(12) United States Patent
Bouaboula et al.

(10) Patent No.: US 11,149,031 B2
(45) Date of Patent: Oct. 19, 2021

(54) SUBSTITUTED N-(3-FLUOROPROPYL)-PYRROLIDINE COMPOUNDS, PROCESSES FOR THEIR PREPARATION AND THERAPEUTIC USES THEREOF

(71) Applicant: SANOFI, Paris (FR)

(72) Inventors: Monsif Bouaboula, Bridegwater, NJ (US); Maurice Brollo, Paris (FR); Victor Certal, Paris (FR); Youssef El-Ahmad, Paris (FR); Bruno Filoche-Romme, Paris (FR); Frank Halley, Paris (FR); Gary McCort, Paris (FR); Laurent Schio, Paris (FR); Michel Tabart, Paris (FR); Corinne Terrier, Paris (FR); Fabienne Thompson, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 16/414,558

(22) Filed: May 16, 2019

(65) Prior Publication Data

US 2020/0361918 A1    Nov. 19, 2020

Related U.S. Application Data

(63) Continuation of application No. PCT/EP2017/068446, filed on Jul. 21, 2017.

(30) Foreign Application Priority Data

Nov. 17, 2016    (EP) .................................... 16306506

(51) Int. Cl.
| | |
|---|---|
| A61P 15/00 | (2006.01) |
| A61P 19/10 | (2006.01) |
| A61P 35/00 | (2006.01) |
| C07D 207/12 | (2006.01) |
| C07D 409/12 | (2006.01) |
| C07D 405/12 | (2006.01) |

(52) U.S. Cl.
CPC ............ *C07D 409/12* (2013.01); *A61P 15/00* (2018.01); *A61P 19/10* (2018.01); *A61P 35/00* (2018.01); *C07D 207/12* (2013.01); *C07D 405/12* (2013.01)

(58) Field of Classification Search
CPC .......... A61P 15/00; A61P 19/10; A61P 35/00; C07D 207/12; C07D 409/12; C07D 405/12
See application file for complete search history.

(56) References Cited

U.S. PATENT DOCUMENTS

| | | | |
|---|---|---|---|
| 6,495,607 B2 | 12/2002 | Bohlmann et al. | |
| 7,612,114 B2 | 11/2009 | Hamaoka et al. | |
| 9,309,211 B2 | 4/2016 | Xiao et al. | |
| 9,540,361 B2 | 1/2017 | Djicks et al. | |
| 9,714,221 B1 | 7/2017 | Bouaboula et al. | |
| 10,570,090 B2 | 2/2020 | Bouaboula et al. | |
| 2013/0252890 A1 | 9/2013 | Wintermantel et al. | |
| 2015/0080438 A1 | 3/2015 | Wintermantel et al. | |
| 2020/0392081 A1 | 12/2020 | Bouaboula et al. | |

FOREIGN PATENT DOCUMENTS

| | | |
|---|---|---|
| CN | 1309635 A | 8/2001 |
| CN | 106924210 A | 7/2017 |
| EP | 1 229 036 | 8/2002 |
| JP | 2002520388 A | 7/2002 |
| JP | 2005528320 A | 9/2005 |
| JP | 2008512348 A | 4/2008 |
| JP | 2008546706 A | 12/2008 |
| JP | 2011500538 A | 1/2011 |
| JP | 2013530973 A | 8/2013 |
| JP | 2015500814 A | 1/2015 |
| WO | 1992015579 A1 | 9/1992 |
| WO | 00/03979 A1 | 1/2000 |
| WO | 2003016270 A2 | 2/2003 |
| WO | WO2003/091239 | 11/2003 |

(Continued)

OTHER PUBLICATIONS

RN1861739-57-2, 2016, registry database compound.*
International Search Report for International Application No. PCT/EP2017/068446, dated Sep. 12, 2017, 5 pages.
Ruff, et al., "Estrogen receptor transcription and transactivation: Structure-function relationship in DNA-and ligand-binding domains of estrogen receptors." Breast Cancer Research, vol. 2, No. 5, p. 353-359.
Franks, et al., "Selective Estrogen Receptor Modulators: Cannabinoid Receptor Inverse Agonists with Differential CB1 and CB2 Selectively," Frontiers in Pharmacology, 7(503): 1-16 (2016).

(Continued)

*Primary Examiner* — Sun Jae Yoo
(74) *Attorney, Agent, or Firm* — McNeill Baur PLLC

(57) ABSTRACT

The present disclosure relates to novel substituted N-(3-fluoropropyl)-pyrrolidine compounds of formula (I-A), wherein R1 and R2 represent independently a hydrogen atom or a deuterium atom; A represents an oxygen or nitrogen atom; and SERM-F represents a selective estrogen receptor modulator fragment comprising an aryl or heteroaryl group linked to the adjacent "A" group. The disclosure also relates to the preparation and to the therapeutic uses of the compounds of formula (I-A) as inhibitors and degraders of estrogen receptors.

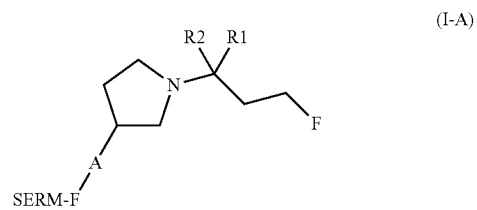

(I-A)

16 Claims, No Drawings

(56) References Cited

FOREIGN PATENT DOCUMENTS

| WO | 2004058682 A1 | 7/2004 |
|---|---|---|
| WO | 2006012135 A1 | 2/2006 |
| WO | 2006138427 A2 | 12/2006 |
| WO | 2009047343 A1 | 4/2009 |
| WO | 2012037410 A2 | 3/2012 |
| WO | WO2012/037411 | 3/2012 |
| WO | 2012068284 A2 | 5/2012 |
| WO | 2013097773 A1 | 7/2013 |
| WO | 2015028409 A1 | 3/2015 |
| WO | 2016097071 A1 | 6/2016 |
| WO | WO2016/097072 | 6/2016 |
| WO | 2016176666 A1 | 11/2016 |
| WO | WO2017/140669 | 8/2017 |
| WO | 2018091153 A1 | 5/2018 |

OTHER PUBLICATIONS

Jordan, Craig V., "Antiestrogens and Selective Estrogen Receptor Modulators as Multifunctional Medicines. 1. Receptor Interactions," Journal of Clinical Chemistry, 46(6): 883-908 (2003).
Miller, Chris P., "SERMs: Evolutionary Chemistry, Revolutionary Biology," Current Pharmaceutical Design, 8(23): 2089-2111 (2002).
Pickar, et al., "SERMs: Progress and future perspectives," Maturitas, Elsevier, 67: 129-138 (2010).
Ullrich, et al., "Estrogen receptor modulator review," Expert Opinion, 16(5):559-572.
Anstead, Gregory M. et al., "2,3-Diarylindenes and 2,3-Diarylindenones: Synthesis, Molecular Structure, Photochemistry, Estrogen Receptor Binging Activity, and Comparisons with Related Triarylethylenes", Journal of Medicinal Chemistry, 1988, vol. 31, No. 7, pp. 1316-1326.
Deroo, B.J., et al., "Estrogen Receptors and Human Disease", The Journal of Clinical Investigation, Mar. 2006, vol. 116, No. 3, pp. 561-570.
Golub et al., "Molecular Classification of Cancer: Class Discovery and Class Prediction by Gene Expression Monitoring", Science, Oct. 15, 1999, vol. 286, pp. 531-537.
International Search Report for International Application No. PCT/EP2017/053282, dated Jul. 6, 2017, 6 pages.
International Search Report for International Application No. PCT/EP2018/069901, dated Oct. 12, 2018, 3 pages.
International Search Report issued in International Application No. PCT/EP2019/073827, dated Oct. 9, 2019, 3 pages.
Lala, P.K., et al., "Role of Nitric Oxide in Tumor Progression: Lessons From Experimental Tumors", Cancer and Metastasis Reviews, 1998, vol. 17, No. 1, pp. 91-106.
McCague, Raymond et al., "Nonisomerizable Analogues of (Z)- and (E)-4-Hydroxytamoxifen. Synthesis and Endocrinological Properties of Substituted Diphenylbenzocycloheptenes", Journal of Medicinal Chemistry, 1988, vol. 31, No. 7, pp. 1285-1290.
International Search Report for PCT/EP2019/073823, dated Oct. 10, 2019, 3 pages.
Pending U.S. Appl. No. 16/634,089, filed Jan. 24, 2020.
Pending U.S. Appl. No. 17/124,852, filed Dec. 17, 2020.
Pending U.S. Appl. No. 17/193,706, filed Mar. 5, 2021.
Pending U.S. Appl. No. 17/193,776, filed Mar. 5, 2021.
Translation of Office Action issued in Japanese Application No. 2018-515615, dated Sep. 18, 2018, 3 pages.
Translation of Search Report issued in Chinese Application No. 201780023008.0, dated Apr. 23, 2020, 3 pages.

\* cited by examiner

SUBSTITUTED N-(3-FLUOROPROPYL)-PYRROLIDINE COMPOUNDS, PROCESSES FOR THEIR PREPARATION AND THERAPEUTIC USES THEREOF

CROSS-REFERENCE TO RELATED APPLICATIONS

This application is a U.S. Continuation application filed under 35 U.S.C. § 111 claiming the benefit of and priority to International Application No. PCT/EP2017/068446, filed Jul. 21, 2017, which claims the benefit of and priority to European Patent Application 16306506.3, filed Nov. 17, 2016, the contents of each of which are incorporated herein by reference in their entireties.

The present invention relates to novel substituted N-(3-fluoropropyl)-pyrrolidine compounds, the processes for their preparation, as well as the therapeutic uses thereof, in particular as anticancer agents via selective antagonism and degradation of estrogen receptors.

The Estrogen Receptors (ERs) belong to the steroid/nuclear receptor superfamily involved in the regulation of eukaryotic gene expression, cellular proliferation and differentiation in target tissues. ERs are in two forms: the estrogen receptor alpha (ERα) and the estrogen receptor beta (ERβ) respectively encoded by the ESR1 and the ESR2 genes. ERα and ERβ are ligand-activated transcription factors which are activated by the hormone estrogen (the most potent estrogen produced in the body is 17β-estradiol). In the absence of hormone, ERs are largely located in the cytosol of the cell. When the hormone estrogen binds to ERs, ERs migrate from the cytosol to the cell nucleus, form dimers and then bind to specific genomic sequences called Estrogen Response Elements (ERE). The DNA/ER complex interacts with co-regulators to modulate the transcription of target genes.

ERα is mainly expressed in reproductive tissues such as uterus, ovary, breast, bone and white adipose tissue. Abnormal ERα signaling leads to development of a variety of diseases, such as cancers, metabolic and cardiovascular diseases, neurodegenerative diseases, inflammation diseases and osteoporosis.

ERα is expressed in not more than 10% of normal breast epithelium but approximately 50-80% of breast tumors. Such breast tumors with high level of ERα are classified as ERα-positive breast tumors. The etiological role of estrogen in breast cancer is well established and modulation of ERα signaling remains the mainstay of breast cancer treatment for the majority ERα-positive breast tumors. Currently, several strategies for inhibiting the estrogen axis in breast cancer exist, including: 1—blocking estrogen synthesis by aromatase inhibitors that are used to treat early and advanced ERα-positive breast cancer patients; 2—antagonizing estrogen ligand binding to ERα by tamoxifen which is used to treat ERα-positive breast cancer patients in both pre- and post-menopausal settings; 3—antagonizing and downregulating ERα levels by fulvestrant, which is used to treat breast cancer in patients that have progressed despite endocrine therapies such as tamoxifen or aromatase inhibitors.

Although these endocrine therapies have contributed enormously to reduction in breast cancer development, about more than one-third of ERα-positive patients display de-novo resistance or develop resistance over time to such existing therapies. Several mechanisms have been described to explain resistance to such hormone therapies. For example, hypersensitivity of ERα to low estrogen level in treatment with aromatase inhibitors, the switch of tamoxifen effects from antagonist to agonist effects in tamoxifen treatments or multiple growth factor receptor signaling pathways. More recently proposed, acquired mutations in ERα occurring after initiation of hormone therapies may play a role in treatment failure and cancer progression. Certain mutations in ERα, particularly those identified in the Ligand Binding Domain (LBD), result in the ability to bind to DNA in the absence of ligand and confer hormone independence in cells harboring such mutant receptors.

Most of the endocrine therapy resistance mechanisms identified rely on ERα-dependent activity. One of the new strategies to counterforce such resistance is to shut down the ERα signaling by removing ERα from the tumor cells using Selective Estrogen Receptors Degraders (SERDs). Clinical and preclinical data showed that a significant number of the resistance pathways can be circumvented by the use SERDs.

There is still a need to provide SERDs with good degradation efficacy.

The objective of the present invention is to provide novel compounds able to selectively antagonize and degrade the estrogen receptors (SERDs compounds), for use in cancer treatment.

The present invention relates to the compounds of the formula (I-A):

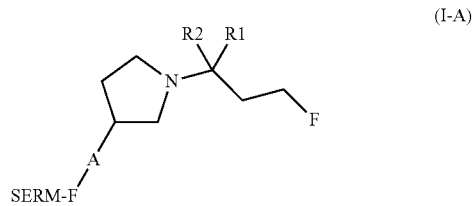

wherein:
R1 and R2 represent independently a hydrogen atom or a deuterium atom;
A represents an oxygen or nitrogen atom (namely, A represents a group of formula —O— or —NH—); and
SERM-F represents a selective estrogen receptor modulator fragment, i.e. a molecule having a selective antagonist activity for estrogen receptors, said SERM-F comprising an aryl or heteroaryl group linked to the adjacent "A" group.

In another embodiment, the present invention relates to the compounds of the formula (I-A) above wherein:
R1 and R2 represent independently a hydrogen atom or a deuterium atom;
A represents an oxygen or nitrogen atom (namely, A represents a group of formula —O— or —NH—); and
SERM-F represents a selective estrogen receptor modulator fragment, i.e. a molecule having a selective antagonist activity for estrogen receptors, said SERM-F comprising an aryl or heteroaryl group linked to the adjacent "A" group;
with the proviso that the compounds of formula (I-B) below are excluded:

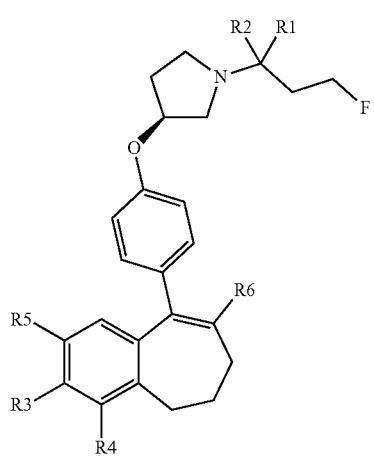

wherein, in formula (I-B):
R1 and R2 represent independently a hydrogen atom or a deuterium atom;
R3 represents a hydrogen atom, a —COOH group, a —OH group or a —OPO(OH)$_2$ group;
R4 represents a hydrogen atom or a fluorine atom;
R5 represents a hydrogen atom or a —OH group;
wherein:
  at least one of R3 or R5 is different from a hydrogen atom;
  when R3 represents a —COOH group, a —OH group or a —OPO(OH)$_2$ group, then R5 represents a hydrogen atom;
  when R5 represents a —OH group, then R3 and R4 represent hydrogen atoms;
R6 is selected from:
  a phenyl group or a heteroaryl group comprising 3 to 9 carbon atoms and comprising from 1 to 3 heteroatoms independently selected from oxygen, nitrogen and sulphur, said phenyl and heteroaryl groups being unsubstituted or substituted with 1 to 3 substituents independently selected from: a (C$_1$-C$_6$)-alkyl group unsubstituted or substituted with one or more (such as 1, 2 or 3) fluorine atoms; a halogen atom; a —OH group; a (C$_1$-C$_6$)-alkoxy group unsubstituted or substituted with one or more (such as 1, 2 or 3) fluorine atoms; a cyano group; a sulphur group substituted with 5 fluorine atoms or (C$_1$-C$_6$)-alkyl groups substituted with two or more (such as 2 or 3) fluorine atoms; a sulfonyl-(C$_1$-C$_6$)-alkyl group wherein said (C$_1$-C$_6$)-alkyl group are unsubstituted or substituted with two or more (such as 2 or 3) fluorine atoms; a silane group substituted with 3 (C$_1$-C$_6$)-alkyl groups; an amine group unsubstituted or substituted with one or more (such as 1 or 2) (C$_1$-C$_6$)-alkyl groups; an amide group unsubstituted or substituted with one or more (such as 1 or 2) (C$_1$-C$_6$)-alkyl groups; a heterocycloalkyl group saturated or partially saturated, comprising 3 to 5 carbon atoms and comprising 1 or 2 heteroatoms independently selected from oxygen, nitrogen or sulphur; or a heteroaryl group comprising 2 to 4 carbon atoms and comprising 1 to 3 heteroatoms selected from oxygen, nitrogen or sulphur and being unsubstituted or substituted with an oxo group; and
  a cycloalkyl group or a heterocycloalkyl group comprising 4 to 9 carbon atoms and comprising 1 or 2 heteroatoms independently selected from oxygen, nitrogen or sulphur, said cycloalkyl or heterocycloalkyl groups being saturated or partially saturated and being unsubstituted or substituted with 1 to 4 substituents independently selected from:
  a fluorine atom; a —OH group; a (C$_1$-C$_6$)-alkyl group; a —COOR7 group wherein R7 is a (C$_1$-C$_6$)-alkyl group; or an oxo group.

In another embodiment, the present invention relates to the compounds of the formula (I-A) above wherein:
R1 and R2 represent independently a hydrogen atom or a deuterium atom;
A represents an oxygen or nitrogen atom (namely, A represents a group of formula —O— or —NH—); and
SERM-F represents a selective estrogen receptor modulator fragment (i.e. a molecule having a selective antagonist activity for estrogen receptors) selected from the following structures (aI), (bII), (cII) and (dIV), provided that when A represents a nitrogen atom then SERM-F represents the structure (aI):

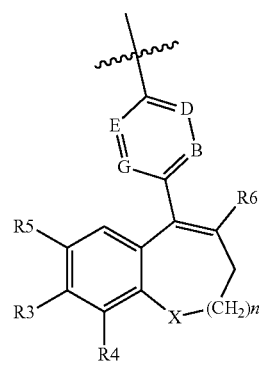

(aI)

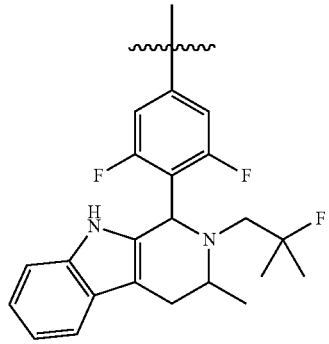

(bII)

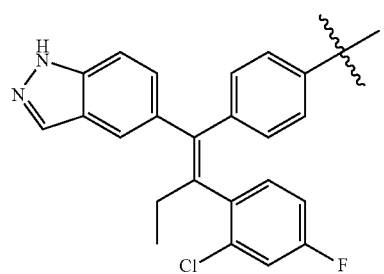

(cIII)

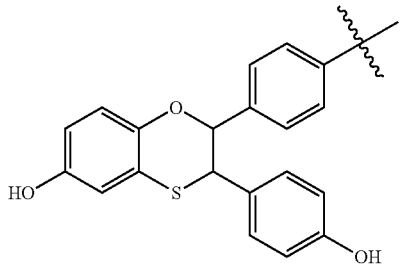

(dIV)

wherein:
B, D, E and G represent independently carbon (═CH—) or nitrogen (N) atoms;
n is an integer selected from 0 and 1;
X represents —CH$_2$—, —O—, —S—, —SO— or —SO$_2$—;
when n=1 and X=CH$_2$, then at least one of A, B, D, E or G is a nitrogen atom;
R3 represents a hydrogen atom or an —OH, —COOH or —OPO(OH)$_2$ group;
R4 represents a hydrogen, fluorine or chlorine atom or a methyl group;
R5 represents a hydrogen, fluorine or chlorine atom, or a methyl or —OH group;
wherein R3 and R5 do not simultaneously represent —OH groups or hydrogen atoms;
R6 is selected from:
  a phenyl group, which is unsubstituted or substituted with 1 to 3 substituents independently selected from:
  a (C$_1$-C$_6$)-alkyl group unsubstituted or substituted with one or more (such as 1, 2 or 3) fluorine atoms or —OH groups; a halogen atom; an —OH group; a (C$_1$-C$_6$)-alkoxy group unsubstituted or substituted with one or more (such as 1, 2 or 3) fluorine atoms, (C$_1$-C$_6$)-alkoxy or heterocycloalkyl groups; a cyano group; a sulphur group substituted with 5 fluorine atoms or with a (C$_1$-C$_6$)-alkyl group substituted with two or more (such as 2 or 3) fluorine atoms; a sulfonyl-(C$_1$-C$_6$)-alkyl group wherein said (C$_1$-C$_6$)-alkyl group is unsubstituted or substituted with two or more (such as 2 or 3) fluorine atoms; a silane group substituted with three (C$_1$-C$_6$)-alkyl groups; an amine group unsubstituted or substituted with one or more (such as 1 or 2) (C$_1$-C$_6$)-alkyl groups; an amide group unsubstituted or substituted with one or more (such as 1 or 2) (C$_1$-C$_6$)-alkyl or (C$_1$-C$_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO$_2$NH$_2$ group; a —COOH group; a —O-cycloalkyl group; a —O-heterocycloalkyl group; and a —OCD$_3$ group;
  a heteroaryl group comprising 3 to 9 carbon atoms and comprising between 1 to 3 heteroatoms independently selected from oxygen, nitrogen and sulphur, said heteroaryl group being unsubstituted or substituted with 1 to 3 substituents independently selected from:
  a (C$_1$-C$_6$)-alkyl group unsubstituted or substituted with one or more (such as 1, 2 or 3) fluorine atoms; a halogen atom; an —OH group; a (C$_1$-C$_6$)-alkoxy group unsubstituted or substituted with one or more (such as 1, 2 or 3) fluorine atoms; a cyano group; a sulphur group substituted with 5 fluorine atoms or with a (C$_1$-C$_6$)-alkyl group substituted with two or more (such as 2 or 3) fluorine atoms; a sulfonyl-(C$_1$-C$_6$)-alkyl group wherein said (C$_1$-C$_6$)-alkyl group is unsubstituted or substituted with two or more (such as 2 or 3) fluorine atoms; a silane group substituted with three (C$_1$-C$_6$)-alkyl groups; an amine group unsubstituted or substituted with one or more (such as 1 or 2) (C$_1$-C$_6$)-alkyl groups; an amide group unsubstituted or substituted with one or more (such as 1 or 2) (C$_1$-C$_6$)-alkyl or (C$_1$-C$_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—(C$_1$-C$_6$)-alkyl group; and an oxo group;
  a cycloalkyl group comprising 4 to 9 carbon atoms, which is saturated or partially saturated, and which is unsubstituted or substituted with 1 to 4 substituents independently selected from:
  a fluorine atom; an —OH group; a (C$_1$-C$_6$)-alkyl group; a —COOR7 group wherein R7 is a (C$_1$-C$_6$)-alkyl group; and an oxo group; and
  a heterocycloalkyl group comprising 4 to 9 carbon atoms and comprising 1 or 2 heteroatoms independently selected from oxygen, nitrogen and sulphur, said heterocycloalkyl group being saturated or partially saturated and being unsubstituted or substituted with 1 to 4 substituents independently selected from:
  a fluorine atom; an —OH group; a (C$_1$-C$_6$)-alkyl group; a —COOR7 group wherein R7 is a (C$_1$-C$_6$)-alkyl group; and an oxo group.
In another embodiment, the invention relates to the compounds of formula (I'):

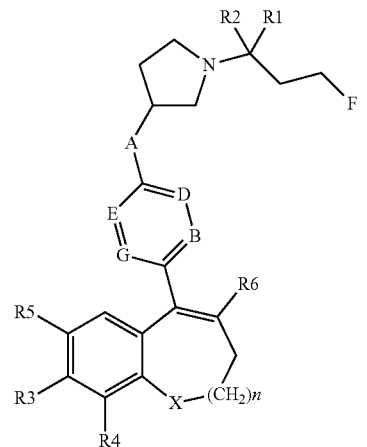

(I')

wherein R1, R2, R3, R4, R5, R6, A, B, D, E, G, X and n are as defined above.
The compounds of formula (I') correspond to the compounds of formula (I-A) as described above, wherein the fragment SERM-F corresponds to the formula (aI) above.

The compounds of the invention, namely the compounds of formulae (I-A) and (I') as defined above, contain one or more asymmetric carbon atoms, more particularly one asymmetric carbon atom on the pyrrolydinyl group. They may therefore exist in the form of enantiomers. These enantiomers form part of the invention. In particular, the carbon 3 of the pyrrolidinyl group linked to the A moiety in formulae (I-A) and (I') above may be in the absolute configuration (R) or (S). The carbon 3 of the pyrrolidinyl group is advantageously in the absolute configuration (S).

Hence, the invention also includes the compounds of formula (I), wherein R1, R2, R3, R4, R5, R6, A, B, D, E, G, X and n are as defined in formula (I') or (I-A) above:

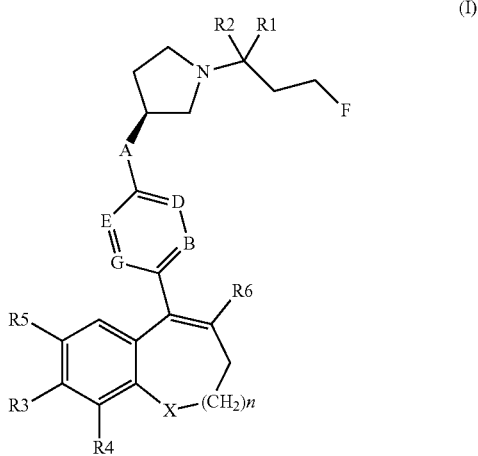

(I)

The compounds of the invention may be present as well under tautomeric forms and are part of the invention.

The compounds of the invention may exist in the form of bases, acids, zwitterion or of addition salts with acids or bases. Such addition salts, bases, acids and zwitterion are part of the invention. Mention may be made for example of hydrochloride salts.

These salts may be prepared with pharmaceutically acceptable acids or bases, although the salts of other acids or bases useful, for example, for purifying or isolating the compounds of the invention also form part of the invention.

In the context of the present invention, the terms below have the following definitions unless otherwise mentioned throughout the specification:
  a halogen atom: a fluorine, a chlorine, a bromine or an iodine atom;
  an oxo: a "=O" group;
  a cyano group: a "—C≡N" group;
  an amine group: a nitrogen atom unsubstituted (—NH$_2$) or substituted with one or more ($C_1$-$C_6$)-alkyl groups;
  an amide group: a —C(O)NRR' or —NH—CO—R" group, wherein R represents a hydrogen atom or a ($C_1$-$C_6$)-alkyl group, R' represents a hydrogen atom or a ($C_1$-$C_6$)-alkoxy group, and R" represents a ($C_1$-$C_6$)-alkyl or ($C_1$-$C_6$)-alkoxy group;
  a silane group: a silicon atom substituted with 3 ($C_1$-$C_6$)-alkyl groups;
  an alkyl group: a linear or branched saturated hydrocarbon-based aliphatic group comprising, unless otherwise mentioned, from 1 to 6 carbon atoms (noted "($C_1$-$C_6$)-alkyl"). By way of examples, mention may be made of, but not limited to: methyl (Me), ethyl (Et), propyl, n-propyl, isopropyl (iPr), butyl, isobutyl, sec-butyl, tert-butyl, pentyl, isopentyl, hexyl and isohexyl groups, and the like;
  an alkoxy group: an —O-alkyl group where the alkyl group is as previously defined. By way of examples, mention may be made of, but not limited to: methoxy (—OMe), ethoxy (—OEt), propoxy, isopropoxy (O-iPr), linear, secondary or tertiary butoxy, isobutoxy, pentoxy or hexoxy groups, and the like;
  a cycloalkyl group: a cyclic alkyl group comprising, unless otherwise mentioned, from 3 to 6 carbon atoms, saturated or partially unsaturated and unsubstituted or substituted. By way of examples, mention may be made of, but not limited to: cyclopropyl, cyclobutyl, cyclopentyl, cyclohexyl, cyclohexen groups, and the like;
  a heterocycloalkyl group: a cyclic alkyl group comprising, unless otherwise mentioned, from 3 to 6 carbon atoms and containing 1 or 2 heteroatoms such as oxygen, nitrogen and sulphur. Such nitrogen atom may be substituted by an oxygen atom in order to form a —N—O bond. Such —N—O bond can be in a form of a N-oxide (—N$^+$—O$^-$). Such heterocycloalkyl group may be saturated or partially saturated, unsubstituted or substituted, and may be monocyclic or bicyclic.

By way of examples of monocyclic heterocycloalkyl groups, mention may be made of, but not limited to: tetrahydropyridinyl, dihydropyridinyl, dihydropyranyl, tetrahydropyranyl groups, and the like.

A bicyclic heterocycloalkyl group means: a phenyl or monocyclic heteroaryl group fused to a monocyclic heterocycloalkyl group as defined above. By way of examples of bicyclic heterocycloalkyl groups, mention may be made of, but not limited to: tetrahydroquinolinyl, indolinyl, indolinone (also named oxindolyl), benzodioxolyl, dihydrobenzodioxinyl (also named benzodioxanyl, such as benzo-1,4-dioxanyl), dihydrobenzoxazinyl (such as 3,4-dihydro-1,4-benz[1,4]oxazine), benzofuranyl, 2,3-dihydrobenzofuranyl, 5,6-dihydro-2H-pyranyl and dihydroazaindolinyl (also named 2,3-dihydro-1H-pyrrolo[2,3-b]pyridinyl) groups, all optionally substituted as above indicated, and the like.

A heteroaryl group: a cyclic aromatic group containing between 4 and 9 carbon atoms and containing between 1 and 3 heteroatoms, such as nitrogen, oxygen and sulphur. Such nitrogen atom may be substituted by an oxygen atom in order to form a —N—O bond. Such —N—O bond can be in a form of a N-oxide (—N$^+$—O$^-$). Said heteroaryl group may be monocyclic or bicyclic. By way of examples of heteroaryl groups, mention may be made of, but not limited to: isoxazole, pyridine (or pyridinyl), pyrimidine (or pyrimidinyl), benzotriazole, benzoxazole, benzimidazole, benzoxadiazole, benzothiazole, benzothiadiazole, benzofuran, indole (also named indolyl), quinolyl, indazole, benzisoxazole, benzisothiazole and thiazolyl groups, and the like;
  A zwitterion: a globally neutral molecule with a positive and a negative electrical charge and having an acid group and a basic group. By way of examples, mention may be made of, but not limited to compounds of the present inventions having R3 which represents a —COOH group or an —OPO(OH)$_2$ group.

In an embodiment, in the compounds of the invention, R1 and R2 both represent hydrogen atoms.

The invention is therefore directed to the compounds of formula (I-A-1) and (1-1) below, wherein SERM-F, A, B, D, E, G, X, n, R3, R4, R5 and R6 are as defined above:

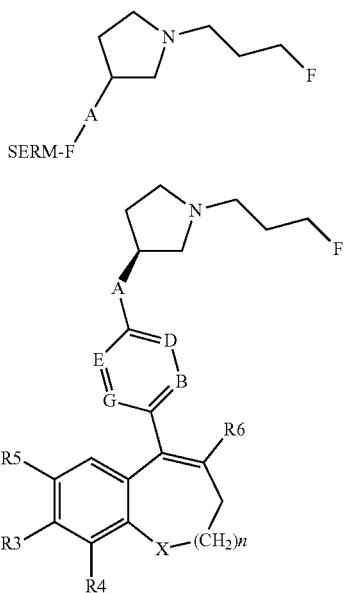

(I-A-1)

(I-1)

In an embodiment of the compounds of formula (I-A-1), (I-1), (I') and (I), when R5 represents an —OH group, then R3 and R4 advantageously represent hydrogen atoms.

In another embodiment, in the compounds of formula (I) and (I'), A represents an oxygen atom. The invention therefore includes the compounds of formula (I-2) below, wherein X, n, R1, R2, R3, R4, R5, R6, B, D, E and G are as defined in formula (I) above:

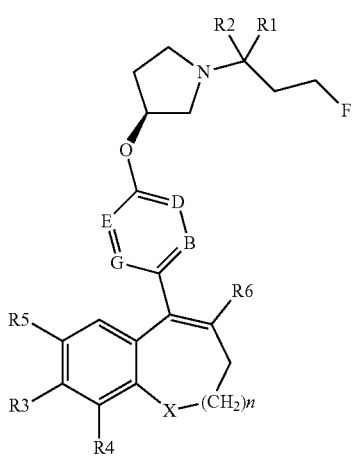

(I-2)

In the compounds of formula (I-2), R1 and R2 advantageously represent hydrogen atoms.

In an embodiment of the compounds of formula (I-2), B, D, E and G represent carbon atoms.

In another embodiment of the compounds of formula (I-2), one or two of B, D, E and G represent nitrogen atoms.

In another embodiment of the compounds of formula (I-2), D represents a nitrogen atom and B, E and G represent carbon atoms.

In another embodiment of the compounds of formula (I-2), E and D represent nitrogen atoms, and B and G represent carbon atoms.

In another embodiment of the compounds of formula (I-2), E and B represent nitrogen atoms, and D and G represent carbon atoms.

In another embodiment of the compounds of formula (I-2), G and B represent nitrogen atoms, and D and E represent carbon atoms.

In another embodiment, in the compounds of formula (I-2) R6 is as defined above.

In the formula (I-2), (I-A-1) and (I-1), as well as in the formula (I') and (1) described above, R6 is advantageously selected from:
 a phenyl group, which is unsubstituted or substituted with 1, 2 or 3 substituents independently selected from:
  a ($C_1$-$C_6$)-alkyl group unsubstituted or substituted with one or more (such as 1, 2 or 3) fluorine atoms or —OH groups (such as methyl, ethyl, tert-butyl, —C(Me)$_2$OH, —CH$_2$F, —CHF$_2$ or —CF$_3$); a halogen atom (such as fluorine or chlorine); an —OH group; a ($C_1$-$C_6$)-alkoxy group unsubstituted or substituted with one or more (such as 1, 2 or 3) fluorine atoms, ($C_1$-$C_6$)-alkoxy or heterocycloalkyl (such as pyrrolidinyl) groups (such as —OMe, —OEt, —O-iPr, —OCH$_2$F, —OCHF$_2$, —OCF$_3$ group, —O—(CH$_2$)$_2$—OCH$_3$ and —O—(CH$_2$)$_2$-pyrrolidin-1-yl); a sulphur group substituted with a ($C_1$-$C_6$)-alkyl group substituted with two or more (such as 2 or 3) fluorine atoms (such as a —SCF$_3$ group); a sulfonyl-($C_1$-$C_6$)-alkyl group (such as a —SO$_2$Me group); an amine group unsubstituted or substituted with one or more (such as 1 or 2) ($C_1$-$C_6$)-alkyl groups (such as a —NHEt or —N(Et)$_2$ group); an amide group substituted with a ($C_1$-$C_6$)-alkoxy group (such as a group —CO—NH—OMe); a —SO$_2$NH$_2$ group; a —COOH group; a —O-cycloalkyl group (such as a —O-cyclopropyl group); a —O-heterocycloalkyl group (such as a —O-oxetanyl group); and a —OCD$_3$ group;
 a heteroaryl group selected from an indole (more particularly indol-4-yl, indol-5-yl or indol-6-yl), pyridinyl (more particularly pyridin-3-yl or pyridin-4-yl), benzofuran, isoxazole (more particularly isoxazol-4-yl), quinolyl (more particularly quinolin-6-yl) and thiazolyl (more particularly thiazol-5-yl) group, said heteroaryl group being unsubstituted or substituted with 1 to 3 substituents independently selected from: a ($C_1$-$C_6$)-alkyl group (such as methyl, ethyl or tert-butyl); a halogen atom (such as fluorine); an —OH group; a ($C_1$-$C_6$)-alkoxy group (such as —OMe or —OEt); an amine group; an amide group substituted with a ($C_1$-$C_6$)-alkoxy group (such as a group —NH—COO-alkyl, in particular-NH—COO(tert-butyl)); and
 a heterocycloalkyl group selected from an indolinyl (more particularly indolin-5-yl or indolin-6-yl), dihydroazaindolinyl (more particularly 2,3-dihydro-1H-pyrrolo[2,3-b]pyridin-5-yl), dihydrobenzodioxinyl (more particularly 2,3-dihydro-1,4-benzodioxin-6-yl), benzodioxolyl (more particularly benzo[1,3]dioxolyl), 2,3-dihydrobenzofuranyl, dihydrobenzoxazinyl (more particularly dihydrobenzoxazin-6-yl and dihydrobenzoxazin-7-yl) and 5,6-dihydro-2H-pyranyl group, the said heterocycloalkyl group being unsubstituted or substituted with 1 to 4 substituents independently selected from:
  a fluorine atom; a ($C_1$-$C_6$)-alkyl group (such as Me or Et); a —COOR7 group wherein R7 is a ($C_1$-$C_6$)-alkyl group (such as a —CO-Me or —COO(tert-butyl) group); and an oxo group.

More specifically, when R6 represents a heteroaryl group, the said heteroaryl is advantageously selected from the following ones:

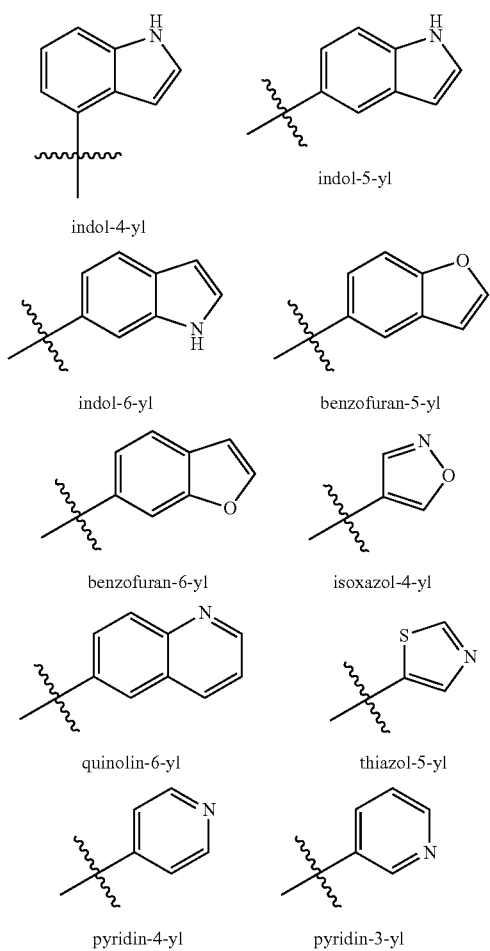

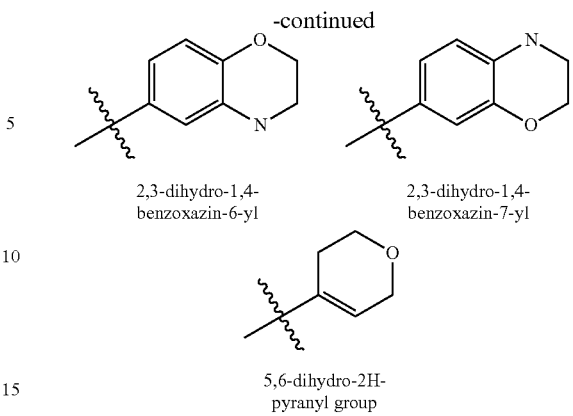

More specifically, when R6 represents a heterocycloalkyl group, said heterocycloalkyl is advantageously selected from the following ones:

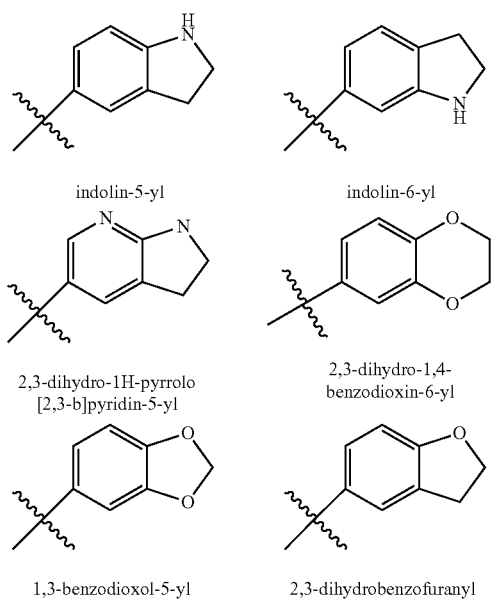

In another embodiment, in the compounds of formula (I), A represents an oxygen atom, B, D, E and G represent carbon atoms, n=0 and X represents —CH$_2$—.

The invention therefore includes the compounds of formula (I-3) below, wherein R1, R2, R3, R4, R5 and R6 are as defined in formula (I) above:

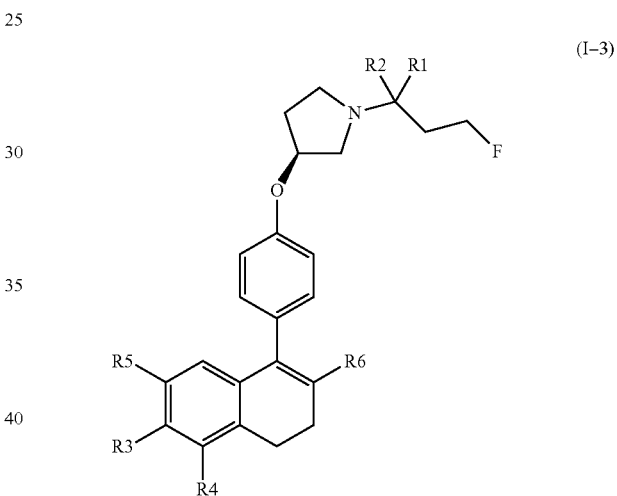

(I-3)

In the compounds of formula (I-3), R1 and R2 advantageously represent hydrogen atoms.

In an embodiment of the compounds of formula (I-3), R4 represents a hydrogen atom, and one of R3 or R5 represents an —OH group while the other of R3 or R5 represents a hydrogen atom.

In another embodiment of the compounds of formula (I-3), R6 is selected from:
a phenyl group, which is unsubstituted or substituted with 1 to 3 substituents independently selected from:
a (C$_1$-C$_6$)-alkyl group unsubstituted or substituted with one or more fluorine atoms or —OH groups; a halogen atom; an —OH group; a (C$_1$-C$_6$)-alkoxy group unsubstituted or substituted with one or more fluorine atoms; a cyano group; a sulphur group substituted with 5 fluorine atoms or with a (C$_1$-C$_6$)-alkyl group substituted with two or more (such as 2 or 3) fluorine atoms; a sulfonyl-(C$_1$-C$_6$)-alkyl group wherein said (C$_1$-C$_6$)-alkyl group is unsubstituted or substituted with two or more fluorine atoms; a silane group substituted with 3 (C$_1$-C$_6$)-alkyl groups; an amine group unsubstituted or substituted with one or more (such as 1 or 2) (C$_1$-C$_6$)-alkyl groups; an amide group unsubstituted or substituted with one or more (such as 1 or 2) (C$_1$-C$_6$)-alkyl or (C$_1$-C$_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a group —$SO_2NH_2$; a group —O-heterocycloalkyl; or a group —$OCD_3$;

a heteroaryl group comprising 3 to 9 carbon atoms and comprising between 1 to 3 heteroatoms independently selected from oxygen, nitrogen and sulphur, said heteroaryl group being unsubstituted or substituted with 1 to 3 substituents independently selected from:

a ($C_1$-$C_6$)-alkyl group unsubstituted or substituted with one or more fluorine atoms; a halogen atom; an —OH group; a ($C_1$-$C_6$)-alkoxy group unsubstituted or substituted with one or more fluorine atoms; a cyano group; a sulphur group substituted with 5 fluorine atoms or with a ($C_1$-$C_6$)-alkyl group substituted with two or more (such as 2 or 3) fluorine atoms; a sulfonyl-($C_1$-$C_6$)-alkyl group wherein said ($C_1$-$C_6$)-alkyl group is unsubstituted or substituted with two or more fluorine atoms; a silane group substituted with 3 ($C_1$-$C_6$)-alkyl groups; an amine group unsubstituted or substituted with one or more (such as 1 or 2) ($C_1$-$C_6$)-alkyl groups; an amide group unsubstituted or substituted with one or more (such as 1 or 2) ($C_1$-$C_6$)-alkyl or ($C_1$-$C_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—($C_1$-$C_6$)-alkyl group; or an oxo group; or a heterocycloalkyl group comprising 4 to 9 carbon atoms and comprising 1 or 2 heteroatoms independently selected from oxygen, nitrogen and sulphur, the said heterocycloalkyl group being saturated or partially saturated and being unsubstituted or substituted with 1 to 4 substituents independently selected from:

a fluorine atom; an —OH group; a ($C_1$-$C_6$)-alkyl group; a —COOR7 group wherein R7 is a ($C_1$-$C_6$)-alkyl group; and an oxo group.

In another embodiment of the compounds of formula (I-3), R6 is selected from:

a phenyl group, which is substituted with 1 or 2 substituents independently selected from:

a ($C_1$-$C_6$)-alkyl group (such as a tert-butyl group); a halogen atom (such as fluorine or chlorine); an —OH group; a ($C_1$-$C_6$)-alkoxy group unsubstituted or substituted with one or more (such as 1, 2 or 3) fluorine atoms (such as a —$OCF_3$ group); a sulphur group substituted with a ($C_1$-$C_6$)-alkyl group substituted with two or more (such as 2 or 3) fluorine atoms (such as a —$SCF_3$ group);

a heteroaryl group selected from a pyridinyl (more particularly pyridinyl-4-yl) and an indole group, the said heteroaryl group being unsubstituted or substituted with 1 to 3 halogen atoms (such as fluorine); and a 5,6-dihydro-2H-pyranyl group.

In another embodiment, in the compounds of formula (I), A represents an oxygen atom, B, D, E and G represent carbon atoms, n=0 and X represents —S— or —SO—.

The invention therefore includes the compounds of formula (I-4) below, wherein R1, R2, R3, R4, R5 and R6 are as defined in formula (I) above:

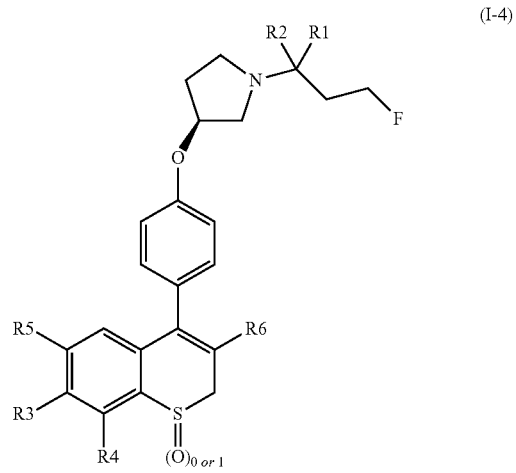

(I-4)

In the compounds of formula (I-4), R1 and R2 advantageously represent hydrogen atoms.

In an embodiment of the compounds of formula (I-4), R4 and R5 represent hydrogen atoms and R3 represents a group of formula —OH, —COOH or —$OPO(OH)_2$.

In another embodiment, in formula (I-4) R3 represents a hydroxyl group.

In another embodiment, in formula (I-4) R6 is selected from:

a phenyl group, which is unsubstituted or substituted with 1 to 3 substituents independently selected from:

a ($C_1$-$C_6$)-alkyl group unsubstituted or substituted with one or more (such as 1, 2 or 3) fluorine atoms or —OH groups; a halogen atom; an —OH group; a ($C_1$-$C_6$)-alkoxy group unsubstituted or substituted with one or more (such as 1, 2 or 3) fluorine atoms, ($C_1$-$C_6$)-alkoxy or heterocycloalkyl groups; a cyano group; a sulphur group substituted with 5 fluorine atoms or with a ($C_1$-$C_6$)-alkyl group substituted with two or more (such as 2 or 3) fluorine atoms; a sulfonyl-($C_1$-$C_6$)-alkyl group wherein the said ($C_1$-$C_6$)-alkyl group is unsubstituted or substituted with two or more (such as 2 or 3) fluorine atoms; a silane group substituted with three ($C_1$-$C_6$)-alkyl groups; an amine group unsubstituted or substituted with one or more (such as 1 or 2) ($C_1$-$C_6$)-alkyl groups; an amide group unsubstituted or substituted with one or more (such as 1 or 2) ($C_1$-$C_6$)-alkyl or ($C_1$-$C_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —$SO_2NH_2$ group; a —COOH group; a —O-cycloalkyl group; a —O-heterocycloalkyl group; and a —$OCD_3$ group;

a heteroaryl group comprising 3 to 9 carbon atoms and comprising between 1 to 3 heteroatoms independently selected from oxygen, nitrogen and sulphur, the said heteroaryl group being unsubstituted or substituted with 1 to 3 substituents independently selected from:

a ($C_1$-$C_6$)-alkyl group unsubstituted or substituted with one or more (such as 1, 2 or 3) fluorine atoms; a halogen atom; an —OH group; a ($C_1$-$C_6$)-alkoxy group unsubstituted or substituted with one or more (such as 1, 2 or 3) fluorine atoms; a cyano group; a sulphur group substituted with 5 fluorine atoms or with a ($C_1$-$C_6$)-alkyl group substituted with two or more (such as 2 or 3) fluorine atoms; a sulfonyl-($C_1$-$C_6$)-alkyl group wherein said ($C_1$-$C_6$)-alkyl group is unsubstituted or substituted with two or more (such as 2 or 3) fluorine atoms; a silane group substituted with three ($C_1$-$C_6$)-alkyl groups; an amine group unsubstituted or substituted with one or more (such as 1 or 2) ($C_1$-$C_6$)-alkyl groups; an amide group unsubstituted or substituted with one or more (such as 1 or 2) ($C_1$-$C_6$)-alkyl or ($C_1$-$C_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—($C_1$-$C_6$)-alkyl group; and an oxo group; and a heterocycloalkyl group comprising 4 to 9 carbon atoms and comprising 1 or 2 heteroatoms independently selected from oxygen, nitrogen and sulphur, said heterocycloalkyl group being saturated or partially saturated and being unsubstituted or substituted with 1 to 4 substituents independently selected from: a fluorine atom; an —OH group; a ($C_1$-$C_6$)-alkyl group; a —COOR7 group wherein R7 is a ($C_1$-$C_6$)-alkyl group; and an oxo group.

In another embodiment, in formula (I-4) R6 is selected from:

a phenyl group substituted with 1, 2 or 3 substituents independently selected from:
a ($C_1$-$C_6$)-alkyl group unsubstituted or substituted with one or more (such as 1, 2 or 3) fluorine atoms or —OH groups (such as methyl, ethyl, tert-butyl, —C(Me)$_2$OH, —CH$_2$F or —CHF$_2$); a halogen atom (such as fluorine or chlorine); a ($C_1$-$C_6$)-alkoxy group unsubstituted or substituted with one or more (such as 1, 2 or 3) fluorine atoms (such as —OMe, —OEt, —OCH$_2$F, —OCHF$_2$ or —OCF$_3$); a sulphur group substituted with a ($C_1$-$C_6$)-alkyl group, which alkyl group is substituted with 2 to 3 fluorine atoms (such as a —SCF$_3$ group); an amine group unsubstituted or substituted with one or two ($C_1$-$C_6$)-alkyl groups (such as a —N(Et)$_2$ group); a —SO$_2$NH$_2$ group; a —O-heterocycloalkyl group (such as a —O-oxetanyl group); or a —OCD$_3$ group;

a heteroaryl group selected from an indole, pyridinyl (more particularly pyridin-3-yl or pyridin-4-yl), quinolyl and thiazolyl group, said heteroaryl group being unsubstituted or substituted with 1 to 3 substituents independently selected from: a ($C_1$-$C_6$)-alkyl group (such as methyl, ethyl or tert-butyl) unsubstituted or substituted with 1 or 2 fluorine atoms; a halogen atom (such as fluorine or chlorine); an —OH group; a ($C_1$-$C_6$)-alkoxy group (such as —OMe or —OEt) unsubstituted or substituted with one or more (such as 1, 2 or 3) fluorine atoms; an amine group; an amide group substituted by a ($C_1$-$C_6$)-alkoxy group (such as a group —NH—COO-alkyl, in particular —NH—COO (tert-butyl)); and a heterocycloalkyl group selected from an indolinyl (more particularly 1-indolinyl), dihydrobenzodioxinyl, benzodioxolyl, 2,3-dihydrobenzofuranyl and dihydrobenzoxazinyl group, said heterocycloalkyl group being unsubstituted or substituted with 1 to 4 substituents independently selected from:
a fluorine atom; a ($C_1$-$C_6$)-alkyl group (such as Me or Et); a —COOR7 group wherein R7 is a ($C_1$-$C_6$)-alkyl group (such as a —CO-Me or —COO(tert-butyl) group); and an oxo group.

In another embodiment, in the compounds of formula (I), A represents an oxygen atom, one or two of B, D, E and G represent a nitrogen atom while the others of B, D, E and G represent carbon atoms, n=0 and X represents —S—.

In this embodiment of the invention, G and B advantageously represent carbon atoms while one or both of E and D represent nitrogen atoms.

The invention therefore includes the compounds of formula (I-5) below, wherein E, D, R1, R2, R3, R4, R5 and R6 are as defined in formula (I) above and wherein one or two of E and D represent nitrogen atoms:

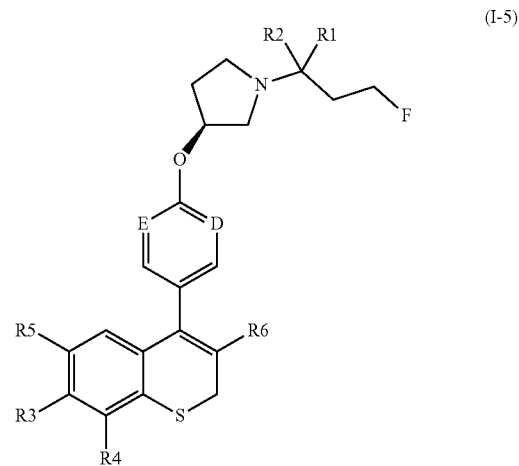

(I-5)

In the compounds of formula (I-5), R1 and R2 advantageously represent hydrogen atoms.

In an embodiment of the compounds of formula (I-5), R4 and R5 represent hydrogen atoms and R3 represents a hydroxyl group.

In another embodiment, in formula (I-5) R6 is selected from:

a phenyl group, which is unsubstituted or substituted with 1 to 3 substituents independently selected from:
a ($C_1$-$C_6$)-alkyl group unsubstituted or substituted with one or more (such as 1, 2 or 3) fluorine atoms or —OH groups; a halogen atom; an —OH group; a ($C_1$-$C_6$)-alkoxy group unsubstituted or substituted with one or more (such as 1, 2 or 3) fluorine atoms, ($C_1$-$C_6$)-alkoxy or heterocycloalkyl groups; a cyano group; a sulphur group substituted with 5 fluorine atoms or with a ($C_1$-$C_6$)-alkyl group substituted with two or more (such as 2 or 3) fluorine atoms; a sulfonyl-($C_1$-$C_6$)-alkyl group wherein said ($C_1$-$C_6$)-alkyl group is unsubstituted or substituted with two or more (such as 2 or 3) fluorine atoms; a silane group substituted with three ($C_1$-$C_6$)-alkyl groups; an amine group unsubstituted or substituted with one or more (such as 1 or 2) ($C_1$-$C_6$)-alkyl groups; an amide group unsubstituted or substituted with one or more (such as 1 or 2) ($C_1$-$C_6$)-alkyl or ($C_1$-$C_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO$_2$NH$_2$ group; a —COOH group; a —O-cycloalkyl group; a —O-heterocycloalkyl group; and a —OCD$_3$ group; and a heteroaryl group comprising 3 to 9 carbon atoms and comprising between 1 to 3 heteroatoms independently selected from oxygen, nitrogen and sulphur, said heteroaryl group being unsubstituted or substituted with 1 to 3 substituents independently selected from:
a $(C_1-C_6)$-alkyl group unsubstituted or substituted with one or more (such as 1, 2 or 3) fluorine atoms; a halogen atom; an —OH group; a $(C_1-C_6)$-alkoxy group unsubstituted or substituted with one or more (such as 1, 2 or 3) fluorine atoms; a cyano group; a sulphur group substituted with 5 fluorine atoms or with a $(C_1-C_6)$-alkyl group substituted with two or more (such as 2 or 3) fluorine atoms; a sulfonyl-$(C_1-C_6)$-alkyl group wherein said $(C_1-C_6)$-alkyl group is unsubstituted or substituted with two or more (such as 2 or 3) fluorine atoms; a silane group substituted with three $(C_1-C_6)$-alkyl groups; an amine group unsubstituted or substituted with one or more (such as 1 or 2) $(C_1-C_6)$-alkyl groups; an amide group unsubstituted or substituted with one or more (such as 1 or 2) $(C_1-C_6)$-alkyl or $(C_1-C_6)$-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—$(C_1-C_6)$-alkyl group; and an oxo group.

In another embodiment, in formula (I-5) R6 is selected from:
a phenyl group substituted with 1 or 2 substituents independently selected from: a $(C_1-C_6)$-alkyl group (such as methyl); a halogen atom (such as fluorine); and a $(C_1-C_6)$-alkoxy group unsubstituted or substituted with one or more fluorine atoms (such as an —OCF$_3$ group); and
a pyridinyl group (more particularly pyridine-3-yl) substituted with 1 or 2 substituents independently selected from a halogen atom (such as fluorine) and a $(C_1-C_6)$-alkoxy group (such as an —OEt group).

In another embodiment, in the compounds of formula (I), A represents an oxygen atom, B, D, E and G represent carbon atoms, n=0 and X represents —O—.

The invention therefore includes the compounds of formula (I-6) below, wherein R1, R2, R3, R4, R5 and R6 are as defined in formula (I) above:

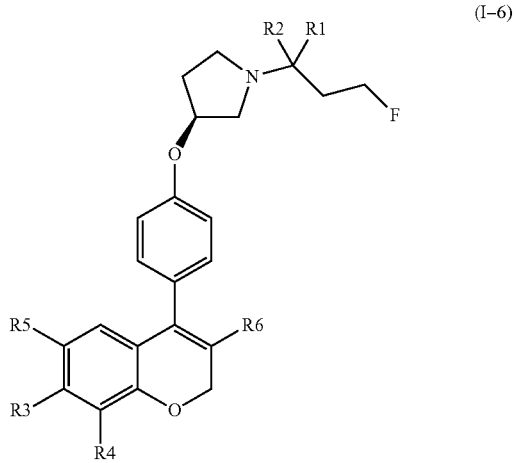

(I-6)

In the compounds of formula (I-6), R1 and R2 advantageously represent hydrogen atoms.

In an embodiment of the compounds of formula (I-6), R4 and R5 advantageously represent hydrogen atoms and R3 a hydroxyl group.

In another embodiment, in formula (I-6) R6 represents a phenyl group which is unsubstituted or substituted with 1 to 3 substituents independently selected from: a $(C_1-C_6)$-alkyl group unsubstituted or substituted with one or more (such as 1, 2 or 3) fluorine atoms or —OH groups; a halogen atom; an —OH group; a $(C_1-C_6)$-alkoxy group unsubstituted or substituted with one or more (such as 1, 2 or 3) fluorine atoms, $(C_1-C_6)$-alkoxy or heterocycloalkyl groups; a cyano group; a sulphur group substituted with 5 fluorine atoms or with a $(C_1-C_6)$-alkyl group substituted with two or more (such as 2 or 3) fluorine atoms; a sulfonyl-$(C_1-C_6)$-alkyl group wherein said $(C_1-C_6)$-alkyl group is unsubstituted or substituted with two or more (such as 2 or 3) fluorine atoms; a silane group substituted with three $(C_1-C_6)$-alkyl groups; an amine group unsubstituted or substituted with one or more (such as 1 or 2) $(C_1-C_6)$-alkyl groups; an amide group unsubstituted or substituted with one or more (such as 1 or 2) $(C_1-C_6)$-alkyl or $(C_1-C_6)$-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO$_2$NH$_2$ group; a —COOH group; a —O-cycloalkyl group; a —O-heterocycloalkyl group; and a —OCD$_3$ group.

In another embodiment, in formula (I-6) R6 represents a phenyl group substituted by 1 or 2 substituents selected from a hydroxyl group and a halogen atom (such as fluorine or chlorine).

In another embodiment, in the compounds of formula (I), A represents a nitrogen atom (A=—NH—), B, D, E and G represent carbon atoms and X represents —CH$_2$—.

The invention therefore includes the compounds of formula (I-7) below, wherein n, R1, R2, R3, R4, R5 and R6 are as defined in formula (I) above:

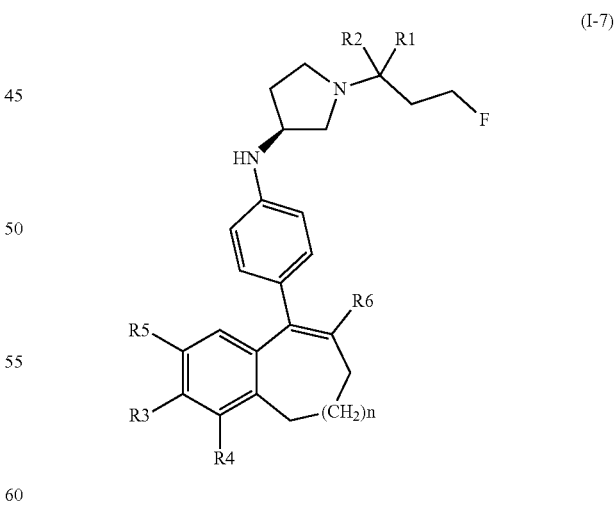

(I-7)

In the compounds of formula (I-7), R1 and R2 advantageously represent hydrogen atoms.

In an embodiment of the compounds of formula (I-7), R4 advantageously represents a hydrogen atom.

In another embodiment, in formula (I-7) one of R3 or R5 represents a hydroxyl group, while the other of R3 or R5 represents a hydrogen atom.

In another embodiment, in formula (I-7) R6 is selected from:
  a phenyl group, which is unsubstituted or substituted with 1 to 3 substituents independently selected from:
a (C$_1$-C$_6$)-alkyl group unsubstituted or substituted with one or more (such as 1, 2 or 3) fluorine atoms or —OH groups; a halogen atom; an —OH group; a (C$_1$-C$_6$)-alkoxy group unsubstituted or substituted with one or more (such as 1, 2 or 3) fluorine atoms, (C$_1$-C$_6$)-alkoxy or heterocycloalkyl groups; a cyano group; a sulphur group substituted with 5 fluorine atoms or with a (C$_1$-C$_6$)-alkyl group substituted with two or more (such as 2 or 3) fluorine atoms; a sulfonyl-(C$_1$-C$_6$)-alkyl group wherein said (C$_1$-C$_6$)-alkyl group is unsubstituted or substituted with two or more (such as 2 or 3) fluorine atoms; a silane group substituted with three (C$_1$-C$_6$)-alkyl groups; an amine group unsubstituted or substituted with one or more (such as 1 or 2) (C$_1$-C$_6$)-alkyl groups; an amide group unsubstituted or substituted with one or more (such as 1 or 2) (C$_1$-C$_6$)-alkyl or (C$_1$-C$_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO$_2$NH$_2$ group; a —COOH group; a —O-cycloalkyl group; a —O-heterocycloalkyl group; and a —OCD$_3$ group; and
  a heteroaryl group comprising 3 to 9 carbon atoms and comprising between 1 to 3 heteroatoms independently selected from oxygen, nitrogen and sulphur, said heteroaryl group being unsubstituted or substituted with 1 to 3 substituents independently selected from:
a (C$_1$-C$_6$)-alkyl group unsubstituted or substituted with one or more (such as 1, 2 or 3) fluorine atoms; a halogen atom; an —OH group; a (C$_1$-C$_6$)-alkoxy group unsubstituted or substituted with one or more (such as 1, 2 or 3) fluorine atoms; a cyano group; a sulphur group substituted with 5 fluorine atoms or with a (C$_1$-C$_6$)-alkyl group substituted with two or more (such as 2 or 3) fluorine atoms; a sulfonyl-(C$_1$-C$_6$)-alkyl group wherein said (C$_1$-C$_6$)-alkyl group is unsubstituted or substituted with two or more (such as 2 or 3) fluorine atoms; a silane group substituted with three (C$_1$-C$_6$)-alkyl groups; an amine group unsubstituted or substituted with one or more (such as 1 or 2) (C$_1$-C$_6$)-alkyl groups; an amide group unsubstituted or substituted with one or more (such as 1 or 2) (C$_1$-C$_6$)-alkyl or (C$_1$-C$_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—(C$_1$-C$_6$)-alkyl group; and an oxo group.

In another embodiment, in formula (I-7) R6 is selected from:
  a phenyl group substituted by 1 or 2 substituents selected from a halogen atom (such as fluorine or chlorine) and a —OCF$_3$, —SCF$_3$ or (C$_1$-C$_6$)-alkyl group (such as tert-butyl); and
  a pyridinyl group (more particularly pyridine-3-yl) substituted by 1 or 2 substituents selected from a halogen atom (such as fluorine) and a (C$_1$-C$_6$)-alkoxy group (such as —OEt).

In another embodiment, in the compounds of formula (I), A represents an oxygen atom, B, D, E and G represent carbon atoms, n=1 and X represents —O—.

The invention therefore includes the compounds of formula (I-8) below, wherein R1, R2, R3, R4, R5 and R6 are as defined in formula (I) above:

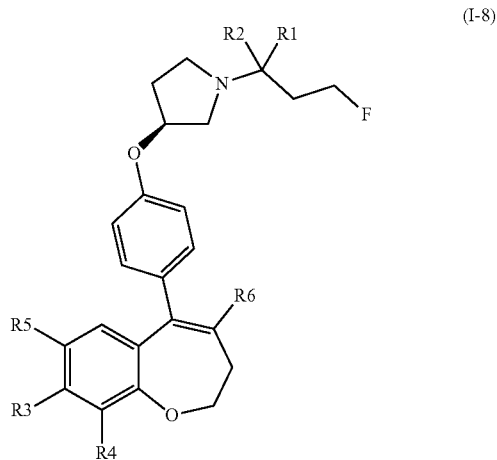

(I-8)

In the compounds of formula (I-8), R1 and R2 advantageously represent hydrogen atoms.

In an embodiment of the compounds of formula (I-8), R3 represents an —OH group.

In another embodiment, in formula (I-8) R4 represents a hydrogen, fluorine or chlorine atom or a methyl group.

In another embodiment, in formula (I-8) R5 represents a hydrogen, fluorine or chlorine atom or a methyl group.

In another embodiment, in formula (I-8) R6 is selected from:
  a phenyl group, which is unsubstituted or substituted with 1 to 3 substituents independently selected from:
a (C$_1$-C$_6$)-alkyl group unsubstituted or substituted with one or more (such as 1, 2 or 3) fluorine atoms or —OH groups; a halogen atom; an —OH group; a (C$_1$-C$_6$)-alkoxy group unsubstituted or substituted with one or more (such as 1, 2 or 3) fluorine atoms, (C$_1$-C$_6$)-alkoxy or heterocycloalkyl groups; a cyano group; a sulphur group substituted with 5 fluorine atoms or with a (C$_1$-C$_6$)-alkyl group substituted with two or more (such as 2 or 3) fluorine atoms; a sulfonyl-(C$_1$-C$_6$)-alkyl group wherein said (C$_1$-C$_6$)-alkyl group is unsubstituted or substituted with two or more (such as 2 or 3) fluorine atoms; a silane group substituted with three (C$_1$-C$_6$)-alkyl groups; an amine group unsubstituted or substituted with one or more (such as 1 or 2) (C$_1$-C$_6$)-alkyl groups; an amide group unsubstituted or substituted with one or more (such as 1 or 2) (C$_1$-C$_6$)-alkyl or (C$_1$-C$_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO$_2$NH$_2$ group; a —COOH group; a —O-cycloalkyl group; a —O-heterocycloalkyl group; and a —OCD group;
  a heteroaryl group comprising 3 to 9 carbon atoms and comprising between 1 to 3 heteroatoms independently selected from oxygen, nitrogen and sulphur, said heteroaryl group being unsubstituted or substituted with 1 to 3 substituents independently selected from:
a $(C_1-C_6)$-alkyl group unsubstituted or substituted with one or more (such as 1, 2 or 3) fluorine atoms; a halogen atom; an —OH group; a $(C_1-C_6)$-alkoxy group unsubstituted or substituted with one or more (such as 1, 2 or 3) fluorine atoms; a cyano group; a sulphur group substituted with 5 fluorine atoms or with a $(C_1-C_6)$-alkyl group substituted with two or more (such as 2 or 3) fluorine atoms; a sulfonyl-$(C_1-C_6)$-alkyl group wherein said $(C_1-C_6)$-alkyl group is unsubstituted or substituted with two or more (such as 2 or 3) fluorine atoms; a silane group substituted with three $(C_1-C_6)$-alkyl groups; an amine group unsubstituted or substituted with one or more (such as 1 or 2) $(C_1-C_6)$-alkyl; an amide group unsubstituted or substituted with one or more (such as 1 or 2) $(C_1-C_6)$-alkyl or $(C_1-C_6)$-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—$(C_1-C_6)$-alkyl group; and an oxo group; and a heterocycloalkyl group comprising 4 to 9 carbon atoms and comprising 1 or 2 heteroatoms independently selected from oxygen, nitrogen and sulphur, said heterocycloalkyl group being saturated or partially saturated and being unsubstituted or substituted with 1 to 4 substituents independently selected from:
a fluorine atom; an —OH group; a $(C_1-C_6)$-alkyl group; a —COOR7 group wherein R7 is a $(C_1-C_6)$-alkyl group; and an oxo group.

In another embodiment, in formula (I-8) R6 is selected from:
a phenyl group substituted with 1 or 2 substituents independently selected from:
a $(C_1-C_6)$-alkyl group unsubstituted or substituted with one or more (such as 1, 2 or 3) fluorine atoms (such as methyl and —CF3); a halogen atom (such as chlorine or fluorine); an —OH group; a $(C_1-C_6)$-alkoxy group unsubstituted or substituted with a $(C_1-C_6)$-alkoxy or a heterocycloalkyl (such as pyrrolidinyl) group (such as —OMe, —OEt, O-iPr, —O—$(CH_2)_2$—$OCH_3$ and —O—$(CH_2)_2$-pyrrolidin-1-yl); a —COOH group; and a —O-cycloalkyl group (such as a —O-cyclopropyl group);
a heteroaryl group selected from an indole, benzofuran and pyridinyl group (more particularly 3-pyridinyl), said heteroaryl group being unsubstituted or substituted with a $(C_1-C_6)$-alkoxy group (such as —OEt); and
an indolinyl (more particularly 1-indolinyl) or 2,3-dihydrobenzofuranyl group.

In another embodiment, in the compounds of formula (I), A represents an oxygen atom, B, E and G represent carbon atoms, D represents a carbon atom or a nitrogen atom, n=1 and X represents —S—.

The invention therefore includes the compounds of formula (I-9) below, wherein D, R1, R2, R3, R4, R5 and R6 are as defined in formula (I) above:

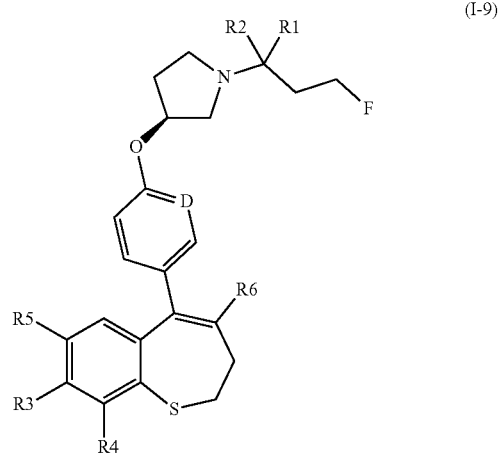

(I-9)

In the compounds of formula (I-9), R1 and R2 advantageously represent hydrogen atoms.

In an embodiment of the compounds of formula (I-9), D represents a carbon atom.

In another embodiment, in formula (I-9) R3 represents a hydrogen atom or an —OH or —COOH group.

In another embodiment, in formula (I-9) R4 represents a hydrogen atom.

In another embodiment, in formula (I-9) R5 represents a hydrogen atom or an —OH group.

In another embodiment, in formula (I-9) R6 is selected from:
a phenyl group, which is unsubstituted or substituted with 1 to 3 substituents independently selected from:
a $(C_1-C_6)$-alkyl group unsubstituted or substituted with one or more (such as 1, 2 or 3) fluorine atoms or —OH groups; a halogen atom; an —OH group; a $(C_1-C_6)$-alkoxy group unsubstituted or substituted with one or more (such as 1, 2 or 3) fluorine atoms, $(C_1-C_6)$-alkoxy or heterocycloalkyl groups; a cyano group; a sulphur group substituted with 5 fluorine atoms or with a $(C_1-C_6)$-alkyl group substituted with two or more (such as 2 or 3) fluorine atoms; a sulfonyl-$(C_1-C_6)$-alkyl group wherein said $(C_1-C_6)$-alkyl group is unsubstituted or substituted with two or more (such as 2 or 3) fluorine atoms; a silane group substituted with three $(C_1-C_6)$-alkyl groups; an amine group unsubstituted or substituted with one or more (such as 1 or 2) $(C_1-C_6)$-alkyl groups; an amide group unsubstituted or substituted with one or more (such as 1 or 2) $(C_1-C_6)$-alkyl or $(C_1-C_6)$-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —$SO_2NH_2$ group; a —COOH group; a —O-cycloalkyl group; a —O-heterocycloalkyl group; and a —$OCD_3$ group;
a heteroaryl group comprising 3 to 9 carbon atoms and comprising between 1 to 3 heteroatoms independently selected from oxygen, nitrogen and sulphur, said heteroaryl group being unsubstituted or substituted with 1 to 3 substituents independently selected from:
a $(C_1-C_6)$-alkyl group unsubstituted or substituted with one or more (such as 1, 2 or 3) fluorine atoms; a halogen atom; an —OH group; a $(C_1-C_6)$-alkoxy group unsubstituted or substituted with one or more (such as 1, 2 or 3) fluorine atoms; a cyano group; a sulphur group substituted with 5 fluorine atoms or with a (C₁-C₆)-alkyl group substituted with two or more (such as 2 or 3) fluorine atoms; a sulfonyl-(C₁-C₆)-alkyl group wherein said (C₁-C₆)-alkyl group is unsubstituted or substituted with two or more (such as 2 or 3) fluorine atoms; a silane group substituted with three (C₁-C₆)-alkyl groups; an amine group unsubstituted or substituted with one or more (such as 1 or 2) (C₁-C₆)-alkyl; an amide group unsubstituted or substituted with one or more (such as 1 or 2) (C₁-C₆)-alkyl or (C₁-C₆)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—(C₁-C₆)-alkyl group; and an oxo group; and a heterocycloalkyl group comprising 4 to 9 carbon atoms and comprising 1 or 2 heteroatoms independently selected from oxygen, nitrogen and sulphur, said heterocycloalkyl group being saturated or partially saturated and being unsubstituted or substituted with 1 to 4 substituents independently selected from: a fluorine atom; an —OH group; a (C₁-C₆)-alkyl group; a —COOR7 group wherein R7 is a (C₁-C₆)-alkyl group; and an oxo group.

In another embodiment, in formula (I-9) R6 is selected from:

a phenyl group substituted with 1, 2 or 3 substituents independently selected from:

a (C₁-C₆)-alkyl group (such as methyl or tert-butyl); a halogen atom (such as fluorine or chlorine); an —OH group; a (C₁-C₆)-alkoxy group unsubstituted or substituted with one or more (such as 1, 2 or 3) fluorine atoms (such as the groups —OMe, —OEt, —OCH₂F, —OCHF₂, —OCF₃); a sulphur group substituted with a (C₁-C₆)-alkyl group substituted with two or more (such as 2 or 3) fluorine atoms (such as a —SCF₃ group); a sulfonyl-(C₁-C₆)-alkyl group (such as a —SO₂Me group); an amine group unsubstituted or substituted with one or more (such as 1 or 2) (C₁-C₆)-alkyl groups (such as the groups —NHEt and —NEt₂); an amide group unsubstituted or substituted with one or more (such as 1 or 2) (C₁-C₆)-alkyl or (C₁-C₆)-alkoxy groups (such as a group —CO—NH—OMe); and a group —OCD₃;

a heteroaryl group selected from an indole, benzofuran, pyridinyl (such as 3-pyridinyl) and isoxazole group, said heteroaryl group being substituted with 1 or 2 substituents independently selected from: a (C₁-C₆)-alkyl group (such as methyl); a halogen atom (such as fluorine); a (C₁-C₆)-alkoxy group (such as —OEt); and an amine group; and a heterocycloalkyl group selected from an indolinyl (more particularly 1-indolinyl), dihydroazaindolinyl, benzodioxolyl (more particularly benzo[1,3]dioxolyl) and 2,3-dihydrobenzofuranyl group, said heterocycloalkyl group being unsubstituted or substituted with 1 or 2 substituents independently selected from a fluorine atom and a (C₁-C₆)-alkyl group (such as methyl).

In another embodiment, in the compounds of formula (I), A represents an oxygen atom, B, D, E and G represent carbon atoms, n=1 and X represents —SO—.

The invention therefore includes the compounds of formula (I-10) below, wherein R1, R2, R3, R4, R5 and R6 are as defined in formula (I) above:

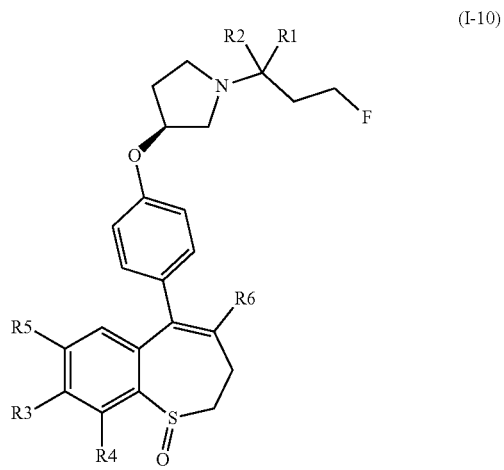

(I-10)

In the compounds of formula (I-10), R1 and R2 advantageously represent hydrogen atoms.

In an embodiment of the compounds of formula (I-10), R3 represents an —OH group.

In another embodiment, in formula (I-10) R4 and R5 represent hydrogen atoms.

In another embodiment, in formula (I-10) R6 represents a phenyl group, which is unsubstituted or substituted with 1 to 3 substituents independently selected from:

a (C₁-C₆)-alkyl group unsubstituted or substituted with one or more (such as 1, 2 or 3) fluorine atoms or —OH groups; a halogen atom; an —OH group; a (C₁-C₆)-alkoxy group unsubstituted or substituted with one or more (such as 1, 2 or 3) fluorine atoms, (C₁-C₆)-alkoxy or heterocycloalkyl groups; a cyano group; a sulphur group substituted with 5 fluorine atoms or with a (C₁-C₆)-alkyl group substituted with two or more (such as 2 or 3) fluorine atoms; a sulfonyl-(C₁-C₆)-alkyl group wherein said (C₁-C₆)-alkyl group is unsubstituted or substituted with two or more (such as 2 or 3) fluorine atoms; a silane group substituted with three (C₁-C₆)-alkyl groups; an amine group unsubstituted or substituted with one or more (such as 1 or 2) (C₁-C₆)-alkyl groups; an amide group unsubstituted or substituted with one or more (such as 1 or 2) (C₁-C₆)-alkyl or (C₁-C₆)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO₂NH₂ group; a —COOH group; a —O-cycloalkyl group; a —O-heterocycloalkyl group; and a —OCD₃ group.

In another embodiment, in formula (I-10) R6 represents a phenyl group substituted with a (C₁-C₆)-alkoxy group unsubstituted or substituted with 1, 2 or 3 fluorine atoms (such as a group —OCF₃).

In another embodiment, in the compounds of formula (I), A represents an oxygen atom, B, D, E and G represent carbon atoms, n=1 and X represents —SO₂—.

The invention therefore includes the compounds of formula (I-11) below, wherein R1, R2, R3, R4, R5 and R6 are as defined in formula (I) above:

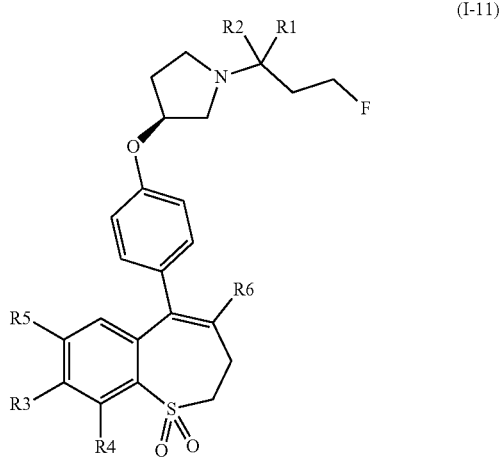

(I-11)

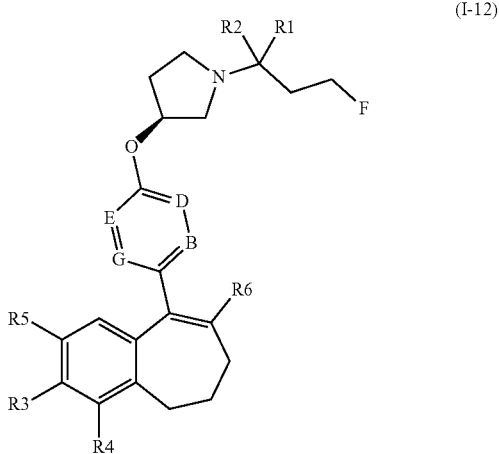

(I-12)

In the compounds of formula (I-11), R1 and R2 advantageously represent hydrogen atoms.

In an embodiment of the compounds of formula (I-11), R3 represents an —OH group.

In another embodiment, in formula (I-11) R4 and R5 represent hydrogen atoms.

In another embodiment, in formula (I-11) R6 represents a phenyl group, which is unsubstituted or substituted with 1 to 3 substituents independently selected from: a $(C_1-C_6)$-alkyl group unsubstituted or substituted with one or more (such as 1, 2 or 3) fluorine atoms or —OH groups; a halogen atom; an —OH group; a $(C_1-C_6)$-alkoxy group unsubstituted or substituted with one or more (such as 1, 2 or 3) fluorine atoms, $(C_1-C_6)$-alkoxy or heterocycloalkyl groups; a cyano group; a sulphur group substituted with 5 fluorine atoms or with a $(C_1-C_6)$-alkyl group substituted with two or more (such as 2 or 3) fluorine atoms; a sulfonyl-$(C_1-C_6)$-alkyl group wherein said $(C_1-C_6)$-alkyl group is unsubstituted or substituted with two or more (such as 2 or 3) fluorine atoms; a silane group substituted with three $(C_1-C_6)$-alkyl groups; an amine group unsubstituted or substituted with one or more (such as 1 or 2) $(C_1-C_6)$-alkyl groups; an amide group unsubstituted or substituted with one or more (such as 1 or 2) $(C_1-C_6)$-alkyl or $(C_1-C_6)$-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO$_2$NH$_2$ group; a —COOH group; a —O-cycloalkyl group; a —O-heterocycloalkyl group; and a —OCD$_3$ group.

In another embodiment, in formula (I-11) R6 represents a phenyl group substituted with 1 or 2 substituents independently selected from: a $(C_1-C_6)$-alkyl group (such as methyl); a halogen atom (such a chlorine or fluorine); and an —OH group.

In another embodiment, in the compounds of formula (I), A represents an oxygen atom, n=1, X represents —CH$_2$—, and one or two of B, D, E and G represent nitrogen atoms.

The invention therefore includes the compounds of formula (I-12) below, wherein B, D, E, G, R1, R2, R3, R4, R5 and R6 are as defined in formula (I) above:

In the compounds of formula (I-12), R1 and R2 advantageously represent hydrogen atoms.

In an embodiment of the compounds of formula (I-12), D represents a nitrogen atom and B, E and G represent carbon atoms.

In another embodiment of the compounds of formula (I-12), D and E represent nitrogen atoms and B and G represent carbon atoms.

In another embodiment of the compounds of formula (I-12), B and E represent nitrogen atoms and D and G represent carbon atoms.

In another embodiment of the compounds of formula (I-12), B and G represent nitrogen atoms and D and E represent carbon atoms.

In another embodiment, in formula (I-12) R3 represents an —OH or —COOH group.

In another embodiment, in formula (I-12) R4 represents a hydrogen or fluorine atom.

In another embodiment, in formula (I-12) R5 represents a hydrogen atom.

In another embodiment, in formula (I-12) R6 is selected from:
  a phenyl group, which is unsubstituted or substituted with
    1 to 3 substituents independently selected from:
  a $(C_1-C_6)$-alkyl group unsubstituted or substituted with one or more (such as 1, 2 or 3) fluorine atoms or —OH groups; a halogen atom; an —OH group; a $(C_1-C_6)$-alkoxy group unsubstituted or substituted with one or more (such as 1, 2 or 3) fluorine atoms, $(C_1-C_6)$-alkoxy or heterocycloalkyl groups; a cyano group; a sulphur group substituted with 5 fluorine atoms or with a $(C_1-C_6)$-alkyl group substituted with two or more (such as 2 or 3) fluorine atoms; a sulfonyl-$(C_1-C_6)$-alkyl group wherein said $(C_1-C_6)$-alkyl group is unsubstituted or substituted with two or more (such as 2 or 3) fluorine atoms; a silane group substituted with three $(C_1-C_6)$-alkyl groups; an amine group unsubstituted or substituted with one or more (such as 1 or 2) $(C_1-C_6)$-alkyl groups; an amide group unsubstituted or substituted with one or more (such as 1 or 2) $(C_1-C_6)$-alkyl or $(C_1-C_6)$-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO$_2$NH$_2$ group; a —COOH group; a —O-cycloalkyl group; a —O-heterocycloalkyl group; and a —OCD$_3$ group;

a heteroaryl group comprising 3 to 9 carbon atoms and comprising between 1 to 3 heteroatoms independently selected from oxygen, nitrogen and sulphur, said heteroaryl group being unsubstituted or substituted with 1 to 3 substituents independently selected from:

a ($C_1$-$C_6$)-alkyl group unsubstituted or substituted with one or more (such as 1, 2 or 3) fluorine atoms; a halogen atom; an —OH group; a ($C_1$-$C_6$)-alkoxy group unsubstituted or substituted with one or more (such as 1, 2 or 3) fluorine atoms; a cyano group; a sulphur group substituted with 5 fluorine atoms or with a ($C_1$-$C_6$)-alkyl group substituted with two or more (such as 2 or 3) fluorine atoms; a sulfonyl-($C_1$-$C_6$)-alkyl group wherein said ($C_1$-$C_6$)-alkyl group is unsubstituted or substituted with two or more (such as 2 or 3) fluorine atoms; a silane group substituted with three ($C_1$-$C_6$)-alkyl groups; an amine group unsubstituted or substituted with one or more (such as 1 or 2) ($C_1$-$C_6$)-alkyl; an amide group unsubstituted or substituted with one or more (such as 1 or 2) ($C_1$-$C_6$)-alkyl or ($C_1$-$C_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—($C_1$-$C_6$)-alkyl group; and an oxo group; and a heterocycloalkyl group comprising 4 to 9 carbon atoms and comprising 1 or 2 heteroatoms independently selected from oxygen, nitrogen and sulphur, said heterocycloalkyl group being saturated or partially saturated and being unsubstituted or substituted with 1 to 4 substituents independently selected from:

a fluorine atom; an —OH group; a ($C_1$-$C_6$)-alkyl group; a —COOR7 group wherein R7 is a ($C_1$-$C_6$)-alkyl group; and an oxo group.

In another embodiment, in formula (I-12) R6 is selected from:

a phenyl group substituted with 1, 2 or 3 substituents independently selected from: a ($C_1$-$C_6$)-alkyl group (such as methyl); a halogen atom (such as chlorine or fluorine); and a ($C_1$-$C_6$)-alkoxy group unsubstituted or substituted with one or more (such as 1, 2 or 3) fluorine atoms (such as the groups —OEt, —OCF$_3$ or —OCHF$_2$);

a pyridinyl (such as 3-pyridinyl) group substituted with 1 or 2 substituents independently selected from a halogen atom (such as fluorine) and a ($C_1$-$C_6$)-alkoxy group (such as —OEt); and an indolinyl group (more particularly an 1-indolinyl group) substituted with 1 or 2 ($C_1$-$C_6$)-alkyl groups (such a methyl).

Among the compounds of formula (I) which are part of the instant invention, mention may be made in particular of the following compounds, described in table 1 hereafter:

8-[4-[(3S)-1-(3-fluoropropyl)pyrrolidin-3-yl]oxyphenyl]-7-(3-fluoro-4-pyridyl)-5,6-dihydronaphthalen-2-ol (example 1 in table 1);

8-[4-[(3S)-1-(3-fluoropropyl)pyrrolidin-3-yl]oxyphenyl]-7-(4-hydroxyphenyl)-5,6-dihydronaphthalen-2-ol (example 2);

7-(3,6-dihydro-2H-pyran-4-yl)-8-[4-[(3S)-1-(3-fluoropropyl)pyrrolidin-3-yl]oxyphenyl]-5,6-dihydronaphthalen-2-ol (example 3);

7-(2-chloro-4-fluoro-phenyl)-8-[4-[(3S)-1-(3-fluoropropyl)pyrrolidin-3-yl]oxyphenyl]-5,6-dihydronaphthalen-2-ol (example 4);

8-[4-[(3S)-1-(3-fluoropropyl)pyrrolidin-3-yl]oxyphenyl]-7-(1H-indol-5-yl)-5,6-dihydronaphthalen-2-ol (example 5);

7-(2-fluoro-4-hydroxy-phenyl)-8-[4-[(3S)-1-(3-fluoropropyl)pyrrolidin-3-yl]oxyphenyl]-5,6-dihydronaphthalen-2-ol (example 6);

7-[2-chloro-4-(trifluoromethoxy)phenyl]-8-[4-[(3S)-1-(3-fluoropropyl)pyrrolidin-3-yl]oxyphenyl]-5,6-dihydronaphthalen-2-ol (example 7);

8-[4-[(3S)-1-(3-fluoropropyl)pyrrolidin-3-yl]oxyphenyl]-7-[4-(trifluoromethoxy)phenyl]-5,6-dihydronaphthalen-2-ol (example 8);

8-[4-[(3S)-1-(3-fluoropropyl)pyrrolidin-3-yl]oxyphenyl]-7-[4-(trifluoromethylsulfanyl)phenyl]-5,6-dihydronaphthalen-2-ol (example 9);

8-[4-[(3S)-1-(3-fluoropropyl)pyrrolidin-3-yl]oxyphenyl]-7-[2-fluoro-4-(trifluoromethoxy)phenyl]-5,6-dihydronaphthalen-2-ol (example 10);

7-(4-tert-butylphenyl)-8-[4-[(3S)-1-(3-fluoropropyl)pyrrolidin-3-yl]oxyphenyl]-5,6-dihydronaphthalen-2-ol (example 11);

5-[4-[(3S)-1-(3-fluoropropyl)pyrrolidin-3-yl]oxyphenyl]-6-[4-(trifluoromethoxy)phenyl]-7,8-dihydronaphthalen-2-ol (example 12);

6-(2-chloro-4-fluoro-phenyl)-5-[4-[(3S)-1-(3-fluoropropyl)pyrrolidin-3-yl]oxyphenyl]-7,8-dihydronaphthalen-2-ol (example 13);

6-(2,4-dichlorophenyl)-5-[4-[(3S)-1-(3-fluoropropyl)pyrrolidin-3-yl]oxyphenyl]-7,8-dihydronaphthalen-2-ol (example 14);

5-[4-[(3S)-1-(3-fluoropropyl)pyrrolidin-3-yl]oxyphenyl]-6-(4-hydroxyphenyl)-7,8-dihydronaphthalen-2-ol (example 15);

3-(2-fluoro-4-methyl-phenyl)-4-[4-[(3S)-1-(3-fluoropropyl)pyrrolidin-3-yl]oxyphenyl]-2H-thiochromen-7-ol (example 16);

3-(4-chloro-3-methyl-phenyl)-4-[4-[(3S)-1-(3-fluoropropyl)pyrrolidin-3-yl]oxyphenyl]-2H-thiochromen-7-ol (example 17);

3-(4-chloro-2-fluoro-phenyl)-4-[4-[(3S)-1-(3-fluoropropyl)pyrrolidin-3-yl]oxyphenyl]-2H-thiochromen-7-ol (example 18);

4-[4-[(3S)-1-(3-fluoropropyl)pyrrolidin-3-yl]oxyphenyl]-3-(1H-indol-5-yl)-2H-thiochromen-7-ol (example 19);

4-[4-[(3S)-1-(3-fluoropropyl)pyrrolidin-3-yl]oxyphenyl]-3-indolin-5-yl-2H-thiochromen-7-ol (example 20);

3-(2,4-dichlorophenyl)-4-[4-[(3S)-1-(3-fluoropropyl)pyrrolidin-3-yl]oxyphenyl]-2H-thiochromen-7-ol (example 21);

3-(2-chloro-4-fluoro-phenyl)-4-[4-[(3S)-1-(3-fluoropropyl)pyrrolidin-3-yl]oxyphenyl]-2H-thiochromen-7-ol (example 22);

3-(3-fluoro-4-methoxy-phenyl)-4-[4-[(3S)-1-(3-fluoropropyl)pyrrolidin-3-yl]oxyphenyl]-2H-thiochromen-7-ol (example 23);

3-(2-fluoro-4-methoxy-phenyl)-4-[4-[(3S)-1-(3-fluoropropyl)pyrrolidin-3-yl]oxyphenyl]-2H-thiochromen-7-ol (example 24);

3-(2-fluoro-4-methyl-phenyl)-4-[4-[(3S)-1-(3-fluoropropyl)pyrrolidin-3-yl]oxyphenyl]-2H-thiochromene-7-carboxylic acid (example 25);

3-(4-ethoxy-2-fluoro-phenyl)-4-[4-[(3S)-1-(3-fluoropropyl)pyrrolidin-3-yl]oxyphenyl]-2H-thiochromen-7-ol (example 26);

3-(6-ethoxy-2-fluoro-3-pyridyl)-4-[4-[(3S)-1-(3-fluoropropyl)pyrrolidin-3-yl]oxyphenyl]-2H-thiochromen-7-ol (example 27);

3-(2,3-dihydro-1,4-benzodioxin-6-yl)-4-[4-[(3S)-1-(3-fluoropropyl)pyrrolidin-3-yl]oxyphenyl]-2H-thiochromen-7-ol (example 28);

3-(2,2-dimethylindolin-5-yl)-4-[4-[(3S)-1-(3-fluoropropyl)pyrrolidin-3-yl]oxyphenyl]-2H-thiochromen-7-ol (example 29);

3-[4-(difluoromethoxy)-3-fluoro-phenyl]-4-[4-[(3S)-1-(3-fluoropropyl)pyrrolidin-3-yl]oxyphenyl]-2H-thiochromen-7-ol (example 30);

3-(2,2-difluoro-1,3-benzodioxol-5-yl)-4-[4-[(3S)-1-(3-fluoropropyl)pyrrolidin-3-yl]oxyphenyl]-2H-thiochromen-7-ol (example 31);

3-(2,2-dimethyl-3H-benzofuran-5-yl)-4-[4-[(3S)-1-(3-fluoropropyl)pyrrolidin-3-yl]oxyphenyl]-2H-thiochromen-7-ol (example 32);

3-[2-fluoro-4-(1-hydroxy-1-methyl-ethyl)phenyl]-4-[4-[(3S)-1-(3-fluoropropyl)pyrrolidin-3-yl]oxyphenyl]-2H-thiochromen-7-ol (example 33);

4-[4-[(3S)-1-(3-fluoropropyl)pyrrolidin-3-yl]oxyphenyl]-3-[2-fluoro-4-(trideuteriomethoxy)phenyl]-2H-thiochromen-7-ol (example 34);

3-[4-(difluoromethoxy)-2-fluoro-phenyl]-4-[4-[(3S)-1-(3-fluoropropyl)pyrrolidin-3-yl]oxyphenyl]-2H-thiochromen-7-ol (example 35);

3-(2-chloro-4-ethoxy-phenyl)-4-[4-[(3S)-1-(3-fluoropropyl)pyrrolidin-3-yl]oxyphenyl]-2H-thiochromen-7-ol (example 36);

4-[4-[(3S)-1-(3-fluoropropyl)pyrrolidin-3-yl]oxyphenyl]-3-[2-fluoro-4-(trifluoromethoxy)phenyl]-2H-thiochromen-7-ol (example 37);

6-[4-[4-[(3S)-1-(3-fluoropropyl)pyrrolidin-3-yl]oxyphenyl]-7-hydroxy-2H-thiochromen-3-yl]-4H-1,4-benzoxazin-3-one (example 38);

3-(4-ethoxy-2-methyl-phenyl)-4-[4-[(3S)-1-(3-fluoropropyl)pyrrolidin-3-yl]oxyphenyl]-2H-thiochromen-7-ol (example 39);

3-(4-ethoxy-2,5-difluoro-phenyl)-4-[4-[(3S)-1-(3-fluoropropyl)pyrrolidin-3-yl]oxyphenyl]-2H-thiochromen-7-ol (example 40);

3-(4-ethoxy-2,3-difluoro-phenyl)-4-[4-[(3S)-1-(3-fluoropropyl)pyrrolidin-3-yl]oxyphenyl]-2H-thiochromen-7-ol (example 41);

4-[4-[4-[(3S)-1-(3-fluoropropyl)pyrrolidin-3-yl]oxyphenyl]-7-hydroxy-2H-thiochromen-3-yl]benzenesulfonamide (example 42);

3-(4-chloro-2-ethoxy-phenyl)-4-[4-[(3S)-1-(3-fluoropropyl)pyrrolidin-3-yl]oxyphenyl]-2H-thiochromen-7-ol (example 43);

4-[4-[(3S)-1-(3-fluoropropyl)pyrrolidin-3-yl]oxyphenyl]-3-[4-(oxetan-3-yloxy)phenyl]-2H-thiochromen-7-ol (example 44);

3-(2-fluoro-6-methoxy-3-pyridyl)-4-[4-[(3S)-1-(3-fluoropropyl)pyrrolidin-3-yl]oxyphenyl]-2H-thiochromen-7-ol (example 45);

6-fluoro-5-[4-[4-[(3S)-1-(3-fluoropropyl)pyrrolidin-3-yl]oxyphenyl]-7-hydroxy-2H-thiochromen-3-yl]pyridin-2-ol (example 46);

4-ethyl-6-[4-[4-[(3S)-1-(3-fluoropropyl)pyrrolidin-3-yl]oxyphenyl]-7-hydroxy-2H-thiochromen-3-yl]-1,4-benzoxazin-3-one (example 47);

[3-(2-fluoro-4-methyl-phenyl)-4-[4-[(3S)-1-(3-fluoropropyl)pyrrolidin-3-yl]oxyphenyl]-2H-thiochromen-7-yl]dihydrogen phosphate (example 48);

3-(2,6-difluoro-3-pyridyl)-4-[4-[(3S)-1-(3-fluoropropyl)pyrrolidin-3-yl]oxyphenyl]-2H-thiochromen-7-ol (example 49);

3-(2,6-dichloro-3-pyridyl)-4-[4-[(3S)-1-(3-fluoropropyl)pyrrolidin-3-yl]oxyphenyl]-2H-thiochromen-7-ol (example 50);

5-[4-[4-[(3S)-1-(3-fluoropropyl)pyrrolidin-3-yl]oxyphenyl]-7-hydroxy-2H-thiochromen-3-yl]indolin-2-one (example 51);

3-(4-tert-butylphenyl)-4-[4-[(3S)-1-(3-fluoropropyl)pyrrolidin-3-yl]oxyphenyl]-2H-thiochromen-7-ol (example 52);

3-(3-chloro-2-ethoxy-4-pyridyl)-4-[4-[(3S)-1-(3-fluoropropyl)pyrrolidin-3-yl]oxyphenyl]-2H-thiochromen-7-ol (example 53);

4-[4-[(3S)-1-(3-fluoropropyl)pyrrolidin-3-yl]oxyphenyl]-3-[4-(trifluoromethoxy)phenyl]-2H-thiochromen-7-ol (example 54);

3-(6-chloro-2-fluoro-3-pyridyl)-4-[4-[(3S)-1-(3-fluoropropyl)pyrrolidin-3-yl]oxyphenyl]-2H-thiochromen-7-ol (example 55);

3-(2-chloro-6-methyl-3-pyridyl)-4-[4-[(3S)-1-(3-fluoropropyl)pyrrolidin-3-yl]oxyphenyl]-2H-thiochromen-7-ol (example 56);

3-(2-fluoro-4-methyl-phenyl)-4-[4-[(3S)-1-(3-fluoropropyl)pyrrolidin-3-yl]oxyphenyl]-1-oxo-2H-thiochromen-7-ol (example 57);

3-(2-chloro-4-methyl-phenyl)-4-[4-[(3S)-1-(3-fluoropropyl)pyrrolidin-3-yl]oxyphenyl]-2H-thiochromen-7-ol (example 58);

tert-butyl 6-[4-[4-[(3S)-1-(3-fluoropropyl)pyrrolidin-3-yl]oxyphenyl]-7-hydroxy-2H-thiochromen-3-yl]-2,3-dihydro-1,4-benzoxazine-4-carboxylate (example 59);

3-[4-(fluoromethoxy)phenyl]-4-[4-[(3S)-1-(3-fluoropropyl)pyrrolidin-3-yl]oxyphenyl]-2H-thiochromen-7-ol (example 60);

3-[4-(fluoromethyl)phenyl]-4-[4-[(3S)-1-(3-fluoropropyl)pyrrolidin-3-yl]oxyphenyl]-2H-thiochromen-7-ol (example 61);

3-[4-(difluoromethyl)-2-fluoro-phenyl]-4-[4-[(3S)-1-(3-fluoropropyl)pyrrolidin-3-yl]oxyphenyl]-2H-thiochromen-7-ol (example 62);

3-(3-chloro-4-ethoxy-2-fluoro-phenyl)-4-[4-[(3S)-1-(3-fluoropropyl)pyrrolidin-3-yl]oxyphenyl]-2H-thiochromen-7-ol (example 63);

3-(2,3-difluoro-4-methyl-phenyl)-4-[4-[(3S)-1-(3-fluoropropyl)pyrrolidin-3-yl]oxyphenyl]-2H-thiochromen-7-ol (example 64);

tert-butyl N-[6-fluoro-5-[4-[4-[(3S)-1-(3-fluoropropyl)pyrrolidin-3-yl]oxyphenyl]-7-hydroxy-2H-thiochromen-3-yl]-2-pyridyl]carbamate (example 65);

4-[4-[(3S)-1-(3-fluoropropyl)pyrrolidin-3-yl]oxyphenyl]-3-[4-(trifluoromethylsulfanyl)phenyl]-2H-thiochromen-7-ol (example 66);

4-[4-[(3S)-1-(3-fluoropropyl)pyrrolidin-3-yl]oxyphenyl]-3-(6-quinolyl)-2H-thiochromen-7-ol (example 67);

3-(2,4-dimethylthiazol-5-yl)-4-[4-[(3S)-1-(3-fluoropropyl)pyrrolidin-3-yl]oxyphenyl]-2H-thiochromen-7-ol (example 68);

3-(2-ethoxy-3-fluoro-4-pyridyl)-4-[4-[(3S)-1-(3-fluoropropyl)pyrrolidin-3-yl]oxyphenyl]-2H-thiochromen-7-ol (example 69);

3-(2-fluoro-4-methyl-phenyl)-4-[4-[(3S)-1-(3-fluoropropyl)pyrrolidin-3-yl]oxyphenyl]-1-oxo-2H-thiochromen-7-ol (example 70);

3-(2-fluoro-4-methyl-phenyl)-4-[4-[(3S)-1-(3-fluoropropyl)pyrrolidin-3-yl]oxyphenyl]-1-oxo-2H-thiochromen-7-ol (example 71);

3-(6-amino-2-fluoro-3-pyridyl)-4-[4-[(3S)-1-(3-fluoropropyl)pyrrolidin-3-yl]oxyphenyl]-2H-thiochromen-7-ol (example 72);

3-(3,3-dimethylindolin-5-yl)-4-[4-[(3S)-1-(3-fluoropropyl)pyrrolidin-3-yl]oxyphenyl]-2H-thiochromen-7-ol (example 73);

3-[4-(diethylamino)-2-fluoro-phenyl]-4-[4-[(3S)-1-(3-fluoropropyl)pyrrolidin-3-yl]oxyphenyl]-2H-thiochromen-7-ol (example 74);

3-(6-tert-butyl-2-fluoro-3-pyridyl)-4-[4-[(3S)-1-(3-fluoropropyl)pyrrolidin-3-yl]oxyphenyl]-2H-thiochromen-7-ol (example 75);

3-(6-ethoxy-2-fluoro-3-pyridyl)-4-[2-[(3S)-1-(3-fluoropropyl)pyrrolidin-3-yl]oxypyrimidin-5-yl]-2H-thiochromen-7-ol (example 76);

3-(2-fluoro-4-methyl-phenyl)-4-[2-[(3S)-1-(3-fluoropropyl)pyrrolidin-3-yl]oxypyrimidin-5-yl]-2H-thiochromen-7-ol (example 77);

3-(2-fluoro-4-methyl-phenyl)-4-[6-[(3S)-1-(3-fluoropropyl)pyrrolidin-3-yl]oxy-3-pyridyl]-2H-thiochromen-7-ol (example 78);

3-(6-ethoxy-2-fluoro-3-pyridyl)-4-[6-[(3S)-1-(3-fluoropropyl)pyrrolidin-3-yl]oxy-3-pyridyl]-2H-thiochromen-7-ol (example 79);

4-[6-[(3S)-1-(3-fluoropropyl)pyrrolidin-3-yl]oxy-3-pyridyl]-3-[4-(trifluoromethoxy)phenyl]-2H-thiochromen-7-ol (example 80);

3-(2,4-dichlorophenyl)-4-[4-[(3S)-1-(3-fluoropropyl)pyrrolidin-3-yl]oxyphenyl]-2H-chromen-7-ol (example 81);

3-(2-chloro-4-fluoro-phenyl)-4-[4-[(3S)-1-(3-fluoropropyl)pyrrolidin-3-yl]oxyphenyl]-2H-chromen-7-ol (example 82);

4-[4-[(3S)-1-(3-fluoropropyl)pyrrolidin-3-yl]oxyphenyl]-3-(4-hydroxyphenyl)-2H-chromen-7-ol (example 83);

7-(2-chloro-4-fluoro-phenyl)-8-[4-[[(3S)-1-(3-fluoropropyl)pyrrolidin-3-yl]amino]phenyl]-5,6-dihydronaphthalen-2-ol (example 84);

6-(2,4-dichlorophenyl)-5-[4-[[(3S)-1-(3-fluoropropyl)pyrrolidin-3-yl]amino]phenyl]-8,9-dihydro-7H-benzo[7]annulen-2-ol (example 85);

6-(6-ethoxy-2-fluoro-3-pyridyl)-5-[4-[[(3S)-1-(3-fluoropropyl)pyrrolidin-3-yl]amino]phenyl]-8,9-dihydro-7H-benzo[7]annulen-2-ol (example 86);

5-[4-[[(3S)-1-(3-fluoropropyl)pyrrolidin-3-yl]amino]phenyl]-6-[4-(trifluoromethoxy)phenyl]-8,9-dihydro-7H-benzo[7]annulen-2-ol (example 87);

5-[4-[[(3S)-1-(3-fluoropropyl)pyrrolidin-3-yl]amino]phenyl]-6-[2-fluoro-4-(trifluoromethoxy)phenyl]-8,9-dihydro-7H-benzo[7]annulen-2-ol (example 88);

6-(4-tert-butylphenyl)-5-[4-[[(3S)-1-(3-fluoropropyl)pyrrolidin-3-yl]amino]phenyl]-8,9-dihydro-7H-benzo[7]annulen-2-ol (example 89);

5-[4-[[(3S)-1-(3-fluoropropyl)pyrrolidin-3-yl]amino]phenyl]-6-[4-(trifluoromethylsulfanyl)phenyl]-8,9-dihydro-7H-benzo[7]annulen-2-ol (example 90);

5-[4-[(3S)-1-(3-fluoropropyl)pyrrolidin-3-yl]oxyphenyl]-4-(3-hydroxyphenyl)-2,3-dihydro-1-benzoxepin-8-ol (example 91);

4-(2-chloro-4-fluoro-phenyl)-5-[4-[(3S)-1-(3-fluoropropyl)pyrrolidin-3-yl]oxyphenyl]-2,3-dihydro-1-benzoxepin-8-ol (example 92);

5-[4-[(3S)-1-(3-fluoropropyl)pyrrolidin-3-yl]oxyphenyl]-4-(1H-indol-5-yl)-2,3-dihydro-1-benzoxepin-8-ol (example 93);

4-(2-fluoro-4-hydroxy-phenyl)-5-[4-[(3S)-1-(3-fluoropropyl)pyrrolidin-3-yl]oxyphenyl]-2,3-dihydro-1-benzoxepin-8-ol (example 94);

4-(2-chloro-3-fluoro-phenyl)-5-[4-[(3S)-1-(3-fluoropropyl)pyrrolidin-3-yl]oxyphenyl]-2,3-dihydro-1-benzoxepin-8-ol (example 95);

4-(2-fluoro-4-methyl-phenyl)-5-[4-[(3S)-1-(3-fluoropropyl)pyrrolidin-3-yl]oxyphenyl]-2,3-dihydro-1-benzoxepin-8-ol (example 96);

4-(4-chloro-3-fluoro-phenyl)-5-[4-[(3S)-1-(3-fluoropropyl)pyrrolidin-3-yl]oxyphenyl]-2,3-dihydro-1-benzoxepin-8-ol (example 97);

4-(4-chloro-2-fluoro-phenyl)-5-[4-[(3S)-1-(3-fluoropropyl)pyrrolidin-3-yl]oxyphenyl]-2,3-dihydro-1-benzoxepin-8-ol (example 98);

4-(4-chloro-3-methyl-phenyl)-5-[4-[(3S)-1-(3-fluoropropyl)pyrrolidin-3-yl]oxyphenyl]-2,3-dihydro-1-benzoxepin-8-ol (example 99);

4-(4-fluoro-2-methyl-phenyl)-5-[4-[(3S)-1-(3-fluoropropyl)pyrrolidin-3-yl]oxyphenyl]-2,3-dihydro-1-benzoxepin-8-ol (example 100);

4-(3-chloro-2-methyl-phenyl)-5-[4-[(3S)-1-(3-fluoropropyl)pyrrolidin-3-yl]oxyphenyl]-2,3-dihydro-1-benzoxepin-8-ol (example 101);

4-(2,4-dichlorophenyl)-5-[4-[(3S)-1-(3-fluoropropyl)pyrrolidin-3-yl]oxyphenyl]-2,3-dihydro-1-benzoxepin-8-ol (example 102);

5-[4-[(3S)-1-(3-fluoropropyl)pyrrolidin-3-yl]oxyphenyl]-4-(1H-indol-6-yl)-2,3-dihydro-1-benzoxepin-8-ol (example 103);

5-[4-[(3S)-1-(3-fluoropropyl)pyrrolidin-3-yl]oxyphenyl]-4-indolin-5-yl-2,3-dihydro-1-benzoxepin-8-ol (example 104);

4-(3-chloro-2-methyl-phenyl)-9-fluoro-5-[4-[(3S)-1-(3-fluoropropyl)pyrrolidin-3-yl]oxyphenyl]-2,3-dihydro-1-benzoxepin-8-ol (example 105);

9-fluoro-4-(2-fluoro-4-methyl-phenyl)-5-[4-[(3S)-1-(3-fluoropropyl)pyrrolidin-3-yl]oxyphenyl]-2,3-dihydro-1-benzoxepin-8-ol (example 106);

9-fluoro-5-[4-[(3S)-1-(3-fluoropropyl)pyrrolidin-3-yl]oxyphenyl]-4-indolin-5-yl-2,3-dihydro-1-benzoxepin-8-ol (example 107);

9-chloro-4-(2-fluoro-4-methyl-phenyl)-5-[4-[(3S)-1-(3-fluoropropyl)pyrrolidin-3-yl]oxyphenyl]-2,3-dihydro-1-benzoxepin-8-ol (example 108);

9-chloro-4-(3-chloro-2-methyl-phenyl)-5-[4-[(3S)-1-(3-fluoropropyl)pyrrolidin-3-yl]oxyphenyl]-2,3-dihydro-1-benzoxepin-8-ol (example 109);

5-[4-[(3S)-1-(3-fluoropropyl)pyrrolidin-3-yl]oxyphenyl]-4-(1H-indol-4-yl)-2,3-dihydro-1-benzoxepin-8-ol (example 110);

4-(2-fluoro-4-methyl-phenyl)-5-[4-[(3S)-1-(3-fluoropropyl)pyrrolidin-3-yl]oxyphenyl]-9-methyl-2,3-dihydro-1-benzoxepin-8-ol (example 111);

4-(3-chloro-2-methyl-phenyl)-5-[4-[(3S)-1-(3-fluoropropyl)pyrrolidin-3-yl]oxyphenyl]-9-methyl-2,3-dihydro-1-benzoxepin-8-ol (example 112);

9-fluoro-5-[4-[(3S)-1-(3-fluoropropyl)pyrrolidin-3-yl]oxyphenyl]-4-(1H-indol-5-yl)-2,3-dihydro-1-benzoxepin-8-ol (example 113);

9-chloro-5-[4-[(3S)-1-(3-fluoropropyl)pyrrolidin-3-yl]oxyphenyl]-4-(1H-indol-5-yl)-2,3-dihydro-1-benzoxepin-8-ol (example 114);

9-chloro-5-[4-[(3S)-1-(3-fluoropropyl)pyrrolidin-3-yl]oxyphenyl]-4-indolin-5-yl-2,3-dihydro-1-benzoxepin-8-ol (example 115);

5-[4-[(3S)-1-(3-fluoropropyl)pyrrolidin-3-yl]oxyphenyl]-4-indolin-6-yl-2,3-dihydro-1-benzoxepin-8-ol (example 116);

5-[4-[(3S)-1-(3-fluoropropyl)pyrrolidin-3-yl]oxyphenyl]-4-indolin-4-yl-2,3-dihydro-1-benzoxepin-8-ol (example 117);

5-[4-[(3S)-1-(3-fluoropropyl)pyrrolidin-3-yl]oxyphenyl]-4-indolin-5-yl-9-methyl-2,3-dihydro-1-benzoxepin-8-ol (example 118);

4-(4-ethoxy-2-methyl-phenyl)-5-[4-[(3S)-1-(3-fluoropropyl)pyrrolidin-3-yl]oxyphenyl]-2,3-dihydro-1-benzoxepin-8-ol (example 119);

4-(benzofuran-5-yl)-5-[4-[(3S)-1-(3-fluoropropyl)pyrrolidin-3-yl]oxyphenyl]-2,3-dihydro-1-benzoxepin-8-ol (example 120);

4-(2-fluoro-4-methoxy-phenyl)-5-[4-[(3S)-1-(3-fluoropropyl)pyrrolidin-3-yl]oxyphenyl]-2,3-dihydro-1-benzoxepin-8-ol (example 121);

4-(2,3-dimethylphenyl)-5-[4-[(3S)-1-(3-fluoropropyl)pyrrolidin-3-yl]oxyphenyl]-2,3-dihydro-1-benzoxepin-8-ol (example 122);

9-chloro-5-[4-[(3S)-1-(3-fluoropropyl)pyrrolidin-3-yl]oxyphenyl]-4-(1H-indol-6-yl)-2,3-dihydro-1-benzoxepin-8-ol (example 123);

9-chloro-5-[4-[(3S)-1-(3-fluoropropyl)pyrrolidin-3-yl]oxyphenyl]-4-(1H-indol-4-yl)-2,3-dihydro-1-benzoxepin-8-ol (example 124);

9-chloro-5-[4-[(3S)-1-(3-fluoropropyl)pyrrolidin-3-yl]oxyphenyl]-4-indolin-6-yl-2,3-dihydro-1-benzoxepin-8-ol (example 125);

4-(3-fluoro-2-methyl-phenyl)-5-[4-[(3S)-1-(3-fluoropropyl)pyrrolidin-3-yl]oxyphenyl]-2,3-dihydro-1-benzoxepin-8-ol (example 126);

4-(6-ethoxy-3-pyridyl)-5-[4-[(3S)-1-(3-fluoropropyl)pyrrolidin-3-yl]oxyphenyl]-2,3-dihydro-1-benzoxepin-8-ol (example 127);

9-chloro-5-[4-[(3S)-1-(3-fluoropropyl)pyrrolidin-3-yl]oxyphenyl]-4-indolin-4-yl-2,3-dihydro-1-benzoxepin-8-ol (example 128);

5-[4-[(3S)-1-(3-fluoropropyl)pyrrolidin-3-yl]oxyphenyl]-4-(1H-indol-6-yl)-9-methyl-2,3-dihydro-1-benzoxepin-8-ol (example 129);

5-[4-[(3S)-1-(3-fluoropropyl)pyrrolidin-3-yl]oxyphenyl]-4-(1H-indol-4-yl)-9-methyl-2,3-dihydro-1-benzoxepin-8-ol (example 130);

9-fluoro-5-[4-[(3S)-1-(3-fluoropropyl)pyrrolidin-3-yl]oxyphenyl]-4-(1H-indol-6-yl)-2,3-dihydro-1-benzoxepin-8-ol (example 131);

9-fluoro-5-[4-[(3S)-1-(3-fluoropropyl)pyrrolidin-3-yl]oxyphenyl]-4-indolin-6-yl-2,3-dihydro-1-benzoxepin-8-ol (example 132);

9-fluoro-5-[4-[(3S)-1-(3-fluoropropyl)pyrrolidin-3-yl]oxyphenyl]-4-(1H-indol-4-yl)-2,3-dihydro-1-benzoxepin-8-ol (example 133);

9-fluoro-5-[4-[(3S)-1-(3-fluoropropyl)pyrrolidin-3-yl]oxyphenyl]-4-indolin-4-yl-2,3-dihydro-1-benzoxepin-8-ol (example 134);

4-(3-chloro-2-methyl-phenyl)-5-[4-[(3S)-1-(3-fluoropropyl)pyrrolidin-3-yl]oxyphenyl]-7-methyl-2,3-dihydro-1-benzoxepin-8-ol (example 135);

5-[4-[(3S)-1-(3-fluoropropyl)pyrrolidin-3-yl]oxyphenyl]-4-(3-hydroxyphenyl)-7-methyl-2,3-dihydro-1-benzoxepin-8-ol (example 136);

5-[4-[(3S)-1-(3-fluoropropyl)pyrrolidin-3-yl]oxyphenyl]-4-indolin-5-yl-7-methyl-2,3-dihydro-1-benzoxepin-8-ol (example 137);

7-fluoro-4-(2-fluoro-4-methyl-phenyl)-5-[4-[(3S)-1-(3-fluoropropyl)pyrrolidin-3-yl]oxyphenyl]-2,3-dihydro-1-benzoxepin-8-ol (example 138);

5-[4-[(3S)-1-(3-fluoropropyl)pyrrolidin-3-yl]oxyphenyl]-4-(1H-indol-5-yl)-7-methyl-2,3-dihydro-1-benzoxepin-8-ol (example 139);

4-(2-fluoro-4-methyl-phenyl)-5-[4-[(3S)-1-(3-fluoropropyl)pyrrolidin-3-yl]oxyphenyl]-7-methyl-2,3-dihydro-1-benzoxepin-8-ol (example 140);

4-(3-fluoro-4-isopropoxy-phenyl)-5-[4-[(3S)-1-(3-fluoropropyl)pyrrolidin-3-yl]oxyphenyl]-2,3-dihydro-1-benzoxepin-8-ol (example 141);

7-fluoro-5-[4-[(3S)-1-(3-fluoropropyl)pyrrolidin-3-yl]oxyphenyl]-4-indolin-5-yl-2,3-dihydro-1-benzoxepin-8-ol (example 142);

7-chloro-5-[4-[(3S)-1-(3-fluoropropyl)pyrrolidin-3-yl]oxyphenyl]-4-indolin-5-yl-2,3-dihydro-1-benzoxepin-8-ol (example 143);

7-chloro-5-[4-[(3S)-1-(3-fluoropropyl)pyrrolidin-3-yl]oxyphenyl]-4-(1H-indol-5-yl)-2,3-dihydro-1-benzoxepin-8-ol (example 144);

7-chloro-4-(2-fluoro-4-methyl-phenyl)-5-[4-[(3S)-1-(3-fluoropropyl)pyrrolidin-3-yl]oxyphenyl]-2,3-dihydro-1-benzoxepin-8-ol (example 145);

5-[4-[(3S)-1-(3-fluoropropyl)pyrrolidin-3-yl]oxyphenyl]-4-[4-(2-methoxyethoxy)phenyl]-2,3-dihydro-1-benzoxepin-8-ol (example 146);

5-[4-[(3S)-1-(3-fluoropropyl)pyrrolidin-3-yl]oxyphenyl]-4-[4-(2-pyrrolidin-1-ylethoxy)phenyl]-2,3-dihydro-1-benzoxepin-8-ol (example 147);

3-[5-[4-[(3S)-1-(3-fluoropropyl)pyrrolidin-3-yl]oxyphenyl]-8-hydroxy-2,3-dihydro-1-benzoxepin-4-yl]-2-methoxy-benzoic acid (example 148);

4-[4-(cyclopropoxy)phenyl]-5-[4-[(3S)-1-(3-fluoropropyl)pyrrolidin-3-yl]oxyphenyl]-2,3-dihydro-1-benzoxepin-8-ol (example 149);

5-[4-[(3S)-1-(3-fluoropropyl)pyrrolidin-3-yl]oxyphenyl]-4-[4-isopropoxy-2-(trifluoromethyl)phenyl]-2,3-dihydro-1-benzoxepin-8-ol hydrochloride (example 150);

4-(2,3-dihydrobenzofuran-5-yl)-5-[4-[(3S)-1-(3-fluoropropyl)pyrrolidin-3-yl]oxyphenyl]-2,3-dihydro-1-benzoxepin-8-ol (example 151);

4-(4-ethoxy-2-fluoro-phenyl)-5-[4-[(3S)-1-(3-fluoropropyl)pyrrolidin-3-yl]oxyphenyl]-2,3-dihydro-1-benzoxepin-8-ol (example 152);

4-(2-chloro-4-ethoxy-phenyl)-5-[4-[(3S)-1-(3-fluoropropyl)pyrrolidin-3-yl]oxyphenyl]-2,3-dihydro-1-benzoxepin-8-ol (example 153);

4-(2-chloro-4-methoxy-phenyl)-5-[4-[(3S)-1-(3-fluoropropyl)pyrrolidin-3-yl]oxyphenyl]-2,3-dihydro-1-benzoxepin-8-ol (example 154);

4-(4-ethoxy-2-methyl-phenyl)-7-fluoro-5-[4-[(3S)-1-(3-fluoropropyl)pyrrolidin-3-yl]oxyphenyl]-2,3-dihydro-1-benzoxepin-8-ol (example 155);

4-(benzofuran-5-yl)-7-fluoro-5-[4-[(3S)-1-(3-fluoropropyl)pyrrolidin-3-yl]oxyphenyl]-2,3-dihydro-1-benzoxepin-8-ol (example 156);

5-[4-[(3S)-1-(3-fluoropropyl)pyrrolidin-3-yl]oxyphenyl]-4-(4-methoxy-2-methyl-phenyl)-2,3-dihydro-1-benzoxepin-8-ol (example 157);

5-[4-[(3S)-1-(3-fluoropropyl)pyrrolidin-3-yl]oxyphenyl]-4-(3-hydroxyphenyl)-2,3-dihydro-1-benzothiepin-8-ol (example 158);

4-(2-chloro-4-fluoro-phenyl)-5-[4-[(3S)-1-(3-fluoropropyl)pyrrolidin-3-yl]oxyphenyl]-2,3-dihydro-1-benzothiepin-8-ol (example 159);

5-[4-[(3S)-1-(3-fluoropropyl)pyrrolidin-3-yl]oxyphenyl]-4-(1H-indol-5-yl)-2,3-dihydro-1-benzothiepin-8-ol (example 160);

4-(4-chloro-3-fluoro-phenyl)-5-[4-[(3S)-1-(3-fluoropropyl)pyrrolidin-3-yl]oxyphenyl]-2,3-dihydro-1-benzothiepin-8-ol (example 161);

4-(4-chloro-3-methyl-phenyl)-5-[4-[(3S)-1-(3-fluoropropyl)pyrrolidin-3-yl]oxyphenyl]-2,3-dihydro-1-benzothiepin-8-ol (example 162);

4-(3-chloro-2-methyl-phenyl)-5-[4-[(3S)-1-(3-fluoropropyl)pyrrolidin-3-yl]oxyphenyl]-2,3-dihydro-1-benzothiepin-8-ol (example 163);

4-(2-fluoro-4-methyl-phenyl)-5-[4-[(3S)-1-(3-fluoropropyl)pyrrolidin-3-yl]oxyphenyl]-2,3-dihydro-1-benzothiepin-8-ol (example 164);

4-(4-fluoro-2-methyl-phenyl)-5-[4-[(3S)-1-(3-fluoropropyl)pyrrolidin-3-yl]oxyphenyl]-2,3-dihydro-1-benzothiepin-8-ol (example 165);

4-(2,4-dichlorophenyl)-5-[4-[(3S)-1-(3-fluoropropyl)pyrrolidin-3-yl]oxyphenyl]-2,3-dihydro-1-benzothiepin-8-ol (example 166);

4-(4-chloro-2-fluoro-phenyl)-5-[4-[(3S)-1-(3-fluoropropyl)pyrrolidin-3-yl]oxyphenyl]-2,3-dihydro-1-benzothiepin-8-ol (example 167);

4-(2-chloro-3-fluoro-phenyl)-5-[4-[(3S)-1-(3-fluoropropyl)pyrrolidin-3-yl]oxyphenyl]-2,3-dihydro-1-benzothiepin-8-ol (example 168);

4-(2-fluoro-4-hydroxy-phenyl)-5-[4-[(3S)-1-(3-fluoropropyl)pyrrolidin-3-yl]oxyphenyl]-2,3-dihydro-1-benzothiepin-8-ol (example 169);

4-(2-chloro-3-fluoro-phenyl)-5-[4-[(3S)-1-(3-fluoropropyl)pyrrolidin-3-yl]oxyphenyl]-2,3-dihydro-1-benzothiepin-7-ol (example 170);

4-(2-fluoro-4-methyl-phenyl)-5-[4-[(3S)-1-(3-fluoropropyl)pyrrolidin-3-yl]oxyphenyl]-2,3-dihydro-1-benzothiepin-7-ol (example 171);

5-[4-[(3S)-1-(3-fluoropropyl)pyrrolidin-3-yl]oxyphenyl]-4-(1H-indol-6-yl)-2,3-dihydro-1-benzothiepin-8-ol (example 172);

4-(3-chloro-2-methyl-phenyl)-5-[4-[(3S)-1-(3-fluoropropyl)pyrrolidin-3-yl]oxyphenyl]-2,3-dihydro-1-benzothiepin-7-ol (example 173);

4-(3-chloro-4-fluoro-phenyl)-5-[4-[(3S)-1-(3-fluoropropyl)pyrrolidin-3-yl]oxyphenyl]-2,3-dihydro-1-benzothiepin-7-ol (example 174);

4-(2-chloro-4-fluoro-phenyl)-5-[4-[(3S)-1-(3-fluoropropyl)pyrrolidin-3-yl]oxyphenyl]-2,3-dihydro-1-benzothiepin-7-ol (example 175);

5-[4-[(3S)-1-(3-fluoropropyl)pyrrolidin-3-yl]oxyphenyl]-4-indolin-5-yl-2,3-dihydro-1-benzothiepin-8-ol (example 176);

5-[4-[(3S)-1-(3-fluoropropyl)pyrrolidin-3-yl]oxyphenyl]-4-(4-hydroxyphenyl)-2,3-dihydro-1-benzothiepin-7-ol (example 177);

5-[4-[(3S)-1-(3-fluoropropyl)pyrrolidin-3-yl]oxyphenyl]-4-(1H-indol-4-yl)-2,3-dihydro-1-benzothiepin-8-ol (example 178);

4-(4-chloro-3-methyl-phenyl)-5-[4-[(3S)-1-(3-fluoropropyl)pyrrolidin-3-yl]oxyphenyl]-2,3-dihydro-1-benzothiepin-7-ol (example 179);

4-(4-fluoro-2-methyl-phenyl)-5-[4-[(3S)-1-(3-fluoropropyl)pyrrolidin-3-yl]oxyphenyl]-2,3-dihydro-1-benzothiepin-7-ol (example 180);

4-(4-chloro-2-fluoro-phenyl)-5-[4-[(3S)-1-(3-fluoropropyl)pyrrolidin-3-yl]oxyphenyl]-2,3-dihydro-1-benzothiepin-7-ol (example 181);

4-(2,4-dichlorophenyl)-5-[4-[(3S)-1-(3-fluoropropyl)pyrrolidin-3-yl]oxyphenyl]-2,3-dihydro-1-benzothiepin-7-ol (example 182);

4-(2,3-dihydro-1H-pyrrolo[2,3-b]pyridin-5-yl)-5-[4-[(3S)-1-(3-fluoropropyl)pyrrolidin-3-yl]oxyphenyl]-2,3-dihydro-1-benzothiepin-8-ol (example 183);

4-(benzofuran-5-yl)-5-[4-[(3S)-1-(3-fluoropropyl)pyrrolidin-3-yl]oxyphenyl]-2,3-dihydro-1-benzothiepin-8-ol (example 184);

4-(4-ethoxy-3-fluoro-phenyl)-5-[4-[(3S)-1-(3-fluoropropyl)pyrrolidin-3-yl]oxyphenyl]-2,3-dihydro-1-benzothiepin-8-ol (example 185);

4-(4-ethoxy-2-methyl-phenyl)-5-[4-[(3S)-1-(3-fluoropropyl)pyrrolidin-3-yl]oxyphenyl]-2,3-dihydro-1-benzothiepin-8-ol (example 186);

4-(6-ethoxy-2-fluoro-3-pyridyl)-5-[4-[(3S)-1-(3-fluoropropyl)pyrrolidin-3-yl]oxyphenyl]-2,3-dihydro-1-benzothiepin-8-ol (example 187);

4-[3-(difluoromethoxy)-4-fluoro-phenyl]-5-[4-[(3S)-1-(3-fluoropropyl)pyrrolidin-3-yl]oxyphenyl]-2,3-dihydro-1-benzothiepin-8-ol (example 188);

4-(2-fluoro-4-methoxy-phenyl)-5-[4-[(3S)-1-(3-fluoropropyl)pyrrolidin-3-yl]oxyphenyl]-2,3-dihydro-1-benzothiepin-8-ol (example 189);

5-[4-[(3S)-1-(3-fluoropropyl)pyrrolidin-3-yl]oxyphenyl]-4-[3-fluoro-4-(trifluoromethoxy)phenyl]-2,3-dihydro-1-benzothiepin-8-ol (example 190);

4-[(difluoromethoxy)-3-fluoro-phenyl]-5-[4-[(3S)-1-(3-fluoropropyl)pyrrolidin-3-yl]oxyphenyl]-2,3-dihydro-1-benzothiepin-8-ol (example 191);

4-(2-fluoro-6-methyl-3-pyridyl)-5-[4-[(3S)-1-(3-fluoropropyl)pyrrolidin-3-yl]oxyphenyl]-2,3-dihydro-1-benzothiepin-8-ol (example 192);

4-(2,2-difluoro-1,3-benzodioxol-5-yl)-5-[4-[(3S)-1-(3-fluoropropyl)pyrrolidin-3-yl]oxyphenyl]-2,3-dihydro-1-benzothiepin-8-ol (example 193);

5-[4-[(3S)-1-(3-fluoropropyl)pyrrolidin-3-yl]oxyphenyl]-4-(4-methylsulfonylphenyl)-2,3-dihydro-1-benzothiepin-8-ol (example 194);

4-(3-ethoxy-4-fluoro-phenyl)-5-[4-[(3S)-1-(3-fluoropropyl)pyrrolidin-3-yl]oxyphenyl]-2,3-dihydro-1-benzothiepin-8-ol (example 195);

4-(4-ethoxy-2-fluoro-phenyl)-5-[4-[(3S)-1-(3-fluoropropyl)pyrrolidin-3-yl]oxyphenyl]-2,3-dihydro-1-benzothiepin-8-ol (example 196);

5-[4-[(3S)-1-(3-fluoropropyl)pyrrolidin-3-yl]oxyphenyl]-4-(2-methyl-2,3-dihydrobenzofuran-5-yl)-2,3-dihydro-1-benzothiepin-8-ol (example 197);

4-(2,2-dimethylindolin-5-yl)-5-[4-[(3S)-1-(3-fluoropropyl)pyrrolidin-3-yl]oxyphenyl]-2,3-dihydro-1-benzothiepin-8-ol (example 198);

2-fluoro-5-[5-[4-[(3S)-1-(3-fluoropropyl)pyrrolidin-3-yl]oxyphenyl]-8-hydroxy-2,3-dihydro-1-benzothiepin-4-yl]-N-methoxy-benzamide (example 199);

4-[4-(ethylamino)-2-fluoro-phenyl]-5-[4-[(3S)-1-(3-fluoropropyl)pyrrolidin-3-yl]oxyphenyl]-2,3-dihydro-1-benzothiepin-8-ol (example 200);

4-(2,2-dimethyl-3H-benzofuran-5-yl)-5-[4-[(3S)-1-(3-fluoropropyl)pyrrolidin-3-yl]oxyphenyl]-2,3-dihydro-1-benzothiepin-8-ol (example 201);

5-[4-[(3S)-1-(3-fluoropropyl)pyrrolidin-3-yl]oxyphenyl]-4-[(2R)-2-methyl-2,3-dihydrobenzofuran-5-yl]-2,3-dihydro-1-benzothiepin-8-ol (example 202);

4-(2,4-dichlorophenyl)-5-[4-[(3S)-1-(3-fluoropropyl)pyrrolidin-3-yl]oxyphenyl]-2,3-dihydro-1-benzothiepine-8-carboxylic acid (example 203);

5-[4-[(3S)-1-(3-fluoropropyl)pyrrolidin-3-yl]oxyphenyl]-4-[(2S)-2-methyl-2,3-dihydrobenzofuran-5-yl]-2,3-dihydro-1-benzothiepin-8-ol (example 204);

4-(2,4-dichlorophenyl)-5-[6-[(3S)-1-(3-fluoropropyl)pyrrolidin-3-yl]oxy-3-pyridyl]-2,3-dihydro-1-benzothiepin-8-ol (example 205);

4-(2-chloro-4-methyl-phenyl)-5-[6-[(3S)-1-(3-fluoropropyl)pyrrolidin-3-yl]oxy-3-pyridyl]-2,3-dihydro-1-benzothiepin-8-ol (example 206);

4-[4-(difluoromethoxy)-3-fluoro-phenyl]-5-[6-[(3S)-1-(3-fluoropropyl)pyrrolidin-3-yl]oxy-3-pyridyl]-2,3-dihydro-1-benzothiepin-8-ol (example 207);

4-(6-ethoxy-2-fluoro-3-pyridyl)-5-[6-[(3S)-1-(3-fluoropropyl)pyrrolidin-3-yl]oxy-3-pyridyl]-2,3-dihydro-1-benzothiepin-8-ol (example 208);

5-[4-[(3S)-1-(3-fluoropropyl)pyrrolidin-3-yl]oxyphenyl]-4-[2-fluoro-4-(trideuteriomethoxy)phenyl]-2,3-dihydro-1-benzothiepin-8-ol (example 209);

4-(2-fluoro-4-methyl-phenyl)-5-[4-[(3S)-1-(3-fluoropropyl)pyrrolidin-3-yl]oxyphenyl]-2,3-dihydro-1-benzothiepine-8-carboxylic acid (example 210);

4-(4-chloro-3-methyl-phenyl)-5-[4-[(3S)-1-(3-fluoropropyl)pyrrolidin-3-yl]oxyphenyl]-2,3-dihydro-1-benzothiepine-8-carboxylic acid (example 211);

5-[4-[(3S)-1-(3-fluoropropyl)pyrrolidin-3-yl]oxyphenyl]-4-[2-fluoro-4-(trifluoromethoxy)phenyl]-2,3-dihydro-1-benzothiepin-8-ol (example 212);

4-[4-(difluoromethoxy)-2-fluoro-phenyl]-5-[4-[(3S)-1-(3-fluoropropyl)pyrrolidin-3-yl]oxyphenyl]-2,3-dihydro-1-benzothiepin-8-ol (example 213);

5-[4-[(3S)-1-(3-fluoropropyl)pyrrolidin-3-yl]oxyphenyl]-4-[4-(trifluoromethoxy)phenyl]-2,3-dihydro-1-benzothiepin-8-ol (example 214);

4-(2,6-difluoro-3-pyridyl)-5-[4-[(3S)-1-(3-fluoropropyl)pyrrolidin-3-yl]oxyphenyl]-2,3-dihydro-1-benzothiepin-8-ol (example 215);

4-(4-tert-butylphenyl)-5-[4-[(3S)-1-(3-fluoropropyl)pyrrolidin-3-yl]oxyphenyl]-2,3-dihydro-1-benzothiepin-8-ol (example 216);

4-(4-ethoxy-2,3-difluoro-phenyl)-5-[4-[(3S)-1-(3-fluoropropyl)pyrrolidin-3-yl]oxyphenyl]-2,3-dihydro-1-benzothiepin-8-ol (example 217);

4-[4-(fluoromethoxy)phenyl]-5-[4-[(3S)-1-(3-fluoropropyl)pyrrolidin-3-yl]oxyphenyl]-2,3-dihydro-1-benzothiepin-8-ol (example 218);

4-(3,5-dimethylisoxazol-4-yl)-5-[4-[(3S)-1-(3-fluoropropyl)pyrrolidin-3-yl]oxyphenyl]-2,3-dihydro-1-benzothiepin-8-ol (example 219);

4-(4-ethoxy-2,5-difluoro-phenyl)-5-[4-[(3S)-1-(3-fluoropropyl)pyrrolidin-3-yl]oxyphenyl]-2,3-dihydro-1-benzothiepin-8-ol (example 220);

4-(3-chloro-4-ethoxy-2-fluoro-phenyl)-5-[4-[(3S)-1-(3-fluoropropyl)pyrrolidin-3-yl]oxyphenyl]-2,3-dihydro-1-benzothiepin-8-ol (example 221);

5-[4-[(3S)-1-(3-fluoropropyl)pyrrolidin-3-yl]oxyphenyl]-4-[4-(trifluoromethylsulfanyl)phenyl]-2,3-dihydro-1-benzothiepin-8-ol (example 222);

4-(6-amino-2-fluoro-3-pyridyl)-5-[4-[(3S)-1-(3-fluoropropyl)pyrrolidin-3-yl]oxyphenyl]-2,3-dihydro-1-benzothiepin-8-ol (example 223);

4-[4-(diethylamino)-2-fluoro-phenyl]-5-[4-[(3S)-1-(3-fluoropropyl)pyrrolidin-3-yl]oxyphenyl]-2,3-dihydro-1-benzothiepin-8-ol (example 224);

5-[4-[(3S)-1-(3-fluoropropyl)pyrrolidin-3-yl]oxyphenyl]-1-oxo-4-[(trifluoromethoxy)phenyl]-2,3-dihydro-1$\lambda^4$-benzothiepin-8-ol (example 225);

5-[4-[(3S)-1-(3-fluoropropyl)pyrrolidin-3-yl]oxyphenyl]-1-oxo-4-[4-(trifluoromethoxy)phenyl]-2,3-dihydro-1$\lambda^4$-benzothiepin-8-ol (example 226);

5-[4-[(3S)-1-(3-fluoropropyl)pyrrolidin-3-yl]oxyphenyl]-1-oxo-4-[4-(trifluoromethoxy)phenyl]-2,3-dihydro-1$\lambda^4$-benzothiepin-8-ol (example 227);

5-[4-[(3S)-1-(3-fluoropropyl)pyrrolidin-3-yl]oxyphenyl]-4-(3-hydroxyphenyl)-1,1-dioxo-2,3-dihydro-1$\lambda^6$-benzothiepin-8-ol (example 228);

4-(2-chloro-4-fluoro-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol (example 229);

4-(2-fluoro-4-methyl-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol (example 230);

4-(2,4-dichlorophenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol (example 231);

4-(2-chloro-3-fluoro-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol (example 232);

4-(4-chloro-2-fluoro-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol (example 233);

4-(4-fluoro-2-methyl-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol (example 234);

4-(3-chloro-2-methyl-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol (example 235);

4-(4-chloro-3-methyl-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol (example 236);

6-(2-fluoro-4-methyl-phenyl)-5-[6-[(3S)-1-(3-fluoropropyl)pyrrolidin-3-yl]oxy-3-pyridyl]-8,9-dihydro-7H-benzo[7]annulen-2-ol (example 237);

6-(2,4-dichlorophenyl)-5-[2-[(3S)-1-(3-fluoropropyl)pyrrolidin-3-yl]oxypyrimidin-5-yl]-8,9-dihydro-7H-benzo[7]annulen-2-ol (example 238);

6-(2,4-dichlorophenyl)-5-[6-[(3S)-1-(3-fluoropropyl)pyrrolidin-3-yl]oxy-3-pyridyl]-8,9-dihydro-7H-benzo[7]annulen-2-ol (example 239);

6-(6-ethoxy-2-fluoro-3-pyridyl)-5-[6-[(3S)-1-(3-fluoropropyl)pyrrolidin-3-yl]oxy-3-pyridyl]-8,9-dihydro-7H-benzo[7]annulen-2-ol (example 240);

6-[4-(difluoromethoxy)-3-fluoro-phenyl]-5-[6-[(3S)-1-(3-fluoropropyl)pyrrolidin-3-yl]oxy-3-pyridyl]-8,9-dihydro-7H-benzo[7]annulen-2-ol (example 241);

6-(2,2-dimethylindolin-5-yl)-5-[6-[(3S)-1-(3-fluoropropyl)pyrrolidin-3-yl]oxy-3-pyridyl]-8,9-dihydro-7H-benzo[7]annulen-2-ol (example 242);

6-(4-chloro-3-fluoro-phenyl)-5-[5-[(3S)-1-(3-fluoropropyl)pyrrolidin-3-yl]oxypyrazin-2-yl]-8,9-dihydro-7H-benzo[7]annulen-2-ol (example 243);

6-(2-fluoro-4-methyl-phenyl)-5-[2-[(3S)-1-(3-fluoropropyl)pyrrolidin-3-yl]oxypyrimidin-5-yl]-8,9-dihydro-7H-benzo[7]annulen-2-ol (example 244);

6-(2,4-dichlorophenyl)-1-fluoro-5-[6-[(3S)-1-(3-fluoropropyl)pyrrolidin-3-yl]oxy-3-pyridyl]-8,9-dihydro-7H-benzo[7]annulen-2-ol (example 245);

6-(4-ethoxy-2,3-difluoro-phenyl)-5-[2-[(3S)-1-(3-fluoropropyl)pyrrolidin-3-yl]oxypyrimidin-5-yl]-8,9-dihydro-7H-benzo[7]annulen-2-ol (example 246);

6-(2,4-dichlorophenyl)-5-[6-[(3S)-1-(3-fluoropropyl)pyrrolidin-3-yl]oxy-3-pyridyl]-8,9-dihydro-7H-benzo[7]annulene-2-carboxylic acid (example 247);

6-[4-(difluoromethoxy)-3-fluoro-phenyl]-5-[6-[(3S)-1-(3-fluoropropyl)pyrrolidin-3-yl]oxy-3-pyridyl]-8,9-dihydro-7H-benzo[7]annulene-2-carboxylic acid (example 248);

6-[4-(difluoromethoxy)-3-fluoro-phenyl]-1-fluoro-5-[6-[(3S)-1-(3-fluoropropyl)pyrrolidin-3-yl]oxy-3-pyridyl]-8,9-dihydro-7H-benzo[7]annulen-2-ol (example 249);
6-(4-chloro-3-methyl-phenyl)-1-fluoro-5-[6-[(3S)-1-(3-fluoropropyl)pyrrolidin-3-yl]oxy-3-pyridyl]-8,9-dihydro-7H-benzo[7]annulen-2-ol (example 250);
6-(6-ethoxy-2-fluoro-3-pyridyl)-5-[2-[(3S)-1-(3-fluoropropyl)pyrrolidin-3-yl]oxypyrimidin-5-yl]-8,9-dihydro-7H-benzo[7]annulen-2-ol (example 251);
6-(6-ethoxy-2-fluoro-3-pyridyl)-1-fluoro-5-[6-[(3S)-1-(3-fluoropropyl)pyrrolidin-3-yl]oxy-3-pyridyl]-8,9-dihydro-7H-benzo[7]annulen-2-ol (example 252);
5-[6-[(3S)-1-(3-fluoropropyl)pyrrolidin-3-yl]oxy-3-pyridyl]-6-[4-(trifluoromethoxy)phenyl]-8,9-dihydro-7H-benzo[7]annulen-2-ol (example 253);
6-(4-chloro-3-fluoro-phenyl)-5-[5-[(3S)-1-(3-fluoropropyl)pyrrolidin-3-yl]oxypyrimidin-2-yl]-8,9-dihydro-7H-benzo[7]annulen-2-ol (example 254);
5-[(E)-2-(2-chloro-4-fluoro-phenyl)-1-[4-[(3S)-1-(3-fluoropropyl)pyrrolidin-3-yl]oxyphenyl]but-1-enyl]-1H-indazole (example 255);
1-[2,6-difluoro-4-[(3S)-1-(3-fluoropropyl)pyrrolidin-3-yl]oxy-phenyl]-2-(2-fluoro-2-methyl-propyl)-3-methyl-1,3,4,9-tetrahydropyrido[3,4-b]indole (example 256);
1-[2,6-difluoro-4-[(3S)-1-(3-fluoropropyl)pyrrolidin-3-yl]oxy-phenyl]-2-(2-fluoro-2-methyl-propyl)-3-methyl-1,3,4,9-tetrahydropyrido[3,4-b]indole (example 257); and
2-[4-[(3S)-1-(3-fluoropropyl)pyrrolidin-3-yl]oxyphenyl]-3-(4-hydroxyphenyl)-2,3-dihydro-1,4-benzoxathiin-6-ol (example 259).

The compounds of the invention can be prepared by the following processes, being understood that solvents, temperatures and other reaction conditions presented below may vary as deemed appropriate to the skilled person in the art.

The general methods described below for the preparation of the compounds of the invention are optionally modified by the use of appropriate reagents and conditions for the introduction of the various moieties found in the formula (I), (1') and (I-A) as described above. Besides, when the reaction schemes below illustrate the synthesis of compounds wherein the "A" moiety is linked to the pyrrolidinyl group in the configuration (S), similar reaction schemes may be used with corresponding reagents in the configuration (R) so as to obtain different enantiomers in the whole scope of formula (I') according to the invention.

The following abbreviations and empirical formulae are used:
AcOH acetic acid
EtOAc ethyl acetate
$AlCl_3$ aluminium trichloride
Boc tert-butyloxycarbonyl
$P(Ph)_2$-$(CH_2)_3$—$P(Ph)_2$ 1,3-bis(diphenylphosphino)propane
$Ph_3P$ triphenylphosphine
$Ph_3P$=O triphenylphosphine oxide
$Cs_2CO_3$ cesium carbonate
CO carbon monoxyde
DCM dichloromethane
DMF N,N-dimethylformamide
DMSO dimethyl sulfoxide
Et ethyl
EtOH ethanol
$Et_2O$ diethyl ether
Hal halogen atom
HCl hydrogen chloride
HPLC high-performance liquid chromatography
iPr isopropyl
$K_2CO_3$ potassium carbonate
LCMS liquid chromatography/mass spectrometry
LiHMDS Lithium HexaMethylDiSilazide
Lutidine 2,6-dimethyl-pyridine
Me methyl
MeCN acetonitrile
MeOH methanol
$MgSO_4$ magnesium sulfate
NaOH sodium hydroxyde
NaCl sodium chloride
$NaHCO_3$ sodium bicarbonate
$Pd(OAc)_2$ palladium acetate
$PdCl_2(PPh_3)_2$ palladium chloride bis triphenylphosphine
$Pd(dppf)Cl_2$ 1,1'bis(diphenylphosphino)ferrocene] dichloropalladium(II)
$Tf_2O$ triflic anhydride
THF tetrahydrofuran
° C. degrees Celsius
RT room temperature
min (mn) minute(s)
mL millilitre(s)
mmol millimole(s)
μmol micromole(s)
μM micromolar
nM nanomolar
ppm parts per million
SCX strong cation exchange SCHEME 1: Preparation of compounds of the formula (I) with A = O: general process

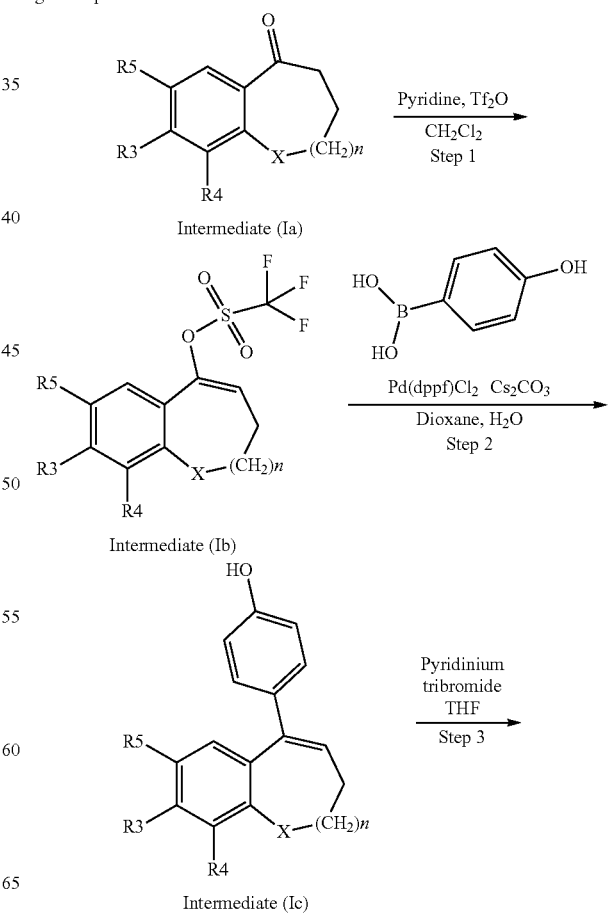

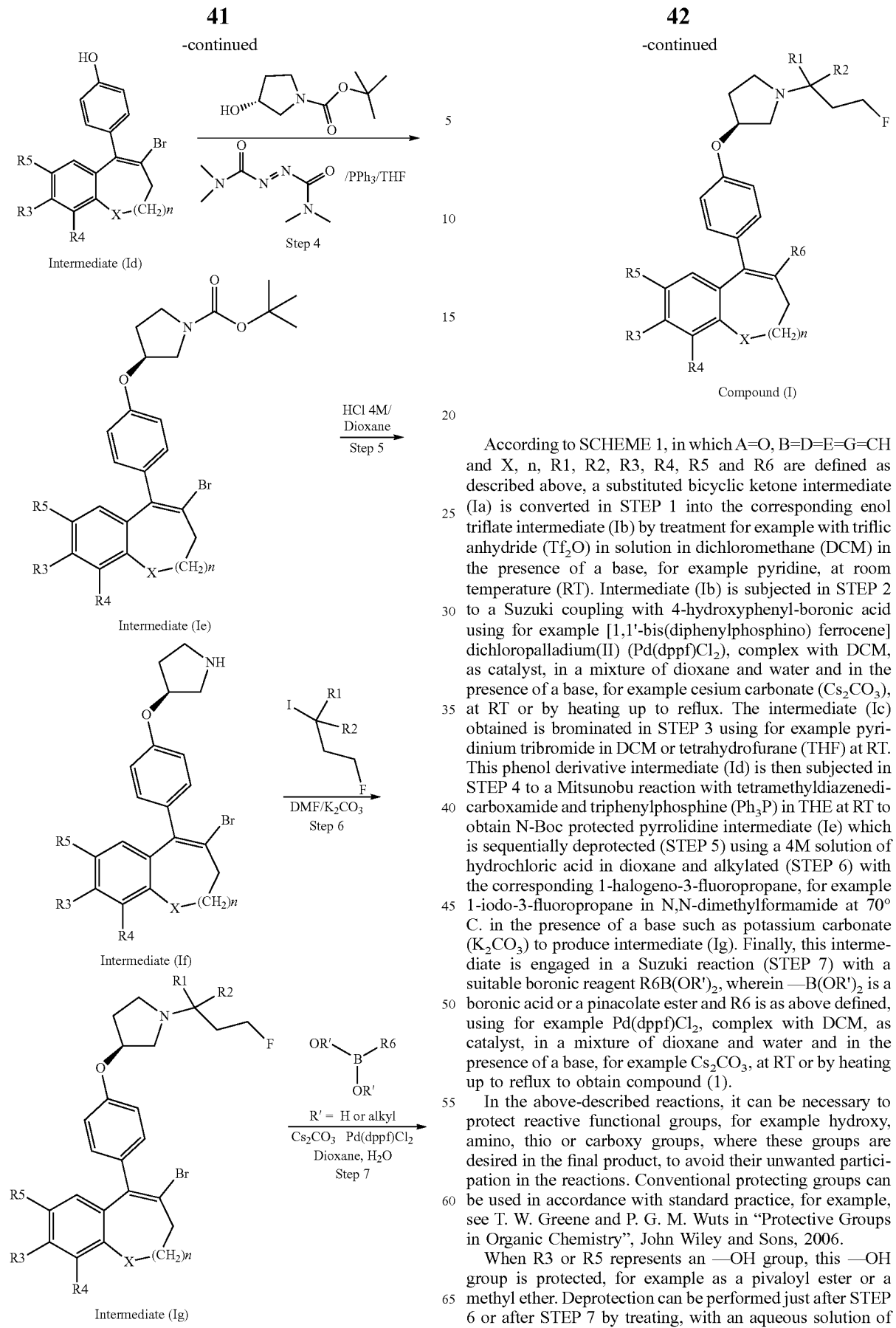

According to SCHEME 1, in which A=O, B=D=E=G=CH and X, n, R1, R2, R3, R4, R5 and R6 are defined as described above, a substituted bicyclic ketone intermediate (Ia) is converted in STEP 1 into the corresponding enol triflate intermediate (Ib) by treatment for example with triflic anhydride (Tf$_2$O) in solution in dichloromethane (DCM) in the presence of a base, for example pyridine, at room temperature (RT). Intermediate (Ib) is subjected in STEP 2 to a Suzuki coupling with 4-hydroxyphenyl-boronic acid using for example [1,1'-bis(diphenylphosphino) ferrocene] dichloropalladium(II) (Pd(dppf)Cl$_2$), complex with DCM, as catalyst, in a mixture of dioxane and water and in the presence of a base, for example cesium carbonate (Cs$_2$CO$_3$), at RT or by heating up to reflux. The intermediate (Ic) obtained is brominated in STEP 3 using for example pyridinium tribromide in DCM or tetrahydrofurane (THF) at RT. This phenol derivative intermediate (Id) is then subjected in STEP 4 to a Mitsunobu reaction with tetramethyldiazenedicarboxamide and triphenylphosphine (Ph$_3$P) in THF at RT to obtain N-Boc protected pyrrolidine intermediate (Ie) which is sequentially deprotected (STEP 5) using a 4M solution of hydrochloric acid in dioxane and alkylated (STEP 6) with the corresponding 1-halogeno-3-fluoropropane, for example 1-iodo-3-fluoropropane in N,N-dimethylformamide at 70° C. in the presence of a base such as potassium carbonate (K$_2$CO$_3$) to produce intermediate (Ig). Finally, this intermediate is engaged in a Suzuki reaction (STEP 7) with a suitable boronic reagent R6B(OR')$_2$, wherein —B(OR')$_2$ is a boronic acid or a pinacolate ester and R6 is as above defined, using for example Pd(dppf)Cl$_2$, complex with DCM, as catalyst, in a mixture of dioxane and water and in the presence of a base, for example Cs$_2$CO$_3$, at RT or by heating up to reflux to obtain compound (1).

In the above-described reactions, it can be necessary to protect reactive functional groups, for example hydroxy, amino, thio or carboxy groups, where these groups are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 2006.

When R3 or R5 represents an —OH group, this —OH group is protected, for example as a pivaloyl ester or a methyl ether. Deprotection can be performed just after STEP 6 or after STEP 7 by treating, with an aqueous solution of sodium hydroxide 2N (NaOH), a solution of the pivaloyl ester in methanol (MeOH) at RT, followed by acidification with an aqueous solution of hydrogen chloride 2N (HCl), or just after STEP 5, by treating a solution of the methyl ether in DCM by boron trifluoride at RT.

When R3 represents a —COOH group, this —COOH group is protected, for example as a methyl ester. Deprotection is performed just after STEP 7 by treating a solution of the methyl ester in MeOH with an aqueous solution of NaOH 2N, at RT, followed by acidification with an aqueous solution of HCl 2N.

In another embodiment of the invention, it can be advantageous for the preparation of intermediate (Ig) from SCHEME 1 to use a variation of SCHEME 1, called SCHEME 1a depicted below.

According to SCHEME 1a, in which A=O, B=D=E=G=CH and X, n, R1, R2, R3, R4 and R5 are defined as described above, an enol triflate intermediate (Ib) (obtained as described in SCHEME 1) is subjected in STEP 1 to a Suzuki coupling with reagent (1) ((S)-1-(3-fluoropropyl)-3-(4-(4,4,5,5-tetramethyl-1,3,2-dioxaborolan-2yl)-phenoxy)pyrrolidine) using for example (Pd(dppf)Cl$_2$), complex with DCM, as catalyst, in a mixture of dioxane and water and in the presence of a base, for example Cs$_2$CO$_3$, at RT or by heating up to reflux. The preparation of reagent (1) is described hereunder in SCHEME 2.

The intermediate (Ih) obtained is brominated in STEP 2 using for example pyridinium tribromide in DCM or THF at RT to produce bromo derivative intermediate (Ig).

SCHEME 1a: Preparation of intermediate (Ig) from SCHEME 1 with A = O: variation

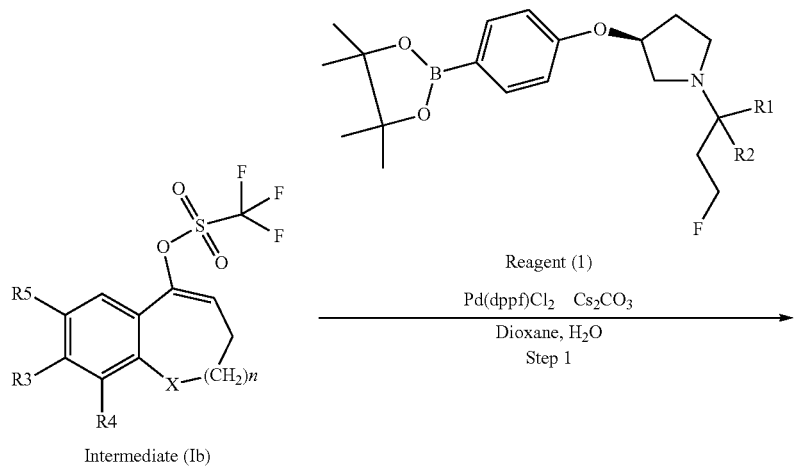

Intermediate (Ih) → Intermediate (Ig)

SCHEME 2: Preparation of reagent (1) of SCHEME 1a

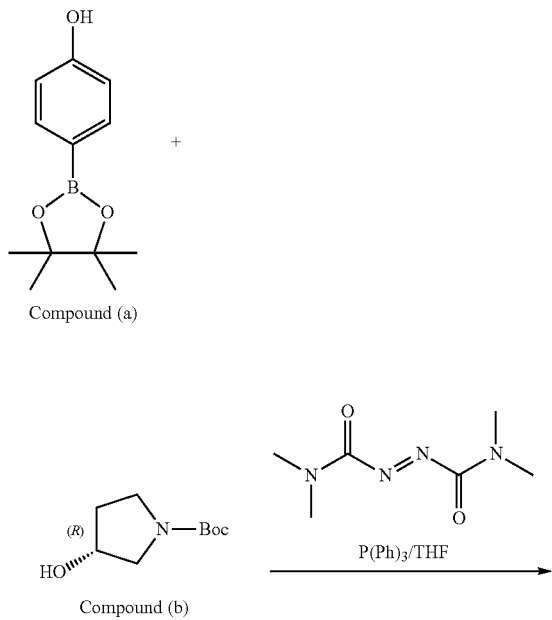

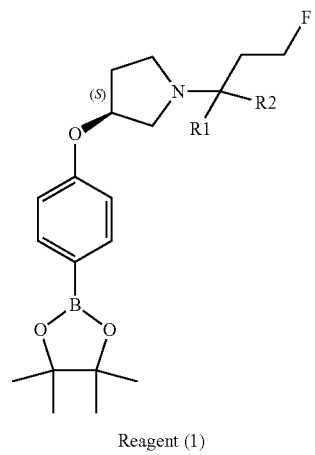

Reagent (1)

According to the above SCHEME 2, commercially available compound (a) (4-(4,4,5,5-tetramethyl-1,3,2-dioxaborolan-2-yl)phenol) is condensed in STEP 1 in THE at RT on compound (b), (R)-1-N-Boc-3-hydroxypyrrolidine, using Ph₃P and N,N,N',N'-tetramethylazodicarboxamide as coupling agent in THE as solvent.

Compound (c) thus obtained is N-deprotected in STEP 2 in MeOH at RT using an acidic agent, for example a solution of HCl 4N in dioxane.

Alkylation of the pyrrolidine nitrogen is then performed in STEP 3 by reacting compound (d) with the corresponding 1-halogeno-3-fluoropropane, for example 1-iodo-3-fluoropropane in acetonitrile (MeCN) in presence of K₂CO₃ at about 40° C.

When A=NH in the compounds of formula (I) according to the invention, then the compounds of formula (I) can be prepared according to SCHEME 3 below.

SCHEME 3: Preparation of compounds of the formula (I) with A = NH: general process

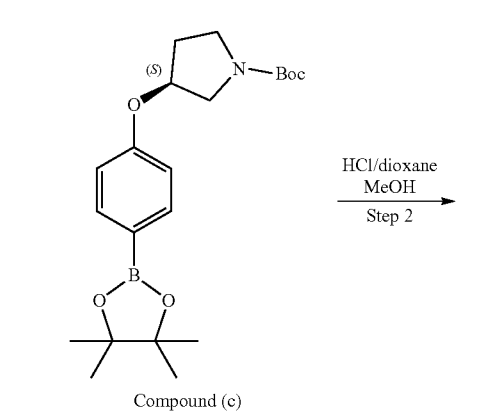

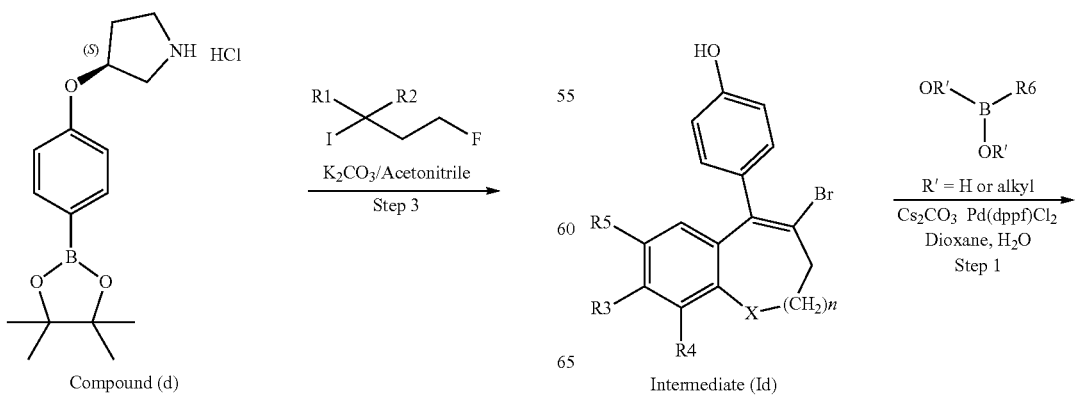

Intermediate (Id)

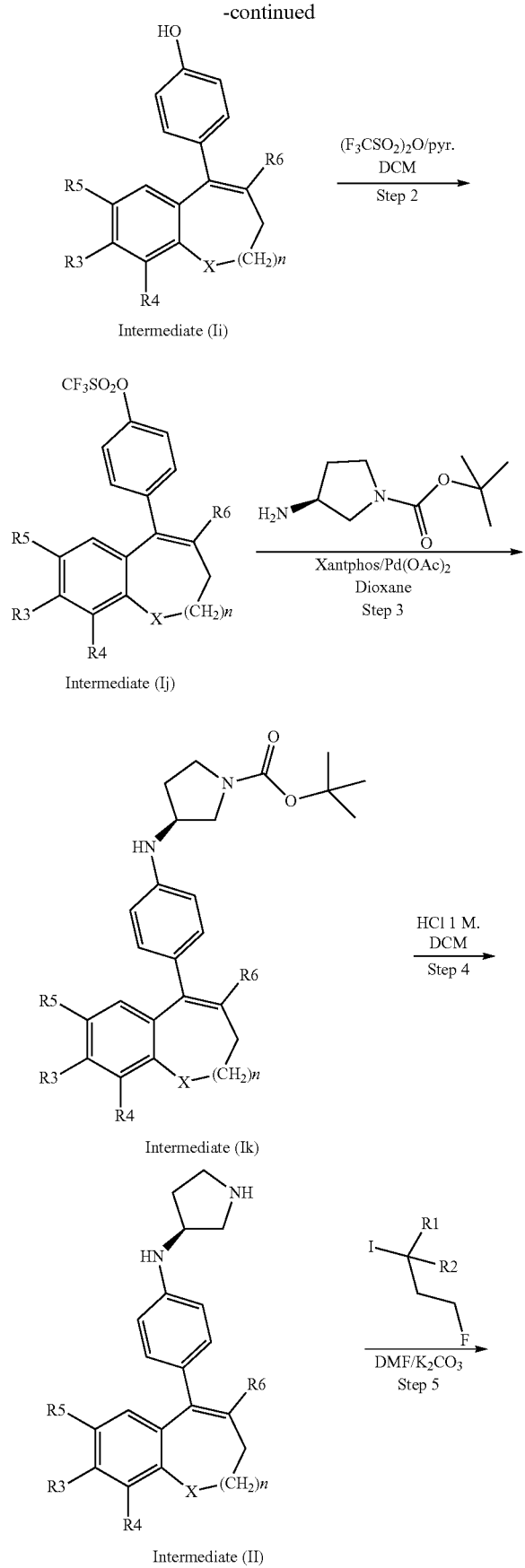

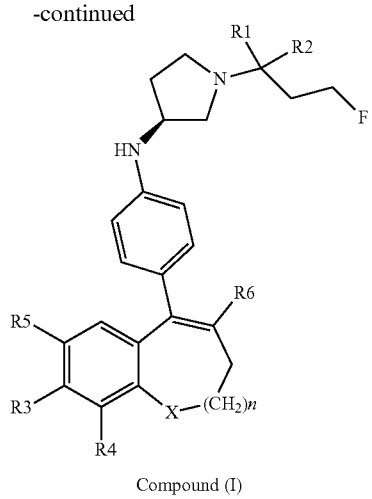

Compound (I)

According to SCHEME 3, in which A=NH, B=D=E=G=CH and X, n, R1, R2, R3, R4, R5 and R6 are defined as described above, a bromo derivative intermediate (Id) as defined in SCHEME 1 is subjected in STEP 1 to a Suzuki coupling with a suitable boronic reagent R6B(OR')$_2$, wherein —B(OR')$_2$ is a boronic acid or a pinacolate ester and R6 is as above defined, using for example Pd(dppf)Cl$_2$, complex with DCM, as catalyst, in a mixture of dioxane and water as solvent and in the presence of a base, for example Cs$_2$CO$_3$, at RT or by heating up to reflux to obtain phenol intermediate (i) which is transformed into a triflate (Ij) in STEP 2 by treatment by Tf$_2$O in DCM in the presence of pyridine. This triflate (Ij) is engaged in a Buchwald coupling (STEP 3) with 3-(S)-amino-pyrrolidine 1-N-Boc protected in dioxane at 140° C. using for example xantphos/Palladium acetate as catalytic system to produce intermediate (Ik). Finally, the Boc protecting group is removed in STEP 4 by a 1M solution of anhydrous hydrochloric acid in DCM and the resulting NH pyrrolidine (Il) is alkylated in STEP 5 with the corresponding disubstituted 1-halogeno-3-fluoropropane, for example 1-iodo-3-fluoropropane in DMF at 70° C. in the presence of K$_2$CO$_3$ as base to produce compound (1) as defined above.

In the above-described reactions, it can be necessary to protect reactive functional groups, for example hydroxy, amino, thio or carboxy groups, where these groups are desired in the final product, to avoid their unwanted participation in the reactions.

Conventional protecting groups can be used in accordance with standard practice, for example, see T. W. Greene and P. G. M. Wuts in "Protective Groups in Organic Chemistry", John Wiley and Sons, 2006.

When R3 or R5 represents an —OH group, this —OH group is protected, for example as a pivaloyl ester or a methyl ether. Deprotection can be performed just after STEP 5 by treating, with an aqueous solution of NaOH 2N, a solution of the pivaloyl ester in MeOH at RT, followed by acidification with an aqueous solution of HCl 2N HCl, or just after STEP 4 by treating a solution of the methyl ether in DCM by boron trifluoride at RT.

When R3 represents a —COOH group, this —COOH group is protected, for example as a methyl ester. Deprotection is performed just after STEP 5 by treating a solution of the methyl ester in MeOH, with an aqueous solution of NaOH 2N at RT, followed by acidification with an aqueous solution of HCl 2N.

In another embodiment of the invention, when A=NH, it can be advantageous for the preparation of the compounds (I) to use a variation of SCHEME 3, called SCHEME 3a depicted below.
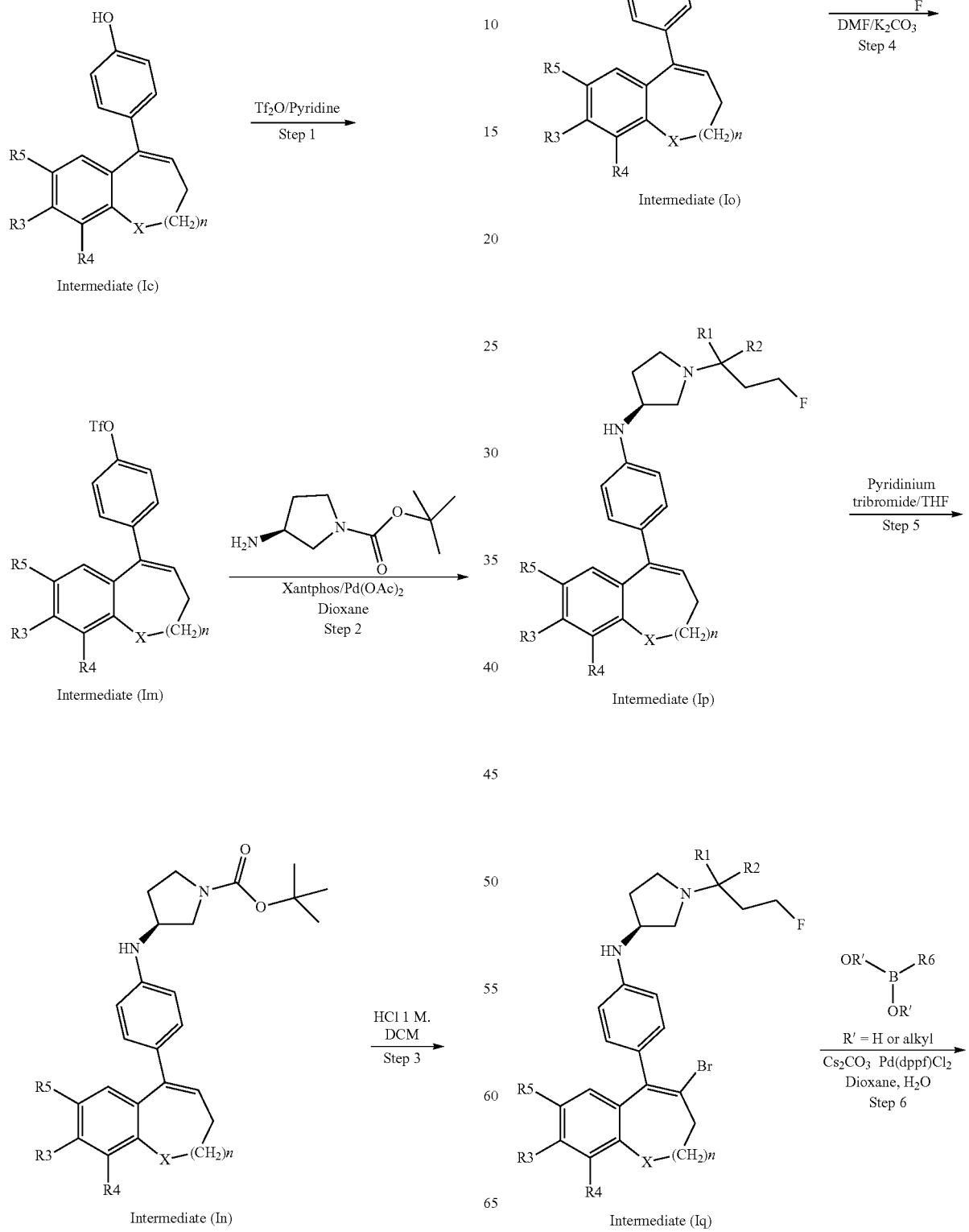

51

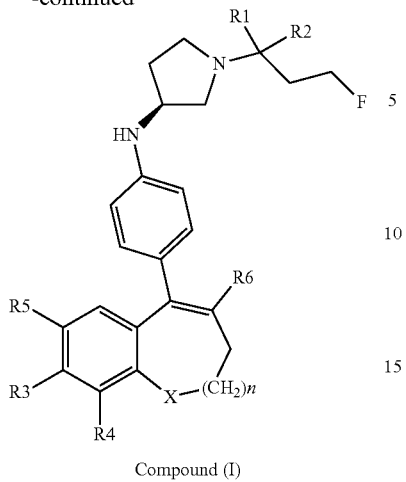

Compound (I)

According to SCHEME 3a, in which A=NH, B=D=E=G=CH and X, n, R1, R2, R3, R4, R5 and R6 are defined as described above, a phenol derivative intermediate (Ic) as described in SCHEME 1 is subjected in STEP 1 to a treatment by $Tf_2O$ in DCM in the presence of pyridine to provide intermediate (Im). This triflate (Im) is engaged in a Buchwald coupling (STEP 2) with 3-(S)-amino-pyrrolidine 1-N-Boc protected in dioxane at 140° C. using for example xantphos/palladium acetate as catalytic system to produce intermediate (In), which is then deprotected in STEP 3 by a 1M solution of anhydrous hydrochloric acid in DCM and the resulting NH pyrrolidine (Io) is alkylated in STEP 4 with the corresponding disubstituted 1-halogeno-3-fluoropropane, for example 1-iodo-3-fluoropropane in DMF at 70° C. in the presence of $K_2CO_3$ as base to produce intermediate (Ip). This intermediate (Ip) obtained is brominated in STEP 5 using for example pyridinium tribromide in DCM or THF at RT. This bromo derivative intermediate (Iq) is then subjected in STEP 6 to a Suzuki coupling with a suitable boronic reagent $R6B(OR')_2$, wherein $—B(OR')_2$ is a boronic acid or a pinacolate ester and R6 is as above defined, using for example $Pd(dppf)Cl_2$, complex with DCM, as catalyst, in a mixture of dioxane and water as solvent and in the presence of a base, for example $Cs_2CO_3$, at RT or by heating up to reflux to obtain compound (I).

In the above-described reactions, it can be necessary to protect reactive functional groups, for example hydroxy, amino, thio or carboxy groups, where these groups are desired in the final product, to avoid their unwanted participation in the reactions.

Conventional protecting groups can be used in accordance with standard practice, for example, see T. W. Greene and P. G. M. Wuts in "Protective Groups in Organic Chemistry", John Wiley and Sons, 2006.

When R3 or R5 represents an —OH group, this —OH group is protected, for example as a pivaloyl ester. Deprotection can be performed just after STEP 5 or STEP 6 by treating, with an aqueous solution of NaOH 2N (NaOH), a solution of the pivaloyl ester in MeOH at RT, followed by acidification with an aqueous solution of HCl 2N.

When R3 represents a —COOH group, this —COOH group is protected, for example as a methyl ester. Deprotection is performed just after STEP 6 by treating a solution of the methyl ester in MeOH, with an aqueous solution of NaOH 2N at RT, followed by acidification with an aqueous solution of HCl 2N.

52

When at least one of B or D or E or G is a nitrogen atom, corresponding compounds of formula (I) can be prepared according to SCHEME 4.

SCHEME 4: Preparation of compounds of the formula (I) with at least one of B, D, E or G = N

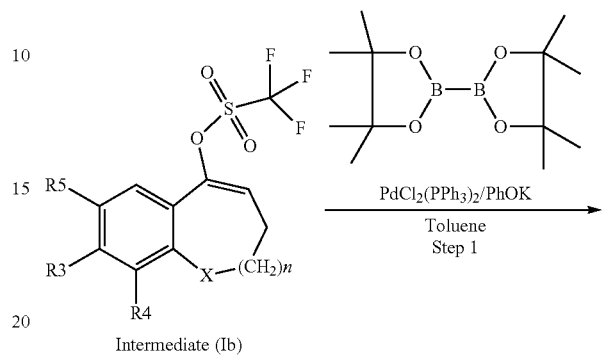

Intermediate (Ib)

Reagent 2
$Cs_2CO_3$ Pd(dppf)$Cl_2$
Dioxane, $H_2O$
Step 2

Intermediate (Ir)

Pyridinium tribromide
THF
Step 3

Intermediate (Is)

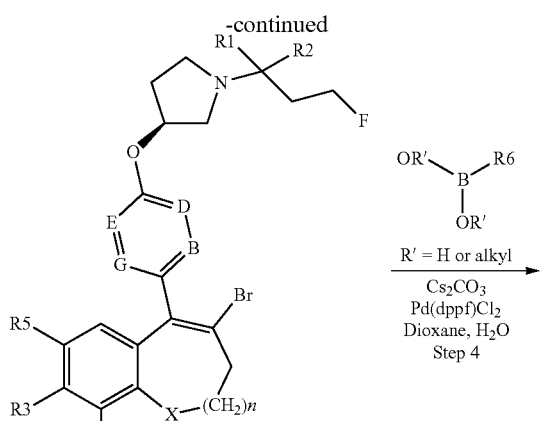

Intermediate (It)

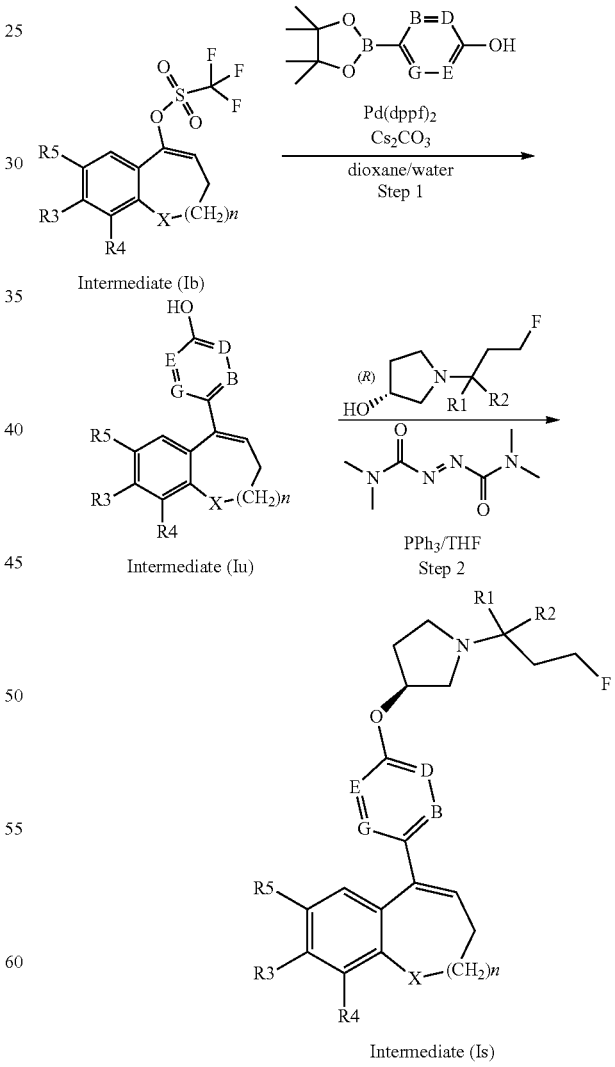

Compound (I)

According to SCHEME 4, in which A=O, at least one of B, D, E or G=N, and X, n, R1, R2, R3, R4, R5 and R6 are defined as described above, an enol triflate intermediate (Ib) is reacted (STEP 1) with bis-pinacolato-diboron using for example PdCl$_2$(PPh$_3$)$_2$, as catalyst, in toluene at 100° C. and in the presence of a base, for example potassium phenate. The preparation of reagent (2) is described hereunder in SCHEME 5.

The intermediate (Ir) thus obtained is subjected in STEP 2 to a Suzuki coupling with reagent (2) (in which Hal is an halogen atom selected between Cl, Br or I) using for example Pd(dppf)Cl$_2$, complex with DCM, as catalyst, in a mixture of dioxane and water as solvent and in the presence of a base, for example Cs$_2$CO$_3$, at RT or by heating up to reflux to obtain intermediate (Is) which is brominated in STEP 3 using for example pyridinium tribromide in DCM or THE at RT. This bromo derivative intermediate (It) is then subjected in STEP 4 to a second Suzuki coupling with a suitable boronic reagent R6B(OR')$_2$, wherein —B(OR')$_2$ is a boronic acid or a pinacolate ester and R6 is as above defined, using for example Pd(dppf)Cl$_2$, complex with DCM, as catalyst, in a mixture of dioxane and water as solvent and in the presence of a base, for example Cs$_2$CO$_3$, at RT or by heating up to reflux to obtain compound of formula (I).

In the above-described reactions, it can be necessary to protect reactive functional groups, for example hydroxy, amino, thio or carboxy groups, where these groups are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 2006.

When R3 or R5 represents an —OH group, this —OH group is protected, for example as a pivaloyl ester. Deprotection can be performed after STEP 4 by treating, with an aqueous solution of NaOH 2N, a solution of the pivaloyl ester in MeOH at RT, followed by acidification with an aqueous solution of HCl 2N.

When R3 represents a —COOH group, this —COOH group is protected, for example as a methyl ester. Deprotection is performed after STEP 4 by treating a solution of the methyl ester in MeOH, with an aqueous solution of NaOH 2N at RT, followed by acidification with an aqueous solution of HCl 2N.

In another embodiment of the invention, when at least one of B, D, E or G is a nitrogen atom, it can be advantageous for the preparation of intermediate (1s) of SCHEME 4 to use a variation of SCHEME 4, called SCHEME 4a depicted below.

SCHEME 4a: Alternative prepration of intermediate (Is) from scheme 4

According to SCHEME 4a, intermediate (Ib) as described in SCHEME 1 is reacted in STEP 1 with the corresponding commercially available boronate ester, using for example Pd(dppf)Cl$_2$, complex with DCM, as catalyst, in a mixture of dioxane and water as solvent and in the presence of a base, for example Cs$_2$CO$_3$, at RT or by heating up to reflux to obtain intermediate (Iu) which is condensed in STEP 2 on the corresponding 3-(R)-hydroxy substituted pyrrolidine using (Ph$_3$P) and N,N,N',N'-tetramethylazodicarboxamide as coupling agent in THF as solvent to provide intermediate (Is).

In another embodiment of the invention, when at least one of B, D, E or G is a nitrogen atom, it is possible for the preparation of compound (I) to use a variation of SCHEME 4, called SCHEME 4b depicted below.

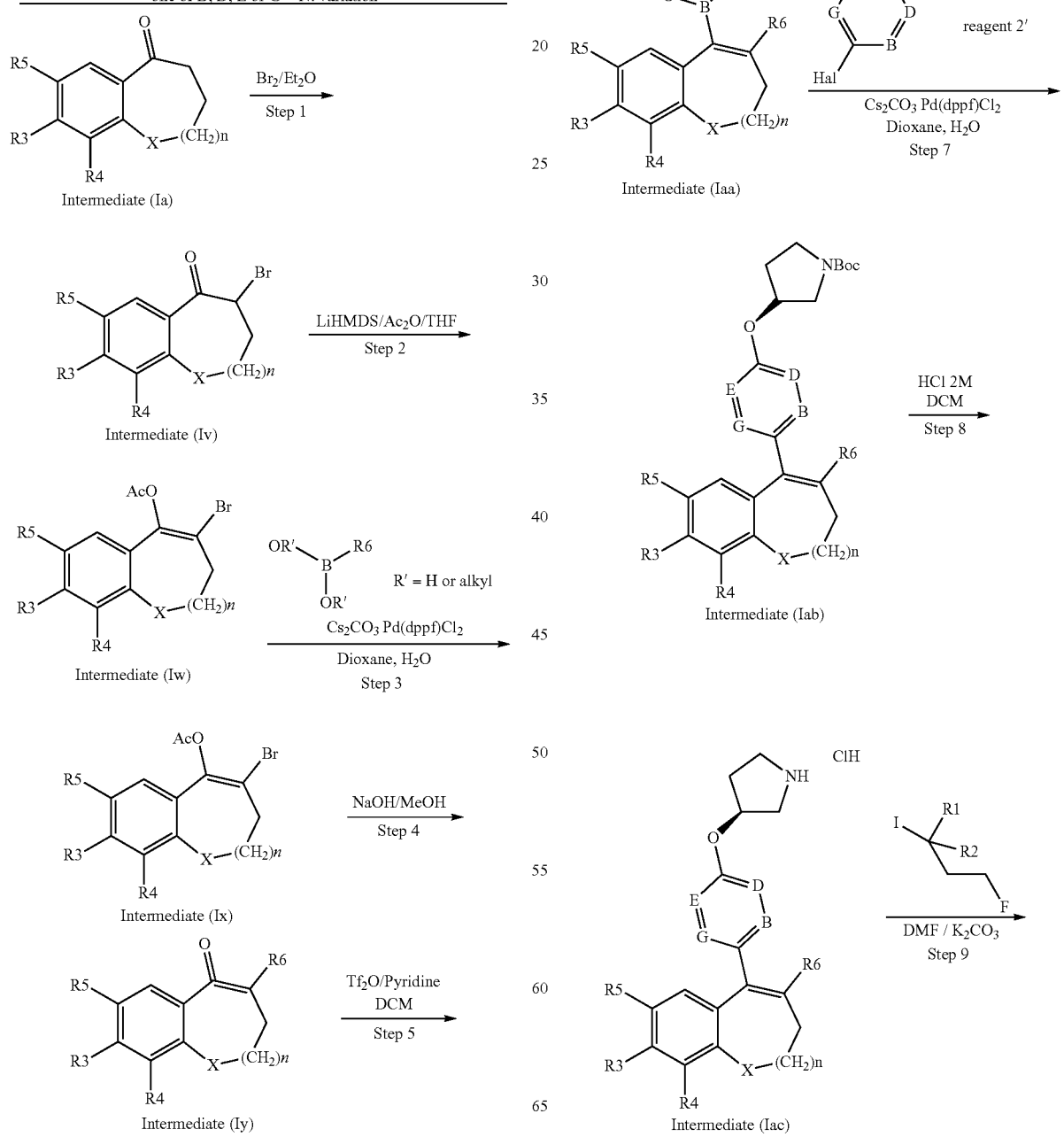

-continued

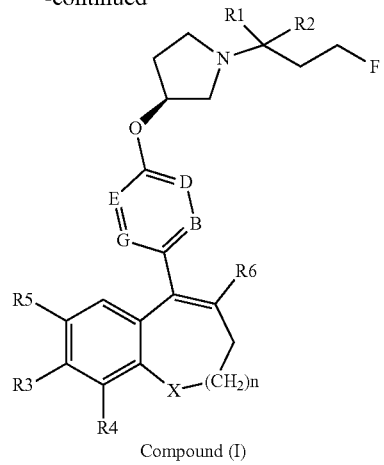

Compound (I)

According to SCHEME 4b, in which A=O, at least one of B, D, E or G=N, and X, n, R1, R2, R3, R4, R5 and R6 are defined as described above, a ketone intermediate (Ia) as defined in SCHEME 1 is alpha brominated (STEP 1) with bromine in a solvent such as diethyl ether (Et$_2$O) and the resulting intermediate (Iv) is treated in STEP 2 by acetic anhydride in the presence of a strong base such as Lithium HexaMethylDiSilazide (LiHMDS) in a solvent such as THF. The resulting enol acetate (Iw) is engaged in a Suzuki coupling (STEP 3) with a suitable boronic reagent R6B (OR')$_2$, wherein —B(OR')$_2$ is a boronic acid or a pinacolate ester and R6 is as above defined, using for example Pd(dppf)Cl$_2$, complex with DCM, as catalyst, in a mixture of dioxane and water as solvent and in the presence of a base, for example Cs$_2$CO$_3$, at RT or by heating up to reflux to provide intermediate (Ix) which is sequentially transformed into a ketone intermediate (Iy) (STEP 4), by treatment with an aqueous solution of NaOH 2M plus MeOH, and then into an enol triflate by treatment (STEP 5) with Tf$_2$O in DCM using pyridine as a base.

The resulting intermediate (Iz) is transformed in STEP 6 into a boronic ester (Iaa) by treatment with bis-pinacolato-diboron using for example palladium chloride bis triphenylphosphine (PdCl$_2$(PPh$_3$)$_2$), as catalyst, in toluene at 100° C. in the presence of a base, for example potassium phenate.

The intermediate (Iaa) is subjected in STEP 7 to a Suzuki coupling with reagent (2') (in which Hal is an halogen atom selected between Cl, Br or I) using for example Pd(dppf)Cl$_2$, complex with DCM, as catalyst, in a mixture of dioxane and water as solvent and in the presence of a base, for example Cs$_2$CO$_3$, at RT or by heating up to reflux to obtain intermediate (Iab) which is first N deprotected (STEP 8, intermediate (Iac) using a solution of hydrogen chloride 2M in DCM and finally (STEP 9) N-alkylated with a 1-fluoro-3-bromo-propane derivative in the presence of a base, for example K$_2$CO$_3$, in DMF at RT or by heating up to 70° C. to obtain compound of formula (I).

In the above-described reactions, it can be necessary to protect reactive functional groups, for example hydroxy, amino, thio or carboxy groups, where these groups are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 2006.

When R3 or R5 represents an —OH group, this —OH group is protected, for example as a pivaloyl ester or a methyl ether. Deprotection can be performed just after STEP 9 by treating, with an aqueous solution of NaOH 2N, a solution of the pivaloyl ester in MeOH at RT, followed by acidification with an aqueous solution of HCl 2N, or just after STEP 8 by treating a solution of the methyl ether in DCM by boron trifluoride at RT.

When R3 represents a —COOH group, this —COOH group is protected, for example as a methyl ester. Deprotection is performed just after STEP 9 by treating a solution of the methyl ester in MeOH, with an aqueous solution of NaOH 2N at RT, followed by acidification with an aqueous solution of HCl 2N.

Reagents (2) and (2') can be prepared according to SCHEME 5.

SCHEME 5: Preparation of reagents 2 and 2' (Hal = I, Br or Cl)

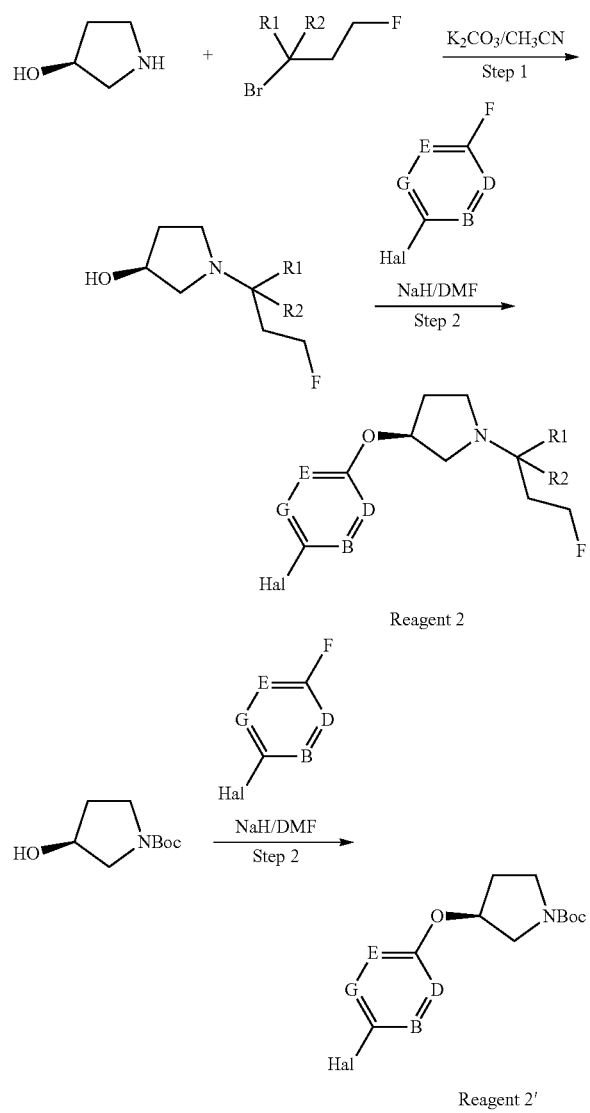

According to SCHEME 5, in which at least one of B, D, E or G=N and Hal is Cl, Br or I, and wherein R1 and R2 are defined as described above, (S)-3-hydroxy-pyrrolidine is reacted (STEP 1) with 1-fluoro-3-bromo-propane derivative in MeCN at 50° C. in the presence of a base, for example K₂CO₃, followed (STEP 2) by condensation on a 1-fluoro-4-halogeno-heteroaromatic derivative in DMF at RT in the presence of a base, for example sodium hydride, to obtain reagent 2. Reagent 2' can be obtained by the same reaction of condensation of N-Boc-(S)-3-hydroxy-pyrrolidine on a 1-fluoro-4-halogeno-heteroaromatic derivative in DMF at RT in the presence of a base, for example sodium hydride In another embodiment of the invention, it is possible for the preparation of reagent 2 or 2' to use a variation of SCHEME 5, called SCHEME 5a depicted below, which consists in performing a Mitsunobu reaction of N-(3-fluoro-propyl)-3-(R)-hydroxy-pyrrolidine derivative (obtained as described in SCHEME 5) or of N-Boc-3-(R)-hydroxy-pyrrolidine on a 1-hydroxy-4-halogeno-heteroaromatic derivative in THF in the presence of triphenylphosphine(Ph₃P) and DEAD (diethyl-aza-dicarboxylate) at RT.

SCHEME 5a: Preparation of reagent 2 or 2' (Hal = I, Br or Cl): variation

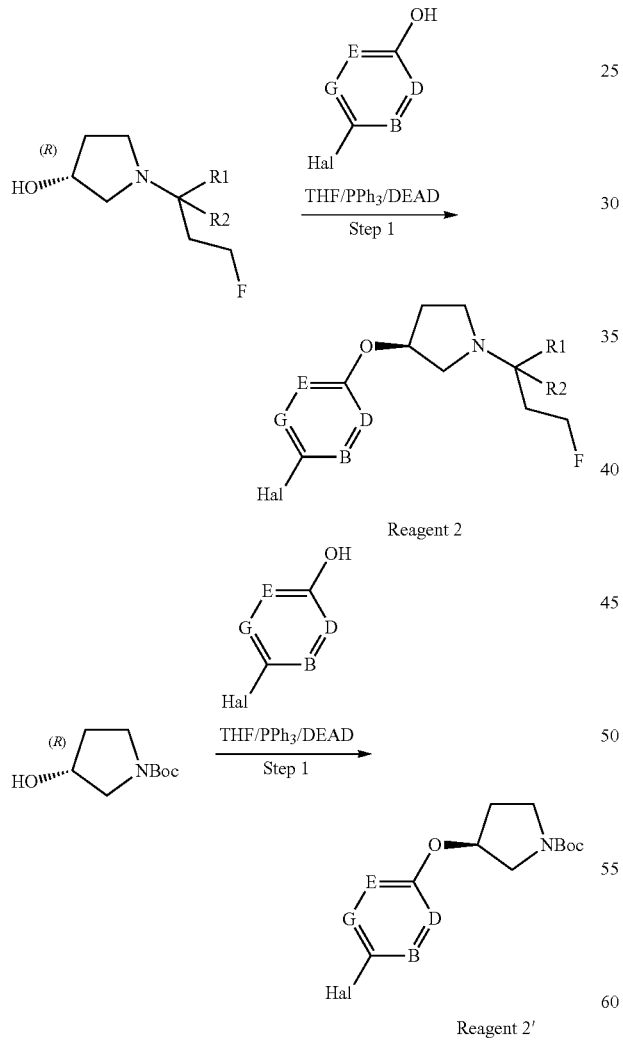

SCHEME 1b: Preparation of compounds of the formula (I)2 and (I)3 where, respectively, X = SO and n = 0 or 1, and X = SO₂ and n = 0 or 1

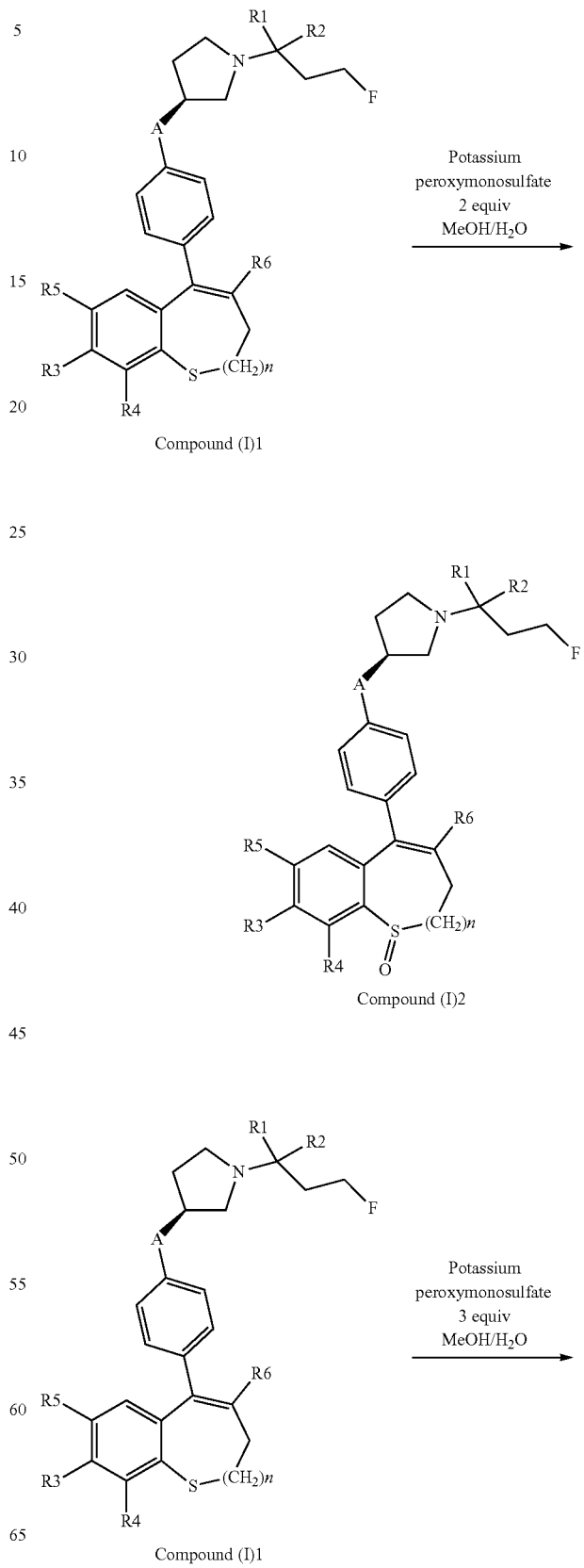

In another embodiment of the invention, when X=SO and n=0 or 1, and when X=SO₂ and n=0 or 1 in formula (I), it is possible to use a variation of SCHEME 1, called SCHEME 1b depicted below.

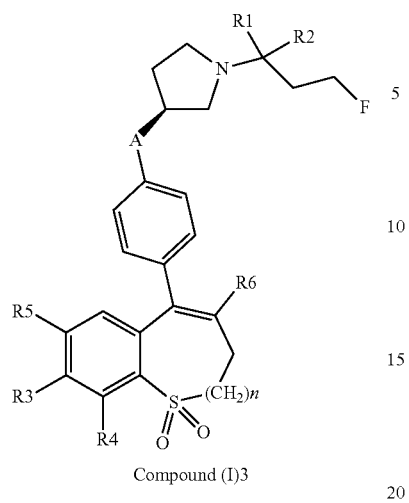

Compound (I)3

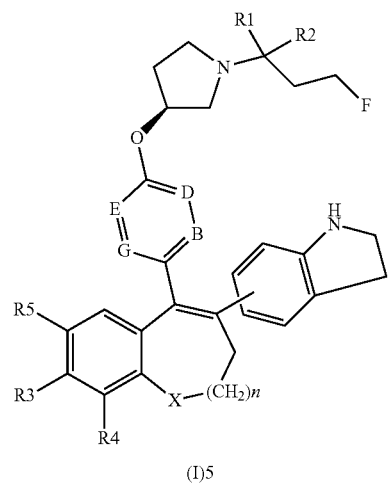

(I)5

According to SCHEME 1b the bicyclic thioether precursor of formula (I)1 is oxidized into the corresponding sulfoxide (compound (I)2) by two equivalents of potassium peroxymonosulfate in MeOH and water at RT. When 3 equivalents of oxidizing agents are used in the same conditions, then the sulfone is obtained (compound (I)3).

In another embodiment of the invention, it is also possible, when R6 is an indolinyl moiety and when A, B, D, G, E, X, n, R1, R2, R3, R4 and R5 are defined in the general formula (I) above, to use a variation of SCHEME 1, called SCHEME 1c depicted below.

SCHEME 1c: Preparation of compounds of the formula (I) where R6 is indolinyl (compounds of formula (I)5)

According to SCHEME 1c, the indolinyl derivative (I)4 is reduced into the indolinyl compound (I)5 by using sodium cyanoborohydride in acetic acid (AcOH).

In another embodiment of the invention, it can be advantageous, when the compounds of the invention are such that R3 is a —COOH group, to generate this carboxylic acid at the last step by carbonylation of a triflate (R3=OTf) as shown in SCHEME 6 depicted below.

SCHEME 6: Preparation of compounds of the formula (I) when R3 = —COOH

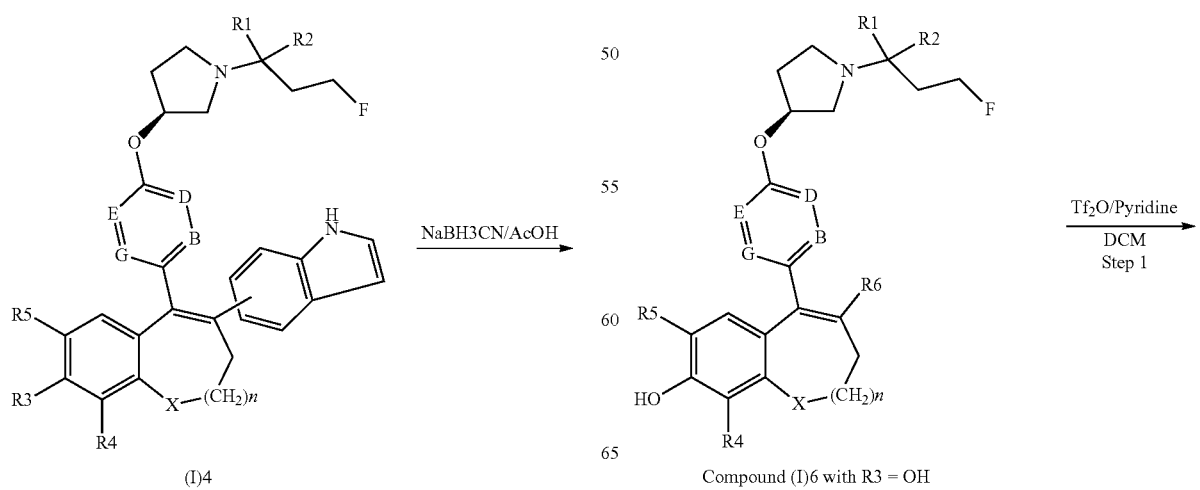

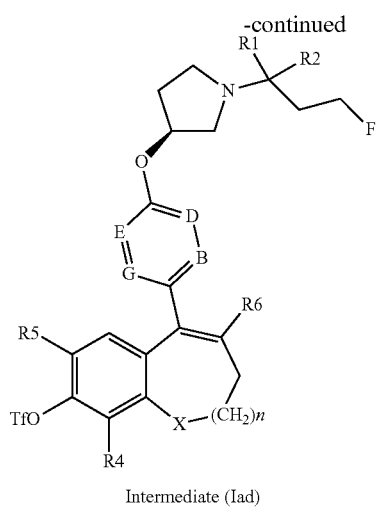

Intermediate (Iad)

Mo(CO)₆/Pd(OAc)₂
pyridine/H₂O
Step 2
→

Compound (I)7 with R3 = COOH

SCHEME 6 describes the synthesis of compounds of the formula (I) wherein A=O, R3 represents a —COOH group, and B, D, G, E, X, n, R1, R2, R4, R5 and R6 are defined in the general formula (I) above, by generating the —COOH group from the —OH group at the R3 position of the compounds of formula (I)6. In STEP 1 of SCHEME 6 the —OH group at the R3 position in the compounds of formula (I)6 is transformed into a triflate group by using Tf₂O in DCM with a base, for example pyridine, at RT. The intermediate (Iad) obtained is then transformed into a carboxylated compound in STEP 2 with Mo(CO)₆ (molybdene hexacarbonyle) at about 150° C. in a mixture of pyridine and water and using for example palladium acetate (Pd(OAc)₂) and 1,1'-bis(diphenylphosphino)ferrocene 1,3-bis(diphenylphosphino)propane (P(Ph)₂-(CH₂)₃—P(Ph)₂) as catalytic system, so as to obtain the compounds of formula (I)7 wherein B, D, G, E, X, n, R1, R2, R4, R5 and R6 are as above defined and R3 is a —COOH group.

In another embodiment of the invention, it is possible as well, when R3 represents a —COOH group, to use a variation of SCHEME 6, called SCHEME 6a depicted below. This SCHEME 6a is an alternative process to the above SCHEME 6.

SCHEME 6a: Preparation of compounds of the formula (I) when R3 = —COOH: variation

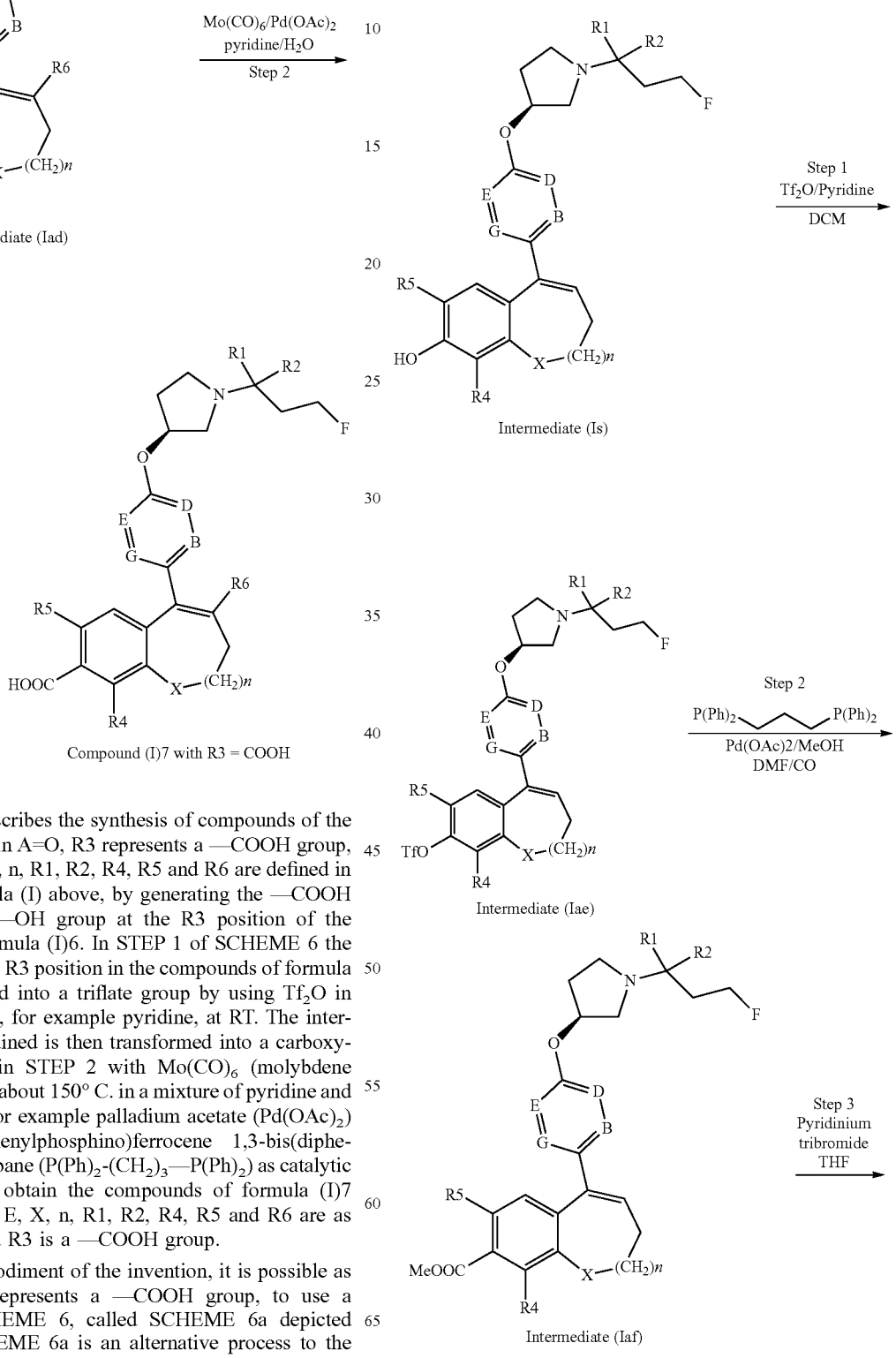

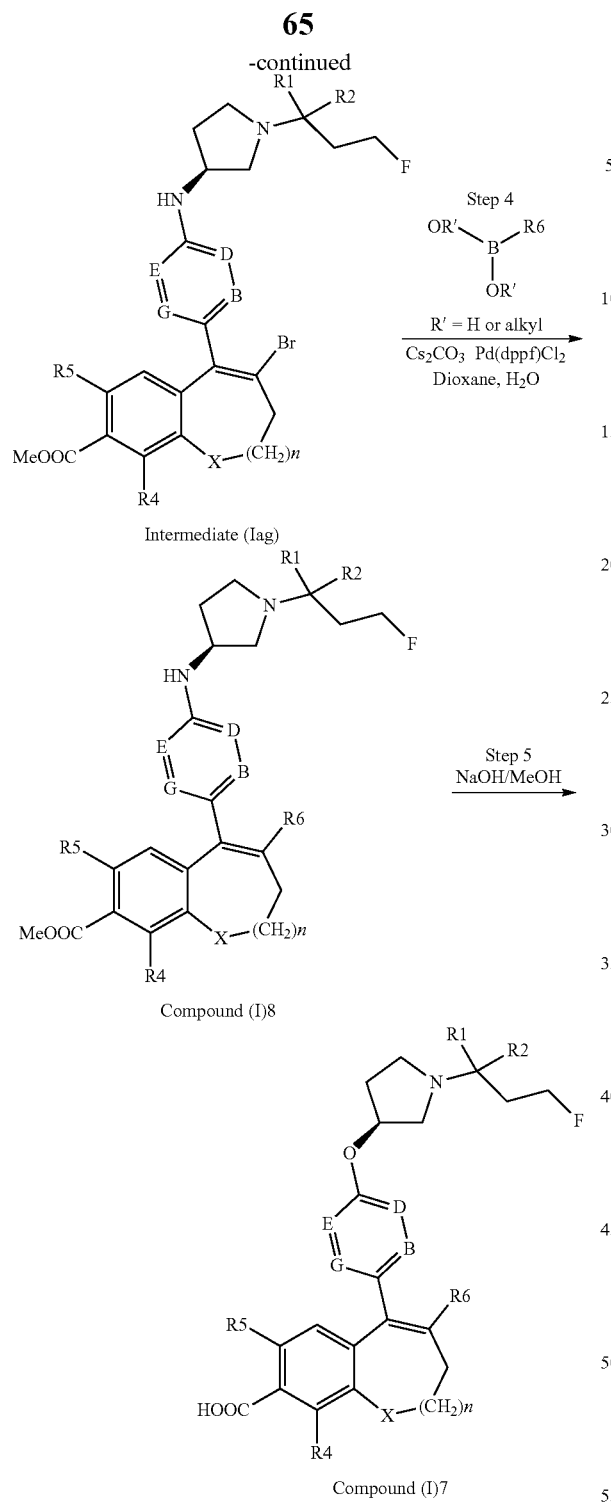

carbon monoxide (CO) at about 70° C. in a mixture of MeOH and DMF using for example Pd(OAc)₂ and (P(Ph)₂-(CH₂)₃—P(Ph)₂) as catalytic system. The intermediate (Iaf) is then subjected to steps 3 and 4 described in SCHEME 6a. The methyl ester (I)8 thus obtained is deprotected using aqueous NaOH in MeOH, so as to obtain compounds of formula (I)7 wherein A=0 and B, D, G, E, X, n, R1, R2, R4, R5 and R6 are defined in the general formula (I) above and R3 is a —COOH group.

The invention also concerns the preparation of the compound (II) depicted below, corresponding to a compound of formula (I-A) as described above wherein R1 and R2 represent hydrogen atoms and wherein SERM-F represents the structure (bII) as described above.

SCHEME 7: Preparation of 1-(S)-(2,6-difluoro-4-(((S)-1-(3-fluoropropyl)pyrrolidin-3-yl)oxy)phenyl)-2-(2-fluoro-2-methylpropyl)-3-(R)-methyl-2,3,4,9-tetrahydro-1H-pyrido[3,4-b]indole of formula (II)

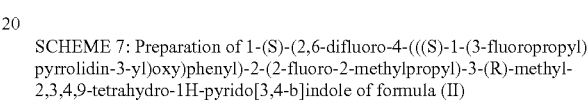

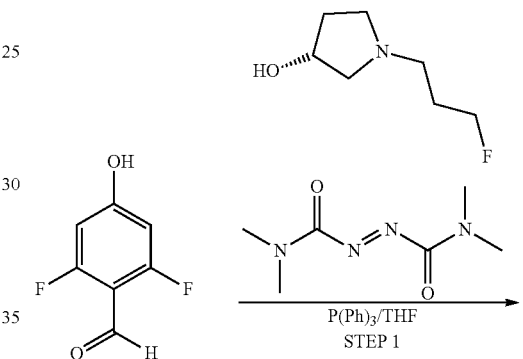

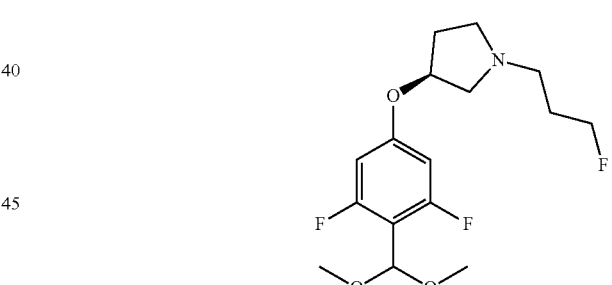

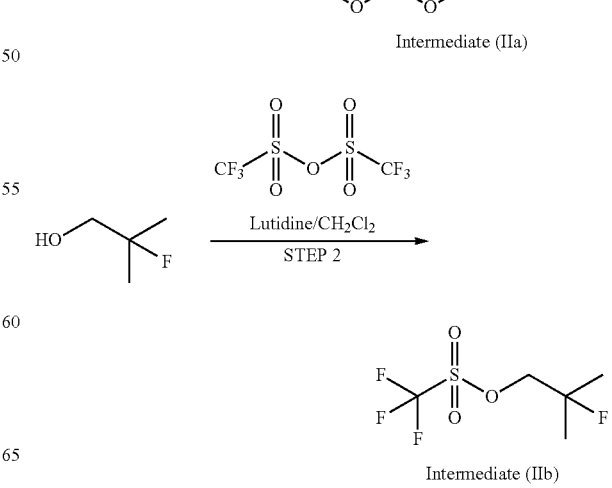

SCHEME 6a describes the synthesis of the intermediates defined above by generating a —COOMe group from the —OH group (R3=OH). In STEP 1 of SCHEME 6a, the —OH group of intermediate (Is), wherein A=0 and B, D, G, E, X, n, R1. R2, R4 and R5 are defined in the general formula (I) above, is transformed into a triflate group with, for example, Tf₂O in DCM with a base, for example pyridine, at RT to provide intermediate (Iae) which is sequentially carbonylated in STEP 2 under 2 to 10 bars of

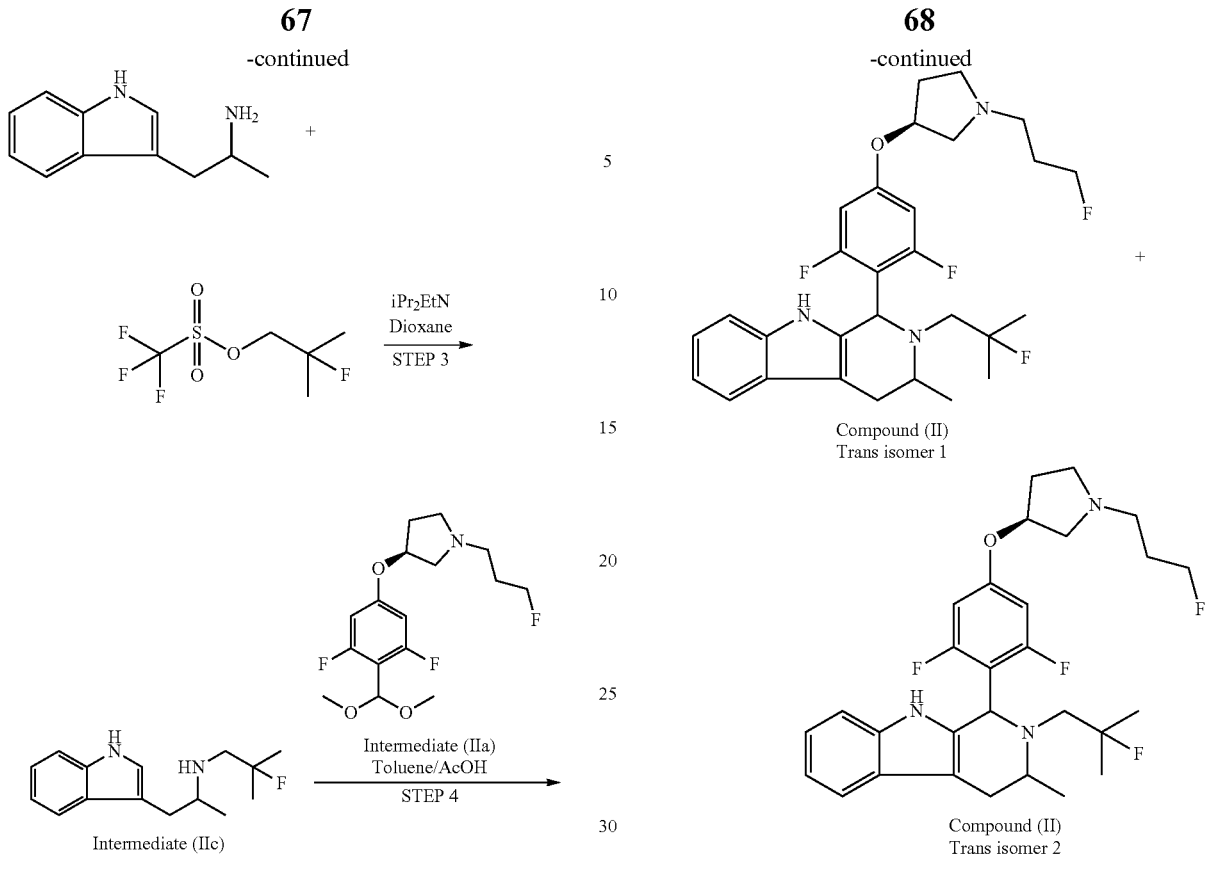

According to SCHEME 7, 2-6-difluoro-4-hydroxy-benzaldehyde is reacted with (R)-1-(3-fluoropropyl)pyrrolidin-3-ol in STEP 1 by a Mitsunobu reaction with tetramethyldiazenedicarboxamide and triphenylphosphine(Ph₃P) in THF at RT to obtain the corresponding phenol ether intermediate (IIa). In parallel, 2-fluoro-2-methyl propanol is condensed in STEP 2 on Tf₂O in DCM in the presence of a base, for example lutidine, and the product of this reaction, intermediate (IIb), is reacted (STEP 3) with 3-(2-aminopropyl)-indole. Then these two moieties (IIa) and (IIc) are assembled in STEP 4 in toluene and AcOH at RT or by heating to reflux to produce intermediate (IId) as a mixture of trans isomers which are separated by chiral HPLC (STEP 5) to obtain compound (II).

The invention also concerns the preparation of the compound (III) depicted below, corresponding to a compound of formula (I-A) as described above wherein R1 and R2 represent hydrogen atoms and wherein SERM-F represents the structure (cIII) as described above.

SCHEME 8: Preparation of (S,E)-5-(2-(2-chloro-4-fluorophenyl)-1-(4-((1-(3-fluoropropyl)pyrrolidin-3-yl)oxy)phenyl)but-1-en-1-yl)-1H-indazole of formula (III)

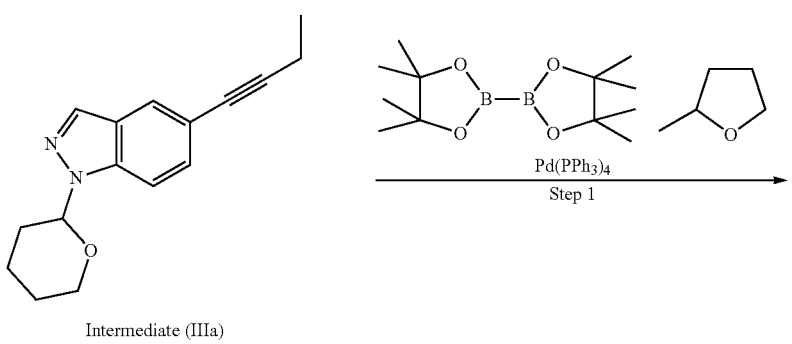

-continued
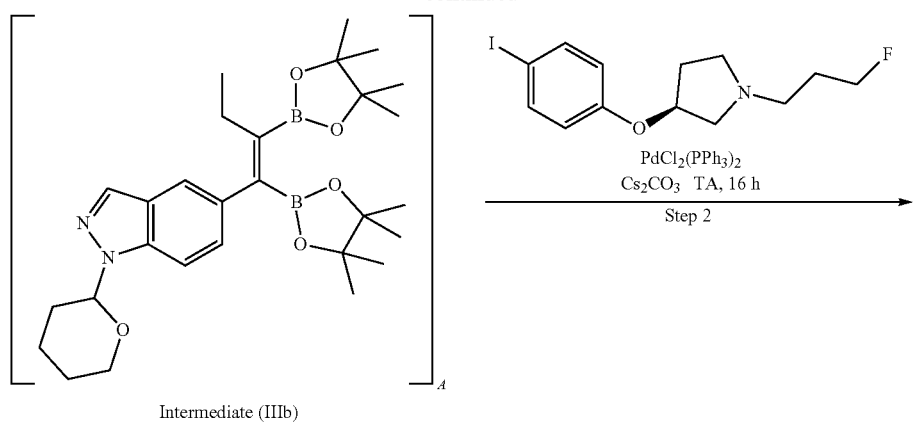
Intermediate (IIIb)
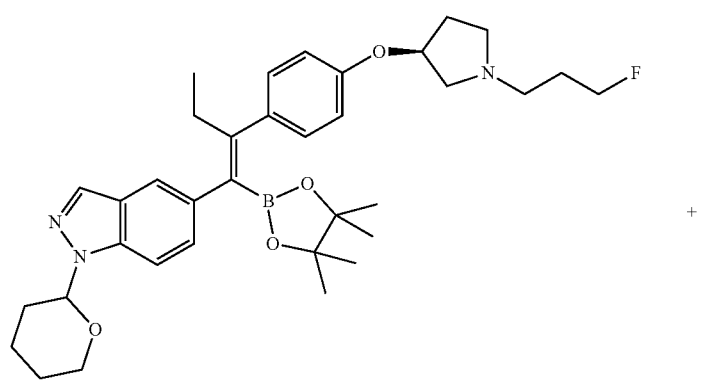
Intermediate (IIIc)
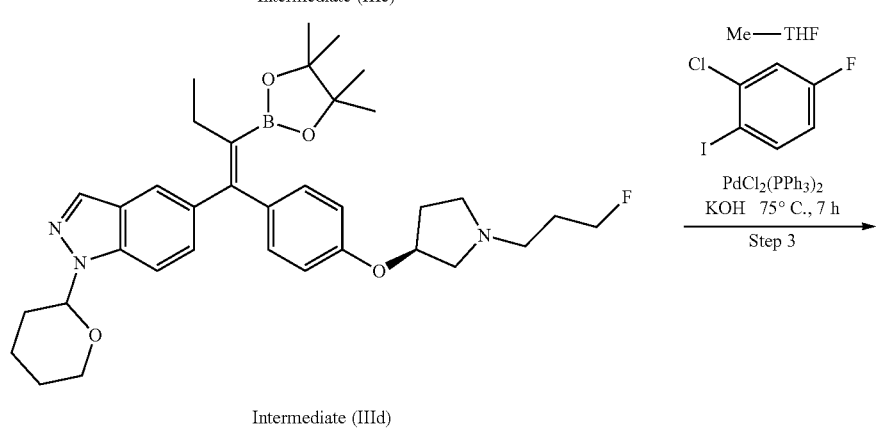
Intermediate (IIId)
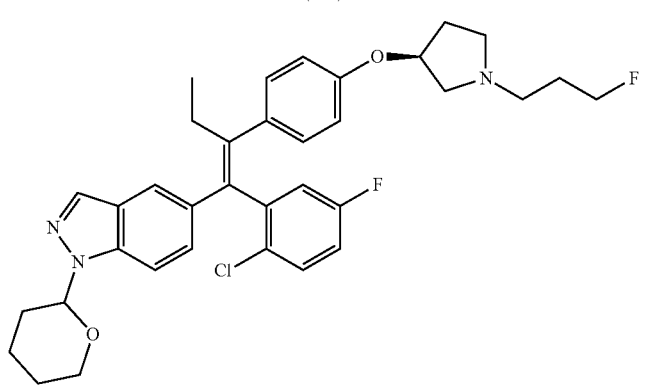
Intermediate (IIIe)

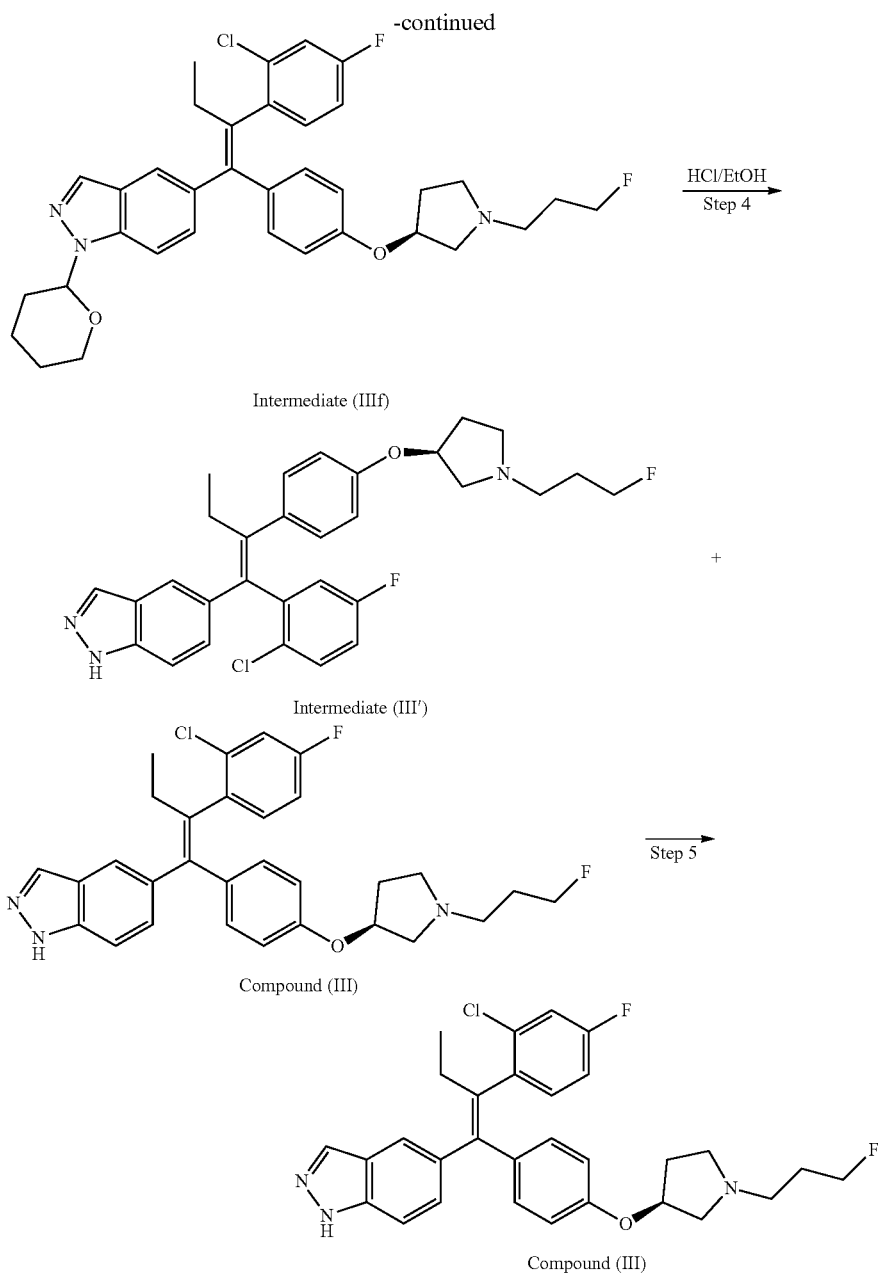

According to Scheme 8, intermediate (IIIa) (preparation described in patent application WO 2012/037410) is reacted in STEP 1 on bis-pinacolatodiboron, using for example tetrakis triphenyl phosphine as catalyst in methyltetrahydrofuran as solvent, at a temperature between RT and reflux. The intermediate (IIIb) obtained is sequentially engaged in two successive Suzuki coupling reactions (STEPS 2 and 3), first with the iodophenoxy N-substituted-3-pyrrolidine, in the presence of $PdCl_2(PPh_3)_2$ as catalyst in the presence of a base such as $Cs_2CO_3$ in methyltetrahydrofuran, at a temperature comprised between RT and reflux, to give intermediates (IIIc) and (IIId), secondly with 2-chloro-4-fluoro-iodobenzene in the presence of $PdCl_2(PPh_3)_2$, in the presence of a base such as potassium hydroxide in methyltetrahydrofuran at a temperature comprised between RT and reflux, to obtain a mixture of intermediates (IIIe) and (IIIf) which are deprotected in STEP 4. Finally the two regioisomers are separated using chiral HPLC in STEP 5 to obtain compound (III).

The invention also concerns the preparation of the compound (IV) depicted below, corresponding to a compound of formula (I-A) as described above wherein R1 and R2 represent hydrogen atoms and wherein SERM-F represents the structure (dIV) as described above.

SCHEME 9: Preparation of 2-(4-(((S)-1-(3-fluoropropyl) pyrrolidin-3-yl)oxy)phenyl)-3-(4-hydroxyphenyl)-2,3-dihydrogenzo[b][1,4]oxathiin-6-ol of formula (IV)

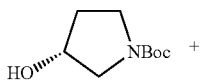

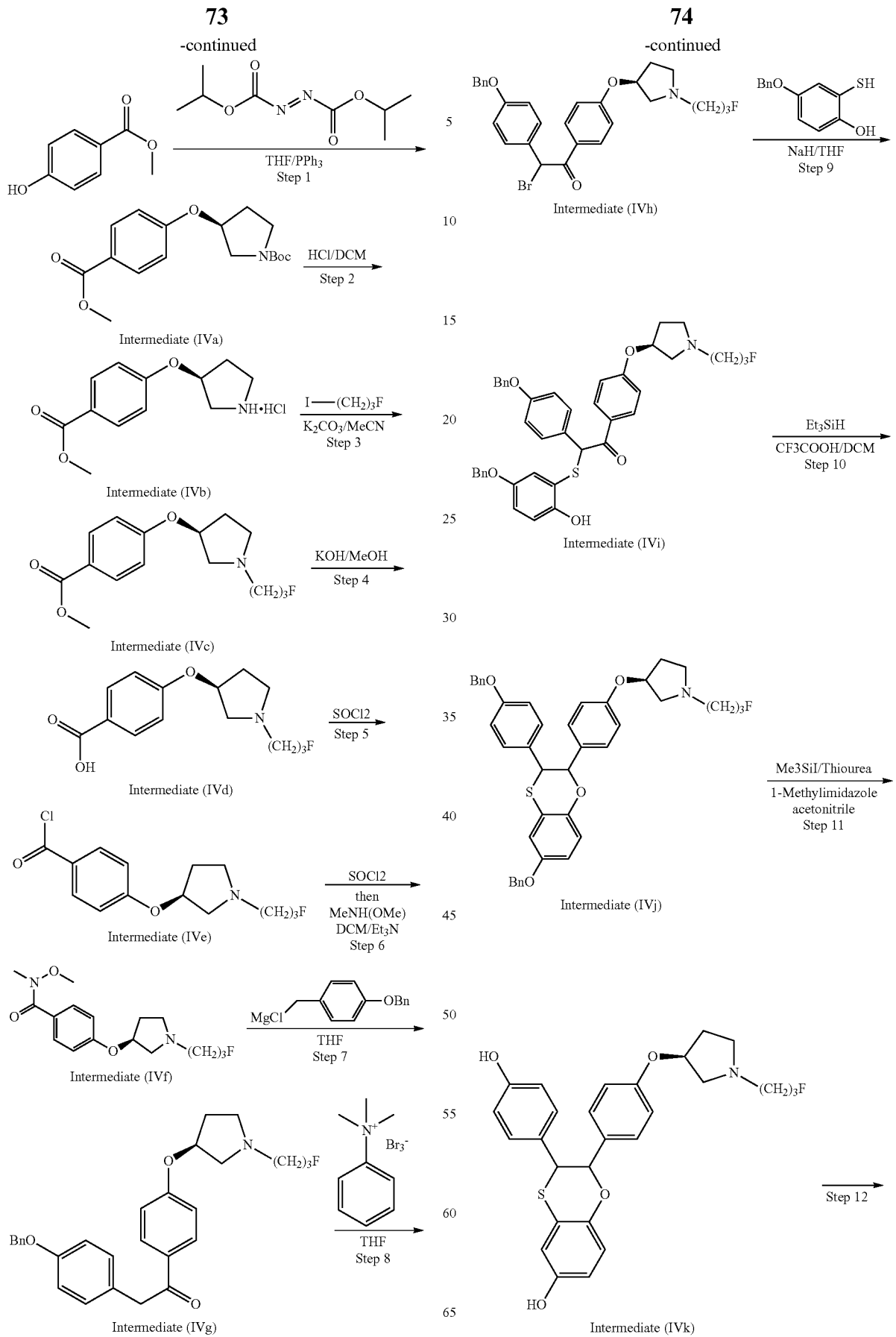

-continued

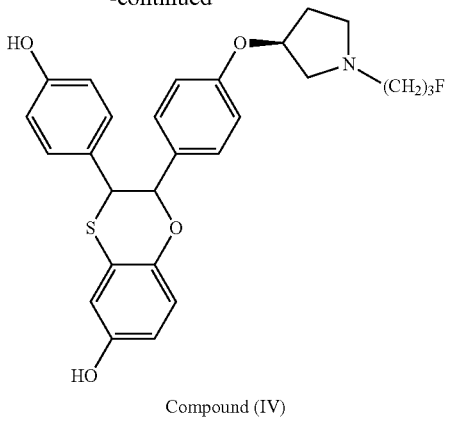

Compound (IV)

According to Scheme 9, 3-(R)-hydroxy-N-Boc-pyrrolidine is reacted in STEP 1 with 4-hydroxy methylbenzoate in THF in the presence of diisopropyl diazene dicarboxylate and triphenyl phosphine to obtain intermediate (IVa), which is sequentially N-deprotected with hydrogen chloride in DCM (STEP 2, intermediate (IVb)) and alkylated with corresponding 3-fluoropropyl derivative in the presence of $K_2CO_3$ as base and in MeCN (STEP 3, intermediate (IVc)). This intermediate is engaged in a saponification using potassium hydroxide in MeOH (STEP 4). The acid intermediate (IVd) is reacted with thionyl chloride (STEP 5), then with methoxy methyl amine in DCM in the presence of a base such as triethylamine (STEP 6) to obtain intermediate (IVf) which is engaged in a Grignard reaction with the corresponding Grignard reagent in THF (STEP 7). The ketone intermediate (IVg) obtained is brominated in STEP 8 with N,N,N-trimethylbenzeneaminium tribromide in THF and the resulting intermediate (IVh) is condensed on the corresponding substituted thiophenol in the presence of a base, NaH for example in a solvent such as THF at a temperature comprised between RT and reflux to produce intermediate (IVi) which is cyclized in STEP 10 into intermediate (IVj) with triethylsilane in a mixture of AcOH and DCM at a temperature comprised between RT and reflux. This intermediate (IVj) is debenzylated in STEP 11 using trimethylsilane iodide with 1-methylimidazole and thiourea in MeCN to produce intermediate (IVk) as a mixture of diastereoisomers which are separated by chiral HPLC (STEP 12) to obtain compound (IV).

Some compounds of the invention are described with their structure, name, method of preparation and analytical data in the below Table 1, which is merely illustrative and does not limit the scope of the present invention. The examples with numbers indicated in bold in below Table 1 are further detailed hereafter.

The methods of preparation A, B and C mentioned in table 1 are respectively described in examples 1, 116 and 228 below.

The 1H NMR spectra at 300, 400 and 500 MHz were performed on a Bruker DPX-300, Bruker Avance DRX-400 and Bruker Avance DPX-500 spectrometer, respectively, with the chemical shifts (δ in ppm) in the solvent dimethyl sulfoxide-d6 (d6-DMSO) referenced at 2.5 ppm at a temperature of 303 K. Coupling constants (J) are given in Hertz.

The liquid chromatography/mass spectra (LC/MS) were obtained on a UPLC Acquity Waters instrument, light scattering detector Sedere and SQD Waters mass spectrometer using UV detection DAD 210<I<400 nm and column Acquity UPLC CSH C18 1.7 μm, dimension 2.1×30 mm, mobile phase $H_2O$+0.1% $HCO_2H$/$CH_3CN$+0.1% $HCO_2H$.

Purities for final compounds were measured using UV detection at 220 nm and are ≥95.0%.

TABLE 1

| Example | Structure | Name | Method | NMR | MASS LC/MS (m/z, MH+) |
|---|---|---|---|---|---|
| 1 | 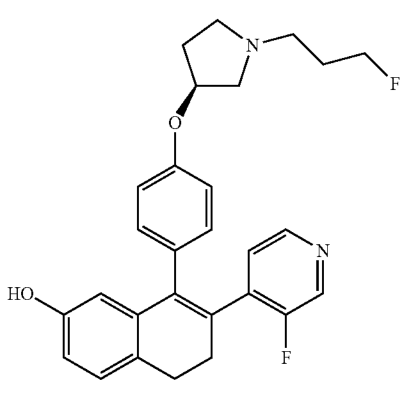 [SMILES: Oc1ccc2c(c1)C(c1ccc(O[C@H]3CCN(CCCF)C3)cc1)=C(c1ccncc1F)CC2] | 8-[4-[(3S)-1-(3-fluoropropyl)pyrrolidin-3-yl]oxyphenyl]-7-(3-fluoro-4-pyridyl)-5,6-dihydronaphthalen-2-ol | A | 1H NMR (400 MHz, DMSO-d6) δ ppm: 1.77 (m, 3 H), 2.19 (m, 1 H), 2.35-2.60 (m, 6 H), 2.66 (m, 1 H), 2.81 (dd, J = 10.2 et 6.2 Hz, 1 H), 3.34 (m, 2 H), 4.47 (dt, J = 47.7 et 6.0 Hz, 2 H), 4.75 (m, 1 H), 6.11 (dd, J = 8.0 et 1.4 Hz, 1 H), 6.23 (s, 2 H), 6.69 (m, 6 H), 7.02 (d, J = 2.2 Hz, 1 H), 7.10 (dd, J = 10.1 et 8.3 Hz, 1 H), 9.71 (s, 1 H) | 463 |

TABLE 1-continued

| Example | Structure | Name | Method | NMR | MASS LC/MS (m/z, MH+) |
|---|---|---|---|---|---|
| 2 | 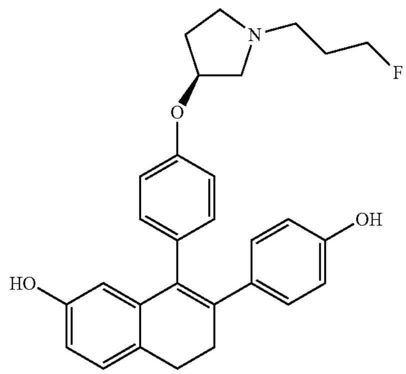 [SMILES: Oc1ccc(C2=C(c3ccc(O[C@H]4CCN(CCCF)C4)cc3)c3cc(O)ccc3CC2)cc1] | 8-[4-[(3S)-1-(3-fluoropropyl)pyrrolidin-3-yl]oxyphenyl]-7-(4-hydroxyphenyl)-5,6-dihydronaphthalen-2-ol | A | 1H NMR (400 MHz, DMSO-d6) δ ppm: 1.80 (m, 3 H), 2.26 (m, 1 H), 2.41 (m, 1 H), 2.48 (m, 2 H), 2.54 à 2.72 (m, 5 H), 2.77 (m, 2 H), 2.85 (dd, J = 10.2 et 6.2 Hz, 1 H), 4.49 (dt, J = 47.4 et 6.0 Hz, 2 H), 4.82 (d, J = 6.7 Hz, 1 H), 6.10 (d, J = 2.3 Hz, 1 H), 6.49 (m, 2 H), 6.80 (m, 4 H), 6.89 (m, 2 H), 6.98 (d, J = 8.1 Hz, 1 H), 8.91 (s, 1 H), 9.23 (s, 1 H) | 460 |
| 3 | 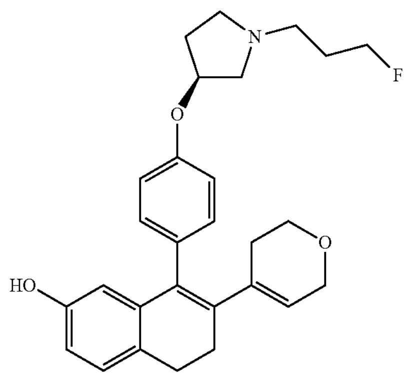 [SMILES: Oc1ccc2c(c1)C(c1ccc(O[C@H]3CCN(CCCF)C3)cc1)=C(C1=CCOCC1)CC2] | 7-(3,6-dihydro-2H-pyran-4-yl)-8-[4-[(3S)-1-(3-fluoropropyl)pyrrolidin-3-yl]oxyphenyl]-5,6-dihydronaphthalen-2-ol | A | 1H NMR (400 MHz, DMSO-d6) δ ppm: 1.82 (m, 5 H), 2.28 (m, 1 H), 2.41 (m, 3 H), 2.61-2.77 (m, 3 H), 2.88 (dd, J = 10.2 et 6.2 Hz, 1 H), 3.48 (m, 2 H), 3.91 (d, J = 2.3 Hz, 2 H), 4.50 (dt, J = 47.4 et 6.0 Hz, 2 H), 4.88 (m, 1 H), 5.38 (m, 1 H), 6.07 (d, J = 2.3 Hz, 1 H), 6.48 (dd, J = 7.9 et 2.4 Hz, 1 H), 6.88 (d, J = 8.7 Hz, 2 H), 6.96 (d, J = 7.9 Hz, 1 H), 7.00 (d, J = 8.6 Hz, 2 H), 8.91 (s, 1 H) | 450 |
| 4 | 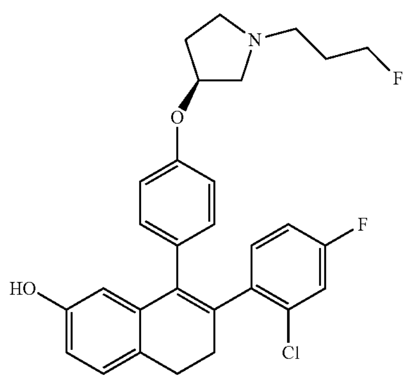 [SMILES: Oc1ccc2c(c1)C(c1ccc(O[C@H]3CCN(CCCF)C3)cc1)=C(c1ccc(F)cc1Cl)CC2] | 7-(2-chloro-4-fluoro-phenyl)-8-[4-[(3S)-1-(3-fluoropropyl)pyrrolidin-3-yl]oxyphenyl]-5,6-dihydronaphthalen-2-ol | A | 1H NMR (400 MHz, DMSO-d6) δ ppm: 1.77 (m, 3 H), 2.23 (m, 1 H), 2.35-2.48 (m, 3 H), 2.52-2.73 (m, 3 H), 2.79 (m, 4 H), 4.47 (dt, J = 47.4 et 6.0 Hz, 2 H), 4.76 (m, 1 H), 6.16 (d, J = 2.4 Hz, 1 H), 6.57 (dd, J = 8.0 et 2.5 Hz, 1 H), 6.73 (d, J = 8.7 Hz, 2 H), 6.92 (d, J = 8.7 Hz, 2 H), 6.95-7.06 (m, 3 H), 7.33 (dd, J = 8.9 et 2.6 Hz, 1 H), 9.02 (s, 1 H) | 496 |
| 5 | 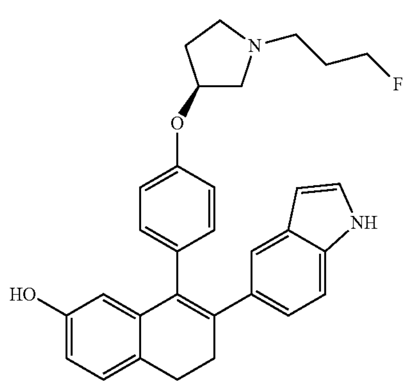 [SMILES: Oc1ccc2c(c1)C(c1ccc(O[C@H]3CCN(CCCF)C3)cc1)=C(c1ccc3[nH]ccc3c1)CC2] | 8-[4-[(3S)-1-(3-fluoropropyl)pyrrolidin-3-yl]oxyphenyl]-7-(1H-indol-5-yl)-5,6-dihydronaphthalen-2-ol | A | 1H NMR (400 MHz, DMSO-d6) δ ppm: 1.78 (m, 3 H), 2.23 (m, 1 H), 2.39 (m, 1 H), 2.46 (m, 2 H), 2.57 (dd, J = 10.4 et 2.4 Hz, 1 H), 2.69 (m, 3 H), 2.80 (m, 3 H), 4.47 (dt, J = 47.4 et 6.0 Hz, 2 H), 4.78 (m, 1 H), 6.12 (d, J = 2.3 Hz, 1 H), 6.24 (s, 1 H), 6.50 (dd, J = 8.0 et 2.4 Hz, 1 H), 6.72 (d, J = 8.6 Hz, 3 H), 6.90 (d, J = 8.6 Hz, 2 H), 7.00 (d, J = 8.1 Hz, 1 H), 7.08 (d, J = 8.4 Hz, 1 H), 7.23 (m, 2 H), 8.91 (s, 1 H), 10.91 (s, 1 H) | 483 |

TABLE 1-continued

| Example | Structure | Name | Method | NMR | MASS LC/MS (m/z, MH+) |
|---|---|---|---|---|---|
| 6 | 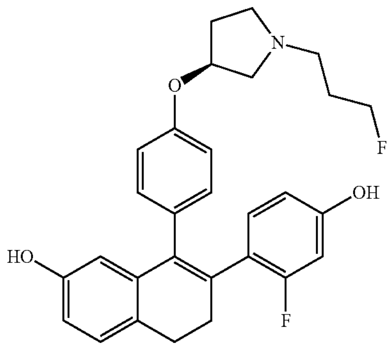 [SMILES: Oc1ccc(C2=C(c3ccc(O[C@H]4CCN(CCCF)C4)cc3)c3cc(O)ccc3CC2)c(F)c1] | 7-(2-fluoro-4-hydroxy-phenyl)-8-[4-[(3S)-1-(3-fluoropropyl)pyr-rolidin-3-yl]oxyphenyl]-5,6-dihydronaphtha-len-2-ol | A | 1H NMR (400 MHz, DMSO-d6) δ ppm: 1.78 (m, 3 H), 2.23 (m, 1 H), 2.40 (m, 1 H), 2.45 (m, 2 H), 2.58 (dd, J = 10.3 et 2.4 Hz, 1 H), 2.67 (m, 3 H), 2.76 (m, 2 H), 2.83 (dd, J = 10.3 et 6.1 Hz, 1 H), 4.48 (dt, J = 47.2 et 6.4 Hz, 2 H), 4.79 (m, 1 H), 6.13 (d, J = 2.4 Hz, 1 H), 6.36 (m, 2 H), 6.53 (dd, J = 8.0 et 2.4 Hz, 1 H), 6.74 (m, 3 H), 6.87 (d, J = 8.4 Hz, 2 H), 7.01 (d, J = 8.1 Hz, 1 H), 8.98 (s, 1 H), 9.69 (s, 1 H) | 478 |
| 7 | 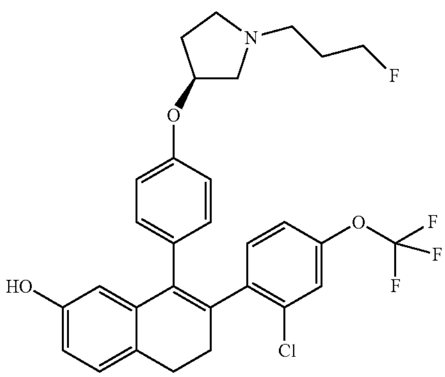 [SMILES: Oc1ccc2c(c1)C(c1ccc(O[C@H]3CCN(CCCF)C3)cc1)=C(c1ccc(OC(F)(F)F)cc1Cl)CC2] | 7-[2-chloro-4-(trifluoromethoxy)phenyl]-8-[4-[(3S)-1-(3-fluoropropyl)pyr-rolidin-3-yl]oxyphenyl]-5,6-dihydronaphtha-len-2-ol | A | 1H NMR (400 MHz, DMSO-d6) δ ppm: 1.77 (m, 3 H), 2.21 (m, 1 H), 2.40 (m, 1 H), 2.48 (m, 2 H), 2.54 (m, 1 H), 2.64 (m, 2 H), 2.85 (m, 2 H), 4.47 (dt, J = 47.4 et 6.0 Hz, 2 H), 4.77 (m, 1 H), 6.18 (d, J = 2.4 Hz, 1 H), 6.58 (dd, J = 8.0, 2.4 Hz, 1 H), 6.73 (d, J = 8.8 Hz, 2 H), 6.91 (d, J = 8.8 Hz, 2 H), 7.04 (d, J = 8.0 Hz, 1 H), 7.18 (m, 2 H), 7.44 (s, 1 H), 9.04 (s, 1 H) | 562 |
| 8 | 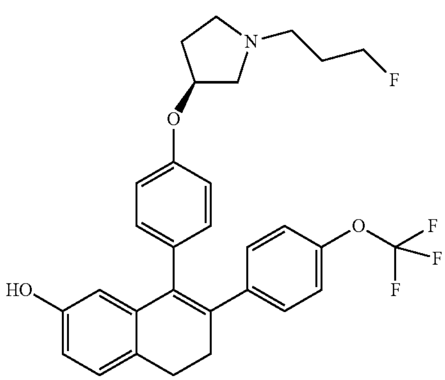 [SMILES: Oc1ccc2c(c1)C(c1ccc(O[C@H]3CCN(CCCF)C3)cc1)=C(c1ccc(OC(F)(F)F)cc1)CC2] | 8-[4-[(3S)-1-(3-fluoropropyl)pyr-rolidin-3-yl]oxyphenyl]-7-[4-(trifluoromethoxy)phenyl]-5,6-dihydronaphtha-len-2-ol | A | 1H NMR (400 MHz, DMSO-d6) δ ppm: 1.81 (m, 3 H), 2.22 (m, 1 H), 2.40 (m, 1 H), 2.48 (m, 2 H), 2.60 (dd, J = 10.3 et 2.6 Hz, 1 H), 2.68 (m, 3 H), 2.82 (m, 3 H), 4.48 (dt, J = 47.4 et 6.0 Hz, 2 H), 4.81 (m, 1 H), 6.14 (d, J = 2.4 Hz, 1 H), 6.55 (dd, J = 8.0, 2.4 Hz, 1 H), 6.78 (d, J = 8.7 Hz, 2 H), 6.89 (d, J = 8.7 Hz, 2 H), 7.03 (d, J = 8.1 Hz, 1 H), 7.11 (s, 4 H), 8.99 (s, 1 H) | 528 |
| 9 | 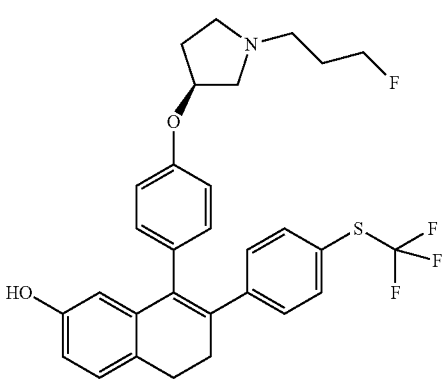 [SMILES: Oc1ccc2c(c1)C(c1ccc(O[C@H]3CCN(CCCF)C3)cc1)=C(c1ccc(SC(F)(F)F)cc1)CC2] | 8-[4-[(3S)-1-(3-fluoropropyl)pyr-rolidin-3-yl]oxyphenyl]-7-[4-(trifluoromethyl-sulfanyl)phenyl]-5,6-dihydronaphtha-len-2-ol | A | 1H NMR (400 MHz, DMSO-d6) δ ppm: 1.79(m, 3 H), 2.24 (m, 1 H), 2.41 (m, 1 H), 2.50 (m, 2 H), 2.57 (m, 1 H), 2.69 (m, 3 H), 2.79 (m, 3 H), 4.48 (dt, J = 47.5 et 6.0 Hz, 2 H), 4.81 (m, 1 H), 6.15 (d, J = 2.4 Hz, 1 H), 6.57 (dd, J = 8.0 et 2.4 Hz, 1 H), 6.77 (d, J = 8.6 Hz, 2 H), 6.88 (d, J = 8.6 Hz, 2 H), 7.04 (d, J = 8.1 Hz, 1 H), 7.14 (d, J = 8.3 Hz, 2 H), 7.46 (d, J = 8.3 Hz, 2 H), 9.01 (s, 1 H) | 544 |

TABLE 1-continued

| Example | Structure | Name | Method | NMR | MASS LC/MS (m/z, MH+) |
|---|---|---|---|---|---|
| 10 | 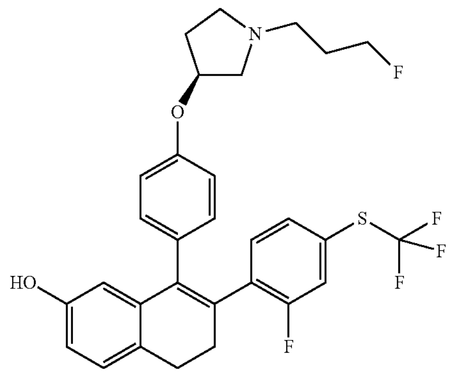 [SMILES: Oc1ccc2c(c1)C(c1ccc(O[C@H]3CCN(CCCF)C3)cc1)=C(c1ccc(SC(F)(F)F)cc1F)CC2] | 8-[4-[(3S)-1-(3-fluoropropyl)pyrrolidin-3-yl]oxyphenyl]-7-[2-fluoro-4-(trifluoromethoxy)phenyl]-5,6-dihydronaphthalen-2-ol | A | 1H NMR (400 MHz, DMSO-d6) δ ppm: 1.78(m, 3 H), 2.26 (m, 1 H), 2.40 (m, 1 H), 2.45-2.60 (m, 5 H), 2.65 (m, 1 H), 2.80 (m, 3 H), 4.48 (dt, J = 47.4 et 6.0 Hz, 2 H) 4.79 (m, 1 H), 6.17 (d, J = 2.0 Hz, 1 H), 6.57 (dd, J = 8.3 et 2.0 Hz, 1 H), 6.76 (d, J = 8.7 Hz, 2 H), 6.89 (d, J = 8.7 Hz, 2 H), 7.05 (m, 2 H), 7.17 (t, J = 8.3 Hz, 1 H), 7.22 (dd, J = 8.3 et 2.2 Hz, 1 H), 9.05 (s, 1 H) | 546 |
| 11 | 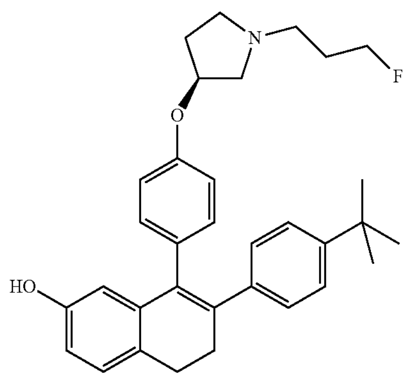 [SMILES: CC(C)(C)c1ccc(C2=C(c3ccc(O[C@H]4CCN(CCCF)C4)cc3)c3cc(O)ccc3CC2)cc1] | 7-(4-tert-butylphenyl)-8-[4-[(3S)-1-(3-fluoropropyl)pyrrolidin-3-yl]oxyphenyl]-5,6-dihydronaphthalen-2-ol | A | 1H NMR (400 MHz, DMSO-d6) δ ppm: 1.20 (s, 9 H), 1.79 (m, 3 H), 2.25 (m, 1 H), 2.39 (m, 3 H), 2.62 (m, 4 H), 2.79 (m, 3 H), 4.48 (dt, J = 47.5 et 6.0 Hz, 2 H), 4.82 (d, J = 6.8 Hz, 1 H), 6.10 (d, J = 2.4 Hz, 1 H), 6.52 (dd, J = 7.9 et 2.4 Hz, 1 H), 6.77 (d, J = 8.7 Hz, 2 H), 6.90 (m, 4 H), 7.02 (m, 1 H), 7.13 (d, J = 8.4 Hz, 2 H), 8.95 (s, 1 H) | 500 |
| 12 | 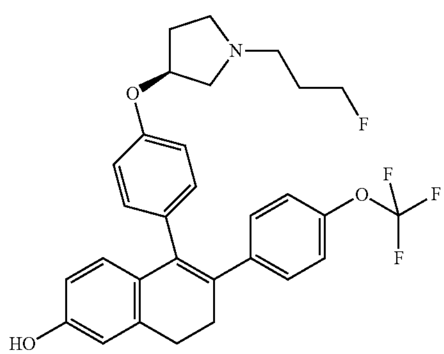 [SMILES: Oc1ccc2c(c1)CCC(c1ccc(OC(F)(F)F)cc1)=C2c1ccc(O[C@H]2CCN(CCCF)C2)cc1] | 5-[4-[(3S)-1-(3-fluoropropyl)pyrrolidin-3-yl]oxyphenyl]-6-[4-(trifluoromethoxy)phenyl]-7,8-dihydronaphthalen-2-ol | A | 1H NMR (400 MHz, DMSO-d6) δ ppm: 1.81 (m, 3 H), 2.22 (m, 1 H), 2.39 (m, 1 H), 2.47 (m, 2 H), 2.59 (dd, J = 10.2 et 2.6 Hz, 1 H), 2.68 (m, 3 H), 2.86 (m, 3 H), 4.48 (dt, J = 47.4 et 6.0 Hz, 2 H), 4.81 (m, 1 H), 6.47 (d, J = 0.9 Hz, 2 H), 6.65 (s, 1 H), 6.77 (d, J = 8.7 Hz, 2 H), 6.87 (d, J = 8.7 Hz, 2 H), 7.09 (s, 4 H), 9.44 (s, 1 H) | 528 |
| 13 | 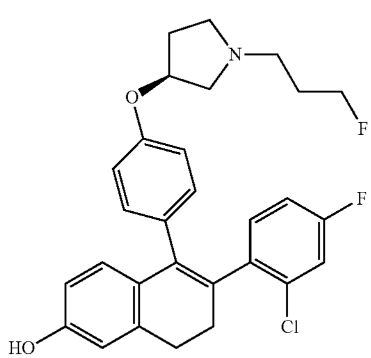 [SMILES: Oc1ccc2c(c1)CCC(c1ccc(F)cc1Cl)=C2c1ccc(O[C@H]2CCN(CCCF)C2)cc1] | 6-(2-chloro-4-fluoro-phenyl)-5-[4-[(3S)-1-(3-fluoropropyl)pyrrolidin-3-yl]oxyphenyl]-7,8-dihydronaphthalen-2-ol | A | 1H NMR (400 MHz, DMSO-d6) δ ppm: 1.78 (m, 3 H), 2.21 (m, 1 H), 2.38 (m, 1 H), 2.48 (t, J = 7.3 Hz, 2 H), 2.50-2.70 (m, 6 H), 2.77 (dd, J = 10.2 et 6.2 Hz, 1 H), 4.46 (dt, J = 47.4 et 6.0 Hz, 2 H), 4.73 (m, 1 H), 6.58 (d, J = 7.8 Hz, 2 H), 6.70 (m, 4 H), 7.05 (d, J = 2.1 Hz, 1 H), 7.31 (d, J = 8.2 Hz, 2 H), 7.53 (d, J = 8.2 Hz, 2 H), 9.80 (m, 1 H) | 496 |

TABLE 1-continued

| Example | Structure | Name | Method | NMR | MASS LC/MS (m/z, MH+) |
|---|---|---|---|---|---|
| 14 | 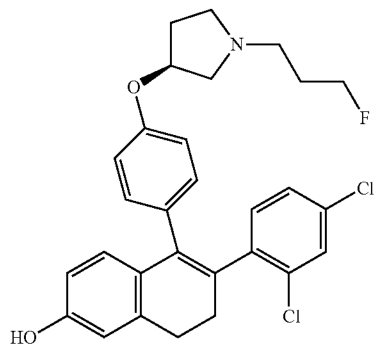 [SMILES: Oc1ccc2c(c1)CCC(c1ccc(Cl)cc1Cl)=C2c1ccc(O[C@H]2CCN(CCCF)C2)cc1] | 6-(2,4-dichlorophenyl)-5-[4-[(3S)-1-(3-fluoropropyl)pyrrolidin-3-yl]oxyphenyl]-7,8-dihydronaphthalen-2-ol | A | 1H NMR (400 MHz, DMSO-d6) δ ppm: 1.78 (m, 3 H), 2.22 (dq, J = 13.6 et 7.0 Hz, 1 H), 2.41 (m, 5 H), 2.62 (m, 2 H), 2.84 (m, 3 H), 4.47 (dt, J = 47.4 et 6.0 Hz, 2 H), 4.77 (d, J = 6.8 Hz, 1 H), 6.49 (s, 2 H), 6.66 (s, 1 H), 6.71 (d, J = 8.7 Hz, 2 H), 6.89 (m, 2 H), 7.04 (d, J = 7.5 Hz, 1 H), 7.17 (d, J = 8.2 Hz, 1 H), 7.50 (d, J = 2.0 Hz, 1 H), 9.46 (s, 1 H) | 512 |
| 15 | 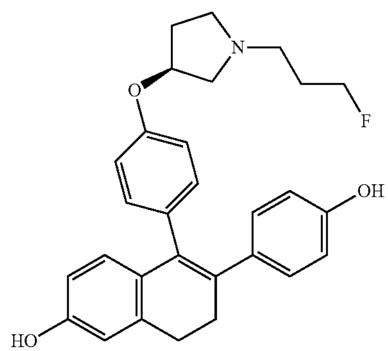 [SMILES: Oc1ccc(C2=C(c3ccc(O[C@H]4CCN(CCCF)C4)cc3)c3ccc(O)cc3CC2)cc1] | 5-[4-[(3S)-1-(3-fluoropropyl)pyrrolidin-3-yl]oxyphenyl]-6-(4-hydroxyphenyl)-7,8-dihydronaphthalen-2-ol | A | 1H NMR (400 MHz, DMSO-d6) δ ppm: 1.80 (m, 3 H), 2.24 (m, 1 H), 2.41 (m, 1 H), 2.46 (m, 2 H), 2.61 (m, 3 H), 2.68 (m, 1 H), 2.81 (m, 3 H), 4.49 (dt, J = 47.4 et 6.4 Hz, 2 H), 4.81 (m, 1 H), 6.43 (m, 2 H), 6.48 (d, J = 8.8 Hz, 2 H), 6.62 (d, J = 1.2 Hz, 1 H), 6.77 (m, 4 H), 6.86 (d, J = 8.8 Hz, 2 H), 9.17 (s, 1 H), 9.32 (s, 1 H) | 460 |
| 16 | 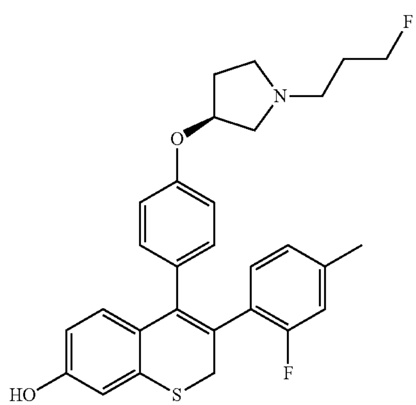 [SMILES: Cc1ccc(C2=C(c3ccc(O[C@H]4CCN(CCCF)C4)cc3)c3ccc(O)cc3SC2)c(F)c1] | 3-(2-fluoro-4-methyl-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.80 (m, 3 H), 2.21 (m, 4 H), 2.37 (m, 1 H), 2.45 (m, 2 H), 2.56 (d, J = 10.8 Hz, 2 H), 2.68 (m, 1 H), 2.80 (dd, J = 10.1 et 6.2 Hz, 1 H), 3.61 (s, 2 H), 4.47 (dt, J = 47.4 et 6.0 Hz, 2 H), 4.77 (m, 1 H), 6.48 (d, J = 7.0 et 1.5 Hz, 1 H), 6.56 (d, J = 7.0 Hz, 1 H), 6.74 (m, 6 H), 6.89 (d, J = 11.1 Hz, 1 H), 9.79 (d, J = 1.6 Hz, 1 H) | 494 |
| 17 | 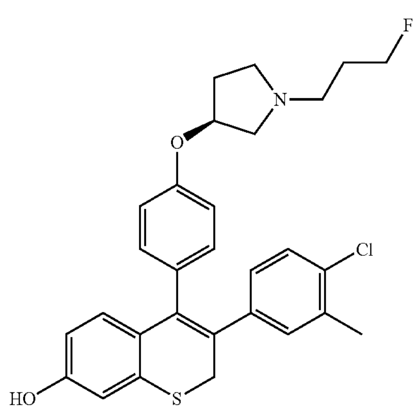 [SMILES: Cc1cc(C2=C(c3ccc(O[C@H]4CCN(CCCF)C4)cc3)c3ccc(O)cc3SC2)ccc1Cl] | 3-(4-chloro-3-methyl-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.76 (m, 3 H), 2.19 (s, 3 H), 2.21 (m, 1 H), 2.37 (m, 1 H), 2.44 (m, 2 H), 2.56 (m, 1 H), 2.66 (m, 2 H), 2.79 (dd, J = 10.3 et 6.2 Hz, 1 H), 3.56 (m, 2 H), 4.47 (dt, J = 47.4 et 6.0 Hz, 2 H), 4.75 (m, 1 H), 6.47 (dd, J = 8.6 et 2.4 Hz, 1 H), 6.56 (d, J = 8.6 Hz, 1 H), 6.67 (d, J = 8.5 Hz, 2 H), 6.77 (d, J = 2.4 Hz, 1 H), 6.81 (d, J = 8.5 Hz, 2 H), 6.98 (dd, J = 8.2 et 2.9 Hz, 1 H), 7.03 (m, 1 H), 7.17 (s, 1 H), 9.77 (s, 1 H) | 510 |

TABLE 1-continued

| Example | Structure | Name | Method | NMR | MASS LC/MS (m/z, MH+) |
|---|---|---|---|---|---|
| 18 | 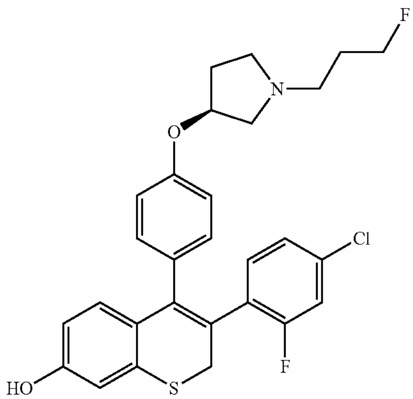 [SMILES: Oc1ccc2c(c1)SCC(c1ccc(Cl)cc1F)=C2c1ccc(O[C@H]2CCN(CCCF)C2)cc1] | 3-(4-chloro-2-fluoro-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.78 (m, 3 H), 2.22 (m, 1 H), 2.38 (q, J = 7.7 Hz, 1 H), 2.47 (m, 2 H), 2.57 (dd, J = 10.4 et 2.6 Hz, 1 H), 2.67 (m, 1 H), 2.80 (dd, J = 10.4 et 6.2 Hz, 1 H), 3.65 (s, 2 H), 4.48 (dt, J = 47.4 et 5.9 Hz, 2 H), 4.79 (m, 1 H), 6.49 (dd, J = 8.6 et 2.4 Hz, 1 H), 6.57 (d, J = 8.6 Hz, 1 H), 6.72 (d, J = 8.8 Hz, 2 H), 6.77 (d, J = 2.4 Hz, 1 H), 6.82 (m, 2 H), 6.99 (t, J = 8.1 Hz, 1 H), 7.05 (m, 1 H), 7.30 (dd, J = 9.8 et 2.0 Hz, 1 H), 9.85 (s, 1 H) | 514 |
| 19 | 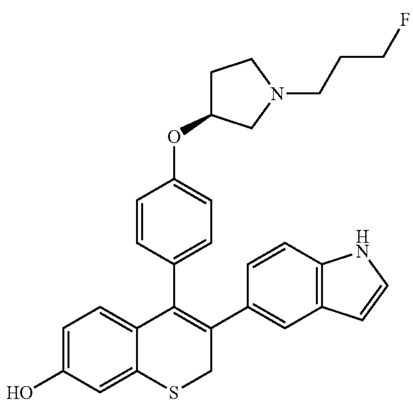 [SMILES: Oc1ccc2c(c1)SCC(c1ccc3[nH]ccc3c1)=C2c1ccc(O[C@H]2CCN(CCCF)C2)cc1] | 4-[4-[(3S)-1-(3-fluoropropyl)pyrrolidin-3-yl]oxyphenyl]-3-(1H-indol-5-yl)-2H-thiochromen-7-ol | A | 1H NMR (400 MHz, DMSO-d6) δ ppm: 1.74 (m, 3 H), 2.20 (m, 1 H), 2.38 (m, 1 H), 2.45 (m, 2 H), 2.55 (dd, J = 10.5 et 2.6 Hz, 1 H), 2.66 (m, 1 H), 2.78 (dd, J = 10.3 et 6.2 Hz, 1 H), 3.78 (s, 2 H), 4.47 (dt, J = 47.4 et 6.0 Hz, 2 H), 4.76 (m, 1 H), 6.26 (s, 1 H), 6.45 (dd, J = 8.6 et 2.5 Hz, 1 H), 6.55 (m, 1 H), 6.67 (d, J = 8.6 Hz, 2 H), 6.72 (dd, J = 8.5 et 1.5 Hz, 1 H), 6.75 (d, J = 2.4 Hz, 1 H), 6.84 (d, J = 8.6 Hz, 2 H), 7.09 (d, J = 8.6 Hz, 1 H), 7.24 (t, J = 2.7 Hz, 1 H), 7.27 (s, 1 H), 9.68 (s, 1 H), 10.96 (s, 1 H) | 501 |
| 20 | 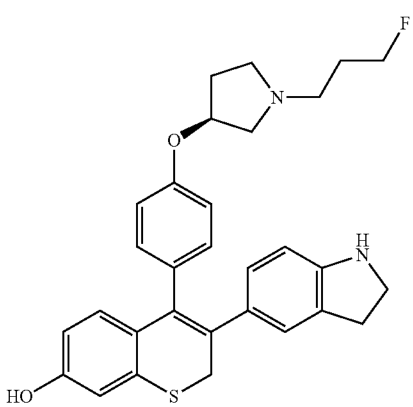 [SMILES: Oc1ccc2c(c1)SCC(c1ccc3c(c1)CCN3)=C2c1ccc(O[C@H]2CCN(CCCF)C2)cc1] | 4-[4-[(3S)-1-(3-fluoropropyl)pyrrolidin-3-yl]oxyphenyl]-3-indolin-5-yl-2H-thiochromen-7-ol | A | 1H NMR (400 MHz, DMSO-d6) δ ppm: 1.78 (m, 3 H), 2.24 (m, 1 H), 2.39 (m, 1 H), 2.47 (m, 2 H), 2.59 (dd, J = 10.3 et 2.5 Hz, 1 H), 2.66 (m, 1 H), 2.73 (t, J = 8.6 Hz, 2 H), 2.82 (dd, J = 10.3 et 6.2 Hz, 1 H), 3.33 (m, 2 H), 3.67 (s, 2 H), 4.48 (dt, J = 47.4 et 6.0 Hz, 2 H), 4.80 (m, 1 H), 5.45 (s, 1 H), 6.19 (d, J = 8.1 Hz, 1 H), 6.43 (dd, J = 8.6 et 2.5 Hz, 1 H), 6.54 (m, 2 H), 6.74 (m, 4 H), 6.85 (d, J = 8 Hz, 2 H), 9.64 (s, 1 H) | 503 |

TABLE 1-continued

| Example | Structure | Name | Method | NMR | MASS LC/MS (m/z, MH+) |
|---|---|---|---|---|---|
| 21 | 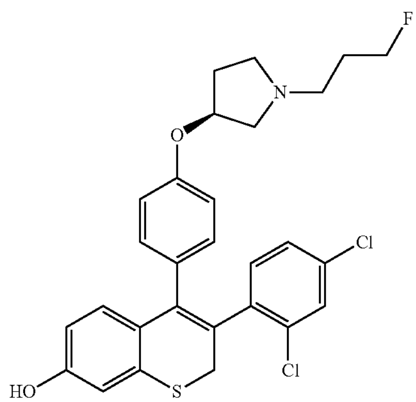 | 3-(2,4-dichlorophenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.75 (m, 3 H), 2.21 (m, 1 H), 2.37 (m, 1 H), 2.45 (m, 2 H), 2.55 (m, 1 H), 2.67 (m, 1 H), 2.78 (m, 1 H), 3.44 (dd, J = 14.6 et 1.8 Hz, 1 H), 3.79 (dd, J = 14.5 et 2.3 Hz, 1 H), 4.47 (dt, J = 47.6 et 5.9 Hz, 2 H), 4.76 (m, 1 H), 6.49 (dd, J = 8.6 et 2.4 Hz, 1 H), 6.58 (d, J = 8.6 Hz, 1 H), 6.71 (d, J = 8.3 Hz, 2 H), 6.77 (d, J = 2.4 Hz, 1 H), 6.83 (d, J = 7.8 Hz, 2 H), 6.99 (dd, J = 8.3 et 2.7 Hz, 1 H), 7.16 (dt, J = 8.3 et 1.7 Hz, 1 H), 7.56 (d, J = 1.7 Hz, 1 H), 9.87 (s, 1 H) | 530 |
| 22 | 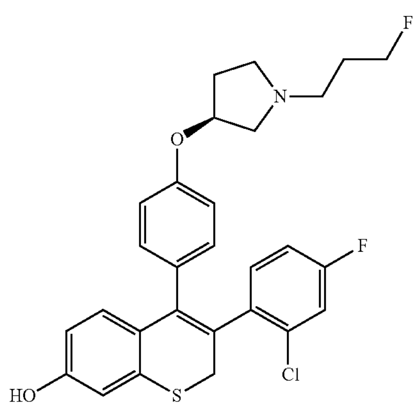 | 3-(2-chloro-4-fluoro-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.75 (m, 3 H), 2.21 (m, 1 H), 2.38 (m, 1 H), 2.45 (m, 2 H), 2.57 (m, 1 H), 2.67 (m, 1 H), 2.78 (m, 1 H), 3.44 (d, J = 14.7 Hz, 1 H), 3.79 (d, J = 14.9 Hz, 1 H), 4.47 (dt, J = 47.5 et 6.0 Hz, 2 H), 4.76 (m, 1 H), 6.49 (dd, J = 8.6, 2.4 Hz, 1 H), 6.58 (d, J = 8.6 Hz, 1 H), 6.70 (d, J = 8.4 Hz, 2 H), 6.77 (d, J = 2.4 Hz, 1 H), 6.83 (d, J = 7.8 Hz, 2 H), 6.99 (m, 2 H), 7.39 (dd, J = 8.8 et 2.4 Hz, 1 H), 9.84 (s, 1 H) | 514 |
| 23 | 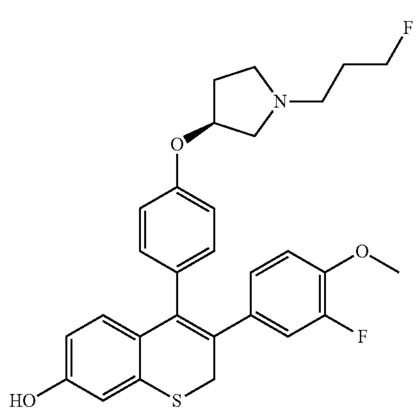 [SMILES: COc1ccc(C2=C(c3ccc(O[C@H]4CCN(CCCF)C4)cc3)c3ccc(O)cc3SC2)cc1F] | 3-(3-fluoro-4-methoxy-phenyl)-4-[4-[(3S)-1-(3-fluoropropyl)pyrrolidin-3-yl]oxyphenyl]-2H-thiochromen-7-ol | A | 1H NMR (500 MHz, DMSO-d6) δ ppm: 1.00 (s, 9 H), 1.80 (m, 3 H), 2.23 (m, 1 H), 2.38-2.50 (m, 3 H), 2.57 (dd, J = 10.3 et 2.3 Hz, 1 H), 2.66 (m, 1 H), 2.83 (dd, J = 10.2 et 6.1 Hz, 1 H), 3.83 (s, 2 H), 4.48 (dt, J = 47.4 et 6.0 Hz, 2 H), 4.82 (m, J = 6.7, 6.7 Hz, 1 H), 6.49 (dd, J = 8.6 et 2.1 Hz, 1 H), 6.57 (s, 1 H), 6.62 (d, J = 8.6 Hz, 1 H), 6.76 (m, 4 H), 6.86 (m, 2 H), 9.95 (s, 1 H) | 510 |

TABLE 1-continued

| Example | Structure | Name | Method | NMR | MASS LC/MS (m/z, MH+) |
|---|---|---|---|---|---|
| 24 | 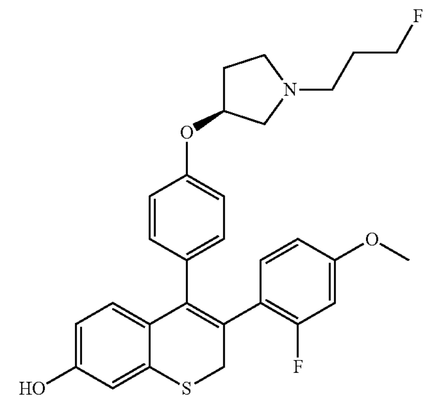 [SMILES: COc1ccc(C2=C(c3ccc(O[C@H]4CCN(CCCF)C4)cc3)c3ccc(O)cc3SC2)c(F)c1] | 3-(2-fluoro-4-methoxy-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.77 (m, 3 H), 2.22 (dd, J = 13.4 et 6.3 Hz, 1 H), 2.40 (m, 3 H), 2.56 (d, J = 10.4 Hz, 1 H), 2.67 (m, 1 H), 2.80 (dd, J = 10.3 et 6.2 Hz, 1 H), 3.60 (s, 2 H), 3.69 (s, 3 H), 4.48 (dt, J = 47.4 et 5.9 Hz, 2 H), 4.78 (s, 1 H), 6.51 (m, 3 H), 6.77 (m, 7 H), 9.80 (s, 1H) | 510 |
| 25 | 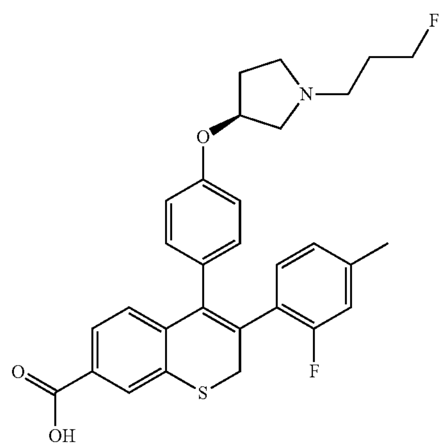 [SMILES: Cc1ccc(C2=C(c3ccc(O[C@H]4CCN(CCCF)C4)cc3)c3ccc(C(=O)O)cc3SC2)c(F)c1] | 3-(2-fluoro-4-methyl-phenyl)-4-[4-[(3S)-1-(3-fluoropropyl)pyrrolidin-3-yl]oxyphenyl]-2H-thiochromene-7-carboxylic acid | | 1H NMR (400 MHz, DMSO-d6) δ ppm: 1.78 (m, 3 H), 2.22 (m, 4 H), 2.39 (m, 1 H), 2.46 (m, 2 H), 2.58 (dd, J = 10.3 et 2.2 Hz, 1 H), 2.67 (d, J = 5.9 Hz, 1 H), 2.81 (dd, J = 10.3 et 6.1 Hz, 1 H), 3.68 (s, 2 H), 4.48 (dt, J = 47.4 et 6.1 Hz, 2 H), 4.78 (m, 1 H), 6.72 (d, J = 8,3 Hz, 2 H), 6.78 (m, 2 H), 6.88 (m, 4 H), 7.57 (dd, J = 8.1 et 1.2 Hz, 1 H), 7.90 (s, 1 H) | 522 |
| 26 | 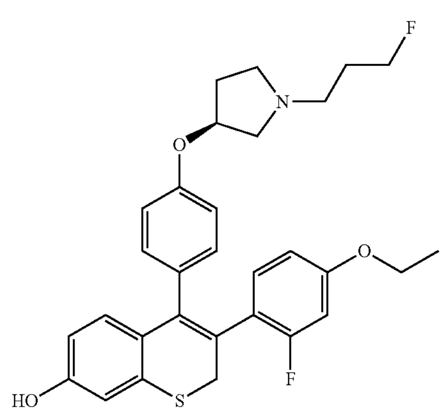 [SMILES: CCOc1ccc(C2=C(c3ccc(O[C@H]4CCN(CCCF)C4)cc3)c3ccc(O)cc3SC2)c(F)c1] | 3-(4-ethoxy-2-fluoro-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.26 (t, J = 6.8 Hz, 3 H), 1.77 (m, 3 H), 2.22 (m, 1 H), 2.39 (q, J = 7.7 Hz, 1 H), 2.46 (m, J = 2.0 Hz, 2 H), 2.57 (dd, J = 10.3 et 2.7 Hz, 1 H), 2.67 (s, 1 H), 2.81 (dd, J = 10.3 et 6.1 Hz, 1 H), 3.60 (s, 2 H), 3.94 (q, J = 6.8 Hz, 2 H), 4.47 (dd, J = 47.4 et 6.1 Hz, 2 H), 4.78 (m, 1 H), 6.48 (m, 2 H), 6.55 (d, J = 8.8 Hz, 1 H), 6.69 (m, 3 H), 6.76 (d, J = 2.4 Hz, 1 H), 6.81 (m, 3 H), 9.77 (s, 1 H) | 524 |

TABLE 1-continued

| Example | Structure | Name | Method | NMR | MASS LC/MS (m/z, MH+) |
|---|---|---|---|---|---|
| 27 | 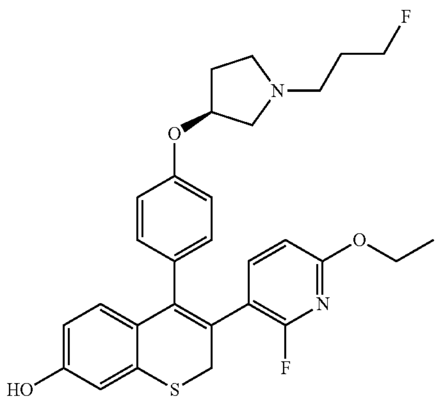 [SMILES: CCOc1ccc(C2=C(c3ccc(O[C@H]4CCN(CCCF)C4)cc3)c3ccc(O)cc3SC2)c(F)n1] | 3-(6-ethoxy-2-fluoro-3-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.26 (t, J = 7.1 Hz, 3 H), 1.78 (m, 3 H), 2.22 (m, 1 H), 2.39 (m, 1 H), 2.46 (m, 2 H), 2.57 (dd, J = 10.4 et 2.6 Hz, 1 H), 2.67 (m, 1 H), 2.81 (dd, J = 10.4 et 6.2 Hz, 1 H), 3.64 (s, 2 H), 4.17 (q, J = 7.1 Hz, 2 H), 4.48 (dt, J = 47.4 et 6.1 Hz, 2 H), 4.79 (m, 1 H), 6.48 (m, 2 H), 6.56 (d, J = 8.8 Hz, 1 H), 6.75 (m, 3 H), 6.83 (d, J = 8.6 Hz, 2 H), 7.33 (dd, J = 9.9 et 8.2 Hz, 1 H), 9.82 (s, 1 H) | 525 |
| 28 | 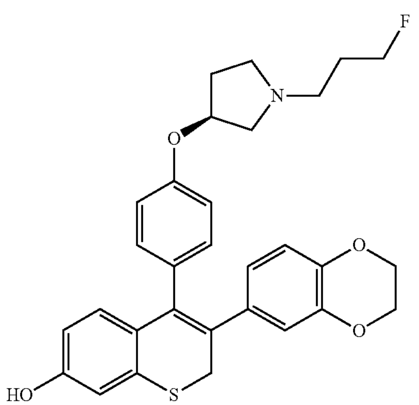 [SMILES: Oc1ccc2c(c1)SCC(c1ccc3c(c1)OCCO3)=C2c1ccc(O[C@H]2CCN(CCCF)C2)cc1] | 3-(2,3-dihydro-1,4-benzodioxin-6-yl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.80 (m, 3 H), 2.23 (m, 1 H), 2.40 (m, 1 H), 2.47 (m, 2 H), 2.60 (dd, J = 10.4 et 2.6 Hz, 1 H), 2.69 (m, 1 H), 2.82 (dd, J = 10.4 et 6.0 Hz, 1 H), 3.68 (s, 2 H), 4.14 (m, 4 H), 4.48 (dt, J = 47.7 et 5.9 Hz, 2 H), 4.80 (m, 1 H), 6.43 (m, 2 H), 6.54 (m, 3 H), 6.74 (m, 3 H), 6.83 (d, J = 8.8 Hz, 2 H), 9.71 (s, 1 H) | 520 |
| 29 | 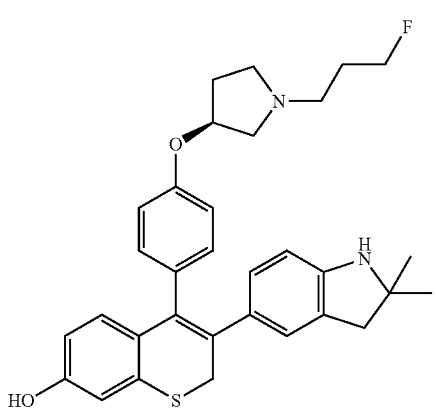 [SMILES: CC1(C)Cc2cc(C3=C(c4ccc(O[C@H]5CCN(CCCF)C5)cc4)c4ccc(O)cc4SC3)ccc2N1] | 3-(2,2-dimethylindolin-5-yl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.15 (s, 6 H), 1.79 (m, 3 H), 2.22 (m, 1 H), 2.41 (m, 1 H), 2.49 (m, 4 H), 2.57 (m, 1 H), 2.68 (m, 1 H), 2.82 (dd, J = 10.3 et 6.1 Hz, 1.0H), 3.67 (s, 2 H), 4.48 (dt, J = 47.4 et 6.0 Hz, 2 H), 4.81 (m, J = 6.8 Hz, 1 H), 5.44 (s, 1 H), 6.13 (d, J = 8.1 Hz, 1 H), 6.42 (dd, J = 8.6 et 2.4 Hz, 1 H), 6.53 (m, 1 H), 6.58 (d, J = 8.1 Hz, 1 H), 6.62 (s, 1 H), 6.72 (m, 3 H), 6.81 (d, J = 8 Hz, 2 H), 9.63 (s, 1 H) | 531 |

TABLE 1-continued

| Example | Structure | Name | Method | NMR | MASS LC/MS (m/z, MH+) |
|---|---|---|---|---|---|
| 30 | 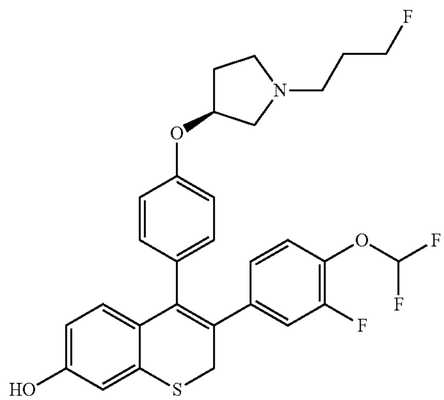 [SMILES: Oc1ccc2c(c1)SCC(c1ccc(OC(F)F)c(F)c1)=C2c1ccc(O[C@H]2CCN(CCCF)C2)cc1] | 3-[4-(difluoromethoxy)-3-fluoro-phenyl]-4-[4-[(3S)-1-(3-fluoropropyl)pyr-rolidin-3-yl]oxyphenyl]-2H-thiochromen-7-ol | A | 1H NMR (400 MHz, DMSO-d6) δ ppm: 1.78 (m, 3 H), 2.23 (m, 1 H), 2.40 (m, 1 H), 2.46 (m, 2 H), 2.59 (dd, J = 10.4 et 2.6 Hz, 1 H), 2.67 (m, 1 H), 2.81 (dd, J = 10.3 et 6.1 Hz, 1 H), 3.75 (s, 2 H), 4.48 (dt, J = 47.7 et 6.1 Hz, 2 H), 4.81 (m, 1 H), 6.47 (dd, J = 8.6 et 2.4 Hz, 1 H), 6.56 (d, J = 8.6 Hz, 1 H), 6.76 (m, 3 H), 6.85 (m, 3 H), 6.99 (m, 1 H), 7.13 (t, J = 8.6 Hz, 1 H), 7.17 (t, J = 73.1 Hz, 1 H), 9.84 (s, 1 H) | 546 |
| 31 | 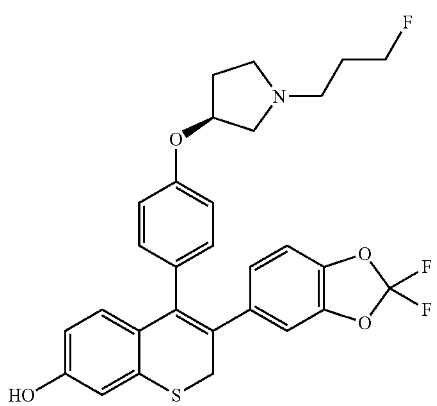 [SMILES: Oc1ccc2c(c1)SCC(c1ccc3c(c1)OC(F)(F)O3)=C2c1ccc(O[C@H]2CCN(CCCF)C2)cc1] | 3-(2,2-difluoro-1,3-benzodioxol-5-yl)-4-[4-[(3S)-1-(3-fluoropropyl)pyr-rolidin-3-yl]oxyphenyl]-2H-thiochromen-7-ol | A | 1H NMR (400 MHz, DMSO-d6) δ ppm: 1.78 (m, 3 H), 2.22 (m, 1 H), 2.40 (m, 1 H), 2.49 (t, J = 7.0 Hz, 2 H), 2.58 (dd, J = 10.3 et 2.5 Hz, 1 H), 2.68 (m, 1 H), 2.81 (dd, J = 10.3 et 6.2 Hz, 1 H), 3.75 (s, 2 H), 4.48 (dt, J = 47.4 et 6.0 Hz, 2 H), 4.81 (m, 1 H), 6.47 (dd, J = 8.6 et 2.4 Hz, 1 H), 6.56 (d, J = 8.6 Hz, 1 H), 6.76 (m, 3 H), 6.87 (m, 3 H), 7.04 (d, J = 1.5 Hz, 1 H), 7.17 (d, J = 8.3 Hz, 1 H), 9.83 (s, 1 H) | 542 |
| 32 | 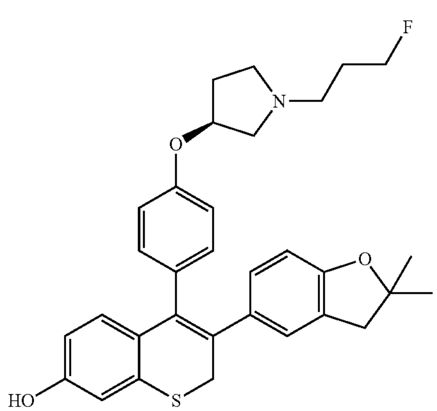 [SMILES: CC1(C)Cc2cc(C3=C(c4ccc(O[C@H]5CCN(CCCF)C5)cc4)c4ccc(O)cc4SC3)ccc2O1] | 3-(2,2-dimethyl-3H-benzofuran-5-yl)-4-[4-[(3S)-1-(3-fluoropropyl)pyr-rolidin-3-yl]oxyphenyl]-2H-thiochromen-7-ol | A | 1H NMR (400 MHz, DMSO-d6) δ ppm: 1.34 (s, 6 H), 1.78 (m, 3 H), 2.22 (m, 1 H), 2.41 (m, 1 H), 2.50 (t, J = 7.0 Hz, 2H), 2.58 (d, J = 10.3 Hz, 1 H), 2.69 (m, 1 H), 2.82 (m, 3 H), 3.70 (s, 2 H), 4.48 (dt, J = 47.4 et 6.0 Hz, 2 H), 4.81 (m, 1 H), 6.43 (m, 2 H), 6.53 (d, J = 8.0 Hz, 1 H), 6.74 (m, 4 H), 6.81 (m, 3 H), 9.71 (s, 1H) | 532 |

TABLE 1-continued

| Example | Structure | Name | Method | NMR | MASS LC/MS (m/z, MH+) |
|---|---|---|---|---|---|
| 33 | 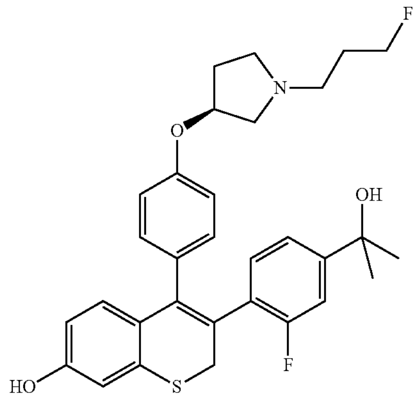 [SMILES: CC(C)(O)c1ccc(C2=C(c3ccc(O[C@H]4CCN(CCCF)C4)cc3)c3ccc(O)cc3SC2)c(F)c1] | 3-[2-fluoro-4-(1-hydroxy-1-methyl-ethyl)phenyl]-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.39 (s, 6 H), 1.78 (m, 3 H), 2.23 (m, 1 H), 2.39 (m, 1 H), 2.47 (m, 2 H), 2.59 (dd, J = 10.3 et 2.5 Hz, 1 H), 2.68 (m, 1 H), 2.81 (dd, J = 10.3, 6.1 Hz, 1 H), 3.74 (s, 2 H), 4.48 (dt, J = 47.4 et 6.0 Hz, 2 H), 4.82 (m, 1 H), 5.14 (s, 1 H), 6.46 (dd, J = 8.6 et 2.5 Hz, 1 H), 6.55 (d, J = 8.6 Hz, 1 H), 6.70 (dd, J = 13.5 et 1.4 Hz, 1 H), 6.75 (dd, J = 5.7 et 3.0 Hz, 3 H), 6.79 (dd, J = 8.2 et 1.6 Hz, 1 H), 6.82-6.91 (m, 2 H), 7.34 (t, J = 8.5 Hz, 1 H), 9.80 (s, 1 H) | 538 |
| 34 | 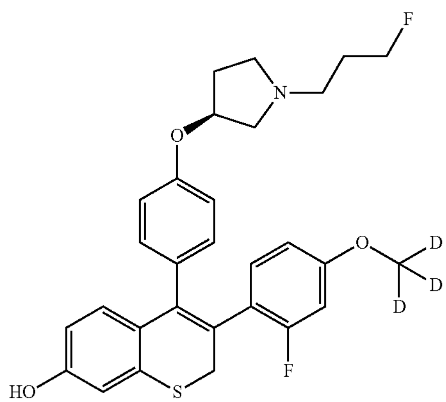 [SMILES: [2H]C([2H])([2H])Oc1ccc(C2=C(c3ccc(O[C@H]4CCN(CCCF)C4)cc3)c3ccc(O)cc3SC2)c(F)c1] | 4-[4-[(3S)-1-(3-fluoropropyl)pyrrolidin-3-yl]oxyphenyl]-3-[2-fluoro-4-(trideuteriomethoxy)phenyl]-2H-thiochromen-7-ol | A | 1H NMR (400 MHz, DMSO-d6) δ ppm: 1.78 (m, 3 H), 2.39 (m, 1 H), 2.49 (m, 2 H), 2.56 (m, 1 H), 2.66 (m, 1 H), 2.81 (dd, J = 10.2 et 6.2 Hz, 1 H), 3.60 (s, 2 H), 4.47 (dt, J = 47.4 et 6.0 Hz, 2 H), 4.77 (m, 1 H), 6.46 (m, 1 H), 6.51 (dd, J = 8.6 et 2.2 Hz, 1 H), 6.55 (m, 1 H), 6.70 (m, 3 H), 6.76 (d, J = 2.3 Hz, 1 H), 6.83 (m, 3 H), 9.78 (s, 1 H) | 513 |
| 35 | 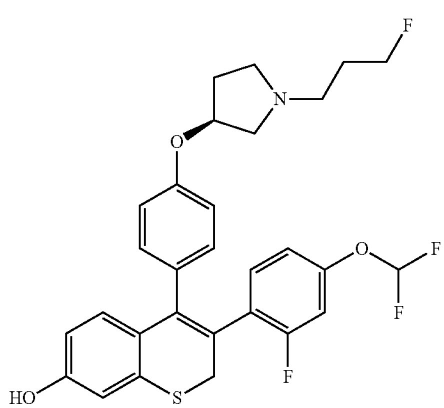 [SMILES: Oc1ccc2c(c1)SCC(c1ccc(OC(F)F)cc1F)=C2c1ccc(O[C@H]2CCN(CCCF)C2)cc1] | 3-[4-(difluoromethoxy)-2-fluoro-phenyl]-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.75 (m, 3 H), 2.21 (m, 1 H), 2.40 (m, 1 H), 2.49 (m, 1 H), 2.56 (dd, J = 10.3 et 2.8 Hz, 1 H), 2.67 (m, 1 H), 2.80 (dd, J = 10.3 et 6.2 Hz, 1 H), 3.64 (s, 2 H), 4.48 (dt, J = 47.4 et 6.0 Hz, 2 H), 4.80 (m, 1 H), 6.48 (dd, J = 8.7 et 2.0 Hz, 1 H), 6.58 (d, J = 8.7 Hz, 1 H), 6.71 (d, J = 8.7 Hz, 2 H), 6.83 (m, 4 H), 6.98 (m, 2 H), 7.25 (t, J = 74.0 Hz, 1 H), 9.88 (s, 1 H) | 546 |

TABLE 1-continued

| Example | Structure | Name | Method | NMR | MASS LC/MS (m/z, MH+) |
|---|---|---|---|---|---|
| 36 | 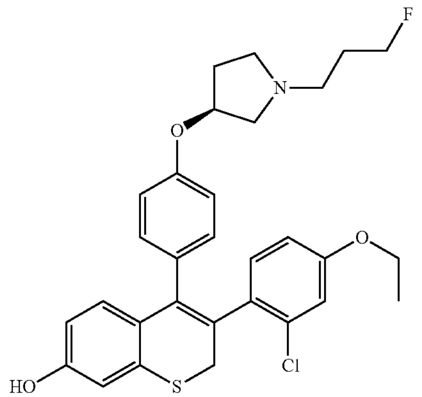 | 3-(2-chloro-4-ethoxy-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.26 (t, J = 7.0 Hz, 3 H), 1.76 (m, 3 H), 2.21 (m, 1 H), 2.38 (m, 1 H), 2.45 (d, J = 2.0 Hz, 2 H), 2.55 (m, 1 H), 2.64 (m, 1 H), 2.80 (m, 1 H), 3.37 (dd, J = 14.8 et 1.1 Hz, 1 H), 3.78 (dd, J = 14.5 et 1.8 Hz, 1 H), 3.95 (q, J = 6.8 Hz, 2 H), 4.47 (dt, J = 47.7 et 5.9 Hz, 2 H), 4.76 (m, 1 H), 6.47 (dd, J = 8.6 et 2.4 Hz, 1 H), 6.56 (d, J = 8.6 Hz, 1 H), 6.62 (dd, J = 8.6 et 2.2 Hz, 1 H), 6.69 (d, J = 8.6 Hz, 2 H), 6.76 (d, J = 2.4 Hz, 1 H), 6.84 (m, 3 H), 6.94 (d, J = 2.4 Hz, 1 H), 9.82 (s, 1 H) | 540 |
| 37 | 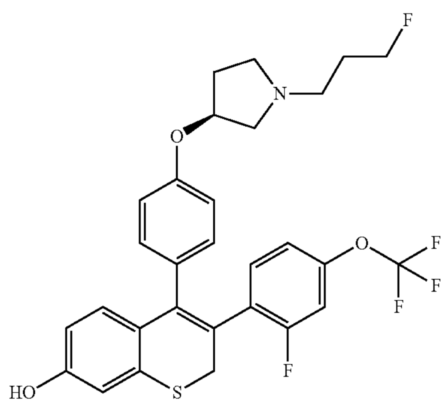 [SMILES: Oc1ccc2c(c1)SCC(c1ccc(OC(F)(F)F)cc1F)=C2c1ccc(O[C@H]2CCN(CCCF)C2)cc1] | 4-[4-[(3S)-1-(3-fluoropropyl)pyrrolidin-3-yl]oxyphenyl]-3-[2-fluoro-4-(trifluoromethoxy)phenyl]-2H-thiochromen-7-ol | A | 1H NMR (400 MHz, DMSO-d6) δ ppm: 1.77(m, 3 H), 2.21 (m, 1 H), 2.40 (m, 1 H), 2.48 (m, 2 H), 2.55 (dd, J = 10.4 et 2.4 Hz, 1 H), 2.67 (m, 1 H), 2.79 (dd, J = 10.3 et 6.1 Hz, 1 H), 3.67 (s, 2 H), 4.47 (dt, J = 47.4 et 6.0 Hz, 2 H), 4.77 (m, 1 H), 6.49 (dd, J = 8.6 et 2.4 Hz, 1 H), 6.60 (d, J = 8.6 Hz, 1 H), 6.71 (d, J = 8.7 Hz, 2 H), 6.78 (d, J = 2.4 Hz, 1 H), 6.82 (d, J = 8.7 Hz, 2 H), 7.00 (d, J = 8.9 Hz, 1 H), 7.10 (t, J = 8.9 Hz, 1 H), 7.24 (d, J = 10.0 Hz, 1 H), 9.85 (s, 1 H) | 564 |
| 38 | 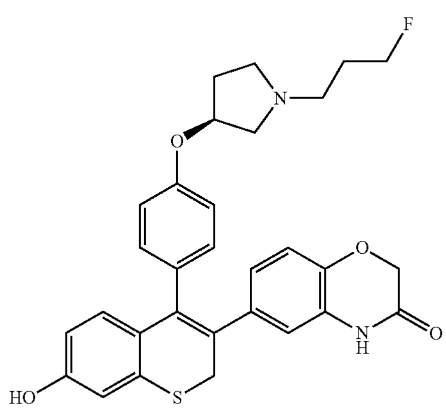 [SMILES: O=C1COc2ccc(C3=C(c4ccc(O[C@H]5CCN(CCCF)C5)cc4)c4ccc(O)cc4SC3)cc2N1] | 6-[4-[4-[(3S)-1-(3-fluoropropyl)pyrrolidin-3-yl]oxyphenyl]-7-hydroxy-2H-thiochromen-3-yl]-4H-1,4-benzoxazin-3-one | A | 1H NMR (400 MHz, DMSO-d6) δ ppm: 1.80 (m, 3 H), 2.22 (m, 1 H), 2.39 (m, 1 H), 2.46 (m, 2 H), 2.59 (dd, J = 10.3 et 2.5 Hz, 1 H), 2.67 (m, 1 H), 2.82 (dd, J = 10.3 et 6.2 Hz, 1 H), 3.68 (s, 2 H), 4.47 (dt, J = 47.4 et 6.0 Hz, 2 H), 4.49 (s, 2 H), 4.80 (m, 1 H), 6.44 (dd, J = 8.7 et 2.0 Hz, 1 H), 6.53 (m, 2 H), 6.59 (d, J = 2.0 Hz, 1 H), 6.69 (d, J = 8.3 Hz, 1 H), 6.75 (m, 3 H), 6.87 (d, J = 8.5 Hz, 2 H), 9.77 (s, 1 H), 10.54 (s, 1 H) | 533 |

TABLE 1-continued

| Example | Structure | Name | Method | NMR | MASS LC/MS (m/z, MH+) |
|---|---|---|---|---|---|
| 39 | 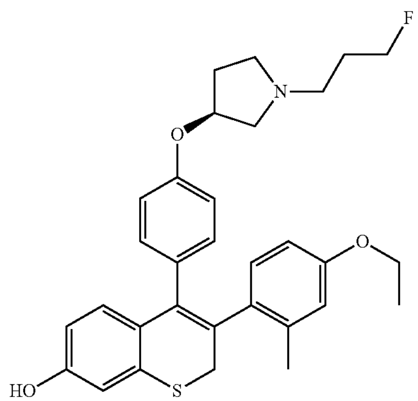 [SMILES: CCOc1ccc(C2=C(c3ccc(O[C@H]4CCN(CCCF)C4)cc3)c3ccc(O)cc3SC2)c(C)c1] | 3-(4-ethoxy-2-methyl-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.25 (t, J = 7.0 Hz, 3 H), 1.76 (m, 3 H), 2.13 (s, 3 H), 2.21 (m, 1 H), 2.38 (m, 1 H), 2.48 (m, 2 H), 2.55 (m, 1 H), 2.66 (m, 1 H), 2.80 (dd, J = 10.3 et 6.1 Hz, 1 H), 3.51 (m, 2 H), 3.90 (q, J = 6.9 Hz, 2 H), 4.47 (dt, J = 47.4 et 6.0 Hz, 2 H), 4.74 (m, 1 H), 6.46 (dd, J = 8.0 et 2.4 Hz, 1 H), 6.52 (m, 2 H), 6.66 (m, 3 H), 6.75 (d, J = 2.4 Hz, 1 H), 6.80 (d, J = 8.4 Hz, 2 H), 6.84 (dd, J = 8.3 et 2.1 Hz, 1 H), 9.71 (s, 1 H) | 520 |
| 40 | 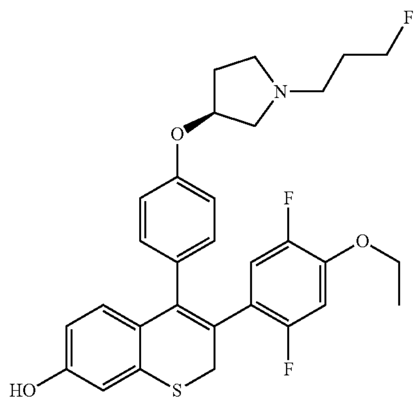 [SMILES: CCOc1cc(F)c(C2=C(c3ccc(O[C@H]4CCN(CCCF)C4)cc3)c3ccc(O)cc3SC2)cc1F] | 3-(4-ethoxy-2,5-difluoro-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.28 (t, J = 7.5 Hz, 3 H), 1.83 (m, 1 H), 2.22 (m, 1 H), 2.39 (m, 1 H), 2.48 (m, 2H), 2.57 (dd, J = 10.3 et 2.6 Hz, 1 H), 2.67 (m, 1 H), 2.81 (dd, J = 10.3 et 6.1 Hz, 1 H), 3.62 (s, 2 H), 4.03 (q, J = 6.9 Hz, 2 H), 4.47 (dt, J = 47.4 et 6.0 Hz, 2 H), 4.80 (m, 1 H), 6.47 (dd, J = 8.7 et 2.0 Hz, 1 H), 6.57 (d, J = 8.7 Hz, 1 H), 6.70-6.85 (m, 6 H), 6.95 (dd, J = 11.4 et 7.3 Hz, 1 H), 9.80 (s, 1 H) | 542 |
| 41 | 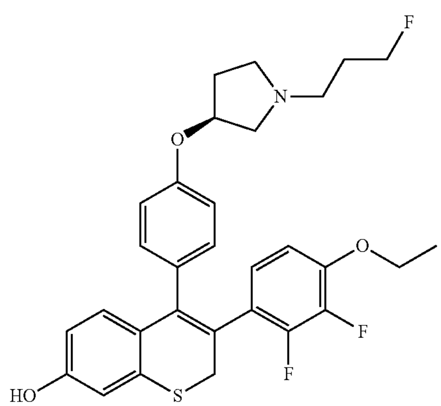 [SMILES: CCOc1ccc(C2=C(c3ccc(O[C@H]4CCN(CCCF)C4)cc3)c3ccc(O)cc3SC2)c(F)c1F] | 3-(4-ethoxy-2,3-difluoro-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.29 (t, J = 7.0 Hz, 3 H), 1.76 (m, 3 H), 2.22 (m, 1 H), 2.39 (m, 1 H), 2.46 (m, 2 H), 2.57 (dd, J = 10.3 et 2.4 Hz, 1 H), 2.67 (m, 1 H), 2.81 (dd, J = 10.3 et 6.1 Hz, 1 H), 3.64 (s, 2 H), 4.05 (q, J = 7.0 Hz, 2 H), 4.47 (dt, J = 47.4 et 6.0 Hz, 2 H), 4.79 (m, 1 H), 6.48 (dd, J = 8.6 Hz, 2.4 Hz, 1 H), 6.58 (d, J = 8.6 Hz, 1 H), 6.70-6.85 (m, 7 H), 9.84 (s, 1 H) | 542 |
| 42 | 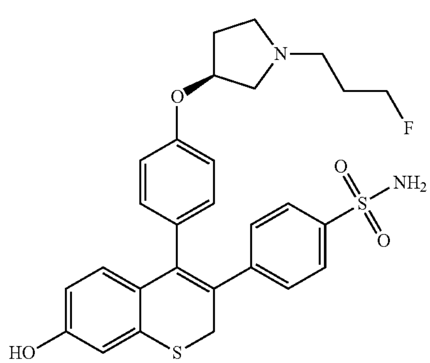 [SMILES: NS(=O)(=O)c1ccc(C2=C(c3ccc(O[C@H]4CCN(CCCF)C4)cc3)c3ccc(O)cc3SC2)cc1] | 4-[4-[4-[(3S)-1-(3-fluoropropyl)pyrrolidin-3-yl]oxyphenyl]-7-hydroxy-2H-thiochromen-3-yl]benzenesulfonamide | A | 1H NMR (400 MHz, DMSO-d6) δ ppm: 1.77 (m, 3 H), 2.23 (m, 1 H), 2.35-2.50 (m, 3 H), 2.59 (m, 1 H), 2.67 (m, 1 H), 2.84 (m, 1 H), 3.77 (s, 2 H), 4.48 (dt, J = 47.4 et 6.0 Hz, 2 H), 4.80 (m, 1 H), 6.48 (m, 1 H), 6.56 (m, 1 H), 6.74 (m, 3 H), 6.85 (d, J = 8.1 Hz, 2 H), 7.20 (d, J = 7.9 Hz, 2 H), 7.30 (s, 2H), 7.57 (d, J = 7.9 Hz, 2 H), 9.83 (s, 1 H) | 541 |

TABLE 1-continued

| Example | Structure | Name | Method | NMR | MASS LC/MS (m/z, MH+) |
|---|---|---|---|---|---|
| 43 | 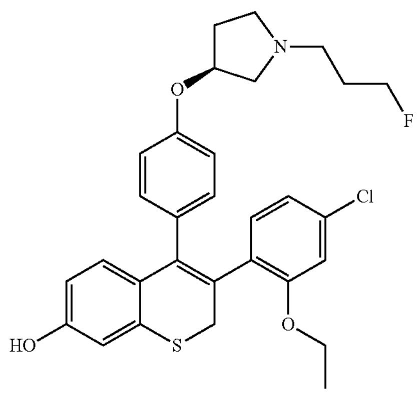 [SMILES: CCOc1cc(Cl)ccc1C1=C(c2ccc(O[C@H]3CCN(CCCF)C3)cc2)c2ccc(O)cc2SC1] | 3-(4-chloro-2-ethoxy-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.32 (t, J = 7.0 Hz, 3 H), 1.77 (m, 3 H), 2.22 (m, 1 H), 2.39 (m, 1 H), 2.46 (m, 2 H), 2.56 (dd, J = 10.3 et 2.4 Hz, 1 H), 2.66 (m, 1 H), 2.80 (dd, J = 10.4 et 6.2 Hz, 1 H), 3.21 (m, 1 H), 3.74 (m, 1 H), 4.06 (m, 2 H), 4.47 (dt, J = 47.4 et 5.9 Hz, 2 H), 4.77 (m, 1 H), 6.47 (dd, J = 8.6 et 2.4 Hz, 1 H), 6.56 (d, J = 8.6 Hz, 1 H), 6.67 (m, 4 H), 6.76 (d, J = 2.4 Hz, 1 H), 6.79 (d, J = 7.8 Hz, 2 H), 6.99 (d, J = 1.2 Hz, 1 H), 9.74 (s, 1 H) | 540 |
| 44 | 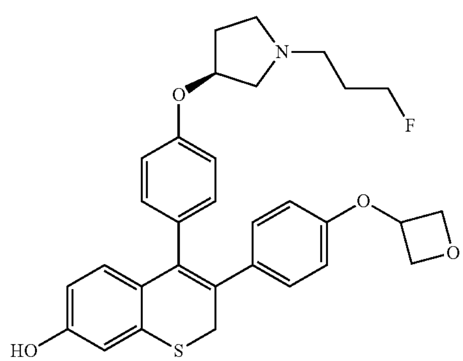 [SMILES: Oc1ccc2c(c1)SCC(c1ccc(OC3COC3)cc1)=C2c1ccc(O[C@H]2CCN(CCCF)C2)cc1] | 4-[4-[(3S)-1-(3-fluoropropyl)pyrrolidin-3-yl]oxyphenyl]-3-[4-(oxetan-3-yloxy)phenyl]-2H-thiochromen-7-ol | A | 1H NMR (400 MHz, DMSO-d6) δ ppm: 1.81 (m, 3 H), 2.23 (m, 1 H), 2.39 (m, 1 H), 2.48 (m, 2 H), 2.59 (dd, J = 10.1 et 2.4 Hz, 1 H), 2.69 (m, 1 H), 2.82 (dd, J = 10.3 et 6.1 Hz, 1 H), 3.71 (s, 2 H), 4.45 (q, J = 5.2 Hz, 2 H), 4.47 (dt, J = 47.4 et 6.0 Hz, 2 H), 4.79 (m, 1 H), 4.85 (q, J = 5.2 Hz, 2 H), 5.18 (quin, J = 5.5 Hz, 1 H), 6.45 (dd, J = 8.7 et 2.4 Hz, 1 H), 6.54 (m, 3 H), 6.73 (m, 3 H), 6.82 (d, J = 8.5 Hz, 2 H), 6.94 (d, J = 8.8 Hz, 2 H), 9.71 (s, 1 H) | 534 |
| 45 | 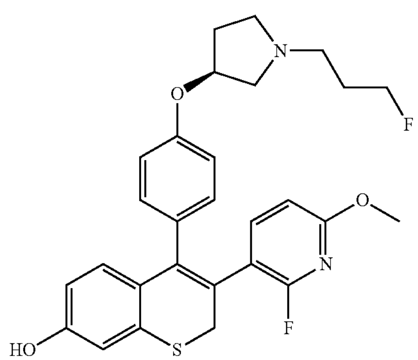 [SMILES: COc1ccc(C2=C(c3ccc(O[C@H]4CCN(CCCF)C4)cc3)c3ccc(O)cc3SC2)c(F)n1] | 3-(2-fluoro-6-methoxy-3-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.79 (m, 3 H), 2.22 (m, 1 H), 2.40 (m, 1 H), 2.48 (m, 2 H), 2.58 (dd, J = 10.2 et 2.5 Hz, 1 H), 2.69 (m, 1 H), 2.81 (dd, J = 10.3 et 6.1 Hz, 1 H), 3.64 (s, 2 H), 3.77 (s, 3 H), 4.48 (dt, J = 47.4 et 6.0 Hz, 2 H), 4.79 (m, 1 H), 6.48 (dd, J = 8.6 et 2.4 Hz, 1 H), 6.53 (d, J = 8.3 Hz, 1 H), 6.57 (m, 1 H), 6.73 (m, 3 H), 6.83 (m, 2 H), 7.35 (dd, J = 9.9 et 8.3 Hz, 1 H), 9.81 (s, 1 H) | 511 |
| 46 | 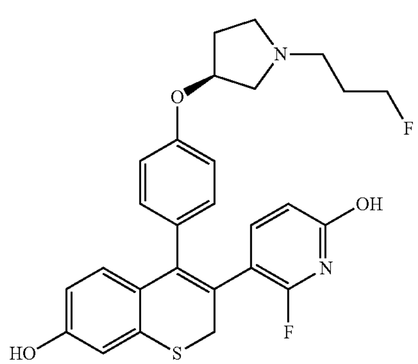 [SMILES: Oc1ccc2c(c1)SCC(c1ccc(O)nc1F)=C2c1ccc(O[C@H]2CCN(CCCF)C2)cc1] | 6-fluoro-5-[4-[4-[(3S)-1-(3-fluoropropyl)pyrrolidin-3-yl]oxyphenyl]-7-hydroxy-2H-thiochromen-3-yl]pyridin-2-ol | A | 1H NMR (400 MHz, DMSO-d6) δ ppm: 1.79 (m, 3 H), 2.23 (m, 1 H), 2.40 (m, 1 H), 2.44 (m, 2 H), 2.58 (d, J = 10.8 Hz, 1 H), 2.66 (m, 1 H), 2.82 (dd, J = 9.5 et 6.4 Hz, 1 H), 3.62 (s, 2 H), 4.48 (dt, J = 47.4 et 5.6 Hz, 2 H), 4.79 (m, 1 H), 6.29 (d, J = 7.8 Hz, 1 H), 6.47 (d, J = 7.8 Hz, 1 H), 6.56 (d, J = 8.6 Hz, 1 H), 6.74 (m, 3 H), 6.83 (d, J = 8.1 Hz, 2 H), 7.24 (t, J = 9.2 Hz, 1 H), 9.78 (s, 1 H), 11.19 (s, 1 H) | 497 |

TABLE 1-continued

| Example | Structure | Name | Method | NMR | MASS LC/MS (m/z, MH+) |
|---|---|---|---|---|---|
| 47 | 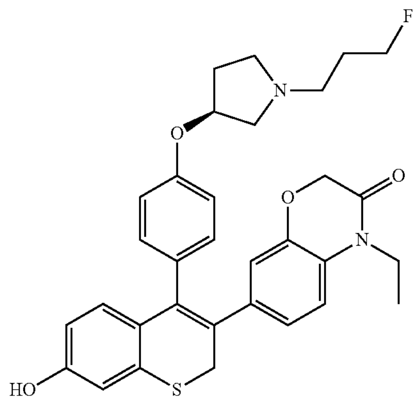 [SMILES: CCN1C(=O)COc2cc(C3=C(c4ccc(O[C@H]5CCN(CCCF)C5)cc4)c4ccc(O)cc4SC3)ccc21] | 4-ethyl-6-[4-[4-[(3S)-1-(3-fluoropropyl)pyrrolidin-3-yl]oxyphenyl]-7-hydroxy-2H-thiochromen-3-yl]-1,4-benzoxazin-3-one | A | 1H NMR (400 MHz, DMSO-d6) δ ppm: 0.85 (t, J = 7.0 Hz, 3 H), 1.77 (m, 3 H), 2.22 (m, 1 H), 2.40 (m, 1 H), 2.48 (m, 2 H), 2.56 (dd, J = 10.3 et 2.5 Hz, 1 H), 2.68 (m, 1 H), 2.82 (dd, J = 10.3 et 6.2 Hz, 1 H), 3.57 (q, J = 6.9 Hz, 2 H), 3.76 (s, 2 H), 4.42 (t, J = 6.1 Hz, 1 H), 4.54 (m, 3 H), 4.79 (d, J = 6.8 Hz, 1 H), 6.43 (m, 1 H), 6.55 (m, 1 H), 6.67 (d, J = 1.1 Hz, 1 H), 6.83 (m, 7 H), 9.76 (s, 1 H) | 561 |
| 48 | 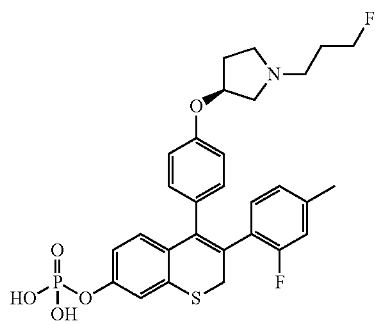 [SMILES: Cc1ccc(C2=C(c3ccc(O[C@H]4CCN(CCCF)C4)cc3)c3ccc(OP(=O)(O)O)cc3SC2)c(F)c1] | [3-(2-fluoro-4-methyl-phenyl)-4-[4-[(3S)-1-(3-fluoropropyl)pyrrolidin-3-yl]oxyphenyl]-2H-thiochromen-7-yl] dihydrogen phosphate | | 1H NMR (400 MHz, DMSO-d6) δ ppm: 1.91 (m, 3 H), 2.20 (s, 3 H), 2.23 (m, 1 H), 2.37-2.41 (m, 1 H), 2.72-3.25 (m, 8 H), 3.62 (s, 2 H), 4.49 (dt, J = 47.5 et 6.0 Hz, 2 H), 4.84 (m, 1 H), 6.56 (d, J = 8.6 Hz, 1 H), 6.72 (m, 3 H), 6.82 (m, 3 H), 6.89 (d, J = 11.4 Hz, 1 H), 7.27 (s, 1 H) | 574 |
| 49 | 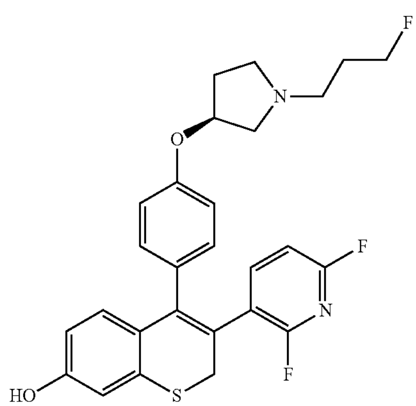 [SMILES: Oc1ccc2c(c1)SCC(c1ccc(F)nc1F)=C2c1ccc(O[C@H]2CCN(CCCF)C2)cc1] | 3-(2,6-difluoro-3-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.77 (m, 3 H), 2.22 (m, 1 H), 2.39 (m, 1 H), 2.47 (m, 2 H), 2.57 (dd, J = 10.4 et 2.4 Hz, 1 H), 2.67 (m, 1 H), 2.81 (dd, J = 10.3 et 6.1 Hz, 1 H), 3.70 (s, 2 H), 4.47 (dt, J = 47.4 et 6.0 Hz, 2 H), 4.79 (m, 1 H), 6.49 (dd, J = 8.7 et 2.4 Hz, 1 H), 6.59 (d, J = 8.7 Hz, 1 H), 6.75 (d, J = 8.4 Hz, 2 H), 6.78 (d, J = 2.4 Hz, 1 H), 6.84 (d, J = 8.4 Hz, 2 H), 6.98 (dd, J = 8.2 et 2.2 Hz, 1 H), 7.71 (m, 1 H), 9.89 (s, 1 H) | 499 |
| 50 | 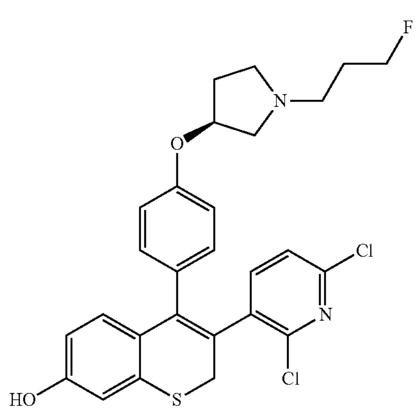 [SMILES: Oc1ccc2c(c1)SCC(c1ccc(Cl)nc1Cl)=C2c1ccc(O[C@H]2CCN(CCCF)C2)cc1] | 3-(2,6-dichloro-3-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.79 (m, 3 H), 2.24 (m, 1 H), 2.41 (m, 3 H), 2.56 (d, J = 9.9 Hz, 1 H), 2.65 (m, 1 H), 2.80 (m, 1 H), 3.55 (d, J = 15.2 Hz, 1 H), 3.81 (d, J = 16.1 Hz, 1 H), 4.47 (dt, J = 47.4, 6.0 Hz, 2 H), 4.78 (d, J = 6.8 Hz, 1 H), 6.50 (dd, J = 8.6, 2.4 Hz, 1 H), 6.60 (d, J = 8.6 Hz, 1 H), 6.74 (d, J = 8.7 Hz, 2 H), 6.78 (d, J = 2.3 Hz, 1 H), 6.85 (d, J = 7.7 Hz, 2 H), 7.33 (d, J = 7.9 Hz, 1 H), 7.47 (d, J = 7.9 Hz, 1 H), 9.87 (s, 1 H) | 531 |

TABLE 1-continued

| Example | Structure | Name | Method | NMR | MASS LC/MS (m/z, MH+) |
|---|---|---|---|---|---|
| 51 | 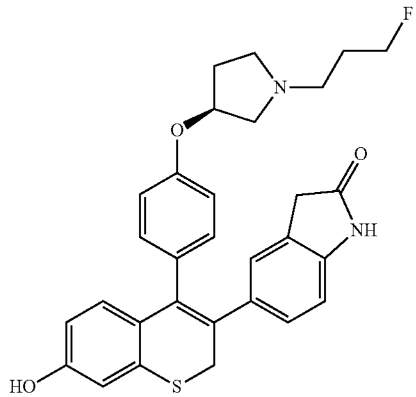 [SMILES: O=C1Cc2cc(C3=C(c4ccc(O[C@H]5CCN(CCCF)C5)cc4)c4ccc(O)cc4SC3)ccc2N1] | 5-[4-[4-[(3S)-1-(3-fluoropropyl)pyrrolidin-3-yl]oxyphenyl]-7-hydroxy-2H-thiochromen-3-yl]indolin-2-one | A | 1H NMR (400 MHz, DMSO-d6) δ ppm: 1.79 (m, 3 H), 2.23 (m, 1 H), 2.41 (m, 1 H), 2.47 (s, 2 H), 2.58 (dd, J = 10.3, 2.6 Hz, 1 H), 2.66 (m, 1 H), 2.82 (dd, J = 10.3, 6.2 Hz, 1 H), 3.31 (s, 2 H), 3.70 (m, 2 H), 4.48 (dt, J = 47.4, 6.0 Hz, 2 H), 4.80 (d, J = 6.8 Hz, 1 H), 6.45 (dd, J = 8.6, 2.5 Hz, 1 H), 6.53 (dd, J = 8.3, 2.1 Hz, 2 H), 6.73 (m, 3 H), 6.78 (d, J = 9.3 Hz, 1 H), 6.83 (m, 2 H), 6.92 (s, 1 H), 9.69 (s, 1 H), 10.26 (s, 1 H) | 517 |
| 52 | 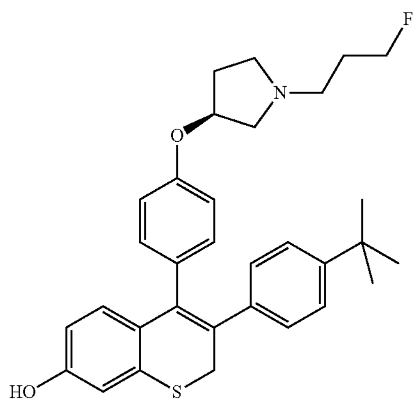 [SMILES: CC(C)(C)c1ccc(C2=C(c3ccc(O[C@H]4CCN(CCCF)C4)cc3)c3ccc(O)cc3SC2)cc1] | 3-(4-tert-butylphenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.73 (m, 9 H), 2.22 (m, 1 H), 2.38 (m, 1 H), 2.46 (m, 2 H), 2.55 (d, J = 2.8 Hz, 3 H), 2.67 (m, 1 H), 2.79 (dd, J = 10.3 et 6.2 Hz, 1 H), 3.73 (s, 2 H), 4.46 (dt, J = 47.4 et 6.0 Hz, 2 H), 4.75 (m, 1 H), 6.46 (dd, J = 8.6 et 2.1 Hz, 1H), 6.55 (d, J = 8.6 Hz, 1 H), 6.73 (m, 3 H), 6.85 (d, J = 8.5 Hz, 2 H), 6.93 (d, J = 8.6 Hz, 2 H), 7.15 (d, J = 8.7 Hz, 2 H), 9.75 (s, 1 H) | 518 |
| 53 | 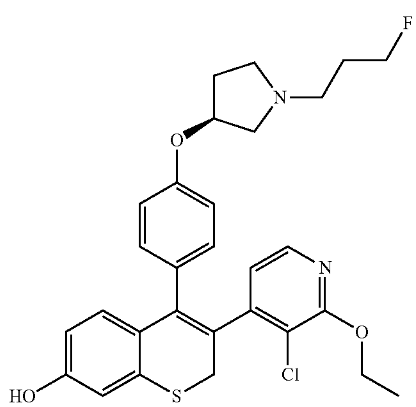 | 3-(3-chloro-2-ethoxy-4-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.32 (t, J = 7.0 Hz, 3 H), 1.75 (m, 3 H), 2.21 (m, 1 H), 2.40 (m, 1 H), 2.47 (m, 2 H), 2.57 (m, 1 H), 2.66 (m, 1 H), 2.80 (m, 1 H), 3.47 (d, J = 14.7 Hz, 1 H), 3.80 (d, J = 14.7 Hz, 1 H), 4.29 (m, 2 H), 4.47 (dt, J = 47.4, 6.0 Hz, 2 H), 4.77 (m, 1 H), 6.50 (dd, J = 8.6, 2.4 Hz, 1 H), 6.55 (d, J = 5.1 Hz, 1 H), 6.60 (d, J = 8.6 Hz, 1 H), 6.72 (d, J = 8.3 Hz, 2 H), 6.78 (d, J = 2.3 Hz, 1 H), 6.85 (d, J = 8.3 Hz, 2 H), 7.79 (d, J = 5.1 Hz, 1 H), 9.75 (s, 1 H) | 541 |

TABLE 1-continued

| Example | Structure | Name | Method | NMR | MASS LC/MS (m/z, MH+) |
|---|---|---|---|---|---|
| 54 | 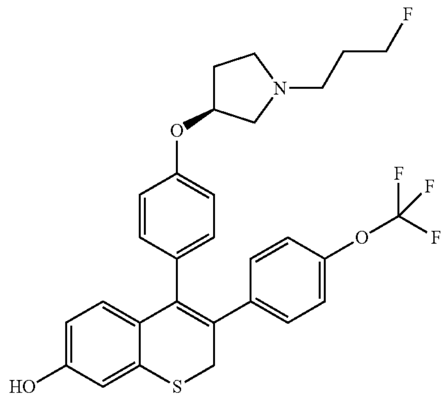 [SMILES: Oc1ccc2c(c1)SCC(c1ccc(OC(F)(F)F)cc1)=C2c1ccc(O[C@H]2CCN(CCCF)C2)cc1] | 4-[4-[(3S)-1-(3-fluoropropyl)pyrrolidin-3-yl]oxyphenyl]-3-[4-(trifluoromethoxy)phenyl]-2H-thiochromen-7-ol | A | 1H NMR (400 MHz, DMSO-d6) δ ppm: 1.75 (m, 3 H), 2.20 (m, 1 H), 2.39 (m, 1 H), 2.49 (m, 2 H), 2.57 (m, 1 H), 2.68 (m, 1 H), 2.80 (dd, J = 10.2 et 6.1 Hz, 1 H), 3.76 (s, 2 H), 4.47 (dt, J = 47.4 et 6.0 Hz, 2 H), 4.79 (m, 1 H), 6.47 (dd, J = 8.6 et 2.4 Hz, 1 H), 6.58 (m, 1 H), 6.73 (m, 3 H), 6.84 (d, J = 7.8 Hz, 2 H), 7.12 (s, 4 H), 9.72 (s, 1 H) | 546 |
| 55 | 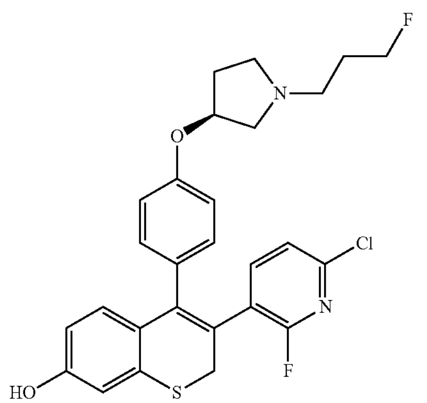 | 3-(6-chloro-2-fluoro-3-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.81 (m, 3 H), 2.24 (m, 1 H), 2.35-2.75 (m, 5 H), 2.86 (m, 1 H), 3.70 (s, 2 H), 4.48 (dt, J = 47.4 et 6.0 Hz, 2 H), 4.81 (m, 1 H), 6.50 (dd, J = 8.7 et 2.4 Hz, 1 H), 6.59 (d, J = 8.7 Hz, 1 H), 6.75-6.90 (m, 5 H), 7.30 (d, J = 7.8 Hz, 1 H), 7.57 (t, J = 8.7 Hz, 1 H), 9.88 (s, 1 H) | 515 |
| 56 | 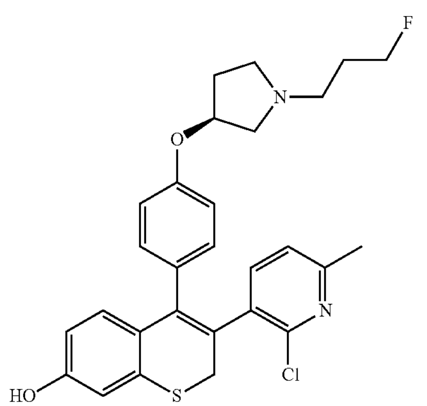 [SMILES: Cc1ccc(C2=C(c3ccc(O[C@H]4CCN(CCCF)C4)cc3)c3ccc(O)cc3SC2)c(Cl)n1] | 3-(2-chloro-6-methyl-3-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.73 (m, 3 H), 2.21 (m, 1 H), 2.38 (m, 6 H), 2.53 (m, 1 H), 2.67 (m, 1 H), 2.82 (m, 1 H), 3.46 (d, J = 14.5 Hz, 1 H), 3.82 (d, J = 14.5 Hz, 1 H), 4.47 (dt, J = 47.4 et 6.0 Hz, 2 H), 4.76 (d, J = 6.7 Hz, 1 H), 6.49 (dd, J = 8.6 et 2.4 Hz, 1 H), 6.58 (d, J = 8.6 Hz, 1 H), 6.71 (d, J = 8.4 Hz, 2 H), 6.77 (d, J = 2.4 Hz, 1 H), 6.85 (d, J = 8.4 Hz, 2 H), 7.01 (d, J = 7.8 Hz, 1 H), 7.27 (d, J = 7.8 Hz, 1 H), 9.88 (s, 1 H) | 511 |

TABLE 1-continued

| Example | Structure | Name | Method | NMR | MASS LC/MS (m/z, MH+) |
|---|---|---|---|---|---|
| 57 | 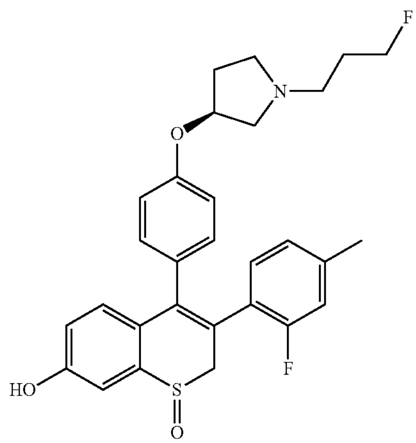 [SMILES: Cc1ccc(C2=C(c3ccc(O[C@H]4CCN(CCCF)C4)cc3)c3ccc(O)cc3S(=O)C2)c(F)c1] | 3-(2-fluoro-4-methyl-phenyl)-4-[4-[(3S)-1-(3-fluoropropyl)pyrrolidin-3-yl]oxyphenyl]-1-oxo-2H-thiochromen-7-ol | | 1H NMR (400 MHz, DMSO-d6) δ ppm: 1.79 (m, 3 H), 2.22 (s, 4 H), 2.39 (m, 1 H), 2.46 (s, 2 H), 2.58 (d, J = 10.1 Hz, 1 H), 2.68 (m, 1 H), 2.81 (dd, J = 9.9, 6.4 Hz, 1 H), 3.93 (d, J = 15.0 Hz, 1 H), 4.18 (d, J = 15.0 Hz, 1 H), 4.48 (dt, J = 47.4, 3.0 Hz, 2 H), 4.81 (m, 1 H), 76 (m, 5 H), 6.90 (m, 4 H), 7.18 (d, J = 2.2 Hz, 1 H), 10.34 (m, 1 H) | 510 |
| 58 | 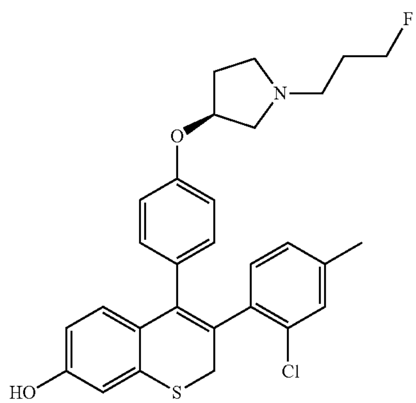 | 3-(2-chloro-4-methyl-phenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.76 (m, 3 H), 2.18 (s, 3 H), 2.20 (m, 1 H), 2.38 (m, 1 H), 2.48 (m, 2 H), 2.56 (m, 1 H), 2.66 (m, 1 H), 2.79 (dd, J = 10.3 et 6.2 Hz, 1 H), 3.45-3.65 (m, 2 H), 4.47 (dt, J = 47.4 et 6.0 Hz, 2 H), 4.75 (m, 1 H), 6.47 (dd, J = 8.6 et 2.3 Hz, 1 H), 6.56 (d, J = 8.6 Hz, 1 H), 6.67 (d, J = 8.6 Hz, 2 H), 6.78 (d, J = 2.3 Hz, 1 H), 6.81 (d, J = 8.3 Hz, 2 H), 6.98 (dd, J = 8.2 et 2.8 Hz, 1 H), 7.04 (d, J = 8.2 Hz, 1 H), 1 H), 7.16 (s, 1 H), 9.76 (s, 1 H) | 510 |
| 59 | 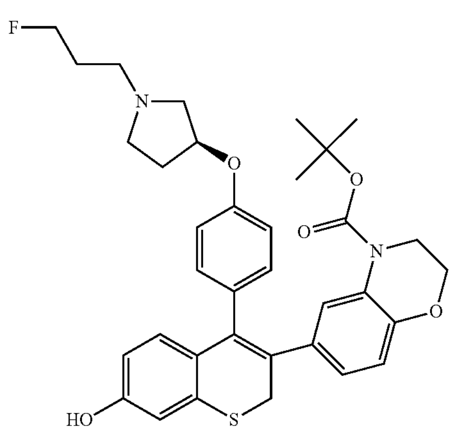 [SMILES: CC(C)(C)OC(=O)N1CCOc2ccc(C3=C(c4ccc(O[C@H]5CCN(CCCF)C5)cc4)c4ccc(O)cc4SC3)cc21] | tert-butyl 6-[4-[4-[(3S)-1-(3-fluoropropyl)pyrrolidin-3-yl]oxyphenyl]-7-hydroxy-2H-thiochromen-3-yl]-2,3-dihydro-1,4-benzoxazine-4-carboxylate | A | 1H NMR (400 MHz, DMSO-d6) δ ppm: 1.47 (s, 9 H), 1.81 (m, 3 H), 2.21 (m, 1 H), 2.40 (m, 1 H), 2.48 (m, 2 H), 2.59 (dd, J = 10.3, 2.6 Hz, 1 H), 2.68 (m, 1 H), 2.82 (dd, J = 10.2 et 6.2 Hz, 1 H), 3.70 (m, 4 H), 4.14 (t, J = 4.5 Hz, 2 H), 4.48 (dt, J = 47.4 et 6.0 Hz, 2 H), 4.80 (d, J = 6.7 Hz, 1 H), 6.50 (m, 4 H), 6.74 (m, 3 H), 6.85 (d, J = 7.8 Hz, 2 H), 7.55 (s, 1 H), 9.72 (s, 1 H) | 619 |

TABLE 1-continued

| Example | Structure | Name | Method | NMR | MASS LC/MS (m/z, MH+) |
|---|---|---|---|---|---|
| 60 | 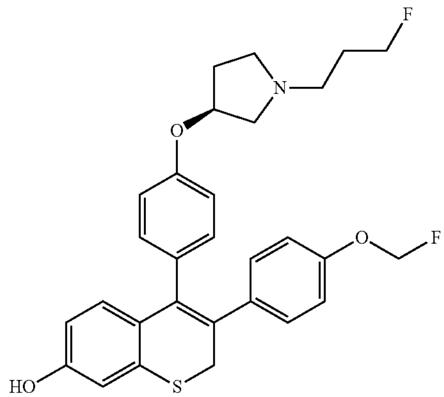 [SMILES: Oc1ccc2c(c1)SCC(c1ccc(OCF)cc1)=C2c1ccc(O[C@H]2CCN(CCCF)C2)cc1] | 3-[4-(fluoromethoxy)phenyl]-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.78 (m, 3 H), 2.24 (m, 1 H), 2.39 (m, 1 H), 2.45 (m, 2 H), 2.59 (dd, J = 10.3 et 2.2 Hz, 1 H), 2.69 (m, 1 H), 2.82 (dd, J = 10.1 et 6.2 Hz, 1 H), 3.73 (s, 2 H), 4.48 (dt, J = 47.4 et 6.0 Hz, 2 H), 4.80 (s, 1 H), 5.79 (d, J = 54.5 Hz, 2 H), 6.46 (dd, J = 8.6 et 2.3 Hz, 1 H), 6.54 (d, J = 8.7 Hz, 1 H), 6.74 (m, 3 H), 6.81 (m, 4 H), 7.02 (d, J = 8.7 Hz, 2 H), 9.75 (s, 1 H) | 510 |
| 61 | 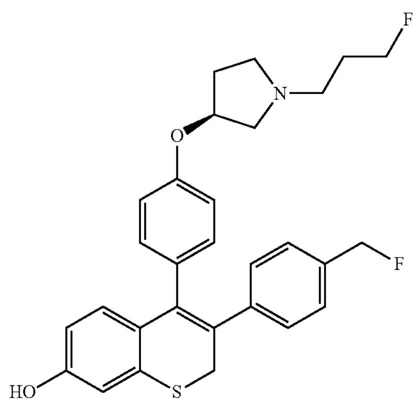 [SMILES: Oc1ccc2c(c1)SCC(c1ccc(CF)cc1)=C2c1ccc(O[C@H]2CCN(CCCF)C2)cc1] | 3-[4-(fluoromethyl)phenyl]-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.79 (m, 3 H), 2.24 (m, 1 H), 2.40 (m, 1 H), 2.49 (m, 2 H), 2.58 (d, J = 10.4 Hz, 1 H), 2.69 (m, 1 H), 2.81 (dd, J = 10.1 et 6.1 Hz, 1 H), 3.76 (s, 2 H), 4.48 (dt, J = 47.4 et 5.9 Hz, 2 H), 4.79 (m, 1 H), 5.30 (d, J = 47.8 Hz, 2 H), 6.47 (dd, J = 8.4 et 2.0 Hz, 1 H), 6.55 (d, J = 8.4 Hz, 1 H), 6.74 (m, 3 H), 6.84 (d, J = 8.4 Hz, 2 H), 7.06 (d, J = 7.8 Hz, 2 H), 7.19 (d, J = 7.8 Hz, 2 H), 9.70 (m, 1 H) | 494 |
| 62 | 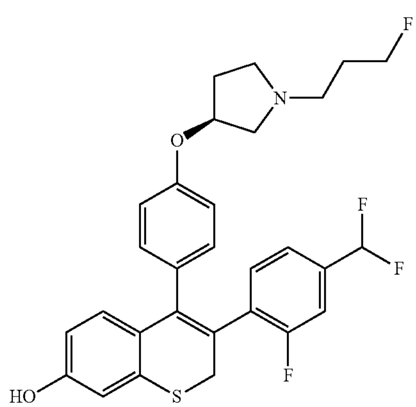 [SMILES: Oc1ccc2c(c1)SCC(c1ccc(C(F)F)cc1F)=C2c1ccc(O[C@H]2CCN(CCCF)C2)cc1] | 3-[4-(difluoromethyl)-2-fluoro-phenyl]-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.76 (m, 3 H), 2.22 (m, 1 H), 2.42 (m, 3 H), 2.57 (m, 1 H), 2.66 (m, 1 H), 2.80 (dd, J = 10.3 et 6.2 Hz, 1 H), 3.68 (s, 2 H), 4.47 (dt, J = 47.4 et 6.0 Hz, 2 H), 4.77 (m, 1 H), 6.49 (dd, J = 8.8 et 2.0 Hz, 1 H), 6.59 (d, J = 8.8 Hz, 1 H), 6.70 (d, J = 8.0 Hz, 2 H), 6.82 (m, 3 H), 6.93 (t, J = 25.0 Hz, 1 H), 7.14 (m, 2 H), 7.30 (d, J = 10.1 Hz, 1 H), 9.85 (s, 1 H) | 530 |

TABLE 1-continued

| Example | Structure | Name | Method | NMR | MASS LC/MS (m/z, MH+) |
|---|---|---|---|---|---|
| 63 | 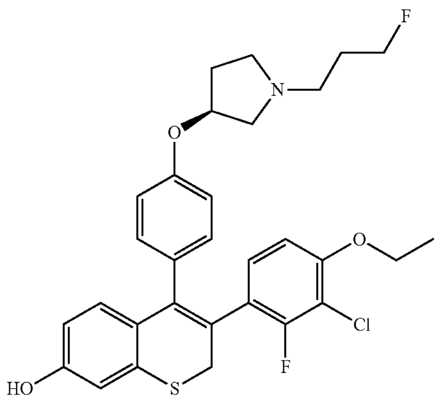 | 3-(3-chloro-4-ethoxy-2-fluorophenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.30 (t, J = 6.9 Hz, 3 H), 1.77 (m, 3 H), 2.22 (m, 1 H), 2.37 (m, 1 H), 2.47 (m, 2 H), 2.56 (d, J = 11.0 Hz, 1 H), 2.67 (m, 1 H), 2.80 (dd, J = 10.3 et 6.1 Hz, 1 H), 3.63 (s, 2 H), 4.05 (q, J = 6.9 Hz, 2 H), 4.47 (dt, J = 47.4 et 6.0 Hz, 2 H), 4.78 (m, 1 H), 6.47 (dd, J = 8.6 et 2.0 Hz, 1 H), 6.57 (d, J = 8.6 Hz, 1 H), 6.70-6.90 (m, 7 H), 9.82 (s, 1 H) | 558 |
| 64 | 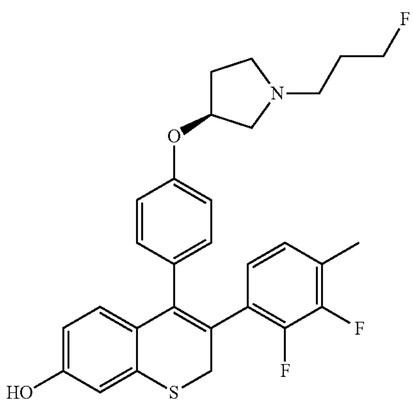 [SMILES: Cc1ccc(C2=C(c3ccc(O[C@H]4CCN(CCCF)C4)cc3)c3ccc(O)cc3SC2)c(F)c1F] | 3-(2,3-difluoro-4-methylphenyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.77 (m, 3 H), 2.18 (s, 3 H), 2.22 (m, 1 H), 2.39 (m, 1 H), 2.47 (m, 2 H), 2.57 (dd, J = 10.3 et 2.7 Hz, 1 H), 2.66 (m, 1 H), 2.80 (dd, J = 10.4 et 6.2 Hz, 1 H), 3.65 (s, 2 H), 4.47 (dt, J = 47.4 et 6.1 Hz, 2 H), 4.78 (m, 1 H), 6.48 (dd, J = 8.6 et 2.4 Hz, 1 H), 6.57 (d, J = 8.6 Hz, 1 H), 6.71 (m, 3 H), 6.77 (d, J = 2.7 Hz, 1 H), 6.83 (m, 3 H), 9.83 (s, 1 H) | 512 |
| 65 | 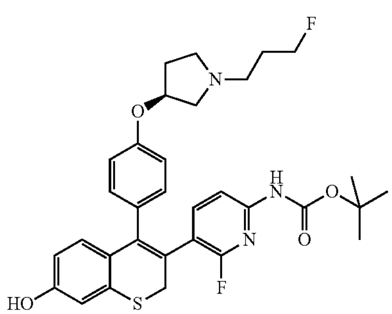 [SMILES: CC(C)(C)OC(=O)Nc1ccc(C2=C(c3ccc(O[C@H]4CCN(CCCF)C4)cc3)c3ccc(O)cc3SC2)c(F)n1] | tert-butyl N-[6-fluoro-5-[4-[4-[(3S)-1-(3-fluoropropyl)pyrrolidin-3-yl]oxyphenyl]-7-hydroxy-2H-thiochromen-3-yl]-2-pyridyl]carbamate | A | 1H NMR (400 MHz, DMSO-d6) δ ppm: 1.44 (s, 9 H), 1.78 (m, 3 H), 2.22 (m, 1 H), 2.39 (m, 1 H), 2.46 (d, J = 1.7 Hz, 2 H), 2.58 (dd, J = 10.3 et 2.6 Hz, 1 H), 2.68 (m, 1 H), 2.81 (dd, J = 10.3 et 6.2 Hz, 1 H), 3.65 (s, 2 H), 4.47 (dt, J = 47.4 et 6.0 Hz, 2 H), 4.79 (m, 1 H), 6.48 (dd, J = 8.6, 2.5 Hz, 1 H), 6.58 (d, J = 8.6 Hz, 1 H), 6.73 (d, J = 8.6 Hz, 2 H), 6.77 (d, J = 2.5 Hz, 1 H), 6.88 (d, J = 8.6 Hz, 2 H), 7.42 (m, 2 H), 9.81 (s, 1 H), 9.93 (s, 1 H) | 596 |
| 66 | 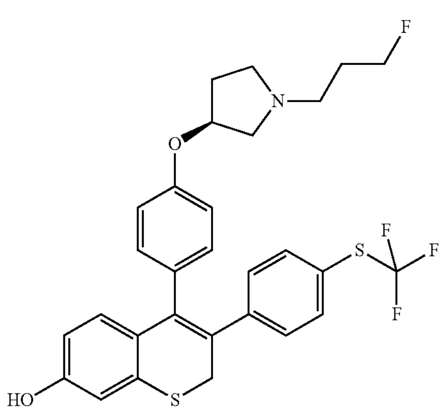 [SMILES: Oc1ccc2c(c1)SCC(c1ccc(SC(F)(F)F)cc1)=C2c1ccc(O[C@H]2CCN(CCCF)C2)cc1] | 4-[4-[(3S)-1-(3-fluoropropyl)pyrrolidin-3-yl]oxyphenyl]-3-[4-(trifluoromethylsulfanyl)phenyl]-2H-thiochromen-7-ol | A | 1H NMR (400 MHz, DMSO-d6) δ ppm: 1.78 (m, 3 H), 2.21 (m, 1 H), 2.39 (m, 1 H), 2.47 (m, 2 H), 2.57 (dd, J = 10.3 et 2.7 Hz, 1 H), 2.67 (m, 1 H), 2.80 (dd, J = 10.3 et 6.1 Hz, 1 H), 3.78 (s, 2 H), 4.47 (dt, J = 47.4 et 6.1 Hz, 2 H), 4.79 (m, 1 H), 6.48 (dd, J = 8.7 et 2.6 Hz, 1 H), 6.58 (d, J = 8.7 Hz, 1 H), 6.72 (d, J = 8.6 Hz, 2 H), 6.77 (d, J = 2.6 Hz, 1 H), 6.82 (d, J = 8.6 Hz, 2 H), 7.15 (d, J = 8.3 Hz, 2 H), 7.47 (d, J = 8.3 Hz, 2 H), 9.83 (s, 1 H) | 562 |

TABLE 1-continued

| Example | Structure | Name | Method | NMR | MASS LC/MS (m/z, MH+) |
|---|---|---|---|---|---|
| 67 | 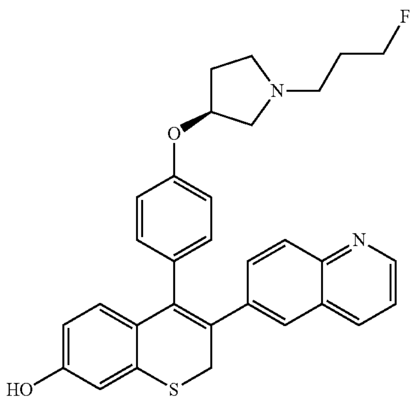 [SMILES: Oc1ccc2c(c1)SCC(c1ccc3ncccc3c1)=C2c1ccc(O[C@H]2CCN(CCCF)C2)cc1] | 4-[4-[(3S)-1-(3-fluoropropyl)pyrrolidin-3-yl]oxyphenyl]-3-(6-quinolyl)-2H-thiochromen-7-ol | A | 1H NMR (400 MHz, DMSO-d6) δ ppm: 1.76 (m, 3 H), 2.20 (m, 1 H), 2.38 (m, 1 H), 2.45 (m, 2 H), 2.55 (m, 1 H), 2.63 (m, 1 H), 2.75 (m, 1 H), 3.89 (s, 2 H), 4.47 (dt, J = 47.4 et 6.0 Hz, 2 H), 4.76 (m, 1 H), 6.50 (dd, J = 8.6, 2.5 Hz, 1 H), 6.62 (d, J = 8.6 Hz, 1 H), 6.70 (d, J = 8.7 Hz, 2 H), 6.79 (d, J = 2.5 Hz, 1 H), 6.87 (d, J = 8.7 Hz, 2 H), 7.30 (dd, J = 8.7 et 2.0 Hz, 1 H), 7.44 (dd, J = 8.3 et 4.2 Hz, 1 H), 7.72 (m, 2 H), 8.14 (d, J = 7.5 Hz, 1 H), 8.79 (dd, J = 4.2 et 1.7 Hz, 1 H), 9.82 (s, 1 H) | 513 |
| 68 | 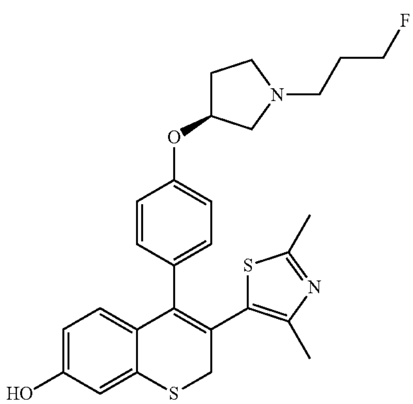 [SMILES: Cc1nc(C)c(C2=C(c3ccc(O[C@H]4CCN(CCCF)C4)cc3)c3ccc(O)cc3SC2)s1] | 3-(2,4-dimethylthiazol-5-yl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.77 (m, 3 H), 1.99 (s, 3 H), 2.23 (m, 1 H), 2.35-2.55 (m, 6 H), 2.60 (dd, J = 10.2 et 2.6 Hz, 1 H), 2.69 (m, 1 H), 2.83 (dd, J = 10.3 et 6.1 Hz, 1 H), 3.62 (s, 2 H), 4.48 (dt, J = 47.4 et 6.0 Hz, 2 H), 4.82 (m, 1 H), 6.48 (dd, J = 8.7 et 2.4 Hz, 1 H), 6.66 (m, 1 H), 6.77 (m, 3 H), 6.89 (d, J = 8.7 Hz, , 2 H), 9.86 (m, 1 H) | 497 |
| 69 | 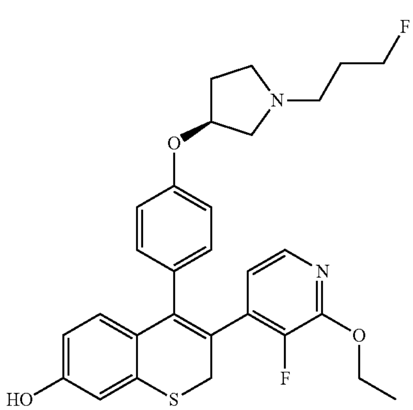 [SMILES: CCOc1nccc(C2=C(c3ccc(O[C@H]4CCN(CCCF)C4)cc3)c3ccc(O)cc3SC2)c1F] | 3-(2-ethoxy-3-fluoro-4-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.30 (t, J = 7.0 Hz, 3 H), 1.78 (m, 3 H), 2.21 (m, 1 H), 2.38 (m, 1 H), 2.46 (m, 2 H), 2.57 (dd, J = 10.3 et 2.6 Hz, 1 H), 2.67 (m, 1 H), 2.81 (dd, J = 10.3 et 6.2 Hz, 1 H), 3.68 (s, 2 H), 4.30 (q, J = 7.1 Hz, 2 H), 4.48 (dt, J = 47.4 et 6.0 Hz, 2 H), 4.80 (m, 1 H), 6.51 (m, 2 H), 6.59 (d, J = 8.5 Hz, 1 H), 6.75 (d, J = 8.5 Hz, 2 H), 6.78 (d, J = 2.5 Hz, 1 H), 6.85 (d, J = 8.5 Hz, 2 H), 7.66 (d, J = 5.1 Hz, 1 H), 9.92 (s, 1 H) | 525 |

TABLE 1-continued

| Example | Structure | Name | Method | NMR | MASS LC/MS (m/z, MH+) |
|---|---|---|---|---|---|
| 70 | 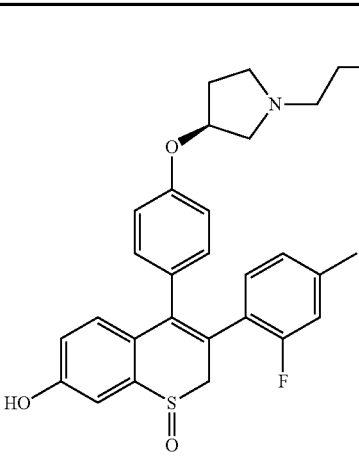<br>Isomer 1 | 3-(2-fluoro-4-methyl-phenyl)-4-[4-[(3S)-1-(3-fluoropropyl)pyrrolidin-3-yl]oxyphenyl]-1-oxo-2H-thiochromen-7-ol | | 1H NMR (400 MHz, DMSO-d6) δ 1.77 (m, 3H), 2.21 (s, 3 H), 2.25 (m, 4H), 2.40 (m, 2H), 2.61 (m, 3H), 2.81 (dd, J = 10.3 et 6.2 Hz, 1H), 3.94 (d, J = 15.0 Hz, 1H), 4.17 (d, J = 15.0 Hz, 1H), 4.48 (dt, J = 47.4 et 6.0 Hz, 2H), 4.79 (m, 1H), 6.75-6.95 (m, 10H), 7.17 (d, J = 2.0 Hz, 1H), 10.40 (s, 1H) | 510 |
| 71 | 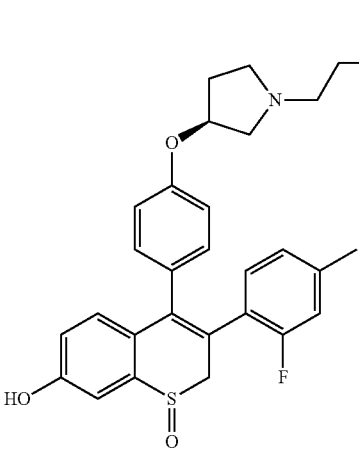<br>Isomer 2 | 3-(2-fluoro-4-methyl-phenyl)-4-[4-[(3S)-1-(3-fluoropropyl)pyrrolidin-3-yl]oxyphenyl]-1-oxo-2H-thiochromen-7-ol | | 1H NMR (400 MHz, DMSO-d6) δ ppm: 1.75 (m, 3 H), 2.21 (s, 3 H), 2.25 (m, 1 H), 2.4 (m, 1 H), 2.49 (m, 1 H), 2.58 (d, J = 8.2 Hz, 2 H), 2.85 (m, 1 H), 3.94 (d, J = 15.0 Hz, 1 H), 4.18 (d, J = 15.2 Hz, 1 H), 4.48 (dt, J = 47.4 et 6.0 Hz, 2 H), 4.80 (m, 1 H), 6.75 (m, 5 H), 6.90 (m, 4 H), 7.18 (d, J = 2.4 Hz, 1 H), 10.32 (s, 1 H) | 510 |
| 72 | 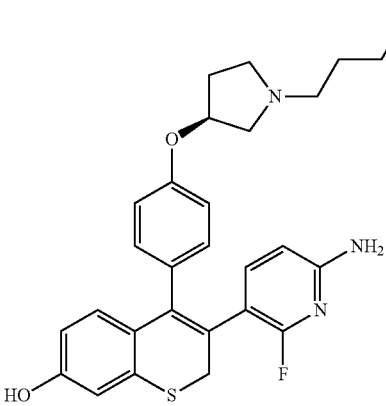 | 3-(6-amino-2-fluoro-3-pyridyl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.79 (m, 3 H), 2.25 (m, 1 H), 2.40 (m, 1 H), 2.49 (m, 2 H), 2.59 (dd, J = 10.2 et 2.5 Hz, 1 H), 2.68 (m, 1 H), 2.83 (dd, J = 10.2 et 6.2 Hz, 1 H), 3.57 (s, 2 H), 4.48 (dt, J = 47.5 et 6.0 Hz, 2 H), 4.80 (m, 1 H), 6.01 (dd, J = 8.1 et 1.8 Hz, 1 H), 6.24 (s, 2 H), 6.46 (dd, J = 8.7 et 2.4 Hz, 1 H), 6.53 (d, J = 8.7 Hz, 1 H), 6.75 (m, 3 H), 6.83 (d, J = 8.5 Hz, 2 H), 6.93 (dd, J = 10.3 et 8.3 Hz, 1 H), 9.77 (s, 1 H) | 496 |

TABLE 1-continued

| Example | Structure | Name | Method | NMR | MASS LC/MS (m/z, MH+) |
|---|---|---|---|---|---|
| 73 | 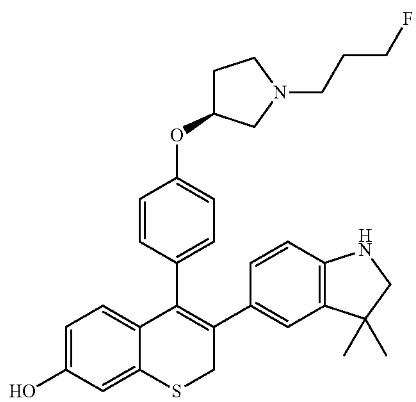 [SMILES: CC1(C)CNc2ccc(C3=C(c4ccc(O[C@H]5CCN(CCCF)C5)cc4)c4ccc(O)cc4SC3)cc21] | 3-(3,3-dimethylindolin-5-yl)-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 0.93 (s, 6 H), 1.77 (m, 3 H), 2.22 (m, 1 H), 2.40-2.55 (m, 3 H), 2.57 (m, 1 H), 2.66 (m, 1 H), 2.83 (dd, J = 10.2 et 6.2 Hz, 1 H), 3.06 (s, 2 H), 3.70 (s, 2 H), 4.48 (dt, J = 47.4 et 6.0 Hz, 2 H), 4.79 (m, 1 H), 5.45 (s, 1 H), 6.31 (d, J = 8.1 Hz, 1 H), 6.39 (s, 1 H), 6.43 (dd, J = 8.6 et 2.4 Hz, 1 H), 6.56 (d, J = 8.7 Hz, 1 H), 6.72 (m, 3 H), 6.82 (m, 3 H), 9.65 (s, 1 H) | 531 |
| 74 | 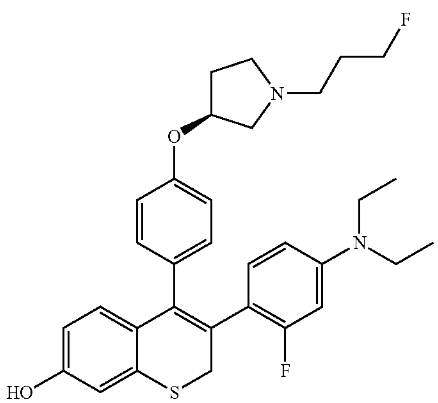 [SMILES: CCN(CC)c1ccc(C2=C(c3ccc(O[C@H]4CCN(CCCF)C4)cc3)c3ccc(O)cc3SC2)c(F)c1] | 3-[4-(diethylamino)-2-fluoro-phenyl]-4-[4-[(3S)-1-(3-fluoropropyl)pyrrolidin-3-yl]oxyphenyl]-2H-thiochromen-7-ol | A | 1H NMR (400 MHz, DMSO-d6) δ ppm: 1.01 (t, J = 6.9 Hz, 6 H), 1.78 (m, 3 H), 2.24 (m, 1 H), 2.41 (m, 1 H), 2.49 (t, J = 7.0 Hz, 2 H), 2.57 (d, J = 10.6 Hz, 1 H), 2.67 (m, 1 H), 2.81 (dd, J = 10.2 et 6.2 Hz, 1 H), 3.24 (m, 4 H), 3.57 (s, 2 H), 4.47 (dt, J = 47.4 et 6.0 Hz, 2 H), 4.79 (m, 1 H), 6.17 (dd, J = 8.7 et 2.2 Hz, 1 H), 6.27 (dd, J = 12.0 et 2.2 Hz, 1 H), 6.45 (dd, J = 8.6 et 2.4 Hz, 1 H), 6.55 (d, J = 8.6 Hz, 1 H), 6.64 (t, J = 9.0 Hz, 1 H), 6.73 (m, 3 H), 6.84 (d, J = 8.4 Hz, 2 H), 9.73 (s, 1 H) | 551 |
| 75 | 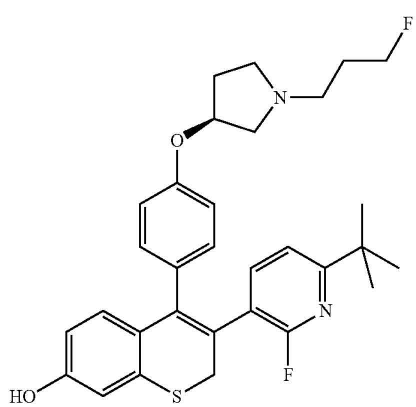 [SMILES: CC(C)(C)c1ccc(C2=C(c3ccc(O[C@H]4CCN(CCCF)C4)cc3)c3ccc(O)cc3SC2)c(F)n1] | 3-(6-tert-butyl-2-fluoro-3-pyridyl)-4-[4-[(3S)-1-(3-fluoropropyl)pyrrolidin-3-yl]oxyphenyl]-2H-thiochromen-7-ol | A | 1H NMR (500 MHz, DMSO-d6) δ ppm: 1.00 (s, 9 H), 1.80 (m, 3 H), 2.23 (m, 1 H), 2.42 (m, 3 H), 2.57 (dd, J = 10.3, 2.3 Hz, 1 H), 2.66 (m, 1 H), 2.83 (dd, J = 10.2, 6.1 Hz, 1 H), 3.83 (s, 2 H), 4.48 (dt, J = 47.4, 6.0 Hz, 2 H), 4.82 (m, J = 6.7, 6.7 Hz, 1 H), 6.49 (dd, J = 8.6, 2.1 Hz, 1 H), 6.57 (s, 1 H), 6.62 (d, J = 8.7 Hz, 1 H), 6.76 (m, 4 H), 6.86 (m, 2 H), 9.95 (m, 1 H) | 537 |
| 76 | 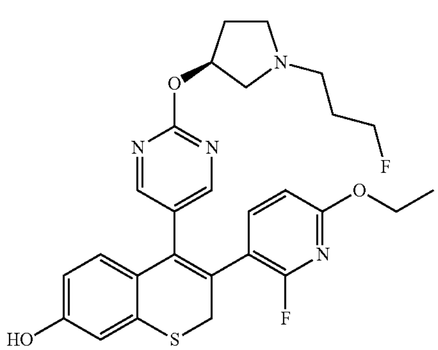 [SMILES: CCOc1ccc(C2=C(c3cnc(O[C@H]4CCN(CCCF)C4)nc3)c3ccc(O)cc3SC2)c(F)n1] | 3-(6-ethoxy-2-fluoro-3-pyridyl)-4-[2-[(3S)-1-(3-fluoropropyl)pyrrolidin-3-yl]oxypyrimidin-5-yl]-2H-thiochromen-7-ol | A | 1H NMR (400 MHz, DMSO-d6) δ ppm: 1.26 (t, J = 7.0 Hz, 3 H), 1.83 (m, 3 H), 2.23 (m, 1 H), 2.37 (m, 1 H), 2.47 (s, 2 H), 2.54 (m, 1 H), 2.63 (m, 1 H), 2.78 (dd, J = 10.7 et 6.2 Hz, 1 H), 3.70 (s, 2 H), 4.19 (q, J = 7.1 Hz, 2 H), 4.48 (dt, J = 47.2 et 6.0 Hz, 2 H), 5.28 (m, 1 H), 6.51 (d, J = 8.8 Hz, 1 H), 6.63 (t, J = 9.3 Hz, 2 H), 6.78 (s, 1 H), 7.56 (dd, J = 9.9 et 8.3 Hz, 1 H), 8.15 (s, 2 H), 10.29 (s, 1 H) | 527 |

TABLE 1-continued

| Example | Structure | Name | Method | NMR | MASS LC/MS (m/z, MH+) |
|---|---|---|---|---|---|
| 77 | 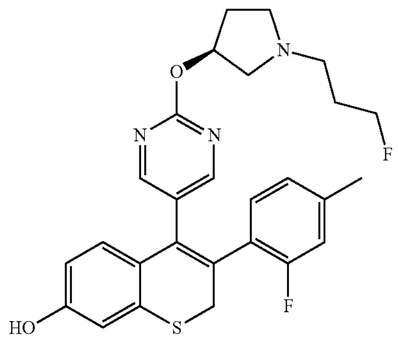 [SMILES: Cc1ccc(C2=C(c3cnc(O[C@H]4CCN(CCCF)C4)nc3)c3ccc(O)cc3SC2)c(F)c1] | 3-(2-fluoro-4-methyl-phenyl)-4-[2-[(3S)-1-(3-fluoropropyl)pyrrolidin-3-yl]oxypyrimidin-5-yl]-2H-thiochromen-7-ol | A | 1H NMR (400 MHz, DMSO-d6) δ ppm: 1.80 (m, 3 H), 2.22 (m, 4 H), 2.36 (m, 1 H), 2.46 (m, 2 H), 2.61 (dd, J = 10.6 et 2.4 Hz, 1 H), 2.75 (m, 2 H), 3.65 (s, 2 H), 4.48 (dt, J = 47.4 et 6.0 Hz, 2 H), 5.28 (m, 1 H), 6.37 (m, 1 H), 6.54 (d, J = 8.6 Hz, 1 H), 6.64 (s, 1 H), 6.85 (d, J = 7.8 Hz, 1 H), 6.90 (d, J = 11.2 Hz, 1 H), 6.97 (t, J = 7.8 Hz, 1 H), 8.10 (s, 2 H) | 496 |
| 78 | 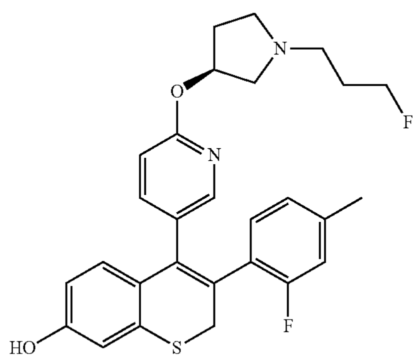 [SMILES: Cc1ccc(C2=C(c3ccc(O[C@H]4CCN(CCCF)C4)nc3)c3ccc(O)cc3SC2)c(F)c1] | 3-(2-fluoro-4-methyl-phenyl)-4-[6-[(3S)-1-(3-fluoropropyl)pyrrolidin-3-yl]oxy-3-pyridyl]-2H-thiochromen-7-ol | A | 1H NMR (400 MHz, DMSO-d6) δ ppm: 1.75 (m, 3 H), 2.21 (m, 4 H), 2.35 (m, 1 H), 2.45 (m, 2 H), 2.56 (dd, J = 10.6, 2.4 Hz, 1 H), 2.74 (m, 2 H), 3.65 (s, 2 H), 4.47 (dt, J = 47.4, 6.0 Hz, 2 H), 5.24 (m, 1 H), 6.48 (m, 1 H), 6.57 (m, 1 H), 6.64 (d, J = 8.6 Hz, 1 H), 6.81 (m, 2 H), 6.93 (m, 2 H), 7.25 (dd, J = 8.5, 2.1 Hz, 1 H), 7.63 (d, J = 2.0 Hz, 1 H), 9.81 (s, 1 H) | 495 |
| 79 | 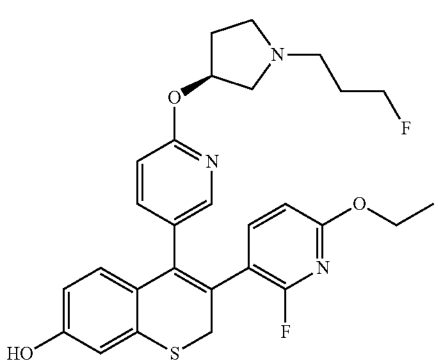 [SMILES: CCOc1ccc(C2=C(c3ccc(O[C@H]4CCN(CCCF)C4)nc3)c3ccc(O)cc3SC2)c(F)n1] | 3-(6-ethoxy-2-fluoro-3-pyridyl)-4-[6-[(3S)-1-(3-fluoropropyl)pyrrolidin-3-yl]oxy-3-pyridyl]-2H-thiochromen-7-ol | A | 1H NMR (400 MHz, DMSO-d6) δ ppm: 1.26 (d, J = 7.0 Hz, 3 H), 1.80 (m, 3 H), 2.19 (m, 1 H), 2.37 (m, 3 H), 2.57 (d, J = 10.8 Hz, 1 H), 2.76 (m, 2 H), 3.68 (s, 2 H), 4.18 (q, J = 6.9 Hz, 2 H), 4.47 (dt, J = 47.4, 6.0 Hz, 2 H), 5.27 (s, 1 H), 6.51 (m, 3 H), 6.69 (d, J = 8.4 Hz, 1 H), 6.78 (s, 1 H), 7.28 (d, J = 7.6 Hz, 1 H), 7.45 (d, J = 9.0 Hz, 1 H), 7.66 (s, 1 H), 9.84 (s, 1 H) | 526 |
| 80 | 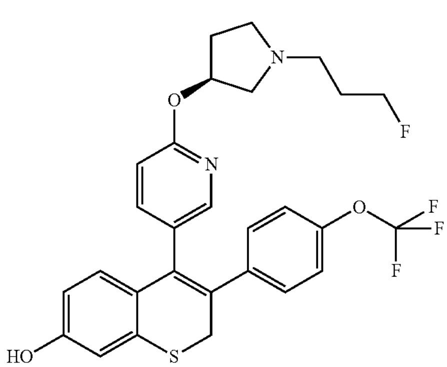 [SMILES: Oc1ccc2c(c1)SCC(c1ccc(OC(F)(F)F)cc1)=C2c1ccc(O[C@H]2CCN(CCCF)C2)nc1] | 4-[6-[(3S)-1-(3-fluoropropyl)pyrrolidin-3-yl]oxy-3-pyridyl]-3-[4-(trifluoromethoxy)phenyl]-2H-thiochromen-7-ol | A | 1H NMR (400 MHz, DMSO-d6) δ 1.78 (m, 3H), 2.21 (m, 1H), 2.34 (m, 1H), 2.44 (m, 2H), 2.56 (d, J = 10.76 Hz, 1H), 2.70 (m, 2H), 3.79 (m, 2H), 4.47 (dt, J = 47.5 et 6.0 Hz, 2 H), 5.26 (m, 1H), 6.50 (dd, J = 8.5 et 2.5 Hz, 1H), 6.58 (d, J = 8.5 Hz, 1H), 6.69 (d, J = 8.5 Hz, 1H), 6.78 (d, J = 2.5 Hz, 1H), 7.18 (m, 4H), 7.30 (dd, J = 8.5 et 2.2 Hz, 1H), 7.62 (d, J = 2.2 Hz, 1H), 9.87 (s, 1H) | 547 |

TABLE 1-continued

| Example | Structure | Name | Method | NMR | MASS LC/MS (m/z, MH+) |
|---|---|---|---|---|---|
| 81 | 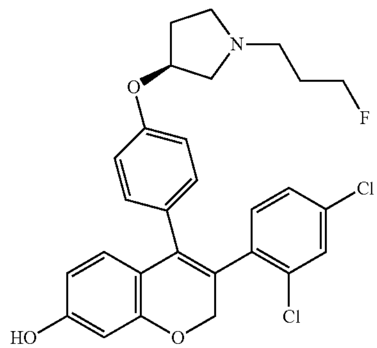 [SMILES: Oc1ccc2c(c1)OCC(c1ccc(Cl)cc1Cl)=C2c1ccc(O[C@H]2CCN(CCCF)C2)cc1] | 3-(2,4-dichlorophenyl)-4-[4-[(3S)-1-(3-fluoropropyl)pyrrolidin-3-yl]oxyphenyl]-2H-chromen-7-ol | A | 1H NMR (400 MHz, DMSO-d6) δ ppm: 1.78 (m, 3 H), 2.23 (m, 1 H), 2.39 (m, 1 H), 2.47 (m, 2 H), 2.58 (m, 1 H), 2.65 (m, 1 H), 2.82 (m, 1 H), 3.37 (m, 2 H), 4.48 (dt, J = 47.6 et 6.0 Hz, 2 H), 4.75-4.95 (m, 3 H), 6.32 (m, 2 H), 6.58 (d, J = 8.6 Hz, 1 H), 6.77 (d, J = 8.2 Hz, 2 H), 6.95 (d, J = 8.2 Hz, 2 H), 7.07 (d, J = 8.4 Hz, 1 H), 7.22 (dd, J = 8.4 et 2.0 Hz, 1 H), 7.56 (d, J = 2.0 Hz, 1 H), 9.74 (s, 1 H) | 514 |
| 82 | 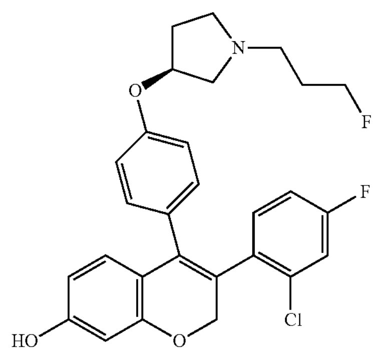 [SMILES: Oc1ccc2c(c1)OCC(c1ccc(F)cc1Cl)=C2c1ccc(O[C@H]2CCN(CCCF)C2)cc1] | 3-(2-chloro-4-fluoro-phenyl)-4-[4-[(3S)-1-(3-fluoropropyl)pyrrolidin-3-yl]oxyphenyl]-2H-chromen-7-ol | A | 1H NMR (400 MHz, DMSO-d6) δ ppm: 1.76 (m, 3 H), 2.21 (m, 1 H), 2.38 (m, 1 H), 2.46 (m, 2 H), 2.56 (dd, J = 10.3 et 2.7 Hz, 1 H), 2.67 (m, 1 H), 2.81 (dd, J = 10.3 et 6.2 Hz, 1 H), 4.47 (dt, J = 47.4 et 6.0 Hz, 2 H), 4.70-4.90 (m, 3 H), 6.31 (m, 2 H), 6.57 (d, J = 8.3 Hz, 1 H), 6.75 (d, J = 8.8 Hz, 2 H), 6.94 (d, J = 8.1 Hz, 2 H), 7.04 (m, 1 H), 7.15 (m, 1 H), 7.39 (dd, J = 8.8, 2.6 Hz, 1 H), 9.73 (s, 1 H) | 498 |
| 83 | 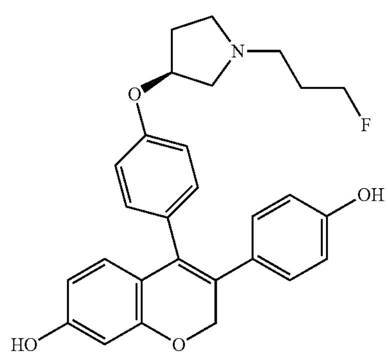 [SMILES: Oc1ccc(C2=C(c3ccc(O[C@H]4CCN(CCCF)C4)cc3)c3ccc(O)cc3OC2)cc1] | 4-[4-[(3S)-1-(3-fluoropropyl)pyrrolidin-3-yl]oxyphenyl]-3-(4-hydroxyphenyl)-2H-chromen-7-ol | A | 1H NMR (400 MHz, DMSO-d6) δ ppm: 1.80 (m, 3 H), 2.26 (m, 1 H), 2.42 (m, 3 H), 2.61 (dd, J = 10.4 et 2.3 Hz, 1 H), 2.70 (m, 1 H), 2.84 (dd, J = 10.3 et 6.2 Hz, 1 H), 4.49 (dt, J = 47.4 et 6.0 Hz, 2 H), 4.82 (m, 1 H), 4.94 (s, 2 H), 6.27 (dd, J = 8.2 et 2.0 Hz, 1 H), 6.30 (d, J = 2.0 Hz, 1 H), 6.49 (d, J = 8.2 Hz, 2 H), 6.80 (m, 4 H), 6.94 (d, J = 8.4 Hz, 2 H), 9.35 (s, 1 H), 9.58 (s, 1 H) | 462 |
| 84 | 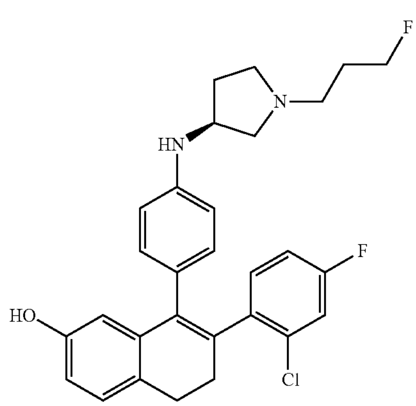 [SMILES: Oc1ccc2c(c1)C(c1ccc(N[C@H]3CCN(CCCF)C3)cc1)=C(c1ccc(F)cc1Cl)CC2] | 7-(2-chloro-4-fluoro-phenyl)-8-[4-[[(3S)-1-(3-fluoropropyl)pyrrolidin-3-yl]amino]phenyl]-5,6-dihydronaphthalen-2-ol | | 1H NMR (400 MHz, DMSO-d6) δ ppm: 1.53 (m, 1 H), 1.76 (m, 2 H), 2.14 (m, 1 H), 2.29 (dd, J = 9.2 et 4.6 Hz, 1 H), 2.35-2.65 (m, 6 H), 2.79 (m, 3 H), 3.76 (m, 1 H), 4.49 (dt, J = 47.6 et 6.0 Hz, 2 H), 5.63 (d, J = 6.6 Hz, 1 H), 6.27 (d, J = 2.3 Hz, 1 H), 6.38 (d, J = 8.3 Hz, 2 H), 6.55 (dd, J = 8.1 et 2.4 Hz, 1 H), 6.71 (d, J = 7.8 Hz, 2 H), 7.02 (m, 3 H), 7.32 (dd, J = 8.9 et 2.4 Hz, 1 H), 8.98 (s, 1 H) | 495 |

TABLE 1-continued

| Example | Structure | Name | Method | NMR | MASS LC/MS (m/z, MH+) |
|---|---|---|---|---|---|
| 85 | 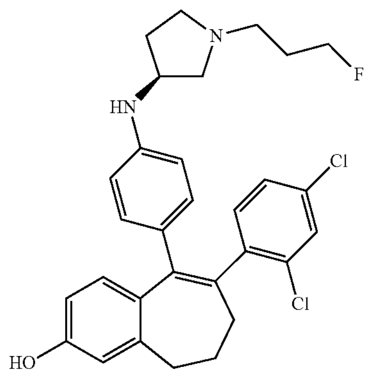 [SMILES: Oc1ccc2c(c1)CCCC(c1ccc(Cl)cc1Cl)=C2c1ccc(N[C@H]2CCN(CCCF)C2)cc1] | 6-(2,4-dichlorophenyl)-5-[4-[[(3S)-1-(3-fluoropropyl)pyrrolidin-3-yl]amino]phenyl]-8,9-dihydro-7H-benzo[7]annulen-2-ol | A | 1H NMR (400 MHz, DMSO-d6) δ ppm: 1.50 (m, 1 H), 1.77 (m, 2 H), 2.06 (m, 5 H), 2.27 (dd, J = 9.1, 4.6 Hz, 1 H), 2.42 (m, 3 H), 2.55 (s, 1 H), 2.68 (m, 3 H), 3.73 (m, 1 H), 4.47 (dt, J = 47.4, 6.0 Hz, 2 H), 5.64 (d, J = 6.5 Hz, 1 H), 6.26 (d, J = 8.6 Hz, 2 H), 6.52 (d, J = 8.6 Hz, 2 H), 6.56 (dd, J = 8.3, 2.2 Hz, 1 H), 6.61 (d, J = 8.3 Hz, 1 H), 6.69 (d, J = 2.2 Hz, 1 H), 7.13 (d, J = 8.3 Hz, 1 H), 7.23 (dd, J = 8.3, 2.0 Hz, 1 H), 7.54 (d, J = 2.0 Hz, 1 H), 9.40 (s, 1 H) | 525 |
| 86 | 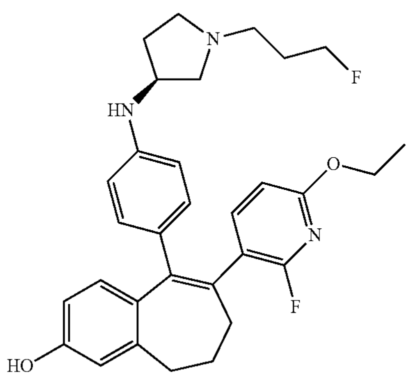 [SMILES: CCOc1ccc(C2=C(c3ccc(N[C@H]4CCN(CCCF)C4)cc3)c3ccc(O)cc3CCC2)c(F)n1] | 6-(6-ethoxy-2-fluoro-3-pyridyl)-5-[4-[[(3S)-1-(3-fluoropropyl)pyrrolidin-3-yl]amino]phenyl]-8,9-dihydro-7H-benzo[7]annulen-2-ol | A | 1H NMR (400 MHz, DMSO-d6) δ ppm: 1.28 (t, J = 7.0 Hz, 3 H), 1.50 (m, 1 H), 1.78 (m, 2 H), 2.01 (m, 5 H), 2.28 (dd, J = 9.2 et 4.5 Hz, 1 H), 2.43 (m, 3 H), 2.7 (m, 1 H), 2.65 (d, J = 7.0 Hz, 2 H), 2.75 (dd, J = 9.0 et 7.0 Hz, 1 H), 3.74 (m, 1 H), 4.18 (q, J = 7.1 Hz, 2 H), 4.47 (dt, J = 47.4 et 6.1 Hz, 2 H), 5.66 (d, J = 6.6 Hz, 1 H), 6.29 (d, J = 8.6 Hz, 2 H), 6.58 (m, 5 H), 6.68 (d, J = 2.3 Hz, 1 H), 7.55 (dd, J = 10.0 et 8.2 Hz, 1 H), 9.39 (s, 1 H) | 520 |
| 87 | 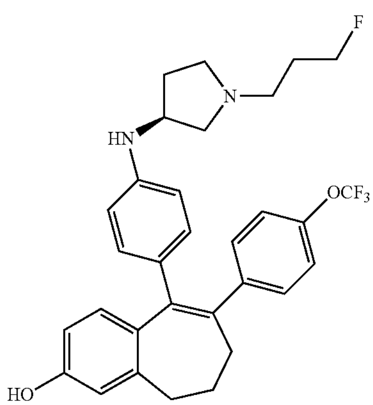 [SMILES: Oc1ccc2c(c1)CCCC(c1ccc(OC(F)(F)F)cc1)=C2c1ccc(N[C@H]2CCN(CCCF)C2)cc1] | 5-[4-[[(3S)-1-(3-fluoropropyl)pyrrolidin-3-yl]amino]phenyl]-6-[4-(trifluoromethoxy)phenyl]-8,9-dihydro-7H-benzo[7]annulen-2-ol | A | 1H NMR (400 MHz, DMSO-d6) δ ppm: 1.51 (d, J = 5.9 Hz, 1 H), 1.78 (m, 2 H), 2.00-2.20 (m, 3 H), 2.27 (m, 3 H), 2.40-2.60 (m, 4 H), 2.65 (t, J = 6.8 Hz, 2 H), 2.74 (t, J = 7.9 Hz, 1 H), 3.74 (m, 1 H), 4.47 (dt, J = 47.4 et 5.9 Hz, 2 H), 5.64 (d, J = 6.5 Hz, 1 H), 6.27 (d, J = 8.3 Hz, 2 H), 6.53 (m, 3 H), 6.61 (m, 1 H), 6.67 (s, 1 H), 7.15 (d, J = 8.0 Hz, 2 H), 7.24 (d, J = 8.0 Hz, 2 H), 9.36 (s, 1 H) | 541 |
| 88 | 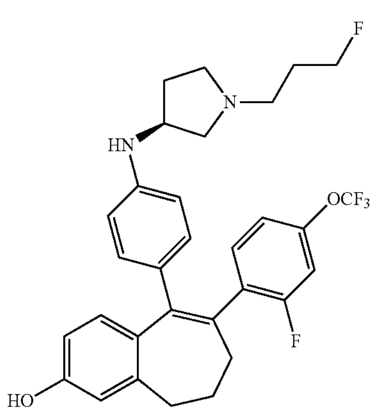 [SMILES: Oc1ccc2c(c1)CCCC(c1ccc(OC(F)(F)F)cc1F)=C2c1ccc(N[C@H]2CCN(CCCF)C2)cc1] | 5-[4-[[(3S)-1-(3-fluoropropyl)pyrrolidin-3-yl]amino]phenyl]-6-[2-fluoro-4-(trifluoromethoxy)phenyl]-8,9-dihydro-7H-benzo[7]annulen-2-ol | A | 1H NMR (400 MHz, CDCl3) δ ppm: 1.32 (m, 1 H), 1.62 (m, 1 H), 1.94 (m, 2 H), 2.13 (m, 2 H), 2.27 (m, 3 H), 2.42 (m, 1 H), 2.56 (m, 3 H), 2.67 (m, 1 H), 2.75 (t, J = 7.0 Hz, 2 H), 2.82 (td, J = 8.6 et 4.8 Hz, 1 H), 3.81 (m, 1 H), 3.92 (d, J = 1.4 Hz, 1 H), 4.50 (dt, J = 47.4 et 6.0 Hz, 2 H), 6.25 (d, J = 8.7 Hz, 2 H), 6.60 (dd, J = 8.4 et 2.5 Hz, 1 H), 6.67 (m, 2 H), 6.73 (d, J = 2.5 Hz, 1 H), 6.88 (m, 3 H), 7.10 (t, J = 8.6 Hz, 1 H) | 559 |

TABLE 1-continued

| Example | Structure | Name | Method | NMR | MASS LC/MS (m/z, MH+) |
|---|---|---|---|---|---|
| 89 | 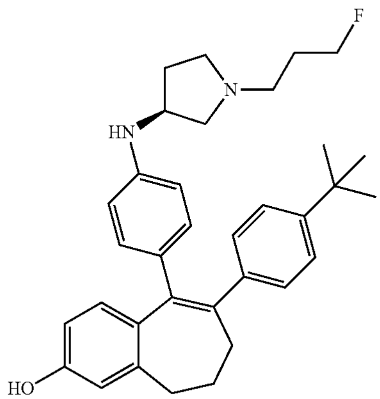 [SMILES: CC(C)(C)c1ccc(C2=C(c3ccc(N[C@H]4CCN(CCCF)C4)cc3)c3ccc(O)cc3CCC2)cc1] | 6-(4-tert-butylphenyl)-5-[4-[[(3S)-1-(3-fluoropropyl)pyrrolidin-3-yl]amino]phenyl]-8,9-dihydro-7H-benzo[7]annulen-2-ol | A | 1H NMR (400 MHz, CDCl3) δ ppm: 1.28 (s, 9 H), 1.64 (m, 1 H), 1.91 (m, 2 H), 2.12 (q, J = 6.9 Hz, 2 H), 2.26 (m, 1 H), 2.38 (m, 3 H), 2.58 (m, 3 H), 2.69 (m, 3 H), 2.82 (m, 1 H), 3.76 (s, 1 H), 3.93 (m, 1 H), 4.49 (dt, J = 47.5 et 6.0 Hz, 2 H), 6.26 (d, J = 8.7 Hz, 2 H), 6.58 (dd, J = 8.4 et 2.8 Hz, 1 H), 6.68 (d, J = 8.7 Hz, 2 H), 6.71 (d, J = 2.8 Hz, 1 H), 6.81 (d, J = 8.4 Hz, 1 H), 7.08 (d, J = 8.5 Hz, 2 H), 7.15 (d, J = 8.5 Hz, 2 H) | 513 |
| 90 | 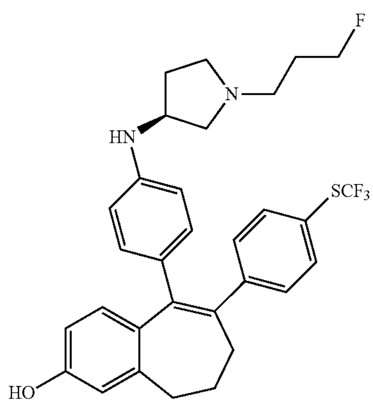 | 5-[4-[[(3S)-1-(3-fluoropropyl)pyrrolidin-3-yl]amino]phenyl]-6-[4-(trifluoromethylsulfanyl)phenyl]-8,9-dihydro-7H-benzo[7]annulen-2-ol | A | 1H NMR (400 MHz, CDCl3) δ ppm: 1.65 (m, 1 H), 1.91 (m, 2 H), 2.14 (d, J = 7.0 Hz, 2 H), 2.26 (m, 1 H), 2.39 (m, 3 H), 2.59 (m, 3 H), 2.66 (m, 1 H), 2.72 (t, J = 7.0 Hz, 2 H), 2.84 (td, J = 8.6, 4.8 Hz, 1 H), 3.78 (m, 1 H), 3.93 (s, 1 H), 4.51 (dt, J = 47.4 et 5.9 Hz, 2 H), 6.23 (d, J = 8.5 Hz, 2 H), 6.59 (dd, J = 8.3 et 2.8 Hz, 1 H), 6.62 (d, J = 8.5 Hz, 1 H), 6.72 (d, J = 2.8 Hz, 1 H), 6.82 (d, J = 8.4 Hz, 1 H), 7.19 (d, J = 8.4 Hz, 2 H), 7.41 (d, J = 8.4 Hz, 2 H) | 557 |
| 91 | 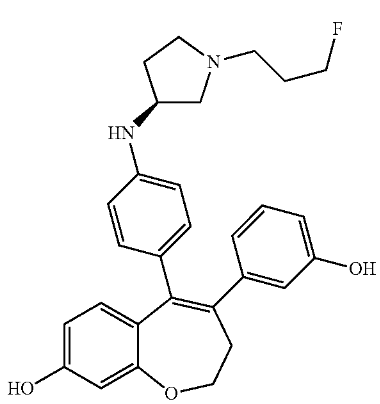 [SMILES: Oc1cccc(C2=C(c3ccc(N[C@H]4CCN(CCCF)C4)cc3)c3ccc(O)cc3OCC2)c1] | 5-[4-[[(3S)-1-(3-fluoropropyl)pyrrolidin-3-yl]oxyphenyl]-4-(3-hydroxyphenyl)-2,3-dihydro-1-benzoxepin-8-ol | A | 1H NMR (400 MHz, DMSO-d6) δ ppm: 1.76 (m, 3 H), 2.23 (m, 1 H), 2.39 (m, 1 H), 2.45 (m, 3 H), 2.56 ( m, 2 H), 2.68 (m, 1 H), 2.81 (dd, J = 10.1 et 6.2 Hz, 1 H), 4.42 (m, 2 H), 4.47 (dt, J = 47.5 et 6.0 Hz, 2 H), 4.75 (m, 1 H), 6.50 (m, 6 H), 6.64 (d, J = 8.7 Hz, 2 H), 6.77 (d, J = 8.6 Hz, 2 H), 6.95 (t, J = 7.9 Hz, 1 H), 9.18 (s, 1 H), 9.59 (s, 1 H) | 476 |

TABLE 1-continued

| Example | Structure | Name | Method | NMR | MASS LC/MS (m/z, MH+) |
|---|---|---|---|---|---|
| 92 | 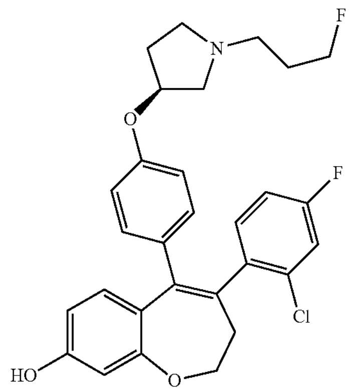 [SMILES: Oc1ccc2c(c1)OCCC(c1ccc(F)cc1Cl)=C2c1ccc(O[C@H]2CCN(CCCF)C2)cc1] | 4-(2-chloro-4-fluoro-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.74 (m, 3 H), 2.20 (m, 1 H), 2.37-2.54 (m, 5 H), 2.66 (m, 2 H), 2.78 (dt, J = 10.4 et 5.4 Hz, 1 H), 4.35-4.55 (m, 4 H), 4.73 (m, 1 H), 6.45-6.55 (m, 3 H), 6.64 (d, J = 8.7 Hz, 2 H), 6.76 (d, J = 8.7 Hz, 2 H), 7.03 (m, 2 H), 7.41 (dd, J = 8.8 et 2.2 Hz, 1 H), 9.67 (s, 1 H) | 512 |
| 93 | 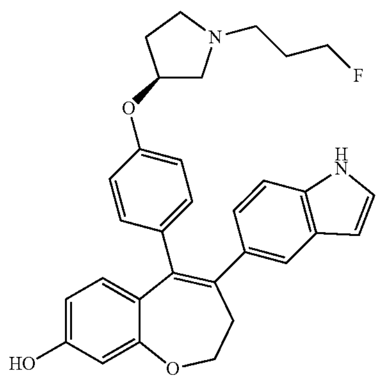 [SMILES: Oc1ccc2c(c1)OCCC(c1ccc3[nH]ccc3c1)=C2c1ccc(O[C@H]2CCN(CCCF)C2)cc1] | 5-[4-[(3S)-1-(3-fluoropropyl)pyrrolidin-3-yl]oxyphenyl]-4-(1H-indol-5-yl)-2,3-dihydro-1-benzoxepin-8-ol | A | 1H NMR (400 MHz, DMSO-d6) δ 1.72 (m, 3H), 2.18 (m, 1H), 2.38 (m, 1H), 2.44 (t, J = 7.2 Hz, 3H), 2.52 (m, 1H), 2.65 (m, 3H), 2.77 (dd, J = 10.2 et 6.2 Hz, 1H), 4.46 (t, J = 6.0 Hz, 2H), 4.47 (dt, J = 47.5 et 6.0 Hz, 2 H), 4.71 (m, 1H), 6.28 (s, 1H), 6.46 (m, 2H), 6.58 (m, 3H), 6.78 (m, 3H), 7.14 (d, J = 8.4 Hz, 1H), 7.25 (t, J = 20 Hz, 1H), 7.31 (s, 1H), 9.52 (s, 1H), 10.95 (s, 1H) | 499 |
| 94 | 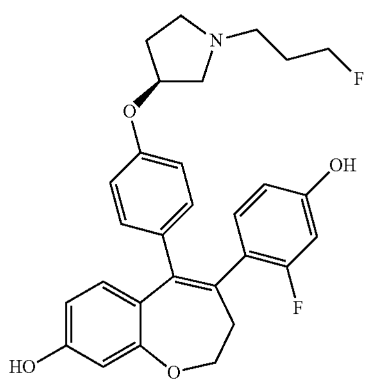 [SMILES: Oc1ccc(C2=C(c3ccc(O[C@H]4CCN(CCCF)C4)cc3)c3ccc(O)cc3OCC2)c(F)c1] | 4-(2-fluoro-4-hydroxy-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.31 (t, J = 7.0 Hz, 3 H), 1.73 (m, 3 H), 2.19 (m, 1 H), 2.38 (m, 1 H), 2.46 (m, 4 H), 2.54 (m, 1 H), 2.66 (m, 1 H), 2.79 (dd, J = 10.3 et 6.2 Hz, 1 H), 3.34 (m, J = 6.7 Hz, 2 H), 4.08 (m, 2 H), 4.46 (dt, J = 47.4 et 6.0 Hz, 2 H), 4.76 (m, 1 H), 6.62-6.75 (m, 6 H), 6.88 (dd, J = 11.7 et 7.0 Hz, 1 H), 6.99 (m, 1 H), 7.04 (d, J = 2.3 Hz, 1 H), 9.76 (s, 1 H) | 494 |
| 95 | 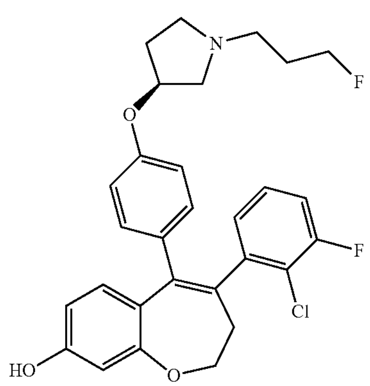 [SMILES: Oc1ccc2c(c1)OCCC(c1cccc(F)c1Cl)=C2c1ccc(O[C@H]2CCN(CCCF)C2)cc1] | 4-(2-chloro-3-fluoro-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.74 (m, 3 H), 2.19 (m, 1 H), 2.37-2.55 (m, 6 H), 2.66 (m, 1 H), 2.78 (m, 1 H), 4.45 (m, 2 H), 4.46 (dt, J = 47.5 et 6.0 Hz, 2 H), 4.73 (m, 1 H), 6.48 (m, 2 H), 6.56 (d, J = 8.0 Hz, 1 H), 6.64 (d, J = 8.8 Hz, 2 H), 6.76 (d, J = 8.8 Hz, 2 H), 6.86 (m, 1 H), 7.15 (m, 2 H), 9.66 (s, 1 H) | 512 |

TABLE 1-continued

| Example | Structure | Name | Method | NMR | MASS LC/MS (m/z, MH+) |
|---|---|---|---|---|---|
| 96 | 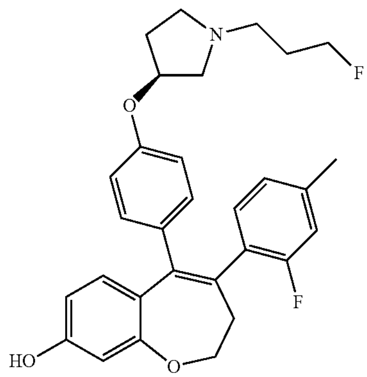 [SMILES: Cc1ccc(C2=C(c3ccc(O[C@H]4CCN(CCCF)C4)cc3)c3ccc(O)cc3OCC2)c(F)c1] | 4-(2-fluoro-4-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.76 (m, 3 H), 2.22 (m, 4 H), 2.38 (m, 1 H), 2.46 (m, 3 H), 2.55 (m, 2 H), 2.65 (m, 1 H), 2.79 (dd, J = 10.3 et 6.1 Hz, 1 H), 4.46 (dt, J = 47.4 et 6.1 Hz, 2 H), 4.44 (t, J = 6.1 Hz, 2 H), 4.46 (dt, J = 47.4 et 6.1 Hz, 2 H), 4.74 (m, 1 H), 6.47 (m, 2 H), 6.53 (m, 1 H), 6.63 (d, J = 8.6 Hz, 2 H), 6.77 (m, 3 H), 6.89 (m, 2 H), 9.62 (s, 1 H) | 492 |
| 97 | 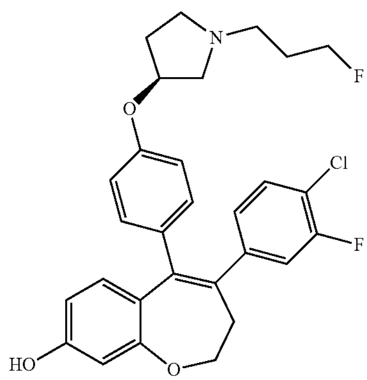 [SMILES: Oc1ccc2c(c1)OCCC(c1ccc(Cl)c(F)c1)=C2c1ccc(O[C@H]2CCN(CCCF)C2)cc1] | 4-(4-chloro-3-fluoro-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.75 (m, 3 H), 2.21 (m, 1 H), 2.38 (m, 1 H), 2.45-2.70 (m, 6 H), 2.80 (dd, J = 10.1 et 6.1 Hz, 1 H), 4.43 (m, 2 H), 4.46 (dt, J = 47.5 et 6.0 Hz, 2 H), 4.78 (m, 1 H), 6.50 (m, 3 H), 6.69 (d, J = 8.6 Hz, 2 H), 6.79 (d, J = 8.6 Hz, 2 H), 6.89 (d, J = 8.3 Hz, 1 H), 7.10 (d, J = 10.9 Hz, 1 H), 7.35 (t, J = 8.1 Hz, 1 H), 9.67 (s, 1 H) | 512 |
| 98 | 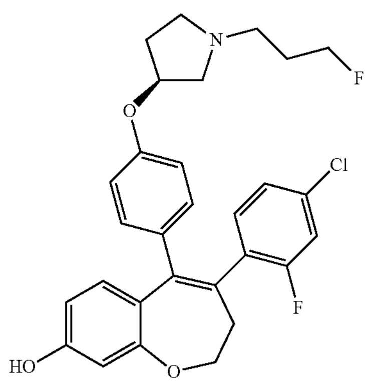 [SMILES: Oc1ccc2c(c1)OCCC(c1ccc(Cl)cc1F)=C2c1ccc(O[C@H]2CCN(CCCF)C2)cc1] | 4-(4-chloro-2-fluoro-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.75 (m, 3 H), 2.21 (m, 1 H), 2.38 (m, 1 H), 2.45 (m, 2 H), 2.57 (m, 3 H), 2.63 (m, 1 H), 2.80 (dd, J = 10.3 et 6.1 Hz, 1 H), 4.44 (m, 2 H), 4.47 (dt, J = 47.8 et 6.0 Hz, 2 H), 4.75 (m, 1 H), 6.48 (m, 2 H), 6.54 (d, J = 8.4 Hz, 1 H), 6.66 (d, J = 8.7 Hz, 2 H), 6.75 (d, J = 8.7 Hz, 2 H), 7.08 (m, 2 H), 7.29 (d, J = 10.0 Hz, 1 H), 9.67 (s, 1 H) | 512 |
| 99 | 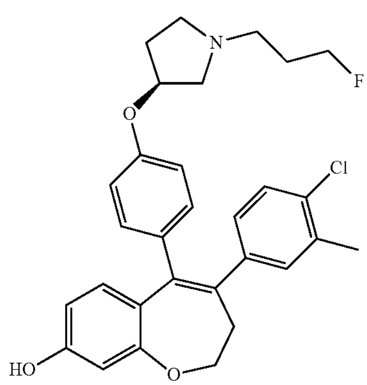 [SMILES: Cc1cc(C2=C(c3ccc(O[C@H]4CCN(CCCF)C4)cc3)c3ccc(O)cc3OCC2)ccc1Cl] | 4-(4-chloro-3-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.31 (t, J = 7.0 Hz, 3 H), 1.75 (m, 3 H), 2.19 (m, 1 H), 2.35-2.55 (m, 6 H), 2.65 (m, 1 H), 2.79 (dd, J = 10.3 et 6.2 Hz, 1 H), 3.34 (m, 2 H), 4.07 (q, J = 6.9 Hz, 2 H), 4.46 (dt, J = 47.4 et 6.0 Hz, 2 H), 4.74 (m, 1 H), 6.64 (m, 2 H), 6.71 (m, 4 H), 6.85 (m, 2 H), 7.05 (d, J = 2.1 Hz, 1 H), 9.77 (s, 1 H) | 508 |

TABLE 1-continued

| Example | Structure | Name | Method | NMR | MASS LC/MS (m/z, MH+) |
|---|---|---|---|---|---|
| 100 | 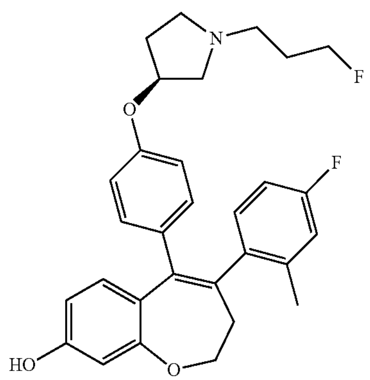 [SMILES: Cc1cc(F)ccc1C1=C(c2ccc(O[C@H]3CCN(CCCF)C3)cc2)c2ccc(O)cc2OCC1] | 4-(4-fluoro-2-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.74 (m, 3 H), 2.10 (s, 3 H), 2.19 (m, 1 H), 2.37 (m, 1 H), 2.44 (m, 2 H), 2.55 (m, 3 H), 2.62 (m, 1 H), 2.78 (dd, J = 10.3 et 6.2 Hz, 1 H), 4.44 (m, 2 H), 4.46 (dt, J = 47.4 et 6.0 Hz, 2 H), 4.73 (m, 1 H), 6.49 (m, 2 H), 6.59 (m, 3 H), 6.70 (d, J = 8.7 Hz, 2 H), 6.90 (m, 2 H), 7.05 (t, J = 6.8 Hz, 1 H), 9.60 (s, 1 H) | 492 |
| 101 | 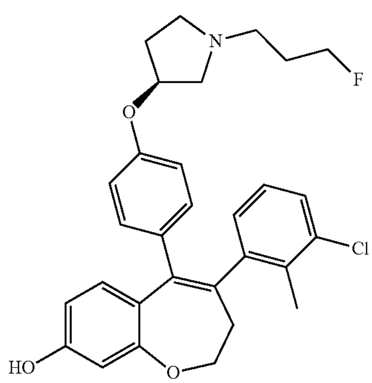 [SMILES: Cc1c(Cl)cccc1C1=C(c2ccc(O[C@H]3CCN(CCCF)C3)cc2)c2ccc(O)cc2OCC1] | 4-(3-chloro-2-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.77 (m, 3 H), 2.15 (s, 3 H), 2.18 (m, 1 H), 2.37 (m, 1 H), 2.44 (m, 2 H), 2.55 (m, 3 H), 2.62 (m, 1 H), 2.77 (m, 1 H), 4.45 (m, 2 H), 4.47 (dt, J = 46.7 et 7.1 Hz, 2 H), 4.73 (m, 1 H), 6.49 (m, 2 H), 6.56 (d, J = 8.6 Hz, 1 H), 6.61 (d, J = 8.6 Hz, 2 H), 6.70 (d, J = 8.6 Hz, 2 H), 7.02 (d, J = 8.3 Hz, 1 H), 7.08 (t, J = 7.6 Hz, 1 H), 7.21 (d, J = 7.7 Hz, 1 H), 9.63 (s, 1 H) | 508 |
| 102 | 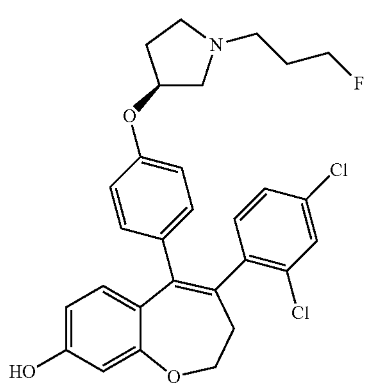 | 4-(2,4-dichlorophenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.76 (m, 3 H), 2.21 (m, 1 H), 2.37 (m, 1 H), 2.45 (d, J = 6.2 Hz, 2 H), 2.54 (m, 3 H), 2.64 (m, 1 H), 2.79 (dt, J = 10.2 et 5.2 Hz, 1 H), 4.45 (m, 2 H), 4.47 (dt, J = 47.9 et 5.9 Hz, 2 H), 4.74 (m, 1 H), 6.48 (m, 2 H), 6.53 (d, J = 8.5 Hz, 1 H), 6.65 (d, J = 8.7 Hz, 2 H), 6.76 (d, J = 8.7 Hz, 2 H), 7.02 (d, J = 8.3 Hz, 1 H), 7.21 (dd, J = 8.3 et 2.0 Hz, 1 H), 7.58 (d, J = 2.1 Hz, 1 H), 9.68 (s, 1 H) | 528 |
| 103 | 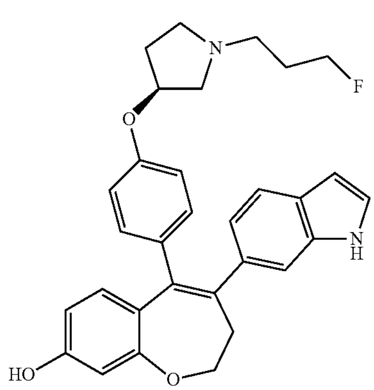 [SMILES: Oc1ccc2c(c1)OCCC(c1ccc3cc[nH]c3c1)=C2c1ccc(O[C@H]2CCN(CCCF)C2)cc1] | 5-[4-[(3S)-1-(3-fluoropropyl)pyrrolidin-3-yl]oxyphenyl]-4-(1H-indol-6-yl)-2,3-dihydro-1-benzoxepin-8-ol | A | 1H NMR (400 MHz, DMSO-d6) δ ppm: 1.74 (m, 3 H), 2.18 (m, 1 H), 2.42-2.55 (m, 8H), 2.64 (m, 1 H), 2.77 (dd, J = 10.3 et 6.2 Hz, 1 H), 4.46 (dt, J = 47.5 et 6.0 Hz, 2 H), 4.71 (m, 1 H), 6.31 (s, 1 H), 6.49 (m, 2 H), 6.55 (d, J = 8.0 Hz, 1 H), 6.59 (d, J = 8.0 Hz, 2 H), 6.77 (m, 3 H), 7.11 (s, 1 H), 7.25 (t, J = 2.6 Hz, 1 H), 7.32 (d, J = 8.2 Hz, 1 H), 9.57 (s, 1 H), 10.92 (s, 1 H) | 499 |

TABLE 1-continued

| Example | Structure | Name | Method | NMR | MASS LC/MS (m/z, MH+) |
|---|---|---|---|---|---|
| 104 | 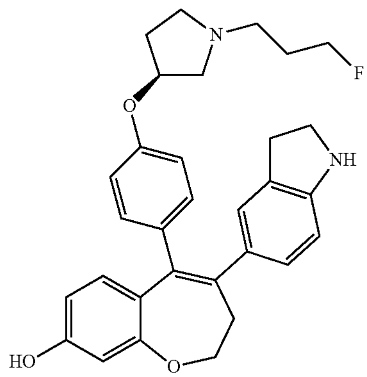 [SMILES: Oc1ccc2c(c1)OCCC(c1ccc3c(c1)CCN3)=C2c1ccc(O[C@H]2CCN(CCCF)C2)cc1] | 5-[4-[(3S)-1-(3-fluoropropyl)pyrrolidin-3-yl]oxyphenyl]-4-indolin-5-yl-2,3-dihydro-1-benzoxepin-8-ol | A | 1H NMR (400 MHz, DMSO-d6) δ ppm: 1.77 (m, 3 H), 2.22 (m, 1 H), 2.39 (m, 1 H), 2.46 (m, 3 H), 2.56 (m, 3 H), 2.66 (m, 1 H), 2.76 (d, J = 8.4 Hz, 1 H), 2.81 (dd, J = 10.3 et 6.2 Hz, 1 H), 3.35 (t, J = 7.8 Hz, 2 H), 4.42 (m, 2 H), 4.46 (dt, J = 47.5 et 6.0 Hz, 2 H), 4.77 (m, 1 H), 5.39 (m, 1 H), 6.25 (d, J = 7.9 Hz, 1 H), 6.45 (m, 2 H), 6.51 (d, J = 8.2 Hz, 1 H), 6.62 (m, 3 H), 6.78 (m, 3 H), 9.46 (s, 1 H) | 501 |
| 105 | 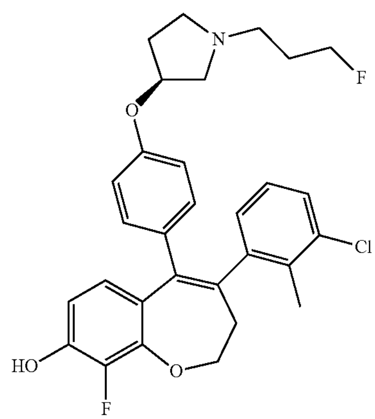 [SMILES: Cc1c(Cl)cccc1C1=C(c2ccc(O[C@H]3CCN(CCCF)C3)cc2)c2ccc(O)c(F)c2OCC1] | 4-(3-chloro-2-methyl-phenyl)-9-fluoro-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.74 (m, 3 H), 2.15 (s, 3 H), 2.20 (m, 1 H), 2.38 (m, 1 H), 2.45 (t, J = 7.0 Hz, 2 H), 2.55 (3H, m), 2.63 (m, 1 H), 2.77 (dd, J = 10.2 et 6.2 Hz, 1 H), 4.47 (dt, J = 47.4 et 6.2 Hz, 2 H), 4.52 (m, 2 H), 4.74 (m, 1 H), 6.37 (d, J = 8.7 Hz, 1 H), 6.63 (m, 3 H), 6.71 (d, J = 8.5 Hz, 2 H), 7.03 (d, J = 7.7 Hz, 1 H), 7.10 (t, J = 7.7 Hz, 1 H), 7.24 (d, J = 7.7 Hz, 1 H), 10.06 (s, 1 H) | 526 |
| 106 | 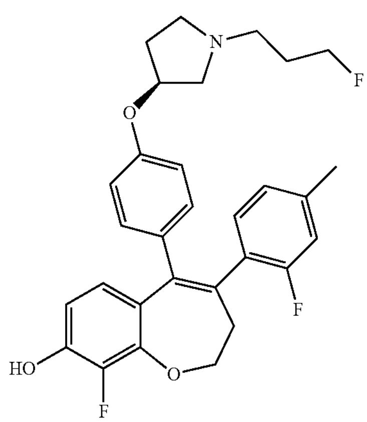 [SMILES: Cc1ccc(C2=C(c3ccc(O[C@H]4CCN(CCCF)C4)cc3)c3ccc(O)c(F)c3OCC2)c(F)c1] | 9-fluoro-4-(2-fluoro-4-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.75 (m, 3 H), 2.20 (m, 1 H), 2.23 (s, 3 H), 2.37 (m, 1 H), 2.45 (m, 2 H), 2.52 (m, 1 H), 2.57 (m, 2 H), 2.65 (m, 1 H), 2.79 (dd, J = 10.3 et 6.4 Hz, 1 H), 4.47 (dt, J = 47.4 et 6.2 Hz, 2 H), 4.52 (m, 2 H), 4.74 (m, 1 H), 6.34 (dd, J = 8.7 et 1.6 Hz, 1 H), 6.62 (m, 3 H), 6.77 (d, J = 8.8 Hz, 2 H), 6.81 (d, J = 7.8 Hz, 1 H), 6.91 (m, 2 H), 10.07 (s, 1 H) | 510 |

TABLE 1-continued

| Example | Structure | Name | Method | NMR | MASS LC/MS (m/z, MH+) |
|---|---|---|---|---|---|
| 107 | 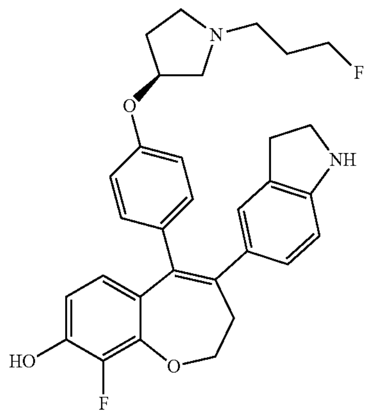 [SMILES: Oc1ccc2c(c1F)OCCC(c1ccc3c(c1)CCN3)=C2c1ccc(O[C@H]2CCN(CCCF)C2)cc1] | 9-fluoro-5-[4-[(3S)-1-(3-fluoropropyl)pyrrolidin-3-yl]oxyphenyl]-4-indolin-5-yl-2,3-dihydro-1-benzoxepin-8-ol | A | 1H NMR (400 MHz, DMSO-d6) δ ppm: 1.77 (m, 3 H), 2.20 (m, 1 H), 2.39 (m, 1 H), 2.47 (m, 3 H), 2.58 (m, 3 H), 2.67 (m, 1 H), 2.75 (m, 4 H), 4.47 (dt, J = 47.4 et 6.2 Hz, 2 H), 4.49 (m, 2 H), 4.77 (m, 1 H), 5.47 (s, 1 H), 6.25 (d, J = 8.2 Hz, 1 H), 6.32 (d, J = 8.9 Hz, 1 H), 6.57-6.73 (m, 4 H), 6.78 (m, 3 H), 9.92 (s, 1 H) | 519 |
| 108 | 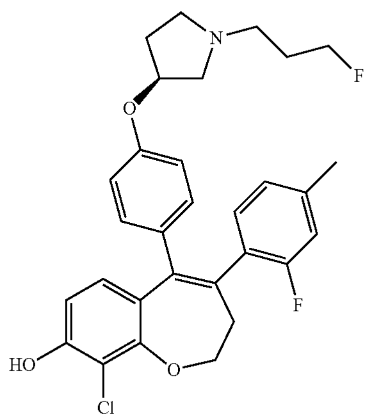 [SMILES: Cc1ccc(C2=C(c3ccc(O[C@H]4CCN(CCCF)C4)cc3)c3ccc(O)c(Cl)c3OCC2)c(F)c1] | 9-chloro-4-(2-fluoro-4-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.75 (m, 3 H), 2.20 (m, 1 H), 2.24 (s, 3 H), 2.38 (m, 1 H), 2.45-2.55 (m, 5 H), 2.65 (m, 1 H), 2.79 (dd, J = 10.2 et 6.2 Hz, 1 H), 4.46 (dt, J = 47.4 et 6.0 Hz, 2 H), 4.53 (m, 2 H), 4.73 (m, 1 H), 6.52 (d, J = 8.7 Hz, 1 H), 6.65 (d, J = 8.5 Hz, 2 H), 6.69 (d, J = 8.7 Hz, 1 H), 6.77 (d, J = 8.5 Hz, 2 H), 6.82 (d, J = 8.9 Hz, 1 H), 6.92 (m, 2 H), 9.35 (s, 1 H) | 526 |
| 109 | 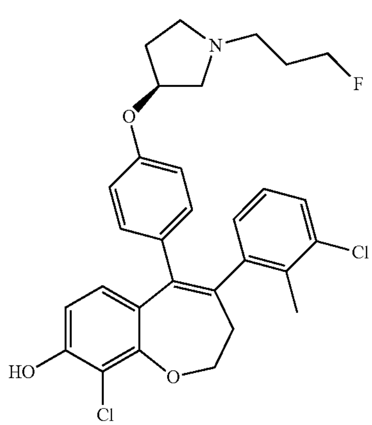 [SMILES: Cc1c(Cl)cccc1C1=C(c2ccc(O[C@H]3CCN(CCCF)C3)cc2)c2ccc(O)c(Cl)c2OCC1] | 9-chloro-4-(3-chloro-2-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.74 (m, 3 H), 2.13 (s, 3 H), 2.20 (m, 1 H), 2.37 (m, 1 H), 2.44 (m, 2 H), 2.55 (m, 3 H), 2.66 (m, 1 H), 2.78 (dd, J = 9.9 et 6.2 Hz, 1 H), 4.47 (dt, J = 47.4 et 6.2 Hz, 2 H), 4.55 (m, 2 H), 4.74 (m, 1 H), 6.55 (d, J = 8.7 Hz, 1 H), 6.62 (d, J = 8.8 Hz, 2 H), 6.72 (m, 3 H), 7.05 (d, J = 7.6 Hz, 1 H), 7.11 (t, J = 7.6 Hz, 1 H), 7.25 (d, J = 7.6 Hz, 1 H), 10.37 (s, 1 H) | 542 |

TABLE 1-continued

| Example | Name | Method | NMR | MASS LC/MS (m/z, MH+) |
|---|---|---|---|---|
| 110 | 5-[4-[(3S)-1-(3-fluoropropyl)pyrrolidin-3-yl]oxyphenyl]-4-(1H-indol-4-yl)-2,3-dihydro-1-benzoxepin-8-ol | A | 1H NMR (400 MHz, DMSO-d6) δ ppm: 1.50(m, 1 H), 1.77(m, 2 H), 2.00-2.20 (m, 5 H), 2.27 (dd, J = 9.1 et 4.6 Hz, 1 H), 2.42 (m, 3 H), 2.55 (m, 1 H), 2.68 (m, 3 H), 3.73 (m, 1 H), 4.47 (dt, J = 47.4 et 6.0 Hz, 2 H), 5.64 (d, J = 6.5 Hz, 1 H), 6.26 (d, J = 8.6 Hz, 2 H), 6.52 (d, J = 8.6 Hz, 2 H), 6.56 (dd, J = 8.3 et 2.2 Hz, 1 H), 6.61 (d, J = 8.3 Hz, 1 H), 6.69 (d, J = 2.2 Hz, 1 H), 7.13 (d, J = 8.3 Hz, 1 H), 7.23 (dd, J = 8.3 et 2.0 Hz, 1 H), 7.54 (d, J = 2.0 Hz, 1 H), 9.40 (s, 1 H) | 499 |
| 111 | 4-(2-fluoro-4-methyl-phenyl)-5-[4-[(3S)-1-(3-fluoropropyl)pyrrolidin-3-yl]oxyphenyl]-9-methyl-2,3-dihydro-1-benzoxepin-8-ol | A | 1H NMR (400 MHz, DMSO-d6) δ ppm: 1.75 (m, 3 H), 2.08 (s, 3 H), 2.21 (m, 1 H), 2.23 (s, 3 H), 2.37 (q, J = 7.7 Hz, 1 H), 2.46 (m, 4 H), 2.55 (m, 1 H), 2.68 (m, 1 H), 2.79 (dd, J = 10.2 et 6.2 Hz, 1 H), 4.42 (m, 2 H), 4.46 (dt, J = 47.5 et 6.0 Hz, 2 H), 4.74 (m, 1 H), 6.38 (d, J = 8.4 Hz, 1 H), 6.52 (d, J = 8.4 Hz, 1 H), 6.62 (d, J = 8.6 Hz, 2 H), 6.75 (d, J = 8.6 Hz, 2 H), 6.80 (d, J = 7.8 Hz, 1 H), 6.89 (m, 2 H), 9.51 (s, 1 H) | 506 |
| 112 | 4-(3-chloro-2-methyl-phenyl)-5-[4-[(3S)-1-(3-fluoropropyl)pyrrolidin-3-yl]oxyphenyl]-9-methyl-2,3-dihydro-1-benzoxepin-8-ol | A | 1H NMR (400 MHz, DMSO-d6) δ ppm: 1.73 (m, 3 H), 2.10 (s, 3 H), 2.14 (s, 3 H), 2.19 (m, 1 H), 2.35 (m, 1 H), 2.45 (m, 4 H), 2.54 (m, 1 H), 2.65 (m, 1 H), 2.77 (dd, J = 10.2 et 6.2 Hz, 1 H), 4.44 (m, 2 H), 4.47 (dt, J = 47.5 et 6.0 Hz, 2 H), 4.75 (m, 1 H), 6.41 (d, J = 8.4 Hz, 1 H), 6.54 (d, J = 8.4 Hz, 1 H), 6.59 (d, J = 8.7 Hz, 2 H), 6.72 (d, J = 8.7 Hz, 2 H), 7.06 (m, 2 H), 7.23 (d, J = 7.6 Hz, 1 H), 9.52 (s, 1 H) | 522 |

TABLE 1-continued

| Example | Structure | Name | Method | NMR | MASS LC/MS (m/z, MH+) |
|---|---|---|---|---|---|
| 113 | 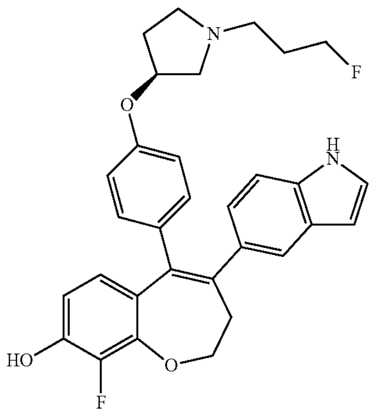 [SMILES: Oc1ccc2c(c1F)OCCC(c1ccc3[nH]ccc3c1)=C2c1ccc(O[C@H]2CCN(CCCF)C2)cc1] | 9-fluoro-5-[4-[(3S)-1-(3-fluoropropyl)pyrrolidin-3-yl]oxyphenyl]-4-(1H-indol-5-yl)-2,3-dihydro-1-benzoxepin-8-ol | A | 1H NMR (400 MHz, DMSO-d6) δ ppm: 1.75 (m, 3 H), 2.19 (m, 1 H), 2.36 (m, 1 H), 2.47 (m, 2 H), 2.50-2.75 (m, 4 H), 2.78 (dd, J = 10.2 et 6.2 Hz, 1 H), 4.46 (dt, J = 47.4 et 6.0 Hz, 2 H), 4.52 (m, 2 H), 4.72 (m, 1 H), 6.29 (m, 1 H), 6.35 (d, J = 8.8 Hz, 1 H), 6.60 (m, 3 H), 6.80 (m, 3 H), 7.16 (d, J = 8.4 Hz, 1 H), 7.26 (t, J = 2.6 Hz, 1 H), 7.33 (s, 1 H), 9.95 (s, 1 H), 10.99 (s, 1 H) | 517 |
| 114 | 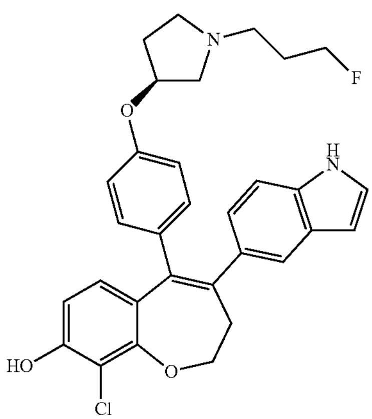 [SMILES: Oc1ccc2c(c1Cl)OCCC(c1ccc3[nH]ccc3c1)=C2c1ccc(O[C@H]2CCN(CCCF)C2)cc1] | 9-chloro-5-[4-[(3S)-1-(3-fluoropropyl)pyrrolidin-3-yl]oxyphenyl]-4-(1H-indol-5-yl)-2,3-dihydro-1-benzoxepin-8-ol | A | 1H NMR (400 MHz, DMSO-d6) δ ppm: 1.75 (m, 3 H), 2.18 (m, 1 H), 2.34 (m, 1 H), 2.45 (t, J = 7.3 Hz, 2 H), 2.53 (m, 1 H), 2.63 (m, 3 H), 2.77 (dd, J = 10.3 et 6.2 Hz, 1 H), 4.46 (dt, J = 47.4 et 6.0 Hz, 2 H), 4.52 (m, 2 H), 4.72 (m, 1 H), 6.29 (s, 1 H), 6.52 (d, J = 8.6 Hz, 1 H), 6.59 (d, J = 8.7 Hz, 2 H), 6.68 (d, J = 8.7 Hz, 1 H), 6.78 (d, J = 8.6 Hz, 2 H), 6.82 (dd, J = 8.5 et 1.3 Hz, 1 H), 7.16 (d, J = 8.4 Hz, 1 H), 7.26 (t, J = 2.7 Hz, 1 H), 7.34 (s, 1 H), 10.25 (s, 1 H), 10.99 (s, 1 H) | 533 |
| 115 | 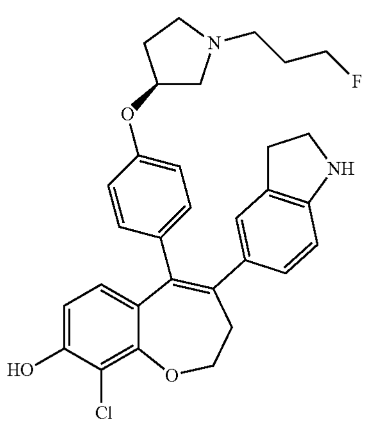 [SMILES: Oc1ccc2c(c1Cl)OCCC(c1ccc3c(c1)CCN3)=C2c1ccc(O[C@H]2CCN(CCCF)C2)cc1] | 9-chloro-5-[4-[(3S)-1-(3-fluoropropyl)pyrrolidin-3-yl]oxyphenyl]-4-indolin-5-yl-2,3-dihydro-1-benzoxepin-8-ol | A | 1H NMR (400 MHz, DMSO-d6) δ ppm: 1.74 (m, 3 H), 2.20 (m, 1 H), 2.38 (m, 1 H), 2.46-2.60 (m, 5 H), 2.67 (m, 1 H), 2.80 (m, 3 H), 3.36 (m, 2 H), 4.46 (dt, J = 47.4 et 6.0 Hz, 2 H), 4.52 (m, 2 H), 4.79 (m, 1 H), 5.47 (s, 1 H), 6.26 (d, J = 8.1 Hz, 1 H), 6.49 (d, J = 8.7 Hz, 1 H), 6.67 (m, 4 H), 6.79 (d, J = 8.8 Hz, 3 H), 10.21 (s, 1 H) | 535 |

TABLE 1-continued

| Example | Structure | Name | Method | NMR | MASS LC/MS (m/z, MH+) |
|---|---|---|---|---|---|
| 116 | 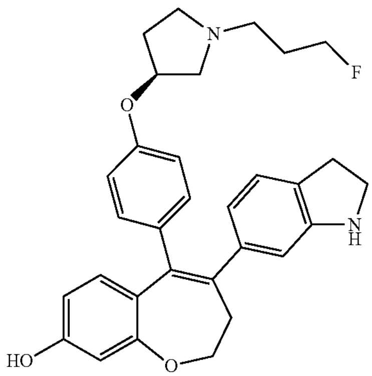 [SMILES: Oc1ccc2c(c1)OCCC(c1ccc3c(c1)NCC3)=C2c1ccc(O[C@H]2CCN(CCCF)C2)cc1] | 5-[4-[(3S)-1-(3-fluoropropyl)pyrrolidin-3-yl]oxyphenyl]-4-indolin-6-yl-2,3-dihydro-1-benzoxepin-8-ol | B | 1H NMR (400 MHz, DMSO-d6) δ ppm: 1.75 (m, 3 H), 2.20 (m, 1 H), 2.38 (m, 1 H), 2.45-2.60 (m, 5 H), 2.66 (m, 1 H), 2.81 (t, J = 8.3 Hz, 3 H), 3.35 (m, 2 H), 4.41 (m, 2 H), 4.47 (dt, J = 47.4 et 6.0 Hz, 2 H), 4.75 (m, 1 H), 5.31 (s, 1 H), 6.26 (m, 2 H), 6.43 (m, 2 H), 6.51 (d, J = 8.5 Hz, 1 H), 6.64 (d, J = 8.8 Hz, 2 H), 6.81 (m, 3 H), 9.55 (s, 1 H) | 501 |
| 117 | 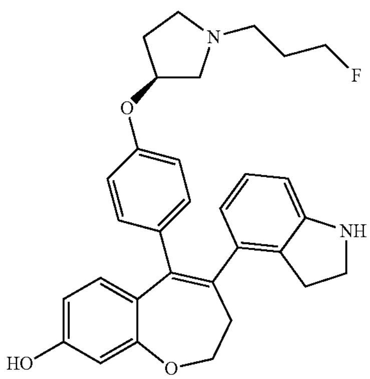 [SMILES: Oc1ccc2c(c1)OCCC(c1cccc3c1CCN3)=C2c1ccc(O[C@H]2CCN(CCCF)C2)cc1] | 5-[4-[(3S)-1-(3-fluoropropyl)pyrrolidin-3-yl]oxyphenyl]-4-indolin-4-yl-2,3-dihydro-1-benzoxepin-8-ol | B | H NMR (400 MHz, DMSO-d6) δ 1.76 (m, 3 H), 2.22 (m, 1 H), 2.38 (m, 1H), 2.45-2.60 (m, 5 H), 2.65 (m, 1 H), 2.79 (dd, J = 10.2 et 6.2 Hz, 1 H), 3.18 (m, 2 H), 4.43 (m, 2 H), 4.47 (dt, J = 47.4 et 6.0 Hz, 2 H), 4.75 (m, 1 H), 5.34 (s, 1 H), 6.29 (d, J = 7.5 Hz, 1 H), 6.35 (d, J = 7.5 Hz, 1 H), 6.48 (m, 2 H), 6.57 (d, J = 8.5 Hz, 1 H), 6.62 (d, J = 8.5 Hz, 2 H), 6.75 (d, J = 8.5 Hz, 2 H), 6.82 (t, J = 8.5 Hz, 1 H), 9.59 (s, 1H) | 501 |
| 118 | 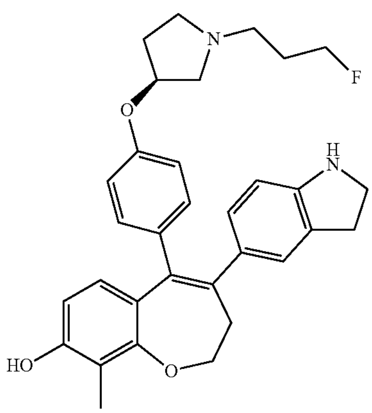 [SMILES: Cc1c(O)ccc2c1OCCC(c1ccc3c(c1)CCN3)=C2c1ccc(O[C@H]2CCN(CCCF)C2)cc1] | 5-[4-[(3S)-1-(3-fluoropropyl)pyrrolidin-3-yl]oxyphenyl]-4-indolin-5-yl-9-methyl-2,3-dihydro-1-benzoxepin-8-ol | A | 1H NMR (400 MHz, DMSO-d6) δ ppm: 1.77 (m, 3 H), 2.07 (s, 3 H), 2.21 (m, 1 H), 2.38 (m, 1H), 2.45-2.85 (m, 9 H), 3.39 (m, 2 H), 4.42 (t, J = 6.0 Hz, 2 H), 4.46 (dt, J = 47.5 et 6.0 Hz, 2 H), 4.77 (m, 1 H), 5.42 (s, 1 H), 6.25 (d, J = 8.1 Hz, 1 H), 6.35 (d, J = 8.4 Hz, 1 H), 6.49 (d, J = 8.4 Hz, 1 H), 6.63 (d, J = 8.7 Hz, 3 H), 6.75 (m, 3 H), 9.39 (s, 1 H) | 515 |
| 119 | 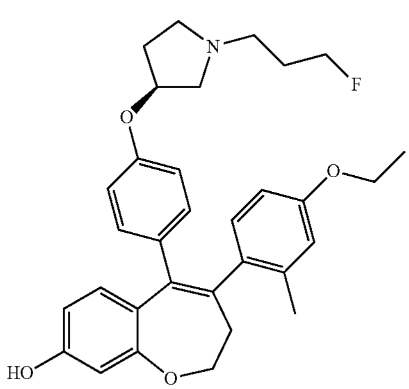 [SMILES: CCOc1ccc(C2=C(c3ccc(O[C@H]4CCN(CCCF)C4)cc3)c3ccc(O)cc3OCC2)c(C)c1] | 4-(4-ethoxy-2-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.28 (t, J = 6.9 Hz, 3 H), 1.73 (m, 3 H), 2.05 (s, 3 H), 2.19 (m, 1 H), 2.35 (m, 1 H), 2.45 (m, 5 H), 2.64 (m, 1 H), 2.78 (dd, J = 10.1 et 6.3 Hz, 1 H), 3.93 (q, J = 6.9 Hz, 2 H), 4.41 (m, 2 H), 4.46 (dt, J = 47.5 et 6.0 Hz, 2 H), 4.72 (m, 1 H), 6.44 (m, 2 H), 6.59 (m, 5 H), 6.70 (d, J = 8.3 Hz, 2 H), 6.92 (d, J = 8.1 Hz, 1 H), 9.60 (s, 1 H) | 518 |

TABLE 1-continued

| Example | Structure | Name | Method | NMR | MASS LC/MS (m/z, MH+) |
|---|---|---|---|---|---|
| 120 | 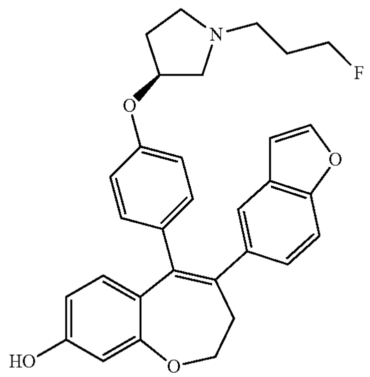 [SMILES: Oc1ccc2c(c1)OCCC(c1ccc3occc3c1)=C2c1ccc(O[C@H]2CCN(CCCF)C2)cc1] | 4-(benzofuran-5-yl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ 1.72 (m, 3H), 2.18 (m, 1H), 2.34 (m, 1H), 2.44 (m, 3H), 2.57 (m, 3H), 2.77 (dd, J = 10.3 et 6.2 Hz, 1H), 4.46 (dt, J = 47.5 et 6.0 Hz, 2 H), 4.47 (d, J = 5.9 Hz, 2H), 4.72 (m, 1H), 6.48 (m, 2H), 6.55 (d, J = 8,0, 1H), 6.60 (d, J = 8.6 Hz, 2H), 6.76 (d, J = 8.6 Hz, 2H), 6.84 (d, J = 1.5 Hz, 1H), 7.01 (dd, J = 8.6 et 1.6 Hz, 1H), 7.37 (d, J = 8.6 Hz, 1H), 7.40 (s, 1H), 7.92 (d, J = 2.1 Hz, 1H), 9.62 (s, 1H) | 500 |
| 121 | 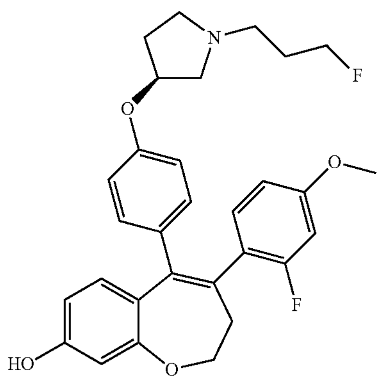 [SMILES: COc1ccc(C2=C(c3ccc(O[C@H]4CCN(CCCF)C4)cc3)c3ccc(O)cc3OCC2)c(F)c1] | 4-(2-fluoro-4-methoxyphenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.60-1.90 (m, 3 H), 2.13 (s, 3H), 2.19 (m, 1 H), 2.37 (m, 1 H), 2.40-2.55 (m, 5 H), 2.61 (m, 1 H), 2.78 (m, 1 H), 3.30 (m, 2 H), 4.46 (dt, J = 47.4 et 6.0 Hz, 2 H), 4.72 (m, 1 H), 6.60 (m, 4 H), 6.70 (m, 2H), 7.05 (d, J = 2.1 Hz, 1 H), 7.16 (m, 3 H), 9.72 (s, 1 H) | 508 |
| 122 | 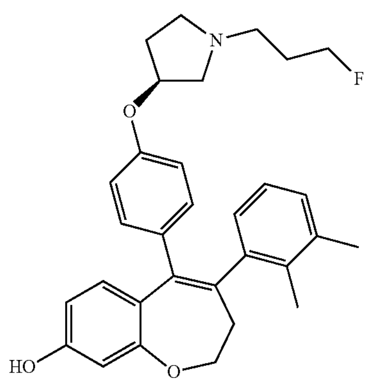 [SMILES: Cc1cccc(C2=C(c3ccc(O[C@H]4CCN(CCCF)C4)cc3)c3ccc(O)cc3OCC2)c1C] | 4-(2,3-dimethylphenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ 1.72 (m, 3H), 2.05 (s, 3H), 2.13 (s, 3H), 2.18 (m, 1H), 2.36 (m, 1H), 2.50 (m, 5H), 2.67 (m, 1H), 2.77 (m, 1H), 4.42 (m, 2H), 4.46 (dt, J = 47.5 et 6.0 Hz, 2 H), 4.72 (m, 1H), 6.48 (m, 2H), 6.56 (m, 3H), 6.69 (d, J = 8.4 Hz, 2H), 6.84 (m, 1H), 6.92 (m, 2H), 9.60 (s, 1H) | 488 |
| 123 | 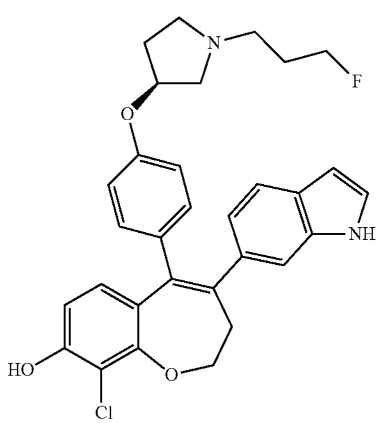 [SMILES: Oc1ccc2c(c1Cl)OCCC(c1ccc3cc[nH]c3c1)=C2c1ccc(O[C@H]2CCN(CCCF)C2)cc1] | 9-chloro-5-[4-[(3S)-1-(3-fluoropropyl)pyrrolidin-3-yl]oxyphenyl]-4-(1H-indol-6-yl)-2,3-dihydro-1-benzoxepin-8-ol | A | 1H NMR (400 MHz, DMSO-d6) δ 1.74 (m, 3H), 2.18 (m, 1H), 2.36 (m, 1H), 2.44 (m, 2H), 2.53 (s, 1H), 2.58-2.71 (m, 3H), 2.78 (dd, J = 10.27 et 6.11 Hz, 1H), 3.38 (m, 1H), 4.40 (t, J = 5.99 Hz, 1H), 4.53 (m, 3H), 4.72 (s, 1H), 6.32 (s, 1H), 6.52 (d, J = 8.5 Hz, 1H), 6.59 (d, J = 8.5 Hz, 2H), 6.69 (d, J = 8.56 Hz, 1H), 6.79 (d, J = 8.5 Hz, 3H), 7.13 (s, 1H), 7.25 (s, 1H), 7.33 (d, J = 8.2 Hz, 1H), 10.92 (s, 1H) | 533 |

TABLE 1-continued

| Example | Name | Method | NMR | MASS LC/MS (m/z, MH+) |
|---|---|---|---|---|
| 124 | 9-chloro-5-[4-[(3S)-1-(3-fluoropropyl)pyrrolidin-3-yl]oxyphenyl]-4-(1H-indol-4-yl)-2,3-dihydro-1-benzoxepin-8-ol | A | 1H NMR (400 MHz, DMSO-d6) δ ppm: 1.67 (m, 3 H), 2.15 (m, 1 H), 2.33 (m, 1 H), 2.44 (t, J = 7.2 Hz, 2 H), 2.64 (m, 4 H), 2.76 (dd, J = 10.2 et 6.2 Hz, 1 H), 4.45 (m, 4 H), 4.67 (t, J = 6.5 Hz, 1 H), 6.29 (s, 1 H), 6.50 (d, J = 8.6 Hz, 2 H), 6.55 (d, J = 8.7 Hz, 1 H), 6.64 (d, J = 7.2 Hz, 1 H), 6.72 (t, J = 8.0 Hz, 3 H), 6.88 (t, J = 7.6 Hz, 1 H), 7.19 (d, J = 8.1 Hz, 1 H), 7.26 (s, 1 H), 10.26 (s, 1 H), 11.02 (s, 1 H) | 533 |
| 125 | 9-chloro-5-[4-[(3S)-1-(3-fluoropropyl)pyrrolidin-3-yl]oxyphenyl]-4-indolin-6-yl-2,3-dihydro-1-benzoxepin-8-ol | B | 1H NMR (400 MHz, DMSO-d6) δ ppm: 1.63 (m, 3 H), 2.18 (m, 1 H), 2.38 (m, 1 H), 2.45 (s, 2 H), 2.56 (d, J = 10.8 Hz, 1 H), 2.67 (m, 1 H), 2.86 (m, 3 H), 3.39 (m, 4 H), 4.46 (m, 4 H), 4.76 (s, 1 H), 5.31 (s, 1 H), 6.25 (m, 2 H), 6.48 (d, J = 8.7 Hz, 1 H), 6.66 (m, 3 H), 6.84 (m, 3 H), 10.24 (s, 1 H) | 535 |
| 126 | 4-(3-fluoro-2-methyl-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ 1.68 (m, 1H), 1.78 (m, 2H), 1.99 (s, 3H), 2.19 (m, 1H), 2.38 (m, 1H), 2.44 (m, 4H), 2.56 (m, 1H), 2.63 (m, 1H), 2.78 (m, 1H), 4.44 (m, 2H), 4.46 (dt, J = 47.5 et 6.0 Hz, 2 H), 4.73 (m, 1H), 6.50 (m, 2H), 6.59 (m, 3H), 6.69 (d, J = 8.0 Hz, 2H), 6.93 (m, 2H), 7.09 (m, 1H), 9.66 (s, 1H) | 492 |

TABLE 1-continued

| Example | Name | Method | NMR | MASS LC/MS (m/z, MH+) |
|---|---|---|---|---|
| 127 | 4-(6-ethoxy-3-pyridyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.26 (t, J = 7.0 Hz, 3 H), 1.76 (m, 3 H), 2.21 (m, 1 H), 2.38 (m, 1 H), 2.46 (m, 2 H), 2.55 (m, 3 H), 2.62 (m, 1 H), 2.80 (dd, J = 10.3 et 6.1 Hz, 1 H), 4.20 (q, J = 7.1 Hz, 2 H), 4.46 (t, J = 5.9 Hz, 2 H), 4.47 (dt, J = 47.4 et 6.1 Hz, 2 H), 4.76 (m, 1 H), 6.48 (m, 2 H), 6.53 (d, J = 8 Hz, 1 H), 6.61 (d, J = 8.6 Hz, 1 H), 6.68 (d, J = 8.6 Hz, 2 H), 6.79 (d, J = 8.6 Hz, 2 H), 7.40 (dd, J = 8.6 et 2.4 Hz, 1 H), 7.82 (d, J = 2.4 Hz, 1 H), 9.64 (s, 1 H) | 505 |
| 128 | 9-chloro-5-[4-[(3S)-1-(3-fluoropropyl)pyrrolidin-3-yl]oxyphenyl]-4-indolin-4-yl-2,3-dihydro-1-benzoxepin-8-ol | B | 1H NMR (400 MHz, DMSO-d6) δ 1.72 (m, 4H), 1.96-2.32 (m, 1H), 2.40 (m, 5H), 2.61 (m, 2H), 2.79 (dd, J = 10.15, 6.24 Hz, 1H), 3.16 (m, 2H), 3.38 (m, 1H), 4.41 (t, J = 5.99 Hz, 1H), 4.49 (m, 3H), 4.75 (s, 1H), 5.34 (s, 1H), 6.30 (d, J = 7.70 Hz, 1H), 6.38 (d, J = 7.58 Hz, 1H), 6.54 (d, J = 8.5 Hz, 1H), 6.61 (d, J = 8.5Hz, 2H), 6.69 (d, J = 8.5 Hz, 1H), 6.77 (d, J = 8.3 Hz, 2H), 6.83 (t, J = 7.64 Hz, 1H), 10.28 (s, 1H) | 535 |
| 129 | 5-[4-[(3S)-1-(3-fluoropropyl)pyrrolidin-3-yl]oxyphenyl]-4-(1H-indol-6-yl)-9-methyl-2,3-dihydro-1-benzoxepin-8-ol | A | 1H NMR (400 MHz, DMSO-d6) δ ppm: 1.75 (m, 3 H), 2.09 (s, 3 H), 2.17 (m, 1 H), 2.38 (m, 1 H), 2.44 (m, 2 H), 2.54 (m, 1 H), 2.62 (m, 3 H), 2.79 (m, 1 H), 4.45 (t, J = 6.0 Hz, 2 H), 4.47 (dt, J = 47.5 et 6.0 Hz, 2 H), 4.71 (m, 1 H), 6.31 (s, 1 H), 6.39 (d, J = 8.4 Hz, 1 H), 6.52 (d, J = 8.4 Hz, 1 H), 6.57 (d, J = 8.7 Hz, 2 H), 6.78 (d, J = 8.6 Hz, 3 H), 7.12 (s, 1 H), 7.24 (t, J = 2.6 Hz, 1 H), 7.32 (d, J = 8.3 Hz, 1 H), 9.44 (s, 1 H), 10.91 (s, 1 H) | 513 |

TABLE 1-continued

| Example | Structure | Name | Method | NMR | MASS LC/MS (m/z, MH+) |
|---|---|---|---|---|---|
| 130 | 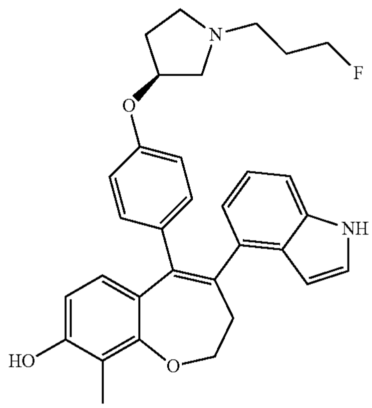 [SMILES: Cc1c(O)ccc2c1OCCC(c1cccc3[nH]ccc13)=C2c1ccc(O[C@H]2CCN(CCCF)C2)cc1] | 5-[4-[(3S)-1-(3-fluoropropyl)pyrrolidin-3-yl]oxyphenyl]-4-(1H-indol-4-yl)-9-methyl-2,3-dihydro-1-benzoxepin-8-ol | A | 1H NMR (400 MHz, DMSO-d6) δ ppm: 1.73 (m, 3 H), 2.10 (s, 3 H), 2.15 (m, 1 H), 2.36 (m, 1 H), 2.44 (t, J = 7.2 Hz, 2 H), 2.62 (m, 4 H), 2.75 (dd, J = 10.1 et 6.2 Hz, 1 H), 4.41 (m, 2 H), 4.44 (dt, J = 47.2 et 5.9 Hz, 2 H), 4.66 (m, 1 H), 6.29 (s, 1 H), 6.41 (d, J = 8.3 Hz, 1 H), 6.48 (d, J = 8.3 Hz, 2 H), 6.54 (d, J = 8.6 Hz, 1 H), 6.62 (d, J = 7.1 Hz, 1 H), 6.71 (d, J = 8.3 Hz, 2 H), 6.87 (t, J = 7.6 Hz, 1 H), 7.17 (d, J = 8.1 Hz, 1 H), 7.25 (s, 1 H), 9.46 (s, 1 H), 11.02 (s, 1 H) | 513 |
| 131 | 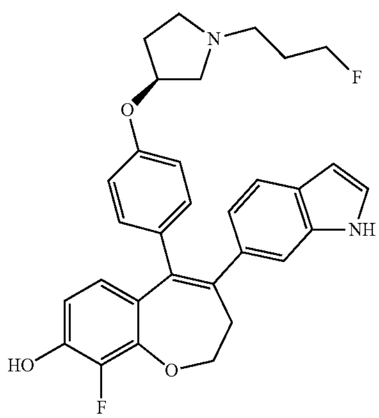 [SMILES: Oc1ccc2c(c1F)OCCC(c1ccc3cc[nH]c3c1)=C2c1ccc(O[C@H]2CCN(CCCF)C2)cc1] | 9-fluoro-5-[4-[(3S)-1-(3-fluoropropyl)pyrrolidin-3-yl]oxyphenyl]-4-(1H-indol-6-yl)-2,3-dihydro-1-benzoxepin-8-ol | A | 1H NMR (300 MHz, DMSO-d6) δ ppm: 1.60-1.90 (m, 3 H), 2.16 (m, 1 H), 2.36 (m, 1 H), 2.44 (t, J = 7 Hz, 2 H), 2.54 (m, 1 H), 2.60-2.80 (m, 4 H), 4.45 (dt, J = 47.6 et 6.0 Hz, 2 H), 4.52 (m, 2 H), 4.71 (m, 1 H), 6.33 (m, 2 H), 6.61 (m, 3 H), 6.79 (m, 3 H), 7.13 (s, 1 H), 7.25 (t, J = 2.7 Hz, 1 H), 7.33 (d, J = 8.2 Hz, 1 H), 9.92 (s, 1 H), 10.92 (s, 1 H) | 517 |
| 132 | 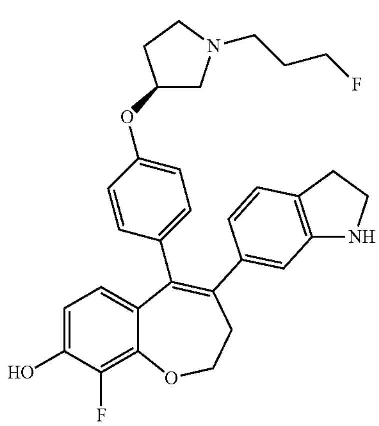 [SMILES: Oc1ccc2c(c1F)OCCC(c1ccc3c(c1)NCC3)=C2c1ccc(O[C@H]2CCN(CCCF)C2)cc1] | 9-fluoro-5-[4-[(3S)-1-(3-fluoropropyl)pyrrolidin-3-yl]oxyphenyl]-4-indolin-6-yl-2,3-dihydro-1-benzoxepin-8-ol | B | 1H NMR (400 MHz, DMSO-d6) δ ppm: 1.78 (m, 3 H), 2.23 (m, 1 H), 2.39 (m, 1 H), 2.47 (m, 2 H), 2.58 (m, 3 H), 2.65 (m, 1 H), 2.82 (m, 3 H), 3.37 (m, 2 H), 4.48 (dt, J = 47.6, 6.0 Hz, 2 H), 4.50 (d, J = 5.9 Hz, 2 H), 4.76 (m, 1 H), 5.32 (s, 1 H), 6.30 (m, 3 H), 6.63 (m, 3 H), 6.82 (m, 3 H), 9.94 (s, 1 H) | 519 |

TABLE 1-continued

| Example | Structure | Name | Method | NMR | MASS LC/MS (m/z, MH+) |
|---|---|---|---|---|---|
| 133 | 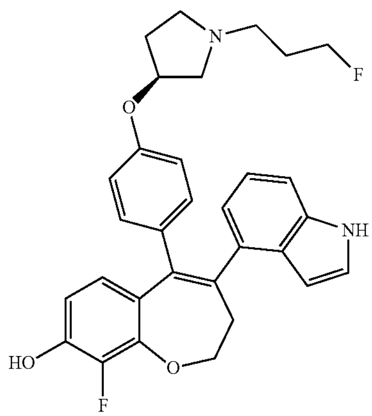 [SMILES: Oc1ccc2c(c1F)OCCC(c1cccc3[nH]ccc13)=C2c1ccc(O[C@H]2CCN(CCCF)C2)cc1] | 9-fluoro-5-[4-[(3S)-1-(3-fluoropropyl)pyrrolidin-3-yl]oxyphenyl]-4-(1H-indol-4-yl)-2,3-dihydro-1-benzoxepin-8-ol | A | 1H NMR (300 MHz, DMSO-d6) δ ppm: 1.74 (m, 3 H), 2.15 (m, 1 H), 2.36 (m, 1 H), 2.44 (m, 4 H), 2.57-2.79 (m, 4 H), 4.37 (t, J = 6.0 Hz, 1 H), 4.52 (q, J = 6.1 Hz, 3 H), 4.67 (m, 1 H), 6.30 (s, 1 H), 6.38 (d, J = 8.7 Hz, 1 H), 6.50 (d, J = 8.6 Hz, 2 H), 6.64 (m, 2 H), 6.73 (d, J = 8.5 Hz, 2 H), 6.88 (t, J = 7.6 Hz, 1 H), 7.19 (d, J = 8.1 Hz, 1 H), 7.27 (s, 1 H), 11.03 (s, 1 H) | 517 |
| 134 | 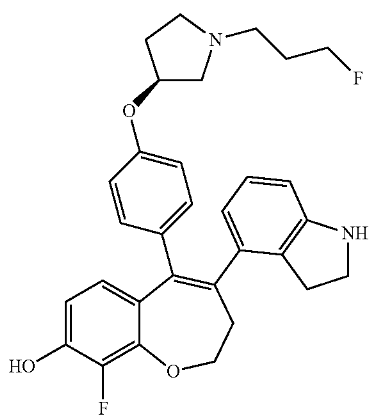 [SMILES: Oc1ccc2c(c1F)OCCC(c1cccc3c1CCN3)=C2c1ccc(O[C@H]2CCN(CCCF)C2)cc1] | 9-fluoro-5-[4-[(3S)-1-(3-fluoropropyl)pyrrolidin-3-yl]oxyphenyl]-4-indolin-4-yl-2,3-dihydro-1-benzoxepin-8-ol | B | 1H NMR (400 MHz, DMSO-d6) δ ppm: 1.76 (m, 3 H), 2.22 (m, 1 H), 2.39 (m, 2 H), 2.46 (m, 4 H), 2.56 (m, 2 H), 2.65 (m, 1 H), 2.80 (dd, J = 10.2 et 6.2 Hz, 1 H), 3.21 (m, 2 H), 4.47 (dt, J = 47.4 et 6.0 Hz, 2 H), 4.50 (m, 2 H), 4.76 (d, J = 6.6 Hz, 1 H), 5.35 (s, 1 H), 6.31 (d, J = 7.7 Hz, 1 H), 6.37 (d, J = 7.7 Hz, 2 H), 6.63 (m, 3 H), 6.78 (d, J = 8.7 Hz, 2 H), 6.83 (t, J = 7.7 Hz, 1 H), 9.97 (s, 1 H) | 519 |
| 135 | 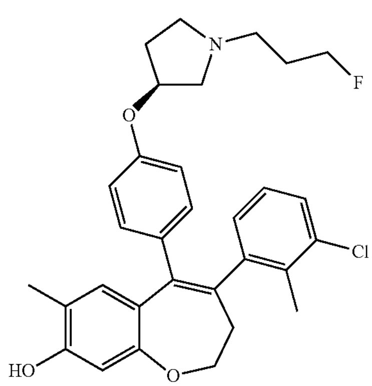 [SMILES: Cc1cc2c(cc1O)OCCC(c1cccc(Cl)c1C)=C2c1ccc(O[C@H]2CCN(CCCF)C2)cc1] | 4-(3-chloro-2-methyl-phenyl)-5-[4-[(3S)-1-(3-fluoropropyl)pyrrolidin-3-yl]oxyphenyl]-7-methyl-2,3-dihydro-1-benzoxepin-8-ol | A | 1H NMR (400 MHz, DMSO-d6) δ ppm: 1.75 (m, 3 H), 1.96 (s, 3 H), 2.13 (s, 3 H), 2.29 (m, 1 H), 2.33 (d, J = 1.6 Hz, 1 H), 2.44 (m, 2 H), 2.54 (m masqué, 3 H), 2.61 (m, 1 H), 2.78 (m, 1 H), 4.42 (m, 2 H), 4.46 (dt, J = 47.5 et 6.0 Hz, 2 H), 4.73 (m, 1 H), 6.45 (s, 1 H), 6.55 (s, 1 H), 6.61 (d, J = 8.6 Hz, 2 H), 6.69 (d, J = 8.6 Hz, 2 H), 7.00 (d, J = 7.6 Hz, 1 H), 7.08 (t, J = 7.6 Hz, 1 H), 7.22 (d, J = 7.6 Hz, 1 H), 9.58 (s, 1 H) | 522 |

TABLE 1-continued

| Example | Structure | Name | Method | NMR | MASS LC/MS (m/z, MH+) |
|---|---|---|---|---|---|
| 136 | 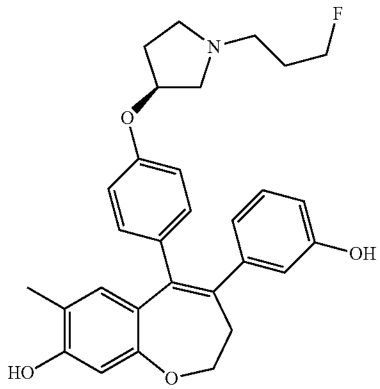 [SMILES: Cc1cc2c(cc1O)OCCC(c1cccc(O)c1)=C2c1ccc(O[C@H]2CCN(CCCF)C2)cc1] | 5-[4-[(3S)-1-(3-fluoropropyl)pyrrolidin-3-yl]oxyphenyl]-4-(3-hydroxyphenyl)-7-methyl-2,3-dihydro-1-benzoxepin-8-ol | A | 1H NMR (400 MHz, DMSO-d6) δ 1.79 (m, 3H), 1.94 (s, 3H), 2.21 (m, 1H), 2.36 (m, 1H), 2.45 (m, 4H), 2.56 (m, 1H), 2.66 (m, 1H), 2.81 (dd, J = 10.3 et 6.2 Hz, 1H), 4.41 (m, 2H), 4.46 (dt, J = 47.5 et 6.0 Hz, 2 H), 4.75 (m, 1H), 6.40 (s, 1H), 6.48 (m, 4H), 6.63 (d, J = 8.7 Hz, 2H), 6.77 (d, J = 8.7 Hz, 2H), 6.95 (m, 1H), 9.17 (s, 1H), 9.53 (s, 1H) | 490 |
| 137 | 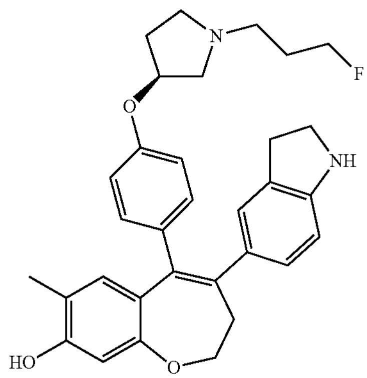 [SMILES: Cc1cc2c(cc1O)OCCC(c1ccc3c(c1)CCN3)=C2c1ccc(O[C@H]2CCN(CCCF)C2)cc1] | 5-[4-[(3S)-1-(3-fluoropropyl)pyrrolidin-3-yl]oxyphenyl]-4-indolin-5-yl-7-methyl-2,3-dihydro-1-benzoxepin-8-ol | A | 1H NMR (400 MHz, DMSO-d6) δ ppm: 1.78 (m, 3 H), 1.93 (s, 3 H), 2.19 (m, 1 H), 2.38 (m, 1 H), 2.46 (m, 2 H), 2.57 (m, 3 H), 2.66 (m, 1 H), 2.77 (m, 3 H), 3.35 (m, 2 H), 4.39 (dt, J = 11.5 et 5.9 Hz, 2 H), 4.46 (dt, J = 47.5 et 6.0 Hz, 2 H), 4.76 (m, 1 H), 5.42 (s, 1 H), 6.24 (d, J = 8.1 Hz, 1 H), 6.39 (s, 1 H), 6.49 (s, 1 H), 6.60 (d, J = 9.0 Hz, 1 H), 6.65 (d, J = 8.7 Hz, 2 H), 6.78 (m, 3 H), 9.44 (s, 1 H) | 515 |
| 138 | 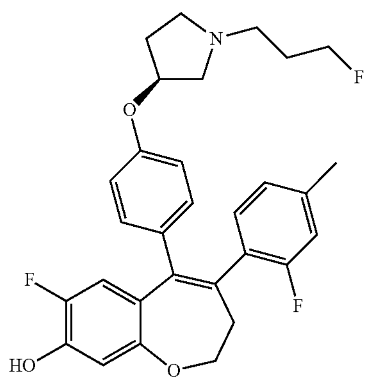 [SMILES: Cc1ccc(C2=C(c3ccc(O[C@H]4CCN(CCCF)C4)cc3)c3cc(F)c(O)cc3OCC2)c(F)c1] | 7-fluoro-4-(2-fluoro-4-methylphenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.80 (m, 3 H), 2.21 (m, 1 H), 2.24 (s, 3 H), 2.38 (m, 1 H), 2.45-2.60 (m, 5 H), 2.65 (m, 1 H), 2.79 (dd, J = 10.3 et 6.2 Hz, 1 H), 4.42 (m, 2 H), 4.46 (dt, J = 47.4 et 6.0 Hz, 2 H), 4.75 (m, 1 H), 6.38 (d, J = 8.9 Hz, 1 H), 6.65 (m, 3 H), 6.80 (m, 3 H), 6.90 (t, J = 8.5 Hz, 1 H), 10.18 (s, 1 H) | 510 |
| 139 | 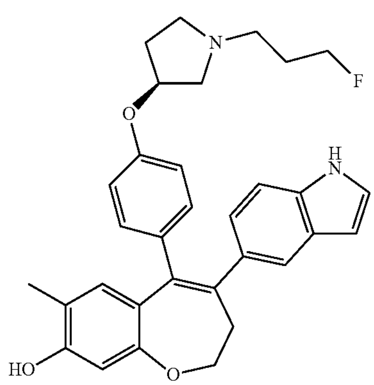 [SMILES: Cc1cc2c(cc1O)OCCC(c1ccc3[nH]ccc3c1)=C2c1ccc(O[C@H]2CCN(CCCF)C2)cc1] | 5-[4-[(3S)-1-(3-fluoropropyl)pyrrolidin-3-yl]oxyphenyl]-4-(1H-indol-5-yl)-7-methyl-2,3-dihydro-1-benzoxepin-8-ol | A | 1H NMR (400 MHz, DMSO-d6) δ ppm: 1.73 (m, 3 H), 1.95 (s, 3 H), 2.18 (m, 1 H), 2.37 (m, 1 H), 2.44 (m, 2 H), 2.54 (m, 1 H), 2.62 (m, 3 H), 2.77 (dd, J = 10.3 et 6.1 Hz, 1 H), 4.41 (m, 2 H), 4.46 (dt, J = 47.2 et 5.6 Hz, 2 H), 4.70 (m, 1 H), 6.28 (t, J = 2.0 Hz, 1 H), 6.42 (s, 1 H), 6.52 (s, 1 H), 6.58 (d, J = 8.8 Hz, 2 H), 6.78 (m, 3 H), 7.14 (d, J = 8.3 Hz, 1 H), 7.25 (t, J = 2.7 Hz, 1 H), 7.30 (s, 1 H), 9.52 (s, 1 H), 10.96 (s, 1 H) | 513 |

TABLE 1-continued

| Example | Structure | Name | Method | NMR | MASS LC/MS (m/z, MH+) |
|---|---|---|---|---|---|
| 140 | 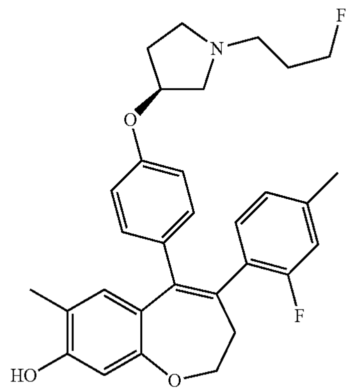 [SMILES: Cc1ccc(C2=C(c3ccc(O[C@H]4CCN(CCCF)C4)cc3)c3cc(C)c(O)cc3OCC2)c(F)c1] | 4-(2-fluoro-4-methyl-phenyl)-5-[4-[(3S)-1-(3-fluoropropyl)pyrrolidin-3-yl]oxyphenyl]-7-methyl-2,3-dihydro-1-benzoxepin-8-ol | A | 1H NMR (400 MHz, DMSO-d6) δ ppm: 1.71 (m, 3 H), 1.94 (s, 3 H), 2.23 (m, 4 H), 2.34 (m, 1 H), 2.45 (m masqué, 4 H), 2.56 (m, 1 H), 2.66 (m, 1 H), 2.79 (dd, J = 10.3, 6.2 Hz, 1 H), 4.40 (t, J = 7.0 Hz, 2H), 4.48 (dt, J = 47.2 et 5.6 Hz, 2 H), 4.74 (d, J = 6.8 Hz, 1 H), 6.40 (s, 1 H), 6.52 (s, 1 H), 6.63 (d, J = 8.8 Hz, 2 H), 6.76 (m, 3 H), 6.88 (m, 2 H), 9.57 (s, 1 H). | 506 |
| 141 | 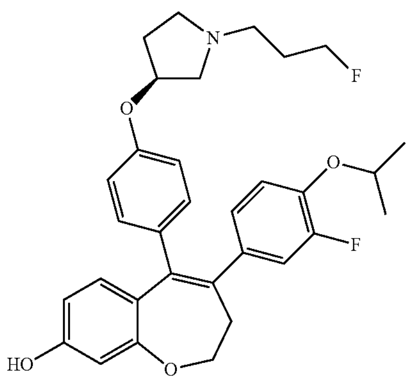 [SMILES: CC(C)Oc1ccc(C2=C(c3ccc(O[C@H]4CCN(CCCF)C4)cc3)c3ccc(O)cc3OCC2)cc1F] | 4-(3-fluoro-4-isopropoxy-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.23 (d, J = 6.0 Hz, 6 H), 1.76 (m, 3 H), 2.22 (m, 1 H), 2.38 (m, 1 H), 2.45 (m, 2 H), 2.65 (m, 4 H), 2.80 (dd, J = 10.3 et 6.2 Hz, 1 H), 4.40-4.55 (m, 5 H), 4.77 (m, 1 H), 6.47 (m, 2 H), 6.53 (d, J = 8.2 Hz, 1 H), 6.68 (d, J = 8.7 Hz, 2 H), 6.78 (m, 3 H), 6.87 (dd, J = 12.8 et 2.0 Hz, 1 H), 6.94 (t, J = 8.8 Hz, 1 H), 9.64 (s, 1 H) | 536 |
| 142 | 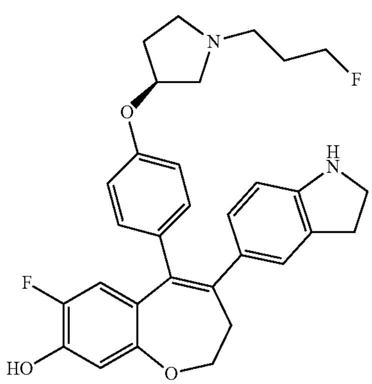 [SMILES: Oc1cc2c(cc1F)C(c1ccc(O[C@H]3CCN(CCCF)C3)cc1)=C(c1ccc3c(c1)CCN3)CCO2] | 7-fluoro-5-[4-[(3S)-1-(3-fluoropropyl)pyrrolidin-3-yl]oxyphenyl]-4-indolin-5-yl-2,3-dihydro-1-benzoxepin-8-ol | A | 1H NMR (400 MHz, DMSO-d6) δ ppm: 1.75 (m, 3 H), 2.22 (m, 1 H), 2.39 (m, 1 H), 2.44 (m, 2 H), 2.58 (m, 3 H), 2.66 (m, 1 H), 2.77 (m, 3 H), 3.30 (m, 2 H), 4.42 (m, 2 H), 4.48 (dt, J = 47.4 et 6.0 Hz, 2 H), 4.78 (m, 1 H), 5.46 (m, 1 H), 6.25 (d, J = 7.1 Hz, 1 H), 6.35 (d, J = 12.1 Hz, 1 H), 6.66 (m, 4 H), 6.80 (m, 3 H), 10.02 (s, 1 H). | 519 |
| 143 | 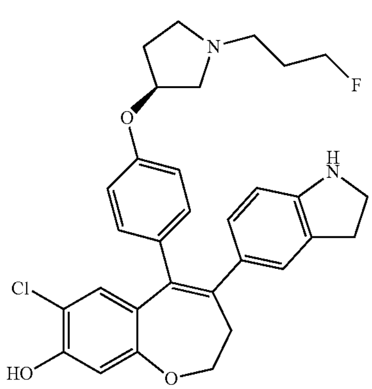 [SMILES: Oc1cc2c(cc1Cl)C(c1ccc(O[C@H]3CCN(CCCF)C3)cc1)=C(c1ccc3c(c1)CCN3)CCO2] | 7-chloro-5-[4-[(3S)-1-(3-fluoropropyl)pyrrolidin-3-yl]oxyphenyl]-4-indolin-5-yl-2,3-dihydro-1-benzoxepin-8-ol | A | 1H NMR (400 MHz, DMSO-d6) δ ppm: 1.76 (m, 3 H), 2.19 (m, 1 H), 2.30-2.80 (m, 8 H), 4.46 (dt, J = 47.4 et 5.9 Hz, 2 H), 4.48 (t, J = 5.7 Hz, 2 H), 4.74 (m, 1 H), 6.29 (s, 1 H), 6.62 (m, 3 H), 6.71 (s, 1 H), 6.79 (m, 3 H), 7.15 (d, J = 8.3 Hz, 1 H), 7.26 (t, J = 2.6 Hz, 1 H), 7.32 (s, 1 H), 10.37 (s, 1 H), 10.99 (s, 1 H). | 535 |

TABLE 1-continued

| Example | Structure | Name | Method | NMR | MASS LC/MS (m/z, MH+) |
|---|---|---|---|---|---|
| 144 | 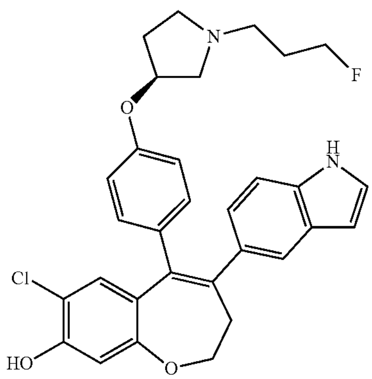 [SMILES: Oc1cc2c(cc1Cl)C(c1ccc(O[C@H]3CCN(CCCF)C3)cc1)=C(c1ccc3[nH]ccc3c1)CCO2] | 7-chloro-5-[4-[(3S)-1-(3-fluoropropyl)pyrrolidin-3-yl]oxyphenyl]-4-(1H-indol-5-yl)-2,3-dihydro-1-benzoxepin-8-ol | A | 1H NMR (400 MHz, DMSO-d6) δ ppm: 1.75 (m, 3 H), 2.18 (m, 1 H), 2.37 (m, 1 H), 2.46 (m, 2 H), 2.53 (m, 1 H), 2.67 (m, 3 H), 2.77 (dd, J = 10.4 et 6.2 Hz, 1 H), 4.46 (dt, J = 47.7 et 6.1 Hz, 2 H), 4.48 (t, J = 5.9 Hz, 2 H), 4.74 (m, 1 H), 6.29 (s, 1 H), 6.61 (m, 3 H), 6.71 (s, 1 H), 6.79 (m, 3 H), 7.15 (d, J = 8.3 Hz, 1 H), 7.26 (t, J = 2.7 Hz, 1 H), 7.32 (s, 1 H), 10.37 (s, 1 H), 10.99 (s, 1 | 533 |
| 145 | 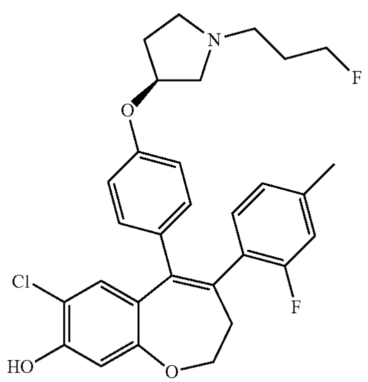 [SMILES: Cc1ccc(C2=C(c3ccc(O[C@H]4CCN(CCCF)C4)cc3)c3cc(Cl)c(O)cc3OCC2)c(F)c1] | 7-chloro-4-(2-fluoro-4-methylphenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.77 (m, 3 H), 2.22 (m, 4 H), 2.37 (m, 1 H), 2.46 (m, 2 H), 2.55 (m, 3 H), 2.64 (m, 1 H), 2.79 (dd, J = 10.0 et 6.1 Hz, 1 H), 4.46 (t, J = 5.6 Hz, 2 H), 4.47 (dt, J = 47.4 et 6.1 Hz, 2 H), 4.75 (m, 1 H), 6.58 (s, 1 H), 6.66 (d, J = 8.3 Hz, 2 H), 6.70 (s, 1 H), 6.78 (m, 3 H), 6.90 (m, 2 H), 10.49 (m, 1 H) | 526 |
| 146 | 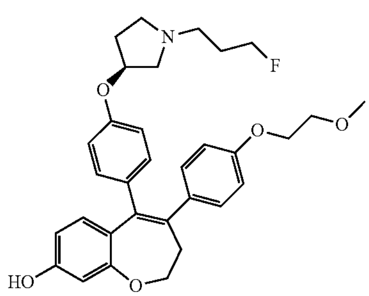 [SMILES: COCCOc1ccc(C2=C(c3ccc(O[C@H]4CCN(CCCF)C4)cc3)c3ccc(O)cc3OCC2)cc1] | 5-[4-[(3S)-1-(3-fluoropropyl)pyrrolidin-3-yl]oxyphenyl]-4-[4-(2-methoxyethoxy)phenyl]-2,3-dihydro-1-benzoxepin-8-ol | A | 1H NMR (400 MHz, DMSO-d6) δ 1.75 (m, 3H), 2.21 (m, 1H), 2.38 (m, 1H), 2.45 (m, 2H), 2.60 (m, 4H), 2.80 (dd, J = 10.3 et 6.17 Hz, 1H), 3.28 (s, 3H), 3.61 (m, 2H), 4.02 (m, 2H), 4.44 (m, 1H), 4.46 (dt, J = 47.5 et 6.0 Hz, 2 H), 4.76 (s, 1H), 6.45 (m, 2H), 6.52 (d, J = 8.0 Hz, 1H), 6.64 (d, J = 8.8 Hz, 2H), 6.74 (m, 4H), 7.00 (d, J = 8.7 Hz, 2H), 9.63 (s, 1H) | 534 |
| 147 | 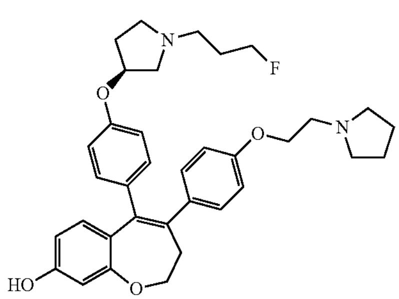 [SMILES: Oc1ccc2c(c1)OCCC(c1ccc(OCCN3CCCC3)cc1)=C2c1ccc(O[C@H]2CCN(CCCF)C2)cc1] | 5-[4-[(3S)-1-(3-fluoropropyl)pyrrolidin-3-yl]oxyphenyl]-4-[4-(2-pyrrolidin-1-ylethoxy)phenyl]-2,3-dihydro-1-benzoxepin-8-ol | A | 1H NMR (400 MHz, DMSO-d6) δ ppm: 1.60-1.85(m, 7 H), 2.19 (m, 1 H), 2.41 (m, 7 H), 2.54 (m, 1 H), 2.61 (m, 3 H), 2.73 (t, J = 5.9 Hz, 2 H), 2.80 (dd, J = 10.2 et 6.2 Hz, 1 H), 3.98 (t, J = 5.9 Hz, 2 H), 4.42 (m, 2 H), 4.48 (dt, J = 47.5 et 6.0 Hz, 2 H), 4.76 (m, 1 H), 6.46 (m, 2 H), 6.52 (d, J = 8.3 Hz, 1 H), 6.64 (d, J = 8.7 Hz, 2 H), 6.75 (dd, J = 14.0 et 8.7 Hz, 4 H), 6.99 (d, J = 8.8 Hz, 2 H), 9.59 (s, 1 H) | 573 |

TABLE 1-continued

| Example | Structure | Name | Method | NMR | MASS LC/MS (m/z, MH+) |
|---|---|---|---|---|---|
| 148 | 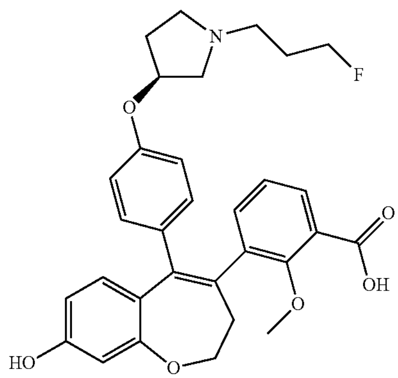 [SMILES: COc1c(C(=O)O)cccc1C1=C(c2ccc(O[C@H]3CCN(CCCF)C3)cc2)c2ccc(O)cc2OCC1] | 3-[5-[4-[(3S)-1-(3-fluoropropyl)pyrrolidin-3-yl]oxyphenyl]-8-hydroxy-2,3-dihydro-1-benzoxepin-4-yl]-2-methoxybenzoicAcid | A | 1H NMR (400 MHz, DMSO-d6) δ ppm: 1.75 (m, 3 H), 2.19 (m, 1 H), 2.38 (m, 1 H), 2.45 (t, J = 6.5 Hz, 2 H), 2.54 (m, 3 H), 2.62 (m, 1 H), 2.79 (dd, J = 10.4 et 6.2 Hz, 1 H), 3.82 (s, 3 H), 4.41 (m, 2 H), 4.46 (dt, J = 47.7 et 5.9 Hz, 2 H), 4.73 (m, 1 H), 6.44 (m, 2 H), 6.54 (d, J = 8.0 Hz, 1 H), 6.64 (m, 4 H), 6.82 (d, J = 8.6 Hz, 2 H), 7.08 (d, J = 4.2 Hz, 1 H), 9.75 (s, 1 H) | 534 |
| 149 | 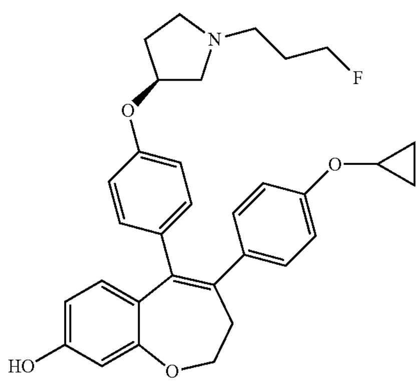 [SMILES: Oc1ccc2c(c1)OCCC(c1ccc(OC3CC3)cc1)=C2c1ccc(O[C@H]2CCN(CCCF)C2)cc1] | 4-[4-(cyclopropoxy)phenyl]-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 0.59 (m, 2 H), 0.73 (m, 2 H), 1.75 (m, 3 H), 2.21 (m, 1 H), 2.39 (m, 1 H), 2.46 (m, 2 H), 2.62 (m, 4 H), 2.80 (dd, J = 10.1 et 6.2 Hz, 1 H), 3.76 (m, 1 H), 4.44 (t, J = 5.9 Hz, 2 H), 4.48 (dt, J = 47.4 et 5.9 Hz, 2 H), 4.77 (m, 1 H), 6.44 (m, 2 H), 6.52 (d, J = 8.3 Hz, 1 H), 6.65 (d, J = 8.8 Hz, 2 H), 6.77 (d, J = 8.6 Hz, 2 H), 6.84 (d, J = 8.6 Hz, 2 H), 7.02 (d, J = 8.6 Hz, 2 H), 9.58 (s, 1 H) | 516 |
| 150 | 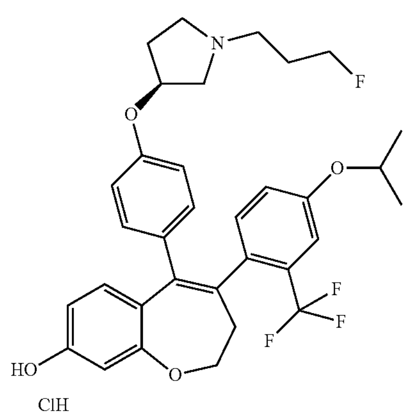 [SMILES: CC(C)Oc1ccc(C2=C(c3ccc(O[C@H]4CCN(CCCF)C4)cc3)c3ccc(O)cc3OCC2)c(C(F)(F)F)c1 ; Cl] | 5-[4-[(3S)-1-(3-fluoropropyl)pyrrolidin-3-yl]oxyphenyl]-4-[4-isopropoxy-2-(trifluoromethyl)phenyl]-2,3-dihydro-1-benzoxepin-8-ol hydrochloride | A | 1H NMR (400 MHz, DMSO-d6) δ ppm: 1.23 (t, J = 7.0 Hz, 6 H), 1.98 (m, 2 H), 2.38-2.75 (m, 4 H), 3.39 (m, 2 H), 3.78 (m, 4 H), 4.42-4.61 (m, 5 H), 4.98 (m, 1 H), 6.48 (m, 3 H), 6.72 (d, J = 7.0 Hz, 2 H), 6.78 (d, J = 7.0 Hz, 2 H), 6.99 (m, 2 H), 7.12 (s, 1 H), 9.65 (s, 1 H), 10.25 (s, 1 H) | 622 |
| 151 | 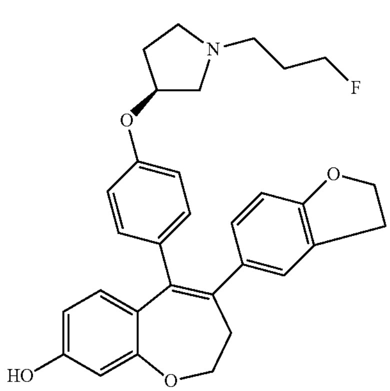 [SMILES: Oc1ccc2c(c1)OCCC(c1ccc3c(c1)CCO3)=C2c1ccc(O[C@H]2CCN(CCCF)C2)cc1] | 4-(2,3-dihydrobenzofuran-5-yl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.76 (m, 3 H), 2.20 (m, 1 H), 2.38 (q, J = 7.7 Hz, 1 H), 2.46 (m, 2 H), 2.56 (m, 3 H), 2.65 (m, 1 H), 2.80 (dd, J = 10.3 et 6.1 Hz, 1 H), 3.04 (t, J = 8.7 Hz, 2 H), 4.36-4.58 (m, 6 H), 4.76 (m, 1 H), 6.46 (m, 2 H), 6.53 (d, J = 7.1 Hz, 2 H), 6.65 (d, J = 8.8 Hz, 2 H), 6.78 (m, 3 H), 6.99 (s, 1 H), 9.58 (s, 1 H) | 502 |

TABLE 1-continued

| Example | Structure | Name | Method | NMR | MASS LC/MS (m/z, MH+) |
|---|---|---|---|---|---|
| 152 | 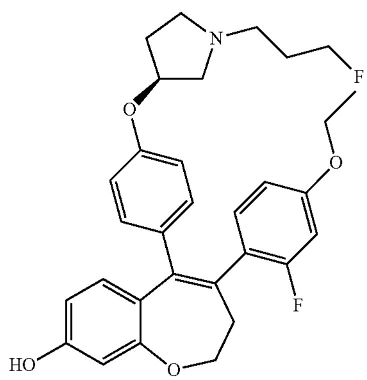 [SMILES: CCOc1ccc(C2=C(c3ccc(O[C@H]4CCN(CCCF)C4)cc3)c3ccc(O)cc3OCC2)c(F)c1] | 4-(4-ethoxy-2-fluoro-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.28 (t, J = 7.0 Hz, 3 H), 1.75 (m, 3 H), 2.20 (m, 1 H), 2.38 (m, 1 H), 2.45 (m, 2 H), 2.55 (m, 3 H), 2.63 (m, 1 H), 2.79 (dd, J = 10.4 et 6.2 Hz, 1 H), 3.96 (q, J = 7.1 Hz, 2 H), 4.44 (t, J = 5.9 Hz, 2 H), 4.47 (dt, J = 47.7 et 6.1 Hz, 2 H), 4.74 (m, 1 H), 6.46 (m, 2 H), 6.53 (d, J = 8.3 Hz, 1 H), 6.56 (dd, J = 8.6 et 2.4 Hz, 1 H), 6.64 (d, J = 8.8 Hz, 2 H), 6.68 (dd, J = 12.2 et 2.4 Hz, 1 H), 6.76 (d, J = 8.8 Hz, 2 H), 6.89 (t, J = 8.8 Hz, 1 H), 9.64 (s, 1 H) | 522 |
| 153 | 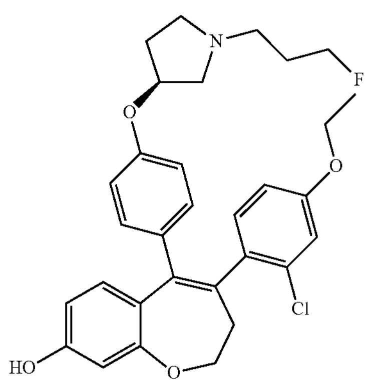 [SMILES: CCOc1ccc(C2=C(c3ccc(O[C@H]4CCN(CCCF)C4)cc3)c3ccc(O)cc3OCC2)c(Cl)c1] | 4-(2-chloro-4-ethoxy-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.27 (t, J = 7.0 Hz, 3 H), 1.74 (m, 3 H), 2.20 (m, 1 H), 2.37 (m, 1 H), 2.45 (m, 2 H), 2.53 (m, 3 H), 2.63 (m, 1 H), 2.79 (m, 1 H), 3.97 (q, J = 6.8 Hz, 2 H), 4.43 (m, 2 H), 4.46 (dd, J = 47.4 et 5.9 Hz, 2 H), 4.73 (m, 1 H), 6.45 (m, 2 H), 6.53 (d, J = 8.0 Hz, 1 H), 6.63 (d, J = 8.8 Hz, 2 H), 6.69 (dd, J = 8.4 et 2.6 Hz, 1 H), 6.76 (d, J = 8.8 Hz, 2 H), 6.88 (d, J = 8.6 Hz, 1 H), 6.97 (d, J = 2.4 Hz, 1 H), 9.65 (s, 1 H) | 538 |
| 154 | 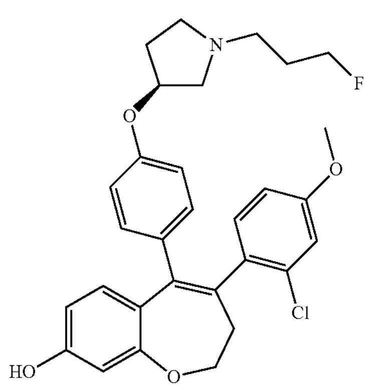 [SMILES: COc1ccc(C2=C(c3ccc(O[C@H]4CCN(CCCF)C4)cc3)c3ccc(O)cc3OCC2)c(Cl)c1] | 4-(2-chloro-4-methoxy-phenyl)-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.74 (m, 3 H), 2.19 (m, 1 H), 2.38 (m, 2 H), 2.45 (m, 2 H), 2.54 (d, J = 2.4 Hz, 2 H), 2.64 (m, 2 H), 2.79 (m, 1 H), 3.71 (s, 3 H), 4.43 (m, 2 H), 4.46 (dt, J = 47.7 et 6.1 Hz, 2 H), 4.73 (m, 1 H), 6.45 (m, 2 H), 6.53 (d, J = 8.0 Hz, 1 H), 6.63 (d, J = 8.6 Hz, 2 H), 6.71 (dd, J = 8.6 et 2.4 Hz, 1 H), 6.76 (d, J = 8.6 Hz, 2 H), 6.90 (d, J = 8.3 Hz, 1 H), 7.00 (d, J = 2.4 Hz, 1 H), 9.64 (s, 1 H) | 524 |
| 155 | 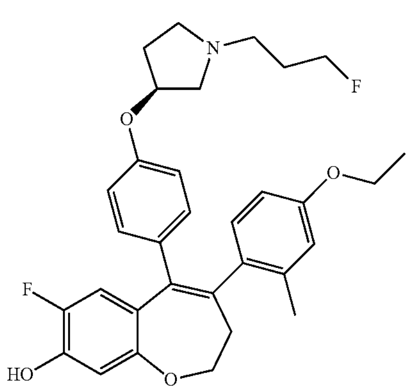 [SMILES: CCOc1ccc(C2=C(c3ccc(O[C@H]4CCN(CCCF)C4)cc3)c3cc(F)c(O)cc3OCC2)c(C)c1] | 4-(4-ethoxy-2-methyl-phenyl)-7-fluoro-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.27 (t, J = 7.0 Hz, 3 H), 1.76 (m, 3 H), 2.04 (s, 3 H), 2.20 (dq, J = 13.3 et 6.8 Hz, 1 H), 2.37 (m, 1 H), 2.43-2.48 (m, 3 H), 2.55 (m, 2 H), 2.64 (m, 1 H), 2.78 (dd, J = 10.1 et 6.2 Hz, 1 H), 3.93 (q, J = 7.0 Hz, 2 H), 4.39 (m, 2 H), 4.47 (dt, J = 47.4 et 5.9 Hz, 2 H), 4.73 (m, 1 H), 6.40 (d, J = 12.2 Hz, 1 H), 6.55-6.75 (m, 7 H), 6.92 (d, J = 7.8 Hz, 1 H), 10.09 (s, 1 H) | 536 |

TABLE 1-continued

| Example | Structure | Name | Method | NMR | MASS LC/MS (m/z, MH+) |
|---|---|---|---|---|---|
| 156 | 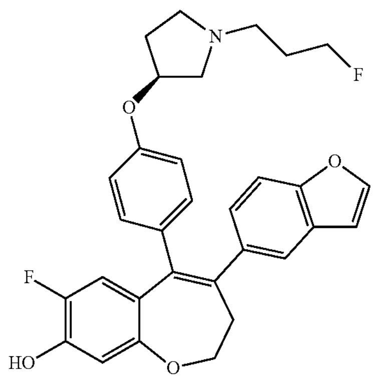 [SMILES: Oc1cc2c(cc1F)C(c1ccc(O[C@H]3CCN(CCCF)C3)cc1)=C(c1ccc3occc3c1)CCO2] | 4-(benzofuran-5-yl)-7-fluoro-5-[4-[(3S)-1-(3-fluoropropyl)pyrrolidin-3-yl]oxyphenyl]-2,3-dihydro-1-benzoxepin-8-ol | A | 1H NMR (400 MHz, DMSO-d6) δ ppm: 1.27 (t, J = 7.0 Hz, 3 H), 1.78 (m, 3 H), 2.08 (m, 2H), 2.19 (m, 4 H), 2.34 (m, 1 H), 2.45 (t, J = 7.2 Hz, 2 H), 2.55 (dd, J = 8.2 et 2.8 Hz, 1 H), 2.72 (m, 4 H), 4.18 (q, J = 7.1 Hz, 2 H), 4.46 (dt, J = 47.4 et 6.0 Hz, 2 H), 5.23 (m, 1 H), 6.55 (m, 3 H), 6.64 (d, J = 7.7 Hz, 1 H), 6.72 (s, 1 H), 7.13 (dd, J = 8.6 et 2.4 Hz, 1 H), 7.58 (d, J = 2.2 Hz, 1 H), 7.66 (dd, J = 10.0 et 8.3 Hz, 1 H), 9.49 (s, 1 H) | 518 |
| 157 | 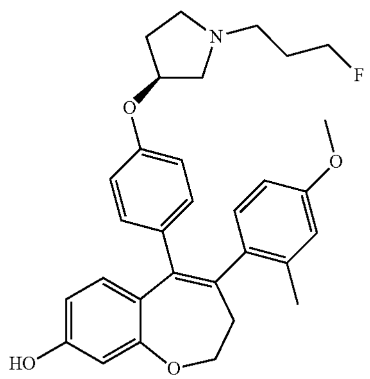 [SMILES: COc1ccc(C2=C(c3ccc(O[C@H]4CCN(CCCF)C4)cc3)c3ccc(O)cc3OCC2)c(C)c1] | 5-[4-[(3S)-1-(3-fluoropropyl)pyrrolidin-3-yl]oxyphenyl]-4-(4-methoxy-2-methyl-phenyl)-2,3-dihydro-1-benzoxepin-8-ol | A | 1H NMR (400 MHz, DMSO-d6) δ ppm: 1.75 (m, 3 H), 2.06 (s, 3 H), 2.19 (m, 1 H), 2.38 (m, 1 H), 2.48 (m, 5 H), 2.62 (m, 1 H), 2.77 (m, 1 H), 3.68 (s, 3 H), 4.43 (m, 2 H), 4.46 (dt, J = 47.5 et 6.0 Hz, 2 H), 4.72 (m, 1 H), 6.49 (m, 2 H), 6.55-6.65 (m, 5 H), 6.71 (d, J = 8.8 Hz, 2 H), 6.94 (d, J = 8.1 Hz, 1 H), 9.60 (s, 1 H) | 504 |
| 158 | 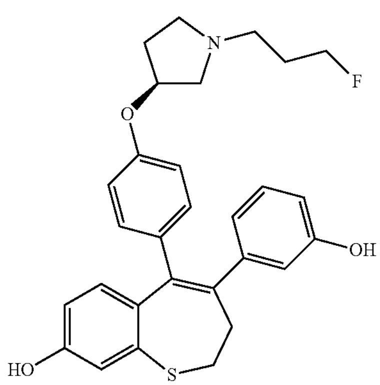 [SMILES: Oc1cccc(C2=C(c3ccc(O[C@H]4CCN(CCCF)C4)cc3)c3ccc(O)cc3SCC2)c1] | 5-[4-[(3S)-1-(3-fluoropropyl)pyrrolidin-3-yl]oxyphenyl]-4-(3-hydroxyphenyl)-2,3-dihydro-1-benzothiepin-8-ol | A | 1H NMR (400 MHz, DMSO-d6) δ ppm: 1.75 (m, 3 H), 2.19 (m, 1 H), 2.38 (m, 1 H), 2.45 (m, 2 H), 2.56 (m, 3 H), 2.64 (m, 1 H), 2.80 (dd, J = 10.3 et 6.2 Hz, 1 H), 3.29 (m, 2 H), 4.46 (dt, J = 47.4 et 6.0 Hz, 2 H), 4.73 (m, 1 H), 6.52 (dd, J = 7. et 2.0 Hz, 1 H), 6.57 (m, 4 H), 6.69 (m, 4 H), 6.98 (t, J = 7.8 Hz, 1 H), 7.03 (d, J = 2.3 Hz, 1 H), 9.17 (s, 1 H), 9.67 (s, 1 H) | 492 |
| 159 | 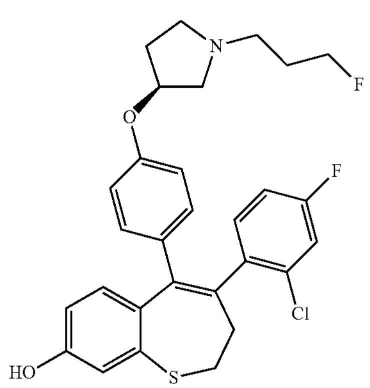 | 4-(2-chloro-4-fluoro-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.74 (m, 3 H), 2.18 (m, 1 H), 2.39 (m, 1 H), 2.45 (d, J = 7.2 Hz, 2 H), 2.55 (m, 3 H), 2.63 (m, 1 H), 2.77 (m, 1 H), 3.22 (m, 1 H), 3.49 (m, 1 H), 4.46 (dt, J = 47.4 et 6.0 Hz, 2 H), 4.71 (m, 1 H), 6.62 (d, J = 8.2 Hz, 2 H), 6.71 (m, 4 H), 7.08 (m, 3 H), 7.45 (dd, J = 8.9, 2.4 Hz, 1 H), 9.75 (s, 1 H) | 528 |

TABLE 1-continued

| Example | Name | Method | NMR | MASS LC/MS (m/z, MH+) |
|---|---|---|---|---|
| 160 | 5-[4-[(3S)-1-(3-fluoropropyl)pyr-rolidin-3-yl]oxyphenyl]-4-(1H-indol-5-yl)-2,3-dihydro-1-benzothiepin-8-ol | A | 1H NMR (400 MHz, DMSO-d6) δ 1.66 (m, 1H), 1.76 (m, 2H), 2.15 (m, 1H), 2.36 (m, 1H), 2.44 (d, J = 7.2 Hz, 3H), 2.58 (m, 3H), 2.76 (dd, J = 10.3 et 6.1 Hz, 1H), 3.31 (s, 2H), 4.45 (dt, J = 47.6 et 6.4 Hz, 2H), 4.69 (m, 1H), 6.29 (s, 1H), 6.54 (d, J = 8.7 Hz, 2H), 6.67 (m, 4H), 6.89 (d, J = 7.8 Hz, 1H), 7.04 (d, J = 2 Hz, 1H), 7.17 (d, J = 8.4 Hz, 1H), 7.25 (t, J = 2.6 Hz, 1H), 7.38 (s, 1H), 9.63 (s, 1H), 10.96 (s, 1H) | 515 |
| 161 | 4-(4-chloro-3-fluoro-phenyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.76 (m, 3 H), 2.21 (m, 1 H), 2.38 (q, J = 7.5 Hz, 1 H), 2.46 (m, 2 H), 2.55 (m, 3 H), 2.68 (m, 1 H), 2.79 (dd, J = 10.1 et 6.2 Hz, 1 H), 3.35 (m, 2 H), 4.47 (dt, J = 48.2 et 6.2 Hz, 2 H), 4.76 (m, 1 H), 6.69 (m, 6 H), 6.97 (d, J = 8.3 Hz, 1 H), 7.05 (s, 1 H), 7.18 (d, J = 10.8 Hz, 1 H), 7.38 (t, J = 8.1 Hz, 1 H), 9.77 (s, 1 H) | 528 |
| 162 | 4-(4-chloro-3-methyl-phenyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.60 à 1.90 (m, 3 H), 2.15 (s, 3H), 2.19 (m, 1 H), 2.37(m, 1 H), 2.40 à 2.55 (m, 5 H), 2.61 (m, 1 H), 2.78 (m, 1 H), 3.37 (m, 2 H), 4.46 (dt, J = 47.4 et 6.0 Hz, 2 H), 4.72 (m, 1 H), 6.60 (m, 4 H), 6.70 (m, 2H), 7.05 (d, J = 2.1 Hz, 1 H), 7.16 (m, 3 H), 9.72 (s, 1 H) | 524 |
| 163 | 4-(3-chloro-2-methyl-phenyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.75 (m, 3 H), 2.20 (m, 1 H), 2.38-2.50 (m, 3 H), 2.54 (m, 3 H), 2.67 (m, 1 H), 2.80 (m, 1 H), 3.37 (t, J = 6.2 Hz, 2 H), 4.47 (dt, J = 47.4 et 6.0 Hz, 2 H), 4.74 (m, 1 H), 6.72 (m, 6 H), 7.03 (m, 2 H), 7.84 (m, 1 H), 9.79 (s, 1 H) | 524 |

TABLE 1-continued

| Example | Structure | Name | Method | NMR | MASS LC/MS (m/z, MH+) |
|---|---|---|---|---|---|
| 164 | 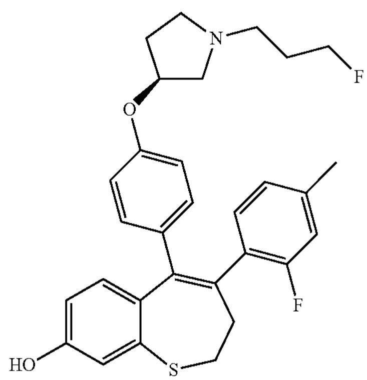 | 4-(2-fluoro-4-methyl-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.75 (m, 3 H), 2.19 (m, 1 H), 2.23 (s, 3 H), 2.37 (m, 1 H), 2.45 (m, 4 H), 2.53 (m, 1 H), 2.62 (m, 1 H), 2.78 (dd, J = 10.3 et 6.1 Hz, 1 H), 3.30 (m, 2 H), 4.46 (dt, J = 47.4 et 6.1 Hz, 2 H), 4.72 (m, 1 H), 6.61 (d, J = 8.8 Hz, 2 H), 6.90 (m, 4 H), 6.81 (d, J = 7.8 Hz, 1 H), 6.95 (m, 2 H), 7.04 (d, J = 2.4 Hz, 1 H), 9.74 (s, 1 H) | 508 |
| 165 | 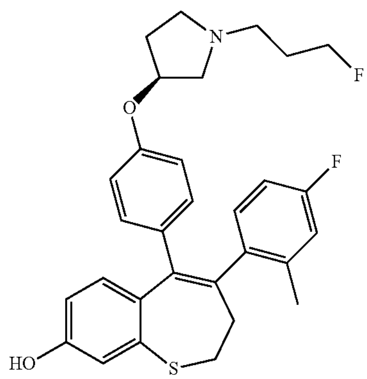 [SMILES: Cc1cc(F)ccc1C1=C(c2ccc(O[C@H]3CCN(CCCF)C3)cc2)c2ccc(O)cc2SCC1] | 4-(4-fluoro-2-methyl-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.74 (m, 3 H), 2.13 (s, 3H), 2.18 (m, 1 H), 2.38 (m, 1H), 2.40-2.55 (m, 5 H), 2.62 (m, 1 H), 2.78 (dd, J = 10.3 et 6.2 Hz, 1 H), 3.36 (m, 2 H), 4.46 (dt, J = 47.5 et 6.0 Hz, 2 H), 4.71 (m, 1 H), 6.60 (q, J = 8.9 Hz, 4 H), 6.69 (m, 2 H), 6.91 (m, 2 H), 7.05 (s, 1 H), 7.15 (t, J = 7.1 Hz, 1 H), 9.71 (s, 1 H) | 508 |
| 166 | 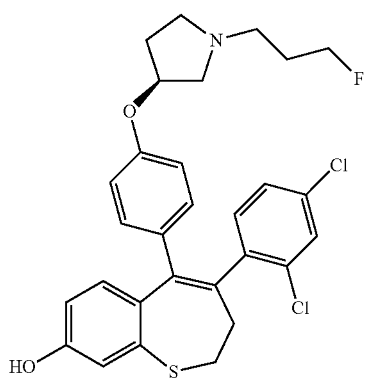 | 4-(2,4-dichlorophenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.75 (m, 3 H), 2.19 (m, 1 H), 2.38 (m, 1 H), 2.45 (t, J = 7.5 Hz, 2 H), 2.52 (d, J = 2.0 Hz, 3 H), 2.62 (m, 1 H), 2.78 (m, 1 H), 3.18 (td, J = 11.9 et 4.6 Hz, 1 H), 3.49 (m, 1 H), 4.46 (dt, J = 47.4 et 5.6 Hz, 2 H), 4.72 (m, 1 H), 6.63 (m, 2 H), 6.70 (m, 4 H), 7.06 (m, 2 H), 7.24 (dd, J = 8.3 et 1.7 Hz, 1 H), 7.64 (d, J = 2.0 Hz, 1 H), 9.80 (s, 1 H) | 545 |
| 167 | 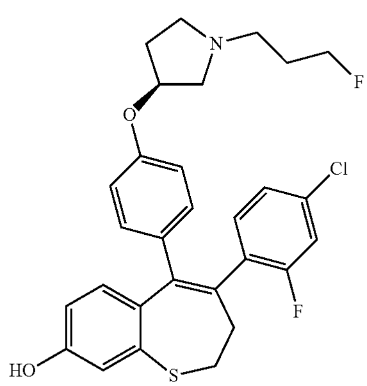 | 4-(4-chloro-2-fluoro-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.75 (m, 3 H), 2.20 (m, 1 H), 2.36 (m, 1 H), 2.46 (m, 2 H), 2.54 (m, 3 H), 2.66 (m, 1 H), 2.79 (dd, J = 10.3 et 6.2 Hz, 1 H), 3.33 (m, 2 H), 4.46 (dt, J = 47.4 et 6.0 Hz, 2 H), 4.73 (m, 1 H), 6.64 (d, J = 9.0 Hz, 2 H), 6.69 (m, 4 H), 7.05 (d, J = 2.3 Hz, 1 H), 7.11 (m, 2 H), 7.35 (d, J = 9.6 Hz, 1 H), 9.80 (s, 1 H) | 528 |

TABLE 1-continued

| Example | Structure | Name | Method | NMR | MASS LC/MS (m/z, MH+) |
|---|---|---|---|---|---|
| 168 | 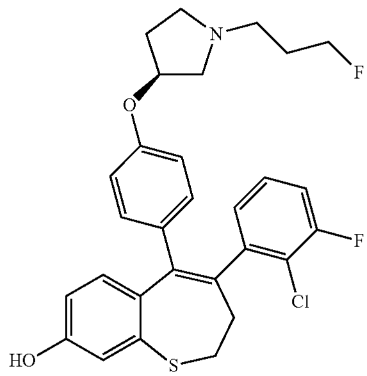 | 4-(2-chloro-3-fluoro-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.73 (m, 3 H), 2.21 (m, 1 H), 2.35 (m, 1 H), 2.45 (t, J = 7.1 Hz, 2 H), 2.52 (m, 3 H), 2.60 (m, 1 H), 2.76 (m, 1 H), 3.21 (m, 1 H), 3.46 (m, 1 H), 4.46 (dt, J = 47.5 et 6.0 Hz, 2 H), 4.71 (m, 1 H), 6.62 (d, J = 8.0 Hz, 2H), 6.65-6.75 (m, 4 H), 6.94 (d, J = 7.2 Hz, 1 H), 7.06 (s, 1 H), 7.22 (m, 2 H), 9.82 (s, 1 H) | 528 |
| 169 | 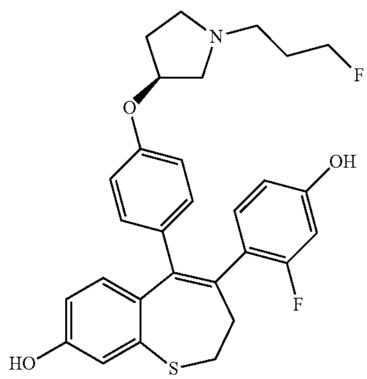 | 4-(2-fluoro-4-hydroxy-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.75 (m, 3 H), 2.20 (m, 1 H), 2.30-2.80 (m, 8 H), 3.00 (dd, J = 11.9 et 6.7 Hz, 1 H), 4.16 (m, 6.2 Hz, 1 H), 4.46 (dt, J = 47.4 et 6.0 Hz, 2 H), 4.75 (m, 1 H), 6.66 (m, 4 H), 6.79 (d, J = 8.4 Hz, 1 H), 6.89 (dd, J = 8.4 et 2.4 Hz, 1 H), 7.23 (m, 5 H), 10.23 (s, 1 H) | 510 |
| 170 | 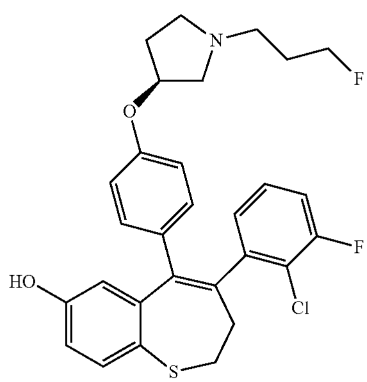 [SMILES: Oc1ccc2c(c1)C(c1ccc(O[C@H]3CCN(CCCF)C3)cc1)=C(c1cccc(F)c1Cl)CCS2] | 4-(2-chloro-3-fluoro-phenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.73 (m, 3 H), 2.20 (m, 1 H), 2.38 (m, 1 H), 2.45 (t, J = 7.2 Hz, 2 H), 2.54 (m, 3 H), 2.62 (m, 1 H), 2.76 (m, 1 H), 3.11 (td, J = 11.8 et 4.8 Hz, 1 H), 3.37-3.48 (m, 1 H), 4.46 (dt, J = 47.4 et 6.0 Hz, 2 H), 4.72 (m, 1 H), 6.34 (d, J = 2.7 Hz, 1 H), 6.66 (t, J = 8.8 Hz, 2 H), 6.72 (m, 3 H), 6.95 (d, J = 7.2 Hz, 1 H), 7.23 (m, 2 H), 7.44 (d, J = 8.3 Hz, 1 H), 9.60 (s, 1 H) | 528 |
| 171 | 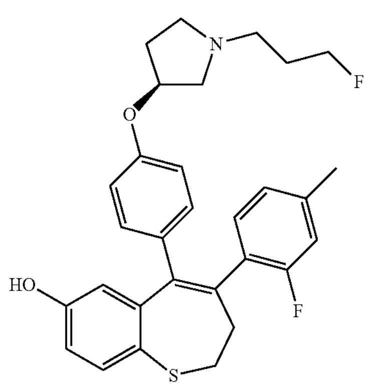 [SMILES: Cc1ccc(C2=C(c3ccc(O[C@H]4CCN(CCCF)C4)cc3)c3cc(O)ccc3SCC2)c(F)c1] | 4-(2-fluoro-4-methyl-phenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.76 (m, 3 H), 2.20 (m, 1 H), 2.25 (s, 3 H), 2.37 (m, 1 H), 2.44 (m, 2 H), 2.54 (m, 3 H), 2.63 (m, 1 H), 2.79 (dd, J = 10.0 et 6.2 Hz, 1 H), 3.25 (t, J = 9.5 Hz, 2 H), 4.46 (dt, J = 47.4 et 6.1 Hz, 2 H), 4.78 (m, 1 H), 6.32 (d, J = 2.7 Hz, 1 H), 6.60-6.75 (m, 5 H), 6.82 (d, J = 7.8 Hz, 1 H), 6.93 (m, 2 H), 7.42 (d, J = 8.3 Hz, 1 H), 9.55 (s, 1 H) | 508 |

TABLE 1-continued

| Example | Structure | Name | Method | NMR | MASS LC/MS (m/z, MH+) |
|---|---|---|---|---|---|
| 172 | 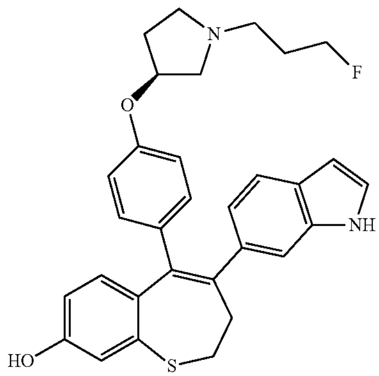 [SMILES: Oc1ccc2c(c1)SCCC(c1ccc3cc[nH]c3c1)=C2c1ccc(O[C@H]2CCN(CCCF)C2)cc1] | 5-[4-[(3S)-1-(3-fluoropropyl)pyrrolidin-3-yl]oxyphenyl]-4-(1H-indol-6-yl)-2,3-dihydro-1-benzothiepin-8-ol | A | 1H NMR (400 MHz, DMSO-d6) δ ppm: 1.74 (m, 3 H), 2.15 (m, 1 H), 2.36 (m, 1 H), 2.44 (t, J = 7.2 Hz, 2 H), 2.52 (m, 1 H), 2.61 (m, 3 H), 2.77 (dd, J = 10.3 et 6.2 Hz, 1 H), 3.32 (m, 2 H), 4.45 (dt, J = 46.6 et 5.9 Hz, 2 H), 4.69 (m, 1 H), 6.32 (s, 1 H), 6.54 (d, J = 8.8 Hz, 2 H), 6.70 (m, 4 H), 6.85 (dd, J = 8.2, 1.2 Hz, 1 H), 7.04 (d, J = 2.1 Hz, 1 H), 7.19 (s, 1 H), 7.25 (t, J = 2.9 Hz, 1 H), 7.34 (d, J = 8.2 Hz, 1 H), 9.63 (s, 1 H), 10.88 (s, 1 H) | 515 |
| 173 | 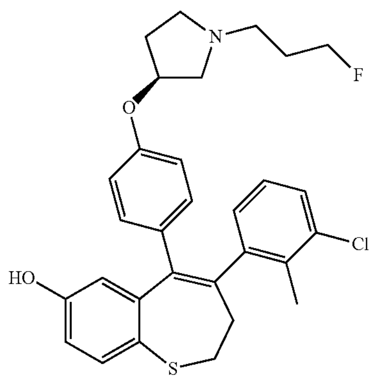 [SMILES: Cc1c(Cl)cccc1C1=C(c2ccc(O[C@H]3CCN(CCCF)C3)cc2)c2cc(O)ccc2SCC1] | 4-(3-chloro-2-methyl-phenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.75 (m, 3 H), 2.22 (m, 4 H), 2.29-2.50 (m, 5 H), 2.53-2.89 (m, 3 H), 3.24 (m, 2 H), 4.46 (dt, J = 47.4 et 5.9 Hz, 2 H), 4.74 (m, 1 H), 6.34 (d, J = 2.6 Hz, 1 H), 6.65 (m, 5 H), 7.11 (m, 2 H), 7.25 (m, 1 H), 7.43 (d, J = 8.3 Hz, 1 H), 9.57 (s, 1 H) | 524 |
| 174 | 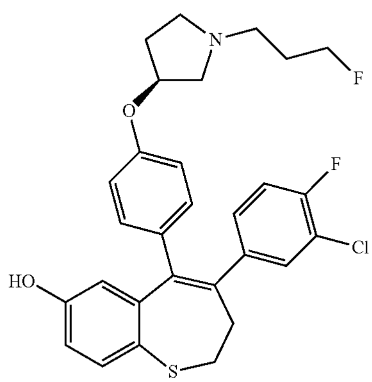 [SMILES: Oc1ccc2c(c1)C(c1ccc(O[C@H]3CCN(CCCF)C3)cc1)=C(c1ccc(F)c(Cl)c1)CCS2] | 4-(3-chloro-4-fluoro-phenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.76 (m, 3 H), 2.20 (m, 1 H), 2.39 (m, 1 H), 2.45 (m, 4 H), 2.56 (s, 1 H), 2.67 (m, 1 H), 2.79 (dd, J = 10.3, 6.2 Hz, 1 H), 3.24 (m, 2 H), 4.47 (dt, J = 47.4 et 6.0 Hz, 2 H), 4.77 (s, 1 H), 6.33 (d, J = 2.6 Hz, 1 H), 6.70 (m, 5 H), 7.15 (td, J = 5.4 et 2.3 Hz, 1 H), 7.26 (m, 1 H), 7.35 (dd, J = 7.2, 1.8 Hz, 1 H), 7.42 (d, J = 8.3 Hz, 1 H), 9.58 (s, 1 H) | 528 |
| 175 | 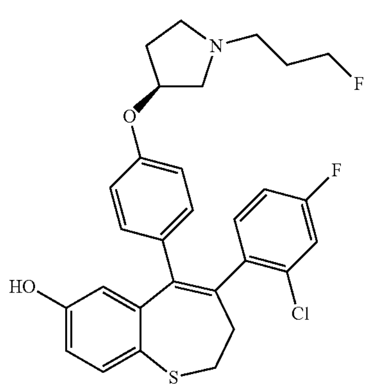 [SMILES: Oc1ccc2c(c1)C(c1ccc(O[C@H]3CCN(CCCF)C3)cc1)=C(c1ccc(F)cc1Cl)CCS2] | 4-(2-chloro-4-fluoro-phenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.63-1.99 (m, 3 H), 2.20 (dt, J = 13.4 et 6.6 Hz, 1 H), 2.27-2.47 (m, 5 H), 2.57 (s, 1 H), 2.65 (m, 1 H), 2.77 (m, 1 H), 3.11 (m, 1 H), 3.43 (m, 1 H), 4.46 (dt, J = 47.4 et 6.0 Hz, 2 H), 4.72 (s, 1 H), 6.34 (d, J = 2.7 Hz, 1 H), 6.68 (m, 5 H), 7.02-7.27 (m, 2 H), 7.43 (d, J = 8.5 Hz, 1 H), 7.48 (d, J = 9.0 Hz, 1 H), 9.59 (s, 1 H) | 528 |

TABLE 1-continued

| Example | Name | Method | NMR | MASS LC/MS (m/z, MH+) |
|---|---|---|---|---|
| 176 | 5-[4-[(3S)-1-(3-fluoropropyl)pyrrolidin-3-yl]oxyphenyl]-4-indolin-5-yl-2,3-dihydro-1-benzothiepin-8-ol | A | 1H NMR (400 MHz, DMSO-d6) δ ppm: 1.76 (m, 3 H), 2.20 (m, 1 H), 2.39 (m, 1 H), 2.45 (m, 2 H), 2.56 (d, J = 2.7 Hz, 2 H), 2.65 (m, 1 H), 2.77 (m, 3 H), 3.36 (m, 4 H), 4.48 (dt, J = 47.4 et 6.0 Hz, 2 H), 4.75 (d, J = 6.7 Hz, 1 H), 5.39 (s, 1 H), 6.27 (d, J = 7.9 Hz, 1 H), 6.68 (m, 7 H), 6.85 (s, 1 H), 7.01 (d, J = 2.2 Hz, 1 H), 9.57 (s, 1 H) | 517 |
| 177 | 5-[4-[(3S)-1-(3-fluoropropyl)pyrrolidin-3-yl]oxyphenyl]-4-(4-hydroxyphenyl)-2,3-dihydro-1-benzothiepin-7-ol | A | 1H NMR (400 MHz, DMSO-d6) δ ppm: 1.78 (m, 3 H), 2.20 (m, 1 H), 2.35-2.60 (m, 6 H), 2.66 (m, 1 H), 2.80 (m, 1 H), 3.22 (m, 2 H), 4.47 (dt, J = 47.4 et 6.0 Hz, 2 H), 4.75 (m, 1 H), 6.30 (d, J = 2.6 Hz, 1 H), 6.57 (d, J = 8.4 Hz, 2 H), 6.63 (m, 3 H), 6.74 (m, 2 H), 6.97 (d, J = 8.4 Hz, 2 H), 7.38 (d, J = 8.4 Hz, 1 H), 9.33 (s, 1 H), 9.49 (s, 1 H) | 492 |
| 178 | 5-[4-[(3S)-1-(3-fluoropropyl)pyrrolidin-3-yl]oxyphenyl]-4-(1H-indol-4-yl)-2,3-dihydro-1-benzothiepin-8-ol | A | 1H NMR (400 MHz, DMSO-d6) δ ppm: 1.60 (m, 1 H), 1.73 (m, 2 H), 2.12 (m, 1 H), 2.34 (q, J = 7.7 Hz, 1 H), 2.43 (m, 4 H), 2.61 (m, 2 H), 2.74 (dd, J = 10.2 et 6.2 Hz, 1 H), 3.28 (t, J = 6.1 Hz, 2 H), 4.44 (dt, J = 47.4 et 6.0 Hz, 2 H), 4.64 (m, 1 H), 6.39 (s, 1 H), 6.45 (d, J = 8.7 Hz, 2 H), 6.65 (d, J = 8.7 Hz, 2 H), 6.71 (m, 2 H), 6.78 (d, J = 7.6 Hz, 1 H), 6.92 (t, J = 7.6 Hz, 1 H), 7.07 (d, J = 1.8 Hz, 1 H), 7.19 (d, J = 8.1 Hz, 1 H), 7.22 (t, J = 2.4 Hz, 1 H), 9.69 (s, 1 H), 10.99 (s, 1 H) | 515 |
| 179 | 4-(4-chloro-3-methyl-phenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.73 (m, 3 H), 2.15 (s, 3 H), 2.20 (m, 1 H), 2.35-2.60 (m, 6 H), 2.65 (m, 1 H), 2.78 (dd, J = 10.2 et 6.2 Hz, 1 H), 3.23 (m, 2 H), 4.46 (dt, J = 47.4 et 6.0 Hz, 2 H), 4.72 (m, 1 H), 6.34 (d, J = 2.7 Hz, 1 H), 6.66 (m, 5 H), 7.20 (m, 3 H), 7.42 (d, J = 8.3 Hz, 1 H), 9.56 (s, 1 H) | 524 |

TABLE 1-continued

| Example | Structure | Name | Method | NMR | MASS LC/MS (m/z, MH+) |
|---|---|---|---|---|---|
| 180 | 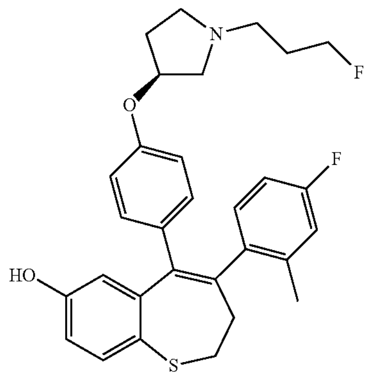 [SMILES: Cc1cc(F)ccc1C1=C(c2ccc(O[C@H]3CCN(CCCF)C3)cc2)c2cc(O)ccc2SCC1] | 4-(4-fluoro-2-methyl-phenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.74 (m, 3 H), 2.18 (s, 3 H), 2.20 (m, 1 H), 2.37 (m, 1 H), 2.45-2.55 (m, 5 H), 2.63 (m, 1 H), 2.80 (m, 1 H), 3.23 (m, 2 H), 4.46 (dt, J = 47.4 et 6.0 Hz, 2 H), 4.72 (m, 1 H), 6.34 (d, J = 2.7 Hz, 1 H), 6.62 (m, 4 H), 6.69 (m, 1 H), 6.93 (m, 2 H), 7.16 (t, J = 6.8 Hz, 1 H), 7.42 (d, J = 8.4 Hz, 1 H), 9.55 (s, 1 H) | 508 |
| 181 | 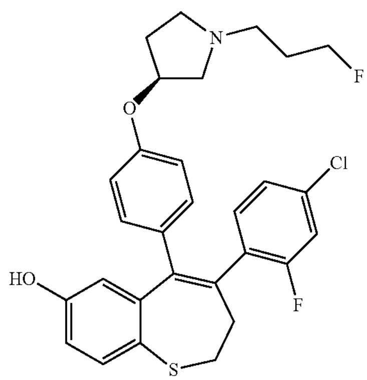 [SMILES: Oc1ccc2c(c1)C(c1ccc(O[C@H]3CCN(CCCF)C3)cc1)=C(c1ccc(Cl)cc1F)CCS2] | 4-(4-chloro-2-fluoro-phenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.74 (m, 3 H), 2.18 (m, 1 H), 2.38 (m, 1 H), 2.46 (t, J = 7.3 Hz, 4 H), 2.55 (m, 1 H), 2.66 (m, 1 H), 2.79 (dd, J = 10.3 et 6.2 Hz, 1 H), 3.26 (t, J = 5.6 Hz, 2 H), 4.47 (dt, J = 47.4 et 6.0 Hz, 2 H), 4.74 (m, 1 H), 6.33 (d, J = 2.7 Hz, 1 H), 6.69 (m, 5 H), 7.12 (m, 2 H), 7.35 (d, J = 8.0 Hz, 1 H), 7.43 (d, J = 8.3 Hz, 1 H), 9.59 (s, 1 H) | 528 |
| 182 | 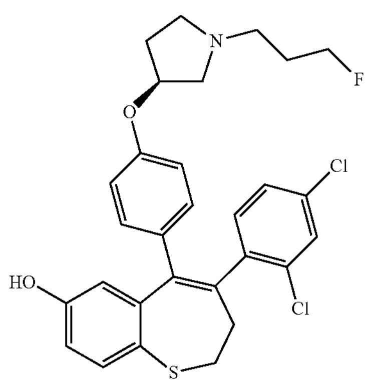 [SMILES: Oc1ccc2c(c1)C(c1ccc(O[C@H]3CCN(CCCF)C3)cc1)=C(c1ccc(Cl)cc1Cl)CCS2] | 4-(2,4-dichlorophenyl)-5-[4-[(3S)-1-(3-fluoropropyl)pyrrolidin-3-yl]oxyphenyl]-2,3-dihydro-1-benzothiepin-7-ol | A | 1H NMR (400 MHz, DMSO-d6) δ ppm: 1.73 (m, 3 H), 2.20 (m, 1 H), 2.39 (m, 5 H), 2.54 (m, 1 H), 2.65 (m, 1 H), 2.79 (dt, J = 10.1 et 6.9 Hz, 1 H), 3.10 (td, J = 11.9 et 4.5 Hz, 1 H), 3.43 (m, 1 H), 4.46 (dt, J = 47.4 et 6.0 Hz, 2 H), 4.73 (m, 1 H), 6.33 (d, J = 2.7 Hz, 1 H), 6.69 (m, 5 H), 7.08 (d, J = 8.2 Hz, 1 H), 7.26 (d, J = 8.2 Hz, 1 H), 7.43 (d, J = 8.4 Hz, 1 H), 7.66 (d, J = 1.8 Hz, 1 H), 9.60 (s, 1 H) | 545 |
| 183 | 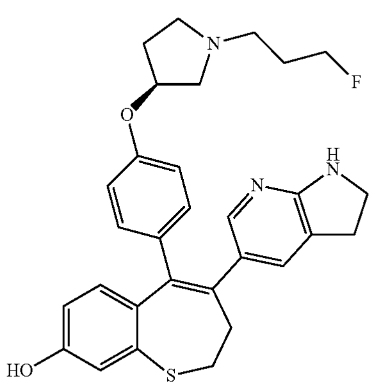 [SMILES: Oc1ccc2c(c1)SCCC(c1cnc3c(c1)CCN3)=C2c1ccc(O[C@H]2CCN(CCCF)C2)cc1] | 4-(2,3-dihydro-1H-pyrrolo[2,3-b]pyridin-5-yl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.76 (m, 3 H), 2.23 (m, 1 H), 2.38 (m, 5 H), 2.55 (dd, J = 10.5 et 2.5 Hz, 1 H), 2.66 (m, 1 H), 2.81 (m, 3 H), 3.24 (m, 2 H), 3.42 (t, J = 7.5 Hz, 2 H), 4.47 (dt, J = 47.4 et 6.0 Hz, 2 H), 4.76 (d, J = 6.8 Hz, 1 H), 6.27 (s, 1 H), 6.69 (m, 6 H), 7.01 (d, J = 2.3 Hz, 1 H), 7.09 (s, 1 H), 7.43 (s, 1 H), 9.67 (s, 1 H) | 518 |

TABLE 1-continued

| Example | Structure | Name | Method | NMR | MASS LC/MS (m/z, MH+) |
|---|---|---|---|---|---|
| 184 | 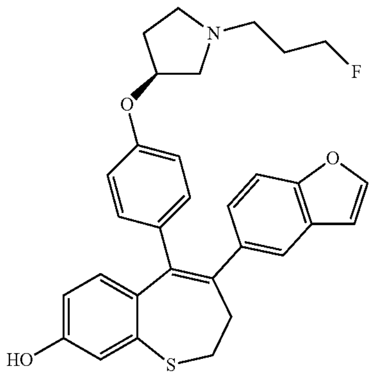 [SMILES: Oc1ccc2c(c1)SCCC(c1ccc3occc3c1)=C2c1ccc(O[C@H]2CCN(CCCF)C2)cc1] | 4-(benzofuran-5-yl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.75 (m, 3 H), 2.21 (m, 4 H), 2.35 (m, 1 H), 2.45 (m, 2 H), 2.56 (dd, J = 10.6 et 2.4 Hz, 1 H), 2.72 (m, 2 H), 3.65 (s, 2 H), 4.47 (dt, J = 47.4 et 6.0 Hz, 2 H), 5.24 (m, 1 H), 6.50 (dd, J = 7.8 et 2.1 Hz, 1 H), 6.57 (d, J = 7.8 Hz, 1 H), 6.64 (d, J = 8.6 Hz, 1 H), 6.81 (m, 2 H), 6.93 (m, 2 H), 7.25 (dd, J = 8.5 et 2.1 Hz, 1 H), 7.63 (d, J = 2.0 Hz, 1 H), 9.81 (s, 1 H) | 516 |
| 185 | 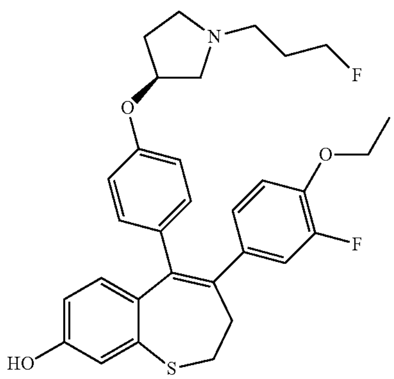 [SMILES: CCOc1ccc(C2=C(c3ccc(O[C@H]4CCN(CCCF)C4)cc3)c3ccc(O)cc3SCC2)cc1F] | 4-(4-ethoxy-3-fluoro-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.30 (t, J = 6.9 Hz, 3 H), 1.76 (m, 3 H), 2.20 (m, 1 H), 2.35 (m, 1 H), 2.44 (m, 2 H), 2.56 (m, 3 H), 2.68 (m, 1 H), 2.79 (dd, J = 10.3 et 6.1 Hz, 1 H), 3.28 (m, 2 H), 4.03 (q, J = 6.9 Hz, 2 H), 4.47 (dt, J = 47.4 et 6.0 Hz, 2 H), 4.75 (m, 1 H), 6.68 (m, 6 H), 6.93 (m, 3 H), 7.03 (d, J = 2.3 Hz, 1 H), 9.73 (s, 1 H) | 538 |
| 186 | 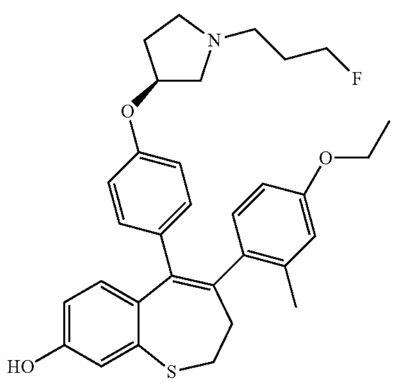 [SMILES: CCOc1ccc(C2=C(c3ccc(O[C@H]4CCN(CCCF)C4)cc3)c3ccc(O)cc3SCC2)c(C)c1] | 4-(4-ethoxy-2-methyl-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.29 (t, J = 7.0 Hz, 3 H), 1.74 (m, 3 H), 2.10 (s, 3 H), 2.17 (m, 1 H), 2.37 (m, 1 H), 2.45 (m, 2 H), 2.53 (m, 3 H), 2.61 (m, 1 H), 2.78 (dd, J = 10.2 et 6.2 Hz, 1 H), 3.24 (m, 2 H), 3.94 (q, J = 6.9 Hz, 2 H), 4.46 (dt, J = 47.4 et 6.0 Hz, 2 H), 4.71 (m, 1 H), 6.52-6.74 (m, 8 H), 7.03 (m, 2 H), 9.69 (s, 1 H) | 534 |
| 187 | 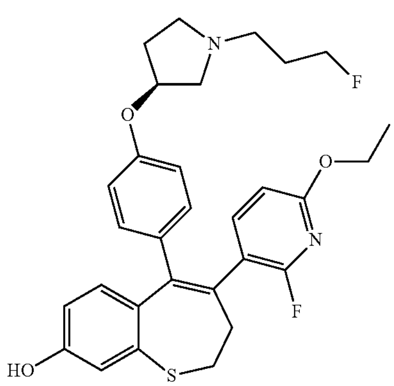 [SMILES: CCOc1ccc(C2=C(c3ccc(O[C@H]4CCN(CCCF)C4)cc3)c3ccc(O)cc3SCC2)c(F)n1] | 4-(6-ethoxy-2-fluoro-3-pyridyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.28 (t, J = 7.1 Hz, 3 H), 1.75 (m, 3 H), 2.20 (m, 1 H), 2.38 (m, 1 H), 2.46 (m, 2 H), 2.54 (m, 3 H), 2.63 (m, 1 H), 2.79 (dd, J = 10.4 et 6.2 Hz, 1 H), 3.36 (m, 2 H), 4.19 (q, J = 7.1 Hz, 2 H), 4.46 (dt, J = 47.0 et 5.9 Hz, 2 H), 4.74 (m, 1 H), 6.58 (dd, J = 8.2 et 0.9 Hz, 1 H), 6.68 (m, 6 H), 7.04 (d, J = 2.2 Hz, 1 H), 7.48 (dd, J = 10.0 et 8.1 Hz, 1 H), 9.83 (s, 1 H) | 539 |

TABLE 1-continued

| Example | Structure | Name | Method | NMR | MASS LC/MS (m/z, MH+) |
|---|---|---|---|---|---|
| 188 | 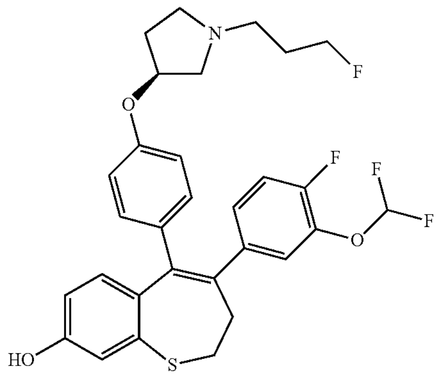 [SMILES: Oc1ccc2c(c1)SCCC(c1ccc(F)c(OC(F)F)c1)=C2c1ccc(O[C@H]2CCN(CCCF)C2)cc1] | 4-[3-(difluoromethoxy)-4-fluoro-phenyl]-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.76 (m, 3 H), 2.21 (m, 1 H), 2.37 (m, 1 H), 2.46 (t, J = 7.3 Hz, 2 H), 2.53 (m, 2 H), 2.58 (m, 3 H), 2.65 (m, 1 H), 2.79 (dd, J = 10.3 et 6.2 Hz, 1 H), 4.47 (dt, J = 47.3 et 6.1 Hz, 2 H), 4.75 (m, 1 H), 6.60-6.75 (m, 6 H), 7.04 (t, J = 66.0 Hz, 1 H), 7.08 (m, 3 H), 7.23 (dd, J = 8.0 et 2.5 Hz, 1 H), 9.76 (s, 1 H) | 560 |
| 189 | 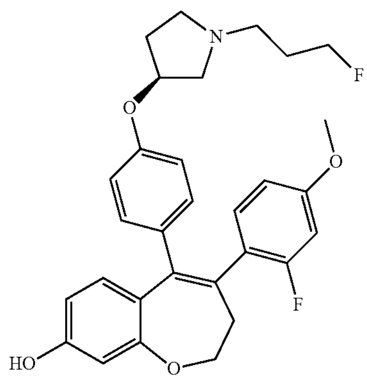 [SMILES: COc1ccc(C2=C(c3ccc(O[C@H]4CCN(CCCF)C4)cc3)c3ccc(O)cc3OCC2)c(F)c1] | 4-(2-fluoro-4-methoxy-phenyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.73 (m, 3 H), 2.19 (m, 1 H), 2.37 (q, J = 7.7 Hz, 1 H), 2.45 (m, 4 H), 2.54 (m, 1 H), 2.65 (m, 1 H), 2.79 (dd, J = 10.3 et 6.2 Hz, 1 H), 3.34 (m, 2 H), 3.71 (s, 3 H), 4.46 (dt, J = 47.4 et 6.0 Hz, 2 H), 4.73 (m, 1 H), 6.55-6.80 (m, 8 H), 6.97 (t, J = 8.7 Hz, 1 H), 7.04 (d, J = 2.3 Hz, 1 H), 9.73 (s, 1 H) | 524 |
| 190 | 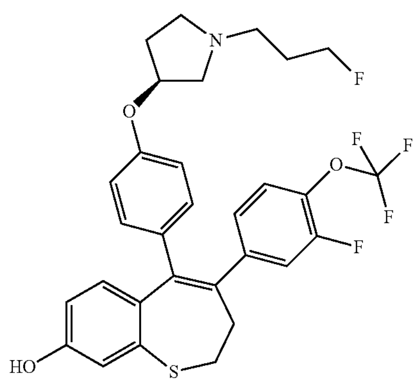 [SMILES: Oc1ccc2c(c1)SCCC(c1ccc(OC(F)(F)F)c(F)c1)=C2c1ccc(O[C@H]2CCN(CCCF)C2)cc1] | 5-[4-[(3S)-1-(3-fluoropropyl)pyr-rolidin-3-yl]oxyphenyl]-4-[3-fluoro-4-(trifluoromethoxy)phenyl]-2,3-dihydro-1-benzothiepin-8-ol | A | 1H NMR (400 MHz, DMSO-d6) δ ppm: 1.75 (m, 3 H), 2.23 (m, 1 H), 2.38 (m, 1 H), 2.44 (m, 4 H), 2.59 (m, 4 H), 2.74 (m, 1 H), 4.48 (dt, J = 47.5 et 6.0 Hz, 2H), 4.76 (d, J = 6.7 Hz, 1 H), 6.69 (m, 6 H), 7.04 (m, 2 H), 7.27 (dd, J = 11.6 et 1.8 Hz, 1 H), 7.37 (t, J = 8.1 Hz, 1 H), 9.83 (s, 1H) | 578 |
| 191 | 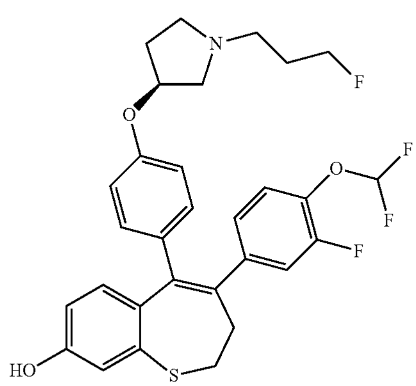 [SMILES: Oc1ccc2c(c1)SCCC(c1ccc(OC(F)F)c(F)c1)=C2c1ccc(O[C@H]2CCN(CCCF)C2)cc1] | 4-[4-(difluoromethoxy)-3-fluoro-phenyl]-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.76 (m, 3 H), 2.20 (m, 1 H), 2.38 (q, J = 7.7 Hz, 1 H), 2.46 (m, 2 H), 2.55 (m, 3 H), 2.65 (m, 1 H), 2.79 (dd, J = 10.1 et 6.2 Hz, 1 H), 3.31 (m, 2 H), 4.47 (dt, J = 47.7 et 5.9 Hz, 2 H), 4.76 (m, 1 H), 6.69 (m, 7 H), 6.99 (d, J = 8.8 Hz, 1 H), 7.05 (d, J = 2.0 Hz, 1 H), 7.17 (m, 2 H), 7.18 (t, J = 73.4 Hz, 1 H), 9.77 (s, 1 H) | 560 |

TABLE 1-continued

| Example | Structure | Name | Method | NMR | MASS LC/MS (m/z, MH+) |
|---|---|---|---|---|---|
| 192 | 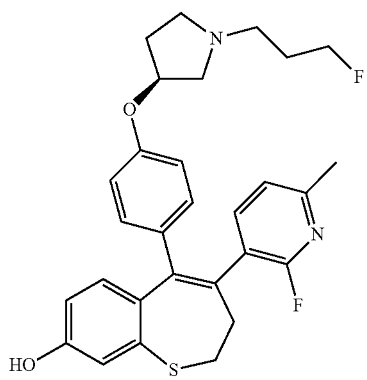 [SMILES: Cc1ccc(C2=C(c3ccc(O[C@H]4CCN(CCCF)C4)cc3)c3ccc(O)cc3SCC2)c(F)n1] | 4-(2-fluoro-6-methyl-3-pyridyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.75 (m, 3 H), 2.18 (m, 1 H), 2.35 (m, 4 H), 2.45-2.55 (m, 5 H), 2.65 (m, 1 H), 2.79 (dd, J = 10.3 et 6.2 Hz, 1 H), 3.33 (s, 2 H), 4.46 (dt, J = 47.4 et 6.0 Hz, 2 H), 4.73 (d, J = 6.5 Hz, 1 H), 6.60-6.75 (m, 6 H), 7.05 (m, 2 H), 7.47 (dd, J = 9.8 et 7.8 Hz, 1 H), 9.83 (s, 1 H) | 509 |
| 193 | 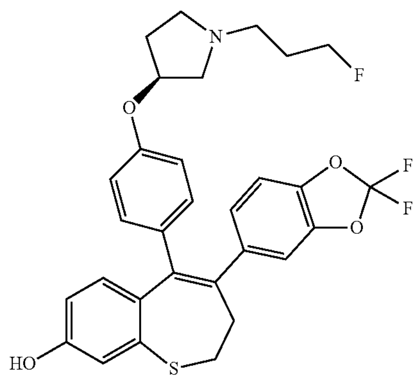 [SMILES: Oc1ccc2c(c1)SCCC(c1ccc3c(c1)OC(F)(F)O3)=C2c1ccc(O[C@H]2CCN(CCCF)C2)cc1] | 4-(2,2-difluoro-1,3-benzodioxol-5-yl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.76 (m, 3 H), 2.20 (m, 1 H), 2.34-2.85 (m, 8 H), 3.35 (m, 2 H), 4.46 (dt, J = 47.4 et 6.0 Hz, 2 H), 5.22 (m, 1 H), 6.68 (m, 5 H), 6.95 (dd, J = 8.6 et 2.3 Hz, 1 H), 7.05 (d, J = 2.1 Hz, 1 H), 7.20 (m, 1 H), 9.75 (s, 1 H) | 556 |
| 194 | 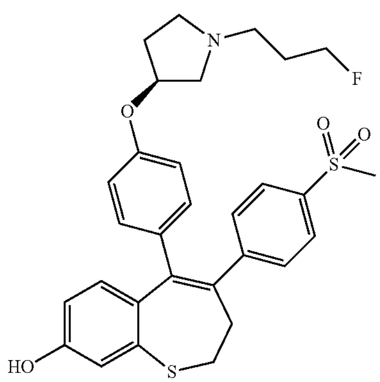 [SMILES: CS(=O)(=O)c1ccc(C2=C(c3ccc(O[C@H]4CCN(CCCF)C4)cc3)c3ccc(O)cc3SCC2)cc1] | 5-[4-[(3S)-1-(3-fluoropropyl)pyrrolidin-3-yl]oxyphenyl]-4-(4-methylsulfonylphenyl)-2,3-dihydro-1-benzothiepin-8-ol | A | 1H NMR (400 MHz, DMSO-d6) δ ppm: 1.74 (m, 3 H), 2.18 (m, 1 H), 2.35 (m, 1 H), 2.45 (d, J = 7.3 Hz, 2 H), 2.55 (m, 1 H), 2.63 (m, 3 H), 2.78 (dd, J = 10.3 et 6.2 Hz, 1 H), 3.18 (s, 3 H), 3.29 (m, 2 H), 4.46 (dt, J = 47.4 et 6.0 Hz, 2 H), 4.73 (m, 1 H), 6.61 (d, J = 8.6 Hz, 2 H), 6.70 (m, 3 H), 6.75 (dd, J = 8.6 et 2.1 Hz, 1 H), 7.06 (d, J = 2.1 Hz, 1 H), 7.42 (d, J = 8.4 Hz, 2 H), 7.74 (d, J = 8.4 Hz, 2 H), 9.82 (s, 1 H) | 554 |
| 195 | 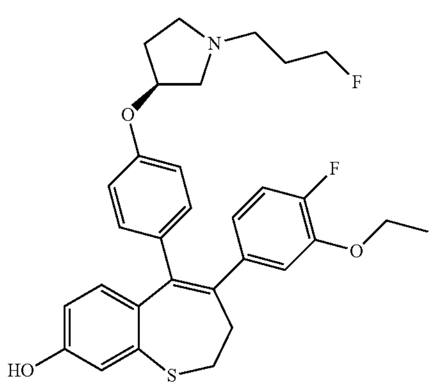 [SMILES: CCOc1cc(C2=C(c3ccc(O[C@H]4CCN(CCCF)C4)cc3)c3ccc(O)cc3SCC2)ccc1F] | 4-(3-ethoxy-4-fluoro-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.18 (t, J = 6.4 Hz, 3 H), 1.73 (m, 3 H), 2.20 (m, 1 H), 2.35-2.70 (m, 7 H), 2.83 (m, 1 H), 3.27 (m, 2 H), 3.82 (d, J = 6.4 Hz, 2 H), 4.47 (dt, J = 47.4, 6.0 Hz, 2 H), 4.75 (m, 1 H), 6.60-7.05 (m, 10 H), 9.74 (s, 1 H) | 538 |

TABLE 1-continued

| Example | Structure | Name | Method | NMR | MASS LC/MS (m/z, MH+) |
|---|---|---|---|---|---|
| 196 | 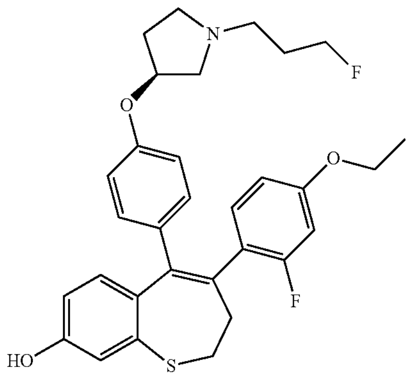 [SMILES: CCOc1ccc(C2=C(c3ccc(O[C@H]4CCN(CCCF)C4)cc3)c3ccc(O)cc3SCC2)c(F)c1] | 4-(4-ethoxy-2-fluoro-phenyl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.28 (t, J = 7.0 Hz, 3 H), 1.75 (m, 3 H), 2.18 (m, 1 H), 2.35 (m, 1 H), 2.45 (m, 4 H), 2.54 (d, J = 1.7 Hz, 1 H), 2.65 (m, 1 H), 2.79 (dd, J = 10.3 et 6.1 Hz, 1 H), 3.34 (m, 2 H), 3.97 (q, J = 7.0 Hz, 2 H), 4.46 (dt, J = 47.4 et 6.0 Hz, 2 H), 4.72 (m, 1 H), 6.58 (dd, J = 8.6 et 2.4 Hz, 1 H), 6.61 (d, J = 8.5 Hz, 2 H), 6.72 (m, 5 H), 6.95 (t, J = 8.7 Hz, 1 H), 7.04 (d, J = 2.3 Hz, 1 H), 9.74 (s, 1 H) | 538 |
| 197 | 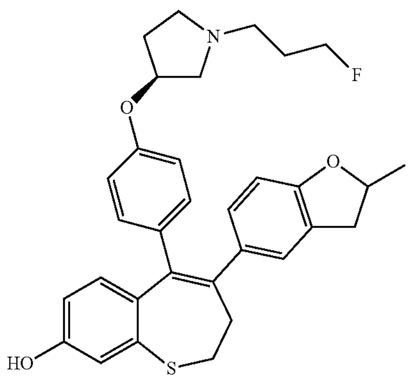 | 5-[4-[(3S)-1-(3-fluoropropyl)pyrrolidin-3-yl]oxyphenyl]-4-(2-methyl-2,3-dihydrobenzofuran-5-yl)-2,3-dihydro-1-benzothiepin-8-ol | A | 1H NMR (400 MHz, DMSO-d6) δ ppm: 1.34 (d, J = 6.2 Hz, 3 H), 1.75 (m, 3 H), 2.20 (m, 1 H), 2.38 (m, 1 H), 2.46 (t, J = 7.3 Hz, 2 H), 2.55 (m, 3 H), 2.65 (dd, J = 15.6 et 7.8 Hz, 2 H), 2.79 (dd, J = 10.3 et 6.2 Hz, 1 H), 3.18 (dd, J = 15.8 et 8.8 Hz, 1 H), 3.27 (m, 2 H), 4.47 (dt, J = 47.4 et 6.0 Hz, 2 H), 4.76 (m, 1 H), 4.84 (m, 1 H), 6.51 (d, J = 8.2 Hz, 1 H), 6.60-6.75 (m, 6 H), 6.84 (d, J = 8.5 Hz, 1 H), 7.00 (s, 1 H), 7.02 (d, J = 2.3 Hz, 1 H), 9.68 (s, 1 H) | 532 |
| 198 | 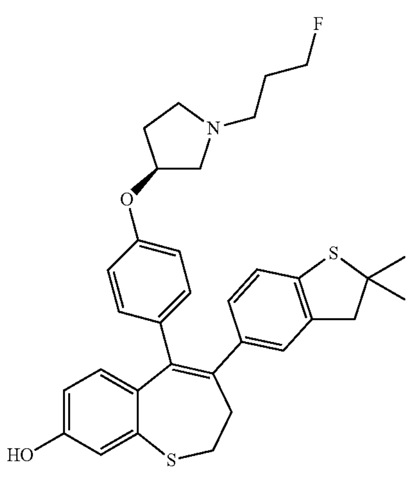 [SMILES: CC1(C)Cc2cc(C3=C(c4ccc(O[C@H]5CCN(CCCF)C5)cc4)c4ccc(O)cc4SCC3)ccc2S1] | 4-(2,2-dimethylindolin-5-yl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.17 (s, 6 H), 1.76 (m, 3 H), 2.19 (m, 1 H), 2.38 (q, J = 7.7 Hz, 1 H), 2.47 (d, J = 7.8 Hz, 2 H), 2.51 (m, 4 H), 2.57 (m, 1 H), 2.65 (m, 1 H), 2.79 (dd, J = 10.3 et 6.1 Hz, 1 H), 3.27 (m, 2 H), 4.47 (dd, J = 48.2 et 5.6 Hz, 2 H), 4.75 (m, 1 H), 5.41 (s, 1 H), 6.21 (d, J = 7.8 Hz, 1 H), 6.60 (d, J = 8.8 Hz, 2 H), 6.69 (m, 6 H), 7.00 (d, J = 2.0 Hz, 1 H), 9.61 (s, 1 H) | 545 |

TABLE 1-continued

| Example | Structure | Name | Method | NMR | MASS LC/MS (m/z, MH+) |
|---|---|---|---|---|---|
| 199 | 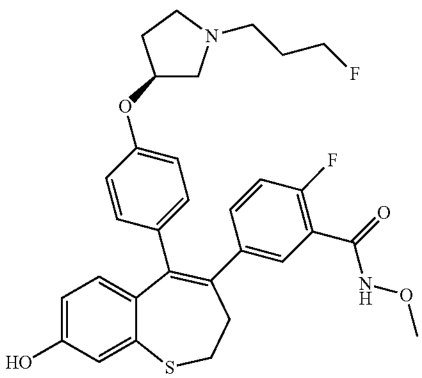 [SMILES: CONC(=O)c1cc(C2=C(c3ccc(O[C@H]4CCN(CCCF)C4)cc3)c3ccc(O)cc3SCC2)ccc1F] | 2-fluoro-5-[5-[4-[(3S)-1-(3-fluoropropyl)pyrrolidin-3-yl]oxyphenyl]-8-hydroxy-2,3-dihydro-1-benzothiepin-4-yl]-N-methoxybenzamide | A | 1H NMR (400 MHz, DMSO-d6) δ ppm: 1.77 (m, 3 H), 2.21 (m, 1 H), 2.38 (m, 1 H), 2.45 (m, 2 H), 2.62 (m, 4 H), 2.79 (dd, J = 10.3 et 6.1 Hz, 1 H), 3.34 (s, 2 H), 3.68 (s, 3 H), 4.47 (dt, J = 47.4 et 6.0 Hz, 2 H), 4.76 (m, 1 H), 6.61 (m, 2 H), 6.74 (m, 4 H), 7.09 (m, 2 H), 7.22 (m, 1 H), 7.42 (d, J = 4.9 Hz, 1 H), 9.74 (s, 1 H), 11.49 (s, 1 H) | 567 |
| 200 | 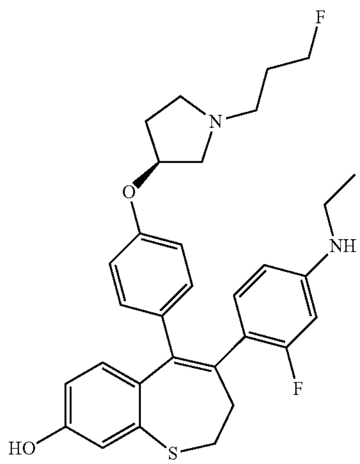 [SMILES: CCNc1ccc(C2=C(c3ccc(O[C@H]4CCN(CCCF)C4)cc3)c3ccc(O)cc3SCC2)c(F)c1] | 4-[4-(ethylamino)-2-fluoro-phenyl]-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.11 (t, J = 7.1 Hz, 3 H), 1.76 (m, 3 H), 2.19 (m, 1 H), 2.38 (m, 1 H), 2.45 (m, 2 H), 2.51 (m, 3 H), 2.64 (m, 1 H), 2.80 (dd, J = 10.3, 6.1 Hz, 1 H), 2.96 (m, 2 H), 3.34 (s, 2 H), 4.46 (dt, J = 46.9 et 6.1 Hz, 2 H), 4.73 (m, 1 H), 5.77 (t, J = 5.3 Hz, 1 H), 6.18 (m, 2 H), 6.61 (d, J = 8.8 Hz, 2 H), 6.69 (m, 5 H), 7.02 (d, J = 2.4 Hz, 1 H), 9.65 (s, 1H) | 537 |
| 201 | 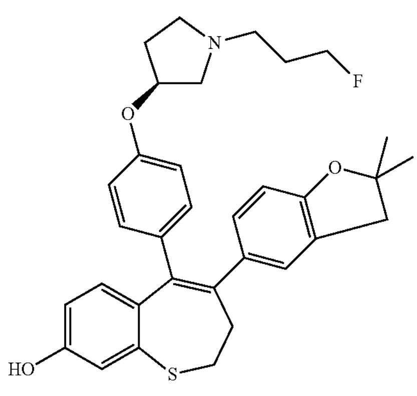 [SMILES: CC1(C)Cc2cc(C3=C(c4ccc(O[C@H]5CCN(CCCF)C5)cc4)c4ccc(O)cc4SCC3)ccc2O1] | 4-(2,2-dimethyl-3H-benzofuran-5-yl)-5-[4-[(3S)-1-(3-fluoropropyl)pyrrolidin-3-yl]oxyphenyl]-2,3-dihydro-1-benzothiepin-8-ol | A | 1H NMR (400 MHz, DMSO-d6) δ ppm: 1.36 (s, 6 H), 1.76 (m, 3 H), 2.19 (m, 1 H), 2.38 (m, 1 H), 2.45 (m, 2 H), 2.55 (m, 3 H), 2.63 (m, 1 H), 2.79 (dd, J = 10.3 6.1 Hz, 1 H), 2.85 (s, 2 H), 3.33 (m, 2 H), 4.46 (dt, J = 47.4 et 6.6 Hz, 2 H), 4.74 (m, 1 H), et 6.49 (d, J = 8.3 Hz, 1 H), 6.61 (m, 2 H), 6.70 (m, 4 H), 6.86 (d, J = 6.8 Hz, 1 H), 6.95 (s, 1 H), 7.02 (d, J = 2.2 Hz, 1 H), 9.65 (s, 1 H) | 546 |

TABLE 1-continued

| Example | Structure | Name | Method | NMR | MASS LC/MS (m/z, MH+) |
|---|---|---|---|---|---|
| 202 | 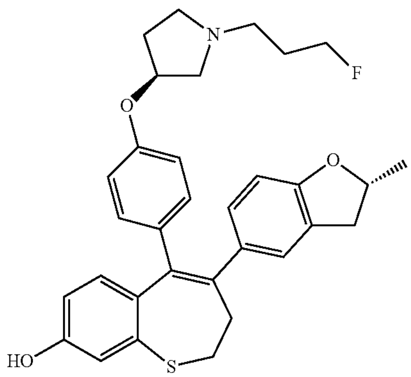 [SMILES: C[C@@H]1Cc2cc(C3=C(c4ccc(O[C@H]5CCN(CCCF)C5)cc4)c4ccc(O)cc4SCC3)ccc2O1] | 5-[4-[(3S)-1-(3-fluoropropyl)pyrrolidin-3-yl]oxyphenyl]-4-[(2R)-2-methyl-2,3-dihydrobenzofuran-5-yl]-2,3-dihydro-1-benzothiepin-8-ol | A | 1H NMR (400 MHz, DMSO-d6) δ 1.34 (d, J = 6.1 Hz, 3H), 1.77 (m, 3H), 2.19 (m, 1H), 2.38 (m, 1H), 2.44 (m, 2H), 2.54 (m masqué, J = 7.58 Hz, 3H), 2.65 (m, 2H), 2.80 (dd, J = 10.0 et 6.24 Hz, 1H), 3.17 (dd, J = 15.5 et 8.74 Hz, 1H), 3.32 (m, 2H), 4.46 (dt, J = 47.5 et 6.0 Hz, 2 H), 4.75 (m, 1H), 4.83 (m, 1H), 6.51 (d, J = 8.2 Hz, 1H), 6.59-6.72 (m, 6H), 6.85 (d, J = 8.3 Hz, 1H), 7.01 (d, J = 11 Hz, 2H), 9.62 (s, 1H) | 532 |
| 203 | 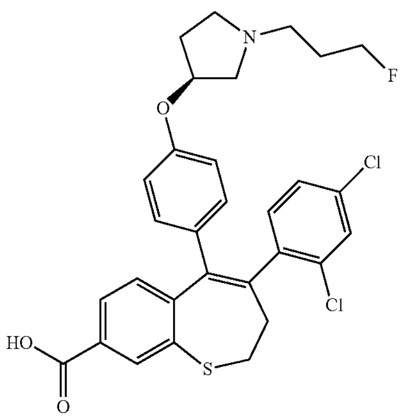 [SMILES: O=C(O)c1ccc2c(c1)SCCC(c1ccc(Cl)cc1Cl)=C2c1ccc(O[C@H]2CCN(CCCF)C2)cc1] | 4-(2,4-dichlorophenyl)-5-[4-[(3S)-1-(3-fluoropropyl)pyrrolidin-3-yl]oxyphenyl]-2,3-dihydro-1-benzothiepine-8-carboxylic acid | | 1H NMR (400 MHz, DMSO-d6) δ ppm: 1.75 (m, 3 H), 2.20 (m, 1 H), 2.35-2.65 (m, 8 H), 2.78 (m, 1 H), 3.33 (m, 1 H), 3.56 (m, 1 H), 4.46 (dt, J = 47.4 et 6.0 Hz, 2 H), 4.73 (m, 1 H), 6.69 (m, 4 H), 7.00 (d, J = 8.1 Hz, 1 H), 7.12 (d, J = 8.3 Hz, 1 H), 7.28 (dd, J = 8.3, 1.9 Hz, 1 H), 7.67 (d, J = 2.0 Hz, 1 H), 7.87 (d, J = 8.1 Hz, 1 H), 8.14 (d, J = 1.5 Hz, 1 H) | 573 |
| 204 | 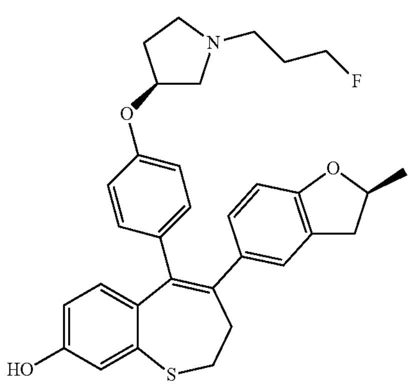 [SMILES: C[C@H]1Cc2cc(C3=C(c4ccc(O[C@H]5CCN(CCCF)C5)cc4)c4ccc(O)cc4SCC3)ccc2O1] | 5-[4-[(3S)-1-(3-fluoropropyl)pyrrolidin-3-yl]oxyphenyl]-4-[(2S)-2-methyl-2,3-dihydrobenzofuran-5-yl]-2,3-dihydro-1-benzothiepin-8-ol | A | 1H NMR (400 MHz, DMSO-d6) δ ppm: 1.34 (d, J = 6.1 Hz, 3 H), 1.79 (m, 3 H), 2.20 (m, 1 H), 2.28 (m, 1 H), 2.44 (m, 2 H), 2.56 (m, 2 H), 2.64 (dd, J = 15.4 et 7.7 Hz, 3 H), 2.79 (dd, J = 10.3 et 6.2 Hz, 1 H), 3.18 (m, 2 H), 4.47 (dt, J = 47.5 et 6.0 Hz, 2 H), 4.75 (d, J = 6.8 Hz, 1 H), 4.83 (m, 1 H), 6.51 (d, J = 8.2 Hz, 1 H), 6.59 (d, J = 7.5 Hz, 2 H), 6.68 (m, 4 H), 6.85 (d, J = 8.3 Hz, 1 H), 6.99 (s, 1 H), 7.02 (d, J = 2.2 Hz, 1 H), 9.64 (s, 1 H) | 532 |
| 205 | 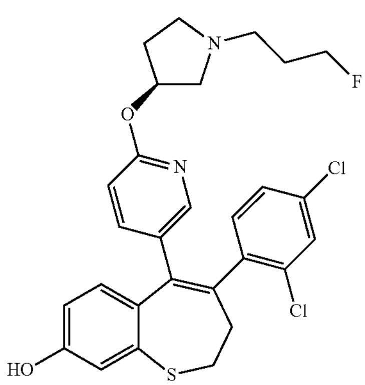 [SMILES: Oc1ccc2c(c1)SCCC(c1ccc(Cl)cc1Cl)=C2c1ccc(O[C@H]2CCN(CCCF)C2)nc1] | 4-(2,4-dichlorophenyl)-5-[(6-[(3S)-1-(3-fluoropropyl)pyrrolidin-3-yl]oxy-3-pyridyl]-2,3-dihydro-1-benzothiepin-8-ol | A | 1H NMR (300 MHz, DMSO-d6) δ ppm: 1.69-2.09 (m, 3 H), 2.25-2.82 (m, 7 H), 3.25 (m, 3 H), 3.51 (m, 1 H), 4.49 (dt, J = 47.3 et 5.5 Hz, 2 H), 5.33 (m, 1 H), 6.63 (d, J = 8.4 Hz, 1 H), 6.74 (m, 2 H), 7.10 (m, 2 H), 7.15 (dd, J = 8.2 Hz, 1 H), 7.30 (dd, J = 8.2 et 2.0 Hz, 1 H), 7.57 (s, 1 H), 7.67 (d, J = 2.0 Hz, 1 H), 9.86 (s, 1 H) | 546 |

TABLE 1-continued

| Example | Structure | Name | Method | NMR | MASS LC/MS (m/z, MH+) |
|---|---|---|---|---|---|
| 206 | 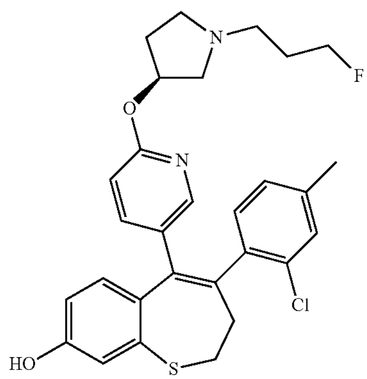 [SMILES: Cc1ccc(C2=C(c3ccc(O[C@H]4CCN(CCCF)C4)nc3)c3ccc(O)cc3SCC2)c(Cl)c1] | 4-(2-chloro-4-methyl-phenyl)-5-[6-[(3S)-1-(3-fluoropropyl)pyrrolidin-3-yl]oxy-3-pyridyl]-2,3-dihydro-1-benzothiepin-8-ol | A | 1H NMR (400 MHz, DMSO-d6) δ ppm: 1.75 (m, 3 H), 2.18 (m, 1 H), 2.25 (s, 3 H), 2.36 (m, 1 H), 2.40-2.60 (m, 5 H), 2.70 (m, 2 H), 3.19 (m, 1 H), 3.53 (m, 1 H), 4.46 (dt, J = 47.4 et 5.9 Hz, 2 H), 5.20 (m, 1 H), 6.54 (d, J = 8.6 Hz, 1 H), 6.73 (s, 2 H), 6.95-7.10 (m, 4 H), 7.30 (s, 1 H), 7.55 (s, 1 H), 9.79 (s, 1 H) | 525 |
| 207 | 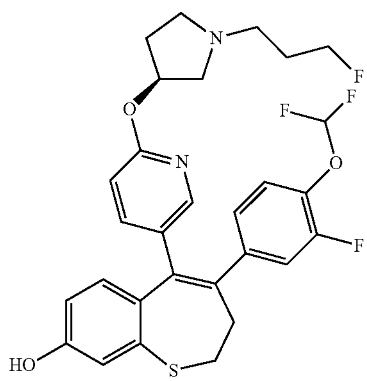 [SMILES: Oc1ccc2c(c1)SCCC(c1ccc(OC(F)F)c(F)c1)=C2c1ccc(O[C@H]2CCN(CCCF)C2)nc1] | 4-[4-(difluoromethoxy)-3-fluoro-phenyl]-5-[6-[(3S)-1-(3-fluoropropyl)pyrrolidin-3-yl]oxy-3-pyridyl]-2,3-dihydro-1-benzothiepin-8-ol | A | 1H NMR (400 MHz, DMSO-d6) δ ppm: 1.77 (m, 3 H), 2.18 (m, 1 H), 2.35 (q, J = 7.5 Hz, 1 H), 2.45 (t, J = 7.3 Hz, 2 H), 2.56 (d, J = 8.6 Hz, 1 H), 2.60 (t, J = 6.1 Hz, 2 H), 2.67 (m, 1 H), 2.75 (dd, J = 10.5 et 6.3 Hz, 1 H), 3.39 (m, 2 H), 4.46 (dt, J = 47.4 et 6.0 Hz, 2 H), 5.21 (m, 1 H), 6.60 (d, J = 8.6 Hz, 1 H), 6.75 (m, 2 H), 6.99 (m, 1 H), 7.10 (m, 2 H), 7.22 (m, 3 H), 7.56 (d, J = 2.2 Hz, 1 H), 9.80 (s, 1 H) | 561 |
| 208 | 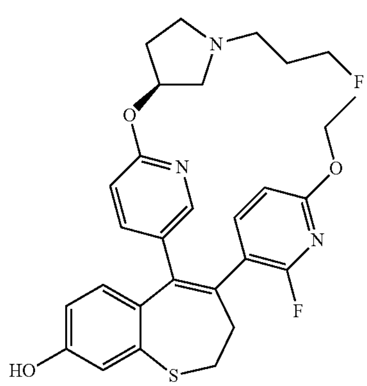 [SMILES: CCOc1ccc(C2=C(c3ccc(O[C@H]4CCN(CCCF)C4)nc3)c3ccc(O)cc3SCC2)c(F)n1] | 4-(6-ethoxy-2-fluoro-3-pyridyl)-5-[6-[(3S)-1-(3-fluoropropyl)pyrrolidin-3-yl]oxy-3-pyridyl]-2,3-dihydro-1-benzothiepin-8-ol | A | 1H NMR (400 MHz, DMSO-d6) δ ppm: 1.28 (m, 3 H), 1.78 (m, 3 H), 2.17 (m, 1 H), 2.35 (m, 1 H), 2.44 (m, 2 H), 2.57 (m, 2 H), 2.67 (m, 1 H), 2.76 (dd, J = 10.3 et 6.3 Hz, 1 H), 3.37 (m, 2 H), 4.20 (q, J = 7.0 Hz, 2 H), 4.46 (dt, J = 47.5 et 6.0 Hz, 2 H), 5.23 (m, 1 H), 6.60 (d, J = 8.6 Hz, 1 H), 6.64 (d, J = 8.1 Hz, 1 H), 6.73 (m, 2 H), 7.07 (m, 2 H), 7.57 (m, 2 H), 9.80 (s, 1 H) | 540 |
| 209 | 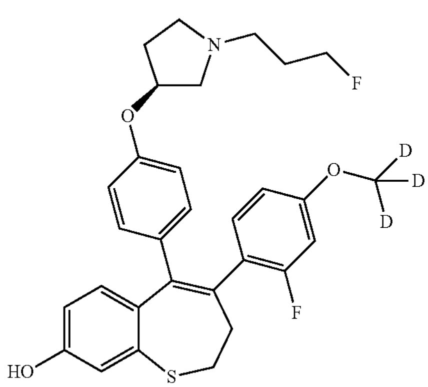 [SMILES: [2H]C([2H])([2H])Oc1ccc(C2=C(c3ccc(O[C@H]4CCN(CCCF)C4)cc3)c3ccc(O)cc3SCC2)c(F)c1] | 5-[4-[(3S)-1-(3-fluoropropyl)pyrrolidin-3-yl]oxyphenyl]-4-[2-fluoro-4-(trideuteriomethoxy)phenyl]-2,3-dihydro-1-benzothiepin-8-ol | A | 1H NMR (400 MHz, DMSO-d6) δ ppm: 1.75 (m, 3 H), 2.21 (m, 1 H), 2.35 (m, 1 H), 2.45 (m, 2 H), 2.56 (m, 3 H), 2.65 (m, 2 H), 2.79 (dd, J = 10.3 et 6.2 Hz, 1 H), 3.37 (m, 2 H), 4.46 (dt, J = 47.5 et 6.0 Hz, 2 H), 4.73 (m, 1 H), 6.61 (m, 3 H), 6.71 (m, 4 H), 6.97 (t, J = 8.7 Hz, 1 H), 7.04 (d, J = 2.2 Hz, 1 H), 9.70 (s, 1 H) | 527 |

TABLE 1-continued

| Example | Name | Method | NMR | MASS LC/MS (m/z, MH+) |
|---|---|---|---|---|
| 210 | 4-(2-fluoro-4-methyl-phenyl)-5-[4-[(3S)-1-(3-fluoropropyl)pyrrolidin-3-yl]oxyphenyl]-2,3-dihydro-1-benzothiepine-8-carboxylic acid | | 1H NMR (400 MHz, DMSO-d6) δ 1.74 (m, 3H), 2.22 (m, 1H), 2.28 (s, 3H), 2.38 (m, 1H), 2.44 (m masqué, 5H), 2.60 (m, 1H), 2.79 (dd, J = 10.5 et 6.2 Hz, 1H), 3.41 (m, 2H), 4.46 (dt, J = 47.5 et 6.0 Hz, 2 H), 4.73 (m, 1H), 6.62 (d, J = 7.5 Hz, 2H), 6.71 (d, J = 7.5 Hz, 2H), 6.85 (d, J = 7.7 Hz, 1H), 6.96 (m, 3H), 7.83 (d, J = 8.4 Hz, 1H), 8.13 (s, 1H), 13 (s, 1H) | 536 |
| 211 | 4-(4-chloro-3-methyl-phenyl)-5-[4-[(3S)-1-(3-fluoropropyl)pyrrolidin-3-yl]oxyphenyl]-2,3-dihydro-1-benzothiepine-8-carboxylic acid | | 1H NMR (400 MHz, DMSO-d6) δ ppm: 1.77 (m, 3 H), 2.15 (s, 3 H), 2.20 (m, 1 H), 2.35-2.55 (m, 6 H), 2.61 (m, 1 H), 2.78 (m, 1 H), 3.42 (m, 2 H), 4.46 (dt, J = 47.5 et 6.0 Hz, 2 H), 4.73 (m, 1 H), 6.63 (m, 4 H), 6.97 (d, J = 8.1 Hz, 1 H), 7.19 (m, 3 H), 7.85 (dd, J = 8.1 et 1.5 Hz, 1 H), 8.15 (d, J = 1.5 Hz, 1 H), 13.1 (s, 1 H) | 552 |
| 212 | 5-[4-[(3S)-1-(3-fluoropropyl)pyrrolidin-3-yl]oxyphenyl]-4-[2-fluoro-4-(trifluoromethoxy)phenyl]-2,3-dihydro-1-benzothiepin-8-ol | A | 1H NMR (400 MHz, DMSO-d6) δ ppm: 1.72 (m, 3 H), 2.17 (m, 1 H), 2.35 (m, 1 H), 2.46 (d, J = 7.5 Hz, 2 H), 2.53 (m, 3 H), 2.65 (m, 1 H), 2.78 (dd, J = 10.3 et 6.1 Hz, 1 H), 3.35 (t, J = 6.3 Hz, 2 H), 4.46 (dt, J = 47.4 et 6.0 Hz, 2 H), 4.73 (m, 1 H), 6.59 (d, J = 8.5 Hz, 2 H), 6.75 (m, 4 H), 7.06 (m, 2 H), 7.22 (t, J = 8.1 Hz, 1 H), 7.29 (d, J = 10.1 Hz, 1 H), 9.83 (s, 1 H) | 578 |

TABLE 1-continued

| Example | Name | Method | NMR | MASS LC/MS (m/z, MH+) |
|---|---|---|---|---|
| 213 | 4-[4-(difluoromethoxy)-2-fluoro-phenyl]-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.75 (m, 3 H), 2.18 (m, 1 H), 2.35-2.60 (m, 6 H), 2.66 (m, 1 H), 2.78 (dd, J = 10.2 et 6.2 Hz, 1 H), 3.35 (m, 2 H), 4.46 (dt, J = 47.4 et 6.0 Hz, 2 H), 4.72 (m, 1 H), 6.61 (m, 2 H), 6.72 (m, 4 H), 6.86 (dd, J = 8.4 et 1.8 Hz, 1 H), 7.05 (m, 2 H), 7.14 (t, J = 8.5 Hz, 1H), 7.25 (t, J = 73.7 Hz, 1 H), 9.80 (s, 1 H) | 560 |
| 214 | 5-[4-[(3S)-1-(3-fluoropropyl)pyr-rolidin-3-yl]oxyphenyl]-4-[4-(trifluoromethoxy)phenyl]-2,3-dihydro-1-benzothiepin-8-ol | A | 1H NMR (400 MHz, DMSO-d6) δ ppm: 1.73 (m, 3 H), 2.17 (m, 1 H), 2.37 (m, 1 H), 2.47 (m, 2 H), 2.61 (m, 4 H), 2.78 (dd, J = 10.2 et 6.2 Hz, 1 H), 3.34 (m, 2 H), 4.46 (dt, J = 47.4, 6.0 Hz, 2 H), 4.73 (m, 1 H), 6.61 (d, J = 8.1 Hz, 2 H), 6.79 (m, 4 H), 7.05 (d, J = 2.2 Hz, 1 H), 7.18 (d, J = 8.1 Hz, 2 H), 7.31 (d, J = 8.1 Hz, 2 H), 9.73 (s, 1 H) | 560 |
| 215 | 4-(2,6-difluoro-3-pyridyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.75 (m, 3 H), 2.20 (dq, J = 13.4, 6.9 Hz, 1 H), 2.41 (m, 3 H), 2.54 (s, 3 H), 2.67 (s, 1 H), 2.80 (s, 1 H), 3.37 (d, J = 6.2 Hz, 2 H), 4.47 (dt, J = 47.4, 6.0 Hz, 2 H), 4.74 (m, 1 H), 6.72 (m, 6 H), 7.03 (m, 2 H), 7.84 (m, 1 H), 9.79 (s, 1 H) | 513 |
| 216 | 4-(4-tert-butylphenyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.23 (s, 9 H), 1.74 (m, 3 H), 2.19 (m, 6.8 Hz, 1 H), 2.37 (m, 1 H), 2.46 (d, J = 7.3 Hz, 2 H), 2.55 (m, 3 H), 2.65 (m, 1 H), 2.78 (dd, J = 10.2 et 6.2 Hz, 1 H), 3.27 (m, 2 H), 4.46 (dt, J = 47.4 et 6.0 Hz, 2 H), 4.73 (m, 1 H), 6.59 (d, J = 8.6 Hz, 2 H), 6.72 (m, 4 H), 7.03 (d, J = 2.2 Hz, 1 H), 7.08 (d, J = 8.2 Hz, 2 H), 7.20 (d, J = 8.2 Hz, 2 H), 9.66 (s, 1 H) | 532 |

TABLE 1-continued

| Example | Structure | Name | Method | NMR | MASS LC/MS (m/z, MH+) |
|---|---|---|---|---|---|
| 217 | 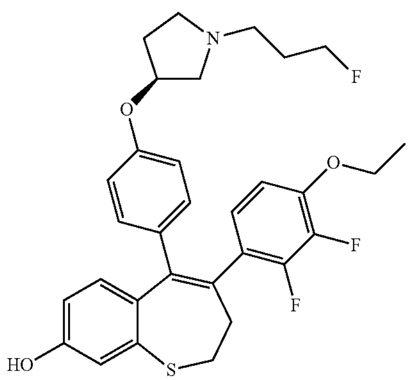 [SMILES: CCOc1ccc(C2=C(c3ccc(O[C@H]4CCN(CCCF)C4)cc3)c3ccc(O)cc3SCC2)c(F)c1F] | 4-(4-ethoxy-2,3-difluoro-phenyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.31 (t, J = 7.0 Hz, 3 H), 1.75 (m, 3 H), 2.19 (m, 1 H), 2.41 (m, 5 H), 2.54 (s, 1 H), 2.65 (m, 1 H), 2.79 (dd, J = 10.3, 6.2 Hz, 1 H), 3.34 (s, 2 H), 4.07 (q, J = 6.9 Hz, 2 H), 4.46 (dt, J = 47.4, 6.0 Hz, 2 H), 4.74 (m, J = 6.5, 6.5 Hz, 1 H), 6.64 (m, 2 H), 6.71 (m, 4 H), 6.85 (m, 2 H), 7.05 (d, J = 2.1 Hz, 1 H), 9.77 (s, 1 H) | 556 |
| 218 | 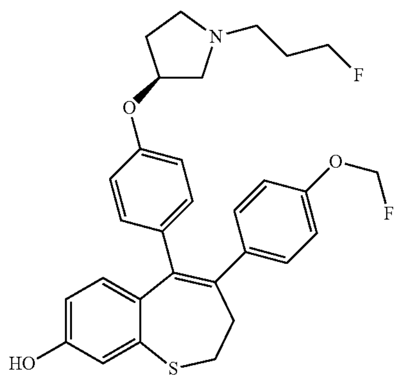 [SMILES: Oc1ccc2c(c1)SCCC(c1ccc(OCF)cc1)=C2c1ccc(O[C@H]2CCN(CCCF)C2)cc1] | 4-[4-(fluoromethoxy)phenyl]-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.75 (m, 3 H), 2.18 (m, 1 H), 2.38 (m, 1 H), 2.45-2.60 (m, 5 H), 2.65 (m, 1 H), 2.79 (dd, J = 10.3 et 6.2 Hz, 1 H), 3.31 (m, 2 H), 4.46 (dt, J = 47.4 et 6.0 Hz, 2 H), 4.75 (m, 1 H), 5.81 (d, J = 54.4 Hz, 2 H), 6.61 (d, J = 8.7 Hz, 2 H), 6.72 (m, 4 H), 6.93 (d, J = 8.6 Hz, 2 H), 7.03 (d, J = 2.2 Hz, 1 H), 7.15 (d, J = 8.7 Hz, 2 H), 9.71 (s, 1 H) | 524 |
| 219 | 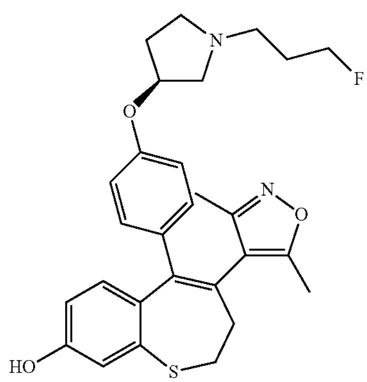 [SMILES: Cc1noc(C)c1C1=C(c2ccc(O[C@H]3CCN(CCCF)C3)cc2)c2ccc(O)cc2SCC1] | 4-(3,5-dimethylisoxazol-4-yl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.77 (m, 3 H), 2.01 (s, 3 H), 2.07 (s, 3 H), 2.21 (m, 1 H), 2.38 (q, J = 6.7 Hz, 3 H), 2.46 (m, 2 H), 2.56 (dd, J = 10.3 et 2.4 Hz, 1 H), 2.65 (m, 1 H), 2.80 (dd, J = 10.3 et 6.2 Hz, 1 H), 3.37 (m, 2 H), 4.47 (dt, J = 47.4 et 6.0 Hz, 2 H), 4.77 (s, 1 H), 6.71 (m, 6 H), 7.06 (d, J = 2.0 Hz, 1 H), 9.77 (s, 1 H) | 495 |
| 220 | 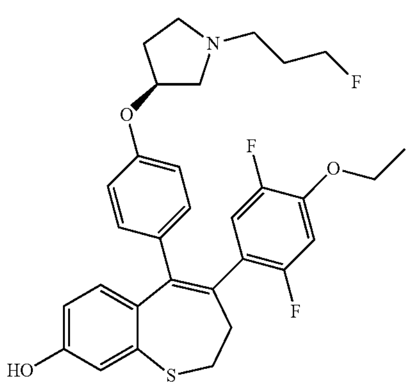 [SMILES: CCOc1cc(F)c(C2=C(c3ccc(O[C@H]4CCN(CCCF)C4)cc3)c3ccc(O)cc3SCC2)cc1F] | 4-(4-ethoxy-2,5-difluoro-phenyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.31 (t, J = 7.0 Hz, 3 H), 1.73 (m, 3 H), 2.19 (m, 1 H), 2.38 (m, 1 H), 2.46 (m, 4 H), 2.54 (m, 1 H), 2.66 (m, 1 H), 2.79 (dd, J = 10.3, 6.2 Hz, 1 H), 3.34 (d, J = 6.7 Hz, 2 H), 4.08 (m, 2 H), 4.46 (dt, J = 47.4, 6.0 Hz, 2 H), 4.76 (m, 1 H), 6.69 (m, 6 H), 6.88 (dd, J = 11.7, 7.0 Hz, 1 H), 6.99 (m, 1 H), 7.04 (d, J = 2.3 Hz, 1 H), 9.76 (s, 1 H) | 556 |

TABLE 1-continued

| Example | Structure | Name | Method | NMR | MASS LC/MS (m/z, MH+) |
|---|---|---|---|---|---|
| 221 | 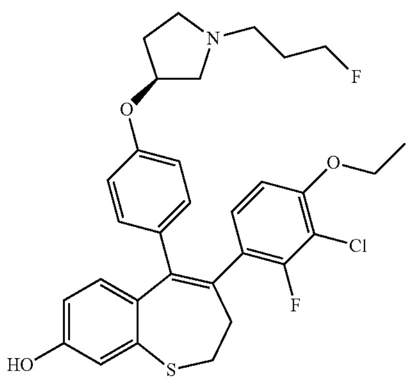 [SMILES: CCOc1ccc(C2=C(c3ccc(O[C@H]4CCN(CCCF)C4)cc3)c3ccc(O)cc3SCC2)c(F)c1Cl] | 4-(3-chloro-4-ethoxy-2-fluoro-phenyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.33 (t, J = 7.0 Hz, 3 H), 1.74 (m, 3 H), 2.15 (s, 1 H), 2.38 (m, 1 H), 2.44 (m, 4 H), 2.55 (m, 1 H), 2.64 (d, J = 6.6 Hz, 1 H), 2.76 (m, 1 H), 3.36 (m, 2 H), 4.07 (q, J = 7.0 Hz, 2 H), 4.46 (dt, J = 47.4 et 6.0 Hz, 2 H), 4.74 (s, 1 H), 6.62-6.78 (m, 6 H), 6.83 (d, J = 8.4 Hz, 1 H), 7.00 (t, J = 8.2 Hz, 1 H), 7.05 (d, J = 2.4 Hz, 1 H), 9.75 (s, 1 H) | 572 |
| 222 | 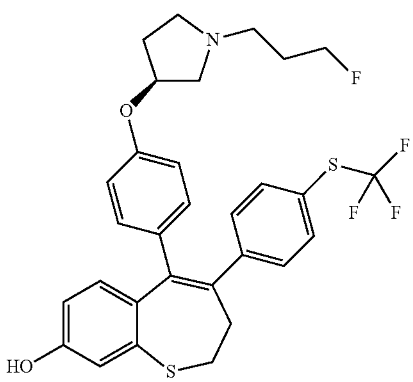 [SMILES: Oc1ccc2c(c1)SCCC(c1ccc(SC(F)(F)F)cc1)=C2c1ccc(O[C@H]2CCN(CCCF)C2)cc1] | 5-[4-[(3S)-1-(3-fluoropropyl)pyr-rolidin-3-yl]oxyphenyl]-4-[4-(trifluoromethyl-sulfanyl)phenyl]-2,3-dihydro-1-benzothiepin-8-ol | A | 1H NMR (400 MHz, DMSO-d6) δ ppm: 1.78 (m, 3 H), 2.21 (m, 1 H), 2.40 (m, 3 H), 2.61 (m, 6 H), 2.77 (dd, J = 10.2, 6.2 Hz, 1 H), 4.46 (dt, J = 47.4, 6.0 Hz, 2 H), 4.73 (m, 1 H), 6.58 (m, 2 H), 6.70 (m, 4 H), 7.05 (d, J = 2.1 Hz, 1 H), 7.31 (d, J = 8.2 Hz, 2 H), 7.53 (d, J = 8.1 Hz, 2 H), 9.80 (m, 1 H) | 576 |
| 223 | 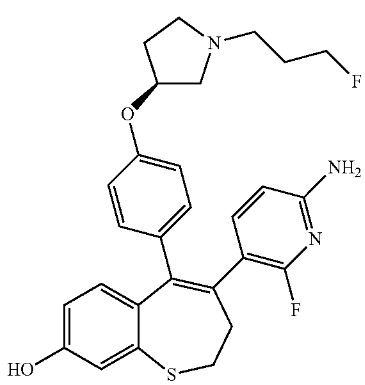 [SMILES: Nc1ccc(C2=C(c3ccc(O[C@H]4CCN(CCCF)C4)cc3)c3ccc(O)cc3SCC2)c(F)n1] | 4-(6-amino-2-fluoro-3-pyridyl)-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.77 (m, 3 H), 2.19 (m, 1 H), 2.41 (m, 5 H), 2.56 (d, J = 2.3 Hz, 1 H), 2.66 (m, 1 H), 2.81 (dd, J = 10.2, 6.2 Hz, 1 H), 3.34 (s, 2 H), 4.47 (dt, J = 47.7, 6.0 Hz, 2 H), 4.75 (m, J = 6.6, 6.6 Hz, 1 H), 6.11 (dd, J = 8.0, 1.4 Hz, 1 H), 6.23 (s, 2 H), 6.69 (m, 6 H), 7.02 (d, J = 2.2 Hz, 1 H), 7.10 (dd, J = 10.1, 8.3 Hz, 1 H), 9.71 (s, 1 H) | 510 |
| 224 | 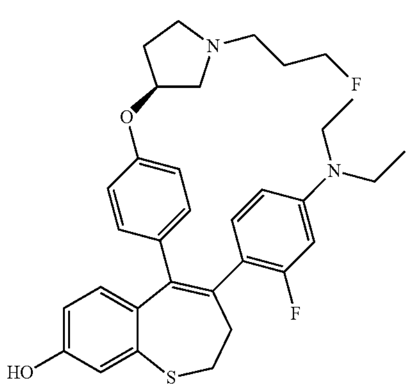 [SMILES: CCN(CC)c1ccc(C2=C(c3ccc(O[C@H]4CCN(CCCF)C4)cc3)c3ccc(O)cc3SCC2)c(F)c1] | 4-[4-(diethylamino)-2-fluoro-phenyl]-5-[4-[(3S)-1-(3-fluoropropyl)pyr-rolidin-3-yl]oxyphenyl]-2,3-dihydro-1-benzothiepin-8-ol | A | 1H NMR (400 MHz, DMSO-d6) δ ppm: 1.04 (t, J = 7.0 Hz, 6 H), 1.75 (m, 3 H), 2.15 (m, 1 H), 2.40 (m, 5 H), 2.54 (s, 1 H), 2.65 (m, 1 H), 2.79 (dd, J = 10.2, 6.2 Hz, 1 H), 3.27 (q, J = 6.9 Hz, 4 H), 3.33 (m, 2 H), 4.46 (dt, J = 47.4, 6.0 Hz, 2 H), 4.73 (d, J = 6.8 Hz, 1 H), 6.27 (dd, J = 8.7, 2.4 Hz, 1 H), 6.32 (dd, J = 14.5, 2.2 Hz, 1 H), 6.64 (m, 6 H), 6.80 (t, J = 8.9 Hz, 1 H), 7.02 (d, J = 2.3 Hz, 1 H), 9.68 (s, 1 H) | 565 |

TABLE 1-continued

| Example | Structure | Name | Method NMR | MASS LC/MS (m/z, MH+) |
|---|---|---|---|---|
| 225 | Racemic | 5-[4-[(3S)-1-(3-fluoropropyl)pyrrolidin-3-yl]oxyphenyl]-1-oxo-4-[4-(trifluoromethoxy)phenyl]-2,3-dihydro-1λ⁴-benzothiepin-8-ol | 1H NMR (400 MHz, DMSO-d6) δ ppm: 1.75 (m, 3 H), 2.18 (m, 1 H), 2.35 (m, 1 H), 2.45 (td, J = 7.3, 2.3 Hz, 2 H), 2.62 (m, 4 H), 2.77 (td, J = 10.1, 6.2 Hz, 1 H), 3.00 (dd, J = 11.9, 6.4 Hz, 1 H), 4.16 (td, J = 12.3, 6.5 Hz, 1 H), 4.46 (dt, J = 47.4, 6.0 Hz, 2 H), 4.74 (m, J = 6.7, 6.7 Hz, 1 H), 6.62 (m, 2 H), 6.69 (m, 2 H), 6.79 (d, J = 8.3 Hz, 1 H), 6.90 (m, 1 H), 7.25 (m, 5 H), 10.26 (s, 1 H) | 576 |
| 226 | Isomer 1 | 5-[4-[(3S)-1-(3-fluoropropyl)pyrrolidin-3-yl]oxyphenyl]-1-oxo-4-[4-(trifluoromethoxy)phenyl]-2,3-dihydro-1λ⁴-benzothiepin-8-ol | 1H NMR (400 MHz, DMSO-d6) δ ppm: 1.73 (m, 3 H), 2.19 (m, 1 H), 2.38 (m, 1 H), 2.48 (m, 2 H), 2.64 (m, 4 H), 2.79 (dd, J = 10.3 et 6.2 Hz, 1 H), 3.01 (m, 1 H), 4.16 (td, J = 12.2 et 6.5 Hz, 1 H), 4.46 (dt, J = 47.4 et 6.0 Hz, 2 H), 4.75 (m, 1 H), 6.64 (d, J = 8.3 Hz, 2H), 6.70 (d, J = 8.3 Hz, 2H), 6.80 (d, J = 8.3 Hz, 1 H), 6.89 (dd, J = 8.3 et 2.6 Hz, 1 H), 7.25 (m, 5 H), 10.24 (s, 1 H) | 576 |
| 227 | Isomer 2 | 5-[4-[(3S)-1-(3-fluoropropyl)pyrrolidin-3-yl]oxyphenyl]-1-oxo-4-[4-(trifluoromethoxy)phenyl]-2,3-dihydro-1λ⁴-benzothiepin-8-ol | 1H NMR (400 MHz, DMSO-d6) δ ppm: 1.75 (m, 3 H), 2.20 (m, 1 H), 2.39 (d, J = 4.8 Hz, 3 H), 2.62 (m, 4 H), 2.80 (m, 1 H), 3.00 (dd, J = 11.9, 6.7 Hz, 1 H), 4.16 (td, J = 12.1, 6.2 Hz, 1 H), 4.46 (dt, J = 47.4, 6.0 Hz, 2 H), 4.75 (s, 1 H), 6.66 (m, 4 H), 6.79 (d, J = 8.4 Hz, 1 H), 6.89 (dd, J = 8.3, 2.4 Hz, 1 H), 7.23 (m, 5 H), 10.23 (s, 1 H) | 576 |

TABLE 1-continued

| Example | Structure | Name | Method | NMR | MASS LC/MS (m/z, MH+) |
|---|---|---|---|---|---|
| 228 | 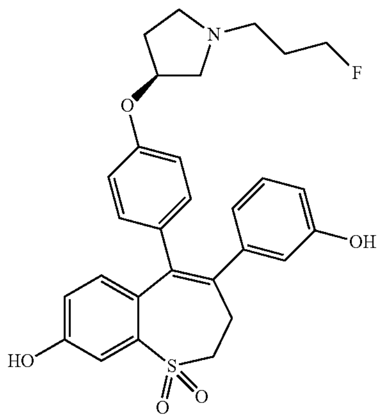 [SMILES: O=S1(=O)CCC(c2cccc(O)c2)=C(c2ccc(O[C@H]3CCN(CCCF)C3)cc2)c2ccc(O)cc21] | 5-[4-[(3S)-1-(3-fluoropropyl)pyrrolidin-3-yl]oxyphenyl]-4-(3-hydroxyphenyl)-1,1-dioxo-2,3-dihydro-1$\lambda^6$-benzothiepin-8-ol | C | 1H NMR (400 MHz, DMSO-d6) δ ppm: 1.74 (m, 3 H), 2.19 (m, 1 H), 2.38 (m, 1 H), 2.45 (m, 2 H), 2.55 (m, 1 H), 2.62 (m, 1 H), 2.73 (d, J = 6.5 Hz, 2 H), 2.80 (dd, J = 10.3 et 6.2 Hz, 1 H), 3.67 (d, J = 6.5 Hz, 2 H), 4.46 (dt, J = 47.4 et 6.1 Hz, 2 H), 4.73 (m, 1 H), 6.52-6.61 (m, 3 H), 6.63 (d, J = 8.8 Hz, 2 H), 6.76 (d, J = 8.8 Hz, 2 H), 6.83 (d, J = 8.4 Hz, 1 H), 7.00 (m, 3 H), 7.40 (d, J = 2.7 Hz, 1 H), 9.22 (s, 1 H), 10.35 (s, 1 H). | 524 |
| 229 | 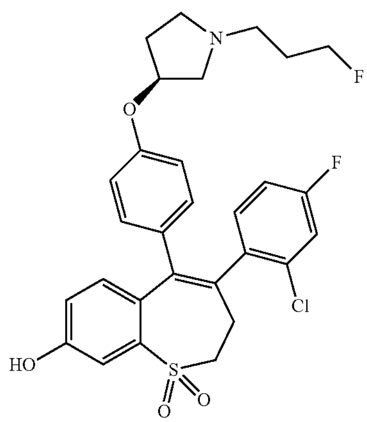 [SMILES: O=S1(=O)CCC(c2ccc(F)cc2Cl)=C(c2ccc(O[C@H]3CCN(CCCF)C3)cc2)c2ccc(O)cc21] | 4-(2-chloro-4-fluoro-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol | C | 1H NMR (400 MHz, DMSO-d6) δ ppm: 1.87 (m, 3 H), 2.20-3.00 (m, 10 H), 3.75 (m, 2 H), 4.48 (d, J = 46.8 Hz, 2 H), 4.84 (m, 1 H), 6.74 (m, 3 H), 6.88 (d, J = 7.9 Hz, 1 H), 7.07 (m, 3 H), 7.43 (m, 1 H), 7.50 (m J = 7.9 Hz, 1 H), 10.44 (s, 1 H) | 560 |
| 230 | 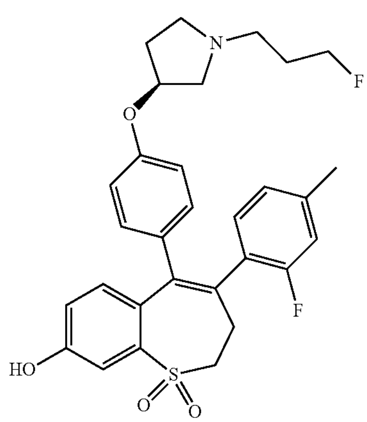 [SMILES: Cc1ccc(C2=C(c3ccc(O[C@H]4CCN(CCCF)C4)cc3)c3ccc(O)cc3S(=O)(=O)CC2)c(F)c1] | 4-(2-fluoro-4-methyl-phenyl)-5-[4-[(3S)-1-(3-fluoropropyl)pyrrolidin-3-yl]oxyphenyl]-1,1-dioxo-2,3-dihydro-1$\lambda^6$-benzothiepin-8-ol | C | 1H NMR (400 MHz, DMSO-d6) δ ppm: 1.74 (m, 3 H), 2.19 (m, 1 H), 2.25 (s, 3 H), 2.37 (m, 1 H), 2.45 (t, J = 7.3 Hz, 2 H), 2.53 (m, 1 H), 2.65 (m, 3 H), 2.78 (dd, J = 10.3 et 6.2 Hz, 1 H), 3.70 (t, J = 6.5 Hz, 2 H), 4.46 (dt, J = 47.4 et 6.0 Hz, 2 H), 4.73 (m, 1 H), 6.65 (d, J = 8.8 Hz, 2 H), 6.78 (m, 3 H), 6.86 (m, 2 H), 7.01 (m, 2 H), 7.40 (d, J = 2.6 Hz, 1 H), 10.47 (s, 1 H) | 540 |

TABLE 1-continued

| Example | Structure | Name | Method | NMR | MASS LC/MS (m/z, MH+) |
|---|---|---|---|---|---|
| 231 | 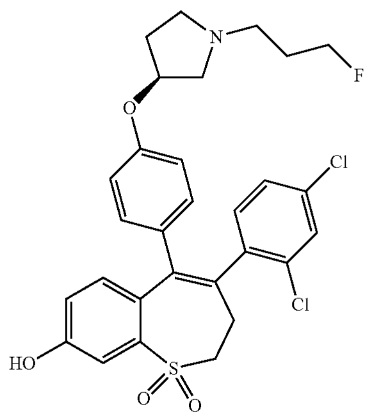 [SMILES: O=S1(=O)CCC(c2ccc(Cl)cc2Cl)=C(c2ccc(O[C@H]3CCN(CCCF)C3)cc2)c2ccc(O)cc21] | 4-(2,4-dichlorophenyl)-5-[4-[(3S)-1-(3-fluoropropyl)pyrrolidin-3-yl]oxyphenyl]-1,1-dioxo-2,3-dihydro-1λ$^6$-benzothiepin-8-ol | C | 1H NMR (400 MHz, DMSO-d6) δ ppm: 1.74 (m, 3 H), 2.19 (m, 1 H), 2.38 (m, 1 H), 2.46 (t, J = 7.0 Hz, 2H), 2,52 (m, 2 H), 2.62 (m, 1 H), 2.83 (m, 2 H), 3.72 (m, 2 H), 4.46 (dt, J = 47.5 et 6.0 Hz, 2 H), 4.73 (m, 1 H), 6.67 (d, J = 8.0 Hz, 2 H), 6.76 (d, J = 8.0 Hz, 2 H), 6.88 (d, J = 8.4 Hz, 1 H), 7.05 (m, 2 H), 7.26 (dd, J = 8.3 et 2.0 Hz, 1 H), 7.42 (d, J = 2.6 Hz, 1 H), 7.66 (d, J = 2.0 Hz, 1 H), 10.45 (s, 1 H) | 577 |
| 232 | 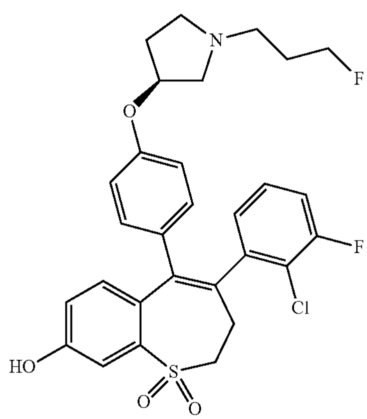 [SMILES: O=S1(=O)CCC(c2cccc(F)c2Cl)=C(c2ccc(O[C@H]3CCN(CCCF)C3)cc2)c2ccc(O)cc21] | 4-(2-chloro-3-fluoro-phenyl)-5-[4-[(3S)-1-(3-fluoropropyl)pyrrolidin-3-yl]oxyphenyl]-1,1-dioxo-2,3-dihydro-1λ$^6$-benzothiepin-8-ol | C | 1H NMR (400 MHz, DMSO-d6) δ ppm: 1.75 (m, 3 H), 2.21 (m, 1 H), 2.40 (m, 1 H), 2.47 (m, 2 H), 2.52-2.70 (m, 4 H), 2.85 (m, 3 H), 4.47 (dt, J = 47.4 et 6.0 Hz, 2 H), 4.75 (m, 1 H), 6.49 (s, 2 H), 6.66 (s, 1 H), 6.70 (d, J = 7.8 Hz, 2 H), 6.89 (d, J = 7.8 Hz, 2 H), 6.97 (td, J = 8.5 et 2.5 Hz, 1 H), 7.08 (m, 1 H), 7.32 (dd, J = 8.9 et 2.5 Hz, 1 H), 9.44 (s, 1 H) | 560 |
| 233 | 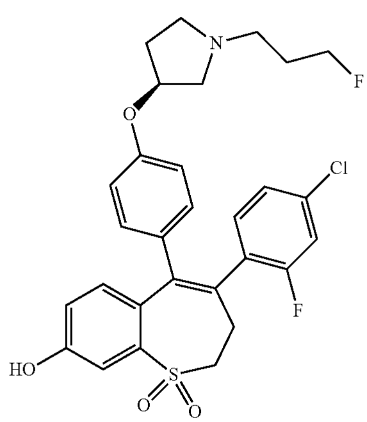 [SMILES: O=S1(=O)CCC(c2ccc(Cl)cc2F)=C(c2ccc(O[C@H]3CCN(CCCF)C3)cc2)c2ccc(O)cc21] | 4-(4-chloro-2-fluoro-phenyl)-5-[4-[(3S)-1-(3-fluoropropyl)pyrrolidin-3-yl]oxyphenyl]-1,1-dioxo-2,3-dihydro-1λ$^6$-benzothiepin-8-ol | C | 1H NMR (400 MHz, DMSO-d6) δ ppm: 1.74 (m, 3 H), 2.22 (m, 1 H), 2.34 (m, 1 H), 2.46 (t, J = 7.3 Hz, 2 H), 2.54 (d, J = 2.6 Hz, 1 H), 2.67 (m, 3 H), 2.79 (dd, J = 10.3 et 6.2 Hz, 1 H), 3.74 (d, J = 6.5 Hz, 2 H), 4.46 (dt, J = 47.4 et 6.0 Hz, 2 H), 4.74 (d, J = 6.8 Hz, 1 H), 6.68 (m, 2 H), 6.76 (m, 2 H), 6.87 (d, J = 8.4 Hz, 1 H), 6.99 (t, J = 8.3 Hz, 1 H), 7.04 (dd, J = 8.4 et 2.6 Hz, 1 H), 7.11 (dd, J = 8.3, 1.9 Hz, 1 H), 7.43 (m, 2 H), 10.48 (s, 1 H) | 560 |

TABLE 1-continued

| Example | Structure | Name | Method | NMR | MASS LC/MS (m/z, MH+) |
|---|---|---|---|---|---|
| 234 | 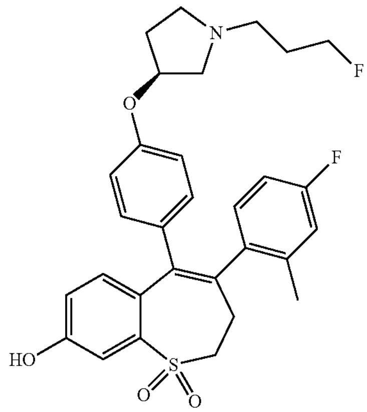 [SMILES: Cc1cc(F)ccc1C1=C(c2ccc(O[C@H]3CCN(CCCF)C3)cc2)c2ccc(O)cc2S(=O)(=O)CC1] | 4-(4-fluoro-2-methyl-phenyl)-5-[4-[(3S)-1-(3-fluoropropyl)pyrrolidin-3-yl]oxyphenyl]-1,1-dioxo-2,3-dihydro-1λ⁶-benzothiepin-8-ol | C | 1H NMR (400 MHz, DMSO-d6) δ ppm: 1.73 (m, 3 H), 2.19 (m, 1 H), 2.26 (s, 3 H), 2.36 (m, 1 H), 2.45 (t, J = 7.1 Hz, 2 H), 2.54 (m, 2 H), 2.64 (m, 1 H), 2.78 (m, 2 H), 3.71 (m, 2 H), 4.46 (dt, J = 47.4 et 6.0 Hz, 2 H), 4.72 (m, 1 H), 6.62 (d, J = 8.7 Hz, 2 H), 6.68 (d, J = 8.7 Hz, 2 H), 6.83 (m, 2 H), 7.02 (m, 3 H), 7.41 (d, J = 2.6 Hz, 1 H), 10.40 (s, 1 H) | 540 |
| 235 | 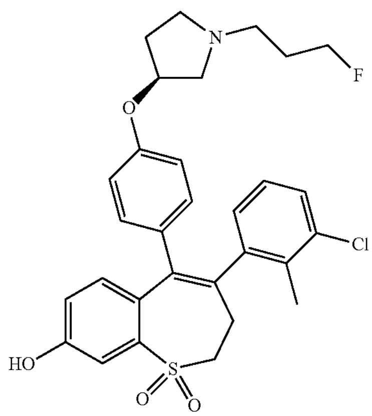 [SMILES: Cc1c(Cl)cccc1C1=C(c2ccc(O[C@H]3CCN(CCCF)C3)cc2)c2ccc(O)cc2S(=O)(=O)CC1] | 4-(3-chloro-2-methyl-phenyl)-5-[4-[(3S)-1-(3-fluoropropyl)pyrrolidin-3-yl]oxyphenyl]-1,1-dioxo-2,3-dihydro-1λ⁶-benzothiepin-8-ol | C | 1H NMR (400 MHz, DMSO-d6) δ ppm: 1.75 (m, 3 H), 2.19 (m, 1 H), 2.29 (s, 3 H), 2.36 (m, 1 H), 2.45 (t, J = 7.5 Hz, 2 H), 2.54 (m, 2 H), 2.62 (m, 1 H), 2.80 (m, 2 H), 3.72 (m, 2 H), 4.46 (dt, J = 47.4 et 6.0 Hz, 2 H), 4.72 (m, 1 H), 6.63 (d, J = 7.0 Hz, 2 H), 6.69 (d, J = 8.8 Hz, 2 H), 6.87 (d, J = 8.4 Hz, 1 H), 7.01 (m, 3 H), 7.25 (d, J = 7.5 Hz, 1 H), 7.42 (d, J = 2.6 Hz, 1 H), 10.43 (s, 1 H) | 556 |
| 236 | 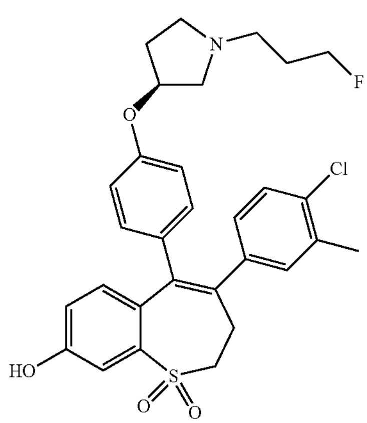 [SMILES: Cc1cc(C2=C(c3ccc(O[C@H]4CCN(CCCF)C4)cc3)c3ccc(O)cc3S(=O)(=O)CC2)ccc1Cl] | 4-(4-chloro-3-methyl-phenyl)-5-[4-[(3S)-1-(3-fluoropropyl)pyrrolidin-3-yl]oxyphenyl]-1,1-dioxo-2,3-dihydro-1λ⁶-benzothiepin-8-ol | C | 1H NMR (400 MHz, DMSO-d6) δ ppm: 1.76 (m, 3 H), 2.19 (m, 1 H), 2.26 (s, 3 H), 2.36 (m, 1 H), 2.45 (t, J = 8.1 Hz, 2 H), 2.52 (m, 2 H), 2.63 (m, 1 H), 2.79 (m, 2 H), 3.72 (m, 2 H), 4.46 (dt, J = 47.8 et 5.8 Hz, 2 H), 4.72 (m, 1 H), 6.63 (d, J = 8.9 Hz, 2 H), 6.69 (d, J = 8.9 Hz, 2 H), 6.87 (d, J = 8.3 Hz, 1 H), 7.01 (m, 2 H), 7.07 (d, J = 8.3 Hz, 1 H), 7.26 (s, 1 H), 7.41 (d, J = 2.6 Hz, 1 H), 10.41 (s, 1 H) | 556 |

TABLE 1-continued

| Example | Structure | Name | Method | NMR | MASS LC/MS (m/z, MH+) |
|---|---|---|---|---|---|
| 237 | 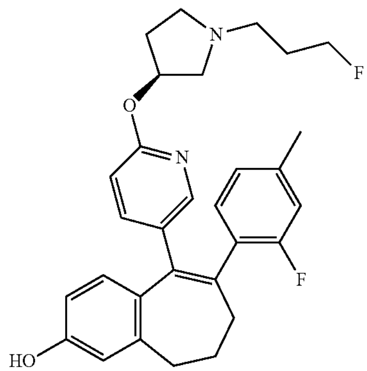 [SMILES: Cc1ccc(C2=C(c3ccc(O[C@H]4CCN(CCCF)C4)nc3)c3ccc(O)cc3CCC2)c(F)c1] | 6-(2-fluoro-4-methyl-phenyl)-5-[6-[(3S)-1-(3-fluoropropyl)pyrrolidin-3-yl]oxy-3-pyridyl]-8,9-dihydro-7H-benzo[7]annulen-2-ol | A | 1H NMR (400 MHz, DMSO-d6) δ ppm: 1.75 (m, 3 H), 2.06 (m, 2 H), 2.18 (m, 2 H), 2.24 (s, 3 H), 2.34 (m, 1 H), 2.45 (t, J = 7.5 Hz, 4 H), 2.54 (d, J = 2.7 Hz, 1 H), 2.70 (m, 3 H), 4.46 (dt, J = 47.4 et 6.1 Hz, 2 H), 5.21 (m, 1 H), 6.54 (d, J = 8.6 Hz, 1 H), 6.59 (d, J = 1.0 Hz, 2 H), 6.72 (s, 1 H), 6.88 (m, 2 H), 7.08 (m, 2 H), 7.56 (d, J = 2.2 Hz, 1 H), 9.47 (s, 1 H) | 491 |
| 238 | 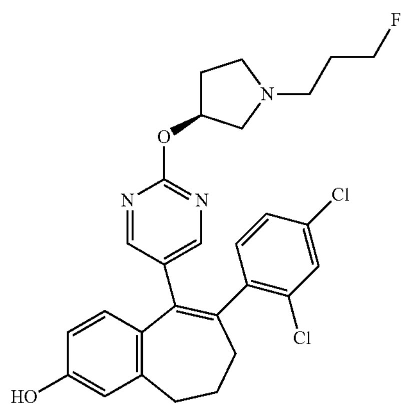 [SMILES: Oc1ccc2c(c1)CCCC(c1ccc(Cl)cc1Cl)=C2c1cnc(O[C@H]2CCN(CCCF)C2)nc1] | 6-(2,4-dichlorophenyl)-5-[2-[(3S)-1-(3-fluoropropyl)pyrrolidin-3-yl]oxypyrimidin-5-yl]-8,9-dihydro-7H-benzo[7]annulen-2-ol | A | 1H NMR (400 MHz, DMSO-d6) δ ppm: 1.77 (m, 3 H), 2.18 (m, 5 H), 2.37 (m, 1 H), 2.45 (m, 2 H), 2.57 (m, 1 H), 2.73 (m, 4 H), 4.46 (dt, J = 47.4 et 6.0 Hz, 2 H), 5.22 (m, 1 H), 6.61 (dd, J = 8.5 et 2.3 Hz, 1 H), 6.66 (d, J = 8.5 Hz, 1 H), 6.75 (d, J = 2.3 Hz, 1 H), 7.34 (s, 2 H), 7.58 (s, 1 H), 7.99 (s, 2 H), 9.57 (s, 1 H) | 528 |
| 239 | 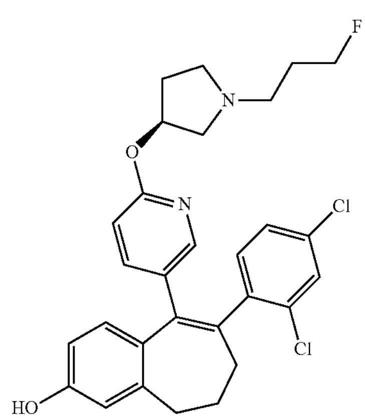 [SMILES: Oc1ccc2c(c1)CCCC(c1ccc(Cl)cc1Cl)=C2c1ccc(O[C@H]2CCN(CCCF)C2)nc1] | 6-(2,4-dichlorophenyl)-5-[6-[(3S)-1-(3-fluoropropyl)pyrrolidin-3-yl]oxy-3-pyridyl]-8,9-dihydro-7H-benzo[7]annulen-2-ol | A | 1H NMR (400 MHz, DMSO-d6) δ ppm: 1.78 (m, 3 H), 2.08 (m, 2 H), 2.18 (m, 1 H), 2.27 (m, 2 H), 2.35 (m, 1 H), 2.46 (m, 2 H), 2.56 (m, 1 H), 2.73 (m, 4 H), 4.47 (dt, J = 47.4 et 6.0 Hz, 2 H), 5.24 (m, 1 H), 6.59 (m, 3 H), 6.72 (s, 1 H), 6.98 (d, J = 8.4 Hz, 1 H), 7.16 (m, 3 H), 7.19 (t, J = 73.3 Hz, 1H), 7.59 (d, J = 2.1 Hz, 1 H), 9.49 (s, 1 H) | 527 |

TABLE 1-continued

| Example | Structure | Name | Method | NMR | MASS LC/MS (m/z, MH+) |
|---|---|---|---|---|---|
| 240 | 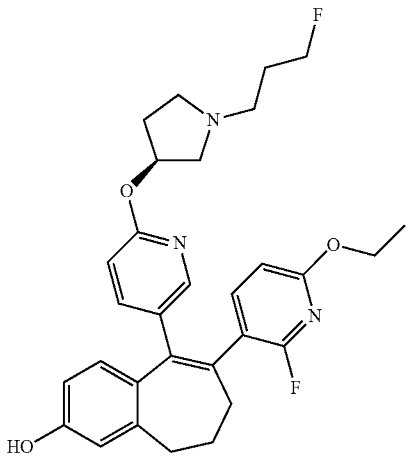 [SMILES: CCOc1ccc(C2=C(c3ccc(O[C@H]4CCN(CCCF)C4)nc3)c3ccc(O)cc3CCC2)c(F)n1] | 6-(6-ethoxy-2-fluoro-3-pyridyl)-5-[6-[(3S)-1-(3-fluoropropyl)pyrrolidin-3-yl]oxy-3-pyridyl]-8,9-dihydro-7H-benzo[7]annulen-2-ol | A | 1H NMR (400 MHz, DMSO-d6) δ ppm: 1.27 (t, J = 7.0 Hz, 3 H), 1.78 (m, 3 H), 2.13 (m, 5 H), 2.34 (m, 1 H), 2.45 (m, 2 H), 2.55 (d, J = 2.8 Hz, 1 H), 2.72 (m, 4 H), 4.18 (q, J = 7.1 Hz, 2 H), 4.46 (dt, J = 47.4, 6.0 Hz, 2 H), 5.23 (m, 1 H), 6.55 (m, 3 H), 6.64 (d, J = 7.7 Hz, 1 H), 6.72 (s, 1 H), 7.13 (dd, J = 8.6, 2.4 Hz, 1 H), 7.58 (d, J = 2.2 Hz, 1 H), 7.66 (dd, J = 10.0, 8.3 Hz, 1 H), 9.49 (s, 1 H) | 522 |
| 241 | 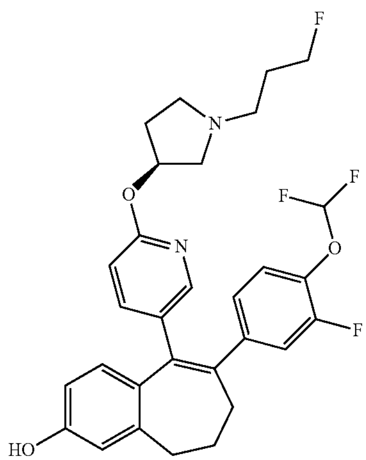 [SMILES: Oc1ccc2c(c1)CCCC(c1ccc(OC(F)F)c(F)c1)=C2c1ccc(O[C@H]2CCN(CCCF)C2)nc1] | 6-[4-(difluoromethoxy)-3-fluorophenyl]-5-[6-[(3S)-1-(3-fluoropropyl)pyrrolidin-3-yl]oxy-3-pyridyl]-8,9-dihydro-7H-benzo[7]annulen-2-ol | A | 1H NMR (400 MHz, DMSO-d6) δ ppm: 1.78 (m, 3 H), 2.08 (d, J = 6.6 Hz, 2 H), 2.18 (m, 1 H), 2.27 (m, 2 H), 2.35 (m, 1 H), 2.44 (m, 2 H), 2.56 (d, J = 2.3 Hz, 1 H), 2.73 (m, 4 H), 4.47 (dt, J = 47.4, 6.0 Hz, 2 H), 5.24 (m, J = 6.8, 6.8 Hz, 1 H), 6.59 (m, 3 H), 6.72 (s, 1 H), 6.98 (d, J = 8.4 Hz, 1 H), 7.16 (m, 3 H), 7.19 (t, J = 73.3 Hz, 1H), 7.59 (d, J = 2.1 Hz, 1 H), 9.49 (s, 1 H) | 543 |
| 242 | 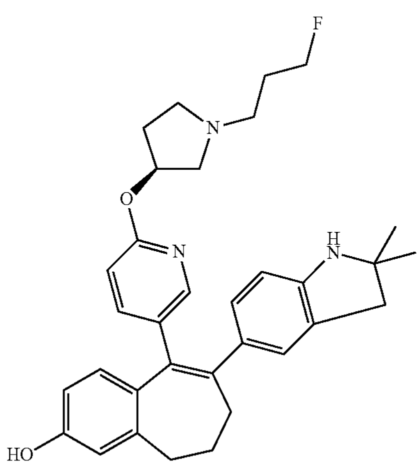 [SMILES: CC1(C)Cc2cc(C3=C(c4ccc(O[C@H]5CCN(CCCF)C5)nc4)c4ccc(O)cc4CCC3)ccc2N1] | 6-(2,2-dimethylindolin-5-yl)-5-[6-[(3S)-1-(3-fluoropropyl)pyrrolidin-3-yl]oxy-3-pyridyl]-8,9-dihydro-7H-benzo[7]annulen-2-ol | | 1H NMR (400 MHz, DMSO-d6) δ ppm: 1.17 (s, 6 H), 1.76 (m, 3 H), 2.04 (d, J = 6.8 Hz, 2 H), 2.20 (m, 3 H), 2.34 (m, 1 H), 2.44 (m, 2 H), 2.56 (m, 3 H), 2.65 (m, 3 H), 2.76 (dd, J = 10.5 et 6.3 Hz, 1 H), 4.46 (dt, J = 47.4 et 6.0 Hz, 2 H), 5.23 (d, J = 6.9 Hz, 1 H), 5.43 (s, 1 H), 6.22 (d, J = 7.9 Hz, 1 H), 6.54 (m, 3 H), 6.68 (m, 2 H), 6.72 (s, 1H), 7.10 (dd, J = 8.5 et 2.4 Hz, 1 H), 7.55 (d, J = 2.2 Hz, 1 H), 9.35 (s, 1 H) | 528 |

TABLE 1-continued

| Example | Structure | Name | Method | NMR | MASS LC/MS (m/z, MH+) |
|---|---|---|---|---|---|
| 243 | 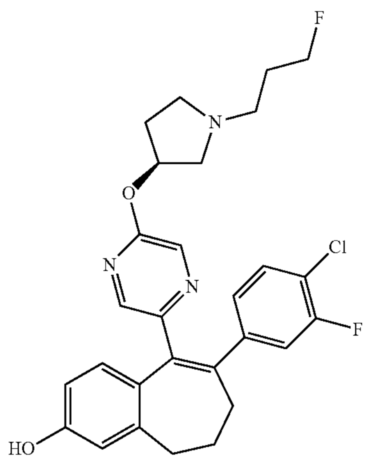 [SMILES: Oc1ccc2c(c1)CCCC(c1ccc(Cl)c(F)c1)=C2c1cnc(O[C@H]2CCN(CCCF)C2)cn1] | 6-(4-chloro-3-fluoro-phenyl)-5-[5-[(3S)-1-(3-fluoropropyl)pyrrolidin-3-yl]oxypyrazin-2-yl]-8,9-dihydro-7H-benzo[7]annulen-2-ol | | 1H NMR (400 MHz, DMSO-d6) δ ppm: 1.77 (m, 3 H), 2.12 (m, 2 H), 2.22 (m, 1 H), 2.34 (m, 3 H), 2.46 (m, 2 H), 2.61 (dd, J = 10.6 et 2.3 Hz, 1 H), 2.70 (m, 4 H), 4.47 (dt, J = 47.4 et 6.0 Hz, 2 H), 5.22 (m, 1 H), 6.57 (m, 2 H), 6.72 (d, J = 2.0 Hz, 1 H), 6.87 (dd, J = 8.4 et 1.7 Hz, 1 H), 7.15 (dd, J = 10.8 et 1.8 Hz, 1 H), 7.37 (t, J = 8.4 Hz, 1 H), 7.66 (d, J = 1.2 Hz, 1 H), 8.12 (d, J = 1.2 Hz, 1 H), 9.50 (s, 1 H) | 512 |
| 244 | 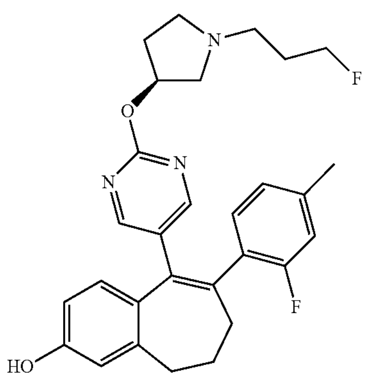 [SMILES: Cc1ccc(C2=C(c3cnc(O[C@H]4CCN(CCCF)C4)nc3)c3ccc(O)cc3CCC2)c(F)c1] | 6-(2-fluoro-4-methyl-phenyl)-5-[2-[(3S)-1-(3-fluoropropyl)pyrrolidin-3-yl]oxypyrimidin-5-yl]-8,9-dihydro-7H-benzo[7]annulen-2-ol | A | 1H NMR (400 MHz, DMSO-d6) δ ppm: 1.77 (m, 3 H), 2.09 (m, 2 H), 2.17-2.41 (m, 7 H), 2.44 (m, 2 H), 2.57 (d, J = 10.8 Hz, 2 H), 2.70 (m, 3 H), 4.47 (dt, J = 47.4 et 5.8 Hz, 2 H), 5.21 (m, 1 H), 6.60 (d, J = 7.5 Hz, 1 H), 6.64 (d, J = 7.5 Hz, 1 H), 6.74 (s, 1 H), 6.91 (m, 2 H), 7.13 (t, J = 7.9 Hz, 1 H), 7.98 (s, 2 H), 9.54 (s, 1 H) | 492 |
| 245 | 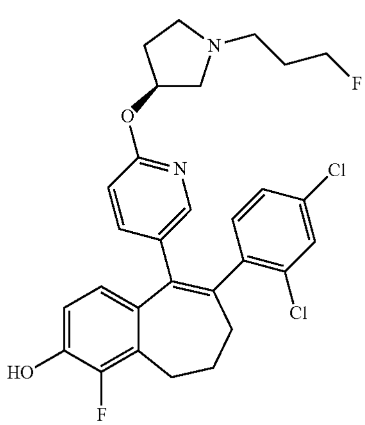 [SMILES: Oc1ccc2c(c1F)CCCC(c1ccc(Cl)cc1Cl)=C2c1ccc(O[C@H]2CCN(CCCF)C2)nc1] | 6-(2,4-dichlorophenyl)-1-fluoro-5-[6-[(3S)-1-(3-fluoropropyl)pyrrolidin-3-yl]oxy-3-pyridyl]-8,9-dihydro-7H-benzo[7]annulen-2-ol | A | 1H NMR (400 MHz, DMSO-d6) δ ppm: 1.75 (m, 3 H), 2.15 (m, 4 H), 2.38 (m, 5 H), 2.64 (m, 2 H), 2.76 (m, 1 H), 2.95 (m, 1 H), 4.46 (dt, J = 47.5 et 5.9 Hz, 2 H), 5.22 (m, 1 H), 6.44 (d, J = 8.4 Hz, 1 H), 6.57 (d, J = 8.6 Hz, 1 H), 6.77 (t, J = 8.7 Hz, 1 H), 7.13 (dd, J = 8.4 et 2.0 Hz, 1 H), 7.23 (d, J = 7.0 HZ, 1 H), 7.29 (d, J = 7.0 HZ, 1 H), 7.58 (s, 2 H), 9.97 (s, 1 H) | 545 |

TABLE 1-continued

| Example | Structure | Name | Method | NMR | MASS LC/MS (m/z, MH+) |
|---|---|---|---|---|---|
| 246 | 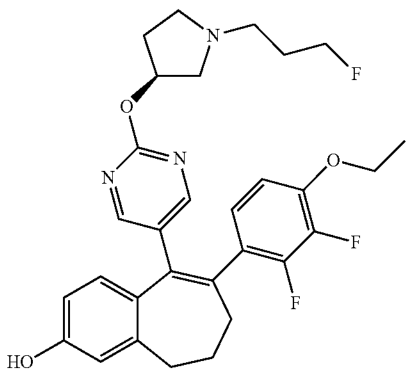 [SMILES: CCOc1ccc(C2=C(c3cnc(O[C@H]4CCN(CCCF)C4)nc3)c3ccc(O)cc3CCC2)c(F)c1F] | 6-(4-ethoxy-2,3-difluorophenyl)-5-[2-[(3S)-1-(3-fluoropropyl)pyrrolidin-3-yl]oxypyrimidin-5-yl]-8,9-dihydro-7H-benzo[7]annulen-2-ol | A | 1H NMR (400 MHz, DMSO-d6) Shift 1.32 (t, J = 6.97 Hz, 3H), 1.78 (m, 3H), 2.07-2.32 (m, 5H), 2.37 (m, 1H), 2.44 (m, 2H), 2.60 (m, 2H), 2.72 (m, 3H), 4.11 (q, J = 7.00 Hz, 2H), 4.46 (dt, J = 47.5 et 6.0 Hz, 2 H), 5.23 (m, 1H), 6.61 (m, 1H), 6.66 (d, J = 8.31 Hz, 1H), 6.75 (d, J = 2.20 Hz, 1H), 6.93 (t, J = 8.0 Hz, 1H), 7.01 (t, J = 7.5 Hz, 1H), 8.01 (s, 2H), 9.56 (s, 1H) | 540 |
| 247 | 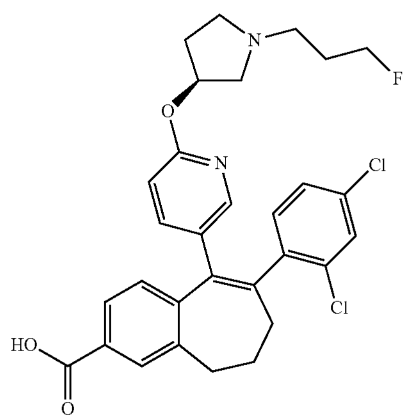 [SMILES: O=C(O)c1ccc2c(c1)CCCC(c1ccc(Cl)cc1Cl)=C2c1ccc(O[C@H]2CCN(CCCF)C2)nc1] | 6-(2,4-dichlorophenyl)-5-[6-[(3S)-1-(3-fluoropropyl)pyrrolidin-3-yl]oxy-3-pyridyl]-8,9-dihydro-7H-benzo[7]annulene-2-carboxylic acid | | 1H NMR (400 MHz, DMSO-d6) δ ppm: 1.77(m, 3 H), 2.19(m, 5 H), 2.37 (m, 3 H), 2.58 (m, 1 H), 2.74 (m, 2 H), 2.94 (m, 2 H), 4.46 (dt, J = 47.4 et 6.0 Hz, 2 H), 5.23 (m, 1 H), 6.60 (d, J = 8.6 Hz, 1 H), 6.92 (d, J = 7.9 Hz, 1 H), 7.14 (d, J = 8.4 Hz, 1 H), 7.31 (q, J = 8.2 Hz, 2 H), 7.61 (s, 2 H), 7.77 (d, J = 7.7 Hz, 1 H), 7.93 (s, 1 H), 12.91 (m, 1 H) | 555 |
| 248 | 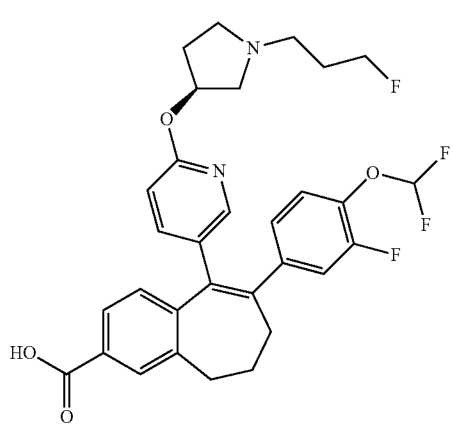 [SMILES: O=C(O)c1ccc2c(c1)CCCC(c1ccc(OC(F)F)c(F)c1)=C2c1ccc(O[C@H]2CCN(CCCF)C2)nc1] | 6-[4-(difluoromethoxy)-3-fluorophenyl]-5-[6-[(3S)-1-(3-fluoropropyl)pyrrolidin-3-yl]oxy-3-pyridyl]-8,9-dihydro-7H-benzo[7]annulene-2-carboxylic acid | | 1H NMR (400 MHz, DMSO-d6) δ ppm: 1.76 (m, 3 H), 2.14 (m, 3 H), 2.26 (m, 2 H), 2.38 (m, 3 H), 2.56 (dd, J = 10.6 et 2.6 Hz, 1 H), 2.68 (m, 1 H), 2.76 (dd, J = 10.5 et 6.2 Hz, 1 H), 2.86 (t, J = 6.7 Hz, 2 H), 4.46 (dt, J = 47.4 et 6.0 Hz, 2 H), 5.24 (m, 1 H), 6.62 (d, J = 8.6 Hz, 1 H), 6.89 (d, J = 7.9 Hz, 1 H), 7.00-7.40 (m, 5 H), 7.62 (d, J = 2.2 Hz, 1 H), 7.75 (dd, J = 8.0 et 1.4 Hz, 1 H), 7.90 (d, J = 1.4 Hz, 1 H), 12.90 (s, 1 H) | 571 |

TABLE 1-continued

| Example | Structure | Name | Method | NMR | MASS LC/MS (m/z, MH+) |
|---|---|---|---|---|---|
| 249 | 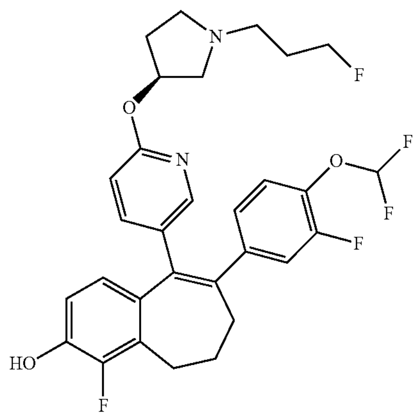 [SMILES: Oc1ccc2c(c1F)CCCC(c1ccc(OC(F)F)c(F)c1)=C2c1ccc(O[C@H]2CCN(CCCF)C2)nc1] | 6-[4-(difluoromethoxy)-3-fluoro-phenyl]-1-fluoro-5-[6-[(3S)-1-(3-fluoropropyl)pyrrolidin-3-yl]oxy-3-pyridyl]-8,9-dihydro-7H-benzo[7]annulen-2-ol | A | 1H NMR (400 MHz, DMSO-d6) δ ppm: 1.76 (m, 3 H), 2.07 (m, 2 H), 2.19 (m, 1 H), 2.25-2.40 (m, 3 H), 2.44 (m, 2 H), 2.55 (dd, J = 10.7 et 2.8 Hz, 1 H), 2.65-2.85 (m, 4 H), 4.46 (dt, J = 47.4 et 6.0 Hz, 2 H), 5.24 (m, 1 H), 6.43 (d, J = 8.4 Hz, 1 H), 6.59 (d, J = 8.7 Hz, 1 H), 6.76 (t, J = 8.7 Hz, 1 H), 7.00 (d, J = 8.3 Hz, 1 H), 7.22 (m, 4 H), 7.61 (d, J = 2.2 Hz, 1 H), 9.94 (s, 1 H) | 561 |
| 250 | 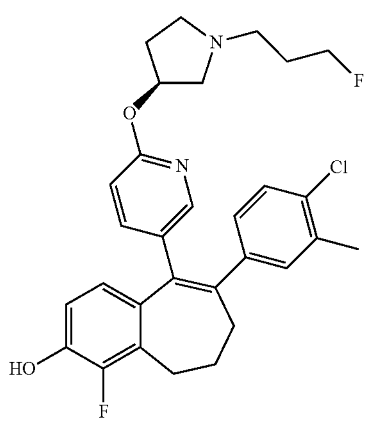 [SMILES: Cc1cc(C2=C(c3ccc(O[C@H]4CCN(CCCF)C4)nc3)c3ccc(O)c(F)c3CCC2)ccc1Cl] | 6-(4-chloro-3-methyl-phenyl)-1-fluoro-5-[6-[(3S)-1-(3-fluoropropyl)pyrrolidin-3-yl]oxy-3-pyridyl]-8,9-dihydro-7H-benzo[7]annulen-2-ol | A | 1H NMR (400 MHz, DMSO-d6) δ ppm: 1.74 (m, 3 H), 2.06 (d, J = 6.7 Hz, 2 H), 2.17 (m, 6 H), 2.35 (m, 1 H), 2.45 (m, 2 H), 2.55 (m, 1 H), 2.77 (m, 4 H), 4.46 (dt, J = 47.4, 6.0 Hz, 2 H), 5.21 (m, 1 H), 6.43 (d, J = 8.3 Hz, 1 H), 6.58 (d, J = 8.6 Hz, 1 H), 6.76 (t, J = 8.7 Hz, 1 H), 6.94 (dd, J = 8.1, 1.7 Hz, 1 H), 7.17 (m, 3 H), 7.58 (d, J = 2.2 Hz, 1 H), 9.92 (s, 1 H) | 525 |
| 251 | 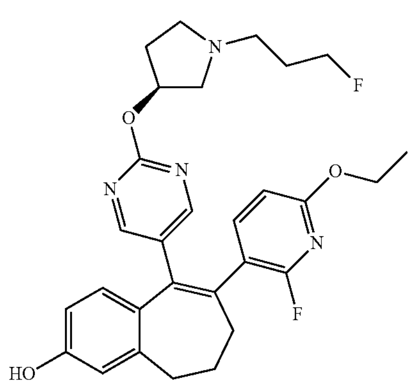 [SMILES: CCOc1ccc(C2=C(c3cnc(O[C@H]4CCN(CCCF)C4)nc3)c3ccc(O)cc3CCC2)c(F)n1] | 6-(6-ethoxy-2-fluoro-3-pyridyl)-5-[2-[(3S)-1-(3-fluoropropyl)pyrrolidin-3-yl]oxypyrimidin-5-yl]-8,9-dihydro-7H-benzo[7]annulen-2-ol | A | 1H NMR (400 MHz, DMSO-d6) δ ppm: 1.27 (t, J = 7.0 Hz, 3 H), 1.79 (m, 3 H), 2.07-2.39 (m, 6 H), 2.46 (m, 2 H), 2.58 (d, J = 10.1 Hz, 1 H), 2.68 (m, 3 H), 2.81 (dd, J = 9.9 et 6.4 Hz, 1 H), 3.93 (d, J = 15.0 Hz, 1 H), 4.18 (q, J = 7.0 Hz, 2 H), 4.48 (dt, J = 47.4 et 3.0 Hz, 2 H), 5.23 (m, 1 H), 6.60-6.75 (m, 4 H), 7.73 (dd, J = 8. et 4.5 Hz, 1 H), 9.60 (s, 1 H) | 523 |

TABLE 1-continued

| Example | Structure | Name | Method | NMR | MASS LC/MS (m/z, MH+) |
|---|---|---|---|---|---|
| 252 | 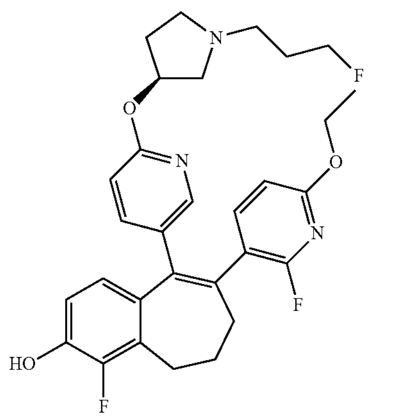 [SMILES: CCOc1ccc(C2=C(c3ccc(O[C@H]4CCN(CCCF)C4)nc3)c3ccc(O)c(F)c3CCC2)c(F)n1] | 6-(6-ethoxy-2-fluoro-3-pyridyl)-1-fluoro-5-[6-[(3S)-1-(3-fluoropropyl)pyrrolidin-3-yl]oxy-3-pyridyl]-8,9-dihydro-7H-benzo[7]annulen-2-ol | A | 1H NMR (400 MHz, DMSO-d6) δ ppm: 1.27 (t, J = 7.1 Hz, 3 H), 1.77 (m, 3 H), 2.08 (m, 2 H), 2.20 (m, 3 H), 2.36 (m, 1 H), 2.44 (m, 2 H), 2.56 (m, 1 H), 2.67 (m, 1 H), 2.78 (m, 3 H), 4.19 (q, J = 7.1 Hz, 2 H), 4.46 (dt, J = 47.4 et 5.9 Hz, 2 H), 5.23 (m, 1 H), 6.44 (d, J = 8.3 Hz, 1 H), 6.60 (d, J = 8.6 Hz, 1 H), 6.65 (d, J = 8.1 Hz, 1 H), 6.76 (t, J = 8.6 Hz, 1 H), 7.15 (dd, J = 8.6 et 2.4 Hz, 1 H), 7.60 (d, J = 2.0 Hz, 1 H), 7.67 (dd, J = 9.7 et 8.4 Hz, 1 H), 9.90 (s, 1 H) | 540 |
| 253 | 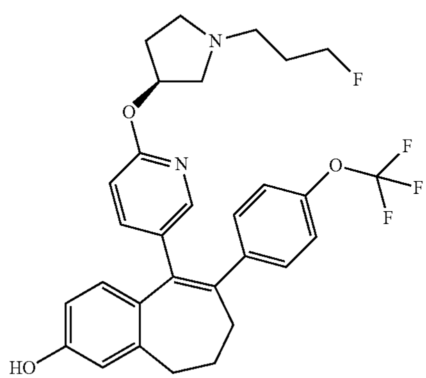 [SMILES: Oc1ccc2c(c1)CCCC(c1ccc(OC(F)(F)F)cc1)=C2c1ccc(O[C@H]2CCN(CCCF)C2)nc1] | 5-[6-[(3S)-1-(3-fluoropropyl)pyrrolidin-3-yl]oxy-3-pyridyl]-6-[4-(trifluoromethoxy)phenyl]-8,9-dihydro-7H-benzo[7]annulen-2-ol | A | 1H NMR (400 MHz, DMSO-d6) δ ppm: 1.73 (m, 3 H), 2.08 (m, 2 H), 2.18 (m, 1 H), 2.31 (m, 3 H), 2.42-2.52 (m, 4 H), 2.71 (m, 3 H), 4.46 (dt, J = 47.4 et 6.0 Hz, 2 H), 5.21 (m, 1 H), 6.58 (m, 3 H), 6.72 (s, 1 H), 7.11 (dd, J = 8.5 et 2.0 Hz, 1 H), 7.19 (d, J = 8.0 Hz, 2 H), 7.25 (d, J = 8.0 Hz, 2 H), 7.55 (d, J = 2.0 Hz, 1 H), 9.48 (s, 1 H) | 543 |
| 254 | 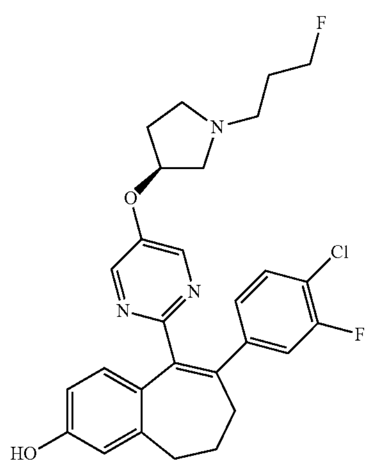 [SMILES: Oc1ccc2c(c1)CCCC(c1ccc(Cl)c(F)c1)=C2c1ncc(O[C@H]2CCN(CCCF)C2)cn1] | 6-(4-chloro-3-fluoro-phenyl)-5-[5-[(3S)-1-(3-fluoropropyl)pyrrolidin-3-yl]oxypyrimidin-2-yl]-8,9-dihydro-7H-benzo[7]annulen-2-ol | | 1H NMR (400 MHz, DMSO-d6) δ ppm: 1.60-1.85 (m, 3 H), 2.20 (m, 1 H), 2.35 (m, 1 H), 2.45 (td, J = 7.3 et 2.3 Hz, 2 H), 2.52-2.70 (m, 4 H), 2.77 (td, J = 10.1 et 6.2 Hz, 1 H), 3.00 (dd, J = 11.9 et 6.4 Hz, 1 H), 4.16 (m, 1 H), 4.46 (dt, J = 47.4 et 6.0 Hz, 2 H), 4.74 (m, 1 H), 6.63 (d, J = 7.8 Hz, 2 H), 6.69 (d, J = 7.8 Hz, 2 H), 6.79 (d, J = 8.3 Hz, 1 H), 6.90 (dd, J = 8.3 et 22 Hz, 1 H), 7.25 (m, 5 H), 10.26 (s, 1 H) | 512 |
| 255 | 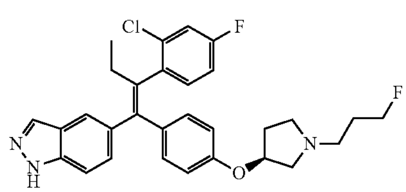 [SMILES: CC/C(=C(/c1ccc(O[C@H]2CCN(CCCF)C2)cc1)c1ccc2[nH]ncc2c1)c1ccc(F)cc1Cl] | 5-[(E)-2-(2-chloro-4-fluoro-phenyl)-1-[4-[(3S)-1-(3-fluoropropyl)pyrrolidin-3-yl]oxyphenyl]but-1-enyl]-1H-indazole | | 1H NMR (400 MHz, DMSO-d6) δ ppm: 0.88 (t, J = 7.6 Hz, 3 H), 1.72 (m, 3 H), 2.15 (m, 1 H), 2.43 (m, 6 H), 2.60 (m, 1 H), 2.75 (dd, J = 10.4 et 6.2 Hz, 1 H), 4.44 (dt, J = 47.4 et 6.1 Hz, 2 H), 4.67 (m, 1 H), 6.56 (d, J = 8.8 Hz, 2 H), 6.80 (d, J = 8.8 Hz, 2 H), 7.15 (m, 2 H), 7.32 (m, 2 H), 7.54 (d, J = 8.6 Hz, 1 H), 7.65 (s, 1 H), 8.09 (s, 1 H), 13.08 (s, 1 H) | 522 |

TABLE 1-continued

| Example | Structure | Name | Method | NMR | MASS LC/MS (m/z, MH+) |
|---|---|---|---|---|---|
| 256 | Trans Isomer 1 | 1-[2,6-difluoro-4-[(3S)-1-(3-fluoropropyl)pyrrolidin-3-yl]oxyphenyl]-2-(2-fluoro-2-methylpropyl)-3-methyl-1,3,4,9-tetrahydropyrido[3,4-b]indole | | 1H NMR (400 MHz, DMSO-d6) δ ppm: 1.04 (d, J = 6.4 Hz, 3 H), 1.18 (m, 6 H), 1.75 (m, 3 H), 2.29-2.40 (m, 3 H), 2.46 (m, 2 H), 2.60-2.75 (m, 3 H), 2.87 (m, 3 H), 3.52 (m, 1 H), 4.47 (dt, J = 47.4 et 6.0 Hz, 2 H), 4.88 (m, 1 H), 5.12 (s, 1 H), 6.60 (d, J = 11.1 Hz, 2 H), 6.98 (m, 2 H), 7.18 (d, J = 7.8 Hz, 1 H), 7.39 (d, J = 7.6 Hz, 1 H), 10.52 (s, 1 H) | 518 |
| 257 | Trans Isomer 2 | 1-[2,6-difluoro-4-[(3S)-1-(3-fluoropropyl)pyrrolidin-3-yl]oxyphenyl]-2-(2-fluoro-2-methylpropyl)-3-methyl-1,3,4,9-tetrahydropyrido[3,4-b]indole | | 1H NMR (400 MHz, DMSO-d6) δ ppm: 1.04 (d, J = 6.4 Hz, 3 H), 1.18 (m, 6 H), 1.75 (m, 3 H), 2.29 (m, 3 H), 2.46 (m, 2 H), 2.64 (m, 3 H), 2.87 (m, 3 H), 3.50 (m, 1 H), 4.47 (dt, J = 47.4 et 6.0 Hz, 2 H), 4.89 (m, 1 H), 5.12 (s, 1 H), 6.60 (d, J = 11.1 Hz, 2 H), 6.98 (m, 2 H), 7.18 (d, J = 7.8 Hz, 1 H), 7.39 (d, J = 7.6 Hz, 1 H), 10.52 (s, 1 H) | 518 |
| 258 | 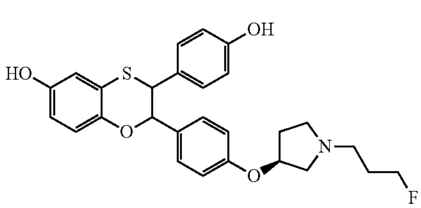 [SMILES: Oc1ccc(C2Sc3cc(O)ccc3OC2c2ccc(O[C@H]3CCN(CCCF)C3)cc2)cc1] | 2-[4-[(3S)-1-(3-fluoropropyl)pyrrolidin-3-yl]oxyphenyl]-3-(4-hydroxyphenyl)-2,3-dihydro-1,4-benzoxathiin-6-ol | | 1H NMR (400 MHz, DMSO-d6) δ ppm: 1.77 (m, 3 H), 2.21 (m, 1 H), 2.39 (m, 1 H), 2.47 (m, 2H), 2.56 (dd, J = 10.3 et 2.6 Hz, 1 H), 2.67 (m, 1 H), 2.81 (dd, J = 10.3 et 6.2 Hz, 1 H), 4.47 (dt, J = 47.4 et 6.0 Hz, 2 H), 4.58 (d, J = 1.8, 1 H), 4.79 (m, 1 H), 5.38 (d, J = 1.8 Hz, 1 H), 6.50 (m, 4 H), 6.72 (t, J = 9.0 Hz, 4 H), 6.80 (d, J = 8.7 Hz, 1 H), 6.97 (d, J = 8.7 Hz, 2 H), 9.15 (s, 1 H), 9.26 (s, 1 H) | 482 |

The examples which follow describe the preparation of some compounds in accordance with the invention. The numbers of the compounds exemplified below match those given in the Table 1 above. All reactions are performed under inert atmosphere unless otherwise stated.

Intermediates:

Intermediate (Ib1). 7-methoxy-3,4-dihydronaphthalen-1-yl-trifluoromethanesulfonate

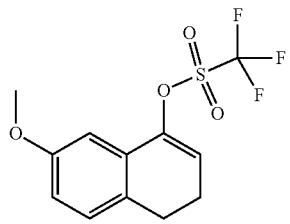 [SMILES: COc1ccc2c(c1)C(OS(=O)(=O)C(F)(F)F)=CCC2]

To a mixture of 7-methoxy-3,4-dihydronaphthalen-1 (2H)-one (32.5 g, 184.44 mmol), THF (500 ml) and N,N-Bis(trifluoromethylsulfonyl)aniline (79.07 g, 221.32 mmol) cooled at −50° C., was added dropwise potassium bis (trimethylsilyl)amide (246 ml, 221.32 mmol) in solution 0.9M in THF. The reaction mixture was stirred for one hour at −50° C. and 20 hours at room temperature. The reaction mixture was cooled to 0° C. and water (500 ml) and EtOAc (200 ml) were added. The organic phase was dried over magnesium sulfate, filtered, and concentrated under reduced pressure. The residue was purified by flash chromatography eluting with a mixture of DCM and n-heptane (10/90; v/v) to give 55 g (96%) of 7-methoxy-3,4-dihydronaphthalen-1-yl trifluoromethanesulfonate (Ib1) as a yellow oil. LC/MS (m/z, MH+): 309

Intermediate (Ic).
4-(7-methoxy-3,4-dihydronaphthalen-1-yl)phenol

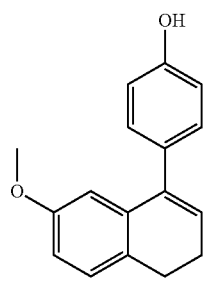 [SMILES: COc1ccc2c(c1)C(c1ccc(O)cc1)=CCC2]

To a mixture of 7-methoxy-3,4-dihydronaphthalen-1-yl trifluoromethanesulfonate (Ib1) (96 g, 311.41 mmol), (4-hydroxyphenyl)boronic acid (42.95 g, 311.41 mmol) and [1,1'-bis(diphenylphosphino)ferrocene]dichloropalladium(II), complex with DCM (11.39 g, 15.57 mmol) in dioxane (1000 ml), was added dropwise a solution of Cs$_2$CO$_3$ 1.5 M (384 ml, 576 mmol). The reaction mixture was stirred for one hour at room temperature. Water (150 ml) and EtOAc (500 ml) were added. The organic phase was dried over magnesium sulfate, filtered, and concentrated under reduced pressure. The residue was purified by flash chromatography eluting with a mixture of EtOAc and n-heptane (10/90; v/v) to give 55 g (70%) of 4-(7-methoxy-3,4-dihydronaphthalen-1-yl)phenol (Ic) as a beige solid. LC/MS (m/z, MH+): 253

Intermediate (Id1). 4-(2-bromo-7-methoxy-3,4-dihydronaphthalen-1-yl)phenol

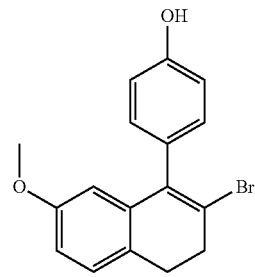 [SMILES: COc1ccc2c(c1)C(c1ccc(O)cc1)=C(Br)CC2]

To a solution of 4-(7-methoxy-3,4-dihydronaphthalen-1-yl)phenol (Ic) (55 g, 217.99 mmol) in THF (1000 ml), was added pyridinium bromide perbromide (69.72 g, 217.99 mmol). The reaction mixture was stirred for 24 hours at room temperature. Water (500 ml) was added, then pH was adjusted to 8 with a solution of NaHCO$_3$. EtOAc was added (500 ml). After decantation, the organic phase was dried over magnesium sulfate, filtered, and concentrated under reduced pressure. The residue was triturated with a mixture of diisopropyl ether and heptane (50/50; v/v). The solid formed was filtered and dried to give 57 g (79%) of 4-(2-bromo-7-methoxy-3,4-dihydronaphthalen-1-yl)phenol (Id1) as a beige solid. LC/MS (m/z, MH+): 331

Intermediate (Ie1). (S)-tert-butyl 3-(4-(2-bromo-7-methoxy-3,4-dihydronaphthalen-1-yl)phenoxy)pyrrolidine-1-carboxylate

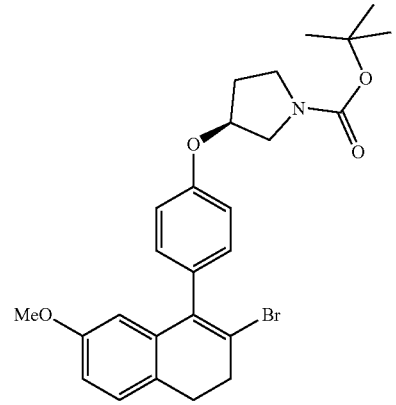 [SMILES: COc1ccc2c(c1)C(c1ccc(O[C@H]3CCN(C(=O)OC(C)(C)C)C3)cc1)=C(Br)CC2]

To a solution of 4-(2-bromo-7-methoxy-3,4-dihydronaphthalen-1-yl)phenol (Id1) (1.01 g, 3.06 mmol) in THF (19 ml), were added (R)-tert-butyl 3-hydroxypyrrolidine-1-carboxylate (635 mg, 3.39 mmol), (E)-N1,N1,N2,N2-tetramethyldiazene-1,2-dicarboxamide (975 mg, 5.66 mmol) and triphenylphosphine (1.48 g, 5.64 mmol). The reaction mixture was stirred for 24 hours at room temperature. Water and EtOAc were added. After decantation, the organic phase was dried over magnesium sulfate, filtered, and concentrated under reduced pressure. The residue was purified by flash chromatography eluting with a gradient of heptane in EtOAc (100/0 to 70/30; v/v) to give 1.46 g (95%) of (S)-tert-butyl 3-(4-(2-bromo-7-methoxy-3,4-dihydronaphthalen-1-yl)phenoxy)pyrrolidine-1-carboxylate (Ie1). LC/MS (m/z, MH⁺): 500

Intermediate (If1). (S)-3-(4-(2-bromo-7-methoxy-3,4-dihydronaphthalen-1-yl)phenoxy)pyrrolidine hydrochloride

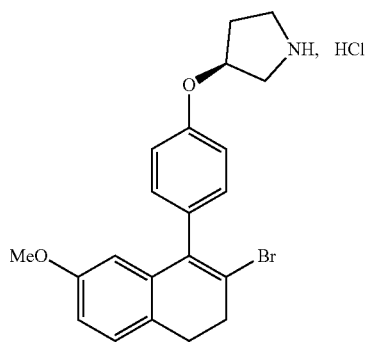 [SMILES: COc1ccc2c(c1)C(c1ccc(O[C@H]3CCNC3)cc1)=C(Br)CC2 ; Cl]

To a solution of (S)-tert-butyl 3-(4-(2-bromo-7-methoxy-3,4-dihydronaphthalen-1-yl)phenoxy)pyrrolidine-1-carboxylate (Ie1) (15 g, 29.97 mmol) in MeOH (260 ml), was added hydrochloric acid in dioxane 4N (70 ml, 280.00 mmol). The reaction mixture was stirred for 2 hours at room temperature. The reaction mixture was concentrated under reduced pressure and the residue obtained was triturated with diisopropyl ether and filtered to give 11.90 g (91%) of (S)-3-(4-(2-bromo-7-methoxy-3,4-dihydronaphthalen-1-yl)phenoxy)pyrrolidine hydrochloride (If) as a beige solid. LC/MS (m/z, MH⁺): 400

Intermediate (If2). (S)-7-bromo-8-(4-(pyrrolidin-3-yloxy)phenyl)-5,6-dihydronaphthalen-2-ol

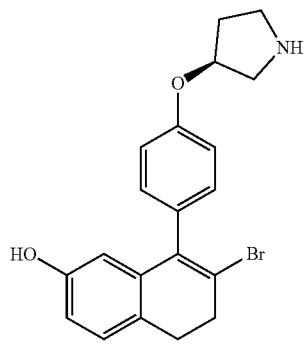 [SMILES: Oc1ccc2c(c1)C(c1ccc(O[C@H]3CCNC3)cc1)=C(Br)CC2]

To a solution of (S)-3-(4-(2-bromo-7-methoxy-3,4-dihydronaphthalen-1-yl)phenoxy)pyrrolidine hydrochloride (If1) (6.59 g, 15.09 mmol) in DCM (200 ml), was added dropwise boron tribromide 1M in DCM (45.26 ml, 45.26 mmol). The reaction mixture was stirred for 24 hours at room temperature. The reaction mixture was cooled at 0° C. and water (10 ml) was added. The pH was adjusted to 8 by adding NaOH 2N. After decantation, the organic phase was dried over magnesium sulfate and concentrated under reduced pressure. The residue obtained was treated on strong cation exchange (SCX) columns (Isolute Flash SCX-2; 20 g): the SCX columns were equilibrated with MeOH and the compound was introduced in solution in MeOH. Elution with MeOH, then with MeOH,NH₃ 2M/dichloromethane to give 5.83 g (100%) of (S)-7-bromo-8-(4-(pyrrolidin-3-yloxy)phenyl)-5,6-dihydronaphthalen-2-ol (If2) which will be used as such in the next step. LC/MS (m/z, MH⁺): 386

Intermediate (Ig1). (S)-7-bromo-8-(4-((1-(3-fluoropropyl)pyrrolidin-3-yl)oxy)phenyl)-5,6-dihydronaphthalen-2-ol

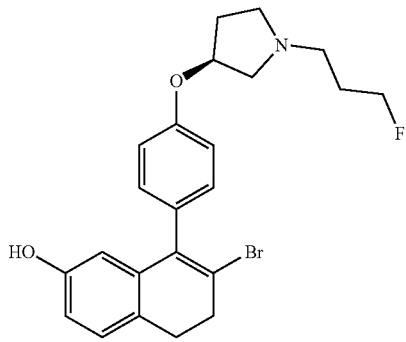 [SMILES: Oc1ccc2c(c1)C(c1ccc(O[C@H]3CCN(CCCF)C3)cc1)=C(Br)CC2]

To a solution of (S)-7-bromo-8-(4-(pyrrolidin-3-yloxy)phenyl)-5,6-dihydronaphthalen-2-ol (If2) (2 g, 5.18 mmol) in DMF (40 ml), were added potassium carbonate (716 mg, 5.18 mmol) and 1-iodo-3-fluoropropane (0.58 ml, 5.18 mmol). The reaction mixture was stirred for one hour at 70° C. After cooling to room temperature, water was added. The gum obtained was filtered, and washed with water and purified by flash chromatography eluting with a mixture of DCM and MeOH (97/03; v/v) to give 520 mg (18%) of (S)-7-bromo-8-(4-((1-(3-fluoropropyl)pyrrolidin-3-yl)oxy)phenyl)-5,6-dihydronaphthalen-2-ol (Ig1). LC/MS (m/z, MH⁺): 446

Compound (c). Tert-butyl (3S)-3-[4-(4,4,5,5-tetramethyl-1,3,2-dioxaborolan-2yl)phenoxy]pyrrolidine-1-carboxylate

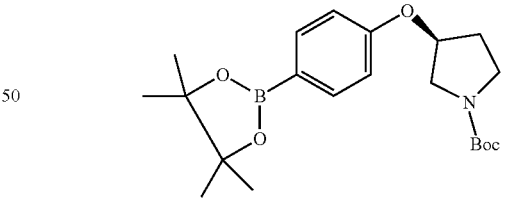

To a solution of 4-(4,4,5,5-tetramethyl-1,3,2-dioxaborolan-2-yl)phenol (82.7 g, 364.51 mmol) in THF (2 L) was added under argon (R)-1-N-Boc-3-hydroxypyrrolidine (84.43 g, 437.41 mmol) followed by N,N,N',N'-tetramethylazodicarboxamide (99.1 g, 546.77 mmol). The clear reaction mixture turned orange and triphenylphosphine (143.41 g, 546.77 mmol) was added. The reaction mixture was stirred at room temperature for 24 hours, meanwhile a precipitate of triphenylphosphine oxide formed (Ph₃P=O). The reaction mixture was poured in water (1.5 L) and extracted with EtOAc (3×1.5 L). Gathered organic phases were dried over magnesium sulfate, filtered, and concentrated under reduced pressure. The residue was taken up into diisopropyl ether (1.5 L) and the solid formed (Ph₃P═O) was filtered. The solvent was concentrated under reduced pressure and the residue purified by column chromatography eluting with a mixture of heptane and EtOAc (90/10; v/v) to give 145 g (100%) of tert-butyl (3S)-3-[4-(4,4,5,5-tetramethyl-1,3,2-dioxaborolan-2-yl)phenoxy]pyrrolidine-1-carboxylate (c) as a colorless oil. LC/MS (m/z, MH$^+$): 390

Compound (d). (3S)-3-[4-(4,4,5,5-tetramethyl-1,3,2-dioxaborolan-2yl)phenoxy]pyrrolidine, hydrochloride

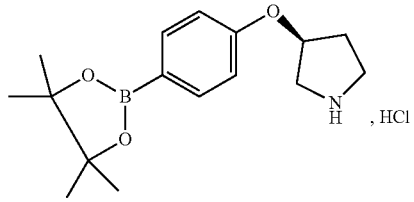 [SMILES: CC1(C)OB(c2ccc(O[C@H]3CCNC3)cc2)OC1(C)C]

To a solution of tert-butyl (3S)-3-[4-(4,4,5,5-tetramethyl-1,3,2-dioxaborolan-2-yl)phenoxy]pyrrolidine-1-carboxylate (c) (80 g, 195.23 mmol) in MeOH (450 ml) was added slowly HCl 4N in dioxane (250 ml). After 1.5 hours, the reaction mixture was concentrated under reduced pressure and the residue was taken up into Et₂O with stirring to give a solid which then was filtered, and dried under vacuum to give 61.8 g (95%) of (3S)-3-[4-(4,4,5,5-tetramethyl-1,3,2-dioxaborolan-2yl)phenoxy]pyrrolidine, hydrochloride (d) as a white powder. LC/MS (m/z, MH$^+$): 290

Reagent (1). (3S)-1-(3-fluoropropyl)-3-[4-(4,4,5,5-tetramethyl-1,3,2-dioxaborolan-2-yl)phenoxy]pyrrolidine

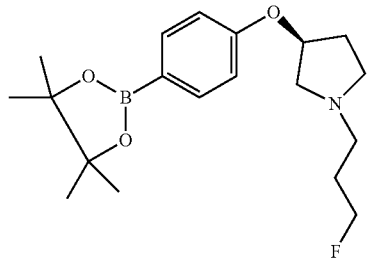 [SMILES: CC1(C)OB(c2ccc(O[C@H]3CCN(CCCF)C3)cc2)OC1(C)C]

To a suspension of (3S)-3-[4-(4,4,5,5-tetramethyl-1,3,2-dioxaborolan-2yl)phenoxy]pyrrolidine, hydrochloride (d) (20 g, 61.42 mmol) in acetonitrile (100 ml), was added K₂CO₃ (21.22 g, 153.54 mmol) and 1-iodo-3-fluoropropane (12.15 g, 61.42 mmol), under argon. The reaction mixture was stirred at 40° C. for 24 hours. After cooling to room temperature, the reaction mixture was filtered, and washed with acetonitrile. The filtrate was concentrated under reduced pressure and the residue was taken up in DCM and the solid formed was filtered, and washed with DCM. The filtrate was concentrated to give 21.5 g (100%) of (3S)-1-(3-fluoropropyl)-3-[4-(4,4,5,5-tetramethyl-1,3,2-dioxaborolan-2-yl) phenoxy]pyrrolidine (1) 21.5 g (100%) as a yellow foam. LC/MS (m/z, MH$^+$): 350

Intermediate (Ia1).
5-oxo-5,6,7,8-tetrahydronaphthalen-2-yl pivalate

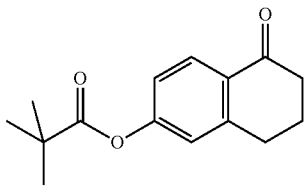 [SMILES: CC(C)(C)C(=O)Oc1ccc2c(c1)CCCC2=O]

To a solution of 8-hydroxy-1-tetralone (2.52 g, 15.23 mmol), in acetone (100 ml), was added potassium carbonate (2.10 g, 15.23 mmol) and pivaloyl chloride (1.88 ml, 15.23 mmol). The reaction mixture was stirred at room temperature for 16 h, filtered, and concentrated under reduced pressure. The residue was purified by flash chromatography eluting with a gradient of heptane in EtOAc (100/0 to 70/30; v/v) to give 3.75 g (100%) of 5-oxo-5,6,7,8-tetrahydronaphthalen-2-yl pivalate (Ia1). LC/MS (m/z, MH$^+$): 247

Intermediate (Ib2). 5-(((trifluoromethyl)sulfonyl)oxy)-7,8-dihydronaphthalen-2-yl pivalate

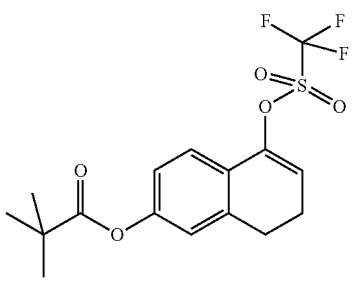 [SMILES: CC(C)(C)C(=O)Oc1ccc2c(c1)CCC=C2OS(=O)(=O)C(F)(F)F]

To a solution of 5-oxo-5,6,7,8-tetrahydronaphthalen-2-yl pivalate (Ia1) (3.75 g, 15.22 mmol) in DCM (125 ml) was added dropwise under argon, pyridine (1.92 ml, 22.84 mmol) and trifluoromethanesulfonic anhydride (5.17 ml, 30.45 mmol). The reaction mixture was stirred at room temperature for two hours and ice (200 g) was added. The phases were separated, the aqueous phase washed with DCM and the gathered organic phases dried over magnesium sulfate, filtered, and evaporated under reduced pressure. The residue was purified by flash chromatography eluting with a gradient of heptane in DCM (80/20 to 60/40; v/v) to give 5.02 g (87%) of 5-(((trifluoromethyl)sulfonyl)oxy)-7,8-dihydronaphthalen-2-yl pivalate (Ib2). LC/MS (m/z, MH$^+$): 379

Intermediate (Ih1). (S)-5-(4-((1-(3-fluoropropyl)pyrrolidin-3-yl)oxy)phenyl)-7,8-dihydronaphthalen-2-yl pivalate

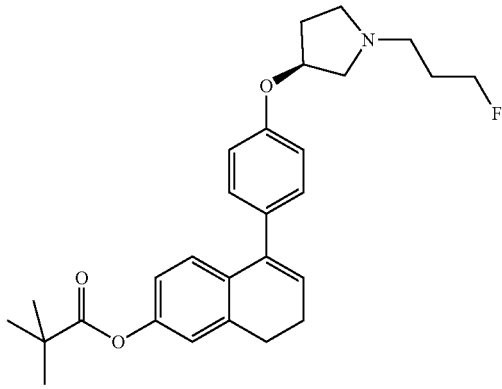 [SMILES: CC(C)(C)C(=O)Oc1ccc2c(c1)CCC=C2c1ccc(O[C@H]2CCN(CCCF)C2)cc1]

To a solution of 5-(((trifluoromethyl)sulfonyl)oxy)-7,8-dihydronaphthalen-2-yl pivalate (Ib2) (2 g, 5.29 mmol) and (S)-1-(3-fluoropropyl)-3-(4-(4,4,5,5-tetramethyl-1,3,2-dioxaborolan-2-yl)phenoxy)pyrrolidine (1) (1.85 g, 5.29 mmol) in dioxane (14 ml) and a solution of $Cs_2CO_3$ 1.5M (7 ml, 10.5 mmol) was added under argon [1,1'-bis(diphenylphosphino) ferrocene]dichloropalladium(II), complex with DCM (273 mg, 0.317 mmol). The reaction mixture was stirred for 30 minutes at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a gradient of MeOH in DCM (0 to 4%; V/V) to give 1.56 g (66%) of (S)-5-(4-((1-(3-fluoropropyl)pyrrolidin-3-yl)oxy)phenyl)-7,8-dihydronaphthalen-2-yl pivalate (Ih1). LC/MS (m/z, MH$^+$): 452

Intermediate (Ig2). (S)-6-bromo-5-(4-((1-(3-fluoropropyl)pyrrolidin-3-yl)oxy)phenyl)-7,8-dihydronaphthalen-2-yl pivalate hydrobromide

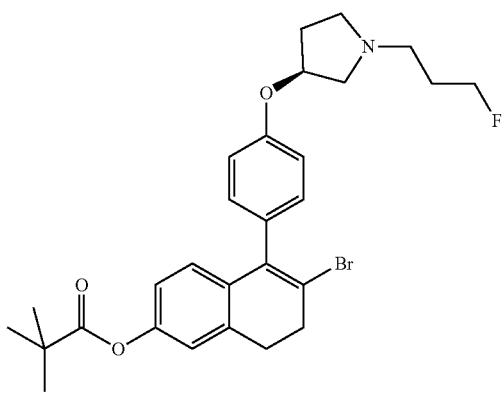 [SMILES: CC(C)(C)C(=O)Oc1ccc2c(c1)CCC(Br)=C2c1ccc(O[C@H]2CCN(CCCF)C2)cc1]

To a solution of (S)-5-(4-((1-(3-fluoropropyl)pyrrolidin-3-yl)oxy)phenyl)-7,8-dihydronaphthalen-2-yl pivalate (Ih1) (1.46 g, 3.23 mmol) in DCM (15 ml), was added pyridinium tribromide (1.26 g, 3.56 mmol). The reaction mixture was stirred for 1 hour at room temperature. Water (30 ml) and DCM (50 ml) were added. The aqueous phase was washed with DCM three times and the gathered organic phases dried over magnesium sulfate, filtered, evaporated under reduced pressure and the residue purified by column chromatography eluting with a gradient of MeOH in DCM (0 to 4%; V/V) to give 1.85 g (94%) of (S)-6-bromo-5-(4-((1-(3-fluoropropyl)pyrrolidin-3-yl)oxy)phenyl)-7,8-dihydronaphthalen-2-yl pivalate hydrobromide (Ig2). LC/MS (m/z, MH$^+$): 530

Intermediate (Ig3). (S)-6-bromo-5-(4-((1-(3-fluoropropyl)pyrrolidin-3-yl)oxy)phenyl)-7,8-dihydronaphthalen-2-ol

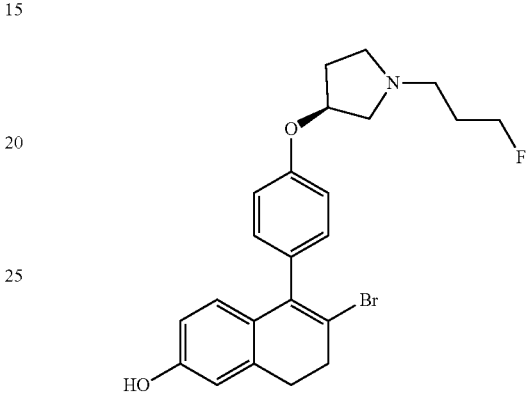

To a solution of (S)-6-bromo-5-(4-((1-(3-fluoropropyl)pyrrolidin-3-yl)oxy)phenyl)-7,8-dihydronaphthalen-2-yl pivalate hydrobromide (Ig2) (1.84 g, 3.01 mmol) in MeOH (30 ml), was added NaOH (2.23 ml, 24.08 mmol) 2N. The reaction mixture was stirred 15 minutes at room temperature and 8 ml of HCl 1N was added. The solvent was removed under reduced pressure and the residue taken up into EtOAc. The phases were separated and the aqueous phase washed with EtOAc. The organic phases were combined and dried over magnesium sulfate, filtered, and evaporated under reduced pressure to give 1.24 g (93%) of (S)-6-bromo-5-(4-((1-(3-fluoropropyl)pyrrolidin-3-yl)oxy)phenyl)-7,8-dihydronaphthalen-2-ol (Ig3). LC/MS (m/z, MH$^+$): 446

Intermediate (Ia2). 4-oxochroman-7-yl pivalate

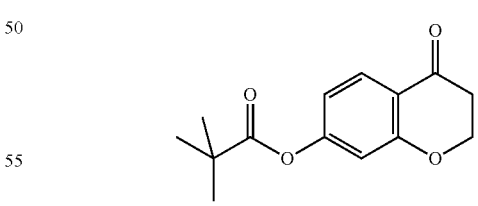

To a solution of 7-hydroxychroman-4-one (2 g, 12.18 mmol), in acetone (50 ml), was added potassium carbonate (1.85 g, 13.40 mmol) and pivaloyl chloride (1.65 ml, 13.40 mmol). The reaction mixture was stirred at room temperature for 16 h, filtered, and concentrated under reduced pressure. The residue was purified by flash chromatography eluting with a gradient of heptane in DCM (100/0 to 0/100; v/v) to give 2.15 g (71%) of 4-oxochroman-7-yl pivalate (Ia2). LC/MS (m/z, MH$^+$): 249

Intermediate (Ib3). 4-(((trifluoromethyl)sulfonyl)oxy)-2H-chromen-7-yl pivalate

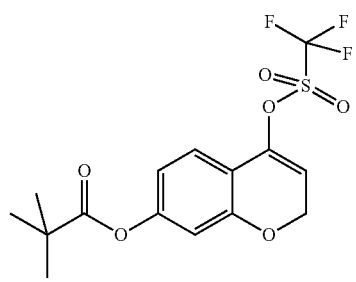 [SMILES: CC(C)(C)C(=O)Oc1ccc2c(c1)OCC=C2OS(=O)(=O)C(F)(F)F]

To a solution of 4-oxochroman-7-yl pivalate (Ia2) (2.15 g, 7.19 mmol) in DCM (80 ml) was added dropwise under argon pyridine (1.05 ml, 12.85 mmol) and trifluoromethanesulfonic anhydride (2.93 ml, 17.30 mmol). The reaction mixture was stirred at room temperature for one hour and ice (200 g) was added. The phases were separated, the aqueous phase washed with DCM and the gathered organic phases dried over magnesium sulfate, filtered, and evaporated under pressure. The residue was purified by flash chromatography eluting with a gradient of heptane in DCM (80/20 to 40/60; v/v) to give 920 mg (34%) of 4-(((trifluoromethyl)sulfonyl)oxy)-2H-chromen-7-yl pivalate (Ib3). LC/MS (m/z, MH+): 381

Intermediate (Ih2). (S)-4-(4-((1-(3-fluoropropyl)pyrrolidin-3-yl)oxy)phenyl)-2H-chromen-7-yl pivalate

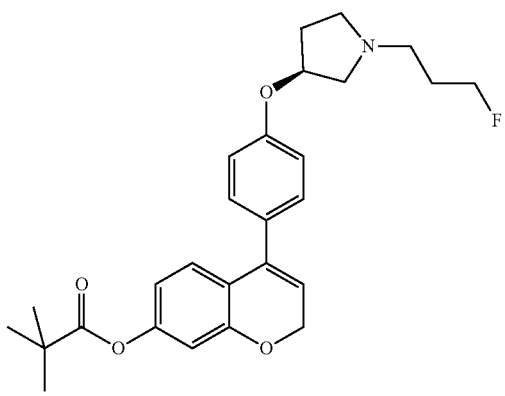 [SMILES: CC(C)(C)C(=O)Oc1ccc2c(c1)OCC=C2c1ccc(O[C@H]2CCN(CCCF)C2)cc1]

To a solution of 4-(((trifluoromethyl)sulfonyl)oxy)-2H-chromen-7-yl pivalate (Ib3) (920 mg, 2.42 mmol) and (S)-1-(3-fluoropropyl)-3-(4-(4,4,5,5-tetramethyl-1,3,2-dioxaborolan-2-yl)phenoxy)pyrrolidine (1) (845 mg, 2.42 mmol) in dioxane (6.5 ml) and a solution of Cs$_2$CO$_3$ 1.5M (3.23 ml, 4.84 mmol) was added under argon [1,1'-bis(diphenylphosphino)ferrocene]dichloropalladium(II), complex with DCM (125 mg, 0.15 mmol). The reaction mixture was stirred for one hour at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a gradient of MeOH in DCM (0 to 4%; V/V) to give 790 mg (72%) of (S)-4-(4-((1-(3-fluoropropyl)pyrrolidin-3-yl)oxy)phenyl)-2H-chromen-7-yl pivalate (Ih2). LC/MS (m/z, MH+): 454

Intermediate (Ig4). (S)-3-bromo-4-(4-((1-(3-fluoropropyl)pyrrolidin-3-yl)oxy)phenyl)-2H-chromen-7-yl pivalate hydrobromide

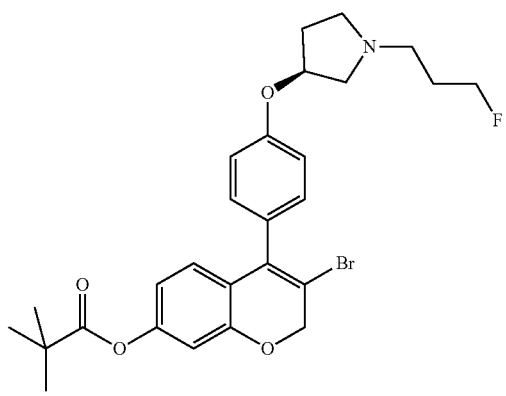 [SMILES: CC(C)(C)C(=O)Oc1ccc2c(c1)OCC(Br)=C2c1ccc(O[C@H]2CCN(CCCF)C2)cc1]

To a solution of (S)-4-(4-((1-(3-fluoropropyl)pyrrolidin-3-yl)oxy)phenyl)-2H-chromen-7-yl pivalate (Ih2) (790 mg, 1.74 mmol) in DCM (10 ml), was added pyridinium tribromide (681 mg, 1.92 mmol). The reaction mixture was stirred for 1 hour at room temperature. Water (30 ml) and DCM (50 ml) were added. The aqueous phase was washed with DCM three times and the gathered organic phases dried over magnesium sulfate, filtered, evaporated under reduced pressure and the residue purified by column chromatography eluting with a gradient of MeOH in DCM (0 to 4%; V/V) to give 0.77 g (72%) of (S)-3-bromo-4-(4-((1-(3-fluoropropyl)pyrrolidin-3-yl)oxy)phenyl)-2H-chromen-7-yl pivalate hydrobromide (Ig4). LC/MS (m/z, MH+): 532

Intermediate (Ig5). (S)-3-bromo-4-(4-((1-(3-fluoropropyl)pyrrolidin-3-yl)oxy)phenyl)-2H-chromen-7-ol

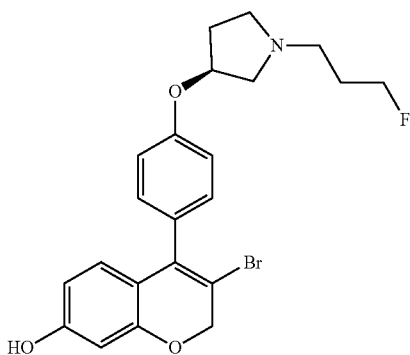 [SMILES: Oc1ccc2c(c1)OCC(Br)=C2c1ccc(O[C@H]2CCN(CCCF)C2)cc1]

To a solution of (S)-3-bromo-4-(4-((1-(3-fluoropropyl)pyrrolidin-3-yl)oxy)phenyl)-2H-chromen-7-yl pivalate hydrobromide (Ig4) (775 mg, 1.26 mmol) in MeOH (15 ml), was added NaOH 2N (0.94 ml, 24.08 mmol). The reaction mixture was stirred 15 minutes at room temperature and 8 ml of HCl 1N was added. The solvent was removed under reduced pressure and the residue partitioned between water and EtOAc. The phases were separated and the aqueous phase washed with EtOAc. The organic phases were combined and dried over magnesium sulfate, filtered, and evaporated under reduced pressure to give 0.57 g (100%) of (S)-3-bromo-4-(4-((1-(3-fluoropropyl)pyrrolidin-3-yl)oxy)phenyl)-2H-chromen-7-ol (Ig5). LC/MS (m/z, MH+): 448

Intermediate (Ia3). 2,2-Dimethyl-propionic acid 4-oxo-thiochroman-7-yl ester

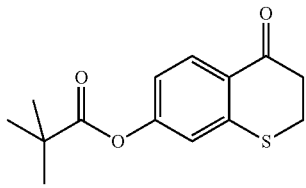 [SMILES: CC(C)(C)C(=O)Oc1ccc2c(c1)SCCC2=O]

To a solution of 7-hydroxythiochroman-4-one (450 mg, 2.5 mmol), in acetone (30 ml), was added potassium carbonate (500 mg, 3.6 mmol) and pivaloyl chloride (0.45 ml, 3.6 mmol). The reaction mixture was stirred at room temperature for 24 h, filtered and concentrated under reduced pressure. The residue was purified by flash chromatography eluting with a gradient of heptane in EtOAc (100/0 to 70/30; v/v) to give 696 mg (74%) of 2,2-dimethyl-propionic acid 4-oxo-thiochroman-7-yl ester (Ia3) as a yellow oil. [MH]+=265

Intermediate (Ib4). 4-(((trifluoromethyl)sulfonyl)oxy)-2H-thiochromen-7-yl pivalate

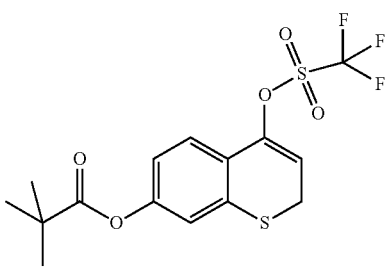 [SMILES: CC(C)(C)C(=O)Oc1ccc2c(c1)SCC=C2OS(=O)(=O)C(F)(F)F]

To a solution under argon of 2,2-dimethyl-propionic acid 4-oxo-thiochroman-7-yl ester (Ia3) (32 g, 121.06 mmol) in DCM (450 ml) and pyridine (14.69 ml, 181.58 mmol), was added dropwise trifluoromethanesulfonic anhydride (40.90 ml, 242.11 mmol). The reaction mixture was stirred at room temperature for 2 h and poured onto ice. The phases were separated, the aqueous phase washed with DCM and the gathered organic phases dried over magnesium sulfate, filtered, and evaporated under reduced pressure. The residue was purified by flash chromatography eluting with DCM to give 30 g (62%) of 4-(((trifluoromethyl)sulfonyl)oxy)-2H-thiochromen-7-yl pivalate (Ib4). LC/MS (m/z, MH+): 397

Intermediate (Ih3). (S)-4-(4-((1-(3-fluoropropyl)pyrrolidin-3-yl)oxy)phenyl)-2H-thiochromen-7-yl pivalate

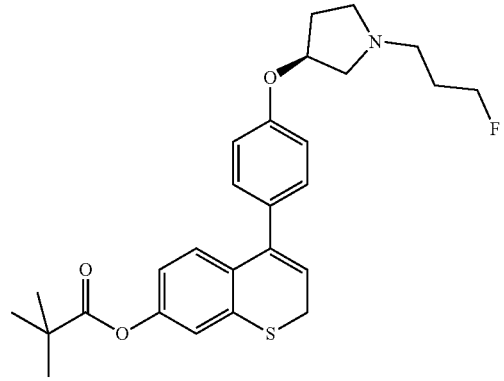 [SMILES: CC(C)(C)C(=O)Oc1ccc2c(c1)SCC=C2c1ccc(O[C@H]2CCN(CCCF)C2)cc1]

To a solution under argon of 4-(((trifluoromethyl)sulfonyl)oxy)-2H-thiochromen-7-yl pivalate (Ib4) (14 g, 35.32 mmol), (S)-1-(3-fluoropropyl)-3-(4-(4,4,5,5-tetramethyl-1,3,2-dioxaborolan-2-yl)phenoxy)pyrrolidine (1) (13 g, 37.22 mmol) in dioxane (375 ml) and water (46 ml), were added $Cs_2CO_3$ (24.17 g, 74.17 mmol) and [1,1'-bis(diphenylphosphino)ferrocene]dichloropalladium(II), complex with DCM (2.31 g, 2.83 mmol). The reaction mixture was stirred for 48 hours at room temperature and partitioned between water and EtOAc. The organic phase was washed with brine, dried over magnesium sulfate, and concentrated under reduced pressure. The residue was purified by flash chromatography eluting with a gradient of DCM in MeOH (100/0 to 95/05; v/v) to give 14.2 g (85%) of (S)-4-(4-((1-(3-fluoropropyl)pyrrolidin-3-yl)oxy)phenyl)-2H-thiochromen-7-yl pivalate (Ih3). LC/MS (m/z, MH+): 470

Intermediate (Ig6). (S)-3-bromo-4-(4-((1-(3-fluoropropyl)pyrrolidin-3-yl)oxy)phenyl)-2H-thiochromen-7-yl pivalate

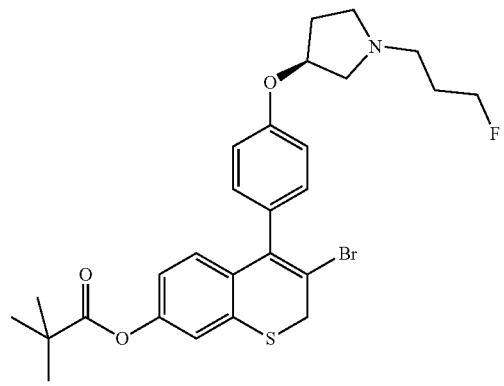 [SMILES: CC(C)(C)C(=O)Oc1ccc2c(c1)SCC(Br)=C2c1ccc(O[C@H]2CCN(CCCF)C2)cc1]

To a solution under argon of (S)-4-(4-((1-(3-fluoropropyl)pyrrolidin-3-yl)oxy)phenyl)-2H-thiochromen-7-yl pivalate (Ih3) (14.22 g, 30.28 mmol), in THF (350 ml) was added pyridinium tribromide (11.62 g, 36.34 mmol). The reaction mixture was stirred for 1 hour at room temperature then partitioned between water and EtOAc. The organic phase was washed with brine, dried over magnesium sulfate, and concentrated under reduced pressure to give 17.57 g (100%) of (S)-3-bromo-4-(4-((1-(3-fluoropropyl)pyrrolidin-3-yl)oxy)phenyl)-2H-thiochromen-7-yl pivalate (Ig6). LC/MS (m/z, MH⁺): 548

Intermediate (Ig7). (S)-3-bromo (-4-(4-((1-(3-fluoropropyl)pyrrolidin-3-yl)oxy)phenyl)-2H-thiochromen-7-ol

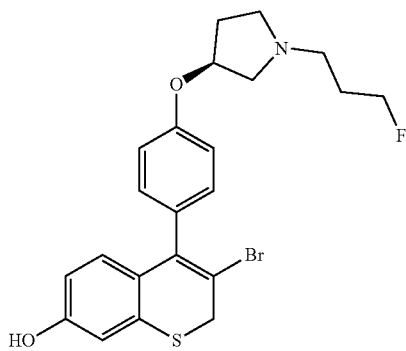 [SMILES: Oc1ccc2c(c1)SCC(Br)=C2c1ccc(O[C@H]2CCN(CCCF)C2)cc1]

To a solution under argon of (S)-3-bromo-4-(4-((1-(3-fluoropropyl)pyrrolidin-3-yl)oxy)phenyl)-2H-thiochromen-7-yl pivalate (Ig6) (17.57 g, 32.03 mmol), in MeOH (350 ml), was added sodium hydroxyde 5M (25.62 ml, 128.11 mmol) and the reaction mixture was stirred at room temperature for 1 hour, then hydrochloric acid 5M (20 ml) was added and the reaction mixture was concentrated under reduced pressure, partitioned between water and EtOAc. The organic phase was washed with brine, dried over magnesium sulfate, and concentrated under reduced pressure. The residue was purified by flash chromatography eluting with a gradient of DCM in MeOH (100/0 to 98/02; v/v) to give 4.8 g (32%) of (S)-3-bromo (-4-(4-((1-(3-fluoropropyl)pyrrolidin-3-yl)oxy)phenyl)-2H-thiochromen-7-ol (Ig7). LC/MS (m/z, MH⁺): 464

Intermediate (Ia4). 8-Hydroxy-3,4-dihydro-2H-benzo[b]oxepin-5-one

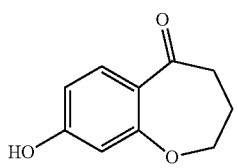 [SMILES: O=C1CCCOc2cc(O)ccc21]

A solution of 8-methoxy-3,4-dihydrobenzo[b]oxepin-5(2H)-one (2.5 g, 13.01 mmol) in 47% aqueous HBr (25 ml) and acetic acid (12.5 ml) was stirred mechanically at 115° C. for 16 hours. The reaction mixture was cooled to room temperature and partitioned between water (100 ml) and EtOAc (200 ml). The organic phase was washed with brine, dried over magnesium sulfate, filtered, and concentrated under reduced pressure. The residue was purified by flash chromatography eluting with a gradient of heptane in EtOAc (100/0 to 70/30; v/v) to give 700 mg (30%) of 8-hydroxy-3,4-dihydrobenzo[b]oxepin-5(2H)-one (Ia4) as an orange powder. LC/MS (m/z, MH⁺): 179

Intermediate (Ia5). 5-oxo-2,3,4,5-tetrahydrobenzo[b]oxepin-8-yl pivalate

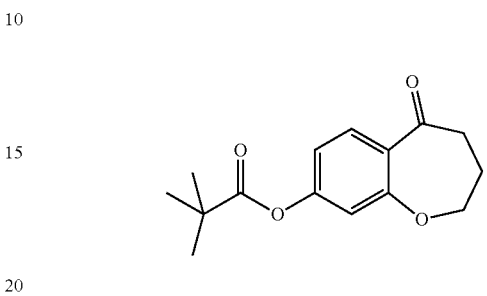

To a solution of 8-hydroxy-3,4-dihydrobenzo[b]oxepin-5(2H)-one (Ia4) (690 mg, 3.87 mmol), in acetone (60 ml), was added potassium carbonate (535 mg, 3.87 mmol) and pivaloyl chloride (0.48 ml, 3.87 mmol). The reaction mixture was stirred at room temperature for 16 h, filtered, and concentrated under reduced pressure. The residue was purified by flash chromatography eluting with a gradient of heptane in EtOAc (100/0 to 85/15; v/v) to give 796 mg (78%) of 5-oxo-2,3,4,5-tetrahydrobenzo[b]oxepin-8-yl pivalate (Ia5) as a yellow oil. LC/MS (m/z, MH⁺): 263

Intermediate (Ib5). 5-(((trifluoromethyl)sulfonyl)oxy)-2,3-dihydrobenzo[b]oxepin-8-yl pivalate

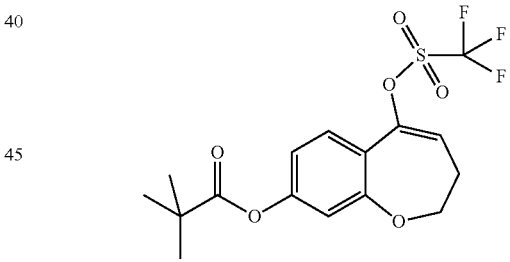

To a solution of 5-oxo-2,3,4,5-tetrahydrobenzo[b]oxepin-8-yl pivalate (Ia5) (4.42 g, 16.85 mmol) in DCM (120 ml) was added under argon pyridine (2.13 ml, 25.28 mmol) and trifluoromethanesulfonic anhydride (5.73 ml, 33.70 mmol) dropwise. The reaction mixture was stirred at room temperature for 16 hours and ice (200 g) was added. The phases were separated, the aqueous phase washed with DCM and the gathered organic phases dried over magnesium sulfate, filtered, and evaporated under reduced pressure. The residue was purified by flash chromatography eluting with a gradient of heptane in EtOAc (100/0 to 90/10; v/v) to give 4.42 g (67%) of 5-(((trifluoromethyl)sulfonyl)oxy)-2,3-dihydrobenzo[b]oxepin-8-yl pivalate (Ib5) as a green oil. LC/MS (m/z, MH⁺): 395

Intermediate (Ih4). (S)-5-(4-((1-(3-fluoropropyl) pyrrolidin-3-yl)oxy)phenyl)-2,3-dihydrobenzo[b] oxepin-8-yl pivalate

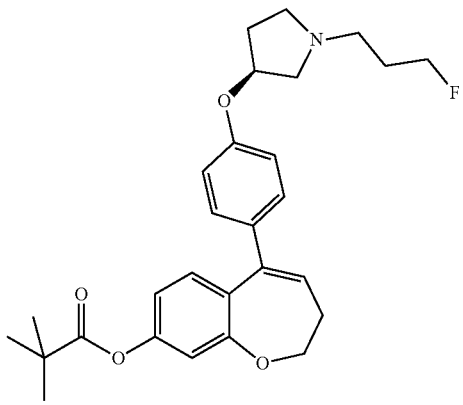 [SMILES: CC(C)(C)C(=O)Oc1ccc2c(c1)OCCC=C2c1ccc(O[C@H]2CCN(CCCF)C2)cc1]

To a solution of 5-(((trifluoromethyl)sulfonyl)oxy)-2,3-dihydrobenzo[b]oxepin-8-yl pivalate (Ib5) (2.2 g, 5.58 mmol) and (S)-1-(3-fluoropropyl)-3-(4-(4,4,5,5-tetramethyl-1,3,2-dioxaborolan-2-yl)phenoxy)pyrrolidine (1) (1.95 g, 5.58 mmol) in dioxane (38 ml) and water (5 ml) were added under argon Cs$_2$CO$_3$ (3.82 g, 11.72 mmol), and [1,1'-bis(diphenylphosphino)ferrocene]dichloropalladium (II), complex with DCM (456 mg, 0.56 mmol). The reaction mixture was stirred for 2 hours at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a gradient of MeOH in DCM (0 to 10%; V/V) to give 2.6 g (99%) of (S)-5-(4-((1-(3-fluoropropyl)pyrrolidin-3-yl)oxy)phenyl)-2,3-dihydrobenzo[b]oxepin-8-yl pivalate (Ih4). LC/MS (m/z, MH$^+$): 468

Intermediate (Ig8). (S)-4-bromo-5-(4-((1-(3-fluoropropyl)pyrrolidin-3-yl)oxy)phenyl)-2,3-dihydrobenzo[b]oxepin-8-yl pivalate

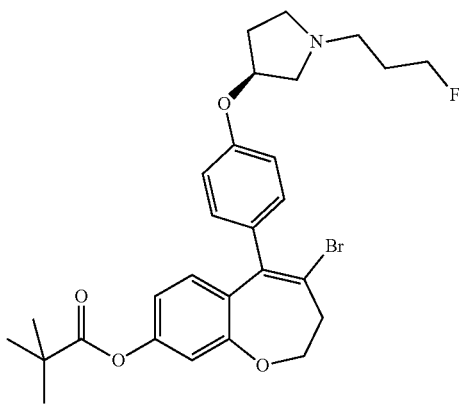 [SMILES: CC(C)(C)C(=O)Oc1ccc2c(c1)OCCC(Br)=C2c1ccc(O[C@H]2CCN(CCCF)C2)cc1]

To a solution of (S)-5-(4-((1-(3-fluoropropyl)pyrrolidin-3-yl)oxy)phenyl)-2,3-dihydrobenzo[b]oxepin-8-yl pivalate (Ih4) (2.6 g, 5.56 mmol) in THF (100 ml), was added pyridinium tribromide (2.37 g, 6.67 mmol). The reaction mixture was stirred for 2 hours at room temperature. Water (20 ml) and DCM (60 ml) were added. The pH was adjusted to 7 by adding saturated solution of NaHCO$_3$. The aqueous phase was washed with DCM three times and the gathered organic phases dried over magnesium sulfate and filtered. The organics were evaporated under reduced pressure to give 3.04 g g (100%) of (S)-4-bromo-5-(4-((1-(3-fluoropropyl)pyrrolidin-3-yl)oxy)phenyl)-2,3-dihydrobenzo[b]oxepin-8-yl pivalate (Ig8) as a black oil. LC/MS (m/z, MH$^+$): 546

Intermediate (Ig9). (S)-4-bromo-5-(4-((1-(3-fluoropropyl)pyrrolidin-3-yl)oxy)phenyl)-2,3-dihydrobenzo[b]oxepin-8-ol

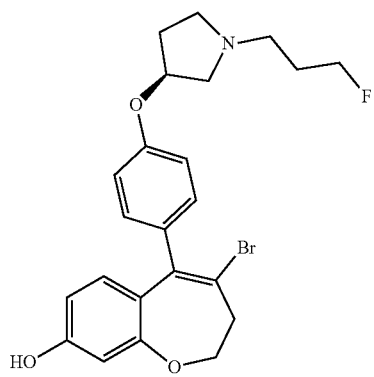

To a solution of (S)-4-bromo-5-(4-((1-(3-fluoropropyl)pyrrolidin-3-yl)oxy)phenyl)-2,3-dihydrobenzo[b]oxepin-8-yl pivalate (Ig8) (3.04 g, 5.56 mmol) in MeOH (75 ml), was added NaOH 5N (4.45 ml, 22.24 mmol). The reaction mixture was stirred for 1 hour at room temperature and 4.5 ml of HCl 5N was added. The solvent was removed under reduced pressure and the residue taken up into EtOAc. The phases were separated and the aqueous phase washed with EtOAc. The organic phases were combined, dried over magnesium sulfate, filtered, and evaporated under reduced pressure. The residue was purified by column chromatography eluting with a gradient of MeOH in DCM (0 to 05%; V/V) to give 1.33 g (52%) of (S)-4-bromo-5-(4-((1-(3-fluoropropyl)pyrrolidin-3-yl)oxy)phenyl)-2,3-dihydrobenzo[b]oxepin-8-ol (Ig9). LC/MS (m/z, MH$^+$): 462

Intermediate (Ia5). 7-fluoro-8-hydroxy-3,4-dihydrobenzo[b]oxepin-5(2H)-one

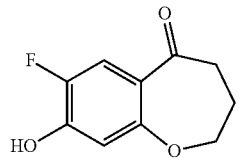 [SMILES: O=C1CCCOc2cc(O)c(F)cc21]

239

Step 1. 7,8-difluoro-3,4-dihydrobenzo[b]oxepin-5 (2H)-one

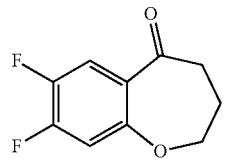 [SMILES: O=C1CCCOc2cc(F)c(F)cc21]

To a solution of 3,4-difluorophenol (5 g, 38.43 mmol) in THF (60 ml), was added potassium carbonate (5.84 g, 42.28 mmol). After 10 minutes of stirring at room temperature, methyl-4-bromobutyrate (8.06 g, 42.28 mmol) was added. The white suspension was heated at 50° C. for two hours. After cooling to room temperature, MeOH (50 ml), water (50 ml) and sodium hydroxide 32% (30 ml) were added. The reaction mixture was heated at 80° C. for 30 minutes. After cooling to room temperature, ice (100 g) was added, then the pH was adjusted to pH 3 by adding HCl 5N. The solid was filtered, and dried by heating under reduced pressure over $P_2O_5$. To the obtained yellow powder, polyphosphoric acid (PPA, 20 g) was added, then the mixture was heated at 80° C. for 30 min. Ice was slowly added and the precipitate was filtered, and dried under reduced pressure over $P_2O_5$ to give 6 g (78%) of 7,8-difluoro-3,4-dihydrobenzo[b]oxepin-5 (2H)-one as a yellow solid. LC/MS (m/z, MH$^+$): 199

Step 2. 7-fluoro-8-hydroxy-3,4-dihydrobenzo[b] oxepin-5(2H)-one (Ia5)

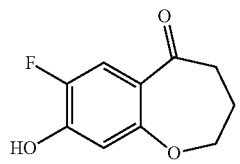 [SMILES: O=C1CCCOc2cc(O)c(F)cc21]

A mixture of but-2-yn-1-ol (2.23 g, 31.82 mmol) and sodium t-butylate (2.23 g, 31.82 mmol) in DMSO (150 ml) was stirred for two minutes. Then, 7,8-difluoro-3,4-dihydrobenzo[b]oxepin-5(2H)-one (3.15 g, 15.89 mmol) was added and the reaction mixture was heated at 125° C. for 20 seconds. After cooling to room temperature, water (50 ml) and EtOAc (100 ml) were added. The organic phase was washed with brine, dried over magnesium sulfate, and concentrated under reduced pressure. The residue was purified by flash chromatography eluting with a gradient of heptane in EtOAc (100/0 to 60/40; v/v) to give (1.36 g) 44% of 7-fluoro-8-hydroxy-3,4-dihydrobenzo[b]oxepin-5(2H)-one (Ia5). LC/MS (m/z, MH$^+$): 197

240

Intermediate (Ia6). 7-fluoro-5-oxo-2,3,4,5-tetrahydrobenzo[b]oxepin-8-yl pivalate

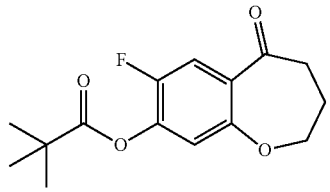

To a solution of 7-fluoro-8-hydroxy-3,4-dihydrobenzo[b]oxepin-5(2H)-one (Ia5) (1.68 g, 8.56 mmol) in acetone (70 ml) was added potassium carbonate (1.30 g, 9.41 mmol). After 10 mn of stirring, pivaloyl chloride (1.13 g/1.16 ml, 9.41 mmol) was added. The suspension was stirred for 1 hour at room temperature. The solids were filtered off and then washed with acetone (10 ml). The filtrate was concentrated under reduced pressure. To the residue obtained, EtOAc (50 ml) and water were added. The organic phase was dried over magnesium sulfate, filtered, and concentrated under reduced pressure. The residue was purified by flash chromatography eluting with a gradient of heptane in EtOAc (100/0 to 85/15; v/v) to give 2.4 g (100%) of 7-fluoro-5-oxo-2,3,4,5-tetrahydrobenzo[b]oxepin-8-yl pivalate (Ia6) as a beige solid. LC/MS (m/z, MH$^+$): 281

Intermediate (Ib6). 7-fluoro-5-(((trifluoromethyl) sulfonyl)oxy)-2,3-dihydrobenzo[b]oxepin-8-yl pivalate

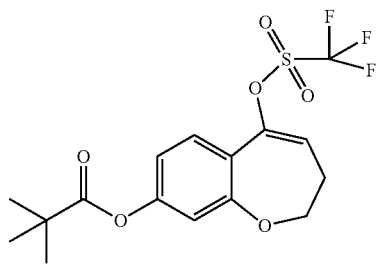 [SMILES: CC(C)(C)C(=O)Oc1ccc2c(c1)OCCC=C2OS(=O)(=O)C(F)(F)F]

To a solution of 7-fluoro-5-oxo-2,3,4,5-tetrahydrobenzo[b]oxepin-8-yl pivalate (Ia6) (2.7 g, 9.63 mmol) in DCM (80 ml) were added dropwise under argon pyridine (1.22 ml, 14.45 mmol) and trifluoromethanesulfonic anhydride (3.27 ml, 19.27 mmol). The reaction mixture was stirred at room temperature for 18 hours and ice (100 g) was added. The phases were separated, the aqueous phase washed with DCM and the gathered organic phases were dried over magnesium sulfate, filtered, and evaporated under reduced pressure. The residue was purified by flash chromatography eluting with a gradient of heptane in DCM (100/0 to 70/30; v/v) to give 2.01 g (51%) of 7-fluoro-5-(((trifluoromethyl)sulfonyl)oxy)-2,3-dihydrobenzo[b]oxepin-8-yl pivalate (Ib6) as an orange oil. LC/MS (m/z, MH$^+$): 413

Intermediate (Ih5). (S)-7-fluoro-5-(4-((1-(3-fluoropropyl)pyrrolidin-3-yl)oxy)phenyl)-2,3-dihydrobenzo[b]oxepin-8-yl pivalate

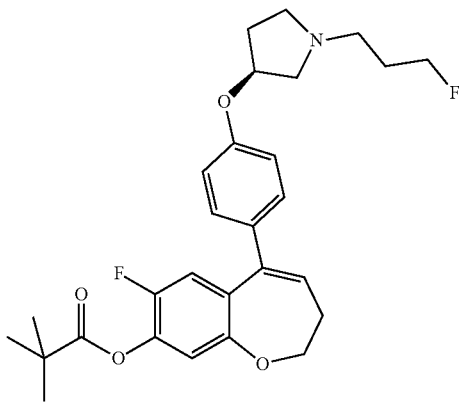 [SMILES: CC(C)(C)C(=O)Oc1cc2c(cc1F)C(c1ccc(O[C@H]3CCN(CCCF)C3)cc1)=CCCO2]

To a solution of 7-fluoro-5-((((trifluoromethyl)sulfonyl)oxy)-2,3-dihydrobenzo[b]oxepin-8-yl pivalate (Ib6) (2 g, 4.85 mmol), and (S)-1-(3-fluoropropyl)-3-(4-(4,4,5,5-tetramethyl-1,3,2-dioxaborolan-2-yl)phenoxy)pyrrolidine (1) (1.86 g, 5.34 mmol) in dioxane (77 ml) and water (19 ml), were added Cs$_2$CO$_3$ (3.16 g, 9.70 mmol) and [1,1'-bis(diphenylphosphino)ferrocene]dichloropalladium(II), complex with DCM (238 mg, 0.29 mmol). The reaction mixture was stirred for 3.5 hours at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a mixture of DCM and MeOH (95/05; v/v) to give 1.91 g (81%) of (S)-7-fluoro-5-(4-((1-(3-fluoropropyl)pyrrolidin-3-yl)oxy)phenyl)-2,3-dihydrobenzo[b]oxepin-8-yl pivalate (Ih5). LC/MS (m/z, MH$^+$): 486

Intermediate (Ig10). (S)-4-bromo-7-fluoro-5-(4-((1-(3-fluoropropyl)pyrrolidin-3-yl)oxy)phenyl)-2,3-dihydrobenzo[b]oxepin-8-yl pivalate

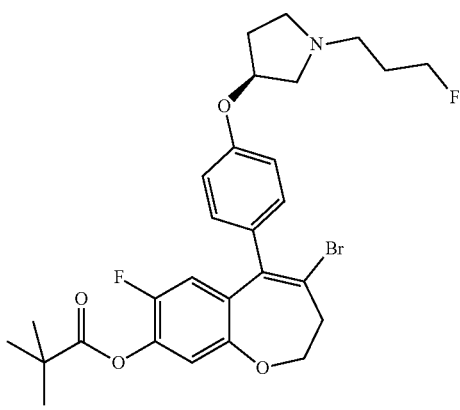 [SMILES: CC(C)(C)C(=O)Oc1cc2c(cc1F)C(c1ccc(O[C@H]3CCN(CCCF)C3)cc1)=C(Br)CCO2]

To a solution of (S)-7-fluoro-5-(4-((1-(3-fluoropropyl)pyrrolidin-3-yl)oxy)phenyl)-2,3-dihydrobenzo[b]oxepin-8-yl pivalate (Ih5) (1.91 g, 3.93 mmol) in THF (85 ml), was added pyridinium tribromide (1.45 g, 4.09 mmol). The reaction mixture was stirred for 1 hour at room temperature. Water (100 ml) and EtOAc were added. The pH was adjusted to 7 with a concentrated solution of NaHCO$_3$. The aqueous phase was washed with EtOAc and the gathered organic phases dried over magnesium sulfate and filtered. The organic phases were evaporated under reduced pressure and the residue obtained was purified by column chromatography eluting with a mixture of DCM and MeOH (95/05; v/v) to give 1.56 g (70%) of (S)-4-bromo-7-fluoro-5-(4-((1-(3-fluoropropyl)pyrrolidin-3-yl)oxy)phenyl)-2,3-dihydrobenzo[b]oxepin-8-yl pivalate (Ig10). LC/MS (m/z, MH$^+$): 564

Intermediate (Ig11). (S)-4-bromo-7-fluoro-5-(4-((1-(3-fluoropropyl)pyrrolidin-3-yl)oxy)phenyl)-2,3-dihydrobenzo[b]oxepin-8-ol

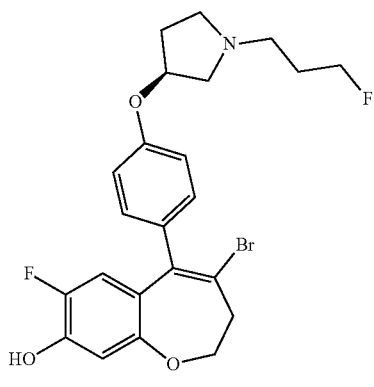 [SMILES: Oc1cc2c(cc1F)C(c1ccc(O[C@H]3CCN(CCCF)C3)cc1)=C(Br)CCO2]

To a solution of (S)-4-bromo-7-fluoro-5-(4-((1-(3-fluoropropyl)pyrrolidin-3-yl)oxy)phenyl)-2,3-dihydrobenzo[b]oxepin-8-yl pivalate (Ig10) (1.56 g, 2.76 mmol) in MeOH (40 ml), was added NaOH 2N (7.55 ml, 15.10 mmol). The reaction mixture was stirred for 30 minutes at room temperature and the pH was adjusted to 7 with 3.5 ml of HCl 4N. The solvent was removed under reduced pressure and to the residue was added DCM. The phases were separated and the aqueous phase washed with DCM. The organic phases were combined and dried over magnesium sulfate, filtered, and evaporated under reduced pressure. The residue obtained was purified by column chromatography eluting with a mixture of DCM and MeOH (95/05; v/v) to give 0.88 g (66%) of (S)-4-bromo-7-fluoro-5-(4-((1-(3-fluoropropyl)pyrrolidin-3-yl)oxy)phenyl)-2,3-dihydrobenzo[b]oxepin-8-ol (Ig11) as gray solid. LC/MS (m/z, MH$^+$): 480

Intermediate (Ia7). 7-chloro-8-hydroxy-3,4-dihydrobenzo[b]oxepin-5(2H)-one

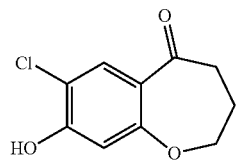

Step 1. 7-Chloro-8-fluoro-3,4-dihydrobenzo[b]oxepin-5(2H)-one

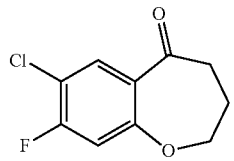 [SMILES: O=C1CCCOc2cc(F)c(Cl)cc21]

To a solution of 3-fluoro-4-chlorophenol (7 g, 45.86 mmol) in DMF (60 ml), was added potassium carbonate (6.97 g, 50.44 mmol). After 10 minutes of stirring at room temperature, methyl-4-bromobutyrate (9.61 g, 50.44 mmol) was added. The white suspension was heated at 50° C. for two hours. After cooling to room temperature, MeOH (50 ml), water (50 ml) and sodium hydroxide 32% (30 ml) were added. The reaction mixture was heated at 80° C. for 30 minutes. After cooling to room temperature, ice (100 g) was added, then HCl 5N was added to pH 3. The solid was filtered, and dried by heating under reduced pressure over $P_2O_5$. To the obtained yellow powder, polyphosphoric acid (PPA, 50 g) was added, then the mixture was heated at 110° C. for two hours. Ice (200 g) was slowly added and the precipitate was filtered, and dried under reduced pressure over $P_2O_5$. The residue was purified by flash chromatography eluting with a mixture of DCM and hexane (80/20; v/v) to give 5.1 g (45%) of 7-chloro-8-fluoro-3,4-dihydrobenzo[b]oxepin-5(2H)-one. LC/MS (m/z, MH$^+$): 215

Step 2. 7-chloro-8-hydroxy-3,4-dihydrobenzo[b]oxepin-5(2H)-one (Ia7)

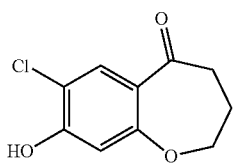 [SMILES: O=C1CCCOc2cc(O)c(Cl)cc21]

A mixture of but-2-yn-1-ol (1.59 g, 22.63 mmol) and sodium t-butylate (2.17 g, 22.63 mmol) in DMSO (25 ml) was stirred for two minutes. Then, 7-chloro-8-fluoro-3,4-dihydrobenzo[b]oxepin-5(2H)-one (2.43 g, 11.31 mmol) was added and the reaction mixture was heated at 125° C. for 40 seconds. After cooling to room temperature, water (50 ml) and EtOAc (100 ml) were added. The organic phase was washed with brine, dried over magnesium sulfate, and concentrated under reduced pressure. The residue was purified by flash chromatography eluting with a gradient of heptane in EtOAc (100/0 to 60/40; v/v) to give 1.32 g (55%) of 7-chloro-8-hydroxy-3,4-dihydrobenzo[b]oxepin-5(2H)-one (Ia7). LC/MS (m/z, MH$^+$): 213

Intermediate (Ia8). 7-chloro-5-oxo-2,3,4,5-tetrahydrobenzo[b]oxepin-8-yl pivalate To a solution of 7-chloro-8-hydroxy-3,4-dihydrobenzo[b]oxepin-5(2H)-one (Ia7) (1.68 g, 7.90 mmol) in acetone (60 ml) was added potassium carbonate (1.2154 g, 8.79 mmol). After 10 mn of stirring, pivaloyl chloride (1.26 ml, 10.20 mmol) was added. The suspension was stirred for 1.5 hour at room temperature. The solids were filtered off and then washed with acetone (10 ml). The filtrate was concentrated under reduced pressure, and partitioned between EtOAc (50 ml) and water (20 ml). The organic phase was dried over magnesium sulfate, filtered, and concentrated under reduced pressure. The residue was purified by flash chromatography eluting with a gradient of heptane in EtOAc (100/0 to 85/15; v/v) to give 2.33 g (99%) of 7-chloro-5-oxo-2,3,4,5-tetrahydrobenzo[b]oxepin-8-yl pivalate (Ia8) as an orange oil. LC/MS (m/z, MH$^+$): 297

Intermediate (Ib7). 7-chloro-5-(((trifluoromethyl)sulfonyl)oxy)-2,3-dihydrobenzo[b]oxepin-8-yl pivalate

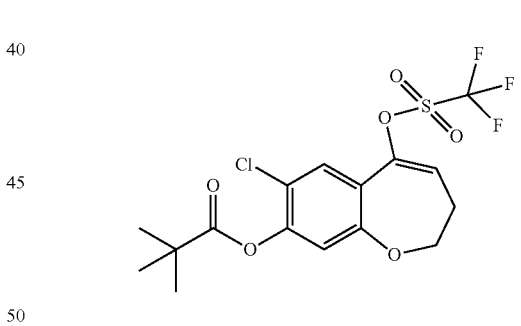

To a solution of 7-chloro-5-oxo-2,3,4,5-tetrahydrobenzo[b]oxepin-8-yl pivalate (Ia8) (2.33 g, 7.85 mmol) in DCM (75 ml) was added under argon pyridine (1 ml, 11.87 mmol) and trifluoromethanesulfonic anhydride (2.67 ml, 15.70 mmol) dropwise. The reaction mixture was stirred at room temperature for 18 hours and ice (100 g) was added. The phases were separated, the aqueous phase washed with DCM and the gathered organic phases dried over magnesium sulfate, filtered, and evaporated under reduced pressure. The residue was purified by flash chromatography eluting with a gradient of heptane in DCM (100/0 to 70/30; v/v) to give 2.05 g (61%) of 7-chloro-5-(((trifluoromethyl)sulfonyl)oxy)-2,3-dihydrobenzo[b]oxepin-8-yl pivalate (Ib7) as an orange oil. LC/MS (m/z, MH$^+$): 429

Intermediate (If6). (S)-7-chloro-5-(4-((1-(3-fluoropropyl)pyrrolidin-3-yl)oxy)phenyl)-2,3-dihydrobenzo[b]oxepin-8-yl pivalate

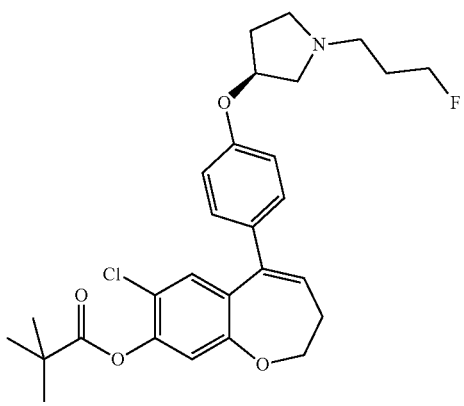 [SMILES: CC(C)(C)C(=O)Oc1cc2c(cc1Cl)C(c1ccc(O[C@H]3CCN(CCCF)C3)cc1)=CCCO2]

To a solution of 7-chloro-5-(((trifluoromethyl)sulfonyl)oxy)-2,3-dihydrobenzo[b]oxepin-8-yl pivalate (Ib7) (2.01 g, 4.69 mmol), (S)-1-(3-fluoropropyl)-3-(4-(4,4,5,5-tetramethyl-1,3,2-dioxaborolan-2-yl)phenoxy)pyrrolidine (1) (1.80 g, 5.16 mmol) in dioxane (75 ml) and water (25 ml), were added Cs$_2$CO$_3$ (3.06 g, 9.37 mmol) and [1,1'-bis(diphenylphosphino)ferrocene]dichloropalladium(II), complex with DCM (229.68 mg, 0.28 mmol). The reaction mixture was stirred for 2 hours at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a mixture of DCM and MeOH (95/05; v/v) to give 2.4 g (100%) of (S)-7-chloro-5-(4-((1-(3-fluoropropyl)pyrrolidin-3-yl)oxy)phenyl)-2,3-dihydrobenzo[b]oxepin-8-yl pivalate (If6). LC/MS (m/z, MH$^+$): 502

Intermediate (Ig12). (S)-4-bromo-7-chloro-5-(4-((1-(3-fluoropropyl)pyrrolidin-3-yl)oxy)phenyl)-2,3-dihydrobenzo[b]oxepin-8-yl pivalate

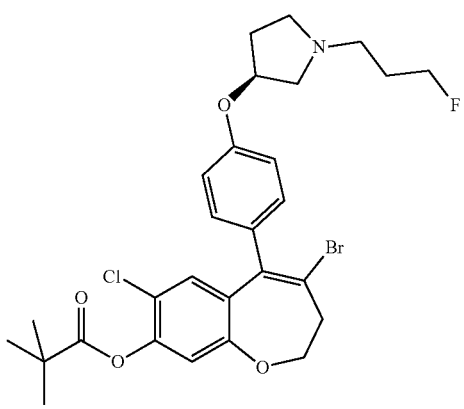 [SMILES: CC(C)(C)C(=O)Oc1cc2c(cc1Cl)C(c1ccc(O[C@H]3CCN(CCCF)C3)cc1)=C(Br)CCO2]

To a solution of (S)-7-chloro-5-(4-((1-(3-fluoropropyl)pyrrolidin-3-yl)oxy)phenyl)-2,3-dihydrobenzo[b]oxepin-8-yl pivalate (If6) (2.35 g, 4.68 mmol) in THF (100 ml), was added pyridinium tribromide (1.73 g, 4.87 mmol). The reaction mixture was stirred for 1.5 hour at room temperature. Water (50 ml) and EtOAc (100 ml) were added. The pH was adjusted to 7 with a concentrated solution of NaHCO$_3$. The aqueous phase was washed with EtOAc and the gathered organic phases dried over magnesium sulfate and filtered. The organic phases were evaporated under reduced pressure. The residue was purified by column chromatography eluting with a mixture of DCM and MeOH (95/05; v/v) to give 1.6 g (59%) of (S)-4-bromo-7-chloro-5-(4-((1-(3-fluoropropyl)pyrrolidin-3-yl)oxy)phenyl)-2,3-dihydrobenzo[b]oxepin-8-yl pivalate (Ig12). LC/MS (m/z, MH$^+$): 580

Intermediate (Ig13). (S)-4-bromo-7-chloro-5-(4-((1-(3-fluoropropyl)pyrrolidin-3-yl)oxy)phenyl)-2-dihydrobenzo[b]oxepin-8-ol

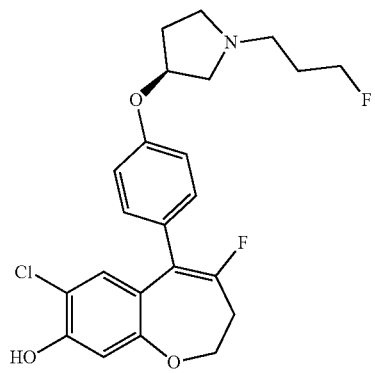

To a solution of (S)-4-bromo-7-chloro-5-(4-((1-(3-fluoropropyl)pyrrolidin-3-yl)oxy)phenyl)-2,3-dihydrobenzo[b]oxepin-8-yl pivalate (Ig12) (1.59 g, 2.74 mmol) in MeOH (170 ml), was added NaOH 2N (29.4 ml, 58.80 mmol). The reaction mixture was stirred for 30 minutes at room temperature and the pH was adjusted to 7 with 15 ml of HCl 4N. The solvent was removed under reduced pressure and the residue taken up into DCM. The phases were separated and the aqueous phase washed with DCM. The organic phases were combined and dried over magnesium sulfate, filtered, and evaporated under reduced pressure. The residue was purified by column chromatography eluting with a mixture of DCM in MeOH: (95/05; v/v) to give 1.17 g (86%) of (S)-4-bromo-7-chloro-5-(4-((1-(3-fluoropropyl)pyrrolidin-3-yl)oxy)phenyl)-2,3-dihydrobenzo[b]oxepin-8-ol (Ig13) as beige solid. LC/MS (m/z, MH$^+$): 496

Intermediate (Ia9). 8-hydroxy-7-methyl-3,4-dihydrobenzo[b]oxepin-5(2H)-one

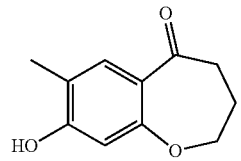

Step 1. 8-fluoro-7-methyl-3,4-dihydrobenzo[b]oxepin-5(2H)-one

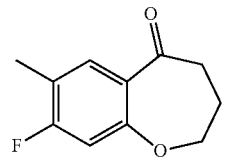

To a solution of 3-fluoro-4-methylphenol (5 g, 39.64 mmol) in DMF (50 ml), was added potassium carbonate (6.03 g, 43.61 mmol). After 10 minutes of stirring at room temperature, methyl-4-bromobutyrate (8.31 g, 43.61 mmol) was added. The white suspension was heated at 50° C. for 24 hours. After cooling to room temperature, MeOH (75 ml), water (50 ml) and sodium hydroxide 32% (25 ml) were added. The reaction mixture was heated at 90° C. for 1 hour. After cooling to room temperature, ice (400 g) was added, then HCl 5N was added to pH 3. The solid was filtered, washed with water (3×50 ml) and dried by heating under reduced pressure over $P_2O_5$. To the obtained yellow powder, polyphosphoric acid (PPA, 130 g) was added, then the mixture was heated at 80° C. for 1 hour. Ice was slowly added and the precipitate was filtered, and dried under reduced pressure over $P_2O_5$ to give 5.86 g (77%) of 8-fluoro-7-methyl-3,4-dihydrobenzo[b]oxepin-5(2H)-one as a yellow solid. LC/MS (m/z, MH$^+$): 195

Step 2. 8-hydroxy-7-methyl-3,4-dihydrobenzo[b]oxepin-5(2H)-one (Ia9)

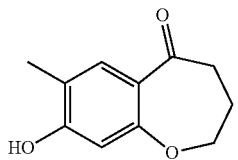

A mixture of but-2-yn-1-ol (1.57 ml, 20.60 mmol) and sodium t-butylate (1.98 g, 20.60 mmol) in DMSO (17 ml) was stirred for two minutes. Then, 8-fluoro-7-methyl-3,4-dihydrobenzo[b]oxepin-5(2H)-one (2 g, 10.30 mmol) was added and the reaction mixture was heated at 125° C. for 2 minutes. After cooling to room temperature, water (150 ml) and DCM (100 ml) were added. The pH was adjusted to 3 by adding HCl 1N. The organic phase was washed with brine, dried over magnesium sulfate, and concentrated under reduced pressure. The residue was purified by flash chromatography eluting with a gradient of heptane in EtOAc (100/0 to 60/40; v/v) to give 0.74 g (37%) of 8-hydroxy-7-methyl-3,4-dihydrobenzo[b]oxepin-5(2H)-one (Ia9). LC/MS (m/z, MH$^+$): 193

Intermediate (Ia10). 7-methyl-5-oxo-2,3,4,5-tetrahydrobenzo[b]oxepin-8-yl pivalate

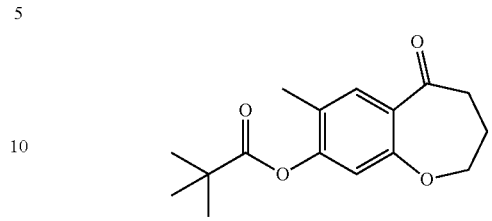

To a solution of 8-hydroxy-7-methyl-3,4-dihydrobenzo[b]oxepin-5(2H)-one (Ia9) (0.74 g, 3.82 mmol) in acetone (30 ml) was added potassium carbonate (581 mg, 4.21 mmol). After 10 mn of stirring, pivaloyl chloride (0.52 ml, 4.21 mmol) was added. The suspension was stirred for 1 hour at room temperature. The solids were filtered off and then washed with acetone (10 ml). The filtrate was concentrated under reduced pressure. To the residue obtained, addition of EtOAc (50 ml) and water. The organic phase was dried over magnesium sulfate, filtered off and concentrated under reduced pressure to give 1 g (100%) of 7-methyl-5-oxo-2,3,4,5-tetrahydrobenzo[b]oxepin-8-yl pivalate (Ia10) as an orange oil. LC/MS (m/z, MH$^+$): 277

Intermediate (Ib8). 7-methyl-5-(((trifluoromethyl)sulfonyl)oxy)-2,3-dihydrobenzo[b]oxepin-8-yl pivalate

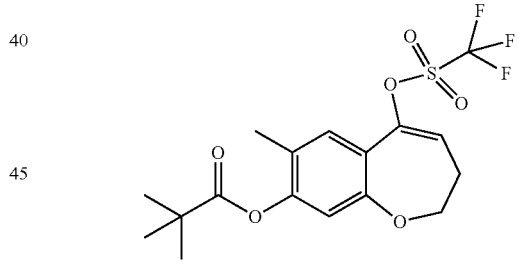

To a solution of 7-methyl-5-oxo-2,3,4,5-tetrahydrobenzo[b]oxepin-8-yl pivalate (Ia10) (1.06 g, 3.84 mmol) in DCM (80 ml) was added dropwise under argon pyridine (0.49 ml, 5.75 mmol) and trifluoromethanesulfonic anhydride (1.30 ml, 7.67 mmol). The reaction mixture was stirred at room temperature for 16 hours and ice (100 g) was added. The phases were separated, the aqueous phase washed with DCM and the gathered organic phases dried over magnesium sulfate, filtered, and evaporated under pressure. The residue was purified by flash chromatography eluting with a gradient of heptane in EtOAc (100/0 to 70/30; v/v) to give 1.34 g (86%) of 7-methyl-5-(((trifluoromethyl)sulfonyl)oxy)-2,3-dihydrobenzo[b]oxepin-8-yl pivalate (Ib8) as an yellow oil. LC/MS (m/z, MH$^+$): 409

Intermediate (If7). (S)-5-(4-((1-(3-fluoropropyl)pyrrolidin-3-yl)oxy)phenyl)-7-methyl-2,3-dihydrobenzo[b]oxepin-8-yl pivalate

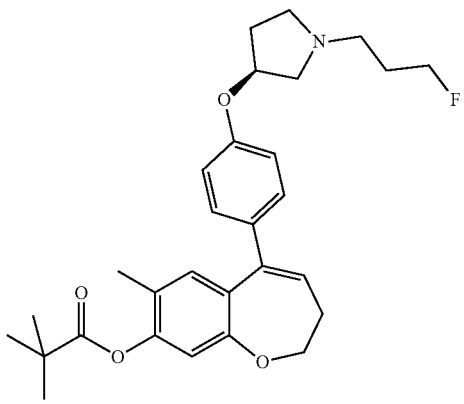 [SMILES: Cc1cc2c(cc1OC(=O)C(C)(C)C)OCCC=C2c1ccc(O[C@H]2CCN(CCCF)C2)cc1]

To a solution of 7-methyl-5-(((trifluoromethyl)sulfonyl)oxy)-2,3-dihydrobenzo[b]oxepin-8-yl pivalate (Ib8) (1.34 g, 3.28 mmol), (S)-1-(3-fluoropropyl)-3-(4-(4,4,5,5-tetramethyl-1,3,2-dioxaborolan-2-yl)phenoxy)pyrrolidine (1) (1.15 g, 3.28 mmol) in dioxane (20 ml) and water (4 ml), were added $Cs_2CO_3$ (2.25 g, 6.89 mmol) and [1,1'-bis(diphenylphosphino)ferrocene]dichloropalladium(II), complex with DCM (268 mg, 0.33 mmol). The reaction mixture was stirred for 5.5 hours at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a mixture of DCM and MeOH (95:05; v/v) to give 1.58 g (100%) of (S)-5-(4-((1-(3-fluoropropyl)pyrrolidin-3-yl)oxy)phenyl)-7-methyl-2,3-dihydrobenzo[b]oxepin-8-yl pivalate (If7). LC/MS (m/z, $MH^+$): 482

Intermediate (Ig14). (S)-4-bromo-5-(4-((1-(3-fluoropropyl)pyrrolidin-3-yl)oxy)phenyl)-7-methyl-2,3-dihydrobenzo[b]oxepin-8-yl pivalate

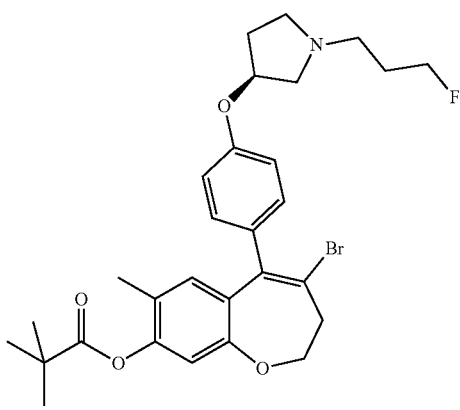

To a solution of (S)-5-(4-((1-(3-fluoropropyl)pyrrolidin-3-yl)oxy)phenyl)-7-methyl-2,3-dihydrobenzo[b]oxepin-8-yl pivalate (If7) (1.58 g, 3.28 mmol) in THF (60 ml), was added pyridinium tribromide (1.40 g, 3.94 mmol). The reaction mixture was stirred for 2 hours at room temperature. Water (100 ml) and EtOAc were added. The pH was adjusted to 7 with a concentrated solution of $NaHCO_3$. The aqueous phase was washed with EtOAc and the gathered organic phases dried over magnesium sulfate and filtered. The organic phases were evaporated under reduced pressure to give 1.84 g (100%) of (S)-4-bromo-5-(4-((1-(3-fluoropropyl)pyrrolidin-3-yl)oxy)phenyl)-7-methyl-2,3-dihydrobenzo[b]oxepin-8-yl pivalate (Ig14) which was used as such in the following step. LC/MS (m/z, $MH^+$): 560

Intermediate (Ig15). (S)-4-bromo-5-(4-((1-(3-fluoropropyl)pyrrolidin-3-yl)oxy)phenyl)-7-methyl-2,3-dihydrobenzo[b]oxepin-8-ol

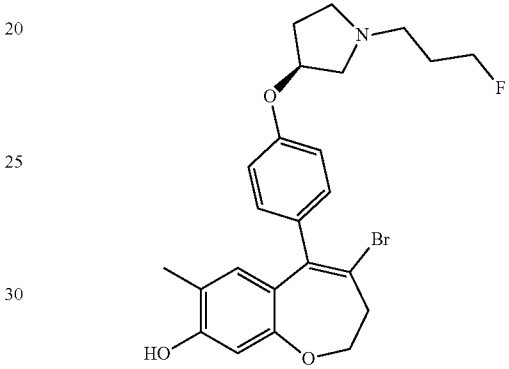

To a solution of (S)-4-bromo-5-(4-((1-(3-fluoropropyl)pyrrolidin-3-yl)oxy)phenyl)-7-methyl-2,3-dihydrobenzo[b]oxepin-8-yl pivalate (Ig14) (1.84 g, 3.28 mmol) in MeOH (30 ml), was added NaOH 5N (2.63 ml, 13.13 mmol). The reaction mixture was stirred for 2 hours at room temperature and the pH was adjusted to 7 with 4.5 ml of HCl 5N. The solvent was removed under reduced pressure and the residue taken up into DCM. The phases were separated and the aqueous phase washed with DCM. The organic phases were combined and dried over magnesium sulfate, filtered, and evaporated under reduced pressure. The residue was purified by column chromatography eluting with a mixture of DCM and MeOH (95:05; v/v) to give 1.19 g (71%) of (S)-4-bromo-5-(4-((1-(3-fluoropropyl)pyrrolidin-3-yl)oxy)phenyl)-7-methyl-2,3-dihydrobenzo[b]oxepin-8-ol (Ig15) as beige meringue. LC/MS (m/z, $MH^+$): 476

Intermediate (Ia11). 9-fluoro-8-hydroxy-3,4-dihydrobenzo[b]oxepin-5(2H)-one

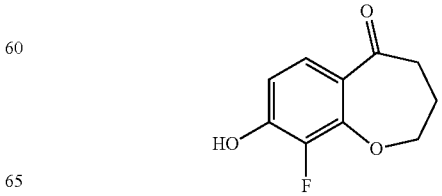

Step 1. 8,9-difluoro-3,4-dihydrobenzo[b]oxepin-5(2H)-one

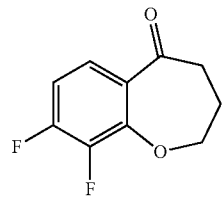 [SMILES: O=C1CCCOc2c1ccc(F)c2F]

To a solution of 2,3-difluorophenol (5 g, 37.67 mmol) in DMF (60 ml) was added potassium carbonate (5.73 g, 41.43 mmol). After 10 minutes of stirring at room temperature, methyl-4-bromobutyrate (7.90 g, 41.43 mmol) was added. The white suspension was heated at 50° C. for 24 hours. After cooling to room temperature, MeOH (50 ml), water (50 ml) and sodium hydroxide 32% (30 ml) were added. The reaction mixture was heated at 80° C. for 1 hour. After cooling to room temperature, ice (100 g) and EtOAc (300 ml) were added, then HCl 5N was added to pH 3. The organic phase was washed with brine, dried over magnesium sulfate, and concentrated under reduced pressure. To the obtained oil, polyphosphoric acid (PPA, 100 g) was added, then the mixture was heated at 80° C. for 1 hour. Ice (300 g) was slowly added and the precipitate was filtered, and dried under reduced pressure. The residue was purified by flash chromatography eluting with a gradient of heptane in EtOAc (100/0 to 70/30; v/v) to give 5.1 g (68%) of 8,9-difluoro-3,4-dihydrobenzo[b]oxepin-5(2H)-one as beige solid. LC/MS (m/z, MH$^+$): 199

Step 2. 9-fluoro-8-hydroxy-3,4-dihydrobenzo[b]oxepin-5(2H)-one (Ia11)

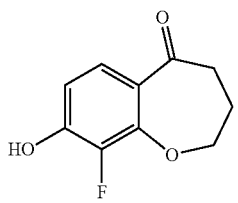 [SMILES: O=C1CCCOc2c1ccc(O)c2F]

A mixture of but-2-yn-1-ol (2.53 g, 35.32 mmol) and sodium t-butylate (3.39 g, 35.32 mmol) in DMSO (35 ml) was stirred for two minutes. Then, 8,9-difluoro-3,4-dihydrobenzo[b]oxepin-5(2H)-one (3.5 g, 17.66 mmol) was added and the reaction mixture was heated at 125° C. for 5 minutes. After cooling to room temperature, water (150 ml) and EtOAc (100 ml) were added. The pH was adjusted to 3 by adding HCl 1N. The organic phase was washed with brine, dried over magnesium sulfate, and concentrated under reduced pressure. The residue was purified by flash chromatography eluting with a gradient of heptane in EtOAc (100:0 to 50:50; v/v) to give 0.99 g (29%) of 9-fluoro-8-hydroxy-3,4-dihydrobenzo[b]oxepin-5(2H)-one (Ia11) as a beige solid. LC/MS (m/z, MH$^+$): 197

Intermediate (Ia12). 9-fluoro-5-oxo-2,3,4,5-tetrahydrobenzo[b]oxepin-8-yl pivalate

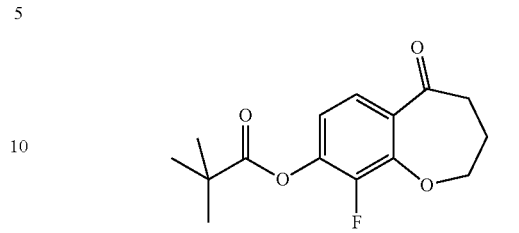

To a solution of 9-fluoro-8-hydroxy-3,4-dihydrobenzo[b]oxepin-5(2H)-one (Ia11) (1.2 g, 6.12 mmol) in acetone (50 ml) was added potassium carbonate (845 mg, 6.12 mmol). After 10 mn of stirring, pivaloyl chloride (0.75 ml, 6.12 mmol) was added. The suspension was stirred for 1 hour at room temperature. The solids were filtered off and then washed with acetone (10 ml). The filtrate was concentrated under reduced pressure. To the residue obtained, addition of EtOAc (50 ml) and water (20 ml). The organic phase was dried over magnesium sulfate, filtered off and concentrated under reduced pressure. The residue was purified by flash chromatography eluting with a gradient of heptane in EtOAc (100/0 to 85/15; v/v) to give 1.69 g (99%) of 9-fluoro-5-oxo-2,3,4,5-tetrahydrobenzo[b]oxepin-8-yl pivalate (Ia12) as a yellow oil. LC/MS (m/z, MH$^+$): 281

Intermediate (Ib9). 9-fluoro-5-(((trifluoromethyl)sulfonyl)oxy)-2,3-dihydrobenzo[b]oxepin-8-yl pivalate

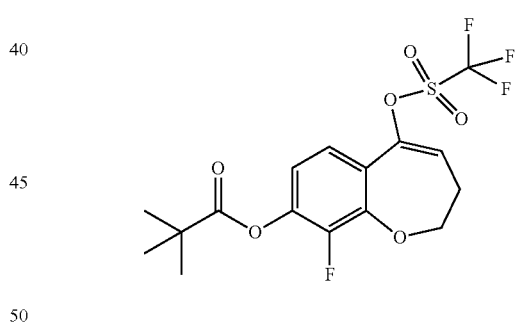

To a solution of 9-fluoro-5-oxo-2,3,4,5-tetrahydrobenzo[b]oxepin-8-yl pivalate (Ia12) (1.68 g, 5.99 mmol) in DCM (40 ml) was added under argon pyridine (1.01 ml, 11.99 mmol) and trifluoromethanesulfonic anhydride (2.04 ml, 11.99 mmol) dropwise. The reaction mixture was stirred at room temperature for 16 hours, then trifluoromethanesulfonic anhydride (1 ml, 5.99 mmol) was added. After 4 hours of stirring at room temperature, ice (100 g) was added. The phases were separated, the aqueous phase washed with DCM and the gathered organic phases dried over magnesium sulfate, filtered, and evaporated under pressure. The residue was purified by flash chromatography eluting with a gradient of heptane in DCM (100/0 to 70/30; v/v) to give 1.84 g (74%) of 9-fluoro-5-(((trifluoromethyl)sulfonyl)oxy)-2,3-dihydrobenzo[b]oxepin-8-yl pivalate (Ib9) as a colorless oil. LC/MS (m/z, MH$^+$): 413

Intermediate (If8). (S)-9-fluoro-5-(4-((1-(3-fluoropropyl)pyrrolidin-3-yl)oxy)phenyl)-2,3-dihydrobenzo[b]oxepin-8-yl pivalate

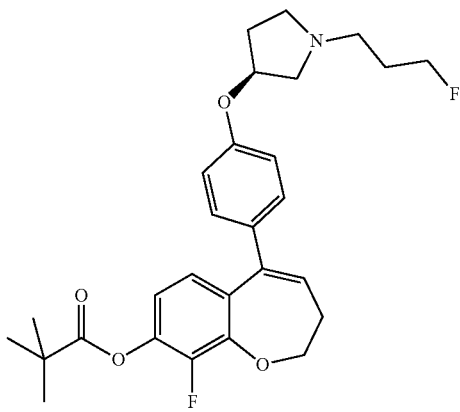 [SMILES: CC(C)(C)C(=O)Oc1ccc2c(c1F)OCCC=C2c1ccc(O[C@H]2CCN(CCCF)C2)cc1]

To a solution of 9-fluoro-5-(((trifluoromethyl)sulfonyl)oxy)-2,3-dihydrobenzo[b]oxepin-8-yl pivalate (Ib9) (1.84 g, 4.46 mmol), (S)-1-(3-fluoropropyl)-3-(4-(4,4,5,5-tetramethyl-1,3,2-dioxaborolan-2-yl)phenoxy)pyrrolidine (1) (1.56 g, 4.46 mmol) in dioxane (80 ml) and water (20 ml), were added Cs$_2$CO$_3$ (3.06 g, 9.37 mmol) and [1,1'-bis(diphenylphosphino)ferrocene]dichloropalladium(II), complex with DCM (219 mg, 0.27 mmol). The reaction mixture was stirred for 2 hours at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a mixture of DCM and MeOH (95/05; v/v) to give 1.9 g (88%) of (S)-9-fluoro-5-(4-((1-(3-fluoropropyl)pyrrolidin-3-yl)oxy)phenyl)-2,3-dihydrobenzo[b]oxepin-8-yl pivalate (If8). LC/MS (m/z, MH$^+$): 486

Intermediate (Ig16). (S)-4-bromo-9-fluoro-5-(4-((1-(3-fluoropropyl)pyrrolidin-3-yl)oxy)phenyl)-2,3-dihydrobenzo[b]oxepin-8-ol

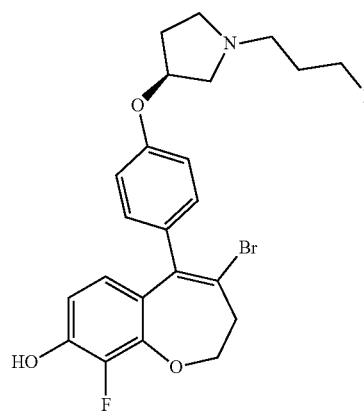

To a solution of (S)-9-fluoro-5-(4-((1-(3-fluoropropyl)pyrrolidin-3-yl)oxy)phenyl)-2,3-dihydrobenzo[b]oxepin-8-yl pivalate (If8) (1.9 g, 3.91 mmol) in THF (100 ml), was added pyridinium tribromide (1.38 g, 4.30 mmol). The reaction mixture was stirred for 1.5 hours at room temperature. MeOH (50 ml) then NaOH 5N (5 ml) were added. After 10 minutes of stirring at room temperature, the pH was adjusted to 6-7 with HCl 5N. The solvent was removed under reduced pressure and the residue taken up into DCM. The phases were separated and the aqueous phase washed with DCM. The organic phases were combined and dried over magnesium sulfate, filtered, and evaporated under reduced pressure. The residue was purified by column chromatography eluting with a mixture of DCM and MeOH (95/05; v/v) to give 1.6 g (85%) of (S)-4-bromo-9-fluoro-5-(4-((1-(3-fluoropropyl)pyrrolidin-3-yl)oxy)phenyl)-2,3-dihydrobenzo[b]oxepin-8-ol (Ig16) as beige meringue. LC/MS (m/z, MH$^+$): 480

Intermediate (Ia13). 9-chloro-8-hydroxy-3,4-dihydrobenzo[b]oxepin-5(2H)-one

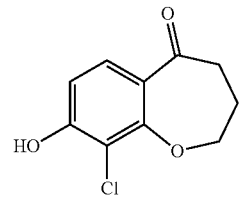 [SMILES: O=C1CCCOc2c1ccc(O)c2Cl]

Step 1. 9-chloro-8-fluoro-3,4-dihydrobenzo[b]oxepin-5(2H)-one

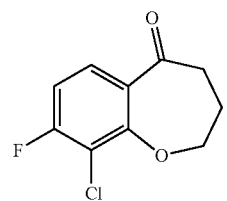 [SMILES: O=C1CCCOc2c1ccc(F)c2Cl]

To a solution of 2-chloro-3-fluorophenol (5 g, 34.12 mmol) in DMF (60 ml) was added potassium carbonate (5.19 g, 37.53 mmol). After 10 minutes of stirring at room temperature, methyl-4-bromobutyrate (7.15 g, 37.53 mmol) was added. The white suspension was heated at 50° C. for 24 hours. After cooling to room temperature, MeOH (50 ml), water (50 ml) and sodium hydroxide 32% (30 ml) were added. The reaction mixture was heated at 80° C. for 30 minutes. After cooling to room temperature, ice (100 g) was added, then HCl 5N was added to pH 3. The solid was filtered, washed with water (3×50 ml) and dried by heating under reduced pressure over P$_2$O$_5$. To the obtained yellow powder, polyphosphoric acid (PPA, 100 g) was added, then the mixture was heated at 90° C. for 15 minutes. Ice (300 g) was slowly added and the precipitate was filtered, and dried under reduced pressure over P$_2$O$_5$ to give 6.44 g (88%) of 9-chloro-8-fluoro-3,4-dihydrobenzo[b]oxepin-5(2H)-one as a white solid. LC/MS (m/z, MH$^+$): 215

Step 2. 9-chloro-8-hydroxy-3,4-dihydrobenzo[b]oxepin-5(2H)-one (Ia13)

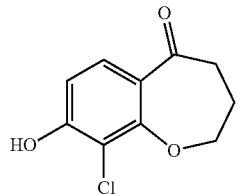 [SMILES: O=C1CCCOc2c1ccc(O)c2Cl]

A mixture of but-2-yn-1-ol (2.67 g, 37.28 mmol) and sodium t-butylate (3.58 g, 37.28 mmol) in DMSO (35 ml) was stirred for two minutes. Then, 9-chloro-8-fluoro-3,4-dihydrobenzo[b]oxepin-5(2H)-one (4 g, 18.64 mmol) was added and the reaction mixture was heated at 125° C. for 5 minutes. After cooling to room temperature, water (150 ml) and DCM (300 ml) were added. The pH was adjusted to 3 by adding HCl 1N. The organic phase was washed with brine, dried over magnesium sulfate, and concentrated under reduced pressure. The residue was purified by flash chromatography eluting with a gradient of heptane in EtOAc (100/0 to 60/40; v/v) to give 2.12 g (54%) of 9-chloro-8-hydroxy-3,4-dihydrobenzo[b]oxepin-5(2H)-one (Ia13) as a beige solid. LC/MS (m/z, MH$^+$): 213

Intermediate (Ia14). 9-chloro-5-oxo-2,3,4,5-tetrahydrobenzo[b]oxepin-8-yl pivalate

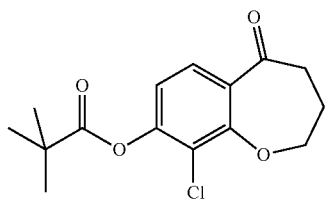 [SMILES: CC(C)(C)C(=O)Oc1ccc2c(c1Cl)OCCCC2=O]

To a solution of 9-chloro-8-hydroxy-3,4-dihydrobenzo[b]oxepin-5(2H)-one (Ia13) (2.05 g, 9.64 mmol) in acetone (100 ml) was added potassium carbonate (1.40 g, 10.12 mmol). After 10 mn of stirring, pivaloyl chloride (1.25 ml, 10.12 mmol) was added. The suspension was stirred for 18 hours at room temperature. The solids were filtered off and then washed with acetone (10 ml). The filtrate was concentrated under reduced pressure. To the residue obtained, addition of EtOAc (50 ml) and water. The organic phase was dried over magnesium sulfate, filtered off and concentrated under reduced pressure to give 2.86 g (100%) of 9-chloro-5-oxo-2,3,4,5-tetrahydrobenzo[b]oxepin-8-yl pivalate (Ia14) as an orange solid. LC/MS (m/z, MH$^+$): 297

Intermediate (Ib10). 9-chloro-5-(((trifluoromethyl)sulfonyl)oxy)-2,3-dihydrobenzo[b]oxepin-8-yl pivalate

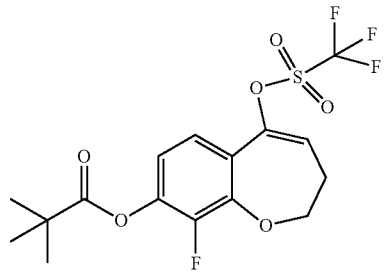 [SMILES: CC(C)(C)C(=O)Oc1ccc2c(c1F)OCCC=C2OS(=O)(=O)C(F)(F)F]

To a solution of 9-chloro-5-oxo-2,3,4,5-tetrahydrobenzo[b]oxepin-8-yl pivalate (Ia14) (2.86 g, 9.64 mmol) in DCM (80 ml) was added under argon pyridine (1.22 ml, 14.46 mmol) and trifluoromethanesulfonic anhydride (3.28 ml, 19.28 mmol) dropwise. The reaction mixture was stirred at room temperature for 16 hours. Ice (100 g) and DCM (200 ml) were added. The phases were separated, the aqueous phase washed with DCM and the gathered organic phases dried over magnesium sulfate, filtered, and evaporated under pressure. The residue was purified by flash chromatography eluting with a gradient of heptane in DCM (100/0 to 50/50; v/v) to give 2.9 g (70%) of 9-chloro-5-(((trifluoromethyl)sulfonyl)oxy)-2,3-dihydrobenzo[b]oxepin-8-yl pivalate (Ib10) as a colorless oil. LC/MS (m/z, MH$^+$): 429

Intermediate (If9). (S)-9-chloro-5-(4-((1-(3-fluoropropyl)pyrrolidin-3-yl)oxy)phenyl)-2,3-dihydrobenzo[b]oxepin-8-yl pivalate

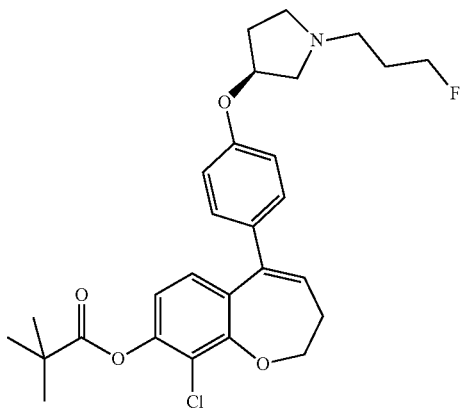

To a solution of 9-chloro-5-(((trifluoromethyl)sulfonyl)oxy)-2,3-dihydrobenzo[b]oxepin-8-yl pivalate (Ib10) (2.84 g, 6.62 mmol), (S)-1-(3-fluoropropyl)-3-(4-(4,4,5,5-tetramethyl-1,3,2-dioxaborolan-2-yl)phenoxy)pyrrolidine (1) (2.31 g, 6.62 mmol) in dioxane (96 ml) and water (24 ml), were added Cs$_2$CO$_3$ (4.54 g, 13.91 mmol) and [1,1'-bis(diphenylphosphino)ferrocene]dichloropalladium(II), complex with DCM (325 mg, 0.40 mmol). The reaction mixture was stirred for 24 hours at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a mixture of DCM and MeOH (95/05; v/v) to give 2.8 g (84%) of (S)-9-chloro-5-(4-((1-(3-fluoropropyl)pyrrolidin-3-yl)oxy)phenyl)-2,3-dihydrobenzo[b]oxepin-8-yl pivalate (If9). LC/MS (m/z, MH+): 502

Intermediate (Ig17). (S)-4-bromo-9-chloro-5-(4-((1-(3-fluoropropyl)pyrrolidin-3-yl)oxy)phenyl)-2,3-dihydrobenzo[b]oxepin-8-ol

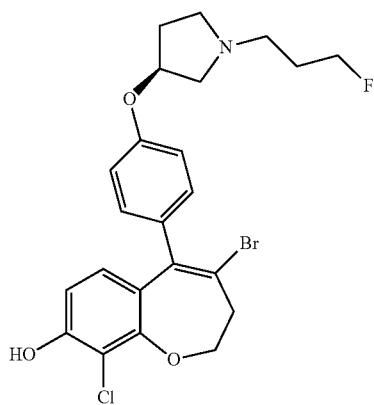 [SMILES: Oc1ccc2c(c1Cl)OCCC(Br)=C2c1ccc(O[C@H]2CCN(CCCF)C2)cc1]

To a solution of (S)-9-chloro-5-(4-((1-(3-fluoropropyl)pyrrolidin-3-yl)oxy)phenyl)-2,3-dihydrobenzo[b]oxepin-8-yl pivalate (If9) (2.8 g, 5.58 mmol) in THF (100 ml), was added pyridinium tribromide (2.14 g, 6.69 mmol). The reaction mixture was stirred for 1 hour at room temperature. MeOH (50 ml) then NaOH 5N (5 ml) were added. After 10 minutes of stirring at room temperature, the pH was adjusted to 6-7 with HCl 5N. The solvent was removed under reduced pressure and the residue taken up into DCM. The phases were separated and the aqueous phase washed with DCM. The organic phases were combined and dried over magnesium sulfate, filtered, and evaporated under reduced pressure. The residue was purified by column chromatography eluting with a mixture of DCM and MeOH (95/05; v/v) to give 1.6 g (58%) of (S)-4-bromo-9-chloro-5-(4-((1-(3-fluoropropyl)pyrrolidin-3-yl)oxy)phenyl)-2,3-dihydrobenzo[b]oxepin-8-ol (Ig17) as beige meringue. LC/MS (m/z, MH+): 496

Intermediate (Ia15). 8-hydroxy-9-methyl-3,4-dihydrobenzo[b]oxepin-5(2H)-one

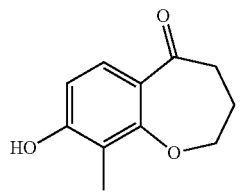

Step 1. 8-fluoro-9-methyl-3,4-dihydrobenzo[b]oxepin-5(2H)-one

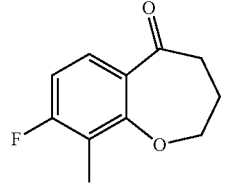

To a solution of 2-methyl-3-fluorophenol (5 g, 39.64 mmol) in DMF (60 ml), was added potassium carbonate (6.03 g, 43.61 mmol). After 10 minutes of stirring at room temperature, methyl-4-bromobutyrate (8.31 g, 43.61 mmol) was added. The white suspension was heated at 50° C. for 24 hours. After cooling to room temperature, MeOH (50 ml), water (50 ml) and sodium hydroxide 32% (30 ml) were added. The reaction mixture was heated at 80° C. for 30 minutes. After cooling to room temperature, ice (100 g) was added, then HCl 5N was added to pH 3. The solid was filtered, washed with water (3×50 ml) and dried by heating under reduced pressure over $P_2O_5$. To the obtained white powder, polyphosphoric acid (PPA, 100 g) was added, then the mixture was heated at 90° C. for 15 minutes. Ice (300 g) was slowly added and the precipitate was filtered, and dried under reduced pressure over $P_2O_5$ to give 6.64 g (86%) of 8-fluoro-9-methyl-3,4-dihydrobenzo[b]oxepin-5(2H)-one as a yellow solid. LC/MS (m/z, MH+): 195

Step 2. 8-hydroxy-9-methyl-3,4-dihydrobenzo[b]oxepin-5(2H)-one (Ia15)

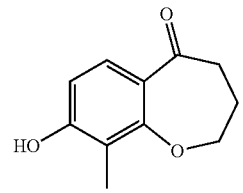

A mixture of but-2-yn-1-ol (1.47 g, 20.60 mmol) and sodium t-butylate (1.98 g, 20.60 mmol) in DMSO (17 ml) was stirred for two minutes. Then, 8-fluoro-9-methyl-3,4-dihydrobenzo[b]oxepin-5(2H)-one (2 g, 10.30 mmol) was added and the reaction mixture was heated at 125° C. for 2 minutes. After cooling to room temperature, water (70 ml) and DCM (150 ml) were added. The pH was adjusted to 3 by adding HCl 1N. The organic phase was washed with brine, dried over magnesium sulfate, and concentrated under reduced pressure. The residue was purified by flash chromatography eluting with a gradient of heptane in EtOAc (100/0 to 60/40; v/v) to give 1.22 g (62%) of 8-hydroxy-9-methyl-3,4-dihydrobenzo[b]oxepin-5(2H)-one (Ia15) as a yellow solid. LC/MS (m/z, MH+): 193

Intermediate (Ia16). 9-methyl-5-oxo-2,3,4,5-tetrahydrobenzo[b]oxepin-8-yl pivalate

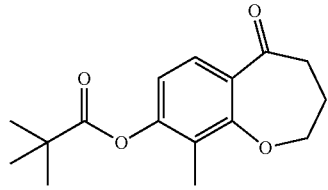 [SMILES: Cc1c(OC(=O)C(C)(C)C)ccc2c1OCCCC2=O]

To a solution of 8-hydroxy-9-methyl-3,4-dihydrobenzo[b]oxepin-5(2H)-one (Ia15) (2.42 g, 12.59 mmol) in acetone (120 ml) was added potassium carbonate (1.83 g, 13.22 mmol).

After 10 min of stirring, pivaloyl chloride (1.63 ml, 13.22 mmol) was added. The suspension was stirred for 24 hours at room temperature. The solids were filtered off and then washed with acetone (10 ml). The filtrate was concentrated under reduced pressure to give 3.15 g (91%) of 9-methyl-5-oxo-2,3,4,5-tetrahydrobenzo[b]oxepin-8-yl pivalate (Ia16) as a yellow oil. LC/MS (m/z, MH$^+$): 277

Intermediate (Ib11). 9-methyl-5-(((trifluoromethyl)sulfonyl)oxy)-2,3-dihydrobenzo[b]oxepin-8-yl pivalate

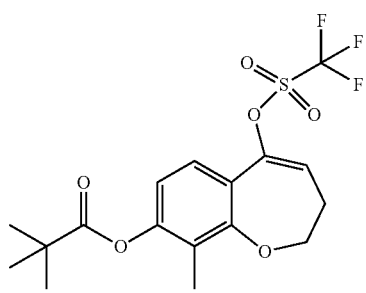 [SMILES: Cc1c(OC(=O)C(C)(C)C)ccc2c1OCCC=C2OS(=O)(=O)C(F)(F)F]

To a solution of 9-methyl-5-oxo-2,3,4,5-tetrahydrobenzo[b]oxepin-8-yl pivalate (Ia16) (2.86 g, 10.35 mmol) in DCM (80 ml) was added under argon pyridine (1.31 ml, 15.53 mmol) and trifluoromethanesulfonic anhydride (3.52 ml, 20.70 mmol) dropwise. The reaction mixture was stirred at room temperature for 3.5 hours. Ice (100 g) and DCM (200 ml) were added. The phases were separated, the aqueous phase washed with DCM and the gathered organic phases dried over magnesium sulfate, filtered, and evaporated under pressure. The residue was purified by flash chromatography eluting with a gradient of heptane in DCM (100/0 to 50/50; v/v) to give 3.4 g (80%) of 9-methyl-5-(((trifluoromethyl)sulfonyl)oxy)-2,3-dihydrobenzo[b]oxepin-8-yl pivalate (Ib11) as a yellow oil. LC/MS (m/z, MH$^+$): 409

Intermediate (If10). (S)-5-(4-((1-(3-fluoropropyl)pyrrolidin-3-yl)oxy)phenyl)-9-methyl-2,3-dihydrobenzo[b]oxepin-8-yl pivalate

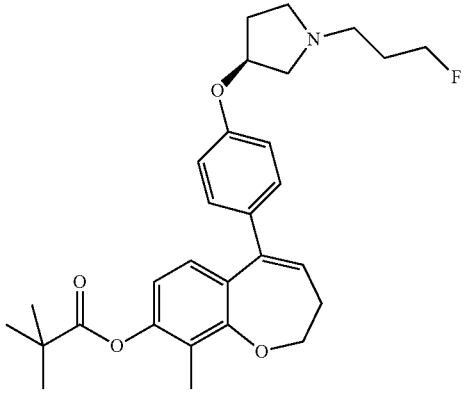 [SMILES: Cc1c(OC(=O)C(C)(C)C)ccc2c1OCCC=C2c1ccc(O[C@H]2CCN(CCCF)C2)cc1]

To a solution of 9-methyl-5-(((trifluoromethyl)sulfonyl)oxy)-2,3-dihydrobenzo[b]oxepin-8-yl pivalate (Ib11) (3.4 g, 8.33 mmol), (S)-1-(3-fluoropropyl)-3-(4-(4,4,5,5-tetramethyl-1,3,2-dioxaborolan-2-yl)phenoxy)pyrrolidine (1) (3.20 g, 9.16 mmol) in dioxane (80 ml) and water (20 ml), were added Cs$_2$CO$_3$ (5.43 g, 16.65 mmol) and [1,1'-bis(diphenylphosphino)ferrocene]dichloropalladium(II), complex with DCM (679.88 mg, 0.83 mmol). The reaction mixture was stirred for 24 hours at room temperature and partitioned between water and EtOAc. The aqueous phase was washed with EtOAc and the gathered organic phases dried over magnesium sulfate, filtered, and concentrated under reduced pressure. The residue was purified by column chromatography eluting with a mixture of DCM and MeOH (95/05; v/v) to give 2.34 g (58%) of (S)-5-(4-((1-(3-fluoropropyl)pyrrolidin-3-yl)oxy)phenyl)-9-methyl-2,3-dihydrobenzo[b]oxepin-8-yl pivalate (If10). LC/MS (m/z, MH$^+$): 482

Intermediate (Ig18). (S)-4-bromo-5-(4-((1-(3-fluoropropyl)pyrrolidin-3-yl)oxy)phenyl)-9-methyl-2,3-dihydrobenzo[b]oxepin-8-ol

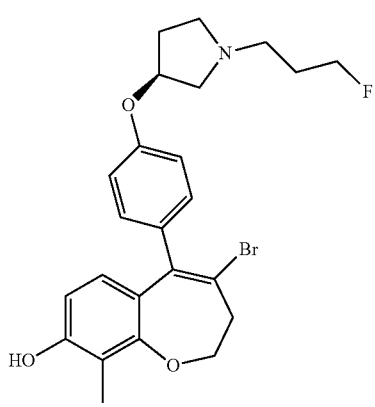 [SMILES: Cc1c(O)ccc2c1OCCC(Br)=C2c1ccc(O[C@H]2CCN(CCCF)C2)cc1]

To a solution of (S)-5-(4-((1-(3-fluoropropyl)pyrrolidin-3-yl)oxy)phenyl)-9-methyl-2,3-dihydrobenzo[b]oxepin-8-yl pivalate (If) (2.34 g, 4.86 mmol) in THF (100 ml), was added pyridinium tribromide (1.86 g, 5.83 mmol). The reaction mixture was stirred for 30 minutes at room temperature. MeOH (50 ml) then NaOH 5N (5 ml) were added. After 10 minutes of stirring at room temperature, the pH was adjusted to 6-7 with HCl 5N. The solvent was removed under reduced pressure and the residue taken up into DCM. The phases were separated and the aqueous phase washed with DCM. The organic phases were combined and dried over magnesium sulfate, filtered, and evaporated under reduced pressure. The residue was purified by column chromatography eluting with a mixture of DCM and MeOH (95/05; v/v) to give 1.73 g (75%) of (S)-4-bromo-5-(4-((1-(3-fluoropropyl)pyrrolidin-3-yl)oxy)phenyl)-9-methyl-2,3-dihydrobenzo[b]oxepin-8-ol (Ig18) as beige meringue. LC/MS (m/z, MH+): 476

Intermediate (Ia7. 8-Methoxy-3,4-dihydro-2H-benzo[b]thiepin-5-one

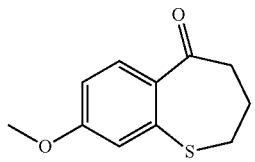

Step 1. 4-(3-Methoxy-phenylsulfanyl)-butyric acid sodium salt

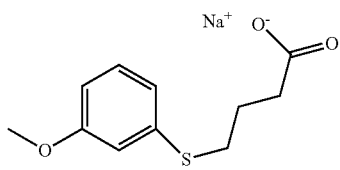

Sodium (1.97 g, 85.59 mmol) was added portionwise to ethanol (50 ml) under argon and stirred until complete dissolution. To this suspension was added 3-methoxybenzenethiol (8.85 ml, 71.33 mmol) followed by the butyrolactone (8.03 ml, 104.5 mmol). The reaction mixture was refluxed for 24 hours, cooled to room temperature, and evaporated to half volume. Diethyl ether (150 ml) was added and the solid filtered, washed with diethyl ether and dried on Buchner to give 17.7 g (100%) of 4-((3-methoxyphenyl)thio)butanoic acid sodium salt as a beige solid. LC/MS (m/z, MH+): 227

Step 2. 8-Methoxy-3,4-dihydro-2H-benzo[b]thiepin-5-one (Ia17)

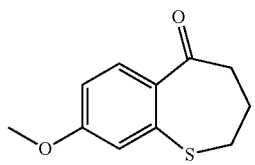

To a slurry of polyphosphoric acid (130 g, 78.66 mmol), heated to 80° C., was added 4-((3-methoxyphenyl)thio)butanoic acid sodium salt (17.7 g, 71 mmol) portionwise. The reaction mixture was stirred for half an hour and poured onto ice. The polyphopshoric acid was left to hydrolyse overnight and the solid formed was filtered, and rinced with water and di-isopropyl ether. The solid was dried on Buchner to give 9 g (55%) of 8-methoxy-3,4-dihydrobenzo[b]thiepin-5(2H)-one (Ia17) as a beige powder. LC/MS (m/z, MH+): 209

Intermediate (Ia18). 8-Hydroxy-3,4-dihydro-2H-benzo[b]thiepin-5-one

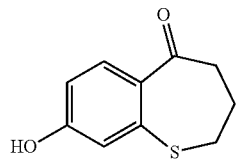 [SMILES: O=C1CCCSc2cc(O)ccc21]

A solution of 8-methoxy-3,4-dihydrobenzo[b]thiepin-5(2H)-one (Ia17) (11.2 g, 53.77 mmol) in 47% aqueous HBr (60 ml) and acetic acid (120 ml) was stirred mechanically at 115° C. for 24 hours. The reaction mixture was cooled to room temperature and partitioned between water (100 ml) and DCM (200 ml). The organic phase was washed with brine, dried over hydrophobic column, and concentrated under reduced pressure. The residue was purified by flash chromatography eluting with a gradient of heptane in EtOAc (100/0 to 70/30; v/v) to give 6.1 g (58%) of 8-hydroxy-3,4-dihydrobenzo[b]thiepin-5(2H)-one (Ia18) as a beige powder. LC/MS (m/z, MH+): 195

Intermediate (Ia19). 5-oxo-2,3,4,5-tetrahydrobenzo[b]thiepin-8-yl pivalate

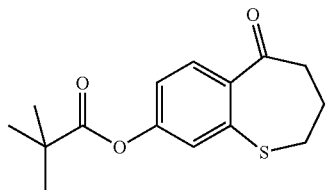 [SMILES: CC(C)(C)C(=O)Oc1ccc2c(c1)SCCCC2=O]

To a solution of 8-hydroxy-3,4-dihydrobenzo[b]thiepin-5(2H)-one (Ia18) (6.1 g, 31.45 mmol), in acetone (250 ml), was added potassium carbonate (potassium carbonate (4.35 g, 31.45 mmol) and pivaloyl chloride (3.87 ml, 31.45 mmol). The reaction mixture was stirred at room temperature for 24 h, filtered, and concentrated under reduced pressure. The residue was purified by flash chromatography eluting with a gradient of heptane in EtOAc (100/0 to 85/15; v/v) to give 5.64 g (64%) of 5-oxo-2,3,4,5-tetrahydrobenzo[b]thiepin-8-yl pivalate (Ia19) as a cream solid. LC/MS (m/z, MH+): 279

Intermediate (Ib12). 5-(((trifluoromethyl)sulfonyl)oxy)-2,3-dihydrobenzo[b]thiepin-8-yl pivalate

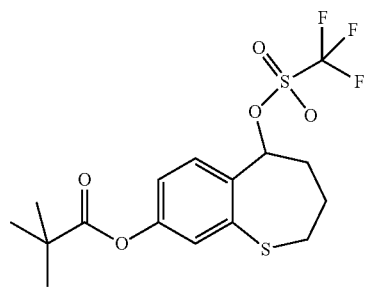

To a solution under argon of 5-oxo-2,3,4,5-tetrahydrobenzo[b]thiepin-8-yl pivalate (Ia19) (20 g, 71.85 mmol) in DCM (250 ml) and pyridine (9.08 ml, 107.77 mmol), was added dropwise trifluoromethanesulfonic anhydride (24.42 ml, 143.70 mmol). The reaction mixture was stirred at room temperature for 1.5 hours then poured onto ice and partitioned between water and DCM. The organic phase was dried over magnesium sulfate, filtered off and concentrated under reduced pressure. The residue was purified by flash chromatography eluting with a gradient of heptane in EtOAc (100/0 to 80/20; v/v) to give 29.5 g (100%) of 5-(((trifluoromethyl)sulfonyl)oxy)-2,3-dihydrobenzo[b]thiepin-8-yl pivalate (Ib12) as a colorless oil. LC/MS (m/z, MH$^+$): 411

Intermediate (If11). (S)-5-(4-((1-(3-fluoropropyl)pyrrolidin-3-yl)oxy)phenyl)-2,3-dihydrobenzo[b]thiepin-8-yl pivalate

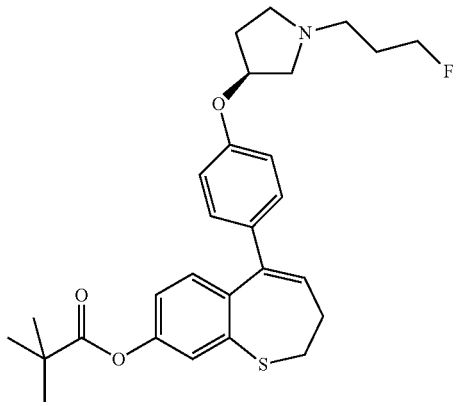 [SMILES: CC(C)(C)C(=O)Oc1ccc2c(c1)SCCC=C2c1ccc(O[C@H]2CCN(CCCF)C2)cc1]

To a solution under argon of 5-(((trifluoromethyl)sulfonyl)oxy)-2,3-dihydrobenzo[b]thiepin-8-yl pivalate (Ib12) (29.5 g, 71.88 mmol), (S)-1-(3-fluoropropyl)-3-(4-(4,4,5,5-tetramethyl-1,3,2-dioxaborolan-2-yl)phenoxy)pyrrolidine (1) (29.07 g, 79.06 mmol), in dioxane (250 ml) and water (50 ml), was added Cs$_2$CO$_3$ (46.88 g, 143.75 mmol). The reaction mixture was degassed by bubbling argon into the solution for 10 minutes then [1,1'-bis(diphenylphosphino)ferrocene]dichloropalladium(II), complex with DCM (2.93 g, 3.59 mmol) was added and the reaction mixture was stirred for 24 hours at room temperature and partitioned between water and EtOAc. The organic phase was washed with brine, dried over magnesium sulfate, and concentrated under reduced pressure. The residue was purified by flash chromatography eluting with a gradient of DCM in MeOH (100/0 to 98/03; v/v) to give 18.9 g (54%) of (S)-5-(4-((1-(3-fluoropropyl)pyrrolidin-3-yl)oxy)phenyl)-2,3-dihydrobenzo[b]thiepin-8-yl pivalate (If11) as a brown oil. LC/MS (m/z, MH$^+$): 484

Intermediate (Ig19). (S)-4-bromo-5-(4-((1-(3-fluoropropyl)pyrrolidin-3-yl)oxy)phenyl)-2,3-dihydrobenzo[b]thiepin-8-yl pivalate hydrobromide

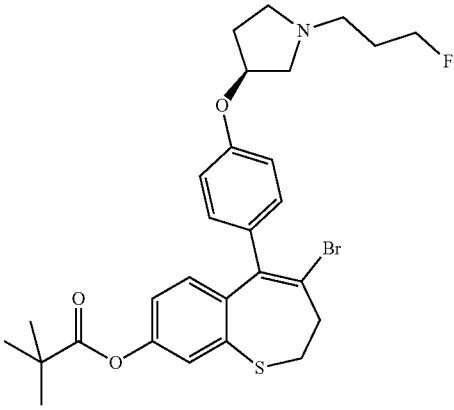 [SMILES: CC(C)(C)C(=O)Oc1ccc2c(c1)SCCC(Br)=C2c1ccc(O[C@H]2CCN(CCCF)C2)cc1]

To a solution under argon of (S)-5-(4-((1-(3-fluoropropyl)pyrrolidin-3-yl)oxy)phenyl)-2,3-dihydrobenzo[b]thiepin-8-yl pivalate (If) (8.11 g, 15.93 mmol), in THF (250 ml) was added pyridinium tribromide (5.94 g, 16.73 mmol). The reaction mixture was stirred for 3.5 hour at room temperature. After LC/MS control, the reaction was not complete. Addition of 0.6 g of pyridinium tribromide. After 48 hours of stirring at room temperature, addition of 0.6 g of pyridinium tribromide. After additional 24 hours of stirring at room temperature the reaction mixture was evaporated under reduced pressure. Addition of concentrated NaHCO$_3$ and a mixture of DCM/MeOH 90/10. The organic phase was dried over magnesium sulfate, and concentrated under reduced pressure to give 6.42 g (69%) of (S)-4-bromo-5-(4-((1-(3-fluoropropyl)pyrrolidin-3-yl)oxy)phenyl)-2,3-dihydrobenzo[b]thiepin-8-yl pivalate (Ig19) as a yellow solid. LC/MS (m/z, MH$^+$): 562

Intermediate (Ig20). (S)-4-bromo-5-(4-((1-(3-fluoropropyl)pyrrolidin-3-yl)oxy)phenyl)-2,3-dihydrobenzo[b]thiepin-8-ol

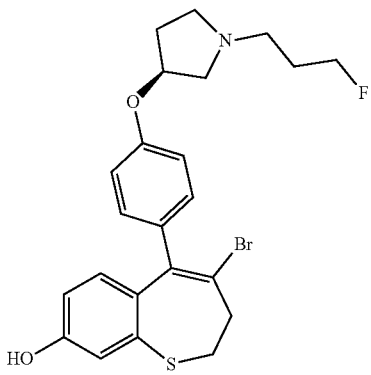 [SMILES: Oc1ccc2c(c1)SCCC(Br)=C2c1ccc(O[C@H]2CCN(CCCF)C2)cc1]

To a solution of (S)-4-bromo-5-(4-((1-(3-fluoropropyl)pyrrolidin-3-yl)oxy)phenyl)-2,3-dihydrobenzo[b]thiepin-8-yl pivalate (Ig19) (3.27 g, 5.81 mmol) in MeOH (80 ml), was added NaOH 5N (5 ml, 25.00 mmol). The reaction mixture was stirred for one hour at room temperature and the pH was adjusted to 7 with 5 ml of HCl 5N. The solvent was removed under reduced pressure and the residue taken up into DCM. The phases were separated and the aqueous phase washed with DCM. The organic phases were combined and dried over magnesium sulfate, filtered, and evaporated under reduced pressure. The residue was purified by column chromatography eluting with a gradient of DCM in MeOH (100/0 to 98/05; v/v) to give 2.14 g (77%) of (S)-4-bromo-5-(4-((1-(3-fluoropropyl)pyrrolidin-3-yl)oxy)phenyl)-2,3-dihydrobenzo[b]thiepin-8-ol (Ig20) as beige solid. LC/MS (m/z, MH+): 478

Intermediate (Ia20). 7-Hydroxy-3,4-dihydro-2H-benzo[b]thiepin-5-one

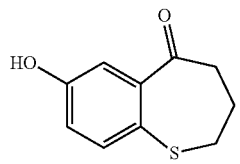 [SMILES: O=C1CCCSc2ccc(O)cc21]

A solution of 7-methoxy-3,4-dihydrobenzo[b]thiepin-5(2H)-one (5 g, 24.01 mmol) in 47% aqueous HBr (50 ml) and acetic acid (25 ml) was stirred mechanically at 115° C. for 24 hours. The reaction mixture was cooled to room temperature and partitioned between water (100 ml) and DCM (200 ml). The organic phase was washed with brine, dried over hydrophobic column, and concentrated under reduced pressure. The residue was purified by flash chromatography eluting with a gradient of heptane in EtOAc (100/0 to 70/30; v/v) to give 3.64 g (78%) of 7-hydroxy-3,4-dihydrobenzo[b]thiepin-5(2H)-one (Ia20) as a beige powder. LC/MS (m/z, MH+): 195

Intermediate (Ia21). 5-oxo-2,3,4,5-tetrahydrobenzo[b]thiepin-7-yl pivalate

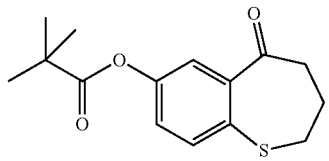 [SMILES: CC(C)(C)C(=O)Oc1ccc2c(c1)C(=O)CCCS2]

To a solution of 7-hydroxy-3,4-dihydrobenzo[b]thiepin-5(2H)-one (Ia20) (3.64 g, 18.74 mmol), in acetone (180 ml), was added potassium carbonate (2.72 g, 19.68 mmol) and pivaloyl chloride (2.42 ml, 19.68 mmol). The reaction mixture was stirred at room temperature for 16 hours, filtered, and concentrated under reduced pressure. The residue was purified by flash chromatography eluting with a gradient of heptane in EtOAc (100/0 to 70/30; v/v) to give 4.78 g (91%) of 5-oxo-2,3,4,5-tetrahydrobenzo[b]thiepin-7-yl pivalate (Ia21) as a yellow oil. LC/MS (m/z, MH+): 279

Intermediate (Ib13). 5-(((trifluoromethyl)sulfonyl)oxy)-2,3-dihydrobenzo[b]thiepin-7-yl pivalate

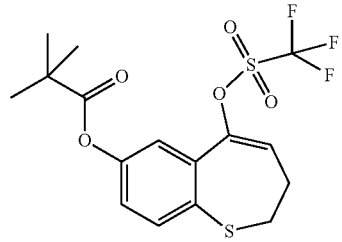 [SMILES: CC(C)(C)C(=O)Oc1ccc2c(c1)C(OS(=O)(=O)C(F)(F)F)=CCCS2]

To a solution under argon of 5-oxo-2,3,4,5-tetrahydrobenzo[b]thiepin-7-yl pivalate (Ia21) (5 g, 17.96 mmol) in DCM (157 ml) and anhydrous pyridine (2.27 ml, 26.94 mmol), cooled at 5° C., was added dropwise trifluoromethanesulfonic anhydride (6.10 ml, 35.92 mmol). The reaction mixture, a thick suspension, was stirred at room temperature for 24 h. Addition of ice and partition between water and DCM. The organic phase was dried over magnesium sulfate, filtered off and concentrated under reduced pressure. The residue was purified by flash chromatography eluting with a gradient of heptane in DCM (80/20 to 40/60; v/v) to give 4.3 g (58%) of 5-(((trifluoromethyl)sulfonyl)oxy)-2,3-dihydrobenzo[b]thiepin-7-yl pivalate (Ib13). LC/MS (m/z, MH+): 411

Intermediate (If12). (S)-5-(4-((1-(3-fluoropropyl)pyrrolidin-3-yl)oxy)phenyl)-2,3-dihydrobenzo[b]thiepin-7-yl pivalate

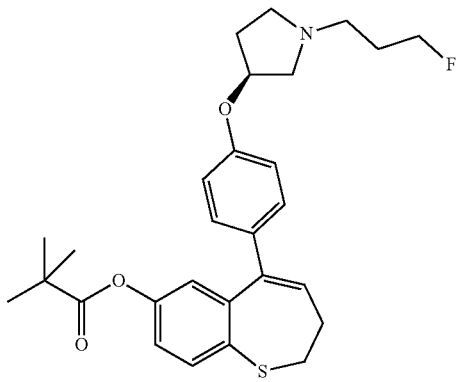 [SMILES: CC(C)(C)C(=O)Oc1ccc2c(c1)C(c1ccc(O[C@H]3CCN(CCCF)C3)cc1)=CCCS2]

To a solution under argon of 5-(((trifluoromethyl)sulfonyl)oxy)-2,3-dihydrobenzo[b]thiepin-7-yl pivalate (Ib13) (4.3 g, 10.48 mmol), (S)-1-(3-fluoropropyl)-3-(4-(4,4,5,5-tetramethyl-1,3,2-dioxaborolan-2-yl)phenoxy)pyrrolidine (1) (3.66 g, 10.48 mmol), in dioxane (30 ml) were added [1,1'-bis(diphenylphosphino)ferrocene]dichloropalladium (II), complex with DCM (901 mg, 1.05 mmol) and Cs₂CO₃ 1.5 M aqueous solution (14 ml, 20.95 mmol). The reaction mixture was stirred for 1 hour at room temperature. After cooling to room temperature, the reaction mixture was poured to a mixture of water (500 ml) and EtOAc (400 ml). The organic phase was washed with brine, dried over magnesium sulfate, filtered on celite and concentrated under reduced pressure. The residue was purified by flash chromatography eluting with a gradient of DCM in MeOH (100/0 to 97/03; v/v) to give 2.6 g (51%) of (S)-5-(4-((1-(3-fluoropropyl)pyrrolidin-3-yl)oxy)phenyl)-2,3-dihydrobenzo[b]thiepin-7-yl pivalate (If12) as a brown oil. LC/MS (m/z, MH+): 484

Intermediate (Ig21). (S)-4-bromo-5-(4-((1-(3-fluoropropyl)pyrrolidin-3-yl)oxy)phenyl)-2,3-dihydrobenzo[b]thiepin-7-yl pivalate

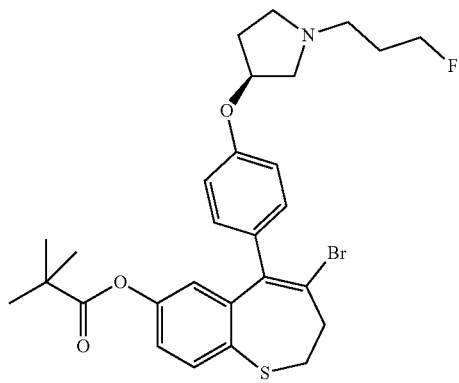 [SMILES: CC(C)(C)C(=O)Oc1ccc2c(c1)C(c1ccc(O[C@H]3CCN(CCCF)C3)cc1)=C(Br)CCS2]

To a solution under argon of (S)-5-(4-((1-(3-fluoropropyl)pyrrolidin-3-yl)oxy)phenyl)-2,3-dihydrobenzo[b]thiepin-7-yl pivalate (If12) (2.6 g, 5.38 mmol), in THF (30 ml) was added pyridinium tribromide (1 g, 5.62 mmol). The reaction mixture was stirred for 24 hours at room temperature. Addition of water (30 ml) and EtOAc (50 ml) then, organic phase was dried over magnesium sulfate, and concentrated under reduced pressure. The obtained meringue was purified by flash chromatography eluting with a gradient of DCM in MeOH (100/0 to 97/03; v/v) to give 2 g (66%) of (S)-4-bromo-5-(4-((1-(3-fluoropropyl)pyrrolidin-3-yl)oxy)phenyl)-2,3-dihydrobenzo[b]thiepin-7-yl pivalate hydrobromide (Ig21). LC/MS (m/z, MH+): 562

Intermediate (Ig22). (S)-4-bromo-5-(4-((1-(3-fluoropropyl)pyrrolidin-3-yl)oxy)phenyl)-2,3-dihydrobenzo[b]thiepin-7-ol

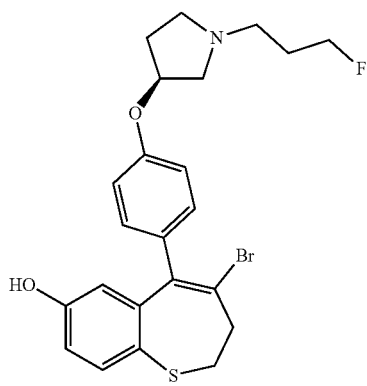 [SMILES: Oc1ccc2c(c1)C(c1ccc(O[C@H]3CCN(CCCF)C3)cc1)=C(Br)CCS2]

To a solution of (S)-4-bromo-5-(4-((1-(3-fluoropropyl)pyrrolidin-3-yl)oxy)phenyl)-2,3-dihydrobenzo[b]thiepin-7-yl pivalate hydrobromide (Ig21) (2.0 g, 3.11 mmol) in MeOH (60 ml), was added NaOH 8N (2.7 ml, 21.60 mmol). The reaction mixture was stirred for 15 minutes at room temperature and the pH was adjusted to 7 with HCl 12N. The solvent was removed under reduced pressure and the residue taken up into DCM. The phases were separated and the aqueous phase washed with DCM. The organic phases were combined and dried over magnesium sulfate, filtered, and evaporated under reduced pressure. The residue was purified by column chromatography eluting with a gradient of DCM in MeOH (100/0 to 96/04; v/v) to give 1.26 g (85%) of (S)-4-bromo-5-(4-((1-(3-fluoropropyl)pyrrolidin-3-yl)oxy)phenyl)-2,3-dihydrobenzo[b]thiepin-7-ol (Ig22). LC/MS (m/z, MH+): 478

Intermediate (Ii1). 4-(2-(2-chloro-4-fluorophenyl)-7-methoxy-3,4-dihydronaphtalen-1-yl)phenol

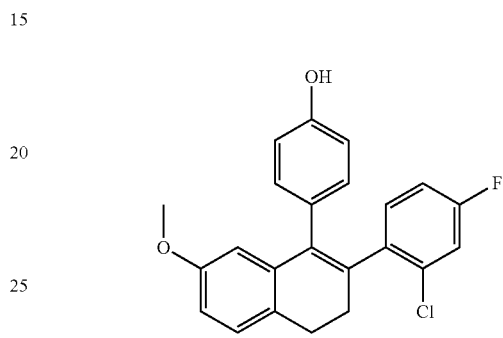

In a 10-20 ml microwave vial was placed a mixture of 4-(2-bromo-7-methoxy-3,4-dihydronaphthalen-1-yl)phenol (Id1) (500 mg, 1.51 mmol), 2-chloro-4-fluorophenylboronic acid (263 mg, 1.51 mmol), Cs$_2$CO$_3$ (1.03 g, 3.17 mmol), 1,1'-bis(diphenylphosphino)ferrocene-palladium(II)dichloride DCM complex (129.8 mg, 150.96 μmol) and 1,4-dioxane (10 ml)/water (2.5 ml). Argon was bubbled during 5 mn and the reaction mixture was irradiated under microwave radiation for 2 h 00 at 120° C. The reaction mixture was cooled and extracted with EtOAc and the organic phase was washed with brine, dried over magnesium sulfate, filtered, and concentrated under reduced pressure. The residue was purified by flash chromatography eluting with a gradient of n-heptane in EtOAc (90/10 to 70/30; v/v), to give 686 mg of 4-(2-(2-chloro-4-fluorophenyl)-7-methoxy-3,4-dihydronaphtalen-1-yl)phenol (ii) as a yellow solid. LC/MS (m/z, MH+): 381

Intermediate (Ij1). 4-(2-(2-chloro-4-fluorophenyl)-7-methoxy-3,4-dihydronaphtalen-1-yl)phenyl trifluoromethane sulfonate

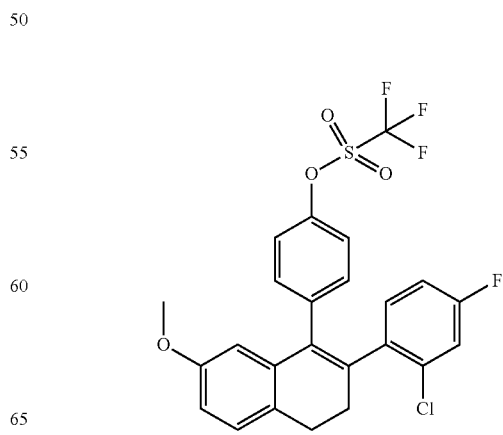

To a mixture of 4-(2-(2-chloro-4-fluorophenyl)-7-methoxy-3,4-dihydronaphtalen-1-yl)phenol (ii) (686 mg, 1.80 mmol) and pyridine (349.6 µl, 4.32 mmol) in DCM (20 ml) at 0° C., was added dropwise trifluoromethanesulfonic anhydride (727.3 µl, 4.32 mmol). The reaction mixture was stirred for 30 min at 0° C., and 1.5 hours at room temperature. The mixture was poured on ice, and the resulting mixture was extracted with DCM. The organic phase was washed with brine, dried over magnesium sulfate, filtered, and concentrated under reduced pressure to give 854 mg (92%) of 4-(2-(2-chloro-4-fluorophenyl)-7-methoxy-3,4-dihydronaphtalen-1-yl)phenyl trifluoromethane sulfonate (Ij1) as an orange oil, which was used as such in the next step. LC/MS (m/z, MH$^+$): 512

Intermediate (Ik1). (S)-tert-butyl 3-((4-(2-(2-chloro-4-fluorophenyl)-7-methoxy-3,4-dihydronaphtalen-1-yl)phenyl)amino)pyrrolidine-1-carboxylate

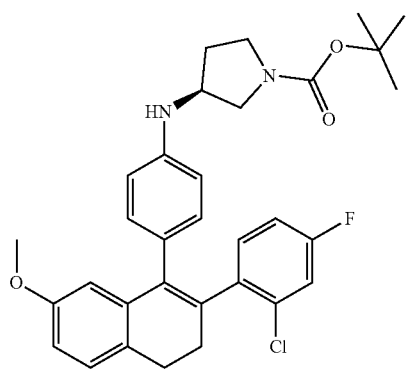 [SMILES: COc1ccc2c(c1)C(c1ccc(N[C@H]3CCN(C(=O)OC(C)(C)C)C3)cc1)=C(c1ccc(F)cc1Cl)CC2]

In a microwave vial was placed a mixture of 4-(2-(2-chloro-4-fluorophenyl)-7-methoxy-3,4-dihydronaphtalen-1-yl)phenyl trifluoromethane sulfonate (Ij1) (265 mg, 516.7 µmol), (S)-tert-butyl 3-aminopyrrolidine-1-carboxylate (289 mg, 1.55 mmol), Cs$_2$CO$_3$ (508 mg, 1.55 mmol), palladium (II) acetate (12 mg, 51.67 µmol) and (9,9-dimethyl-9H-xanthene-4,5-diyl)bis(diphenylphosphine) (42 mg, 72.33 µmol) in 1,4-dioxane (16 ml). Argon was bubbled during 10 min and the reaction mixture was irradiated under microwave radiation for 2 hours at 140° C. The reaction mixture was cooled at room temperature and silica (40-60 µm) (4 g) was added. The mixture was concentrated under reduced pressure and the solid residue was purified by flash chromatography eluting with a mixture of n-heptane and EtOAc (80/20; v/v), to give 165 mg (58%) of (S)-tert-butyl 3-((4-(2-(2-chloro-4-fluorophenyl)-7-methoxy-3,4-dihydronaphtalen-1-yl)phenyl)amino)pyrrolidine-1-carboxylate (Ik1) as a pale yellow solid. LC/MS (m/z, MH$^+$): 549

Intermediate (II1). (S)—N-(4-(2-(2-chloro-4-fluorophenyl)-7-methoxy-3,4-dihydronaphtalen-1-yl)phenyl)pyrrolidin-3-amine hydrochloride

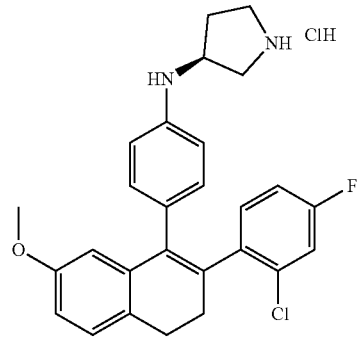 [SMILES: COc1ccc2c(c1)C(c1ccc(N[C@H]3CCNC3)cc1)=C(c1ccc(F)cc1Cl)CC2 ; Cl]

To a solution of (S)-tert-butyl 3-((4-(2-(2-chloro-4-fluorophenyl)-7-methoxy-3,4-dihydronaphtalen-1-yl)phenyl)amino)pyrrolidine-1-carboxylate (Ik1) (156 mg, 284.11 µmol) in DCM (4.2 ml), was added dropwise a hydrochloric acid solution (1M) in ether (2.84 ml, 2.84 mmol). The reaction mixture was stirred for 24 hours at room temperature. The reaction mixture was dissolved with MeOH and concentrated under reduced pressure to give 114 mg (89%) of (S)—N-(4-(2-(2-chloro-4-fluorophenyl)-7-methoxy-3,4-dihydronaphtalen-1-yl)phenyl)pyrrolidin-3-amine hydrochloride (Il1) as a pale yellow solid, which was used as such in the next step. LC/MS (m/z, MH$^+$): 449

Intermediate (II2). (S)-7-(2-chloro-4-fluorophenyl)-8-(4-(pyrrolidin-3-ylamino)phenyl)-5,6-dihydronaphtalen-2-ol

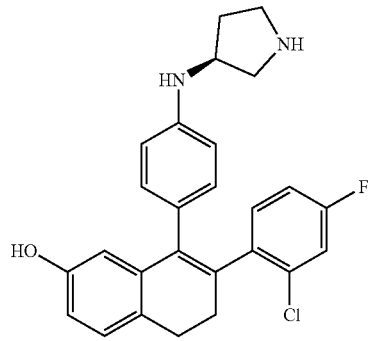 [SMILES: Oc1ccc2c(c1)C(c1ccc(N[C@H]3CCNC3)cc1)=C(c1ccc(F)cc1Cl)CC2]

To a suspension of (S)—N-(4-(2-(2-chloro-4-fluorophenyl)-7-methoxy-3,4-dihydronaphtalen-1-yl)phenyl)pyrrolidin-3-amine hydrochloride (Il1) (113 mg, 232.79 µmol) in DCM (3.5 ml) at 0° C., was added dropwise boron tribromide solution 1M (698.4 µl, 698.4 µmol). The reaction mixture was stirred for 1 hour at 0° C. The reaction mixture was treated on ice, and the pH was adjusted to 8 by adding sodium hydrogenocarbonate. The mixture was extracted (3×) with DCM (5% MeOH) and washed with brine. The organic phase was dried over magnesium sulfate and concentrated under reduced pressure to give 79 mg (72%) of (S)-7-(2-chloro-4-fluorophenyl)-8-(4-(pyrrolidin-3-ylamino)phenyl)-5,6-dihydronaphtalen-2-ol (Il2) as a brown solid. LC/MS (m/z, MH$^+$): 435

Intermediate (Ia22). 5-oxo-6,7,8,9-tetrahydro-5H-benzo[7]annulen-2-yl 2,2-dimethylpropanoate

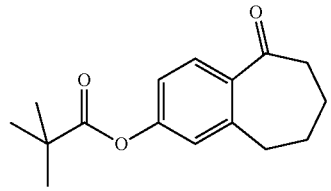 [SMILES: CC(C)(C)C(=O)Oc1ccc2c(c1)CCCCC2=O]

To a solution of 2-hydroxy-6,7,8,9-tetrahydro-5H-benzo[7]annulen-5-one (1.52 g, 8.63 mmol), in acetone (60 ml), was added $K_2CO_3$ (1.19 g, 8.63 mmol) and pivaloyl chloride (1.06 ml, 8.63 mmol). The reaction mixture was stirred at room temperature for 16 hours, filtered, and concentrated under reduced pressure. The residue was purified by flash chromatography eluting with a gradient of heptane in EtOAc (100/0 to 85/15; v/v) to give 1.55 g (69%) of 5-oxo-6,7,8,9-tetrahydro-5H-benzo[7]annulen-2-yl 2,2-dimethylpropanoate (Ia22) as a colorless oil. LC/MS (m/z, MH$^+$): 261

Intermediate (Ib14). 9-(trifluoromethanesulfonyloxy)-6,7-dihydro-5H-benzo[7]annulen-3-yl 2,2-dimethylpropanoate

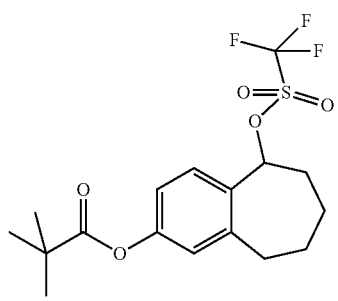 [SMILES: CC(C)(C)C(=O)Oc1ccc2c(c1)CCCCC2OS(=O)(=O)C(F)(F)F]

To a solution of 5-oxo-6,7,8,9-tetrahydro-5H-benzo[7]annulen-2-yl 2,2-dimethylpropanoate (Ia22) (15 g, 57.62 mmol) in DCM (500 ml) was added dropwise under argon pyridine (7.28 ml, 86.43 mmol) and trifluoromethanesulfonic anhydride (19.58 ml, 115.24 mmol).

The reaction mixture was stirred at room temperature for 2 hours and ice (200 g) was added. The phases were separated, the aqueous phase was washed with DCM and the gathered organic phases were dried over magnesium sulfate, filtered, and evaporated under reduced pressure to give 22 g (97%) of 9-(trifluoromethanesulfonyloxy)-6,7-dihydro-5H-benzo[7]annulen-3-yl 2,2-dimethylpropanoate (Ib14) as a white solid. LC/MS (m/z, MH$^-$): 391

Intermediate (Ic2). 9-(4-hydroxyphenyl)-6,7-dihydro-5H-benzo[7]annulen-3-yl pivalate

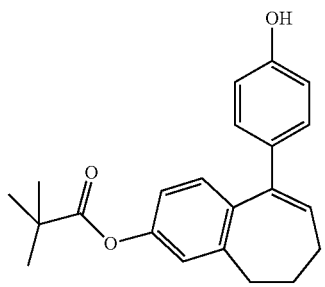 [SMILES: CC(C)(C)C(=O)Oc1ccc2c(c1)CCCC=C2c1ccc(O)cc1]

To a mixture of 9-(trifluoromethanesulfonyloxy)-6,7-dihydro-5H-benzo[7]annulen-3-yl 2,2-dimethylpropanoate (Ib14) (6.925 g, 17.65 mmol), (4-hydroxyphenyl)boronic acid (2.73 g, 19.41 mmol) and [1,1'-bis(diphenylphosphino)ferrocene]dichloropalladium(II), complex with DCM (1.52 g, 1.76 mmol) in dioxane (60 ml), was added dropwise a solution of $Cs_2CO_3$ 1.5 M (23.6 ml, 35.3 mmol). The reaction mixture was stirred for two hours at room temperature. Water (60 ml) and EtOAc (100 ml) were added. The organic phase was dried over magnesium sulfate, filtered, and concentrated under reduced pressure. The residue was purified by flash chromatography eluting with a mixture of EtOAc and n-heptane (10/90; v/v) to give 2.84 g (48%) of 9-(4-hydroxyphenyl)-6,7-dihydro-5H-benzo[7]annulen-3-yl pivalate (Ic2) as a yellow solid. LC/MS (m/z, MH$^+$): 337

Intermediate (Im1). 9-(4-(((trifluoromethyl)sulfonyl)oxy)phenyl)-6,7-dihydro-5H-benzo[7]annulen-3-yl pivalate

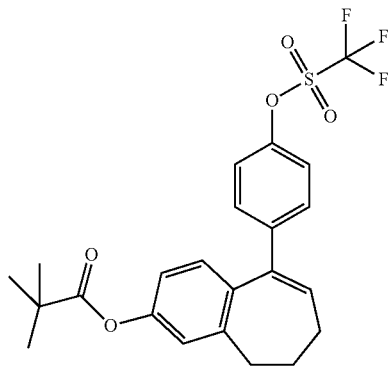 [SMILES: CC(C)(C)C(=O)Oc1ccc2c(c1)CCCC=C2c1ccc(OS(=O)(=O)C(F)(F)F)cc1]

To a mixture of 9-(4-hydroxyphenyl)-6,7-dihydro-5H-benzo[7]annulen-3-yl pivalate (Ic2) (2.84 g, 8.44 mmol) and pyridine (1.64 ml, 20.26 mmol) in DCM (90 ml) at 0° C., was added dropwise trifluoromethanesulfonic anhydride (3.41 ml, 20.26 mmol). The reaction mixture was stirred for 2 hours at room temperature. Ice was added, and the resulting mixture was extracted with DCM. The organic phase was washed with brine, dried over magnesium sulfate, filtered, and concentrated under reduced pressure to give 4.05 g of a yellow solid. The solid residue was purified by flash chromatography eluting with a mixture of n-heptane and EtOAc (98/2; v/v), to give 2.16 g (55%) of 9-(4-(((trifluoromethyl)sulfonyl)oxy)phenyl)-6,7-dihydro-5H-benzo[7]annulen-3-yl pivalate (Im1) as a yellow oil. LC/MS (m/z, MH$^+$): 469

Intermediate (In1). (S)-tert-butyl 3-((4-(3-(pivaloyloxy)-6,7-dihydro-5H-benzo[7]annulen-9-yl)phenyl)amino)pyrrolidine-1-carboxylate

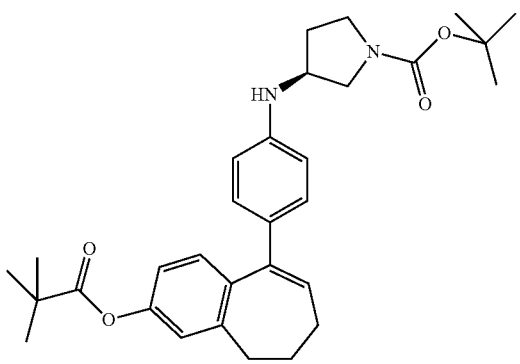 [SMILES: CC(C)(C)OC(=O)N1CC[C@H](Nc2ccc(C3=CCCCc4cc(OC(=O)C(C)(C)C)ccc43)cc2)C1]

In a microwave vial, a mixture of 9-(4-(((trifluoromethyl)sulfonyl)oxy)phenyl)-6,7-dihydro-5H-benzo[7]annulen-3-yl pivalate (Im1) (1.71 g, 3.65 mmol), (S)-tert-butyl 3-aminopyrrolidine-1-carboxylate (2.04 g, 10.95 mmol), Cs$_2$CO$_3$ (3.59 g, 10.95 mmol), palladium(II) acetate (84 mg, 365 µmol) and (9,9-dimethyl-9H-xanthene-4,5-diyl)bis(diphenylphosphine) (296 mg, 511 µmol) in 1,4-dioxane (85 ml) was stirred at 140° C. for 3 hours. The reaction mixture was cooled to room temperature and silica (40-60 µm) (7 g) was added. The mixture was concentrated under reduced pressure and the solid residue was purified by flash chromatography eluting with a gradient of n-heptane in EtOAc (90/10 to 85/15; v/v), to give 1.05 g (57%) of (S)-tert-butyl 3-((4-(3-(pivaloyloxy)-6,7-dihydro-5H-benzo[7]annulen-9-yl)phenyl)amino)pyrrolidine-1-carboxylate (In1) as a yellow oil. LC/MS (m/z, MH$^+$): 505

Intermediate (Io1). (S)-9-(4-pyrrolidin-3-ylamino)phenyl)-6,7-dihydro-5H-benzo[7]annulen-3-yl pivalate

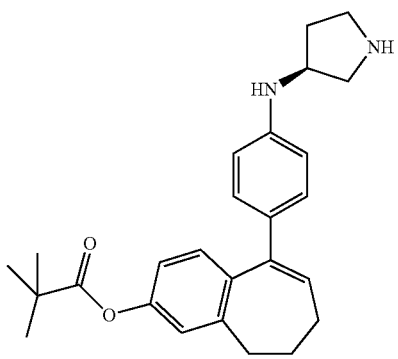 [SMILES: CC(C)(C)C(=O)Oc1ccc2c(c1)CCCC=C2c1ccc(N[C@H]2CCNC2)cc1]

To a solution of (S)-tert-butyl 3-((4-(3-(pivaloyloxy)-6,7-dihydro-5H-benzo[7]annulen-9-yl)phenyl)amino)pyrrolidine-1-carboxylate (In1) (1.33 g, 2.64 mmol) in DCM (36 ml), was added dropwise a HCl 1M in ether (26.3 ml, 26.3 mmol). The reaction mixture was stirred at room temperature for 3 hours, under argon. The reaction mixture was concentrated under reduced pressure to give 1.07 g of a yellow solid. The solid was dissolved in DCM/MeOH: 95/5 (v/v) and treated with a solution of sodium hydrogenocarbonate. After decantation and separation, the aqueous phase was extracted with DCM (5% MeOH). The organic phase was dried over magnesium sulfate and concentrated under reduced pressure to give 912 mg (85%) of (S)-9-(4-pyrrolidin-3-ylamino)phenyl)-6,7-dihydro-5H-benzo[7]annulen-3-yl pivalate (Io1) as a yellow oil, which was used as such in the next step. LC/MS (m/z, MH$^+$): 405

Intermediate (Ip1). (S)-9-(4-((1-(3-fluoropropyl)pyrrolidin-3-yl)amino)phenyl)-6,7-dihydro-5H-benzo[7]annulen-3-yl pivalate

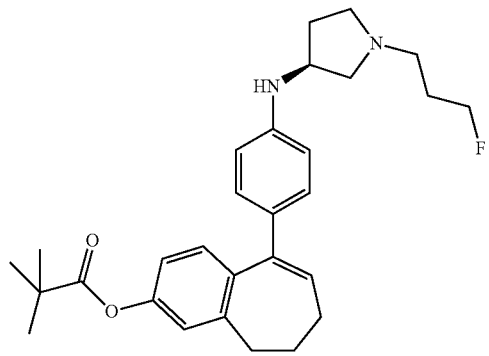 [SMILES: CC(C)(C)C(=O)Oc1ccc2c(c1)CCCC=C2c1ccc(N[C@H]2CCN(CCCF)C2)cc1]

To a solution of (S)-9-(4-pyrrolidin-3-ylamino)phenyl)-6,7-dihydro-5H-benzo[7]annulen-3-yl pivalate (Io1) (912 mg, 2.25 mmol) in DMF (41 ml), were added potassium carbonate (234 mg, 1.69 mmol) and 1-iodo-3-fluoropropane (254.9 µl, 2.37 mmol). The reaction mixture was stirred for 1 h 15 mn at 70° C. After cooling to room temperature, the reaction mixture was treated with water (60 ml) and extracted with EtOAc. After decantation, the organic phase was washed with brine, dried over magnesium sulfate and concentrated under reduced pressure. The residue was purified by flash chromatography eluting with a mixture of DCM and MeOH (97/3; v/v), to give 833 mg (80%) of (S)-9-(4-((1-(3-fluoropropyl)pyrrolidin-3-yl)amino)phenyl)-6,7-dihydro-5H-benzo[7]annulen-3-yl pivalate (Ip1) as an orange oil. LC/MS (m/z, MH$^+$): 465

Intermediate (Iq1). (S)-8-bromo-9-(4-((1-(3-fluoropropyl)pyrrolidin-3-yl)amino)phenyl)-6,7-dihydro-5H-benzo[7]annulen-3-yl pivalate

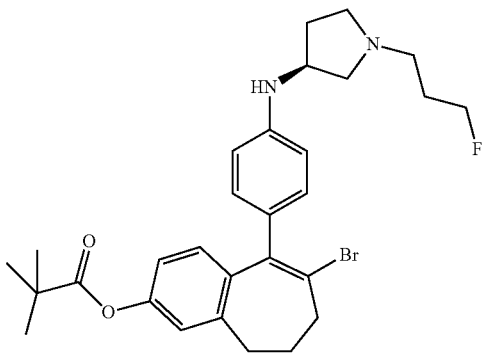 [SMILES: CC(C)(C)C(=O)Oc1ccc2c(c1)CCCC(Br)=C2c1ccc(N[C@H]2CCN(CCCF)C2)cc1]

To a solution of (S)-9-(4-((1-(3-fluoropropyl)pyrrolidin-3-yl)amino)phenyl)-6,7-dihydro-5H-benzo[7]annulen-3-yl pivalate (Ip1) (400 mg, 860.9 µmol) in THF (8 ml) at 0° C., was added pyridinium tribromide (238.6 mg, 671.5 µmol). The reaction mixture was stirred for 25 min at −10° C. The reaction mixture was poured over a solution of sodium hydrogenocarbonate and extracted with DCM. The organic phase was dried over magnesium sulfate and concentrated under reduced pressure to give a yellow resin (450 mg) which was purified by flash chromatography eluting with EtOAc, to give 242 mg (52%) of (S)-8-bromo-9-(4-((1-(3-fluoropropyl)pyrrolidin-3-yl)amino)phenyl)-6,7-dihydro-5H-benzo[7]annulen-3-yl pivalate (Iq1) as a resin. LC/MS (m/z, MH$^+$): 544

Intermediate (Iq2). (S)-8-bromo-9-(4-((1-(3-fluoropropyl)pyrrolidin-3-yl)amino)phenyl)-6,7-dihydro-5H-benzo[7]annulen-3-ol

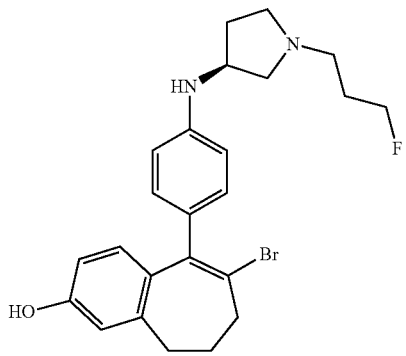 [SMILES: Oc1ccc2c(c1)CCCC(Br)=C2c1ccc(N[C@H]2CCN(CCCF)C2)cc1]

A solution of (S)-8-bromo-9-(4-((1-(3-fluoropropyl)pyrrolidin-3-yl)amino)phenyl)-6,7-dihydro-5H-benzo[7]annulen-3-yl pivalate (Iq1) (280 mg, 515 µmol) in MeOH (7 ml) and sodium hydroxide 5M (443 µl, 2.22 mmol) was stirred for 20 mn at room temperature. Aqueous hydrochloric acid 5M (0.42 ml) was added to adjust the pH to 7/8. The mixture was concentrated under reduced pressure to obtain an off-white solid which was taken up with DCM/MeOH: 95/5 (v/v) and, after filtration, partly concentrated under reduced pressure. The concentrated solution was purified by flash chromatography eluting with a mixture of DCM and MeOH (96/4; v/v), to give 214 mg (90%) of (S)-8-bromo-9-(4-((1-(3-fluoropropyl)pyrrolidin-3-yl)amino)phenyl)-6,7-dihydro-5H-benzo[7]annulen-3-ol (Iq2) as a resin. LC/MS (m/z, MH$^+$): 459

Reagent 2a. (S)-2-((1-(3-fluoropropyl)pyrrolidin-3-yl)oxy)-5-iodopyridine

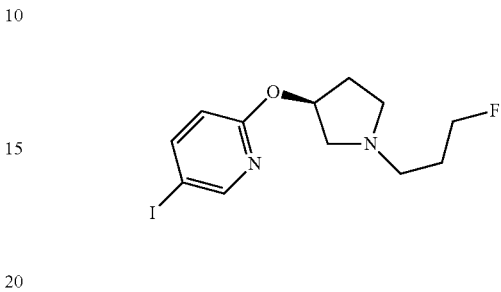

Step 1. (S)-1-(3-fluoropropyl)pyrrolidin-3-ol

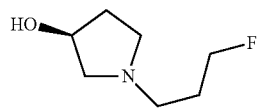

A suspension of (S)-3-hydroxypyrrolidine (5 g, 56.82 mmol), bromofluoropropane (9.28 g, 62.5 mmol), potassium carbonate (23.56 g, 170.45 mmol) and acetonitrile (50 ml) was stirred at 50° C. for 8 h. After cooling to room temperature, the suspension was filtered and concentrated under reduced pressure. To the residue obtained, addition of DCM (200 ml) and saturated solution of sodium chloride (50 ml). The organic phase was dried over magnesium sulfate, filtered, and concentrated under reduced pressure to give 6.7 g (80%) of (S)-1-(3-fluoropropyl)pyrrolidin-3-ol as a pale yellow oil. LC/MS (m/z, MH$^+$): 148

Step 2. (S)-2-((1-(3-fluoropropyl)pyrrolidin-3-yl)oxy)-5-iodopyridine (2a)

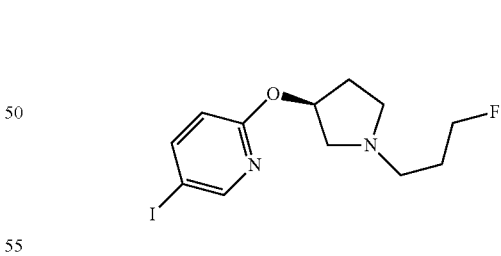

A mixture of (S)-1-(3-fluoropropyl)pyrrolidin-3-ol (1 g, 6.79 mmol), 2-fluoro-5-iodopyridine (1.75 g; 7.47 mmol), sodium hydride (815 mg, 20.38 mmol) and DMF (24 ml) was stirred at room temperature for 18 hours. Addition of EtOAc (100 ml) and saturated solution of NH$_4$Cl (50 ml). The organic phase was dried over magnesium sulfate, filtered, and concentrated under reduced pressure. The residue was purified by column chromatography eluting with a mixture of heptane and EtOAc (50/50; v/v) to give 1.25 g (53%) of (S)-2-((1-(3-fluoropropyl)pyrrolidin-3-yl)oxy)-5-iodopyridine (2a). LC/MS (m/z, MH$^+$): 351

Intermediate (Ir1). 9-(4,4,5,5-tetramethyl-1,3,2-di-oxaborolan-2-yl)-6,7-dihydro-5H-benzo[7]annulen-3-yl pivalate

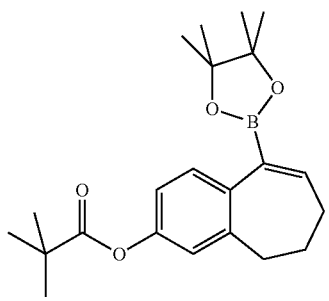 [SMILES: CC(C)(C)C(=O)Oc1ccc2c(c1)CCCC=C2B1OC(C)(C)C(C)(C)O1]

A suspension of 9-(((trifluoromethyl)sulfonyl)oxy)-6,7-dihydro-5H-benzo[7]annulen-3-yl pivalate (Ib14) (1 g, 2.55 mmol), palladium chloride bis triphenylphosphine (90 mg, 0.13 mmol), triphenylphosphine (41 mg, 0.15 mmol), bis (pinacolato)diboron (647 mg, 2.55 mmol) and potassium phenolate (505 mg, 3.82 mmol) in toluene (20 ml) was stirred at 55° C. for 24 hours. After cooling to room temperature, addition of EtOAc and water. The organic phase was dried over magnesium sulfate, filtered, and concentrated under reduced pressure. The residue was purified by column chromatography eluting with a gradient of DCM in heptane (80/20 to 60/40; V/V) to give 616 mg (65%) of 9-(4,4,5,5-tetramethyl-1,3,2-dioxaborolan-2-yl)-6,7-dihydro-5H-benzo[7]annulen-3-yl pivalate (Ir1). LC/MS (m/z, MH+): 371

Intermediate (Is1). (S)-9-(6-((1-(3-fluoropropyl) pyrrolidin-3-yl)oxy)pyridin-3-yl)-6,7-dihydro-5H-benzo[7]annulen-3-yl pivalate

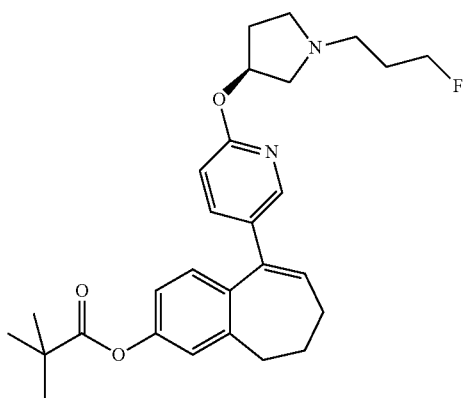 [SMILES: CC(C)(C)C(=O)Oc1ccc2c(c1)CCCC=C2c1ccc(O[C@H]2CCN(CCCF)C2)nc1]

To a solution of 9-(4,4,5,5-tetramethyl-1,3,2-dioxaborolan-2-yl)-6,7-dihydro-5H-benzo[7]annulen-3-yl pivalate (Ir1) (500 mg, 1.35 mmol) and (S)-2-((1-(3-fluoropropyl) pyrrolidin-3-yl)oxy)-5-iodopyridine (2a) (520 mg, 1.49 mmol), in dioxane (7 ml) was added under argon [1,1'-bis (diphenylphosphino)ferrocene]dichloropalladium(II), complex with DCM (104.00 mg, 0.14 mmol) and a solution of Cs₂CO₃ 1.5 M (3.60 ml, 5.40 mmol). The reaction mixture was stirred for one hour at 80° C. After cooling to room temperature, addition of EtOAc and water. The organic phase was dried over magnesium sulfate, filtered, and concentrated under reduced pressure. The residue was purified by column chromatography eluting with a gradient of MeOH in DCM (2 to 6%; V/V) to give 503 mg (80%) of (S)-9-(6-((1-(3-fluoropropyl)pyrrolidin-3-yl)oxy)pyridin-3-yl)-6,7-dihydro-5H-benzo[7]annulen-3-yl pivalate (Is1). LC/MS (m/z, MH+): 467

Intermediate (It1). (S)-8-bromo-9-(6-((1-(3-fluoropropyl)pyrrolidin-3-yl)oxy)pyridin-3-yl)-6,7-dihydro-5H-benzo[7]annulen-3-yl pivalate

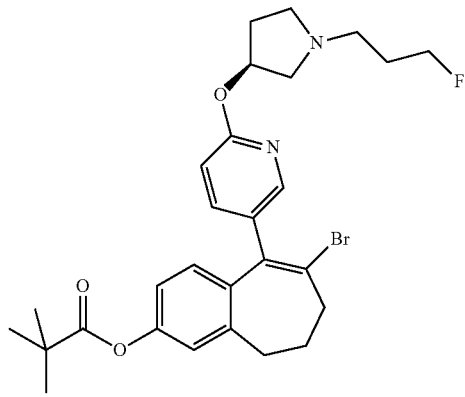 [SMILES: CC(C)(C)C(=O)Oc1ccc2c(c1)CCCC(Br)=C2c1ccc(O[C@H]2CCN(CCCF)C2)nc1]

To a solution of (S)-9-(6-((1-(3-fluoropropyl)pyrrolidin-3-yl)oxy)pyridin-3-yl)-6,7-dihydro-5H-benzo[7]annulen-3-yl pivalate (Is1) (500 mg, 1.07 mmol) in THF (10 ml), was added pyridinium tribromide (420 mg, 1.18 mmol). The reaction mixture was stirred for 1 hour at room temperature and 20 ml of EtOAc and 5 ml of water were added followed by a 5 ml of sodium hydroxide 32%. The organic phase was dried over magnesium sulfate, filtered, evaporated under reduced pressure to give 584 mg (99%) of (S)-8-bromo-9-(6-((1-(3-fluoropropyl)pyrrolidin-3-yl)oxy)pyridin-3-yl)-6, 7-dihydro-5H-benzo[7]annulen-3-yl pivalate (It1). LC/MS (m/z. MH+): 545

Intermediate (It2). (S)-8-bromo-9-(6-((1-(3-fluoropropyl)pyrrolidin-3-yl)oxy)pyridin-3-yl)-6,7-dihydro-H-benzo[7]annulen-3-ol

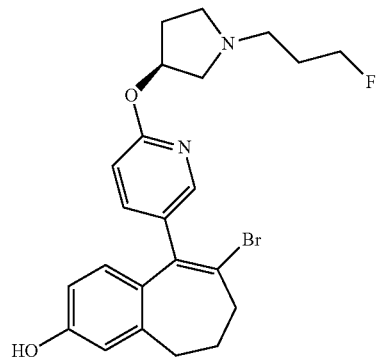 [SMILES: Oc1ccc2c(c1)CCCC(Br)=C2c1ccc(O[C@H]2CCN(CCCF)C2)nc1]

To a solution of (S)-8-bromo-9-(6-((1-(3-fluoropropyl) pyrrolidin-3-yl)oxy)pyridin-3-yl)-6,7-dihydro-5H-benzo[7] annulen-3-yl pivalate (It1) (584 mg, 1.07 mmol) in MeOH (10 ml), was added NaOH 2N (1 ml, 8.00 mmol). The reaction mixture was stirred 30 minutes at room temperature and 8 ml of HCL 1N were added. The solvent was removed under reduced pressure and the residue taken up into DCM. The phases were separated and the aqueous phase washed with DCM and EtOAc. The organic phase was dried over magnesium sulfate, filtered, and evaporated under reduced pressure. The residue was purified by column chromatography eluting with a gradient of MeOH in DCM (0 to 05%; V/V) to give 277 mg (56%) of (S)-8-bromo-9-(6-((1-(3-fluoropropyl)pyrrolidin-3-yl)oxy)pyridin-3-yl)-6,7-dihydro-5H-benzo[7]annulen-3-ol (It2). LC/MS (m/z, MH$^+$): 462

Intermediate (Ia23). 1-fluoro-2-hydroxy-6,7,8,9-tetrahydro-5H-benzo[7]annulen-5-one

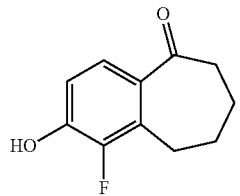 [SMILES: O=C1CCCCc2c1ccc(O)c2F]

To a solution of 1-fluoro-2-methoxy-6,7,8,9-tetrahydro-5H-benzo[7]annulen-5-one (6.2 g, 29.8 mmol) in toluene (100 ml) was added AlCl$_3$ (4.76 g, 35.7 mmol). The brown suspension was stirred for 1 hour at 90° C. After cooling to room temperature, the hot mixture was poured into 900 g of iced water. The solid obtained was filtered off, washed with water, aqueous HCl 0.1 N and dried to give 5.3 g (92%) of 1-fluoro-2-hydroxy-6,7,8,9-tetrahydro-5H-benzo[7]annulen-5-one (Ia23) as a beige solid. LC/MS (m/z, MH$^+$): 195

Intermediate (Ia24). 1-fluoro-5-oxo-6,7,8,9-tetrahydro-5H-benzo[7]annulen-2-yl 2,2-dimethylpropanoate

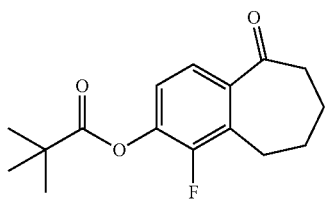 [SMILES: CC(C)(C)C(=O)Oc1ccc2c(c1F)CCCCC2=O]

To a solution of 1-fluoro-2-hydroxy-6,7,8,9-tetrahydro-5H-benzo[7]annulen-5-one (Ia23) (5.3 g, 27.3 mmol) in acetone (150 ml) were added K$_2$CO$_3$ (3.77 g, 27.29 mmol) and pivaloyl chloride (2.29 g/3.36 ml, 27.3 mmol). The orange suspension was stirred for 2 hours at room temperature. The solids were filtered off and then washed with acetone (10 ml). The filtrate was concentrated under reduced pressure. EtOAc (100 ml) and water were added to the residue obtained. The organic phase was dried over magnesium sulfate, filtered off and concentrated under reduced pressure to give 7.2 g (95%) of 1-fluoro-5-oxo-6,7,8,9-tetrahydro-5H-benzo[7]annulen-2-yl-2,2-dimethylpropanoate (Ia24) as a beige solid. LC/MS (m/z, MH$^+$): 279

Intermediate (Ib15). 4-fluoro-9-(trifluoromethanesulfonyloxy)-6,7-dihydro-5H-benzo[7]annulen-3-yl 2,2-dimethylpropanoate

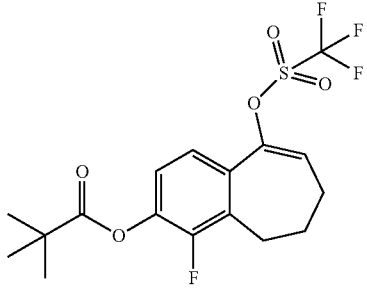 [SMILES: CC(C)(C)C(=O)Oc1ccc2c(c1F)CCCC=C2OS(=O)(=O)C(F)(F)F]

To a solution of 1-fluoro-5-oxo-6,7,8,9-tetrahydro-5H-benzo[7]annulen-2-yl-2,2-dimethylpropanoate (Ia24) (2.05 g, 7.37 mmol) in DCM (50 ml) was added under argon pyridine (0.93 ml, 11.05 mmol) and trifluoromethanesulfonic anhydride (2.5 ml, 14.73 mmol) dropwise. The reaction mixture was stirred at room temperature for 2 hours and ice (100 g) was added. The phases were separated, the aqueous phase was washed with DCM and the gathered organic phases were dried over magnesium sulfate, filtered, and evaporated under pressure. The residue was purified by flash chromatography eluting with DCM to give 2.5 g (83%) of 4-fluoro-9-(trifluoromethanesulfonyloxy)-6,7-dihydro-5H-benzo[7]annulen-3-yl-2,2-dimethylpropanoate (Ib15) as a yellow oil. LC/MS (m/z, MH$^+$): 411

Intermediate (Ir2). 4-fluoro-9-(4,4,5,5-tetramethyl-1,3,2-dioxaborolan-2-yl)-6,7-dihydro-5H-benzo[7]annulen-3-yl pivalate

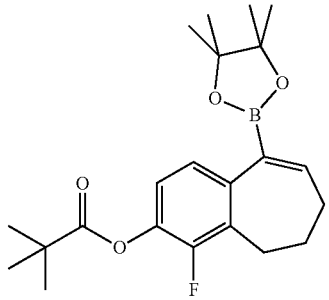 [SMILES: CC(C)(C)C(=O)Oc1ccc2c(c1F)CCCC=C2B1OC(C)(C)C(C)(C)O1]

A suspension of 4-fluoro-9-(((trifluoromethyl)sulfonyl)oxy)-6,7-dihydro-5H-benzo[7]annulen-3-yl pivalate (Ib15) (1.6 g, 3.90 mmol), bis(triphenylphosphine) palladium(II) dichloride (138 mg, 0.195 mmol), triphenylphosphine (62 mg, 0.23 mmol), bis(pinacolato)diboron (990 mg, 3.90 mmol) and potassium phenolate (773 mg, 5.85 mmol) in toluene (4 ml) was stirred at 60° C. for 4 hours. After cooling to room temperature, EtOAc and water were added. The organic phase was dried over magnesium sulfate, filtered, and concentrated under reduced pressure. The residue was purified by column chromatography eluting with a gradient of DCM in heptane (80/20 to 50/50; V/V) to give 1.09 g (72%) of 4-fluoro-9-(4,4,5,5-tetramethyl-1,3,2-dioxaborolan-2-yl)-6,7-dihydro-5H-benzo[7]annulen-3-yl pivalate (Ir2). LC/MS (m/z, MH$^+$): 389

Intermediate (Is2). (S)-4-fluoro-9-(6-((1-(3-fluoropropyl)pyrrolidin-3-yl)oxy)pyridin-3-yl)-6,7-dihydro-5H-benzo[7]annulen-3-yl pivalate

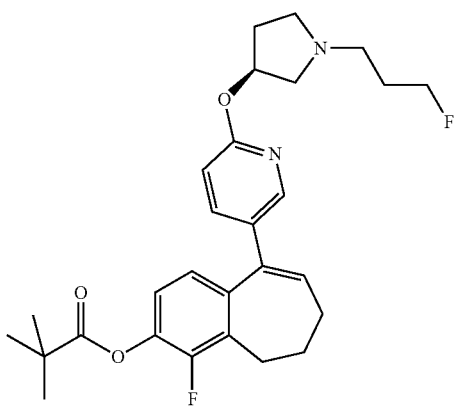 [SMILES: CC(C)(C)C(=O)Oc1ccc2c(c1F)CCCC=C2c1ccc(O[C@H]2CCN(CCCF)C2)nc1]

To a solution of 4-fluoro-9-(4,4,5,5-tetramethyl-1,3,2-dioxaborolan-2-yl)-6,7-dihydro-5H-benzo[7]annulen-3-yl pivalate (Ir2) (1.08 g, 2.78 mmol) and (S)-2-((1-(3-fluoropropyl)pyrrolidin-3-yl)oxy)-5-iodopyridine (2a) (1.07 g, 3.06 mmol), in dioxane (20 ml) was added under argon [1,1'-bis(diphenylphosphino)ferrocene]dichloropalladium (II), complex with DCM (129 mg, 0.17 mmol) and a solution of $Cs_2CO_3$ 1.5 M (7.4 ml, 11.12 mmol). The reaction mixture was stirred for one hour at 80° C. After cooling to room temperature, EtOAc and water were added. The organic phase was dried over magnesium sulfate, filtered, and concentrated under reduced pressure. The residue was purified by column chromatography eluting with a gradient of MeOH in DCM (2 to 6%; V/V) to give 1.35 g (100%) of (S)-4-fluoro-9-(6-((1-(3-fluoropropyl)pyrrolidin-3-yl)oxy)pyridin-3-yl)-6,7-dihydro-5H-benzo[7]annulen-3-yl pivalate (Is2). LC/MS (m/z, $MH^+$): 485

Intermediate (It3). (S)-8-bromo-4-fluoro-9-(6-((1-(3-fluoropropyl)pyrrolidin-3-yl)oxy)pyridin-3-yl)-6,7-dihydro-5H-benzo[7]annulen-3-yl pivalate

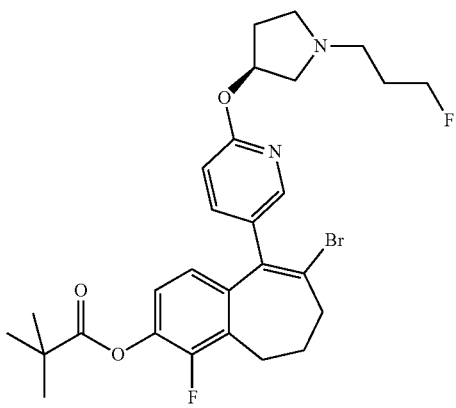 [SMILES: CC(C)(C)C(=O)Oc1ccc2c(c1F)CCCC(Br)=C2c1ccc(O[C@H]2CCN(CCCF)C2)nc1]

To a solution of (S)-4-fluoro-9-(6-((1-(3-fluoropropyl)pyrrolidin-3-yl)oxy)pyridin-3-yl)-6,7-dihydro-5H-benzo[7]annulen-3-yl pivalate (Is2) (1.35 g, 2.79 mmol) in THF (40 ml), was added pyridinium tribromide (891 mg, 2.79 mmol). The reaction mixture was stirred for 3 hours at room temperature and 60 ml of EtOAc and 20 ml of water were added followed by a concentrated solution of $NaHCO_3$ until pH7. The organic phase was dried over magnesium sulfate, filtered, evaporated under reduced pressure to give 1.1 g (74%) of (S)-8-bromo-4-fluoro-9-(6-((1-(3-fluoropropyl)pyrrolidin-3-yl)oxy)pyridin-3-yl)-6,7-dihydro-5H-benzo[7]annulen-3-yl pivalate (It3). LC/MS (m/z, $MH^+$): 563

Intermediate (It4). (S)-8-bromo-4-fluoro-9-(6-((1-(3-fluoropropyl)pyrrolidin-3-yl)oxy)pyridin-3-yl)-6,7-dihydro-5H-benzo[7]annulen-3-ol

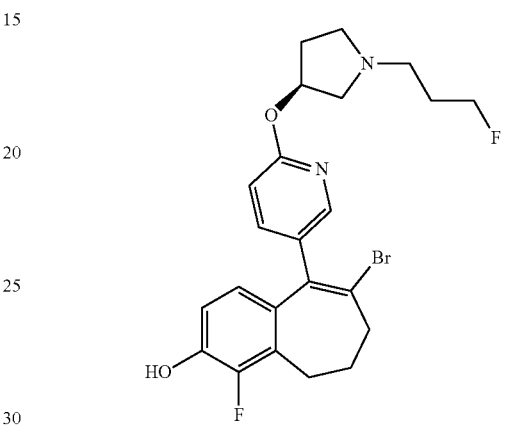

To a solution of (S)-8-bromo-4-fluoro-9-(6-((1-(3-fluoropropyl)pyrrolidin-3-yl)oxy)pyridin-3-yl)-6,7-dihydro-5H-benzo[7]annulen-3-yl pivalate (It3) (1.2 g, 2.13 mmol) in MeOH (30 ml), was added NaOH 2N (5.4 ml, 10.8 mmol). The reaction mixture was stirred 30 minutes at room temperature and 3 ml of HCl 4N were added. The solvent was removed under reduced pressure and the residue taken up into DCM. The phases were separated and the aqueous phase washed with DCM and EtOAc. The organic phase was dried over magnesium sulfate, filtered, and evaporated under reduced pressure. The residue was purified by column chromatography eluting with a gradient of MeOH in DCM (0 to 05%; V/V) to give 459 mg (45%) of (S)-8-bromo-4-fluoro-9-(6-((1-(3-fluoropropyl)pyrrolidin-3-yl)oxy)pyridin-3-yl)-6,7-dihydro-5H-benzo[7]annulen-3-ol (It4). LC/MS (m/z, $MH^+$): 479

Intermediate (Ir3). 5-(4,4,5,5-tetramethyl-1,3,2-dioxaborolan-2-yl)-2,3-dihydrobenzo[b]thiepin-8-yl pivalate

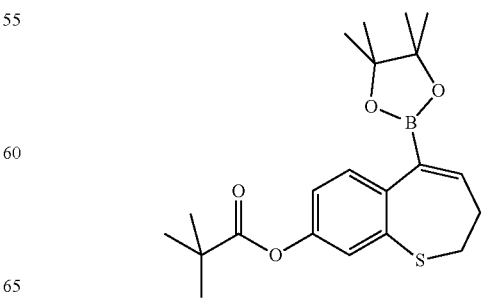

A suspension of 5-(((trifluoromethyl)sulfonyl)oxy)-2,3-dihydrobenzo[b]thiepin-8-yl pivalate (Ib12) (2.8 g, 6.82 mmol), bis(triphenylphosphine)palladium(II)dichloride (0.24 g, 0.34 mmol), triphenylphosphine (0.11 g, 0.41 mmol), bis(pinacolato)diboron (1.73 g, 6.82 mmol) and potassium phenolate (1.35 mg, 6.82 mmol) in toluene (60 ml) was stirred at 58° C. for 30 minutes. After cooling to room temperature, EtOAc and water were added. The organic phase was separated and the aqueous phase extracted with DCM. The gathered organic phases were dried over magnesium sulfate, filtered, and concentrated under reduced pressure. The residue was purified by column chromatography eluting with a gradient of DCM in heptane (0 to 40%; V/V) to give 2.05 g (77%) of 5-(4,4,5,5-tetramethyl-1,3,2-dioxaborolan-2-yl)-2,3-dihydrobenzo[b]thiepin-8-yl pivalate (Ir3). LC/MS (m/z, MH+): 389

Intermediate (Is3). (S)-5-(6-((1-(3-fluoropropyl) pyrrolidin-3-yl)oxy)pyridin-3-yl)-2,3-dihydrobenzo [b]thiepin-8-yl pivalate

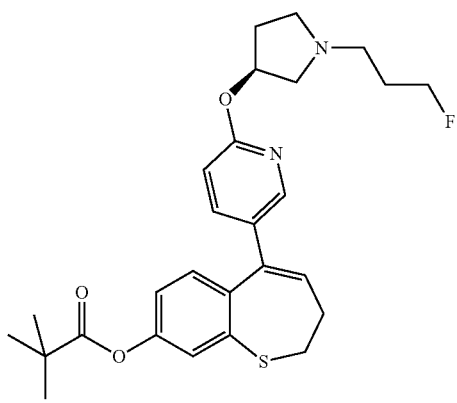 [SMILES: CC(C)(C)C(=O)Oc1ccc2c(c1)SCCC=C2c1ccc(O[C@H]2CCN(CCCF)C2)nc1]

To a solution of 5-(4,4,5,5-tetramethyl-1,3,2-dioxaborolan-2-yl)-2,3-dihydrobenzo[b]thiepin-8-yl pivalate (Ir3) (2 g, 4.64 mmol) and (S)-2-((1-(3-fluoropropyl)pyrrolidin-3-yl)oxy)-5-iodopyridine (2a) (1.79 g, 5.1 mmol), in dioxane (50 ml) was added under argon [1,1'-bis(diphenylphosphino) ferrocene]dichloropalladium(II), complex with DCM (0.36 g, 0.46 mmol) and a solution of Cs2CO3 (4.53 g, 13.91 mmol) in water (10 ml). The reaction mixture was stirred for one hour at 60° C. After cooling to room temperature, the reaction mixture was partitioned between water and DCM. The aqueous phase was washed twice with DCM and the gathered organic phases dried over magnesium sulfate, filtered, and concentrated under reduced pressure The residue was purified by column chromatography eluting with a gradient of MeOH in DCM (0 to 5%; V/V) to give 2.37 g (100%) of crude (S)-5-(6-((1-(3-fluoropropyl)pyrrolidin-3-yl)oxy)pyridin-3-yl)-2,3-dihydrobenzo[b]thiepin-8-yl pivalate (Is3). LC/MS (m/z, MH+): 485

Intermediate (It5). (S)-4-bromo-5-(6-((1-(3-fluoropropyl)pyrrolidin-3-yl)oxy)pyridin-3-yl)-2,3-dihydrobenzo[b]thiepin-8-yl pivalate

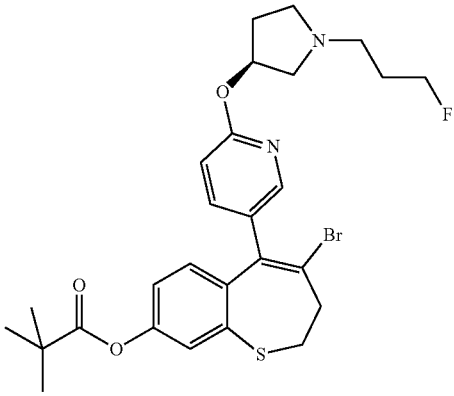 [SMILES: CC(C)(C)C(=O)Oc1ccc2c(c1)SCCC(Br)=C2c1ccc(O[C@H]2CCN(CCCF)C2)nc1]

To a solution of (S)-5-(6-((1-(3-fluoropropyl)pyrrolidin-3-yl)oxy)pyridin-3-yl)-2,3-dihydrobenzo[b]thiepin-8-yl pivalate (Is3) (2.37 g, 3.42 mmol) in THF (250 ml), was added pyridinium tribromide (1.34 g, 3.77 mmol). The reaction mixture was stirred for 16 hours at room temperature and water (100 ml) was added. The pH was adjusted to 7 with a concentrated solution of NaHCO3. The aqueous phase was washed with 3 times with DCM and the gathered organic phases dried over magnesium sulfate and filtered. The organic phases were evaporated under reduced pressure and the residue was purified by column chromatography eluting with a gradient of MeOH in DCM (0 to 5%; V/V) to give 1.68 g (87%) of crude (S)-4-bromo-5-(6-((1-(3-fluoropropyl)pyrrolidin-3-yl)oxy)pyridin-3-yl)-2,3-dihydrobenzo [b]thiepin-8-yl pivalate (It5) which will be used as such in the next step. LC/MS (m/z, MH+): 563

Intermediate (It6). (S)-4-bromo-5-(6-((1-(3-fluoropropyl)pyrrolidin-3-yl)oxy)pyridin-3-yl)-2,3-dihydrobenzo[b]thiepin-8-ol

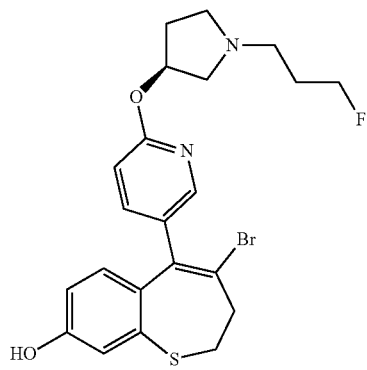 [SMILES: Oc1ccc2c(c1)SCCC(Br)=C2c1ccc(O[C@H]2CCN(CCCF)C2)nc1]

To a solution of (S)-4-bromo-5-(6-((1-(3-fluoropropyl)pyrrolidin-3-yl)oxy)pyridin-3-yl)-2,3-dihydrobenzo[b]thiepin-8-yl pivalate (It5) (1.67 g, 2.37 mmol) in MeOH (24 ml), was added aqueous NaOH 2N (5 ml, 10.00 mmol). The reaction mixture was stirred for 2 minutes at room temperature and was added aqueous HCl 5N to adjust pH. The solvent was removed under reduced pressure and the residue taken up into DCM. The phases were separated and the aqueous phase washed twice with DCM/MeOH 95/05; V/V and EtOAc. The organic phases were combined and dried over magnesium sulfate, filtered, and evaporated under reduced pressure. The residue was purified by column chromatography eluting with a gradient of MeOH in DCM (0 to 5%; V/V) to give 0.93 g (82%) of crude (S)-4-bromo-5-(6-((1-(3-fluoropropyl)pyrrolidin-3-yl)oxy)pyridin-3-yl)-2,3-dihydrobenzo[b]thiepin-8-ol (It6). LC/MS (m/z, MH+): 479

Reagent 2b. (S)-5-bromo-2-((1-(3-fluoropropyl)pyrrolidin-3-yl)oxy)pyrimidine

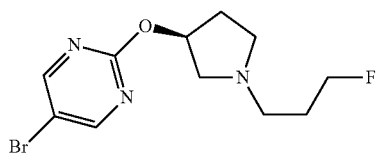 [SMILES: FCCCN1CC[C@H](Oc2ncc(Br)cn2)C1]

Step 1. (R)-1-(3-fluoropropyl)pyrrolidin-3-ol

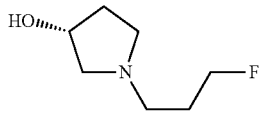

A suspension of (R)-3-hydroxypyrrolidine (5 g, 54.52 mmol), 1-fluoro-3-iodopropane (11.27 g, 59.97 mmol), potassium carbonate (22.61 g, 163.57 mmol) and acetonitrile (50 ml) was stirred at 50° C. for 4 h. After cooling to room temperature, the suspension was filtered, and concentrated under reduced pressure. To the residue obtained, addition of DCM (200 ml) and saturated solution of sodium chloride (50 ml). The organic phase was dried over magnesium sulfate, filtered, and concentrated under reduced pressure to give 5 g (62%) of (R)-1-(3-fluoropropyl)pyrrolidin-3-ol as a pale yellow oil. LC/MS (m/z, MH+): 148

Step 2. (S)-5-bromo-2-((1-(3-fluoropropyl)pyrrolidin-3-yl)oxy)pyrimidine (2b)

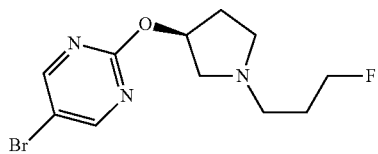 [SMILES: FCCCN1CC[C@H](Oc2ncc(Br)cn2)C1]

A mixture of (R)-1-(3-fluoropropyl)pyrrolidin-3-ol (1.53 g, 10.39 mmol), 5-bromo-2-hydroxypyrimidine (1.74 g; 9.45 mmol), triphenylphosphine (4.25 g, 16.06 mmol), (E)-N1,N1,N2,N2-tetramethyldiazene-1,2-dicarboxamide (2.91 g, 16.06 mmol) and THF (5 ml) was stirred at room temperature for 18 h. Addition of EtOAc (50 ml) and water (20 ml).

The organic phase was dried over magnesium sulfate, filtered, and concentrated under reduced pressure. The residue was purified by column chromatography eluting with a mixture of DCM and MeOH (95/05; v/v) to give 1.7 g (59%) of (S)-5-bromo-2-((1-(3-fluoropropyl)pyrrolidin-3-yl)oxy)pyrimidine (2b). LC/MS (m/z, MH+): 204

Intermediate (Is4). (S)-9-(2-((1-(3-fluoropropyl)pyrrolidin-3-yl)oxy)pyrimidin-5-yl)-6,7-di hydro-5H-benzo[7]annulen-3-yl pivalate

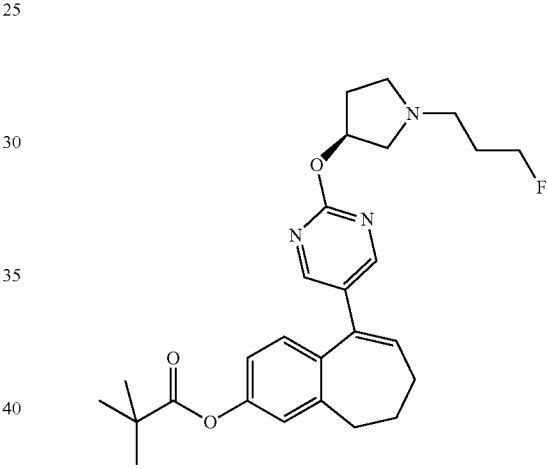

To a solution of 9-(4,4,5,5-tetramethyl-1,3,2-dioxaborolan-2-yl)-6,7-dihydro-5H-benzo[7]annulen-3-yl pivalate (Ir1) (300 mg, 0.81 mmol) and (S)-5-bromo-2-((1-(3-fluoropropyl)pyrrolidin-3-yl)oxy)pyrimidine (2b) (246.42 mg, 810.18 μmol), in dioxane (2 ml) was added under argon [1,1'-bis(diphenylphosphino)ferrocene]dichloropalladium (II), complex with DCM (40.00 mg, 0.49 mmol) and a solution of $Cs_2CO_3$ 1.5 M (2.16 ml, 3.24 mmol). The reaction mixture was stirred for one hour at 80° C. After cooling to room temperature, EtOAc and water were added. The organic phase was dried over magnesium sulfate, filtered, and concentrated under reduced pressure. The residue was purified by column chromatography eluting with a gradient of MeOH in DCM (2 to 6%; V/V) to give 380 mg (100%) of (S)-9-(2-((1-(3-fluoropropyl)pyrrolidin-3-yl)oxy)pyrimidin-5-yl)-6,7-dihydro-5H-benzo[7]annulen-3-yl pivalate (Is4). LC/MS (m/z, MH+): 468

Intermediate (It7). (S)-8-bromo-9-(2-((1-(3-fluoropropyl)pyrrolidin-3-yl)oxy)pyrimidin-5-yl)-6,7-dihydro-5H-benzo[7]annulen-3-yl pivalate

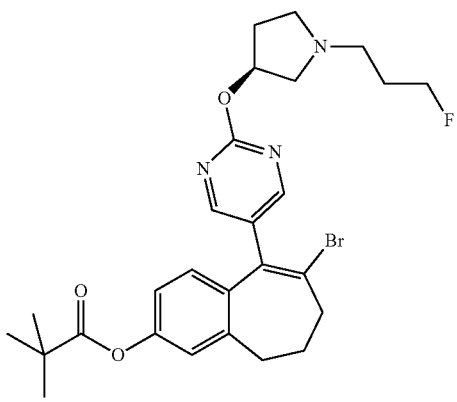 [SMILES: CC(C)(C)C(=O)Oc1ccc2c(c1)CCCC(Br)=C2c1cnc(O[C@H]2CCN(CCCF)C2)nc1]

To a solution of (S)-9-(2-((1-(3-fluoropropyl)pyrrolidin-3-yl)oxy)pyrimidin-5-yl)-6,7-dihydro-5H-benzo[7]annulen-3-yl pivalate (Is4) (100 mg, 0.21 mmol) in DCM (5 ml), was added pyridinium tribromide (288 mg, 0.82 mmol). The reaction mixture was stirred for 1 hour at room temperature and 20 ml of EtOAc and 5 ml of water were added. The organic phase was dried over magnesium sulfate, filtered, evaporated under reduced pressure to give 130 mg (98%) of (S)-8-bromo-9-(2-((1-(3-fluoropropyl)pyrrolidin-3-yl)oxy)pyrimidin-5-yl)-6,7-dihydro-5H-benzo[7]annulen-3-yl pivalate hydrobromide salt (It7) which was used as such in the next step. LC/MS (m/z, MH+): 546

Intermediate (It8). (S)-8-bromo-9-(2-((1-(3-fluoropropyl)pyrrolidin-3-yl)oxy)pyrimidin-5-yl)-6,7-dihydro-5H-benzo[7]annulen-3-ol

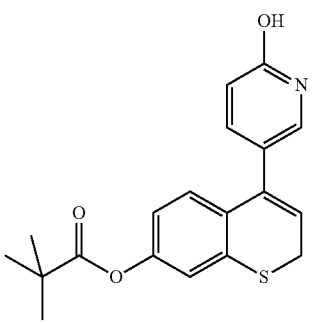 [SMILES: CC(C)(C)C(=O)Oc1ccc2c(c1)SCC=C2c1ccc(O)nc1]

To a solution of (S)-8-bromo-9-(2-((1-(3-fluoropropyl)pyrrolidin-3-yl)oxy)pyrimidin-5-yl)-6,7-dihydro-5H-benzo[7]annulen-3-yl pivalate hydrobromide salt (It7) (130 mg, 0.21 mmol) in MeOH (5 ml), was added NaOH 2N (0.5 ml, 4 mmol). The reaction mixture was stirred 30 minutes at room temperature and 0.5 ml of HCl 1N were added. The solvent was removed under reduced pressure and the residue taken up into DCM. The phases were separated and the aqueous phase washed with DCM. The organic phase was dried over magnesium sulfate, filtered, and evaporated under reduced pressure. The residue was purified by column chromatography eluting with a gradient of MeOH in DCM (0 to 05%; V/V) to give 70 mg (71%) of (S)-8-bromo-9-(2-((1-(3-fluoropropyl)pyrrolidin-3-yl)oxy)pyrimidin-5-yl)-6,7-dihydro-5H-benzo[7]annulen-3-ol (It8). LC/MS (m/z, MH+): 462

Intermediate (Iu1). 4-(6-hydroxypyridin-3-yl)-2H-thiochromen-7-yl pivalate

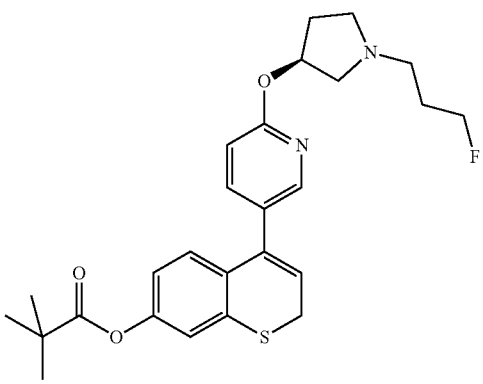 [SMILES: CC(C)(C)C(=O)Oc1ccc2c(c1)SCC=C2c1ccc(O[C@H]2CCN(CCCF)C2)nc1]

In a mixture of 4-(((trifluoromethyl)sulfonyl)oxy)-2H-thiochromen-7-yl pivalate (Ib4) (1.2 g, 3.03 mmol) in 1,4-dioxane/water: 80/20 (v/v) (15 ml) were added 5-(4,4,5,5-tetramethyl-1,3,2-dioxaborolan-2-yl)pyridin-2-ol (736 mg, 3.33 mmol), $Cs_2CO_3$ (2.10 g, 6.45 mmol) and [1,1'-bis(diphenylphosphino)ferrocene]dichloropalladium(II), complex with DCM (247 mg, 302.7 μmol) and the mixture was stirred at 120° C. for 30 min. The reaction mixture was cooled to room temperature and silica Si60 (40-60 μm) (4.4 g) was added. The mixture was concentrated under reduced pressure and the solid residue was purified by flash chromatography eluting with a gradient of n-heptane in EtOAc (10/90; v/v) to pure EtOAc, to give 401 mg (39%) of 4-(6-hydroxypyridin-3-yl)-2H-thiochromen-7-yl pivalate (Iu1). LC/MS (m/z, MH+): 342

Intermediate (Is5). (S)-4-(6-((1-(3-fluoropropyl)pyrrolidin-3-yl)oxy)pyridin-3-yl)-2H-thiochromen-7-yl pivalate To a mixture of 4-(6-hydroxypyridin-3-yl)-2H-thiochromen-7-yl pivalate (Iu1) (455 mg, 1.33 mmol), (R)-1-(3-fluoropropyl)pyrrolidin-3-ol (216 mg, 1.47 mmol) and triphenylphosphine (603 mg, 2.27 mmol) in THF (11 ml), was added diisopropyl azodicarboxylate (446 μl, 2.27 mmol). The reaction mixture was stirred for 4.5 hours at room temperature. After completion, the mixture was concentrated under reduced pressure and the residue was purified by flash chromatography eluting with a gradient of DCM in MeOH (99/1 to 98/2; v/v), to give 339 mg (54%) of (S)-4-(6-((1-(3-fluoropropyl)pyrrolidin-3-yl)oxy)pyridin-3-yl)-2H-thiochromen-7-yl pivalate (Is5) as a yellow resin. LC/MS (m/z, MH+): 471

Intermediate (It9). (S)-3-bromo-4-(6-((1-(3-fluoropropyl)pyrrolidin-3-yl)oxy)pyridin-3-yl)-2H-thiochromen-7-yl pivalate

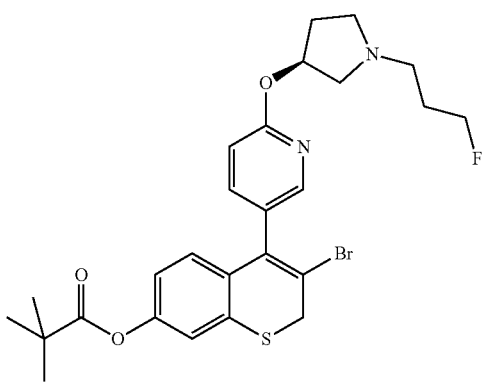 [SMILES: CC(C)(C)C(=O)Oc1ccc2c(c1)SCC(Br)=C2c1ccc(O[C@H]2CCN(CCCF)C2)nc1]

To a solution of (S)-4-(6-((1-(3-fluoropropyl)pyrrolidin-3-yl)oxy)pyridin-3-yl)-2H-thiochromen-7-yl pivalate (Is5) (336 mg, 714 μmol) in DCM (7 ml) at room temperature, was added pyridinium tribromide (304 mg, 857 μmol). The reaction mixture was stirred for 1 hour at room temperature. Then, it was washed with water (2 ml) and brine (2 ml). The organic phase was dried over magnesium sulfate and concentrated under reduced pressure and the residue was purified by flash chromatography eluting with a mixture of DCM and B (95/5 to 90/10; v/v) (B: DCM/MeOH/ammonia solution 7N in MeOH: 85/15/1; v/v) to give 306 mg (78%) of (S)-3-bromo-4-(6-((1-(3-fluoropropyl)pyrrolidin-3-yl)oxy)pyridin-3-yl)-2H-thiochromen-7-yl pivalate (It9). LC/MS (m/z, MH+): 549

Intermediate (It0). (S)-3-bromo-4-(6-((1-(3-fluoropropyl)pyrrolidin-3-yl)oxy)pyridin-3-yl)-2H-thiochromen-7-ol

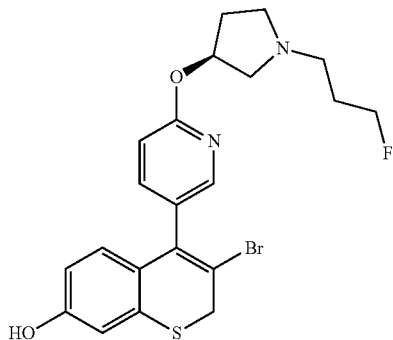 [SMILES: Oc1ccc2c(c1)SCC(Br)=C2c1ccc(O[C@H]2CCN(CCCF)C2)nc1]

A solution of (S)-3-bromo-4-(6-((1-(3-fluoropropyl)pyrrolidin-3-yl)oxy)pyridin-3-yl)-2H-thiochromen-7-yl pivalate (It9) (336 mg, 611.5 μmol) in MeOH (7 ml) and sodium hydroxide 2M (1.35 ml, 2.70 mmol) was stirred for 30 min at room temperature. Aqueous hydrochloric acid 2M was added to adjust the pH to 6/7. The mixture was extracted with DCM and the organic phase was dried over magnesium sulfate and concentrated under reduced pressure. The residue was purified by flash chromatography eluting with a mixture of DCM and MeOH (95/5; v/v), to give 300 mg (100%) of (S)-3-bromo-4-(6-((1-(3-fluoropropyl)pyrrolidin-3-yl)oxy)pyridin-3-yl)-2H-thiochromen-7-ol (It10) as a light brown solid. LC/MS (m/z, MH+): 465

Intermediate (Iu2). 4-(2-hydroxypyrimidin-5-yl)-2H-thiochromen-7-yl pivalate

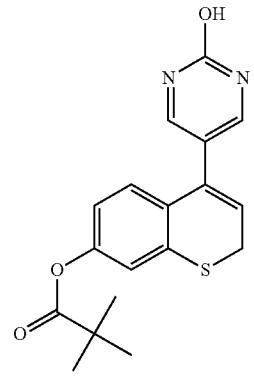 [SMILES: CC(C)(C)C(=O)Oc1ccc2c(c1)SCC=C2c1cnc(O)nc1]

To a mixture of 4-(((trifluoromethyl)sulfonyl)oxy)-2H-thiochromen-7-yl pivalate (Ib4) (1.5 g, 3.78 mmol), 2-hydroxypyrimidine-5-boronic acid pinacolester (973 mg, 4.16 mmol) and [1,1'-bis(diphenylphosphino)ferrocene]dichloropalladium(II), complex with DCM (154 mg, 0.19 mmol) in dioxane (30 ml), was added dropwise a solution of Cs$_2$CO$_3$ 1.5 M (10 ml, 15 mmol). The reaction mixture was stirred for one hour at 100° C. After cooling to room temperature, water (20 ml) and EtOAc (50 ml) were added. The organic phase was dried over magnesium sulfate, filtered, and concentrated under reduced pressure. The residue was purified by flash chromatography eluting with a gradient of MeOH in DCM (0 to 05%; V/V) to give 200 mg (15%) of 4-(2-hydroxypyrimidin-5-yl)-2H-thiochromen-7-yl pivalate (Iu2) as a beige solid. LC/MS (m/z, MH+): 343

Intermediate (Is6). (S)-4-(2-((1-(3-fluoropropyl) pyrrolidin-3-yl)oxy)pyrimidin-5-yl)-2H-thiochromen-7-yl pivalate

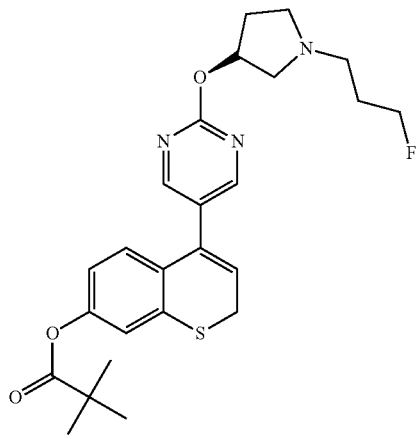

To a solution of 4-(2-hydroxypyrimidin-5-yl)-2H-thiochromen-7-yl pivalate (Iu2) (200 mg, 0.584 mmol) in THF (5 ml), were added (R)-1-(3-fluoropropyl)pyrrolidin-3-ol (95 mg, 0.642 mmol), (E)-N1,N1,N2,N2-tetramethyldiazene-1,2-dicarboxamide (173 mg, 0.993 mmol) and triphenylphosphine (263 mg, 0.993 mmol). The reaction mixture was stirred for 24 hours at room temperature. Water and EtOAc were added. After decantation, the organic phase was dried over magnesium sulfate, filtered, and concentrated under reduced pressure. The residue was purified by flash chromatography eluting with a gradient of MeOH in DCM (0 to 05%; V/V) to give 250 mg (91%) of (S)-4-(2-((1-(3-fluoropropyl)pyrrolidin-3-yl)oxy)pyrimidin-5-yl)-2H-thiochromen-7-yl pivalate (Is6). LC/MS (m/z, MH⁺): 472

Intermediate (It11). 3-bromo-4-(2-{[1-(3-fluoropropyl)pyrrolidin-3-yl]oxy}pyrimidin-5-yl)-2H-thiochromen-7-yl 2,2-dimethylpropanoate, hydrobromide salt

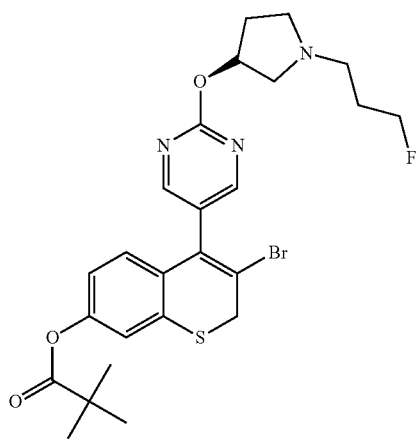

To a solution of (S)-4-(2-((1-(3-fluoropropyl)pyrrolidin-3-yl)oxy)pyrimidin-5-yl)-2H-thiochromen-7-yl pivalate (Is6) (250 mg, 0.53 mmol) in DCM (5 ml), was added pyridinium tribromide (288 mg, 0.82 mmol). The reaction mixture was stirred for 1 hour at room temperature and 2 ml of water were added. The organic phase was dried over magnesium sulfate, filtered, evaporated under reduced pressure to give 300 mg (90%) of 3-bromo-4-(2-{[1-(3-fluoropropyl)pyrrolidin-3-yl]oxy}pyrimidin-5-yl)-2H-thiochromen-7-yl 2,2-dimethylpropanoate hydrobromide salt (It11) which was used as such in the next step. LC/MS (m/z, MH⁺): 550

Intermediate (It12). (S)-3-bromo-4-(2-((1-(3-fluoropropyl)pyrrolidin-3-yl)oxy)pyrimidin-5-yl)-2H-thiochromen-7-ol

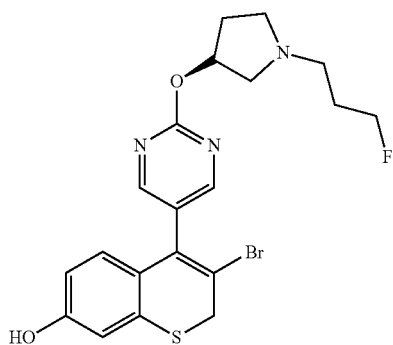

To a solution of 3-bromo-4-(2-{[1-(3-fluoropropyl)pyrrolidin-3-yl]oxy}pyrimidin-5-yl)-2H-thiochromen-7-yl 2,2-dimethylpropanoate hydrobromide salt (It11) (300 mg, 0.48 mmol) in MeOH (5 ml), was added NaOH 2N (1 ml, 8 mmol). The reaction mixture was stirred 30 minutes at room temperature and 2 ml of HCl 1N were added. The solvent was removed under reduced pressure and the residue taken up into DCM. The phases were separated and the aqueous phase washed with DCM. The organic phase was dried over magnesium sulfate, filtered, and evaporated under reduced pressure. The residue was purified by column chromatography eluting with a gradient of MeOH in DCM (0 to 05%; V/V) to give 170 mg (69%) of (S)-3-bromo-4-(2-((1-(3-fluoropropyl)pyrrolidin-3-yl)oxy)pyrimidin-5-yl)-2H-thiochromen-7-ol (It12). LC/MS (m/z, MH⁺): 466

Reagent 2a'. (S)-tert-butyl 3-((5-bromopyrazin-2-yl)oxy)pyrrolidine-1-carboxylate

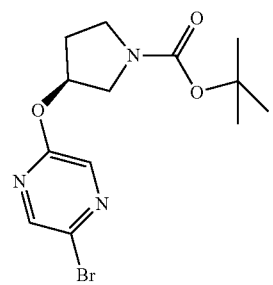 [SMILES: CC(C)(C)OC(=O)N1CC[C@H](Oc2cnc(Br)cn2)C1]

A mixture of (R)-1-N-Boc-3-hydroxypyrrolidine (5 g, 25.90 mmol), 5-bromopyrazin-2-ol (5.44 g, 31.08 mmol), triphenylphosphine (8.15 g, 31.08 mmol), (E)-N1,N1,N2, N2-tetramethyldiazene-1,2-dicarboxamide (6.12 ml, 31.08 mmol) and THF (150 ml) was stirred at room temperature for 24 h. After addition of EtOAc and water, the organic phase was dried over magnesium sulfate, filtered, and concentrated under reduced pressure. The residue was purified by flash chromatography eluting with a mixture of DCM and MeOH (98/02; v/v) to give 7.4 g (83%) (S)-tert-butyl 3-((5-bromopyrazin-2-yl)oxy)pyrrolidine-1-carboxylate (2a'). LC/MS (m/z, MH+): 344

Intermediate (Iv). 6-bromo-2-methoxy-6,7,8,9-tetrahydro-5H-benzo[7]annulen-5-one

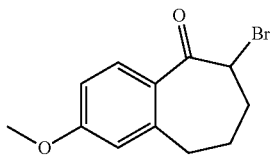

To a solution of 2-methoxy-6,7,8,9-tetrahydro-benzocyclohepten-5-one (10 g, 50.99 mmol) in diethyl ether (100 ml), was added dropwise at 0° C. a solution of bromine (2.80 ml, 54.05). The reaction mixture was stirred for 1 hour at 0° C. then EtOAc and water were added. The organic phase was dried over magnesium sulfate, filtered, evaporated under reduced pressure to give a residue which was purified by flash chromatography eluting with a gradient of EtOAc in heptane (0 to 10%; V/V) to give 10.29 g (75%) of 6-bromo-2-methoxy-6,7,8,9-tetrahydro-5H-benzo[7]annulen-5-one (Iv). LC/MS (m/z, MH+): 269

Intermediate (Iw1). 8-bromo-3-methoxy-6,7-dihydro-5H-benzo[7]annulen-9-yl acetate

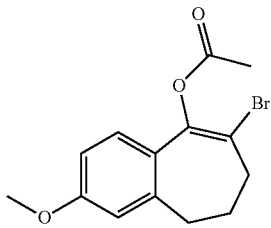 [SMILES: COc1ccc2c(c1)CCCC(Br)=C2OC(C)=O]

To a solution under argon of 6-bromo-2-methoxy-6,7,8, 9-tetrahydro-5H-benzo[7]annulen-5-one (Iv1) (15.47 g, 57.48 mmol) (10 g, 50.99 mmol) in THF (130 ml), was added dropwise at −70° C. a solution of lithium bis(trimethylsilyl)amide (63.23 ml, 63.23 mmol) 1M in THF. After 15 minutes, acetic anhydride (16.43 ml, 172.44 mmol) was added and the reaction mixture was stirred for 20 hours at room temperature. EtOAc and water were added and the organic phase was dried over magnesium sulfate, filtered, evaporated under reduced pressure to give a residue which was purified by flash chromatography eluting with a gradient of EtOAc in heptane (0 to 10%; V/V) to give 16.23 g (91%) of 8-bromo-3-methoxy-6,7-dihydro-5H-benzo[7]annulen-9-yl acetate (Iw1). LC/MS (m/z, MH+): 311

Intermediate (Ix1). 8-(4-chloro-3-fluorophenyl)-3-methoxy-6,7-dihydro-5H-benzo[7]annulen-9-yl cetate

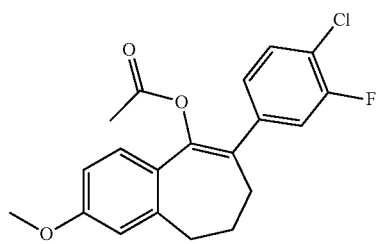 [SMILES: COc1ccc2c(c1)CCCC(c1ccc(Cl)c(F)c1)=C2OC(C)=O]

To a solution under argon of 8-bromo-3-methoxy-6,7-dihydro-5H-benzo[7]annulen-9-yl acetate (Iw1) (8 g, 25.71 mmol), in dioxane (200 ml) and water (50 ml), was introduced 4-chloro-3-fluorophenylboronic acid (4.93 g, 28.28 mmol), Cs$_2$CO$_3$ (17.61 g, 53.99 mmol), and [1,1'-bis(diphenylphosphino)ferrocene]dichloropalladium(II), complex with DCM (1.26 g, 1.54 mmol). The reaction mixture was heated at 90° C. for 40 minutes. After cooling, EtOAc and water were added and the organic phase was dried over magnesium sulfate, filtered, evaporated under reduced pressure to give a residue which was purified by cristallisation in MeOH to give 6.73 g (72%) of 8-(4-chloro-3-fluorophenyl)-3-methoxy-6,7-dihydro-5H-benzo[7]annulen-9-yl cetate (Ix1). LC/MS (m/z, MH+): 361

Intermediate (Iy1). 6-(4-chloro-3-fluorophenyl)-2-methoxy-6,7,8,9-tetrahydro-5H-benzo[7]annulen-5-one

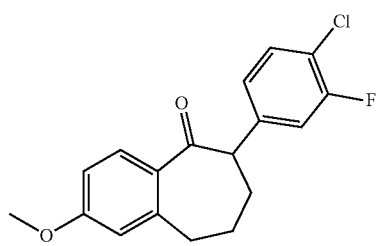 [SMILES: COc1ccc2c(c1)CCCC(c1ccc(Cl)c(F)c1)C2=O]

To a solution of methyl 8-(4-chloro-3-fluorophenyl)-3-methoxy-6,7-dihydro-5H-benzo[7]annulen-9-yl acetate (Ix1) (6.73 g, 18.65 mmol), in MeOH (130 mL), was added dropwise an aqueous solution of sodium hydroxide 2M (18.65 ml, 37.31 mmol). The reaction mixture was heated at 50° C. for 1 hour. After cooling to room temperature, the reaction mixture was neutralized with HCl 2N then the MeOH was concentrated under reduced pressure, EtOAc and water were added and the organic phase was dried over magnesium sulfate, filtered, evaporated under reduced pressure to give a residue which was purified by flash chromatography eluting with a gradient of EtOAc in heptane (0 to 10%; V/V) to give 3.73 g (62%) of 6-(4-chloro-3-fluorophenyl)-2-methoxy-6,7,8,9-tetrahydro-5H-benzo[7]annulen-5-one (Iy1). LC/MS (m/z, MH+): 319

295

Intermediate (Iz1). 8-(4-chloro-3-fluorophenyl)-3-methoxy-6,7-dihydro-5H-benzo[7]annulen-9-yl trifluoromethanesulfonate

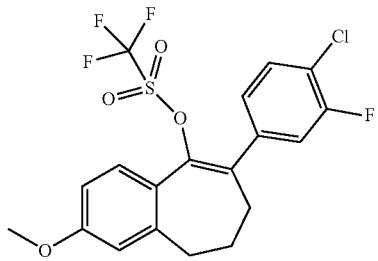 [SMILES: COc1ccc2c(c1)CCCC(c1ccc(Cl)c(F)c1)=C2OS(=O)(=O)C(F)(F)F]

To a solution of 6-(4-chloro-3-fluorophenyl)-2-methoxy-6,7,8,9-tetrahydro-5H-benzo[7]annulen-5-one (Iy1) (4.13 g, 12.96 mmol) in DCM (70 ml) was added under argon pyridine (1.57 ml, 19.43 mmol) and trifluoromethanesulfonic anhydride (5.47 ml, 32.39 mmol) dropwise. The reaction mixture was stirred at room temperature for 1 hour and water was added. The phases were separated, the aqueous phase was washed with DCM and the gathered organic phases were dried over magnesium sulfate, filtered, and evaporated under pressure. The residue was purified by flash chromatography eluting with a gradient of EtOAc in heptane (0 to 10%; V/V) to give 3.2 g (66%) of 8-(4-chloro-3-fluorophenyl)-3-methoxy-6,7-dihydro-5H-benzo[7]annulen-9-yl trifluoromethanesulfonate (Iz1). LC/MS (m/z, MH$^+$): 451

Intermediate (Iaa1). 2-(8-(4-chloro-3-fluorophenyl)-3-methoxy-6,7-dihydro-5H-benzo[7]annulen-9-yl)-4,4,5,5-tetramethyl-1,3,2-dioxaborolane

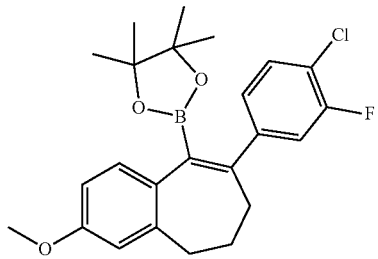 [SMILES: COc1ccc2c(c1)CCCC(c1ccc(Cl)c(F)c1)=C2B1OC(C)(C)C(C)(C)O1]

A suspension of 8-(4-chloro-3-fluorophenyl)-3-methoxy-6,7-dihydro-5H-benzo[7]annulen-9-yl trifluoromethanesulfonate (Iz1) (2.85 g, 6.32 mmol), bis(triphenylphosphine)palladium(II)dichloride (113 mg, 0.189 mmol), triphenylphosphine (99.41 mg, 0.379 mmol), bis(pinacolato) diboron (2.41 g, 9.48 mmol), potassium phenolate (1.67 g, 12.63 mmol) and potassium bromide (1.13 g, 9.48 mmol) in toluene (75 ml) was stirred at 50° C. for 2 hours. After cooling to room temperature, addition of EtOAc and water. The organic phase was dried over magnesium sulfate, filtered, and concentrated under reduced pressure. The residue was purified by flash chromatography eluting with a gradient of EtOAc in heptane (0/100 to 10/90; V/V) to give 2.28 g (84%) of 2-(8-(4-chloro-3-fluorophenyl)-3-methoxy-6,7-dihydro-5H-benzo[7]annulen-9-yl)-4,4,5,5-tetramethyl-1,3,2-dioxaborolane (Iaa1) as an yellow oil. LC/MS (m/z, MH$^+$): 429

296

Intermediate (Iab1). (S)-tert-butyl 3-((5-(8-(4-chloro-3-fluorophenyl)-3-methoxy-6,7-dihydro-5H-benzo[7]annulen-9-yl)pyrazin-2-yl)oxy)pyrrolidine-1-carboxylate

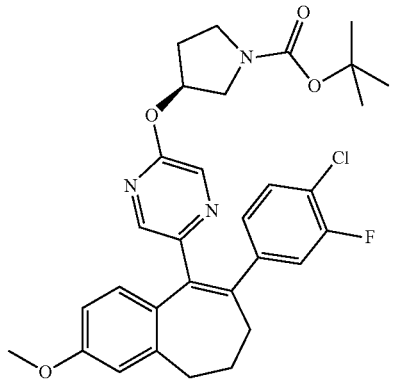 [SMILES: COc1ccc2c(c1)CCCC(c1ccc(Cl)c(F)c1)=C2c1cnc(O[C@H]2CCN(C(=O)OC(C)(C)C)C2)cn1]

To a solution of 2-(8-(4-chloro-3-fluorophenyl)-3-methoxy-6,7-dihydro-5H-benzo[7]annulen-9-yl)-4,4,5,5-tetramethyl-1,3,2-dioxaborolane (Iaa1) (2.1 g, 4.90 mmol) and S)-tert-butyl 3-((5-bromopyrazin-2-yl)oxy)pyrrolidine-1-carboxylate (2a') (3.37 g, 9.80 mmol), in dioxane (40 ml)/water (10 ml) was added under argon [1,1'-bis(diphenylphosphino)ferrocene]dichloropalladium(II), complex with DCM (400 mg, 0.489 mmol) and Cs$_2$CO$_3$ (3.35 g, 10.29 mmol). The reaction mixture was stirred for 24 hours at 90° C. After cooling to room temperature, addition of EtOAc and water, the organic phase was dried over magnesium sulfate, filtered, and concentrated under reduced pressure. The residue was purified by column chromatography eluting with a gradient of EtOAc in heptane (0 to 30%; V/V) to give 1.1 g (40%) of (S)-tert-butyl 3-((5-(8-(4-chloro-3-fluorophenyl)-3-methoxy-6,7-dihydro-5H-benzo[7]annulen-9-yl)pyrazin-2-yl)oxy) pyrrolidine-1-carboxylate (Iab1). LC/MS (m/z, MH$^+$): 566

Intermediate (Iac1). (S)-2-(8-(4-chloro-3-fluorophenyl)-3-methoxy-6,7-dihydro-5H-benzo[7]annulen-9-yl)-5-(pyrrolidin-3-yloxy)pyrazine hydrochloride

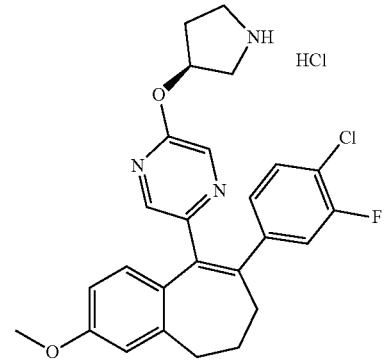 [SMILES: COc1ccc2c(c1)CCCC(c1ccc(Cl)c(F)c1)=C2c1cnc(O[C@H]2CCNC2)cn1 ; Cl]

To a solution of (S)-tert-butyl 3-((5-(8-(4-chloro-3-fluorophenyl)-3-methoxy-6,7-dihydro-5H-benzo[7]annulen-9-yl)pyrazin-2-yl)oxy)pyrrolidine-1-carboxylate (Iab1) (1.1 g, 1.94 mmol) in DCM (30 ml), was added dropwise HCl 2N in ether (10 ml, 20 mmol). The reaction mixture was stirred at room temperature for 48 h then concentrated under reduced pressure. The residue obtained was triturated with ethyl ether and the solid was filtered, and dried to give 980 mg (100%) of (S)-2-(8-(4-chloro-3-fluorophenyl)-3-methoxy-6,7-dihydro-5H-benzo[7]annulen-9-yl)-5-(pyrrolidin-3-yloxy)pyrazine hydrochloride (Iac1). LC/MS (m/z, MH+): 466

Intermediate (Iac2). (S)-8-(4-chloro-3-fluorophenyl)-9-(5-(pyrrolidin-3-yloxy)pyrazin-2-yl)-6,7-dihydro-5H-benzo[7]annulen-3-ol

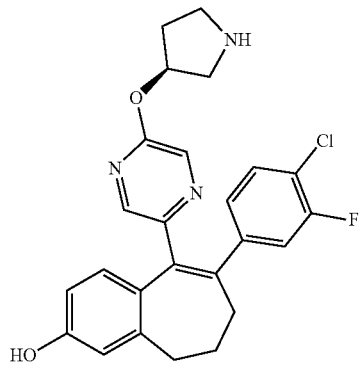 [SMILES: Oc1ccc2c(c1)CCCC(c1ccc(Cl)c(F)c1)=C2c1cnc(O[C@H]2CCNC2)cn1]

To a solution cooled at 0° C. of (S)-2-(8-(4-chloro-3-fluorophenyl)-3-methoxy-6,7-dihydro-5H-benzo[7]annulen-9-yl)-5-(pyrrolidin-3-yloxy)pyrazine hydrochloride (Iac1) (980 mg, 1.95 mmol) in DCM (20 ml), boron tribromide (5.85 ml, 5.85 mmol) was added dropwise. After stirring for 1 hour, the reaction mixture was poured onto aqueous HCl 1N, neutralize with aqueous NaOH 1M and EtOAc was added. The organic phase was dried over magnesium sulfate, filtered, and concentrated under reduced pressure to give 696 mg (80%) of (S)-8-(4-chloro-3-fluorophenyl)-9-(5-(pyrrolidin-3-yloxy)pyrazin-2-yl)-6,7-dihydro-5H-benzo[7]annulen-3-ol (Iac2). LC/MS (m/z, MH+): 452

Reagent 2b'. (S)-tert-butyl 3-((2-iodopyrimidin-5-yl)oxy)pyrrolidine-1-carboxylate

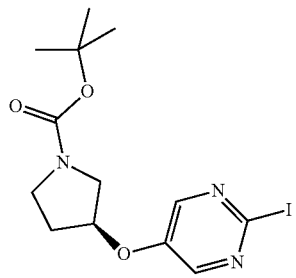 [SMILES: CC(C)(C)OC(=O)N1CC[C@H](Oc2cnc(I)nc2)C1]

To a solution of 2-iodopyrimidin-5-ol (200 mg, 900.97 μmol) in THE (3 ml), were added (R)-1-N-Boc-3-hydroxypyrrolidine (208.69 mg, 1.08 mmol) and triphenylphosphine (283.57 g, 1.08 mmol). After cooling at 0° C., (E)-N1,N1,N2,N2-tetramethyldiazene-1,2-dicarboxamide (0.2 ml, 1.08 mmol) was added dropwise and the reaction mixture is stirred for 24 hours. Water and EtOAc were added. After decantation, the organic phase was dried over magnesium sulfate, filtered, and concentrated under reduced pressure. The residue was purified by flash chromatography eluting with a gradient of EtOAc in heptane (0 to 100%; V/V) to give 340 mg (96%) of (S)-tert-butyl 3-((2-iodopyrimidin-5-yl)oxy)pyrrolidine-1-carboxylate. LC/MS (m/z, MH+): 392

Intermediate (Iab2). (S)-tert-butyl 3-((2-(8-(4-chloro-3-fluorophenyl)-3-methoxy-6,7-dihydro-5H-benzo[7]annulen-9-yl)pyrimidin-5-yl)oxy)pyrrolidine-1-carboxylate

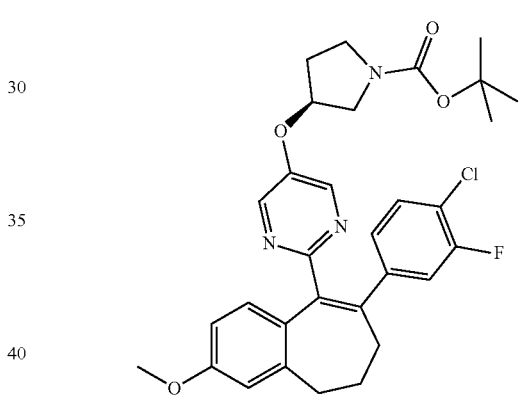

To a solution of 2-(8-(4-chloro-3-fluorophenyl)-3-methoxy-6,7-dihydro-5H-benzo[7]annulen-9-yl)-4,4,5,5-tetramethyl-1,3,2-dioxaborolane (Iaa1) (560 mg, 1.31 mmol) and —(S)-tert-butyl 3-((2-iodopyrimidin-5-yl)oxy)pyrrolidine-1-carboxylate (2b') (3.36 g, 8.58 mmol), in dioxane (40 ml)/water (10 ml) was added under argon [1,1'-bis(diphenylphosphino)ferrocene]dichloropalladium(II), complex with DCM (85.33 mg, 104.49 μmol) and Cs₂CO₃ (893.72 mg, 2.74 mmol). The reaction mixture was stirred for 24 hours at 80° C. After cooling to room temperature, addition of EtOAc and water, the organic phase was dried over magnesium sulfate, filtered, and concentrated under reduced pressure. The residue was purified by column chromatography eluting with a gradient of EtOAc in heptane (0 to 50%; V/V) to give 192 mg (26%) of (S)-tert-butyl 3-((2-(8-(4-chloro-3-fluorophenyl)-3-methoxy-6,7-dihydro-5H-benzo[7]annulen-9-yl)pyrimidin-5-yl)oxy)pyrrolidine-1-carboxylate (Iab2). LC/MS (m/z, MH+): 566

Intermediate (Iac3). (S)-2-(8-(4-chloro-3-fluorophenyl)-3-methoxy-6,7-dihydro-5H-benzo[7]annulen-9-yl)-5-(pyrrolidin-3-yloxy)pyrimidine hydrochloride

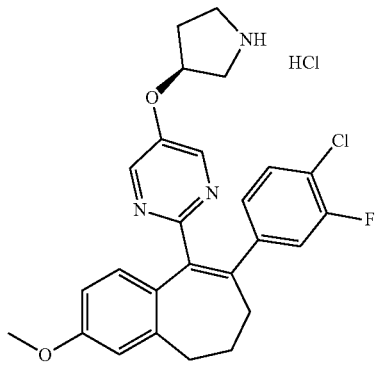 [SMILES: COc1ccc2c(c1)CCCC(c1ccc(Cl)c(F)c1)=C2c1ncc(O[C@H]2CCNC2)cn1 ; Cl]

To a solution of (S)-tert-butyl 3-((2-(8-(4-chloro-3-fluorophenyl)-3-methoxy-6,7-dihydro-5H-benzo[7]annulen-9-yl)pyrimidin-5-yl)oxy)pyrrolidine-1-carboxylate (Iab2) (338 mg, 597.11 µmol) in DCM (5 ml), was added dropwise HCl 2N in ether (3 ml, 6.0 mmol). The reaction mixture was stirred at room temperature for 24 h then concentrated under reduced pressure. The residue obtained was triturated with ethyl ether and the solid was filtered, and dried to give 330 mg of (S)-2-(8-(4-chloro-3-fluorophenyl)-3-methoxy-6,7-dihydro-5H-benzo[7]annulen-9-yl)-5-(pyrrolidin-3-yloxy)pyrimidine hydrochloride (Iac3). LC/MS (m/z, MH$^+$): 466

Intermediate (Iac4). (S)-8-(4-chloro-3-fluorophenyl)-9-(5-(pyrrolidin-3-yloxy)pyrimidin-2-yl)-6,7-dihydro-5H-benzo[7]annulen-3-ol

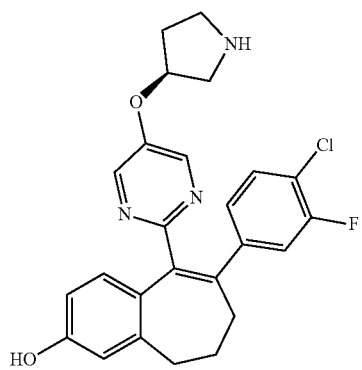 [SMILES: Oc1ccc2c(c1)CCCC(c1ccc(Cl)c(F)c1)=C2c1ncc(O[C@H]2CCNC2)cn1]

To a solution cooled at 0° C. of (S)-2-(8-(4-chloro-3-fluorophenyl)-3-methoxy-6,7-dihydro-5H-benzo[7]annulen-9-yl)-5-(pyrrolidin-3-yloxy)pyrimidine hydrochloride (Iac3) (330 mg, 656.84 µmol) in DCM (3.5 ml), boron tribromide (1.97 ml, 1.97 mmol) was added dropwise. After stirring for 1 hour, the reaction mixture was poured onto a saturated aqueous solution of NaHCO$_3$, and DCM was added. The organic phase was dried over magnesium sulfate, filtered, and concentrated under reduced pressure to give 248 mg (83%) of (S)-8-(4-chloro-3-fluorophenyl)-9-(5-(pyrrolidin-3-yloxy)pyrimidin-2-yl)-6,7-dihydro-5H-benzo[7]annulen-3-ol (Iac4). LC/MS (m/z, MH$^+$): 452

Intermediate (Is7). (S)-9-(6-((1-(3-fluoropropyl)pyrrolidin-3-yl)oxy)pyridin-3-yl)-6,7-dihydro-5H-benzo[7]annulen-3-ol

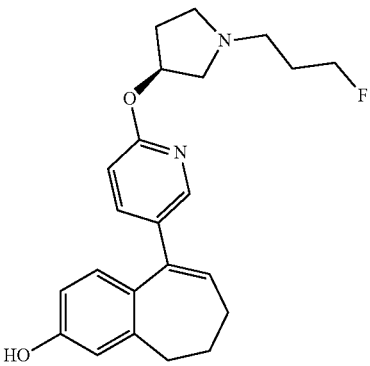 [SMILES: Oc1ccc2c(c1)CCCC=C2c1ccc(O[C@H]2CCN(CCCF)C2)nc1]

To a solution of 9-(4,4,5,5-tetramethyl-1,3,2-dioxaborolan-2-yl)-6,7-dihydro-5H-benzo[7]annulen-3-yl pivalate (Ir1) (0.90 g, 2.43 mmol) and (S)-2-((1-(3-fluoropropyl)pyrrolidin-3-yl)oxy)-5-iodopyridine (2a) (0.86 g, 2.45 mmol), in dioxane/water (50 ml; 4/1; V/V) were added Cs$_2$CO$_3$ (1.66 g, 5.10 mmol) and [1,1'-bis(diphenylphosphino)ferrocene]dichloropalladium(II), complex with DCM (0.12 g, 0.15 mmol) and the reaction mixture was stirred for 90 minutes at 60° C. After cooling to room temperature, MeOH (50 ml) and NaOH 5N (5 ml, 40.00 mmol) were added and the reaction mixture was stirred for 5 minutes. Aqueous HCl (5 M) was added to adjust pH 7 then the solution was partitioned between water and DCM. The organic layer was dried over hydrophobic column, and concentrated under reduced pressure. The residue was purified by flash chromatography eluting with a gradient of MeOH in DCM (0 to 5%; V/V) to give 789 mg (85%) of crude (S)-9-(6-((1-(3-fluoropropyl)pyrrolidin-3-yl)oxy)pyridin-3-yl)-6,7-dihydro-5H-benzo[7]annulen-3-ol (Is7). LC/MS (m/s, MH$^+$): 383

Intermediate (Iae1). (S)-9-(6-((1-(3-fluoropropyl)pyrrolidin-3-yl)oxy)pyridin-3-yl)-6,7-dihydro-5H benzo[7]annulen-3-yl trifluoromethanesulfonate

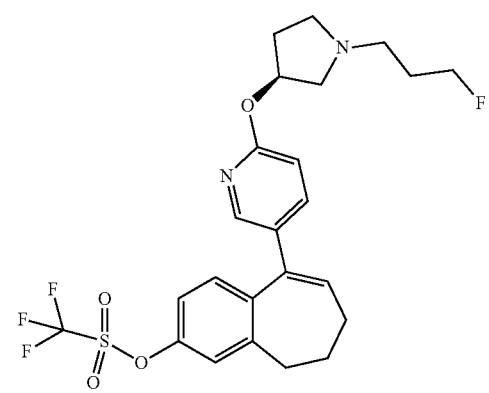 [SMILES: O=S(=O)(Oc1ccc2c(c1)CCCC=C2c1ccc(O[C@H]2CCN(CCCF)C2)nc1)C(F)(F)F]

To a solution of (S)-9-(6-((1-(3-fluoropropyl)pyrrolidin-3-yl)oxy)pyridin-3-yl)-6,7-dihydro-5H-benzo[7]annulen-3-ol (Is7) (1.6 g, 4.18 mmol) in DCM (20 ml) and pyridine (1.02 ml, 12.55 mmol), cooled to 5° C. (ice bath), was added dropwise trifluoromethanesulfonic anhydride (2.20 ml, 12.55 mmol) under argon. The reaction mixture was stirred at room temperature for 18 hours. Ice (50 g) and DCM (50 ml) were added and the phases separated. The organic phase was dried over magnesium sulfate, and concentrated under reduced pressure. The residue was purified by flash chromatography eluting with a gradient of DCM in MeOH (100/0 to 95/05; v/v) to give 700 mg (32%) of (S)-9-(6-((1-(3-fluoropropyl)pyrrolidin-3-yl)oxy)pyridin-3-yl)-6,7-dihydro-5H benzo[7]annulen-3-yl trifluoromethanesulfonate (Iae1). LC/MS (m/s, MH+): 515

Intermediate (Iaf1). (S)-methyl 9-(6-((1-(3-fluoropropyl)pyrrolidin-3-yl)oxy)pyridin-3-yl)-6,7-dihydro-5H-benzo[7]annulene-3-carboxylate

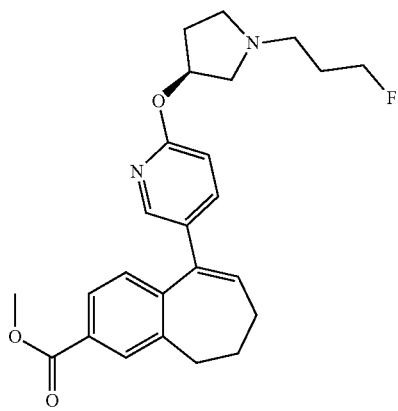 [SMILES: COC(=O)c1ccc2c(c1)CCCC=C2c1ccc(O[C@H]2CCN(CCCF)C2)nc1]

In an autoclave, to a solution of (S)-9-(6-((1-(3-fluoropropyl)pyrrolidin-3-yl)oxy)pyridin-3-yl)-6,7-dihydro-5H benzo[7]annulen-3-yl trifluoromethanesulfonate (Iae1) (0.65 g, 1.26 mmol) in DMF (8 ml) and MeOH (4 ml), were added 1,3-bis(diphenylphosphino)propane (0.16 g, 0.38 mmol), Pd(OAc)$_2$ (0.085 g, 0.38 mmol) and triethylamine (0.93 ml, 6.32 mmol). The black suspension was carbonylated at 40° C. under 3 bars of CO for 16 hours. The reaction mixture was diluted with DCM (50 ml), filtered, and concentrated under reduced pressure. The residue was purified by flash chromatography eluting with a gradient of DCM in MeOH (100/0 to 95/05; v/v) to give 490 mg (92%) of ((S)-methyl 9-(6-((1-(3-fluoropropyl)pyrrolidin-3-yl)oxy)pyridin-3-yl)-6,7-dihydro-5H-benzo[7]annulene-3-carboxylate (Iaf1). LC/MS (m/s, MH+): 425

Intermediate (Iag1). (S)-methyl 8-bromo-9-(6-((1-(3-fluoropropyl)pyrrolidin-3-yl)oxy)pyridin-3-yl)-6,7-dihydro-5H-benzo[7]annulene-3-carboxylate

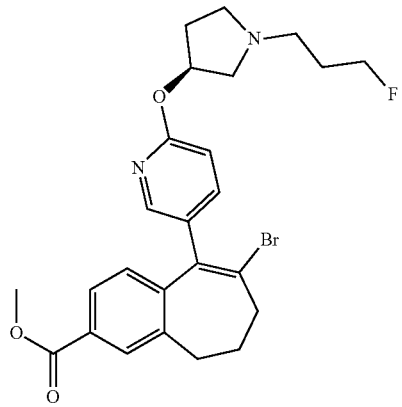 [SMILES: COC(=O)c1ccc2c(c1)CCCC(Br)=C2c1ccc(O[C@H]2CCN(CCCF)C2)nc1]

To a solution of (S)-methyl 9-(6-((1-(3-fluoropropyl)pyrrolidin-3-yl)oxy)pyridin-3-yl)-6,7-dihydro-5H-benzo[7]annulene-3-carboxylate (Iaf1) (490 mg, 1.15 mmol) in THF (25 ml), was added pyridinium tribromide (387 mg, 1.21 mmol). The reaction mixture was stirred for 16 hours at room temperature and 0.5 molar equivalents pyridinium tribromide were added. After one hour water (30 ml) was added. The pH was adjusted to 7 with a concentrated solution of NaHCO$_3$. The aqueous phase was washed twice with DCM and the gathered organic phases dried over hydrophobic column, and concentrated under reduced pressure. The residue was purified by flash chromatography eluting with a gradient of MeOH in DCM (0 to 5%; V/V) to give 210 mg of crude (S)-methyl 8-bromo-9-(6-((1-(3-fluoropropyl)pyrrolidin-3-yl)oxy)pyridin-3-yl)-6,7-dihydro-5H benzo[7]annulene-3-carboxylate (Iag1) which was used as such in the following step. LC/MS (m/s, MH+): 504

Intermediate (I)8. (S)-methyl 8-(2,4-dichlorophenyl)-9-(6-((1-(3-fluoropropyl)pyrrolidin-3-yl)oxy)pyridin-3-yl)-6,7-dihydro-5H-benzo[7]annulene-3-carboxylate

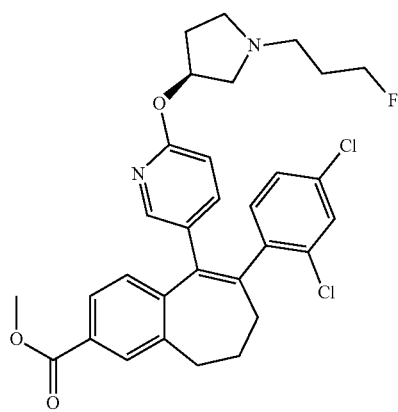 [SMILES: COC(=O)c1ccc2c(c1)CCCC(c1ccc(Cl)cc1Cl)=C2c1ccc(O[C@H]2CCN(CCCF)C2)nc1]

A mixture of (S)-methyl 8-bromo-9-(6-((1-(3-fluoropropyl)pyrrolidin-3-yl)oxy)pyridin-3-yl)-6,7-dihydro-5H-benzo[7]annulene-3-carboxylate (Iag1) (100 mg, 198.65 µmol), 2,4-dichlorophenyl-boronic acid (42.99 mg, 218.51 µmol), Cs₂CO₃ (136.06 mg, 417.16 µmol), [1,1'-bis(diphenylphosphino)ferrocene]dichloropalladium(II), complex with DCM (9.73 mg, 11.92 µmol) and a solution of dioxane/water (3 ml; 4/1) was microwaved at 90° C. for 30 minutes. After cooling, DCM (5 ml) the reaction mixture was concentrated under reduced pressure. The residue was purified by column chromatography eluting with a gradient of MeOH in DCM (0% to 5%; v/v) to give a residue which was further purified on strong cation exchange (SCX) column to give 89 mg (79%) of (S)-methyl 8-(2,4-dichlorophenyl)-9-(6-((1-(3-fluoropropyl)pyrrolidin-3-yl)oxy)pyridin-3-yl)-6,7-dihydro-5H-benzo[7]annulene-3-carboxylate (I)8 which was engaged as such in the following step. LC/MS (m/s, MH⁺): 569

Intermediate (IIa). (S)-3-(4-(dimethoxymethyl)-3,5-difluorophenoxy)-1-(3-fluoropropyl)pyrrolidine

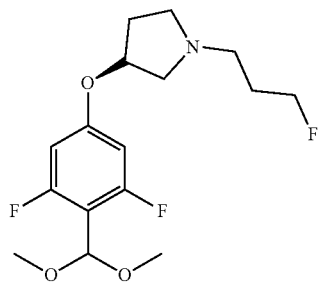

To a solution of 2,6-difluoro-4-hydroxybenzaldehyde (474 mg, 3 mmol) in THF (15 ml), were added (R)-1-(3-fluoropropyl)pyrrolidin-3-ol (552 mg, 3.75 mmol), (E)-N1,N1,N2,N2-tetramethyldiazene-1,2-dicarboxamide (1.03 g, 6 mmol) and triphenylphosphine (1.57 g, 6 mmol). The reaction mixture was stirred for 24 hours at room temperature. Water and EtOAc were added. After decantation, the organic phase was dried over magnesium sulfate, filtered, and concentrated under reduced pressure. The residue was purified by flash chromatography eluting with a mixture of DCM and MeOH (98/02; v/v) to give 285 mg (29%) of (S)-3-(4-(dimethoxymethyl)-3,5-difluorophenoxy)-1-(3-fluoropropyl)pyrrolidine (IIa). LC/MS (m/z, MH⁺): 334

Intermediate (IIb). 2-fluoro-2-methylpropyl trifluoromethanesulfonate

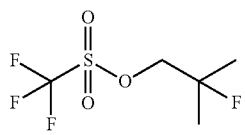

To a solution of 2-fluoro-2-methyl-propan-1-ol (4 g, 43.42 mmol) and 2,6-dimethylpyridine (5.83 g, 52.22 mmol) in DCM (30 ml) cooled at 0° C., was added dropwise trifluoromethanesulfonic anhydride (13.76 g, 46.82 mmol). The reaction mixture was stirred for 1 hour at 0° C. HCl 2N (33 ml) was added. After decantation, the organic phase was dried over magnesium sulfate, filtered, and concentrated under reduced pressure to give 6.8 g (70%) of 2-fluoro-2-methylpropyl trifluoromethanesulfonate (IIb) which was used as such in the following step. LC/MS (m/z, MH⁺): 225

Intermediate (IIc). N-(1-(1H-indol-3-yl)propan-2-yl)-2-fluoro-2-methylpropan-1-amine

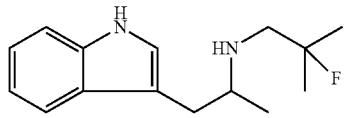 [SMILES: CC(Cc1c[nH]c2ccccc12)NCC(C)(C)F]

To a solution of 1-(1H-indol-3-yl)propan-2-amine (4.5 g, 25.83 mmol) and N,N-diisopropylamine (7.51 g, 45.2 mmol) in dioxane (50 ml), was added 2-fluoro-2-methylpropyl trifluoromethanesulfonate (IIb) (7.43 g, 33.14 mmol). The reaction mixture was stirred for 18 hour at 75° C. EtOAc and water were added. After decantation, the organic phase was dried over magnesium sulfate, filtered, and concentrated under reduced pressure. The residue was purified by flash chromatography eluting with a mixture of DCM and MeOH (98/05; v/v) to give 5.6 g (87%) of N-(1-(1H-indol-3-yl)propan-2-yl)-2-fluoro-2-methylpropan-1-amine (IIc). LC/MS (m/z, MH⁺): 249

Intermediate (IId). 1-(2,6-difluoro-4-(((S)-1-(3-fluoropropyl)pyrrolidin-3-yl)oxy)phenyl)-2-(2-fluoro-2-methylpropyl)-3-methyl-2,3,4,9-tetrahydro-1H-pyrido[3,4-b]indole

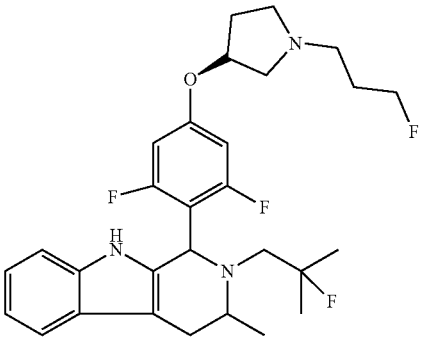

To a solution of (S)-3-(4-(dimethoxymethyl)-3,5-difluorophenoxy)-1-(3-fluoropropyl)pyrrolidine (IIa) (230 mg, 0.69 mmol) and N-(1-(1H-indol-3-yl)propan-2-yl)-2-fluoro-2-methylpropan-1-amine (IIc) (210 mg, 0.85 mmol) in toluene (50 ml), was added acetic acid (1 ml, 22.3 mmol). The reaction mixture was microwaved at 130° C. for 50 minutes. After cooling, EtOAc and saturated solution of NaHCO₃ were added. After decantation, the organic phase was dried over magnesium sulfate, filtered, and concentrated under reduced pressure. The residue was purified by flash chromatography eluting with a gradient of MeOH in DCM (0 to 03%; V/V) to give 157 mg (44%) of 1-(2,6-difluoro-4-(((S)-1-(3-fluoropropyl)pyrrolidin-3-yl)oxy)phenyl)-2-(2-fluoro-2-methylpropyl)-3-methyl-2,3,4,9-tetrahydro-1H-pyrido[3,4-b]indole (IId) as a mixture of trans isomers which will be separated by chiral chromatography. LC/MS (m/z, MH⁺): 518

Reagent (2c). (S)-1-(3-fluoropropyl)-3-(4-iodophenoxy)pyrrolidine

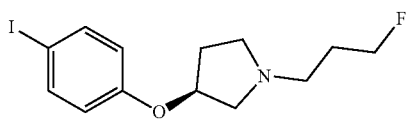 [SMILES: FCCCN1CC[C@H](Oc2ccc(I)cc2)C1]

Step 1. (S)-tert-butyl 3-(4-iodophenoxy)pyrrolidine-1-carboxylate

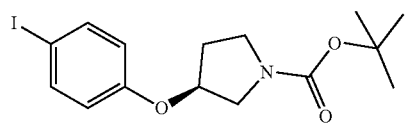 [SMILES: CC(C)(C)OC(=O)N1CC[C@H](Oc2ccc(I)cc2)C1]

To a solution of 4-iodophenol (2 g, 9.09 mmol) in THF (20 ml), were added (R)-1-N-boc-3-hydroxypyrrolidine (2.11 g, 10.91 mmol), (E)-N1,N1,N2,N2-tetramethyldiazene-1,2-dicarboxamide (2.47 g, 13.64 mmol) and triphenylphosphine (3.58 g, 13.64 mmol). The reaction mixture was stirred for 24 hours at room temperature. Water and EtOAc were added. After decantation, the organic phase was dried over magnesium sulfate, filtered, and concentrated under reduced pressure. The residue was purified by flash chromatography eluting with a gradient of EtOAc in heptane (0 to 15%; V/V) to give 2.29 g (65%) of (S)-tert-butyl 3-(4-iodophenoxy)pyrrolidine-1-carboxylate. LC/MS (m/z, MH$^+$): 390

Step 2. (S)-3-(4-iodophenoxy)pyrrolidine, hydrochloride

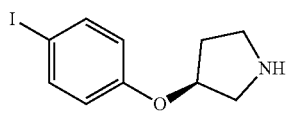 [SMILES: Ic1ccc(O[C@H]2CCNC2)cc1]

To a solution of (S)-tert-butyl 3-(4-iodophenoxy)pyrrolidine-1-carboxylate (2.29 g, 2.94 mmol) in MeOH (20 mL), was added dropwise HCl 4N in dioxane (5 ml). The reaction mixture was stirred at room temperature for 18 hours. To the reaction mixture was concentrated under reduced pressure. The residue obtained was triturated with ethyl ether and the solid was filtered, and dried to give 976 mg (52%) of (S)-3-(4-iodophenoxy)pyrrolidine, hydrochloride. LC/MS (m/z, MH$^+$): 290

Step 3. (S)-1-(3-fluoropropyl)-3-(4-iodophenoxy)pyrrolidine (2c)

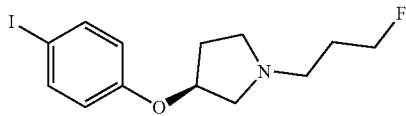 [SMILES: FCCCN1CC[C@H](Oc2ccc(I)cc2)C1]

To a solution of (S)-3-(4-iodophenoxy)pyrrolidine hydrochloride (970 mg, 2.98 mmol), in acetonitrile (20 mL), was added potassium carbonate (1.03 g, 7.45 mmol), followed by 1-fluoro-3-iodopropane (560 mg, 2.98 mmol). The reaction mixture was heated at 45° C. for 18 h. After cooling to room temperature, the solid was filtrated and the filtrate was concentrated under reduced pressure. The residue obtained was treated with DCM and the solid formed was filtrated. The filtrate was concentrated under reduced pressure to give 990 mg (95%) of (S)-1-(3-fluoropropyl)-3-(4-iodophenoxy)pyrrolidine (2c). LC/MS (m/z, MH$^+$): 350

Intermediate (IIb). (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole

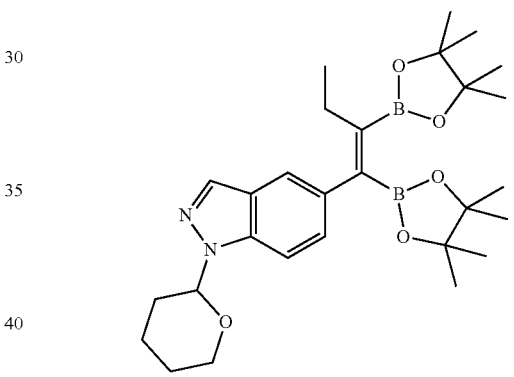

To a solution of 5-(but-1-yn-1-yl)-1-(tetrahydro-2H-pyran-2-yl)-1H-indazole (IIIa) (3.2 g, 11.95 mmol), in anhydrous 2-methyl-THF (50 mL), was added under argon, bis(pinacolato)diboron (3.68 g, 14.34 mmol), followed by tetrakis(triphenylphosphine)platinum (153 mg, 0.12 mmol). The reaction mixture was degassed 10 minutes with argon and heated at reflux (oil bath 95° C.) for 4 h, and then allowed to cool to room temperature. EtOAc and water were added to the reaction mixture. The layers were separated and the organic layer was dried over magnesium sulfate, filtered, and concentrated under reduced pressure to give 4.9 g (81%) of (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole (IIIb) which was engaged as such in the next step. LC/MS (m/z, MH$^+$): 509

307

Intermediates (IIIc) and (IIId). 5-[(1Z)-1-(4-{[(3S)-1-(3-fluoropropyl)pyrrolidin-3-yl]oxy}phenyl)-2-(tetramethyl-1,3,2-dioxaborolan-2-yl)but-1-en-1-yl]-1-(oxan-2-yl)-1H-indazole and 5-[(1E)-2-(4-{[(3S)-1-(3-fluoropropyl)pyrrolidin-3-yl]oxy}phenyl)-1-(tetramethyl-1,3,2-dioxaborolan-2-yl)but-1-en-1-yl]-1-(oxan-2-yl)-1H-indazole

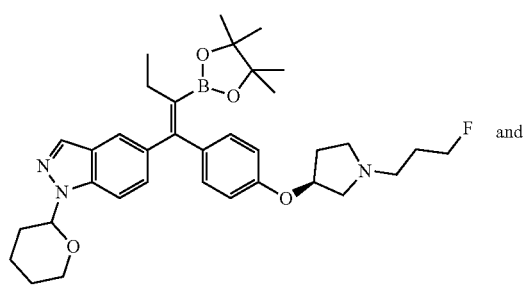

and

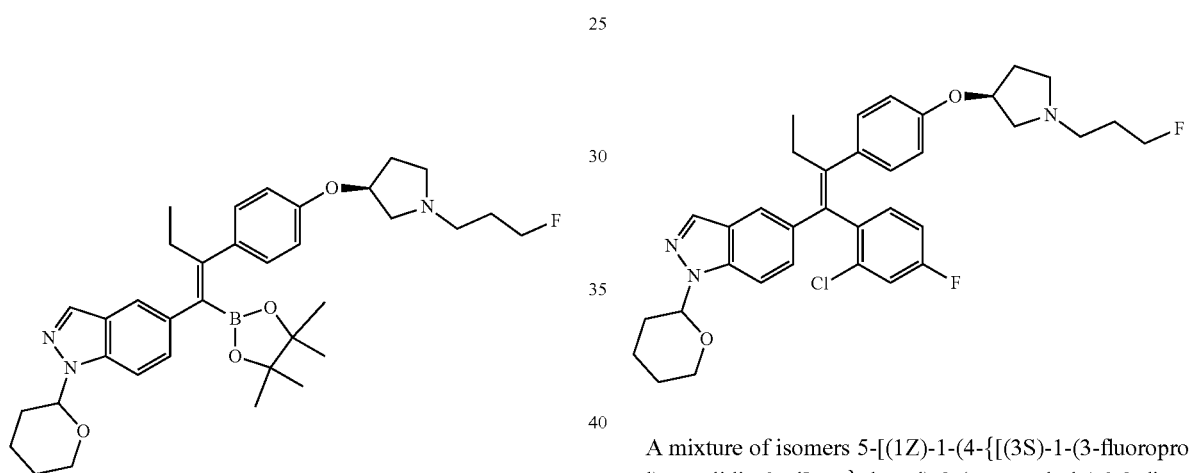

A mixture of (Z)-5-(1,2-bis(4,4,5,5-tetramethyl-1,3,2-dioxaborolan-2-yl)but-1-en-1-yl)-1-(tetrahydro-2H-pyran-2-yl)-1H-indazole (IIb) (1.5 g, 2.95 mmol), (S)-1-(3-fluoropropyl)-3-(4-iodophenoxy)pyrrolidine (2c) (1.5 g, 4.30 mmol), toluene (30 ml), water (0.25 ml), Cs$_2$CO$_3$ (1.92 g, 5.9 mmol), and [1,1'-bis(diphenylphosphino)ferrocene]dichloropalladium(II), complex with DCM (144 mg, 0.18 mmol) was degassed with argon then heated at 80° C. for 24 hours. After cooling to room temperature, EtOAc and water were added. The layers were separated, and the organic layer was dried over magnesium sulfate, filtered, and concentrated under reduced pressure to give 819 mg (46%) of a mixture of isomers 5-[(1Z)-1-(4-{[(3S)-1-(3-fluoropropyl)pyrrolidin-3-yl]oxy}phenyl)-2-(tetramethyl-1,3,2-dioxaborolan-2-yl)but-1-en-1-yl]-1-(oxan-2-yl)-1H-indazole (IIIc) and 5-[(1E)-2-(4-{[(3S)-1-(3-fluoropropyl)pyrrolidin-3-yl]oxy}phenyl)-1-(tetramethyl-1,3,2-dioxaborolan-2-yl)but-1-en-1-yl]-1-(oxan-2-yl)-1H-indazole (IIId) which was engaged as such in the next step. LC/MS (m/z, MH$^+$): 604

308

Intermediates (IIIe) and (IIIf). 5-[(1E)-2-(2-chloro-4-fluorophenyl)-1-(4-{[(3S)-1-(3-fluoropropyl)pyrrolidin-3-yl]oxy}phenyl)but-1-en-1-yl]-1-(oxan-2-yl)-1H-indazole and 5-[(1Z)-1-(2-chloro-5-fluorophenyl)-2-(4-{[(3S)-1-(3-fluoropropyl)pyrrolidin-3-yl]oxy}phenyl)but-1-en-1-yl]-1-(oxan-2-yl)-1H-indazole A mixture of isomers 5-[(1Z)-1-(4-{[(3S)-1-(3-fluoropropyl)pyrrolidin-3-yl]oxy}phenyl)-2-(tetramethyl-1,3,2-dioxaborolan-2-yl)but-1-en-1-yl]-1-(oxan-2-yl)-1H-indazole (IIIc) and 5-[(1E)-2-(4-{[(3S)-1-(3-fluoropropyl)pyrrolidin-3-yl]oxy}phenyl)-1-(tetramethyl-1,3,2-dioxaborolan-2-yl)but-1-en-1-yl]-1-(oxan-2-yl)-1H-indazole (IIId) (819 mg, 1.36 mmol), 2-chloro-4-fluorobenzene (487 mg, 1.90 mmol), 2-methylTHF (20 ml), potassium hydroxyde (419 mg, 7.46 mmol), water (1.8 ml), and [1,1'-bis(diphenylphosphino)ferrocene]dichloropalladium(II), complex with DCM (49 mg, 0.068 mmol) was degassed with argon then heated at 90° C. for 4.5 hours. After cooling to room temperature, addition of EtOAc and water. The layers were separated, and the organic layer was dried over magnesium sulfate, filtered, and concentrated under reduced pressure to give 770 mg (94%) of a mixture of isomers 5-[(1E)-2-(2-chloro-4-fluorophenyl)-1-(4-{[(3S)-1-(3-fluoropropyl)pyrrolidin-3-yl]oxy}phenyl)but-1-en-1-yl]-1-(oxan-2-yl)-1H-indazole (IIIe) and 5-[(1Z)-1-(2-chloro-5-fluorophenyl)-2-(4-{[(3S)-1-(3-fluoropropyl)pyrrolidin-3-yl]oxy}phenyl)but-1-en-1-yl]-1-(oxan-2-yl)-1H-indazole (IIIf) which was engaged as such in the next step. LC/MS (m/z, MH$^+$): 606

Intermediates (III) and (III'). 5-[(1E)-2-(2-chloro-4-fluorophenyl)-1-(4-{[(3S)-1-(3-fluoropropyl)pyrrolidin-3-yl]oxy}phenyl)but-1-en-1-yl]-1H-indazole and 5-[(1Z)-1-(2-chloro-5-fluorophenyl)-2-(4-{[(3S)-1-(3-fluoropropyl)pyrrolidin-3-yl]oxy}phenyl)but-1-en-1-yl]-1H-indazole

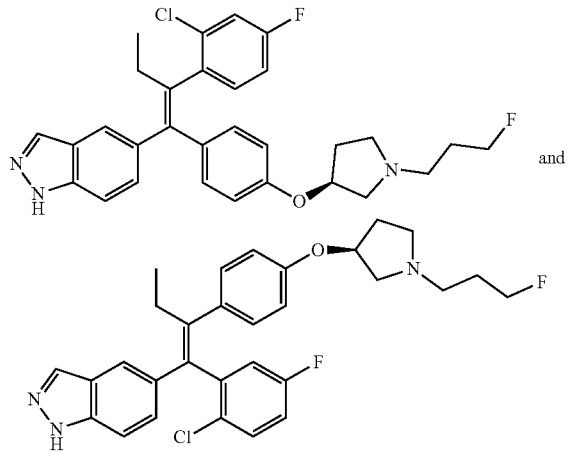

and

A mixture of isomers 5-[(1E)-2-(2-chloro-4-fluorophenyl)-1-(4-{[(3S)-1-(3-fluoropropyl)pyrrolidin-3-yl]oxy}phenyl)but-1-en-1-yl]-1-(oxan-2-yl)-1H-indazole (IIIe) and 5-[(1Z)-1-(2-chloro-5-fluorophenyl)-2-(4-{[(3S)-1-(3-fluoropropyl)pyrrolidin-3-yl]oxy}phenyl) but-1-en-1-yl]-1-(oxan-2-yl)-1H-indazole (IIIf) (770 mg, 1.27), MeOH (5 ml) and hydrogen chloride 4N in dioxan (25 ml) was stirred at room temperature for 18 hours. The reaction mixture was concentrated under reduced pressure and the residue obtained was treated on strong cation exchange (SCX) column to give 524 mg (79%) of a mixture of isomers 5-[(1E)-2-(2-chloro-4-fluorophenyl)-1-(4-{[(3S)-1-(3-fluoropropyl)pyrrolidin-3-yl]oxy}phenyl)but-1-en-1-yl]-1H-indazole (III) and 5-[(1Z)-1-(2-chloro-5-fluorophenyl)-2-(4-{[(3S)-1-(3-fluoropropyl) pyrrolidin-3-yl]oxy}phenyl)but-1-en-1-yl]-1H-indazole (III') which will be separated by chiral chromatography. LC/MS (m/z, MH$^+$): 522

Intermediate (IVa). tert-butyl (S)-3-(4-(methoxycarbonyl)phenoxy)pyrrolidine-1-carboxylate

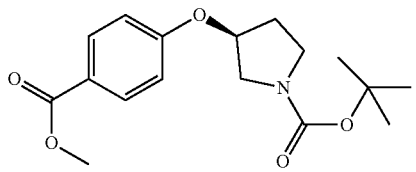 [SMILES: COC(=O)c1ccc(O[C@H]2CCN(C(=O)OC(C)(C)C)C2)cc1]

To a solution of methyl 4-hydroxybenzoate (3 g, 19.72 mmol) in THF (75 ml), were added (R)-1-N-boc-3-hydroxypyrrolidine (4.43 g, 23.66 mmol), diisopropyl(E)-diazene-1,2-dicarboxylate (4.78 g, 23.66 mmol) and triphenylphosphine (6.21 g, 23.66 mmol). The reaction mixture was heated at 60° C. for 24 hours. Water and EtOAc were added. After decantation, the organic phase was dried over magnesium sulfate, filtered, and concentrated under reduced pressure. The residue was purified by flash chromatography eluting with a gradient of EtOAc in cyclohexane (0 to 15%; V/V) to give 6.18 g (98%) of tert-butyl (S)-3-(4-(methoxycarbonyl)phenoxy)pyrrolidine-1-carboxylate (IVa). LC/MS (m/z, MH$^+$): 322

Intermediate (IVb). methyl (S)-4-(pyrrolidin-3-yloxy)benzoate, hydrochloride

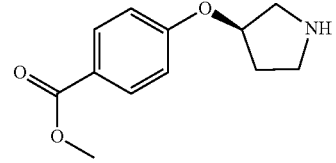 [SMILES: COC(=O)c1ccc(O[C@@H]2CCNC2)cc1]

To a solution of tert-butyl (S)-3-(4-(methoxycarbonyl) phenoxy)pyrrolidine-1-carboxylate (IVa) (6 g, 18.67 mmol) in DCM (80 ml), was added dropwise HCl 4N in dioxane (20 ml). The reaction mixture was stirred at room temperature for 8 h. The reaction mixture was concentrated under reduced pressure. The residue obtained was triturated with DCM and the solid was filtered, and dried to give 4.67 g (97%) of methyl (S)-4-(pyrrolidin-3-yloxy)benzoate, hydrochloride (IVb). LC/MS (m/z, MH$^+$): 222

Intermediate (IVc). methyl (S)-4-((1-(3-fluoropropyl)pyrrolidin-3-yl)oxy)benzoate

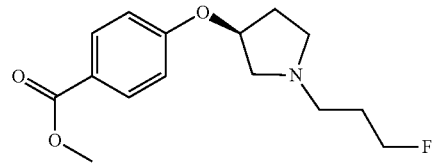 [SMILES: COC(=O)c1ccc(O[C@H]2CCN(CCCF)C2)cc1]

To a solution of (S)-4-(pyrrolidin-3-yloxy)benzoate, hydrochloride (IVb) (4.2 g, 16.30 mmol), in acetonitrile (80 mL), was added potassium carbonate (5.63 g, 40.74 mmol), followed by 1-fluoro-3-iodopropane (3.98 g, 21.19 mmol). The reaction mixture was heated at 40° C. for 24 h. After cooling to room temperature, the solid was filtrated and the filtrate was concentrated under reduced pressure. To the residue obtained, addition of water and EtOAc. After decantation, the organic phase was dried over magnesium sulfate, filtered, and concentrated under reduced pressure. The oil obtained was purified by flash chromatography eluting with a mixture of DCM, MeOH and acetonitrile (94/03/03; v/v/v) to give 3.8 g (83%) of methyl (S)-4-((1-(3-fluoropropyl) pyrrolidin-3-yl)oxy)benzoate (IVc). LC/MS (m/z, MH$^+$): 282

Intermediate (IVd). 4-{[(3S)-1-(3-fluoropropyl)pyrrolidin-3-yl]oxy}benzoic acid, hydrochloride

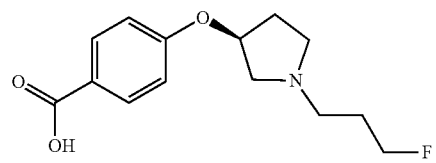 [SMILES: O=C(O)c1ccc(O[C@H]2CCN(CCCF)C2)cc1]

To a solution of methyl (S)-4-((1-(3-fluoropropyl)pyrrolidin-3-yl)oxy)benzoate (IVc) (2.5 g, 8.89 mmol), in MeOH (15 ml), was added potassium hydroxide (1.45 g, 25.84 mmol). The reaction mixture was heated at 35° C. for 24 h. After cooling to room temperature, the reaction mixture was concentrated under reduced pressure and residue obtained was treated with ethyl ether. The solid formed was filtrated and solubilized in dioxane (30 ml). Addition of HCl 4N in dioxane (6.5 ml). The solid formed was filtrated to give 3.85 g (99%) of 4-{[(3S)-1-(3-fluoropropyl)pyrrolidin-3-yl]oxy}benzoic acid, hydrochloride (IVd). LC/MS (m/z, MH$^+$): 268

Intermediate (IVe). (S)-4-((1-(3-fluoropropyl)pyrrolidin-3-yl)oxy)benzoyl chloride, hydrochloride

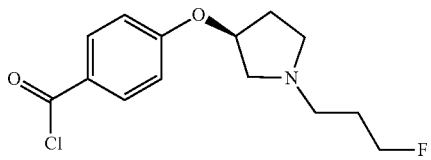 [SMILES: O=C(Cl)c1ccc(O[C@H]2CCN(CCCF)C2)cc1]

To a mixture of 4-{[(3S)-1-(3-fluoropropyl)pyrrolidin-3-yl]oxy}benzoic acid, hydrochloride (IVd) (3.3 g, 12.3 mmol), in DCM (30 mL), was added thionyl chloride (2.2 g, 18.52 mmol). The reaction mixture was heated at 35° C. for 3 hours. After cooling to room temperature, the reaction mixture was concentrated under reduced pressure to give 3.3 g (99%) of (S)-4-((1-(3-fluoropropyl)pyrrolidin-3-yl)oxy)benzoyl chloride, hydrochloride (IVe) which was used as such in the next step.

Intermediate (IVf). (S)-4-((1-(3-fluoropropyl)pyrrolidin-3-yl)oxy)-N-methoxy-N-methylbenzamide

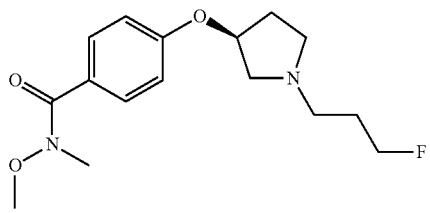 [SMILES: CON(C)C(=O)c1ccc(O[C@H]2CCN(CCCF)C2)cc1]

To a mixture of (S)-4-((1-(3-fluoropropyl)pyrrolidin-3-yl)oxy)benzoyl chloride (IVe), hydrochloride (3.3 g, 10 mmol), in DCM (35 ml) cooled at 0° C., were added N,O-dimethylhydroxylamine hydrochloride (2.47 g, 25.41 mmol) and triethylamine (4.67 g, 46.2 mmol). The reaction mixture was stirred at room temperature for 3 hours. Water was added, then after decantation, the organic phase was dried over magnesium sulfate, filtered, and concentrated under reduced pressure. The residue was purified by flash chromatography eluting with a mixture of DCM, MeOH and acetonitrile (92/04/04; v/v/v) to give 3.4 g (95%) of (S)-4-((1-(3-fluoropropyl)pyrrolidin-3-yl)oxy)-N-methoxy-N-methylbenzamide (IVf). LC/MS (m/z, MH$^+$): 311

Intermediate (IVg). (S)-2-(4-(benzyloxy)phenyl)-1-(4-((1-(3-fluoropropyl)pyrrolidin-3-yl)oxy)phenyl)ethan-1-one

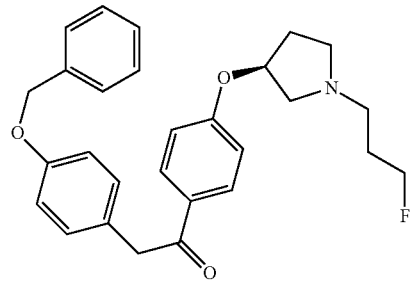 [SMILES: O=C(Cc1ccc(OCc2ccccc2)cc1)c1ccc(O[C@H]2CCN(CCCF)C2)cc1]

To a solution of (S)-4-((1-(3-fluoropropyl)pyrrolidin-3-yl)oxy)-N-methoxy-N-methylbenzamide (IVf) (1 g, 3.22 mmol), in THE (5 ml) cooled at 0° C., were added dropwise (4-(benzyloxy)benzyle magnesium chloride 0.25 M in THE (77 ml, 19.33 mmol). The reaction mixture was stirred at 0° C. for 3 hours. A saturated solution of ammonium chloride (10 ml) and EtOAc (30 ml) were added, then after decantation, the organic phase was dried over magnesium sulfate, filtered, and concentrated under reduced pressure. The residue was purified by flash chromatography eluting with a mixture of DCM, MeOH and acetonitrile (94/03/03; v/v/v) to give 1.02 g (71%) of (S)-2-(4-(benzyloxy)phenyl)-1-(4-((1-(3-fluoropropyl)pyrrolidin-3-yl)oxy)phenyl)ethan-1-one (IVg). LC/MS (m/z, MH$^+$): 448

Intermediate (IVh). 2-(4-(benzyloxy)phenyl)-2-bromo-1-(4-(((R)-1-(3-fluoropropyl)pyrrolidin-3-yl)oxy)phenyl)ethan-1-one

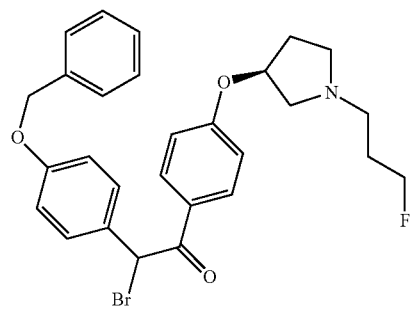 [SMILES: O=C(c1ccc(O[C@H]2CCN(CCCF)C2)cc1)C(Br)c1ccc(OCc2ccccc2)cc1]

To a solution of (S)-2-(4-(benzyloxy)phenyl)-1-(4-((1-(3-fluoropropyl)pyrrolidin-3-yl)oxy)phenyl)ethan-1-one (IVg) (1.02 g, 2.28 mmol) in DCM (20 ml) was added trimethylammoniumbenzene tribromide (1.55 g, 4.10 mmol). The reaction mixture was stirred at 40° C. for 1 h. After cooling to room temperature, the solid was filtered, and the filtrate was concentrated under reduced pressure to give 1.2 g (100%) of 2-(4-(benzyloxy)phenyl)-2-bromo-1-(4-(((R)-1-(3-fluoropropyl)pyrrolidin-3-yl)oxy)phenyl)ethan-1-one (IVh) which was used as such in the next step. LC/MS (m/z, MH$^+$): 526

313

Intermediate (IVi). 2-((5-(benzyloxy)-2-hydroxyphenyl)thio)-2-(4-(benzyloxy)phenyl)-1-(4-(((R)-1-(3-fluoropropyl)pyrrolidin-3-yl)oxy)phenyl)ethan-1-one

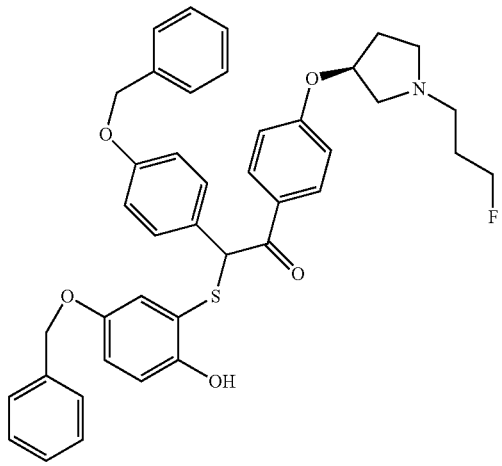 [SMILES: O=C(c1ccc(O[C@H]2CCN(CCCF)C2)cc1)C(Sc1cc(OCc2ccccc2)ccc1O)c1ccc(OCc2ccccc2)cc1]

To a suspension of sodium hydride (114 mg, 2.85 mmol) in THF (5 ml) cooled at 0° C., was added dropwise of 4-(benzyloxy)-2-mercaptophenol (662 mg, 2.85 mmol) in solution in THF (5 ml). After stirring for 15 min at 0° C., a solution of 2-(4-(benzyloxy)phenyl)-2-bromo-1-(4-(((R)-1-(3-fluoropropyl)pyrrolidin-3-yl)oxy)phenyl)ethan-1-one (IVh) (1 g, 1.9 mmol) in THF (15 ml) was added dropwise. The reaction mixture was stirred for 6 h at 0° C. and then 1 h at room temperature. A saturated solution of sodium chloride (30 ml) and EtOAc (30 ml) were added, then after decantation, the organic phase was dried over magnesium sulfate, filtered, and concentrated under reduced pressure. The residue was purified by flash chromatography eluting with a mixture of DCM and isopropanol (96.5/3.5; v/v) to give 400 mg (31%) of 2-((5-(benzyloxy)-2-hydroxyphenyl)thio)-2-(4-(benzyloxy)phenyl)-1-(4-(((R)-1-(3-fluoropropyl)pyrrolidin-3-yl)oxy)phenyl)ethan-1-one (IVi). LC/MS (m/z, MH+): 678

Intermediate (IVj). (3S)-3-{4-[6-(benzyloxy)-3-[4-(benzyloxy)phenyl]-2,3-dihydro-1,4-benzoxathiin-2-yl]phenoxy}-1-(3-fluoropropyl)pyrrolidine

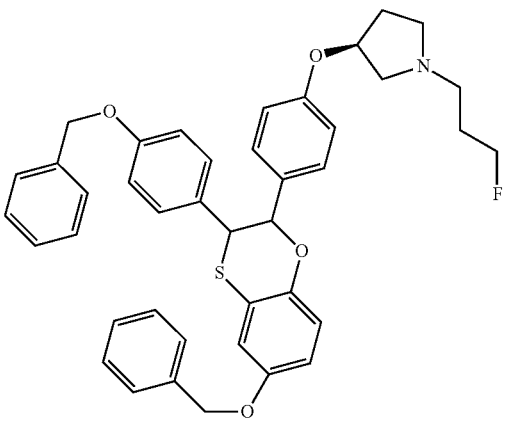 [SMILES: FCCCN1CC[C@H](Oc2ccc(C3Oc4ccc(OCc5ccccc5)cc4SC3c3ccc(OCc4ccccc4)cc3)cc2)C1]

314

To a solution of 2-((5-(benzyloxy)-2-hydroxyphenyl)thio)-2-(4-(benzyloxy)phenyl)-1-(4-(((R)-1-(3-fluoropropyl)pyrrolidin-3-yl)oxy)phenyl)ethan-1-one (IVi) (400 mg, 0.59 mmol) in DCM (12 ml) cooled at 0° C., were added dropwise trifluoroacetic acid (0.72 ml, 9.44 mmol) in solution in DCM (1 ml), then triethylsilane (0.53 ml, 3.54 mmol) in DCM (1 ml). After stirring for 7 h at 0° C., a saturated solution of sodium hydrogenocarbonate (30 ml) and DCM (30 ml) were added, then after decantation, the organic phase was dried over magnesium sulfate, filtered, and concentrated under reduced pressure. The residue was purified by flash chromatography eluting with a mixture of DCM and isopropanol (97/3; v/v) to give 274 mg (70%) of (3S)-3-{4-[6-(benzyloxy)-3-[4-(benzyloxy)phenyl]-2,3-dihydro-1,4-benzoxathiin-2-yl]phenoxy}-1-(3-fluoropropyl)pyrrolidine (IVj). LC/MS (m/z, MH+): 662

Intermediate (IVk). 2-(4-(((S)-1-(3-fluoropropyl)pyrrolidin-3-yl)oxy)phenyl)-3-(4-hydroxyphenyl)-2,3-dihydrobenzo[b][1,4]oxathiin-6-ol

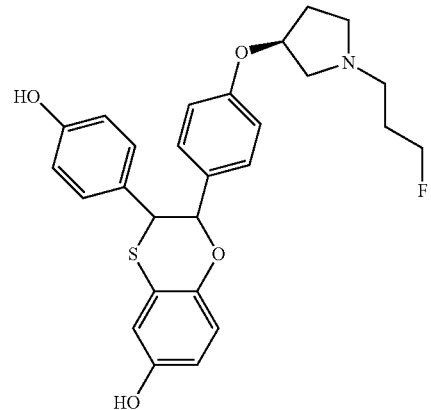 [SMILES: Oc1ccc(C2Sc3cc(O)ccc3OC2c2ccc(O[C@H]3CCN(CCCF)C3)cc2)cc1]

To a solution of (3S)-3-{4-[6-(benzyloxy)-3-[4-(benzyloxy)phenyl]-2,3-dihydro-1,4-benzoxathiin-2-yl]phenoxy}-1-(3-fluoropropyl)pyrrolidine (IVj) (273 mg, 0.41 mmol) in acetonitrile (10 ml), were added diisopropylethylamine (0.36 ml, 2.06 mmol) and thiourea (157 mg, 2.06 mmol). The reaction mixture was cooled at 0° C. before addition dropwise of iodotrimethylsilane (1.2 ml, 8.46 mmol) and N-methylimidazole (0.1 ml, 1.24 mmol). The reaction mixture was stirred at room temperature for 24 h and heated at reflux for 3 h. After cooling to 10° C., a saturated solution of sodium hydrogenocarbonate (5 ml) and EtOAc (20 ml) were added, then after decantation, the organic phase was dried over magnesium sulfate, filtered, and concentrated under reduced pressure. The residue was purified by flash chromatography eluting with a mixture of DCM and isopropanol (96/04; v/v) to give 68 mg (34%) of 2-(4-(((S)-1-(3-fluoropropyl)pyrrolidin-3-yl)oxy)phenyl)-3-(4-hydroxyphenyl)-2,3-dihydrobenzo[b][1,4]oxathiin-6-ol (IVk) as a mixture of isomers which will be separated by chiral chromatography. LC/MS (m/z, MH+): 482

EXAMPLES

Example 1. 8-[4-[(3S)-1-(3-fluoropropyl)pyrrolidin-3-yl]oxyphenyl]-7-(3-fluoro-4-pyridyl)-5,6-dihydronaphthalen-2-ol

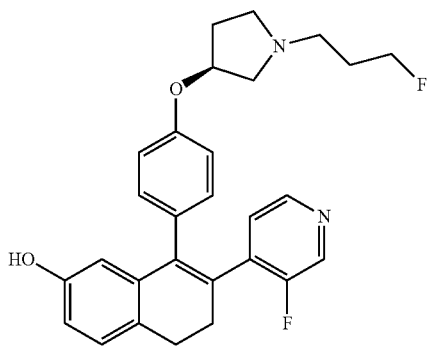 [SMILES: Oc1ccc2c(c1)C(c1ccc(O[C@H]3CCN(CCCF)C3)cc1)=C(c1ccncc1F)CC2]

Method A:

To a solution of 7-bromo-8-[4-[(3S)-1-(3-fluoropropyl)pyrrolidin-3-yl]oxyphenyl]-5,6-dihydronaphthalen-2-ol (Intermediate Ig1, 150 mg, 336.06 µmol) in dioxane (1.6 ml), was added 3-fluoropyridin-4-yl boronic acid (52.09 mg, 369.66 µmol), Cs$_2$CO$_3$ (0.8 ml of a 1.5 N aqueous solution, 1.20 mmol), and Pd(dppf)Cl$_2$ (12.94 mg, 16.80 µmol). The reaction mixture was heated at 70° C. for 2 hours. Water was added, and the reaction mixture was extracted with EtOAc. The organic phase was dried over magnesium sulfate, filtered, and concentrated under reduced pressure. The residue was purified by column chromatography eluting with a gradient of diisopropyl ether and MeOH (95/5 and 90/10; V:V) to give 56 mg (36%) of 8-[4-[(3S)-1-(3-fluoropropyl)pyrrolidin-3-yl]oxyphenyl]-7-(3-fluoro-4-pyridyl)-5,6-dihydronaphthalen-2-ol.

Example 16. 3-(2-fluoro-4-methyl-phenyl)-4-[4-[(3S)-1-(3-fluoropropyl)pyrrolidin-3-yl]oxyphenyl]-2H-thiochromen-7-ol

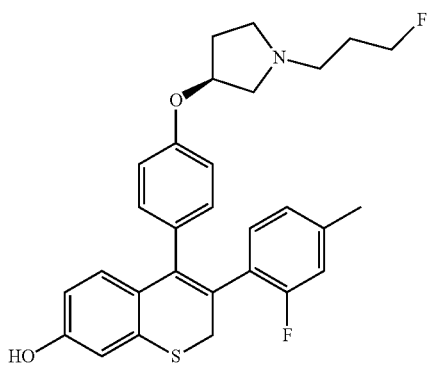 [SMILES: Cc1ccc(C2=C(c3ccc(O[C@H]4CCN(CCCF)C4)cc3)c3ccc(O)cc3SC2)c(F)c1]

To a solution of 3-bromo-4-[4-[(3S)-1-(3-fluoropropyl)pyrrolidin-3-yl]oxyphenyl]-2H-thiochromen-7-ol (Intermediate Ig7, 80 mg, 0.17 mmol), in dioxane (2.6 ml) and water (0.7 ml), was added 2-fluoro-4-methylphenyl boronic acid (30 mg, 0.19 mmol), Cs$_2$CO$_3$ (118 mg, 0.36 mmol), and Pd(dppf)Cl$_2$ (8 mg, 0.01 mmol). The reaction mixture was microwaved at 90° C. for 30 minutes. After cooling, the reaction mixture was concentrated under reduced pressure. The residue obtained was partitioned between water and DCM. The organic phase was concentrated under reduced pressure and the residue was purified by column chromatography eluting with a gradient of MeOH in DCM (0% to 05%; v/v) to give 20 mg (23%) of 3-(2-fluoro-4-methyl-phenyl)-4-[4-[(3S)-1-(3-fluoropropyl)pyrrolidin-3-yl]oxyphenyl]-2H-thiochromen-7-ol as a beige solid.

Example 25. 3-(2-fluoro-4-methyl-phenyl)-4-[4-[(3S)-1-(3-fluoropropyl)pyrrolidin-3-yl]oxyphenyl]-2H-thiochromene-7-carboxylic acid Step 1. [3-(2-fluoro-4-methyl-phenyl)-4-[4-[(3S)-1-(3-fluoropropyl)pyrrolidin-3-yl]oxyphenyl]-2H-thiochromen-7-yl]trifluoromethanesulfonate

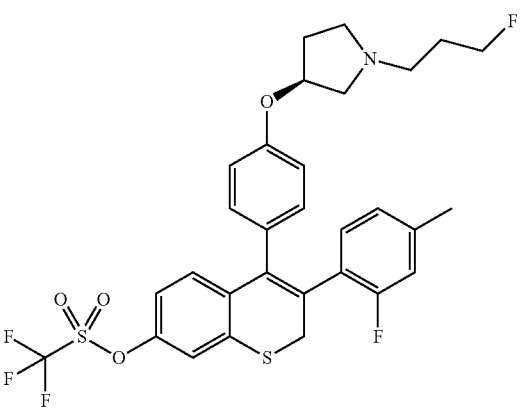 [SMILES: Cc1ccc(C2=C(c3ccc(O[C@H]4CCN(CCCF)C4)cc3)c3ccc(OS(=O)(=O)C(F)(F)F)cc3SC2)c(F)c1]

To a solution of 3-(2-fluoro-4-methyl-phenyl)-4-[4-[(3S)-1-(3-fluoropropyl)pyrrolidin-3-yl]oxyphenyl]-2H-thiochromen-7-ol (Example 16, 426 mg, 863.03 µmol) in DCM (15 ml), was added pyridine (139.60 µl, 1.73 mmol) and trifluoromethanesulfonic anhydride (302.49 µl, 1.73 mmol). The reaction mixture was stirred at room temperature for 1 hour, and poured onto ice. The aqueous phase was extracted with DCM, dried over magnesium sulfate, filtered, and concentrated under reduced pressure. The residue was purified by flash chromatography eluting with a gradient of MeOH in DCM (2 to 5%; V/V) to give 132 mg (70%) of [3-(2-fluoro-4-methyl-phenyl)-4-[4-[(3S)-1-(3-fluoropropyl)pyrrolidin-3-yl]oxyphenyl]-2H-thiochromen-7-yl]trifluoromethanesulfonate. LC/MS (m/z, MH+): 626

Step 2. 3-(2-fluoro-4-methyl-phenyl)-4-[4-[(3S)-1-(3-fluoropropyl)pyrrolidin-3-yl]oxyphenyl]-2H-thiochromene-7-carboxylic acid

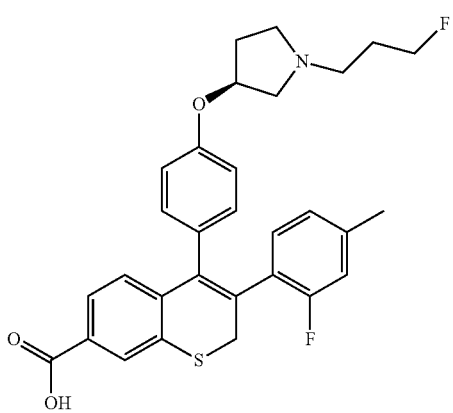 [SMILES: Cc1ccc(C2=C(c3ccc(O[C@H]4CCN(CCCF)C4)cc3)c3ccc(C(=O)O)cc3SC2)c(F)c1]

To a solution of [3-(2-fluoro-4-methyl-phenyl)-4-[4-[(3S)-1-(3-fluoropropyl)pyrrolidin-3-yl]oxyphenyl]-2H-thiochromen-7-yl]trifluoromethanesulfonate (277 mg, 442.73 µmol) in water (1.3 ml) was added pyridine (144 µL, 1.77 mmol), 1,1'-bis(diphenylphosphino)ferrocene (25.30 mg, 44.27 µmol), Pd(OAc)$_2$ (9.94 mg, 44.27 µmol), and molybdenum hexacarbonyl (58.50 mg, 221.36 µmol). The reaction mixture was microwaved at 150° C. for 20 minutes, and poured into water. The aqueous phase was extracted with EtOAc and the organic extracts were dried over magnesium sulfate, filtered, and concentrated under reduced pressure. The residue was purified by flash chromatography eluting with a gradient of MeOH in DCM (0 to 20%; V/V) to give 65 mg (28.1%) of 3-(2-fluoro-4-methyl-phenyl)-4-[4-[(3S)-1-(3-fluoropropyl)pyrrolidin-3-yl]oxyphenyl]-2H-thiochromene-7-carboxylicacid.

Example 29. 3-(2,2-dimethylindolin-5-yl)-4-[4-[(3S)-1-(3-fluoropropyl)pyrrolidin-3-yl]oxyphenyl]-2H-thiochromen-7-ol Step 1. 1-[5-[4-[4-[(3S)-1-(3-fluoropropyl)pyrrolidin-3-yl]oxyphenyl]-7-hydroxy-2H-thiochromen-3-yl]-2,2-dimethyl-indolin-1-yl]ethanone

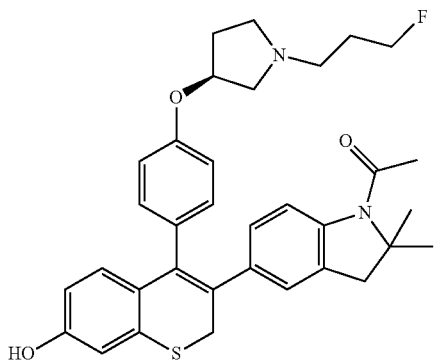 [SMILES: CC(=O)N1c2ccc(C3=C(c4ccc(O[C@H]5CCN(CCCF)C5)cc4)c4ccc(O)cc4SC3)cc2CC1(C)C]

To a solution of 3-bromo-4-[4-[(3S)-1-(3-fluoropropyl)pyrrolidin-3-yl]oxyphenyl]-2H-thiochromen-7-ol (Intermediate Ig7, 160 mg, 344.54 µmol) in a mixture of dioxane and water (8 ml; 80/20; V/V), was added 1-(2,2-dimethyl-5-(4,4,5,5-tetramethyl-1,3,2-dioxaborolan-2-yl)indolin-1-yl)ethanone (130.32 mg, 413.44 µmo), Pd(dppf)Cl$_2$ (16.88 mg, 20.67 µmol), and Cs$_2$CO$_3$ (235.98 mg, 723.53 µmol). The reaction mixture was heated at reflux for 30 minutes, and evaporated to dryness under reduced pressure. The residue was purified by flash chromatography eluting with a gradient of MeOH in DCM (2 to 5%; V/V) to give 140 mg 70.9%) of 1-[5-[4-[4-[(3S)-1-(3-fluoropropyl)pyrrolidin-3-yl]oxyphenyl]-7-hydroxy-2H-thiochromen-3-yl]-2,2-dimethyl-indolin-1-yl]ethanone. LC/MS (m/z, MH+): 573

Step 2. 3-(2,2-dimethylindolin-5-yl)-4-[4-[(3S)-1-(3-fluoropropyl)pyrrolidin-3-yl]oxyphenyl]-2H-thiochromen-7-ol

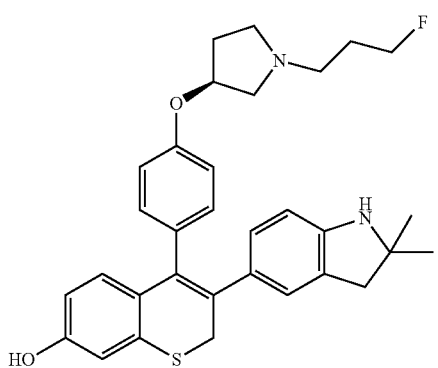 [SMILES: CC1(C)Cc2cc(C3=C(c4ccc(O[C@H]5CCN(CCCF)C5)cc4)c4ccc(O)cc4SC3)ccc2N1]

To a solution of 1-[5-[4-[4-[(3S)-1-(3-fluoropropyl)pyrrolidin-3-yl]oxyphenyl]-7-hydroxy-2H-thiochromen-3-yl]-2,2-dimethyl-indolin-1-yl]ethanone (121 mg, 211.27 µmol) in dioxane (2.5 ml), was added hydrochloric acid (2N, 1.24 ml). The reaction mixture was microwaved at 120° C. for 1 hour and poured onto a saturated aqueous solution of sodium bicarbonate. The aqueous phase was extracted with EtOAc and the gathered organic extracts were dried over magnesium sulfate, filtered, and concentrated under reduced pressure. The residue was purified by flash chromatography eluting with a gradient of MeOH in DCM (2 to 5%; V/V) to give 60 mg (53.5%) of 3-(2,2-dimethylindolin-5-yl)-4-[4-[(3S)-1-(3-fluoropropyl)pyrrolidin-3-yl]oxyphenyl]-2H-thiochromen-7-ol.

Example 48. [3-(2-fluoro-4-methyl-phenyl)-4-[4-[(3S)-1-(3-fluoropropyl)pyrrolidin-3-yl]oxyphenyl]-2H-thiochromen-7-yl]dihydrogen phosphate Step 1. diethyl [3-(2-fluoro-4-methyl-phenyl)-4-[4-[(3S)-1-(3-fluoropropyl)pyrrolidin-3-yl]oxyphenyl]-2H-thiochromen-7-yl]phosphate

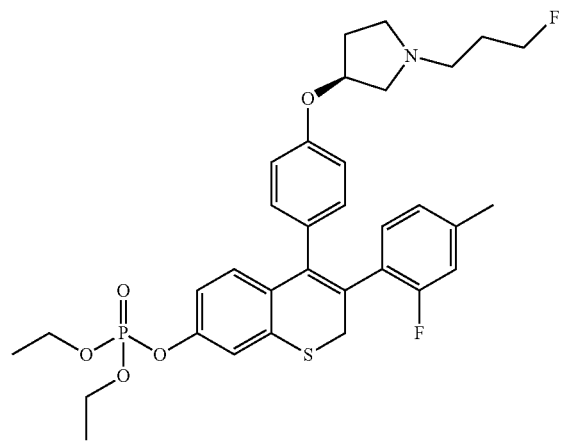 [SMILES: CCOP(=O)(OCC)Oc1ccc2c(c1)SCC(c1ccc(C)cc1F)=C2c1ccc(O[C@H]2CCN(CCCF)C2)cc1]

To a solution of 3-(2-fluoro-4-methyl-phenyl)-4-[4-[(3S)-1-(3-fluoropropyl)pyrrolidin-3-yl]oxyphenyl]-2H-thiochromen-7-ol (Example 16, 160 mg, 0.32 mmol), in tetrachloromethane (8 ml), was added diisopropylethylamine (0.21 ml, 1.04 mmol), and diethyl chlorophosphate (0.11 ml, 0.81 mmol). The reaction mixture was heated at 105° C. for 2 hours, and concentrated under reduced pressure. The residue was purified by strong cation exchange (SCX) column to give 160 mg (88%) of diethyl [3-(2-fluoro-4-methyl-phenyl)-4-[4-[(3S)-1-(3-fluoropropyl)pyrrolidin-3-yl]oxyphenyl]-2H-thiochromen-7-yl]phosphate.

LC/MS (m/z, MH+): 629

Step 2 [3-(2-fluoro-4-methyl-phenyl)-4-[4-[(3S)-1-(3-fluoropropyl)pyrrolidin-3-yl]oxyphenyl]-2H-thiochromen-7-yl]dihydrogen phosphate

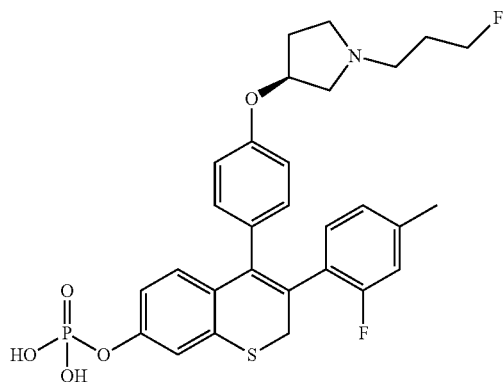 [SMILES: Cc1ccc(C2=C(c3ccc(O[C@H]4CCN(CCCF)C4)cc3)c3ccc(OP(=O)(O)O)cc3SC2)c(F)c1]

To a solution of diethyl [3-(2-fluoro-4-methyl-phenyl)-4-[4-[(3S)-1-(3-fluoropropyl)pyrrolidin-3-yl]oxyphenyl]-2H-thiochromen-7-yl]phosphate (80 mg, 0.13 mmol), in acetonitrile (3 ml), was added iodotrimethylsilane (0.09 ml, 0.64 mmol). The reaction mixture was stirred at 60° C. for 1.5 hours, and concentrated under reduced pressure. The residue was purified by strong cation exchange (SCX) column and reverse phase column chromatography, eluting with a gradient of acetonitrile in water (20% to 80%; v/v) to give 37 mg (51%) of [3-(2-fluoro-4-methyl-phenyl)-4-[4-[(3S)-1-(3-fluoropropyl)pyrrolidin-3-yl]oxyphenyl]-2H-thiochromen-7-yl]dihydrogen phosphate.

Example 57. 3-(2-fluoro-4-methyl-phenyl)-4-[4-[(3S)-1-(3-fluoropropyl)pyrrolidin-3-yl]oxyphenyl]-1-oxo-2H-thiochromen-7-ol

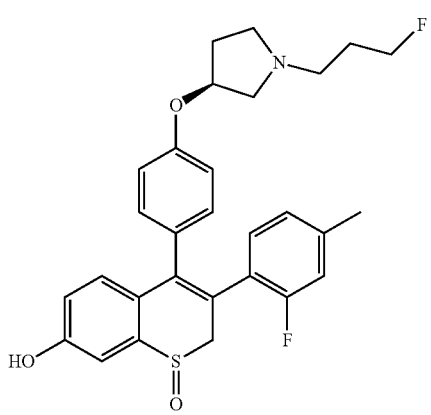 [SMILES: Cc1ccc(C2=C(c3ccc(O[C@H]4CCN(CCCF)C4)cc3)c3ccc(O)cc3S(=O)C2)c(F)c1]

To a solution of 3-(2-fluoro-4-methyl-phenyl)-4-[4-[(3S)-1-(3-fluoropropyl)pyrrolidin-3-yl]oxyphenyl]-2H-thiochromen-7-ol (Example 16, 50 mg, 101.29 µmol) in MeOH (4 ml) was added a solution of potassium peroxymonosulfate (OXONE®, 124.55 mg, 202.59 µmol) in water (1 ml) at 0° C. (ice bath). The reaction mixture was stirred for 30 minutes, and a solution of saturated sodium thiosulphate was added (5 ml) followed by a saturated solution of sodium bicarbonate until pH 7-8. The aqueous phase was extracted with DCM and the gathered organic extracts, dried over magnesium sulfate, filtered, and concentrated under reduced pressure. The residue was purified by flash chromatography eluting with a mixture of DCM and MeOH (97/3; V/V) to give 35 mg (67.8%) of 3-(2-fluoro-4-methyl-phenyl)-4-[4-[(3S)-1-(3-fluoropropyl)pyrrolidin-3-yl]oxyphenyl]-1-oxo-2H-thiochromen-7-ol as a racemate.

Example 70. 3-(2-fluoro-4-methyl-phenyl)-4-[4-[(3S)-1-(3-fluoropropyl)pyrrolidin-3-yl]oxyphenyl]-1-oxo-2H-thiochromen-7-ol

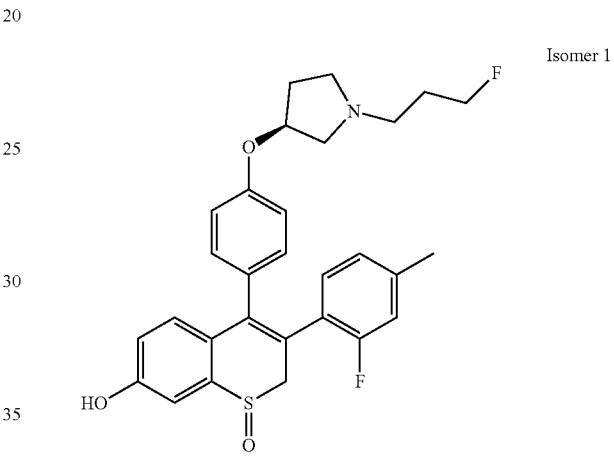

Isomer 1

3-(2-fluoro-4-methyl-phenyl)-4-[4-[(3S)-1-(3-fluoropropyl)pyrrolidin-3-yl]oxyphenyl]-1-oxo-2H-thiochromen-7-ol (Example 57, 210 mg, 412.08 µmol) was separated by chiral HPLC on Chiralpak IC 20 µm column, eluting with a mixture of heptane, ethanol and triethylamine (70/30/0.1; V/V/V) to give 82.9 mg (39.5%) of diastereomer 1.

Example 71. 3-(2-fluoro-4-methyl-phenyl)-4-[4-[(3S)-1-(3-fluoropropyl)pyrrolidin-3-yl]oxyphenyl]-1-oxo-2H-thiochromen-7-ol

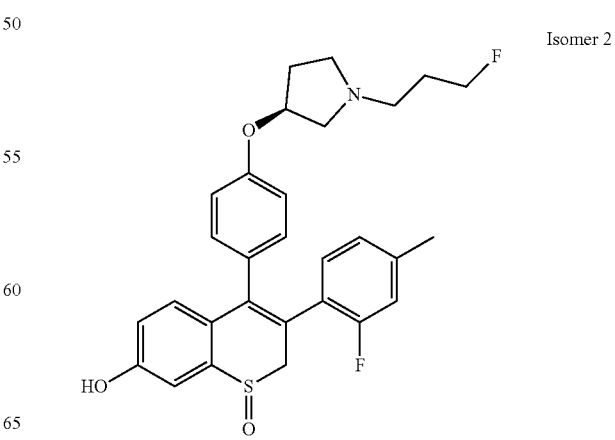

Isomer 2

3-(2-fluoro-4-methyl-phenyl)-4-[4-[(3S)-1-(3-fluoropropyl)pyrrolidin-3-yl]oxyphenyl]-1-oxo-2H-thiochromen-7-ol (Example 57, 210 mg, 412.08 µmol) was separated by chiral HPLC on Chiralpak IC 20 µm column, eluting with a mixture of heptane, ethanol and triethylamine (70/30/0.1; V/V/V) to give 80.4 mg (38.3%) of diastereomer 2.

Example 72. 3-(6-amino-2-fluoro-3-pyridyl)-4-[4-[(3S)-1-(3-fluoropropyl)pyrrolidin-3-yl]oxyphenyl]-2H-thiochromen-7-ol

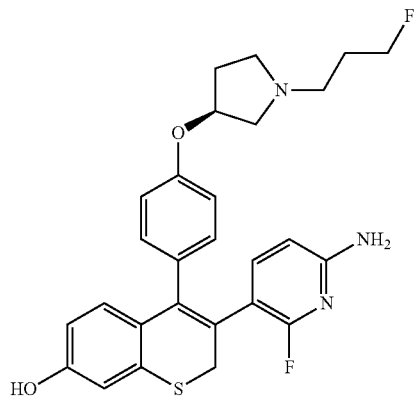

To a solution of tert-butyl N-[6-fluoro-5-[4-[4-[(3S)-1-(3-fluoropropyl)pyrrolidin-3-yl]oxyphenyl]-7-hydroxy-2H-thiochromen-3-yl]-2-pyridyl]carbamate (Example 65, 94 mg, 157.80 µmol) in THF (5 ml) was added Hydrochloric acid (1.5 ml, 4M in dioxane, 40 eq.). The reaction mixture was heated at 50° C. for 16 hours, and poured into a saturated sodium bicarbonate solution. The aqueous phase was extracted with EtOAc and the gathered organic extracts were dried over magnesium sulfate, filtered, and concentrated under reduced pressure. The residue was purified by flash chromatography eluting with EtOAc to give 53 mg (67.8%) of 3-(6-amino-2-fluoro-3-pyridyl)-4-[4-[(3S)-1-(3-fluoropropyl)pyrrolidin-3-yl]oxyphenyl]-2H-thiochromen-7-ol.

Example 84. 7-(2-chloro-4-fluoro-phenyl)-8-[4-[[(3S)-1-(3-fluoropropyl)pyrrolidin-3-yl]amino]phenyl]-5,6-dihydronaphthalen-2-ol

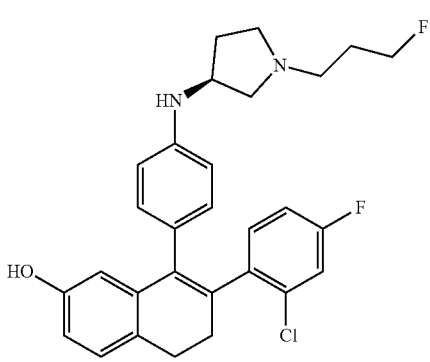 [SMILES: Oc1ccc2c(c1)C(c1ccc(N[C@H]3CCN(CCCF)C3)cc1)=C(c1ccc(F)cc1Cl)CC2]

To a solution of 7-(2-chloro-4-fluoro-phenyl)-8-[4-[[(3S)-pyrrolidin-3-yl]amino]phenyl]-5,6-dihydronaphthalen-2-ol (Intermediate I2, 78.6 mg, 180.72 µmol) in N,N-dimethylformamide (3.5 ml) was added potassium carbonate (18.73 mg, 135.54 µmol), and 1-fluoro-3-iodopropane (20.44 µl, 189.75 µmol). The reaction mixture was heated at 70° C. for 1 hour, and 30 ml of water was added. The aqueous phase was extracted with EtOAc, and the gathered organic extracts, were dried over magnesium sulfate, filtered, and concentrated under reduced pressure. The residue was purified by flash chromatography eluting with a mixture of DCM and MeOH (97/3; V) to give 41.5 mg (46%) of 7-(2-chloro-4-fluoro-phenyl)-8-[4-[[(3S)-1-(3-fluoropropyl)pyrrolidin-3-yl]amino]phenyl]-5,6-dihydronaphthalen-2-ol.

Example 116. 5-[4-[(3S)-1-(3-fluoropropyl)pyrrolidin-3-yl]oxyphenyl]-4-indolin-6-yl-2,3-dihydro-1-benzoxepin-8-ol

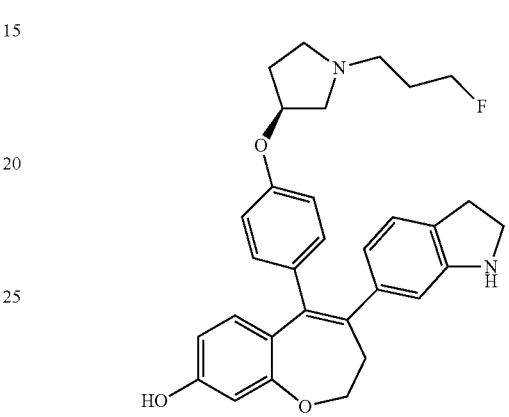

Method B:

To a solution of 5-[4-[(3S)-1-(3-fluoropropyl)pyrrolidin-3-yl]oxyphenyl]-4-(1H-indol-6-yl)-2,3-dihydro-1-benzoxepin-8-ol (Example 103, 60 mg, 120.34 µmol) in acetic acid (6 ml), was added sodium cyanoborohydride (22.29 mg, 336.95 µmol). The reaction mixture was stirred at room temperature for 24 hours, and 20 ml of an aqueous sodium bicarbonate solution was added to reach pH 7. The aqueous phase was extracted with DCM, and the gathered organic phases dried over an hydrophobic column, and concentrated under reduced pressure. The residue was purified by flash chromatography, eluting with a gradient of MeOH in DCM (0 to 10%; V/V) to give 36 mg (59.8%) of 5-[4-[(3S)-1-(3-fluoropropyl)pyrrolidin-3-yl]oxyphenyl]-4-indolin-6-yl-2,3-dihydro-1-benzoxepin-8-ol.

Example 166. 4-(2,4-dichlorophenyl)-5-[4-[(3S)-1-(3-fluoropropyl)pyrrolidin-3-yl]oxyphenyl]-2,3-dihydro-1-benzothiepin-8-ol

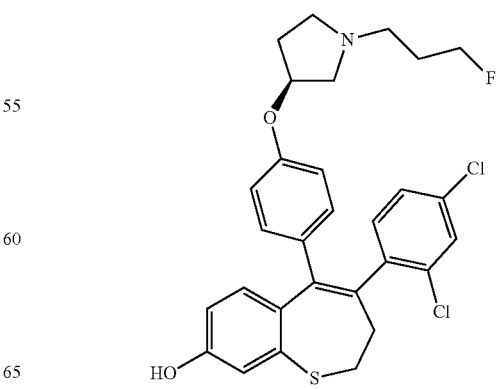

To a solution of 4-bromo-5-[4-[(3S)-1-(3-fluoropropyl)pyrrolidin-3-yl]oxyphenyl]-2,3-dihydro-1-benzothiepin-8-ol (Intermediate Ig20, 600 mg, 1.25 mmol), in dioxane (16 ml) and water (4 ml), was added 2,4-dichlorophenyl boronic acid (260 mg, 1.34 mmol), Cs₂CO₃ (859 mg, 2.63 mmol), and Pd(dppf)Cl₂ (61 mg, 0.75 mmol). The reaction mixture was heated at 120° C. for 1 hour, and concentrated under reduced pressure. The residue was partitioned between water and DCM, and the organic phase was concentrated under reduced pressure. The residue was purified by column chromatography eluting with a gradient of MeOH in DCM (0% to 05%; v/v) to give a solid which was further purified on strong cation exchange (SCX) column to give 409 mg (60%) of 4-(2,4-dichlorophenyl)-5-[4-[(3S)-1-(3-fluoropropyl)pyrrolidin-3-yl]oxyphenyl]-2,3-dihydro-1-benzothiepin-8-ol.

Example 198. 4-(2,2-dimethylindolin-5-yl)-5-[4-[(3S)-1-(3-fluoropropyl)pyrrolidin-3-yl]oxyphenyl]-2,3-dihydro-1-benzothiepin-8-ol Step 1. 1-[5-[5-[4-[(3S)-1-(3-fluoropropyl)pyrrolidin-3-yl]oxyphenyl]-8-hydroxy-2,3-dihydro-1-benzothiepin-4-yl]-2,2-dimethyl-indolin-1-yl]ethanone

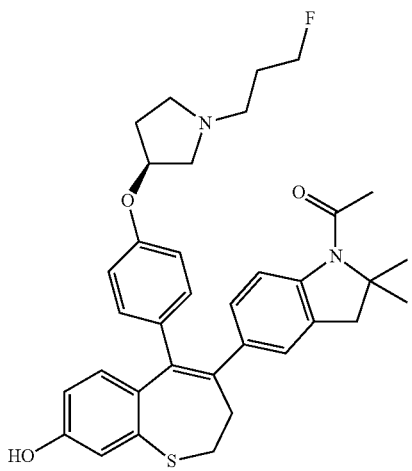 [SMILES: CC(=O)N1c2ccc(C3=C(c4ccc(O[C@H]5CCN(CCCF)C5)cc4)c4ccc(O)cc4SCC3)cc2CC1(C)C]

To a solution of 4-bromo-5-[4-[(3S)-1-(3-fluoropropyl)pyrrolidin-3-yl]oxyphenyl]-2,3-dihydro-1-benzothiepin-8-ol (Intermediate Ig20, 160 mg, 334.44 µmol) in a mixture of dioxane and water (8 ml; 80/20; V/V), was added 1-(2,2-dimethyl-5-(4,4,5,5-tetramethyl-1,3,2-dioxaborolan-2-yl)indolin-1-yl)ethanone (126.50 mg, 401.32 µmol), Pd(dppf)Cl₂ (16.39 mg, 20.07 µmol), and Cs₂CO₃ (229.06 mg, 702.32 µmol). The reaction mixture was heated at reflux for 1 hour, and evaporated to dryness under reduced pressure. The residue was purified by flash chromatography eluting with a gradient of MeOH in DCM (2 to 5%; V/V) to give 112 mg (62.2%) of 1-[5-[5-[4-[(3S)-1-(3-fluoropropyl)pyrrolidin-3-yl]oxyphenyl]-8-hydroxy-2,3-dihydro-1-benzothiepin-4-yl]-2,2-dimethyl-indolin-1-yl]ethanone. LC/MS (m/z, MH+): 587

Step 2. 4-(2,2-dimethylindolin-5-yl)-5-[4-[(3S)-1-(3-fluoropropyl)pyrrolidin-3-yl]oxyphenyl]-2,3-dihydro-1-benzothiepin-8-ol

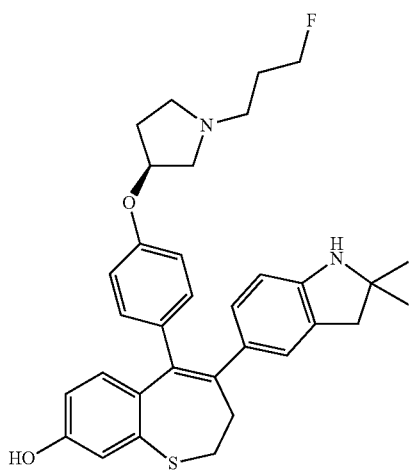 [SMILES: CC1(C)Cc2cc(C3=C(c4ccc(O[C@H]5CCN(CCCF)C5)cc4)c4ccc(O)cc4SCC3)ccc2N1]

To a solution of 1-[5-[5-[4-[(3S)-1-(3-fluoropropyl)pyrrolidin-3-yl]oxyphenyl]-8-hydroxy-2,3-dihydro-1-benzothiepin-4-yl]-2,2-dimethyl-indolin-1-yl]ethanone (100 mg, 170.43 µmol) in dioxane (2.5 ml), was added hydrochloric acid (2N, 1 ml). The reaction mixture was microwaved at 120° C. for 1 hour and poured onto a saturated aqueous solution of sodium bicarbonate. The aqueous phase was extracted with EtOAc and the gathered organic extracts were dried over magnesium sulfate, filtered, and concentrated under reduced pressure The residue was purified by flash chromatography eluting with a gradient of MeOH in DCM (2 to 5%; V/V) to give 81 mg (87.3%) of 4-(2,2-dimethylindolin-5-yl)-5-[4-[(3S)-1-(3-fluoropropyl)pyrrolidin-3-yl]oxyphenyl]-2,3-dihydro-1-benzothiepin-8-ol.

Example 203. 4-(2,4-dichlorophenyl)-5-[4-[(3S)-1-(3-fluoropropyl)pyrrolidin-3-yl]oxyphenyl]-2,3-dihydro-1-benzothiepine-8-carboxylic acid Step 1. [4-(2,4-dichlorophenyl)-5-[4-[(3S)-1-(3-fluoropropyl)pyrrolidin-3-yl]oxyphenyl]-2,3-dihydro-1-benzothiepin-8-yl]trifluoromethanesulfonate

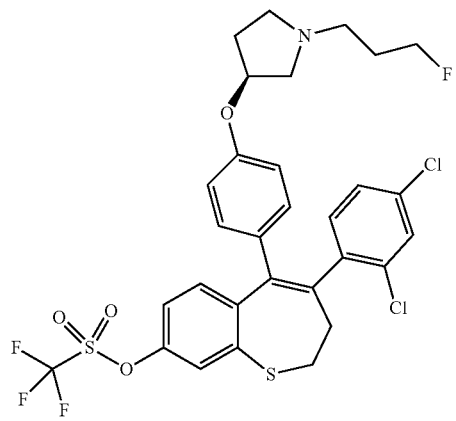 [SMILES: O=S(=O)(Oc1ccc2c(c1)SCCC(c1ccc(Cl)cc1Cl)=C2c1ccc(O[C@H]2CCN(CCCF)C2)cc1)C(F)(F)F]

To a solution of 4-(2,4-dichlorophenyl)-5-[4-[(3S)-1-(3-fluoropropyl)pyrrolidin-3-yl]oxyphenyl]-2,3-dihydro-1-benzothiepin-8-ol (Example 166, 100 mg, 183.65 µmol) in DCM (5 ml), was added pyridine (23.21 µl, 275.48 µmol) and trifluoromethanesulfonic anhydride (62.42 µl, 367.30 µmol). The reaction mixture was stirred at room temperature for 1 hour, and poured onto ice. The aqueous phase was extracted with DCM, dried over magnesium sulfate, filtered, and concentrated under reduced pressure. The residue was purified by flash chromatography eluting with a gradient of MeOH in DCM (2 to 5%; V/V) to give 100 mg (80.5%) of [4-(2,4-dichlorophenyl)-5-[4-[(3S)-1-(3-fluoropropyl)pyrrolidin-3-yl]oxyphenyl]-2,3-dihydro-1-benzothiepin-8-yl]trifluoromethanesulfonate. LC/MS (m/z, MH+): 676

Step 2. 4-(2,4-dichlorophenyl)-5-[4-[(3S)-1-(3-fluoropropyl)pyrrolidin-3-yl]oxyphenyl]-2,3-dihydro-1-benzothiepine-8-carboxylic acid

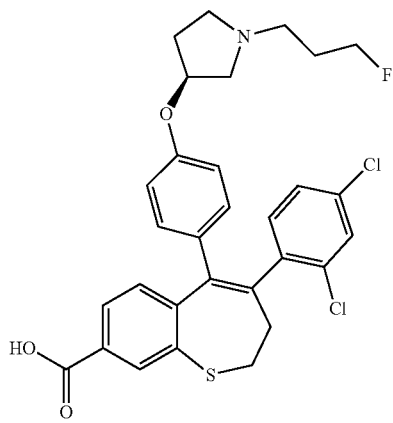 [SMILES: O=C(O)c1ccc2c(c1)SCCC(c1ccc(Cl)cc1Cl)=C2c1ccc(O[C@H]2CCN(CCCF)C2)cc1]

A mixture of [4-(2,4-dichlorophenyl)-5-[4-[(3S)-1-(3-fluoropropyl)pyrrolidin-3-yl]oxyphenyl]-2,3-dihydro-1-benzothiepin-8-yl]trifluoromethanesulfonate (100 mg, 0.15 mmol), pyridine (0.12 ml, 1.48 mmol), water (0.5 ml), 1,1'-bis(diphenylphosphino)ferrocene (8 mg, 0.015 mmol), palladium acetate (3 mg, 0.015 mmol) and molybdenum hexacarbonyl (19 mg, 0.074 mmol) was microwaved at 150° C. for 20 minutes. The reaction mixture was partitioned between DCM (25 ml) and water (25 ml) and the phases were separated. The organic phase was dried over magnesium sulfate, filtered, and concentrated under reduced pressure. The residue was purified by flash chromatography eluting with a gradient of MeOH in DCM (0 to 10%; V/V) to give 7 mg (8%) of 4-(2,4-dichlorophenyl)-5-[4-[(3S)-1-(3-fluoropropyl)pyrrolidin-3-yl]oxyphenyl]-2,3-dihydro-1-benzothiepine-8-carboxylic acid.

Example 210. 4-(2-fluoro-4-methyl-phenyl)-5-[4-[(3S)-1-(3-fluoropropyl)pyrrolidin-3-yl]oxyphenyl]-2,3-dihydro-1-benzothiepine-8-carboxylic acid Step 1. [4-(2-fluoro-4-methyl-phenyl)-5-[4-[(3S)-1-(3-fluoropropyl)pyrrolidin-3-yl]oxyphenyl]-2,3-dihydro-1-benzothiepin-8-yl]trifluoromethanesulfonate

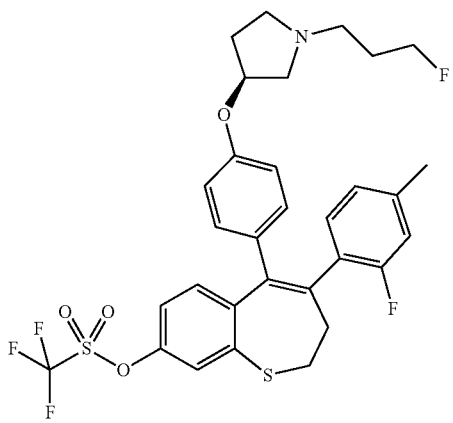 [SMILES: Cc1ccc(C2=C(c3ccc(O[C@H]4CCN(CCCF)C4)cc3)c3ccc(OS(=O)(=O)C(F)(F)F)cc3SCC2)c(F)c1]

To a solution of 4-(2-fluoro-4-methyl-phenyl)-5-[4-[(3S)-1-(3-fluoropropyl)pyrrolidin-3-yl]oxyphenyl]-2,3-dihydro-1-benzothiepin-8-ol (Example 164, 50 mg, 295.49 µmol) in DCM (7 ml), was added pyridine (37.34 µl, 443.23 µmol) and trifluoromethanesulfonic anhydride (100.43 µl, 590.98 µmol). The reaction mixture was stirred at room temperature for 1 hour, and poured onto ice. The aqueous phase was extracted with DCM, dried over magnesium sulfate, filtered, and concentrated under reduced pressure. The residue was purified by flash chromatography eluting with a gradient of MeOH in DCM (2 to 5%; V/V) to give 128 mg (67.7%) of [4-(2-fluoro-4-methyl-phenyl)-5-[4-[(3S)-1-(3-fluoropropyl)pyrrolidin-3-yl]oxyphenyl]-2,3-dihydro-1-benzothiepin-8-yl]trifluoromethanesulfonate. LC/MS (m/z, MH+): 639

Step 2. 4-(2-fluoro-4-methyl-phenyl)-5-[4-[(3S)-1-(3-fluoropropyl)pyrrolidin-3-yl]oxyphenyl]-2,3-dihydro-1-benzothiepine-8-carboxylicacid

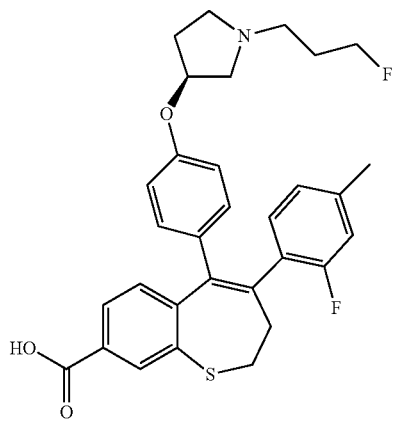 [SMILES: Cc1ccc(C2=C(c3ccc(O[C@H]4CCN(CCCF)C4)cc3)c3ccc(C(=O)O)cc3SCC2)c(F)c1]

A mixture of [4-(2-fluoro-4-methyl-phenyl)-5-[4-[(3S)-1-(3-fluoropropyl)pyrrolidin-3-yl]oxyphenyl]-2,3-dihydro-1-benzothiepin-8-yl]trifluoromethanesulfonate (127 mg, 198.53 µmol), pyridine (161.38 µl, 1.99 mmol), water (0.5 ml), 1,1'-bis(diphenylphosphino)ferrocene (11.35 mg, 19.85 µmol)), palladium acetate (4.46 mg, 19.85 µmol) and molybdenum hexacarbonyl (26.23 mg, 99.27 µmol) was microwaved at 150° C. for 20 minutes. The reaction mixture was partitioned between DCM (25 ml) and water (25 ml) was the phases were separated. The organic phase was dried over magnesium sulfate, filtered, and concentrated under reduced pressure. The residue was purified by flash chromatography eluting with a gradient of MeOH in DCM (0 to 10%; V/V) to give 41 mg (38.6%) of 4-(2-fluoro-4-methyl-phenyl)-5-[4-[(3S)-1-(3-fluoropropyl)pyrrolidin-3-yl]oxyphenyl]-2,3-dihydro-1-benzothiepine-8-carboxylicacid.

Example 211. 4-(4-chloro-3-methyl-phenyl)-5-[4-[(3S)-1-(3-fluoropropyl)pyrrolidin-3-yl]oxyphenyl]-2,3-dihydro-1-benzothiepine-8-carboxylic acid Step 1. [4-(4-chloro-3-methyl-phenyl)-5-[4-[(3S)-1-(3-fluoropropyl)pyrrolidin-3-yl]oxyphenyl]-2,3-dihydro-1-benzothiepin-8-yl]trifluoromethanesulfonate

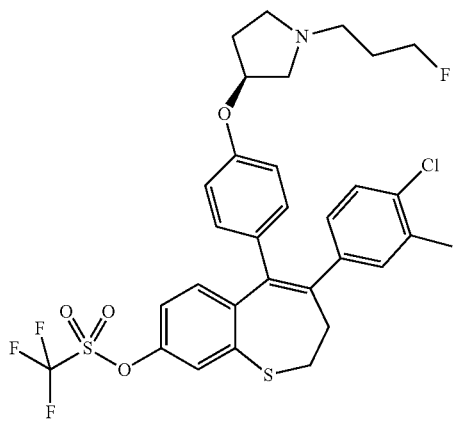 [SMILES: Cc1cc(C2=C(c3ccc(O[C@H]4CCN(CCCF)C4)cc3)c3ccc(OS(=O)(=O)C(F)(F)F)cc3SCC2)ccc1Cl]

To a solution of 4-(4-chloro-3-methyl-phenyl)-5-[4-[(3S)-1-(3-fluoropropyl)pyrrolidin-3-yl]oxyphenyl]-2,3-dihydro-1-benzothiepin-8-ol (Example 162, 150 mg, 286.21 µmol) in DCM (7 ml), was added pyridine (36.17 µl, 429.32 µmol) and trifluoromethanesulfonic anhydride (97.28 µl, 572.42 µmol). The reaction mixture was stirred at room temperature for 1 hour, and poured onto ice. The aqueous phase was extracted with DCM, dried over magnesium sulfate, filtered, and concentrated under reduced pressure. The residue was purified by flash chromatography eluting with a gradient of MeOH in DCM (2 to 5%; V/V) to give 180 mg (95.8) of [4-(4-chloro-3-methyl-phenyl)-5-[4-[(3S)-1-(3-fluoropropyl)pyrrolidin-3-yl]oxyphenyl]-2,3-dihydro-1-benzothiepin-8-yl]trifluoromethanesulfonate. LC/MS (m/z, MH+): 657

Step 2. 4-(4-chloro-3-methyl-phenyl)-5-[4-[(3S)-1-(3-fluoropropyl)pyrrolidin-3-yl]oxyphenyl]-2,3-dihydro-1-benzothiepine-8-carboxylicacid

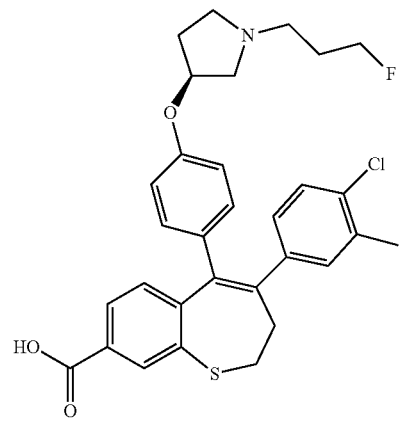 [SMILES: Cc1cc(C2=C(c3ccc(O[C@H]4CCN(CCCF)C4)cc3)c3ccc(C(=O)O)cc3SCC2)ccc1Cl]

A mixture of [4-(4-chloro-3-methyl-phenyl)-5-[4-[(3S)-1-(3-fluoropropyl)pyrrolidin-3-yl]oxyphenyl]-2,3-dihydro-1-benzothiepin-8-yl]trifluoromethanesulfonate (180 mg, 274.33 µmol), pyridine (222.99 µl, 2.74 mmol), water (0.5 ml), 1,1'-bis(diphenylphosphino)ferrocene (15.68 mg, 27.43 µmol), palladium acetate (6.16 mg, 27.43 µmol) and molybdenum hexacarbonyl (36.25 mg, 137.16 µmol) was microwaved at 150° C. for 20 minutes. The reaction mixture was partitioned between DCM (25 ml) and water (25 ml), and the phases were separated. The organic phase was dried over magnesium sulfate, filtered, and concentrated under reduced pressure. The residue was purified by flash chromatography eluting with a gradient of MeOH in DCM (0 to 10%; V/V) to give 60 mg (39.6%) of 4-(4-chloro-3-methyl-phenyl)-5-[4-[(3S)-1-(3-fluoropropyl)pyrrolidin-3-yl]oxyphenyl]-2,3-dihydro-1-benzothiepine-8-carboxylicacid.

Example 225. 5-[4-[(3S)-1-(3-fluoropropyl)pyrrolidin-3-yl]oxyphenyl]-1-oxo-4-[4-(trifluoromethoxy)phenyl]-2,3-dihydro-benzothiepin-8-ol

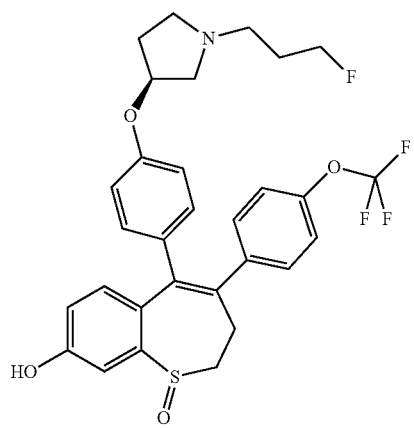 [SMILES: O=S1CCC(c2ccc(OC(F)(F)F)cc2)=C(c2ccc(O[C@H]3CCN(CCCF)C3)cc2)c2ccc(O)cc21]

To a solution of 5-[4-[(3S)-1-(3-fluoropropyl)pyrrolidin-3-yl]oxyphenyl]-4-[4-(trifluoromethoxy)phenyl]-2,3-dihydro-1-benzothiepin-8-ol (Example 214, 450 mg, 804.12 µmol) in MeOH (40 ml) was added dropwise a solution of potassium peroxymonosulfate (OXONE®, 988.69 mg, 1.61 mmol) in water (10 ml) at 0° C. (ice bath). The reaction mixture was stirred for 20 minutes, and a saturated solution of sodium thiosulfate (50 ml) was added, followed by a saturated aqueous solution of sodium bicarbonate until pH 7-8. The aqueous phase was extracted with DCM and the gathered organic extracts were dried over magnesium sulfate, filtered, and concentrated under reduced pressure. The residue was purified by column chromatography eluting with a gradient of MeOH in dichloromethane (3 to 5%; V/V) to give 235 mg (50.8%) of 5-[4-[(3S)-1-(3-fluoropropyl)pyrrolidin-3-yl]oxyphenyl]-1-oxo-4-[4-(trifluoromethoxy)phenyl]-2,3-dihydro-benzothiepin-8-ol as a racemate.

Example 226. 5-[4-[(3S)-1-(3-fluoropropyl)pyrrolidin-3-yl]oxyphenyl]-1-oxo-4-[4-(trifluoromethoxy)phenyl]-2,3-dihydro-benzothiepin-8-ol Isomer 1

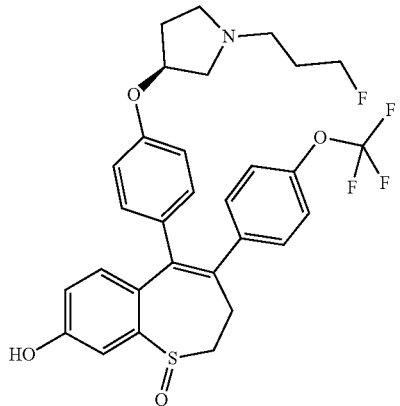

5-[4-[(3S)-1-(3-fluoropropyl)pyrrolidin-3-yl]oxyphenyl]-1-oxo-4-[4-(trifluoromethoxy)phenyl]-2,3-dihydro-benzothiepin-8-ol (Example 225, 210 mg, 363.95 µmol) was separated by chiral HPLC on Chiralpak AD 20 µm column, eluting with a mixture of heptane, ethanol and triethylamine (75/25/0.1; V/V/V) to give 101.9 mg (48%) of diastereomer 1. 5-[4-[(3S)-1-(3-fluoropropyl)pyrrolidin-3-yl]oxyphenyl]-1-oxo-4-[(trifluoromethoxy)phenyl]-2,3-dihydro-benzothiepin-8-ol.

Example 227. 5-[4-[(3S)-1-(3-fluoropropyl)pyrrolidin-3-yl]oxyphenyl]-1-oxo-4-[4-(trifluoromethoxy)phenyl]-2,3-dihydro-benzothiepin-8-ol Isomer 2

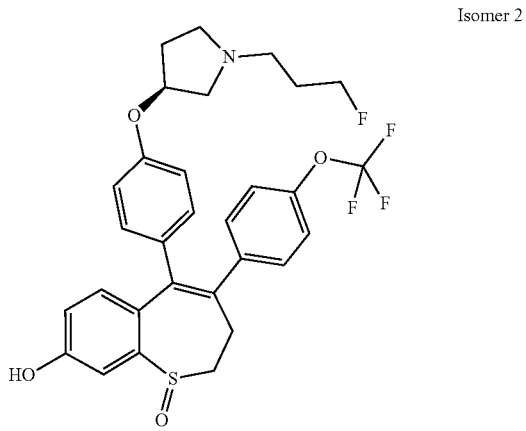 [SMILES: O=S1CCC(c2ccc(OC(F)(F)F)cc2)=C(c2ccc(O[C@H]3CCN(CCCF)C3)cc2)c2ccc(O)cc21]

5-[4-[(3S)-1-(3-fluoropropyl)pyrrolidin-3-yl]oxyphenyl]-1-oxo-4-[4-(trifluoromethoxy)phenyl]-2,3-dihydro-benzothiepin-8-ol (Example 225, 210 mg, 363.95 µmol) was separated by chiral HPLC on Chiralpak AD 20 µm column, eluting with a mixture of heptane, ethanol and triethylamine (75/25/0.1; V/V/V) to give 98.8 mg (47%) of 5-[4-[(3S)-1-(3-fluoropropyl)pyrrolidin-3-yl]oxyphenyl]-1-oxo-4-[4-(trifluoromethoxy)phenyl]-2,3-dihydro-benzothiepin-8-ol, diastereomer 2.

Example 228. 5-[4-[(3S)-1-(3-fluoropropyl)pyrrolidin-3-yl]oxyphenyl]-4-(3-hydroxyphenyl)-1,1-dioxo-2,3-dihydro-benzothiepin-8-ol

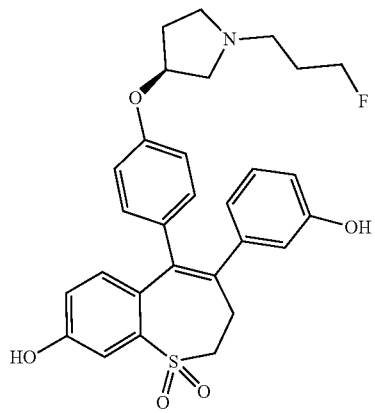 [SMILES: O=S1(=O)CCC(c2cccc(O)c2)=C(c2ccc(O[C@H]3CCN(CCCF)C3)cc2)c2ccc(O)cc21]

Method C:

To a solution of 5-[4-[(3S)-1-(3-fluoropropyl)pyrrolidin-3-yl]oxyphenyl]-4-(3-hydroxyphenyl)-2,3-dihydro-1-benzothiepin-8-ol (Example 158, 59 mg, 120.01 µmol) in MeOH (2 ml), was added potassium peroxymonosulfate (OXONE®, 221.34 mg, 360.04 µmol) in solution in water (2 ml). The reaction mixture was stirred at room temperature for 3 hours, and 10 ml of a saturated thiosulfate solution was added, followed by a saturated sodium bicarbonate aqueous solution until pH 7-8 is reached. The aqueous phase was extracted with DCM, and the organic phase was dried over hydrophobic column, and evaporated under reduced pressure The residue was purified by flash chromatography eluting with a gradient of MeOH in DCM (from 0 to 10% V/V) to give 55 mg (87.5%) of 5-[4-[(3S)-1-(3-fluoropropyl)pyrrolidin-3-yl]oxyphenyl]-4-(3-hydroxyphenyl)-1,1-dioxo-2,3-dihydro-benzothiepin-8-ol.

Example 242. 6-(2,2-dimethylindolin-5-yl)-5-[6-[(3S)-1-(3-fluoropropyl)pyrrolidin-3-yl]oxy-3-pyridyl]-8,9-dihydro-7H-benzo[7]annulen-2-ol Step 1. 1-[5-[5-[6-[(3S)-1-(3-fluoropropyl)pyrrolidin-3-yl]oxy-3-pyridyl]-2-hydroxy-8,9-dihydro-7H-benzo[7]annulen-6-yl]-2,2-dimethyl-indolin-1-yl]ethanone

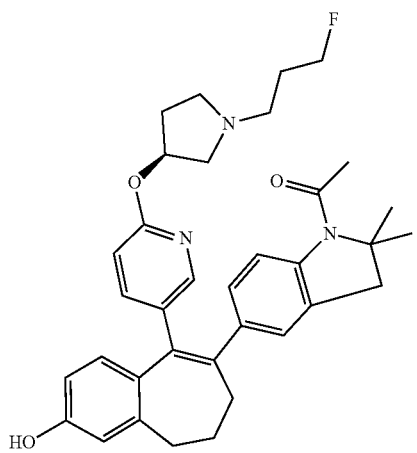 [SMILES: CC(=O)N1c2ccc(C3=C(c4ccc(O[C@H]5CCN(CCCF)C5)nc4)c4ccc(O)cc4CCC3)cc2CC1(C)C]

To a solution of 6-bromo-5-[6-[(3S)-1-(3-fluoropropyl)pyrrolidin-3-yl]oxy-3-pyridyl]-8,9-dihydro-7H-benzo[7]annulen-2-ol (Intermediate It2, 80 mg, 173.40 µmol) in a mixture of dioxane and water (8 ml; 80/20; V/V), was added 1-(2,2-dimethyl-5-(4,4,5,5-tetramethyl-1,3,2-dioxaborolan-2-yl)indolin-1-yl)ethanone (130.32 mg, 413.44 µmol), Pd(dppf)Cl$_2$ (16.88 mg, 20.67 µmol), and Cs$_2$CO$_3$ (235.98 mg, 723.53 µmol). The reaction mixture was heated at 60° C. for 1 hour, and concentrated under reduced pressure. The residue was purified by flash chromatography eluting with a mixture of MeOH and di-isopropyl ether (10/90; V/V) to give 81 mg (82%) of 1-[5-[5-[6-[(3S)-1-(3-fluoropropyl)pyrrolidin-3-yl]oxy-3-pyridyl]-2-hydroxy-8,9-dihydro-7H-benzo[7]annulen-6-yl]-2,2-dimethyl-indolin-1-yl]ethanone. LC/MS (m/z, MH$^+$): 570

Step 2. 6-(2,2-dimethylindolin-5-yl)-5-[6-[(3S)-1-(3-fluoropropyl)pyrrolidin-3-yl]oxy-3-pyridyl]-8,9-dihydro-7H-benzo[7]annulen-2-ol

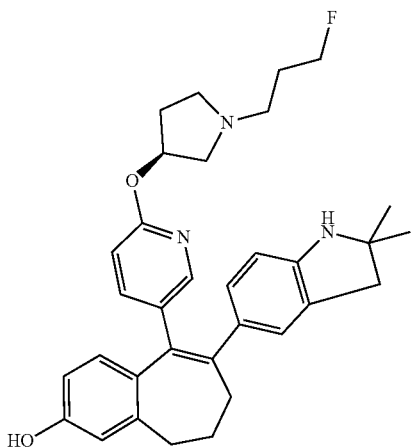 [SMILES: CC1(C)Cc2cc(C3=C(c4ccc(O[C@H]5CCN(CCCF)C5)nc4)c4ccc(O)cc4CCC3)ccc2N1]

To a solution of 1-[5-[5-[6-[(3S)-1-(3-fluoropropyl)pyrrolidin-3-yl]oxy-3-pyridyl]-2-hydroxy-8,9-dihydro-7H-benzo[7]annulen-6-yl]-2,2-dimethyl-indolin-1-yl]ethanone (80 mg, 140.42 µmol) in dioxane (2 ml), was added hydrochloric acid (2N, 0.8 ml). The reaction mixture was microwaved at 120° C. for 1 hour and poured onto a saturated aqueous solution of sodium bicarbonate. The aqueous phase was extracted with EtOAc and the gathered organic extracts were dried over magnesium sulfate, filtered, and concentrated under reduced pressure The residue was purified by flash chromatography eluting with a mixture of MeOH and di-isopropyl ether (10/90; V/V) to give 42 mg (56.7%) of 6-(2,2-dimethylindolin-5-yl)-5-[6-[(3S)-1-(3-fluoropropyl)pyrrolidin-3-yl]oxy-3-pyridyl]-8,9-dihydro-7H-benzo[7]annulen-2-ol.

Example 243. 6-(4-chloro-3-fluoro-phenyl)-5-[5-[(3S)-1-(3-fluoropropyl)pyrrolidin-3-yl]oxypyrazin-2-yl]-8,9-dihydro-7H-benzo[7]annulen-2-ol

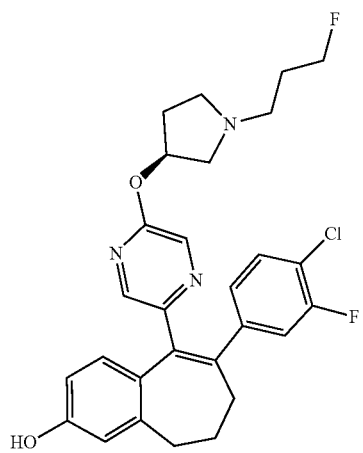 [SMILES: Oc1ccc2c(c1)CCCC(c1ccc(Cl)c(F)c1)=C2c1cnc(O[C@H]2CCN(CCCF)C2)cn1]

To a solution of 6-(4-chloro-3-fluoro-phenyl)-5-[5-[(3S)-pyrrolidin-3-yl]oxypyrazin-2-yl]-8,9-dihydro-7H-benzo[7]annulen-2-ol (Intermediate Iac2, 696 mg, 1.54 mmol) n N,N-dimethylformamide (20 ml) was added potassium carbonate (212.85 mg, 11.54 mmol), and 1-fluoro-3-iodopropane (182.48 µl, 1.69 mmol). The reaction mixture was heated at 70° C. for 1 hour, and poured into water. The aqueous phase was extracted with EtOAc, and the gathered organic extracts, were dried over magnesium sulfate, filtered, and concentrated under reduced pressure The residue was purified by flash chromatography eluting with a gradient of heptane and EtOAc (50/50 to 0/100; V/V) to give 482 mg (61.1%) of 6-(4-chloro-3-fluoro-phenyl)-5-[5-[(3S)-1-(3-fluoropropyl)pyrrolidin-3-yl]oxypyrazin-2-yl]-8,9-dihydro-7H-benzo[7]annulen-2-ol.

Example 247. 6-(2,4-dichlorophenyl)-5-[6-[(3S)-1-(3-fluoropropyl)pyrrolidin-3-yl]oxy-3-pyridyl]-8,9-dihydro-7H-benzo[7]annulene-2-carboxylic acid

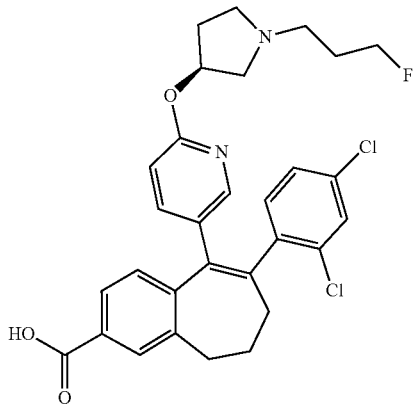 [SMILES: O=C(O)c1ccc2c(c1)CCCC(c1ccc(Cl)cc1Cl)=C2c1ccc(O[C@H]2CCN(CCCF)C2)nc1]

To a solution of methyl 6-(2,4-dichlorophenyl)-5-[6-[(3S)-1-(3-fluoropropyl)pyrrolidin-3-yl]oxy-3-pyridyl]-8,9-dihydro-7H-benzo[7]annulene-2-carboxylate (Intermediate (I)8, 80 mg, 140.48 µmol) in MeOH (5 ml) was added a solution of NaOH 5M (280.95 µl, 1.40 mmol) and the reaction mixture was heated to 60° C. for 1 hour and the solvent removed under reduced pressure. The residue was taken up in water (10 ml) and aqueous hydrochloric acid (5 M) added to pH 7. The slurry was extracted with DCM, dried over hydrophobic column and concentrated under reduced pressure. The residue was purified by column chromatography eluting first with a with a gradient of MeOH in DCM (0 to 15%; V/V) then a mixture of DCM/ammoniac 7N in MeOH (2/1; V/V), to give 56 mg (72%) of (S)-8-(2,4-dichlorophenyl)-9-(6-((1-(3-fluoropropyl)pyrrolidin-3-yl)oxy)pyridin-3-yl)-6,7-dihydro-5H-benzo[7]annulene-3-carboxylic acid as a white powder.

Example 248. 6-[4-(difluoromethoxy)-3-fluoro-phenyl]-5-[6-[(3S)-1-(3-fluoropropyl) pyrrolidin-3-yl]oxy-3-pyridyl]-8,9-dihydro-7H-benzo[7]annulene-2-carboxylicacid Step 1. methyl 6-[4-(difluoromethoxy)-3-fluoro-phenyl]-5-[6-[(3S)-1-(3-fluoropropyl)pyrrolidin-3-yl]oxy-3-pyridyl]-8,9-dihydro-7H-benzo[7]annulene-2-carboxylate

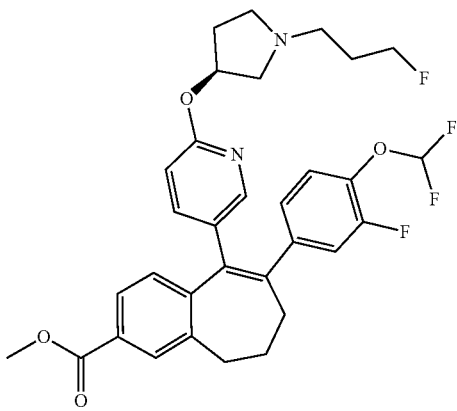 [SMILES: COC(=O)c1ccc2c(c1)CCCC(c1ccc(OC(F)F)c(F)c1)=C2c1ccc(O[C@H]2CCN(CCCF)C2)nc1]

To a solution of methyl 6-bromo-5-[6-[(3S)-1-(3-fluoropropyl)pyrrolidin-3-yl]oxy-3-pyridyl]-8,9-dihydro-7H-benzo[7]annulene-2-carboxylate (Intermediate Iag1, 100 mg, 198.65 µmol), in dioxane and water (3 ml; 80/20; V/V) was added 2-(4-difluoromethoxy-3-fluoro-phenyl)-4,4,5,5-tetramethyl-[1,3,2]dioxaborolane (57.22 mg, 198.65 µmol), $Cs_2CO_3$ (136.06 mg, 417.16 µmol), and Pd(dppf)Cl$_2$ (9.73 mg, 11.92 µmol). The reaction mixture was microwaved at 90° C. for 30 minutes, and concentrated under reduced pressure. The residue was purified by flash chromatography eluting with a gradient of MeOH in DCM (0 to 5%; V/V) to give 85 mg (73.2%) of methyl 6-[4-(difluoromethoxy)-3-fluoro-phenyl]-5-[6-[(3S)-1-(3-fluoropropyl)pyrrolidin-3-yl]oxy-3-pyridyl]-8,9-dihydro-7H-benzo[7]annulene-2-carboxylate. LC/MS (m/z, MH$^+$): 585

Step 2. 6-[4-(difluoromethoxy)-3-fluoro-phenyl]-5-[6-[(3S)-1-(3-fluoropropyl)pyrrolidin-3-yl]oxy-3-pyridyl]-8,9-dihydro-7H-benzo[7]annulene-2-carboxylic acid

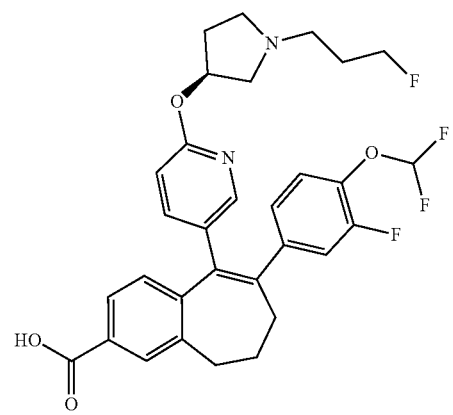 [SMILES: O=C(O)c1ccc2c(c1)CCCC(c1ccc(OC(F)F)c(F)c1)=C2c1ccc(O[C@H]2CCN(CCCF)C2)nc1]

335

To a solution of methyl 6-[4-(difluoromethoxy)-3-fluoro-phenyl]-5-[6-[(3S)-1-(3-fluoropropyl)pyrrolidin-3-yl]oxy-3-pyridyl]-8,9-dihydro-7H-benzo[7]annulene-2-carboxylate (90 mg, 153.95 µmol) in MeOH (5 ml), was added sodium hydroxide (307.90 µl, 1.54 mmol). The reaction mixture was stirred at 60° C. for 1 hour, and water and hydrochloric acid (5M) were added until pH 7. The aqueous phase was extracted with DCM and the gathered organic extracts, dried over hydrophobic column and evaporated under reduced pressure. The residue was purified by flash chromatography eluting with a gradient of MeOH in DCM (0 to 40%; V/V) to give 66 mg (75.1%) of 6-[4-(difluoromethoxy)-3-fluoro-phenyl]-5-[6-[(3S)-1-(3-fluoropropyl)pyrrolidin-3-yl]oxy-3-pyridyl]-8,9-dihydro-7H-benzo[7]annulene-2-carboxylic acid.

Example 254. 6-(4-chloro-3-fluoro-phenyl)-5-[5-[(3S)-1-(3-fluoropropyl)pyrrolidin-3-yl]oxypyrimi-din-2-yl]-8,9-dihydro-7H-benzo[7]annulen-2-ol

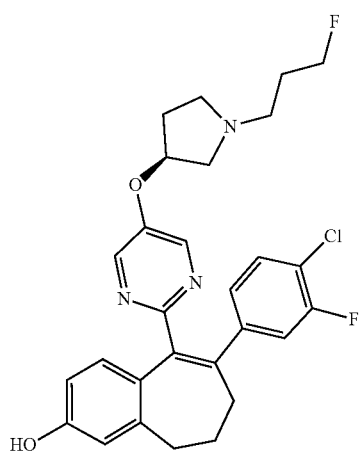 [SMILES: Oc1ccc2c(c1)CCCC(c1ccc(Cl)c(F)c1)=C2c1ncc(O[C@H]2CCN(CCCF)C2)cn1]

To a solution of 6-(4-chloro-3-fluoro-phenyl)-5-[5-[(3S)-pyrrolidin-3-yl]oxypyrimidin-2-yl]-8,9-dihydro-7H-benzo[7]annulen-2-ol (Intermediate Iac4, 248 mg, 548.77 µmol) in N,N-dimethylformamide (5 ml) was added potassium carbonate (75.84 mg, 548.77 µmol), and 1-fluoro-3-iodopropane (65.02 µl, 603.65 µmol). The reaction mixture was heated at 70° C. for 3 hour, and poured over water. The aqueous phase was extracted with EtOAc, and the gathered organic extracts were dried over magnesium sulfate, filtered, and concentrated under reduced pressure. The residue was purified by flash chromatography eluting with a gradient of EtOAc in heptane (50 to 100%; V/V) to give 125 mg (44.5%) of 6-(4-chloro-3-fluoro-phenyl)-5-[5-[(3S)-1-(3-fluoropropyl)pyrrolidin-3-yl]oxypyrimidin-2-yl]-8,9-dihydro-7H-benzo[7]annulen-2-ol.

Example 255. 5-[(E)-2-(2-chloro-4-fluoro-phenyl)-1-[4-[(3S)-1-(3-fluoropropyl)pyrrolidin-3-yl]oxyphe-nyl]but-1-enyl]-1H-indazole

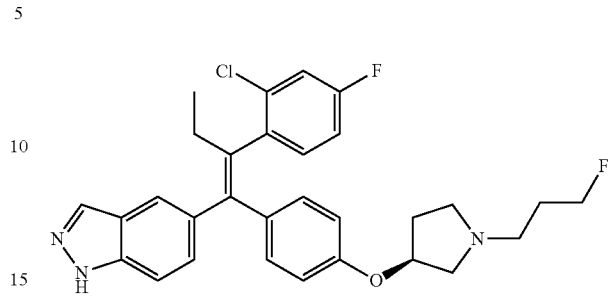

The mixture of isomers 5-[(1E)-2-(2-chloro-4-fluorophe-nyl)-1-(4-{[(3S)-1-(3-fluoropropyl)pyrrolidin-3-yl]oxy}phenyl)but-1-en-1-yl]-1H-indazole and 5-[(1Z)-1-(2-chloro-5-fluorophenyl)-2-(4-{[(3S)-1-(3-fluoropropyl)pyrrolidin-3-yl]oxy}phenyl)but-1-en-1-yl]-1H-indazole (Intermediates III and III', 523 mg, 0.1 mmol) was separated by chiral chromatography (column Chiralcel OD 10 µm, Dimension 250×30 mm, mobile phase: CO₂ 65% [MeOH 0.1% TEA] 35% to give 195 mg (37%) of 5-[(1E)-2-(2-chloro-4-fluo-rophenyl)-1-(4-{[(3S)-1-(3-fluoropropyl)pyrrolidin-3-yl]oxy}phenyl)but-1-en-1-yl]-1H-indazole.

Example 256. 1-[2,6-difluoro-4-[(3S)-1-(3-fluoro-propyl)pyrrolidin-3-yl]oxy-phenyl]-2-(2-fluoro-2-methyl-propyl)-3-methyl-1,3,4,9-tetrahydropyrido[3,4-b]indole Trans Isomer 1

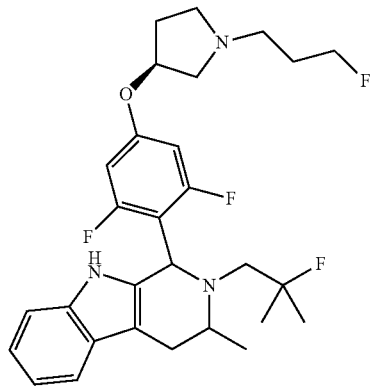

The mixture of trans isomers 1-[2,6-difluoro-4-[(3S)-1-(3-fluoropropyl)pyrrolidin-3-yl]oxy-phenyl]-2-(2-fluoro-2-methyl-propyl)-3-methyl-1,3,4,9-tetrahydropyrido[3,4-b]in-dole (Intermediate IId, 130 mg, 0.25 mmol) was separated by chiral chromatography (column Chiralpak AD-H 5 µm, Dimension 3×25 cm, mobile phase: heptane 75% EtOH 25% TEA 0.1%) to give the first trans isomer 1 levogyre: 50.7 mg (39%). [α]$_D^{20}$=−38.8+/−2.9, c=0.0958 in DMSO at 589 nm.

Example 257. 1-[2,6-difluoro-4-[(3S)-1-(3-fluoropropyl)pyrrolidin-3-yl]oxy-phenyl]-2-(2-fluoro-2-methyl-propyl)-3-methyl-1,3,4,9-tetrahydropyrido[3,4-b]indole

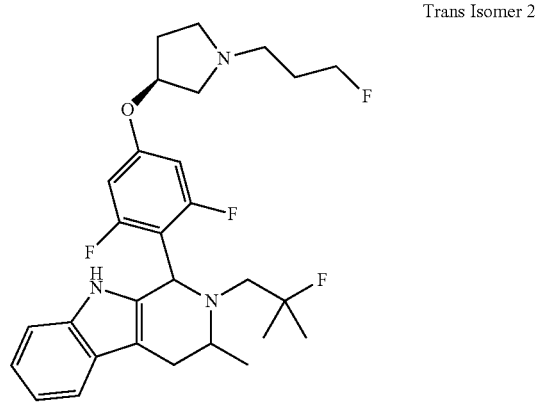 [SMILES: CC1Cc2c([nH]c3ccccc23)C(c2c(F)cc(O[C@H]3CCN(CCCF)C3)cc2F)N1CC(C)(C)F]

Trans Isomer 2

The mixture of trans isomers 1-[2,6-difluoro-4-[(3S)-1-(3-fluoropropyl)pyrrolidin-3-yl]oxy-phenyl]-2-(2-fluoro-2-methyl-propyl)-3-methyl-1,3,4,9-tetrahydropyrido[3,4-b]indole (Intermediate IId, 130 mg, 0.25 mmol) were separated by chiral chromatography (column Chiralpak AD-H 5 μm, Dimension 3×25 cm, mobile phase: heptane 75% EtOH 25% TEA 0.1%) to give the second trans isomer 2 dextrogyre: 50.6 mg (39%). $[\alpha]_D^{20}$=+39.2+/−2.7, c=0.056 in DMSO at 589 nm.

Example 258. 2-[4-[(3S)-1-(3-fluoropropyl)pyrrolidin-3-yl]oxyphenyl]-3-(4-hydroxyphenyl)-2,3-dihydro-1,4-benzoxathiin-6-ol

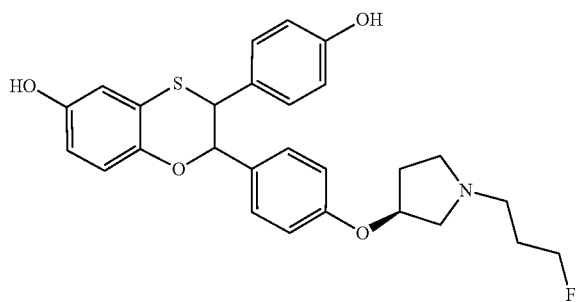 [SMILES: Oc1ccc(C2Sc3cc(O)ccc3OC2c2ccc(O[C@H]3CCN(CCCF)C3)cc2)cc1]

The mixture of isomers 2-[4-[(3S)-1-(3-fluoropropyl)pyrrolidin-3-yl]oxyphenyl]-3-(4-hydroxyphenyl)-2,3-dihydro-1,4-benzoxathiin-6-ol (Intermediate IVk, 52 mg, 0.108 mmol) were separated by chiral chromatography (column Chiralpak AD 10 μm, Dimension 250×30 mm, mobile phase: heptane/ethanol/triethylamine 70/30/0.1) to give the stereomer 1: 13.5 mg (26%).

The compounds according to the invention were subjected to pharmacological tests for determining their antagonist, antiproliferative and degradation effects on estrogen receptors.

Test A: Biochemical Antagonist Activity on Wild Type (WT) and Mutants

Estrogen Receptors Test A involves measuring the in vitro antagonist activity of the compounds of the invention on estrogen receptors.

The measurements of the antagonist activities were made using an estrogen receptor coactivator assay as described hereunder.

Antagonistic potency of compounds was evaluated using LanthaScreen® TR-FRET ERα Coactivator Assay (ThermoFisher) with modifications. It is a competition assay, where binding of a test compound to a complex comprised of (i) His6-ERα298-554 protein representing ERα ligand-binding domain, (ii) Tb-labeled His6 antibody, (iii) a fluorescein-labeled PGC1a coactivator peptide (EAEEPSLLKKLLLAPANTQ), and (iv) estradiol, results in a decrease of the TR-FRET signal due to dissociation of the coactivator peptide. His6-ERα298-554 proteins were expressed as WT or D538G or Y537S mutants in E. coli and purified by affinity chromatography. The assay works in a homogeneous mix-and-read format. In a typical experiment, a 4 μL mixture of 0.5 nM His6-ERα298-554, 0.5 nM Tb-labeled His6 antibody, 250 nM PGC1a peptide, and 3 nM estradiol (or 10 nM estradiol) in 100 mM potassium phosphate, pH 7.4, 0.01% Tween-20, 0.02% $NaN_3$, 5 mM DTT, was added to 40 nL test compound in DMSO and incubated overnight at room temperature. The TR-FRET 520:495 nm emission ratio was calculated and used to determine the IC50 value from a dose response curve fit to the 4-parameter logistic equation.

The antagonist activity with respect to estrogen receptors in this test is given by the concentration which inhibits 50% of the estrogen receptor activity (or IC50) in nM.

The Table 2 below indicates the biochemical results of antagonist activity on WT and mutants estrogen receptors for the compounds according to the invention, and demonstrates that the compounds tested have an antagonist activity regarding estrogen receptors. In table 2, the figures indicated have been obtained using the above protocol with 3 nM estradiol, unless they are noted with an asterisk (*), which indicates a protocol using 10 nM estradiol.

TABLE 2

| Examples | Antagonism WT $IC_{50}$ (nM) | Antagonism D538G $IC_{50}$ (nM) | Antagonism Y537S $IC_{50}$ (nM) |
|---|---|---|---|
| 1 | 460 | N/A | N/A |
| 2 | 11 | 60.0 | 37.0 |
| 3 | 1511 | N/A | N/A |
| 4 | 284 | N/A | N/A |
| 5 | 28 | 209.0 | 72 |
| 6 | 2 | 13 | 8 |
| 7 | 1474* | >4000* | >4000* |
| 8 | 1391* | >4000* | >4000* |
| 9 | 2288* | >4000* | >4000* |
| 10 | 1273* | >4000* | >4000* |
| 11 | >4000* | >4000* | >4000* |
| 12 | 585 | >4000* | >4000* |
| 13 | 151* | 2010* | 1561* |
| 14 | 225* | 3310* | 2303* |
| 15 | 9 | 161 | 83 |
| 16 | 4 | 16 | 6 |
| 17 | 7 | 39 | 14 |
| 18 | 9 | 39 | 15 |
| 19 | 7 | 23 | 11 |
| 20 | 15 | 46 | 21 |
| 21 | 9 | 47 | 19 |
| 22 | 6 | 27 | 9 |
| 23 | 50* | 803* | 678* |
| 24 | 5* | 80* | 44* |
| 25 | 1420* | >4000* | >4000* |
| 26 | 3 | 67 | 39 |
| 27 | 2* | 38* | 21* |
| 28 | 4* | 68* | 41* |
| 29 | 14* | 240* | 130* |
| 30 | 34 | 694 | 415 |

TABLE 2-continued

| Examples | Antagonism WT IC$_{50}$ (nM) | Antagonism D538G IC$_{50}$ (nM) | Antagonism Y537S IC$_{50}$ (nM) |
|---|---|---|---|
| 31 | 5 | 101 | 59 |
| 32 | 19* | 314* | 168* |
| 33 | 66* | 1691* | 596* |
| 34 | 4* | 83* | 46* |
| 35 | 16* | 421* | 220* |
| 36 | 11* | 257* | 154* |
| 37 | 41 | 745 | 475 |
| 38 | 604* | >4000* | 3708* |
| 39 | 9* | 221* | 127* |
| 40 | 44* | 901* | 605* |
| 41 | 27* | 740* | 407* |
| 42 | 674* | >4000* | >4000* |
| 43 | 96* | 1135* | 673* |
| 44 | 172* | 2926* | 1818* |
| 45 | 1* | 34* | 14* |
| 46 | 5* | 101* | 59* |
| 47 | 388* | >4000* | 3051* |
| 48 | >4000* | >4000* | >4000* |
| 49 | 37* | 888* | 472* |
| 50 | 72* | 1553* | 1172* |
| 51 | 350* | >4000* | 3598* |
| 52 | 351* | >4000* | 2914* |
| 53 | 2* | 36* | 25* |
| 54 | 246* | 3032* | 2641* |
| 55 | 48* | 971* | 444* |
| 56 | 37* | 721* | 358* |
| 57 | 1071* | >4000* | >4000* |
| 58 | 27* | 590* | 295* |
| 59 | 879* | >4000* | >4000* |
| 60 | 9* | 215* | 103* |
| 61 | 37* | 686* | 437* |
| 62 | 27* | 523* | 271* |
| 63 | 318* | >4000* | 2450* |
| 64 | 24* | 492* | 204* |
| 65 | 1223* | >4000* | >4000* |
| 66 | 59 | 1801 | 362 |
| 67 | 120* | 1812* | 1275* |
| 68 | 104* | 1835* | 1151* |
| 69 | 1568* | >4000* | >4000* |
| 70 | 1658* | >4000* | >4000* |
| 71 | 2744* | >4000* | >4000* |
| 72 | 11* | 202* | 108* |
| 73 | 1107* | >4000* | >4000* |
| 74 | 322* | >4000* | 2385* |
| 75 | 2486* | >4000* | >4000* |
| 76 | 4* | 100* | 61* |
| 77 | 16* | 323* | 197* |
| 78 | 1* | 29* | 15* |
| 79 | 0.5* | 6* | 5* |
| 80 | 12* | 283* | 154* |
| 81 | 520* | >4000* | >4000* |
| 82 | 297* | >4000* | 2293* |
| 83 | 81 | 1324 | 1162 |
| 84 | 30 | 1746 | 958 |
| 85 | 1* | 21* | 15* |
| 86 | 0.5* | 7* | 5* |
| 87 | 23* | 568* | 294* |
| 88 | 12* | 293* | 159* |
| 89 | 27* | 726* | 423* |
| 90 | 12* | 293* | 165* |
| 91 | 2 | 10 | 6 |
| 92 | 7 | 59 | 22 |
| 93 | 8 | 59 | 26 |
| 94 | 2 | 10 | 6 |
| 95 | 6 | 43 | 20 |
| 96 | 7 | 47 | 19 |
| 97 | 50 | 358 | 18 |
| 98 | 14 | 106 | 40 |
| 99 | 5 | 36 | 25 |
| 100 | 7 | 54 | 25 |
| 101 | 6 | 50 | 25 |
| 102 | 12 | 106 | 51 |
| 103 | 38 | 252 | 101 |
| 104 | 12 | 54 | 23 |
| 105 | 5 | 38 | 23 |
| 106 | 5 | 31 | 16 |
| 107 | 19 | 79 | 55 |
| 108 | 30 | 221 | 129 |
| 109 | 29 | 215 | 150 |
| 110 | 5 | 39 | 26 |
| 111 | 91 | 822 | 407 |
| 112 | 91 | 838 | 543 |
| 113 | 6 | 32 | 19 |
| 114 | 29 | 178 | 104 |
| 115 | 88 | 322 | 200 |
| 116 | 31 | 120 | 86 |
| 117 | 32 | 309 | 214 |
| 118 | 152 | 442 | 237 |
| 119 | 2 | 10 | 6 |
| 120 | 2 | 7 | 4 |
| 121 | 2 | 27 | 13 |
| 122 | 3 | 41 | 24 |
| 123 | 156 | 2287 | 1428 |
| 124 | 22 | 849 | 1243 |
| 125 | 190 | 1342 | 945 |
| 126 | 5 | 94 | 55 |
| 127 | 3 | 49 | 24 |
| 128 | 96 | 1212 | 933 |
| 129 | 502 | >4000 | 2676 |
| 130 | 70 | 1193 | 777 |
| 131 | 19 | 340 | 276 |
| 132 | 28 | 473 | 334 |
| 133 | 4 | 64 | 39 |
| 134 | 19 | 328 | 225 |
| 135 | 21 | 591 | 352 |
| 136 | 4 | 59 | 44 |
| 137 | 250 | 1712 | 1218 |
| 138 | 18 | 360 | 253 |
| 139 | 68 | 1170 | 819 |
| 140 | 36 | 644 | 542 |
| 141 | 23 | 1504 | 1124 |
| 142 | 41 | 1820 | 1154 |
| 143 | 464 | 4000 | 4000 |
| 144 | 528 | 4000 | 4000 |
| 145 | 256 | 4000 | 3274 |
| 146 | 51* | 1171* | 845* |
| 147 | 390* | >4000* | 3814* |
| 148 | >4000* | >4000* | >4000* |
| 149 | 23* | 303* | 289* |
| 150 | 31* | 489* | 425* |
| 151 | 6* | 88* | 68* |
| 152 | 9* | 154* | 107* |
| 153 | 6* | 117* | 86* |
| 154 | 5* | 77* | 51* |
| 155 | 21* | 365* | 228* |
| 156 | 19* | 409* | 254* |
| 157 | 2* | 56* | 36* |
| 158 | 1 | 4 | 3 |
| 159 | 3 | 17 | 10 |
| 160 | 3 | 13 | 8 |
| 161 | 6 | 31 | 22 |
| 162 | 4 | 24 | 19 |
| 163 | 5 | 24 | 19 |
| 164 | 3 | 13 | 9 |
| 165 | 3 | 11 | 8 |
| 166 | 6 | 34 | 25 |
| 167 | 5 | 26 | 16 |
| 168 | 3 | 14 | 9 |
| 169 | 2 | 5 | 3 |
| 170 | 18 | 129 | 82 |
| 171 | 24 | 140 | 87 |
| 172 | 6 | 24 | 18 |
| 173 | 21 | 145 | 87 |
| 174 | 53 | 422 | 222 |
| 175 | 20 | 116 | 65 |
| 176 | 6 | 28 | 20 |
| 177 | 4 | 41 | 29 |
| 178 | 2 | 10 | 7 |
| 179 | 12 | 114 | 80 |
| 180 | 7 | 36 | 16 |
| 181 | 25 | 135 | 54 |
| 182 | 21 | 110 | 45 |

TABLE 2-continued

| Examples | Antagonism WT IC$_{50}$ (nM) | Antagonism D538G IC$_{50}$ (nM) | Antagonism Y537S IC$_{50}$ (nM) |
|---|---|---|---|
| 183 | 7 | 122 | 70 |
| 184 | 1 | 6 | 4 |
| 185 | 2.9 | 104 | 65 |
| 186 | 1* | 21* | 16* |
| 187 | 1.5 | 43 | 22 |
| 188 | 8.2 | 266 | 157 |
| 189 | 2* | 31* | 19* |
| 190 | 39* | 638* | 425* |
| 191 | 3 | 51 | 32 |
| 192 | 9* | 205* | 109* |
| 193 | 1* | 25* | 20* |
| 194 | 10* | 206* | 141* |
| 195 | 14* | 335* | 170* |
| 196 | 3* | 63* | 36* |
| 197 | 1* | 20* | 13* |
| 198 | 1 | 8 | 6 |
| 199 | 21* | 456* | 316* |
| 200 | 3* | 51* | 33* |
| 201 | 1* | 21* | 15* |
| 202 | 1* | 15* | 11* |
| 203 | 65* | 1446* | 803* |
| 204 | 24* | 24* | 15* |
| 205 | 1* | 16* | 11* |
| 206 | 0.7* | 13* | 9* |
| 207 | 2* | 9* | 6* |
| 208 | 0.6* | 7* | 5* |
| 209 | 2* | 35* | 20* |
| 210 | 103* | 2224* | 1334* |
| 211 | 39* | 964* | 475* |
| 212 | 34* | 800* | 412* |
| 213 | 4* | 96* | 55* |
| 214 | 38* | 539* | 457* |
| 215 | 8* | 190* | 86* |
| 216 | 33* | 662* | 543* |
| 217 | 4* | 61* | 39* |
| 218 | 1* | 25* | 22* |
| 219 | 12* | 233* | 149* |
| 220 | 8* | 164* | 84* |
| 221 | 11* | 265* | 133* |
| 222 | 18* | 371* | 238* |
| 223 | 2* | 42* | 24* |
| 224 | 71* | 1478* | 1029* |
| 225 | 750* | >4000* | >4000* |
| 226 | >4000* | >4000* | >4000* |
| 227 | 392* | 3333* | 3499* |
| 228 | 6 | 73 | 38 |
| 229 | 12 | 85 | 34 |
| 230 | 14 | 99 | 41 |
| 231 | 38 | 240 | 141 |
| 232 | 16 | 99 | 78 |
| 233 | 20 | 128 | 70 |
| 234 | 9 | 59 | 33 |
| 235 | 13 | 100 | 83 |
| 236 | 8 | 54 | 29 |
| 237 | 0.6* | 7* | 5* |
| 238 | 3* | 59* | 33* |
| 239 | 13* | 13* | 9* |
| 240 | 6* | 6* | 4* |
| 241 | 1* | 27* | 16* |
| 242 | 1* | 9* | 7* |
| 243 | 12* | 386* | 179* |
| 244 | 3* | 67* | 34* |
| 245 | 0.4 | 4 | 3 |
| 246 | 2* | 42* | 26* |
| 247 | 5* | 136* | 72* |
| 248 | 141* | 3443* | 1917* |
| 249 | 1* | 24* | 14* |
| 250 | 7* | 113* | 70* |
| 251 | 4* | 104* | 57* |
| 252 | 0.7* | 8* | 9* |
| 253 | 7* | 155* | 95* |
| 254 | 2848* | >4000* | >4000* |
| 255 | 15* | 190* | 140* |
| 256 | 6* | 120* | 101* |
| 257 | 3310* | >4000* | >4000* |
| 258 | 203* | >4000* | 2423* |

N/A: not available

Test B: Cell Proliferation/Viability Assay on MCF7 (Breast Tumor Cells) WT and Mutants Cell Lines Test B involves measuring the in vitro proliferation activity of the compounds of the invention by analyzing the viability of the tumor cells.

The measurements of the viability were made using a breast cancer cell viability assay as described hereunder.

MCF7 cells expressing (and dependent) on mutants estrogen receptor Tyr 537 Ser or Asp 538 Gly were generated by transfection of MCF7 parental cells (ATCC) with expression vectors coding for different mutants of estrogen receptor Tyr 537 Ser or Asp 538 Gly. The cells were first selected by antibiotic (related to vector expression) and then selected for their growth dependence on estrogen receptor based on their ability to grow in vitro in absence of estradiol (parental cell line die in absence of estradiol).

MCF7 cells (ATCC) or MCF7 cells expressing (and dependent) on mutants estrogen receptor Tyr 537 Ser or Asp 538 Gly were seeded in 384 wells microplate at concentration of >999 cells/30 µL per well in red phenol free MEM medium containing 5% charcoal dextran striped FBS. The following day, 9 points serial 1:5 dilution of each compound were added to the cells in 20 µL at final concentrations ranging from 3-0.000001 µM. After 7 days of compound exposure, 50 µL of CellTiter-Glo (promega) was added to the cells and relative luminescence arbitrary units (RLUs) were determined in luminescence plate reader (Envision device). CellTiter-Glo was added to 50 µL medium without cells to determine the background signal.

The percent of viability of each sample was determined as follows: (RLU sample−RLU background/RLU untreated−RLU background)*100=% viability.

The viability activity with respect to estrogen receptors in this test is given by the concentration which inhibits 50% of the viability activity (or IC50) in nM.

The Table 3 below indicates the cell proliferation/viability assay results on MCF7 (breast tumor cells) WT and mutants cell lines, for some of the compounds according to the invention, and demonstrates that the compounds tested have a significant antiproliferative activity regarding estrogen receptors.

TABLE 3

| Examples | proliferation MCF7 (WT) IC$_{50}$ (nM) | proliferation MCF7 Y537S IC$_{50}$ (nM) | proliferation MCF7 D538G IC$_{50}$ (nM) |
|---|---|---|---|
| 1 | N/A | N/A | N/A |
| 2 | N/A | N/A | N/A |
| 3 | N/A | N/A | N/A |
| 4 | N/A | N/A | N/A |
| 5 | N/A | N/A | N/A |
| 6 | N/A | N/A | N/A |
| 7 | 13 | >999 | 18 |
| 8 | >999 | >999 | >999 |
| 9 | 44 | >999 | 47 |
| 10 | 85 | >999 | 29 |
| 11 | 44 | >999 | 162 |

TABLE 3-continued

| Examples | proliferation MCF7 (WT) IC$_{50}$ (nM) | proliferation MCF7 Y537S IC$_{50}$ (nM) | proliferation MCF7 D538G IC$_{50}$ (nM) |
|---|---|---|---|
| 12 | 1 | 9 | 5 |
| 13 | 0.4 | 8 | 3 |
| 14 | 0.5 | 6 | 1 |
| 15 | 0.2 | 30 | 25 |
| 16 | 0.9 | 10 | 2 |
| 17 | 0.4 | 3 | 1 |
| 18 | 0.5 | 7 | 1 |
| 19 | N/A | N/A | N/A |
| 20 | N/A | N/A | N/A |
| 21 | N/A | N/A | N/A |
| 22 | N/A | N/A | N/A |
| 23 | 7 | >999 | 14 |
| 24 | 0.3 | 6 | 0.9 |
| 25 | 16 | 160 | 31 |
| 26 | 0.9 | 10 | 2 |
| 27 | 0.4 | 6 | 2 |
| 28 | 0.7 | 11 | 2 |
| 29 | 0.4 | 6 | 0.9 |
| 30 | 1 | 16 | 2 |
| 31 | 0.4 | 6 | 1 |
| 32 | 0.4 | 6 | 1 |
| 33 | 4 | 22 | 2 |
| 34 | 0.5 | 4 | 0.5 |
| 35 | 0.2 | 2 | 0.3 |
| 36 | 0.5 | 3 | 0.5 |
| 37 | 0.6 | 4 | 0.6 |
| 38 | 12.00 | >999 | 16 |
| 39 | 0.4 | 2 | 0.5 |
| 40 | 1 | 20 | 2 |
| 41 | 0.9 | 4 | 1 |
| 42 | 46 | 809 | 31 |
| 43 | 0.4 | 11 | 1 |
| 44 | >999 | >999 | >999 |
| 45 | 0.1 | 2 | 0.6 |
| 46 | 0.1 | 2 | 0.5 |
| 47 | 17 | 103 | 38 |
| 48 | 1 | 17 | 6 |
| 49 | 0.3 | 3 | 0.9 |
| 50 | 0.6 | 7 | 2 |
| 51 | 91 | 230 | 148 |
| 52 | 2 | 41 | 3 |
| 53 | 0.2 | 5 | 0.2 |
| 54 | 3 | 21 | 3 |
| 55 | 0.7 | 5 | 0.3 |
| 56 | 0.6 | 14 | 0.7 |
| 57 | 33 | >999 | >999 |
| 58 | 2 | 5 | 0.8 |
| 59 | 27 | >999 | >999 |
| 60 | 0.5 | 3 | 0.4 |
| 61 | 2 | 17 | 0.6 |
| 62 | 0.4 | 6 | 0.2 |
| 63 | 5 | >999 | 5 |
| 64 | 1 | 5 | 0.7 |
| 65 | 21 | 572 | 21 |
| 66 | 2 | 8 | 2 |
| 67 | 12 | 86 | 16 |
| 68 | 14 | 125 | 7 |
| 69 | 0.2 | 0.8 | 0.2 |
| 70 | 64 | 478 | 97 |
| 71 | 12 | 414 | 88 |
| 72 | 2 | 1 | 0.5 |
| 73 | 95 | 377 | 119 |
| 74 | 12 | 173 | 16 |
| 75 | 63 | >999 | 74 |
| 76 | 0.6 | 6 | 1 |
| 77 | 2 | 29 | 5 |
| 78 | 0.3 | 4 | 0.9 |
| 79 | 0.3 | 0.8 | 5 |
| 80 | 0.3 | 3 | 0.4 |
| 81 | 18 | 17 | 3.5 |
| 82 | 15 | 18 | 1 |
| 83 | 2 | 18 | 13 |
| 84 | 0.4 | 6 | 2 |
| 85 | 0.4 | 7 | 0.7 |
| 86 | 0.2 | 1 | 0.2 |
| 87 | 0.2 | 3 | 1 |
| 88 | 0.3 | 3 | 0.6 |
| 89 | 0.4 | 5 | 1 |
| 90 | 0.3 | 4 | 0.5 |
| 91 | N/A | N/A | N/A |
| 92 | N/A | N/A | N/A |
| 93 | N/A | N/A | N/A |
| 94 | N/A | N/A | N/A |
| 95 | N/A | N/A | N/A |
| 96 | 2 | 16 | 5 |
| 97 | N/A | N/A | N/A |
| 98 | 0.5 | 5 | 2 |
| 99 | N/A | N/A | N/A |
| 100 | N/A | N/A | N/A |
| 101 | N/A | N/A | N/A |
| 102 | 0.5 | 5 | 0.8 |
| 103 | 0.3 | 4 | 1 |
| 104 | N/A | N/A | N/A |
| 105 | 0.5 | 11 | 2 |
| 106 | 0.7 | 12 | 3 |
| 107 | 19 | 147 | 33 |
| 108 | N/A | N/A | N/A |
| 109 | N/A | N/A | N/A |
| 110 | 1 | 45 | 6 |
| 111 | N/A | N/A | N/A |
| 112 | N/A | N/A | N/A |
| 113 | 5 | 31 | 14 |
| 114 | N/A | N/A | N/A |
| 115 | N/A | N/A | N/A |
| 116 | 6 | 150 | 17 |
| 117 | N/A | N/A | N/A |
| 118 | N/A | N/A | N/A |
| 119 | 0.6 | 5 | 0.5 |
| 120 | 1 | 10 | 2 |
| 121 | 0.3 | 3 | 1 |
| 122 | N/A | N/A | N/A |
| 123 | N/A | N/A | N/A |
| 124 | 8 | 165 | 33 |
| 125 | N/A | N/A | N/A |
| 126 | N/A | N/A | N/A |
| 127 | N/A | N/A | N/A |
| 128 | N/A | N/A | N/A |
| 129 | 245 | >999 | 456 |
| 130 | N/A | N/A | N/A |
| 131 | N/A | N/A | N/A |
| 132 | N/A | N/A | N/A |
| 133 | N/A | N/A | N/A |
| 134 | N/A | N/A | N/A |
| 135 | N/A | N/A | N/A |
| 136 | N/A | N/A | N/A |
| 137 | N/A | N/A | N/A |
| 138 | 2 | 51 | 7 |
| 139 | N/A | N/A | N/A |
| 140 | N/A | N/A | N/A |
| 141 | 1 | 22 | 4 |
| 142 | 8 | 154 | 34 |
| 143 | 24 | 357 | 63 |
| 144 | 38 | 653 | 64 |
| 145 | 9 | 124 | 17 |
| 146 | 6 | 69 | 12 |
| 147 | 52 | >999 | 90 |
| 148 | 222 | >999 | 314 |
| 149 | 0.5 | 12 | 2 |
| 150 | 0.4 | 14 | 2 |
| 151 | 0.3 | 7 | 1 |
| 152 | 0.5 | 4 | 3 |
| 153 | 0.3 | 3 | 0.7 |
| 154 | 0.2 | 4 | 0.6 |
| 155 | 0.4 | 6 | 1 |
| 156 | 0.6 | 14 | 2 |
| 157 | 0.2 | 4 | 0.6 |
| 158 | N/A | N/A | N/A |
| 159 | N/A | N/A | N/A |
| 160 | N/A | N/A | N/A |
| 161 | N/A | N/A | N/A |

TABLE 3-continued

| Examples | proliferation MCF7 (WT) IC$_{50}$ (nM) | proliferation MCF7 Y537S IC$_{50}$ (nM) | proliferation MCF7 D538G IC$_{50}$ (nM) |
|---|---|---|---|
| 162 | 0.4 | 5 | 1 |
| 163 | N/A | N/A | N/A |
| 164 | 0.6 | 5 | 0.6 |
| 165 | N/A | N/A | N/A |
| 166 | 0.2 | 8 | 1 |
| 167 | N/A | N/A | N/A |
| 168 | N/A | N/A | N/A |
| 169 | N/A | N/A | N/A |
| 170 | N/A | N/A | N/A |
| 171 | N/A | N/A | N/A |
| 172 | 0.2 | 12 | 2 |
| 173 | N/A | N/A | N/A |
| 174 | N/A | N/A | N/A |
| 175 | N/A | N/A | N/A |
| 176 | 3 | 48 | 9 |
| 177 | N/A | N/A | N/A |
| 178 | 0.5 | 16 | 2 |
| 179 | N/A | N/A | N/A |
| 180 | N/A | N/A | N/A |
| 181 | N/A | N/A | N/A |
| 182 | N/A | N/A | N/A |
| 183 | 1 | 73 | 5 |
| 184 | 0.3 | 4 | 0.7 |
| 185 | 0.4 | 6 | 1 |
| 186 | 0.3 | 5 | 0.4 |
| 187 | 0.2 | 4 | 0.7 |
| 188 | 0.2 | 4 | 2 |
| 189 | 0.2 | 4 | 1 |
| 190 | 0.2 | 6 | 0.8 |
| 191 | 0.3 | 3 | 0.4 |
| 192 | 0.3 | 5 | 0.9 |
| 193 | 0.3 | 5 | 0.5 |
| 194 | 0.2 | 3 | 0.4 |
| 195 | 0.3 | 3 | 0.7 |
| 196 | 0.4 | 6 | 1 |
| 197 | 0.3 | 5 | 0.6 |
| 198 | 0.4 | 6 | 1 |
| 199 | 0.2 | 4 | 0.2 |
| 200 | 0.7 | 12 | 2 |
| 201 | 0.2 | 8 | 1 |
| 202 | 0.4 | 6 | 1 |
| 203 | 0.8 | 13 | 1 |
| 204 | 0.4 | 5 | 0.8 |
| 205 | 0.2 | 3 | 0.2 |
| 206 | 0.3 | 4 | 0.7 |
| 207 | 0.1 | 2 | 0.3 |
| 208 | 0.2 | 4 | 0.7 |
| 209 | 0.3 | 4 | 0.7 |
| 210 | 0.8 | 15 | 1 |
| 211 | 0.4 | 10 | 0.6 |
| 212 | 0.4 | 3 | 0.5 |
| 213 | 0.3 | 2 | 0.2 |
| 214 | 0.4 | 6 | 0.7 |
| 215 | 0.1 | 3 | 0.2 |
| 216 | 0.6 | 13 | 1 |
| 217 | 0.1 | 5 | 0.6 |
| 218 | 0.1 | 1 | 0.1 |
| 219 | 0.1 | 2 | 0.4 |
| 220 | 0.4 | 5 | 0.5 |
| 221 | 0.5 | 8 | 0.6 |
| 222 | 4 | 1 | 0.4 |
| 223 | 1 | 0.1 | 0.2 |
| 224 | 3 | 83 | 8 |
| 225 | 18 | 249 | 36 |
| 226 | 87 | >999 | 288 |
| 227 | 6 | 134 | 9 |
| 228 | N/A | N/A | N/A |
| 229 | N/A | N/A | N/A |
| 230 | N/A | N/A | N/A |
| 231 | N/A | N/A | N/A |
| 232 | N/A | N/A | N/A |
| 233 | N/A | N/A | N/A |
| 234 | N/A | N/A | N/A |
| 235 | N/A | N/A | N/A |
| 236 | N/A | N/A | N/A |
| 237 | 0.3 | 5 | 0.7 |
| 238 | 0.3 | 3 | 0.5 |
| 239 | 0.3 | 3 | 1 |
| 240 | 0.3 | 3 | 0.5 |
| 241 | 0.1 | 2 | 0.2 |
| 242 | 0.7 | 11 | 2 |
| 243 | 0.2 | 3 | 0.5 |
| 244 | 0.9 | 6 | 2 |
| 245 | 0.3 | 3 | 0.1 |
| 246 | 0.4 | 7 | 0.4 |
| 247 | 0.2 | 6 | 0.4 |
| 248 | 0.7 | 15 | 1 |
| 249 | 0.3 | 4 | 0.6 |
| 250 | 0.3 | 4 | 0.3 |
| 251 | 0.4 | 5 | 0.5 |
| 252 | 0.6 | 9 | 0.4 |
| 253 | 0.1 | 2 | 0.1 |
| 254 | 16 | 129 | 17 |
| 255 | 0.1 | 6 | 0.9 |
| 256 | 0.1 | 2 | 0.7 |
| 257 | 18 | 272 | 85 |
| 258 | 6 | 17 | 1 |

N/A: not available

Test C: Estrogen Receptor Degradation Activity

Test C involves measuring the in vitro degradation activity of the compounds of the invention.

The measurements of the degradation activities were made using a breast cancer cell ERα in cell western assay as described hereunder.

MCF7 cells (ATCC) were seeded in 384 wells microplate (collagen coated) at concentration of >9990 cells/30 μL per well in red phenol free MEM alpha medium (invitrogen) containing 5% charcoal dextran striped FBS. The following day, 9 points serial 1:5 dilution of each compound were added to the cells in 2.5 μL at final concentrations ranging from 3-0.000018 μM or 0.1 μM for fulvestrant (using as positive control). At 4 hours post compounds addition the cells were fixed by adding 25 μL of formalin (final concentration 5% formalin containing 0.1% triton) for 10 minutes at room temperature and then washed twice with PBS. Then, 50 μL of LI-COR blocking buffer containing 0.1% Triton was added to plate for 30 minutes at room temperature. LI-COR blocking buffer was removed and cells were incubated overnight at cold room with 50 μL anti-ER rabbit monoclonal antibody (Thermo scientific MA1-39540) diluted at 1:>999 in LI-COR blocking buffer containing 0.1% tween-20. Wells which were treated with blocking but no antibody were used as background control. Wells were washed twice with PBS (0.1% tween-20) and incubated at 37° C. for 60 minutes in LI-COR (0.1% tween-20) containing goat anti-rabbit antibody Alexa 488 (1:>999) and Syto-64 a DNA dye (2 μM final concentration). Cells were then washed 3 times in PBS and scanned in ACUMEN explorer (TTP-Labtech). Integrated intensities in the green fluorescence and red fluorescence were measured to determine the levels of ERα and DNA respectively.

The degradation activity with respect to estrogen receptors in this test is given by the concentration which degrades 50% of the estrogen receptor (or IC50) in nM.

The % of ERα levels decrease were determined as follows: % inhibition=100*(1−(sample−fulvestrant:DM−fulvestrant)).

The Table 4 below indicates the estrogen receptor degradation activity results for some of the compounds according to the invention, and demonstrates that compounds tested have a significant degradation activity on estrogen receptors, namely more than 70%, and more than 80% for most of the tested compounds.

TABLE 4

| Examples | Degradation IC$_{50}$ (nM) | % Degradation at 3 μM |
| --- | --- | --- |
| 1 | 34 | 84 |
| 2 | 0.3 | 84 |
| 3 | 85 | 80 |
| 4 | 12 | 87 |
| 5 | 0.5 | 81 |
| 6 | 0.2 | 84 |
| 7 | 22 | 82 |
| 8 | 25 | 84 |
| 9 | 28 | 79 |
| 10 | 15 | 78 |
| 11 | 49 | 80 |
| 12 | 5 | 89 |
| 13 | 2 | 87 |
| 14 | 3 | 89 |
| 15 | 0.3 | 89 |
| 16 | 1 | 90 |
| 17 | 2 | 87 |
| 18 | 0.6 | 90 |
| 19 | 3 | 78 |
| 20 | 3 | 86 |
| 21 | 3 | 92 |
| 22 | 1 | 95 |
| 23 | 0.3 | 93 |
| 24 | 0.2 | 91 |
| 25 | 19 | 93 |
| 26 | 0.8 | 90 |
| 27 | 0.6 | 94 |
| 28 | 0.3 | 80 |
| 29 | 0.2 | 92 |
| 30 | 1 | 91 |
| 31 | 0.7 | 86 |
| 32 | 0.8 | 87 |
| 33 | 1 | 84 |
| 34 | 0.4 | 85 |
| 35 | 1 | 89 |
| 36 | 0.2 | 83 |
| 37 | 3 | 83 |
| 38 | 12 | 86 |
| 39 | 0.7 | 86 |
| 40 | 0.2 | 81 |
| 41 | 1 | 85 |
| 42 | 11 | 89 |
| 43 | 0.8 | 97 |
| 44 | 8 | 89 |
| 45 | 0.2 | 87 |
| 46 | 0.2 | 83 |
| 47 | 1 | 84 |
| 48 | 0.8 | 89 |
| 49 | 0.2 | 89 |
| 50 | 0.2 | 84 |
| 51 | 12 | 85 |
| 52 | 1 | 84 |
| 53 | 0.2 | 84 |
| 54 | 1 | 74 |
| 55 | 0.2 | 88 |
| 56 | 0.2 | 86 |
| 57 | 3 | 89 |
| 58 | 0.2 | 78 |
| 59 | 0.9 | 81 |
| 60 | 0.2 | 73 |
| 61 | 0.2 | 82 |
| 62 | 0.2 | 80 |
| 63 | 0.3 | 86 |
| 64 | 0.2 | 81 |
| 65 | 38 | 71 |
| 66 | 0.2 | 84 |
| 67 | 1 | 90 |
| 68 | 0.6 | 87 |
| 69 | 0.2 | 81 |
| 70 | 25 | 73 |
| 71 | 11 | 75 |
| 72 | 0.2 | 91 |
| 73 | 6 | 86 |
| 74 | 4 | 83 |
| 75 | 27 | 92 |
| 76 | 0.6 | 88 |
| 77 | 1 | 91 |
| 78 | 0.2 | 88 |
| 79 | 0.2 | 89 |
| 80 | 0.2 | 89 |
| 81 | 7 | 77 |
| 82 | 7 | 86 |
| 83 | 2 | 75 |
| 84 | 2 | 78 |
| 85 | 1 | 86 |
| 86 | 0.5 | 95 |
| 87 | 0.4 | 83 |
| 88 | 0.2 | 88 |
| 89 | 1 | 91 |
| 90 | 0.4 | 91 |
| 91 | 0.4 | 91 |
| 92 | 0.5 | 96 |
| 93 | 0.4 | 87 |
| 94 | 0.2 | 87 |
| 95 | 0.2 | 93 |
| 96 | 0.6 | 91 |
| 97 | 0.2 | 94 |
| 98 | 0.5 | 93 |
| 99 | 0.7 | 89 |
| 100 | 0.2 | 88 |
| 101 | 0.6 | 92 |
| 102 | 2 | 87 |
| 103 | 3 | 89 |
| 104 | 0.2 | 88 |
| 105 | 0.2 | 91 |
| 106 | 0.5 | 90 |
| 107 | 2 | 82 |
| 108 | 3 | 86 |
| 109 | 1 | 90 |
| 110 | 0.2 | 87 |
| 111 | 6 | 86 |
| 112 | 4 | 87 |
| 113 | 0.7 | 80 |
| 114 | 5 | 71 |
| 115 | 6 | 77 |
| 116 | 2 | 88 |
| 117 | 3 | 92 |
| 118 | 126 | 74 |
| 119 | 1 | 91 |
| 120 | 0.7 | 91 |
| 121 | 0.2 | 90 |
| 122 | 0.3 | 91 |
| 123 | 15 | 81 |
| 124 | 5 | 76 |
| 125 | 4 | 84 |
| 126 | 0.3 | 91 |
| 127 | 0.8 | 90 |
| 128 | 14 | 72 |
| 129 | 44 | 75 |
| 130 | 18 | 73 |
| 131 | 3 | 83 |
| 132 | 2 | 88 |
| 133 | 2 | 83 |
| 134 | 3 | 85 |
| 135 | 3 | 87 |
| 136 | 1 | 79 |
| 137 | 5 | 75 |
| 138 | 0.5 | 89 |
| 139 | 9 | 73 |
| 140 | 3 | 85 |
| 141 | 2 | 87 |
| 142 | 2 | 83 |
| 143 | 14 | 74 |
| 144 | 18 | 75 |
| 145 | 0.5 | 82 |
| 146 | 2 | 86 |
| 147 | 49 | 77 |
| 148 | 448 | 77 |

TABLE 4-continued

| Examples | Degradation IC$_{50}$ (nM) | % Degradation at 3 μM |
|---|---|---|
| 149 | 0.9 | 91 |
| 150 | 4 | 82 |
| 151 | 0.4 | 90 |
| 152 | 0.2 | 92 |
| 153 | 0.2 | 91 |
| 154 | 0.2 | 92 |
| 155 | 0.2 | 81 |
| 156 | 0.4 | 85 |
| 157 | 0.2 | 90 |
| 158 | 0.2 | 88 |
| 159 | 0.5 | 89 |
| 160 | 0.2 | 75 |
| 161 | 0.7 | 93 |
| 162 | 0.8 | 90 |
| 163 | 0.6 | 94 |
| 164 | 0.5 | 91 |
| 165 | 0.2 | 90 |
| 166 | 2 | 90 |
| 167 | 0.5 | 87 |
| 168 | 0.7 | 86 |
| 169 | 0.2 | 85 |
| 170 | 1 | 81 |
| 171 | 0.2 | 85 |
| 172 | 0.4 | 87 |
| 173 | 4 | 82 |
| 174 | 4 | 81 |
| 175 | 0.3 | 83 |
| 176 | 0.2 | 85 |
| 177 | 0.2 | 75 |
| 178 | 0.4 | 87 |
| 179 | 4 | 80 |
| 180 | 3 | 80 |
| 181 | 3 | 83 |
| 182 | 5 | 79 |
| 183 | 1 | 83 |
| 184 | 0.7 | 87 |
| 185 | 0.7 | 84 |
| 186 | 0.6 | 85 |
| 187 | 0.5 | 92 |
| 188 | 0.8 | 90 |
| 189 | 0.3 | 88 |
| 190 | 0.5 | 91 |
| 191 | 0.2 | 95 |
| 192 | 0.4 | 91 |
| 193 | 0.2 | 91 |
| 194 | 0.2 | 89 |
| 195 | 0.4 | 97 |
| 196 | 0.3 | 93 |
| 197 | 0.2 | 88 |
| 198 | 0.2 | 87 |
| 199 | 0.4 | 94 |
| 200 | 0.5 | 91 |
| 201 | 0.8 | 85 |
| 202 | 0.5 | 89 |
| 203 | 0.6 | 93 |
| 204 | 0.6 | 88 |
| 205 | 0.4 | 84 |
| 206 | 0.4 | 85 |
| 207 | 0.5 | 85 |
| 208 | 0.4 | 86 |
| 209 | 0.4 | 92 |
| 210 | 2 | 89 |
| 211 | 0.3 | 93 |
| 212 | 2 | 90 |
| 213 | 0.9 | 86 |
| 214 | 1 | 82 |
| 215 | 0.2 | 93 |
| 216 | 0.2 | 88 |
| 217 | 0.2 | 87 |
| 218 | 0.2 | 78 |
| 219 | 0.2 | 90 |
| 220 | 0.2 | 89 |
| 221 | 0.2 | 84 |
| 222 | 1 | 80 |
| 223 | 0.2 | 85 |
| 224 | 3 | 85 |
| 225 | 6 | 82 |
| 226 | 103 | 93 |
| 227 | 4 | 90 |
| 228 | 0.2 | 87 |
| 229 | 0.2 | 89 |
| 230 | 0.8 | 93 |
| 231 | 2 | 96 |
| 232 | 0.2 | 95 |
| 233 | 0.2 | 94 |
| 234 | 0.2 | 90 |
| 235 | 0.9 | 95 |
| 236 | 0.3 | 91 |
| 237 | 0.2 | 92 |
| 238 | 0.5 | 87 |
| 239 | 0.6 | 87 |
| 240 | 0.3 | 89 |
| 241 | 0.2 | 85 |
| 242 | 0.8 | 83 |
| 243 | 0.3 | 91 |
| 244 | 0.4 | 92 |
| 245 | 0.5 | 87 |
| 246 | 0.5 | 82 |
| 247 | 0.2 | 93 |
| 248 | 0.7 | 95 |
| 249 | 0.3 | 87 |
| 250 | 0.5 | 87 |
| 251 | 0.5 | 89 |
| 252 | 0.2 | 86 |
| 253 | 0.2 | 85 |
| 254 | 10 | 84 |
| 255 | 0.6 | 92 |
| 256 | 0.2 | 91 |
| 257 | 37 | 87 |
| 258 | 5 | 77 |

It is therefore apparent that the compounds of the invention have degradation activities for estrogen receptors, and that most of them have as well antagonist and/or antiproliferative activity. The compounds according to the invention can therefore be used for preparing medicaments, especially medicaments which are antagonists and degraders of estrogen receptors.

Accordingly, in another of its aspects, the invention provides medicaments which comprise a compound of the formula (I-A), (I) or (I') or a pharmaceutically acceptable salt thereof.

The invention also relates to the compounds of formula (I-A), (I) or (I') defined above, or a pharmaceutically acceptable salt thereof, for use in therapy, especially as inhibitors and degraders of estrogen receptors.

The invention also relates to the compounds of formula (I-A), (I) or (I') defined above, or a pharmaceutically acceptable salt thereof, for use in the treatment of ovulatory dysfunction, cancer, endometriosis, osteoporosis, benign prostatic hypertrophy or inflammation.

In particular, the invention relates to the compounds of formula (I-A), (I) or (I') defined above, or a pharmaceutically acceptable salt thereof, for use in the treatment of cancer.

In an embodiment, the cancer is a hormone dependent cancer.

In another embodiment, the cancer is an estrogen receptor dependent cancer, particularly the cancer is an estrogen receptor α dependent cancer.

In another embodiment, the cancer is a cancer with wild type estrogen receptors.

In another embodiment, the cancer is a cancer with deregulated function of estrogen receptors related to, but not limited to, at least one epigenetic and genetic alteration of estrogen receptors such us mutation, amplification, splice variant.

In another embodiment, the cancer is a cancer with mutated estrogen receptors.

In another embodiment, the mutations of estrogen receptors can include, but not limited to, new or known mutations such us Leu536Arg, Tyr537Ser, Tyr537Asn, Asp538Gly.

In another embodiment, the cancer is an estrogen-sensitive cancer.

In another embodiment, the cancer is selected from breast, ovarian, endometrial, prostate, uterine, cervical or lung cancer, or a metastasis thereof.

In another embodiment, the metastasis is a cerebral metastasis.

In another embodiment, the cancer is breast cancer. Particularly, the breast cancer is an estrogen receptor positive breast cancer (ERα positive breast cancer).

In another embodiment, the cancer is resistant to anti-hormonal treatment.

In a further embodiment, the anti-hormonal treatment is as single agent or in combination with other agents such as CDK4/6 or PI3K inhibitors.

In a further embodiment, the anti-hormonal treatment includes treatment with at least one agent selected from tamoxifen, fulvestrant, a steroidal aromatase inhibitor, and a non-steroidal aromatase inhibitor.

The present invention, according to another of its aspects, also relates to a method of treating the pathological conditions indicated above, comprising administering to a subject in need thereof a therapeutically effective amount of a compound of the formula (I-A), (I) or (I') defined above, or a pharmaceutically acceptable salt thereof. In an embodiment of this method of treatment, the subject is a human.

The present invention also relates to the use of a compound of the formula (I-A), (I) or (I') defined above, or a pharmaceutically acceptable salt thereof, for the manufacture of a medicament useful for treating any of the pathological conditions indicated above, more particularly for treating cancer.

According to another of its aspects, the present invention relates to pharmaceutical compositions comprising as active principle a compound of the formula (I-A), (I) or (I') defined above, or a pharmaceutically acceptable salt thereof. These pharmaceutical compositions comprise an effective dose of at least one compound of the formula (I-A), (I) or (I'), or a pharmaceutically acceptable salt thereof, and also at least one pharmaceutically acceptable excipient.

The said excipients are selected, in accordance with the pharmaceutical form and method of administration desired, from the customary excipients, which are known to a person skilled in the art.

In the pharmaceutical compositions of the present invention for oral, sublingual, subcutaneous, intramuscular, intravenous, topical, local, intra-tracheal, intranasal, transdermal or rectal administration, the active principle of formula (I-A), (I) or (I') above, or its pharmaceutically acceptable salt thereof, may be administered in a unit administration form, in a mixture with conventional pharmaceutical excipients, to animals and to human beings for the treatment of the above disorders or diseases.

The unit administration forms appropriate include oral forms such as tablets, soft or hard gel capsules, powders, granules and oral solutions or suspensions, sublingual, buccal, intra-tracheal, intra-ocular and intra-nasal administration forms, forms for inhalative, topical, transdermal, subcutaneous, intra-muscular or intravenous administration, rectal administration forms and implants. For topical application it is possible to use the compounds according to the invention in creams, gels, ointments or lotions.

As an example, a unit administration form of a compound according to the invention in tablet form may comprise the following components:

| Compound according to the invention | 50.0 mg |
|---|---|
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate; such dosages do not depart from the scope of the invention. According to usual practice, the dosage that is appropriate for each patient is determined by the doctor according to the mode of administration and the weight and response of the said patient.

The invention claimed is:
1. The compound of formula (I-A):

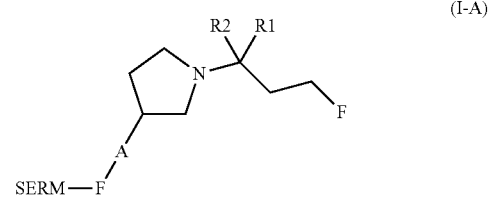

(I-A)

wherein:
R1 and R2 represent independently a hydrogen atom or a deuterium atom;
A represents an oxygen or nitrogen atom; and
SERM-F represents a selective estrogen receptor modulator fragment comprising an aryl or heteroaryl group linked to the adjacent "A" group;
wherein SERM-F is selected from the group consisting of structures (aI), (cIII) and (dIV), provided that when A represents a nitrogen atom then SERM-F represents the structure (aI):

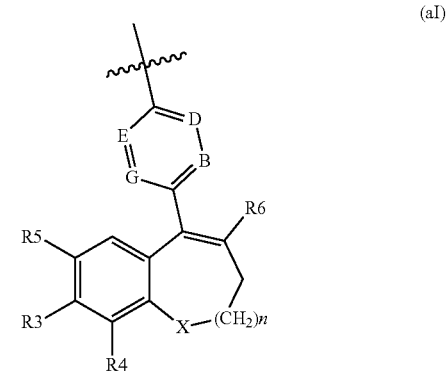

(aI)

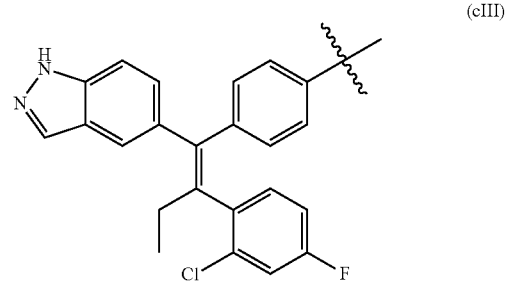

(cIII)

-continued

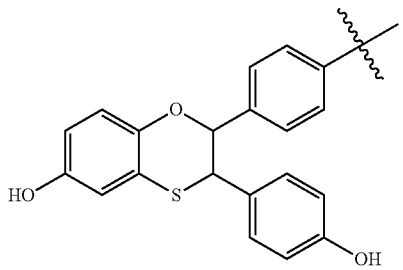
(dIV)

wherein:
B, D, E and G represent independently =CH— or nitrogen atoms;
n is an integer selected from 0 and 1;
X represents —CH$_2$—, —O—, —S—, —SO— or —SO$_2$—;
when n=1 and X=CH$_2$, then at least one of A, B, D, E or G is a nitrogen atom;
R3 represents a hydrogen atom or an —OH, —COOH or —OPO(OH)$_2$ group;
R4 represents a hydrogen, fluorine or chlorine atom or a methyl group;
R5 represents a hydrogen, fluorine or chlorine atom, or a methyl or —OH group;
wherein R3 and R5 do not simultaneously represent —OH groups or hydrogen atoms;
R6 is selected from:
a phenyl group, which is unsubstituted or substituted with 1 to 3 substituents independently selected from:
a (C$_1$-C$_6$)-alkyl group unsubstituted or substituted with one or more fluorine atoms or —OH groups; a halogen atom; an —OH group; a (C$_1$-C$_6$)-alkoxy group unsubstituted or substituted with one or more fluorine atoms, (C$_1$-C$_6$)-alkoxy or heterocycloalkyl groups; a cyano group; a sulphur group substituted with 5 fluorine atoms or with a (C$_1$-C$_6$)-alkyl group substituted with two or more fluorine atoms; a sulfonyl-(C$_1$-C$_6$)-alkyl group wherein said (C$_1$-C$_6$)-alkyl group is unsubstituted or substituted with two or more fluorine atoms; a silane group substituted with three (C$_1$-C$_6$)-alkyl groups; an amine group unsubstituted or substituted with one or more (C$_1$-C$_6$)-alkyl groups; an amide group unsubstituted or substituted with one or more (C$_1$-C$_6$)-alkyl or (C$_1$-C$_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —SO$_2$NH$_2$ group; a —COOH group; a —O-cycloalkyl group; a —O-heterocycloalkyl group; and a OCD$_3$ group;
a heteroaryl group comprising 3 to 9 carbon atoms and comprising between 1 to 3 heteroatoms independently selected from oxygen, nitrogen and sulphur, said heteroaryl group being unsubstituted or substituted with 1 to 3 substituents independently selected from:
a (C$_1$-C$_6$)-alkyl group unsubstituted or substituted with one or more fluorine atoms; a halogen atom; an —OH group; a (C$_1$-C$_6$)-alkoxy group unsubstituted or substituted with one or more fluorine atoms; a cyano group; a sulphur group substituted with 5 fluorine atoms or with a (C$_1$-C$_6$)-alkyl group substituted with two or more fluorine atoms; a sulfonyl-(C$_1$-C$_6$)-alkyl group wherein said (C$_1$-C$_6$)-alkyl group is unsubstituted or substituted with two or more fluorine atoms; a silane group substituted with three (C$_1$-C$_6$)-alkyl groups; an amine group unsubstituted or substituted with one or more (C$_1$-C$_6$)-alkyl groups; an amide group unsubstituted or substituted with one or more (C$_1$-C$_6$)-alkyl or (C$_1$-C$_6$)-alkoxy groups; a heterocycloalkyl group saturated or partially saturated, comprising 3 to 5 carbon atoms and comprising 1 or 2 heteroatoms independently selected from oxygen, nitrogen and sulphur; a heteroaryl group comprising 2 to 4 carbon atoms and comprising 1 to 3 heteroatoms selected from oxygen, nitrogen and sulphur and being unsubstituted or substituted with an oxo group; a —COO—(C$_1$-C$_6$)-alkyl group; and an oxo group;
a cycloalkyl group comprising 4 to 9 carbon atoms, which is saturated or partially saturated, and which is unsubstituted or substituted with 1 to 4 substituents independently selected from:
a fluorine atom; an —OH group; a (C$_1$-C$_6$)-alkyl group; a —COOR7 group wherein R7 is a (C$_1$-C$_6$)-alkyl group; and an oxo group; and
a heterocycloalkyl group comprising 4 to 9 carbon atoms and comprising 1 or 2 heteroatoms independently selected from oxygen, nitrogen and sulphur, said heterocycloalkyl group being saturated or partially saturated and being unsubstituted or substituted with 1 to 4 substituents independently selected from:
a fluorine atom; an —OH group; a (C$_1$-C$_6$)-alkyl group; a —COOR7 group wherein R7 is a (C$_1$-C$_6$)-alkyl group; and an oxo group;
or a pharmaceutically acceptable salt thereof.

2. The compound according to claim 1, wherein the compound is a compound of formula (I), wherein
R1 and R2 represent independently a hydrogen atom or a deuterium atom;
A represents an oxygen or nitrogen atom; and wherein R3, R4, R5, R6, B, D, E, G, X and n are as defined in claim 1:

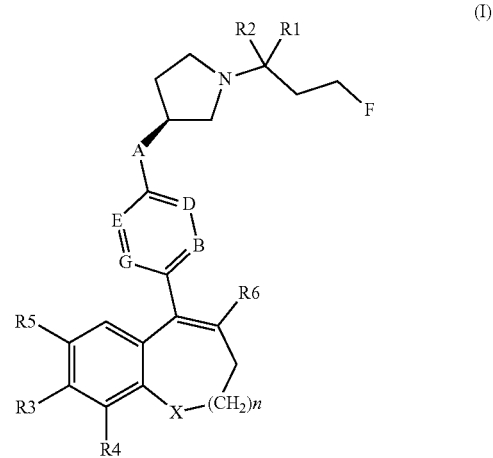
(I)

or a pharmaceutically acceptable salt thereof.

3. The compound according to claim 2, wherein R6 is selected from:
a phenyl group, which is unsubstituted or substituted with 1, 2 or 3 substituents independently selected from:
a (C$_1$-C$_6$)-alkyl group unsubstituted or substituted with one or more fluorine atoms or —OH groups; a halogen atom; an —OH group; a (C$_1$-C$_6$)-alkoxy group unsubstituted or substituted with one or more fluorine atoms, (C$_1$-C$_6$)-alkoxy or heterocycloalkyl groups; a sulphur group substituted with a (C$_1$-C$_6$)-alkyl group substituted with two or more fluorine atoms; a sulfonyl-(C$_1$-C$_6$)-alkyl group; an amine group unsubstituted or substituted with one or more (C$_1$-C$_6$)-alkyl groups; an amide group substituted with an (C$_1$-C$_6$)-alkoxy groups; a —SO$_2$NH$_2$ group; a —COOH group; a —O-cycloalkyl group; a —O-heterocycloalkyl group; and a —OCD$_3$ group;

a heteroaryl group selected from an indole, pyridinyl, benzofuran, isoxazole, quinolyl and thiazolyl group, said heteroaryl group being unsubstituted or substituted with 1 to 3 substituents independently selected from: a ($C_1$-$C_6$)-alkyl group; a halogen atom; an —OH group; a ($C_1$-$C_6$)-alkoxy group; an amine group; an amide group substituted with a ($C_1$-$C_6$)-alkoxy group; and a heterocycloalkyl group selected from an indolinyl, dihydroazaindolinyl, dihydrobenzodioxinyl, benzodioxolyl, 2,3-dihydrobenzofuranyl, dihydrobenzoxazinyl and 5,6-dihydro-2H-pyranyl group, said heterocycloalkyl group being unsubstituted or substituted with 1 to 4 substituents independently selected from:

a fluorine atom; a ($C_1$-$C_6$)-alkyl group; a —COOR7 group wherein R7 is a ($C_1$-$C_6$)-alkyl group; and an oxo group; or a pharmaceutically acceptable salt thereof.

4. The compound according to claim 1, wherein the compound is a compound of formula (I-2), wherein R1 and R2 represent independently a hydrogen atom or a deuterium atom, and X, n, R3, R4, R5, R6, B, D, E and G are as defined in claim 1:

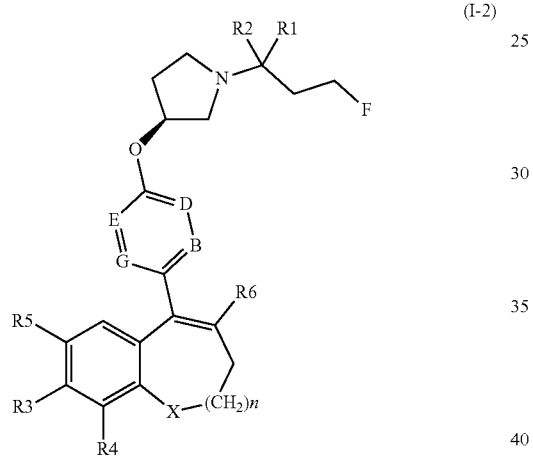

(I-2)

or a pharmaceutically acceptable salt thereof.

5. The compound according to claim 1, wherein the compound is a compound of formula (I-3), wherein R1 and R2 represent independently a hydrogen atom or a deuterium atom, and R3, R4, R5 and R6 are as defined in claim 1:

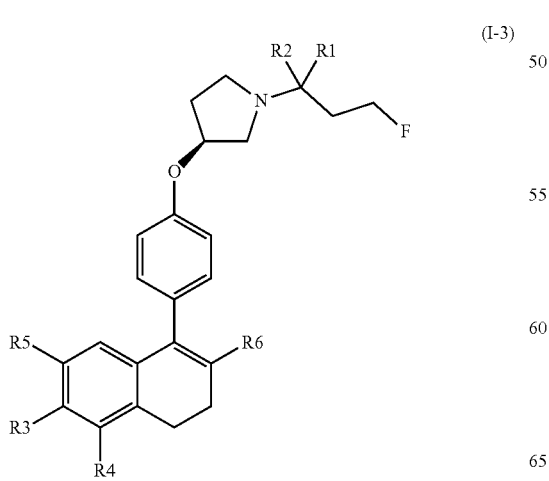

(I-3)

or a pharmaceutically acceptable salt thereof.

6. The compound according to claim 1, wherein the compound is a compound of formula (I-4), wherein R1 and R2 represent independently a hydrogen atom or a deuterium atom, and R3, R4, R5 and R6 are as defined in claim 1:

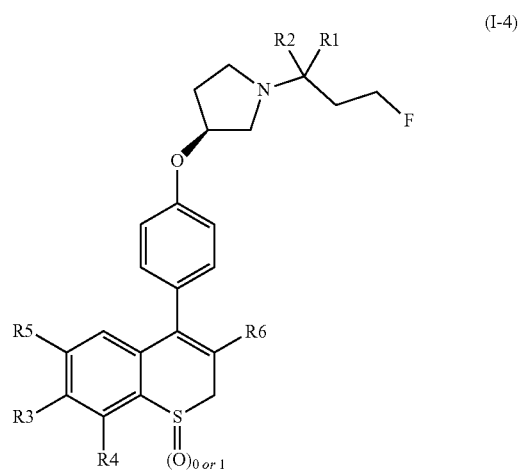

(I-4)

or a pharmaceutically acceptable salt thereof.

7. The compound according to claim 1, wherein the compound is a compound of formula (I-5), wherein R1 and R2 represent independently a hydrogen atom or a deuterium atom, and E, D, R3, R4, R5 and R6 are as defined in claim 1 and wherein one or two of E and D represent nitrogen atoms:

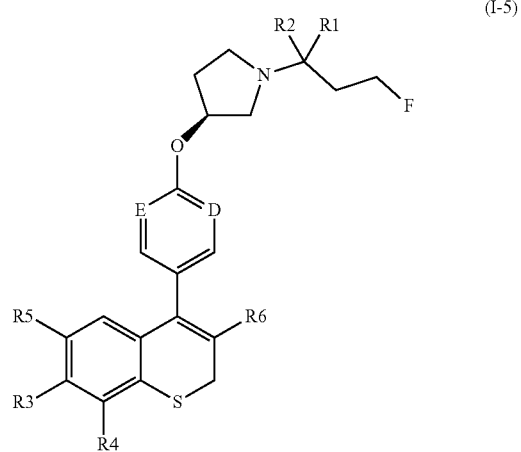

(I-5)

or a pharmaceutically acceptable salt thereof.

8. The compound according to claim 1, wherein the compound is a compound of formula (I-6), wherein R1 and R2 represent independently a hydrogen atom or a deuterium atom, and R3, R4, R5 and R6 are as defined in claim 1:

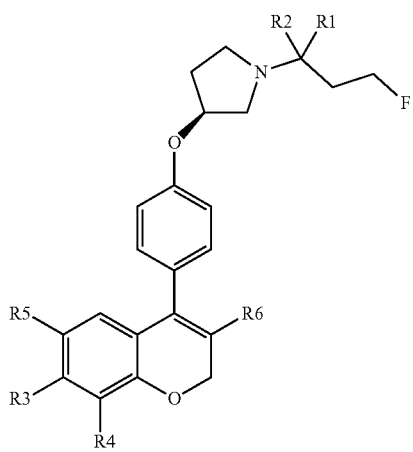

(I-6)

or a pharmaceutically acceptable salt thereof.

9. The compound according to claim 1, wherein the compound is a compound of formula (I-7), wherein R1 and R2 represent independently a hydrogen atom or a deuterium atom, and n, R3, R4, R5 and R6 are as defined in claim 1:

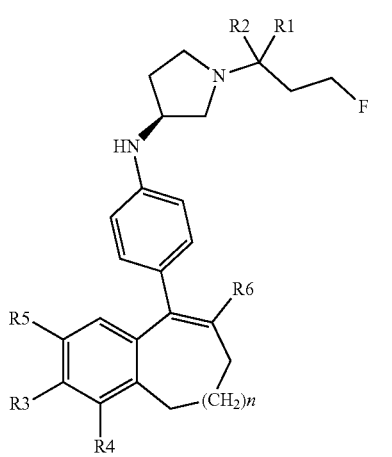

(I-7)

or a pharmaceutically acceptable salt thereof.

10. The compound according to claim 1, wherein the compound is a compound of formula (I-8), wherein R1 and R2 represent independently a hydrogen atom or a deuterium atom, and R3, R4, R5 and R6 are as defined in claim 1:

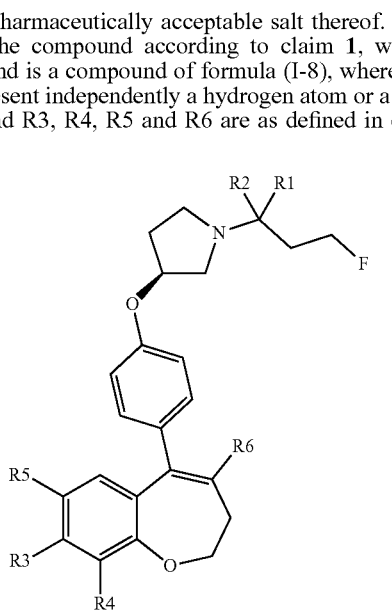

(I-8)

or a pharmaceutically acceptable salt thereof.

11. The compound according to claim 1, wherein the compound is a compound of formula (I-9), wherein R1 and R2 represent independently a hydrogen atom or a deuterium atom, and D, R3, R4, R5 and R6 are as defined in claim 1:

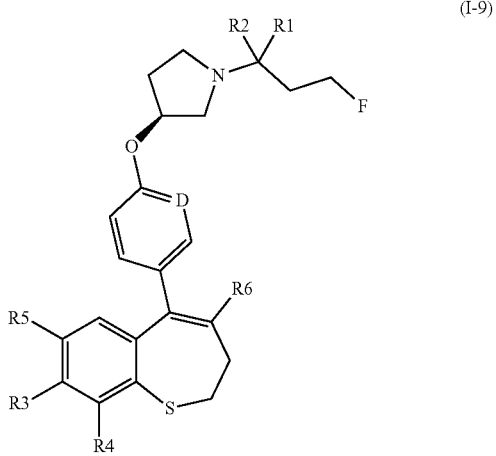

(I-9)

or a pharmaceutically acceptable salt thereof.

12. The compound according to claim 1, wherein the compound is a compound of formula (I-10), wherein R1 and R2 represent independently a hydrogen atom or a deuterium atom, and R3, R4, R5 and R6 are as defined in claim 1:

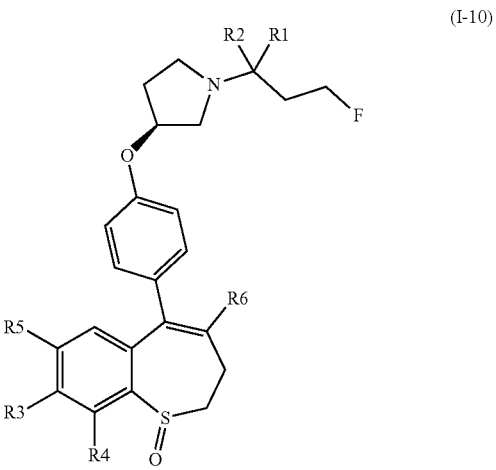

(I-10)

or a pharmaceutically acceptable salt thereof.

13. The compound according to claim 1, wherein the compound is a compound of formula (I-11), wherein R1 and R2 represent independently a hydrogen atom or a deuterium atom, and R3, R4, R5 and R6 are as defined in claim 1:

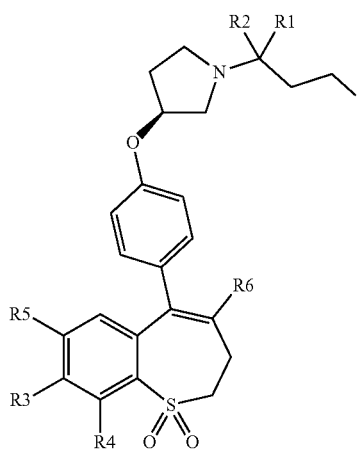

(I-11)

or a pharmaceutically acceptable salt thereof.

14. The compound according to claim 1, wherein the compound is a compound of formula (I-12), wherein R1 and R2 represent independently a hydrogen atom or a deuterium atom, and B, D, E, G, R3, R4, R5 and R6 are as defined in claim 1:

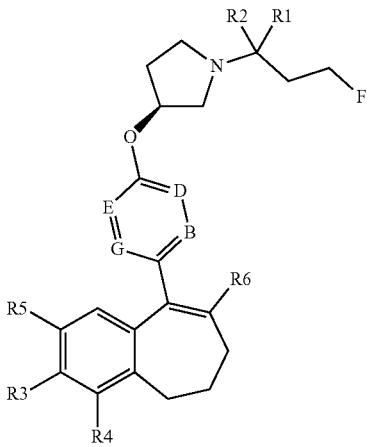

(I-12)

or a pharmaceutically acceptable salt thereof.

15. A pharmaceutical composition comprising a compound according to claim 1, or a pharmaceutically acceptable salt thereof, and at least one pharmaceutically acceptable excipient.

16. The compound according to claim 1, wherein the compound is selected from 6-(2,4-dichlorophenyl)-5-[6-[(3S)-1-(3-fluoropropyl)pyrrolidin-3-yl]oxy-3-pyridyl]-8,9-dihydro-7H-benzo[7]annulene-2-carboxylic acid, and 6-(2,4-dichlorophenyl)-5-[6-[(3S)-1-(3-fluoropropyl)pyrrolidin-3-yl]oxy-3-pyridyl]-8,9-dihydro-7H-benzo[7]annulen-2-ol.

* * * * *